United States Patent
Mitsuya et al.

(10) Patent No.: US 7,285,552 B2
(45) Date of Patent: *Oct. 23, 2007

(54) DRUGS CONTAINING TRIAZASPIRO[5.5]UNDECANE DERIVATIVES AS THE ACTIVE INGREDIENT

(75) Inventors: Hiroaki Mitsuya, Kumamoto (JP); Kenji Maeda, Kumamoto (JP); Shiro Shibayama, Mishima-gun (JP); Yoshikazu Takaoka, Mishima-gun (JP)

(73) Assignee: Ono Pharmaceuticals Co., Ltd., Osaka (JP)

( * ) Notice: Subject to any disclaimer, the term of this patent is extended or adjusted under 35 U.S.C. 154(b) by 68 days.

This patent is subject to a terminal disclaimer.

(21) Appl. No.: 10/472,626

(22) PCT Filed: Mar. 18, 2002

(86) PCT No.: PCT/JP02/02553

§ 371 (c)(1), (2), (4) Date: Sep. 22, 2003

(87) PCT Pub. No.: WO02/074769

PCT Pub. Date: Sep. 26, 2002

(65) Prior Publication Data

US 2004/0106619 A1 Jun. 3, 2004

(30) Foreign Application Priority Data

Mar. 19, 2001 (JP) ............................. 2001-079611

(51) Int. Cl.
*A61K 31/497* (2006.01)
(52) U.S. Cl. ................................. 514/253.01
(58) Field of Classification Search ............ 514/253.01
See application file for complete search history.

(56) References Cited

U.S. PATENT DOCUMENTS

| | | | |
|---|---|---|---|
| 6,288,083 B1 * | 9/2001 | Luly et al. | 514/318 |
| 6,288,084 B1 * | 9/2001 | Luly et al. | 514/318 |
| 7,053,090 B2 | 5/2006 | Habashita et al. | |
| 7,119,091 B2 | 10/2006 | Habashita et al. | |
| 2005/0215557 A1 | 9/2005 | Habashita et al. | |

FOREIGN PATENT DOCUMENTS

| | | |
|---|---|---|
| EP | 1 123 726 A1 | 9/2002 |
| GB | 2 127 807 A | 4/1984 |
| JP | 59-89671 A | 5/1984 |
| WO | WO93-13101 A1 | 7/1993 |
| WO | WO97-11940 A1 | 4/1997 |
| WO | WO 01/40227 A1 | 6/2001 |

OTHER PUBLICATIONS

Liu et al, "Homozygous Defect in HIV-1 Coreceptor Accounts for Resistance of Some Multiply-Exposed Individuals to HIV-1 Infection" Cell, vol. 86, pp. 367-377 (1996).*
Samson et al, "Resistance to HIV-1 infection in caucasian individuals bearing mutant alleles of the CCR-5 chemokine receptor gene" Nature, vol. 382, pp. 722-725 (1996).*
Maeda, K. et al., "Novel Low Molecular Weight Spirodiketopiperazin Derivatives Potently Inhibit $R^5$ HIV-1 Infection through Their Antagonistic Effects on CCR5", Journal of Biological Chemistry, 276 (37), pp. 35194 to 35200 (2001).

* cited by examiner

Primary Examiner—Zachary C Tucker
(74) Attorney, Agent, or Firm—Sughrue Mion Pllc.

(57) ABSTRACT

A pharmaceutical composition for prevention and/or treatment for HIV infection or AIDS induced by the infection which comprises, as an active ingredient, a triazaspiro[5.5] undecane derivative, a quaternary ammonium salt thereof, an N-oxide thereof, or a non-toxic salt thereof, and if necessary, it may be combined with at least one member of other agents for prevention and/or treatment for HIV infection (wherein all symbols are as defined in the specification.)

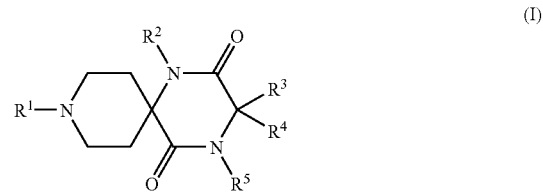

(I)

The triazaspiro[5.5]undecane derivatives, the quaternary ammonium salts thereof or the N-oxides thereof, or the non-toxic salts thereof are useful in preventing and/or treating HIV infection and AIDS induced by the infection.

7 Claims, No Drawings

DRUGS CONTAINING TRIAZASPIRO[5.5]UNDECANE DERIVATIVES AS THE ACTIVE INGREDIENT

TECHNICAL FIELD

The present invention relates to a pharmaceutical composition for prevention and/or treatment for human immunodeficiency virus (hereinafter referred to as "HIV") infection or acquired immune deficiency syndrome (called AIDS) induced by the infection which comprises, as an active ingredient, at least one selected from triazaspiro[5.5]undecane derivatives, quaternary ammonium salts thereof and N-oxides thereof, and non-toxic salts thereof, and if necessary, other agents for prevention and/or treatment for HIV infection.

More particularly, it relates to a pharmaceutical composition for prevention and/or treatment for HIV infection or AIDS induced by the infection which comprises, as an active ingredient, at least one selected from triazaspiro[5.5]undecane derivatives represented by formula (I)

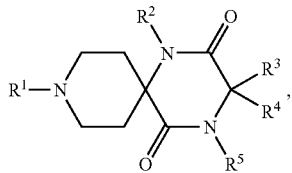

quaternary ammonium salts thereof or N-oxides thereof, or non-toxic salts thereof, and if necessary, a protease inhibitor, a reverse transcriptase inhibitor, a fusion inhibitor and/or a chemokine regulator.

BACKGROUND ART

In the publication of International Publication No. 01/40227, it is reported that the compounds represented by formula (I) regulate the effect of chemokine/chemokine receptor, so they are used for prevention and/or treatment of various inflammatory diseases, asthma, atopic dermatitis, urticaria, allergic diseases (allergic bronchopulmonary aspergillosis or allergic eosinophilic gastroenteritis etc.), nephritis, nephropathy, hepatitis, arthritis, rheumatoid arthritis, psoriasis, rhinitis, conjunctivitis, ischemic reperfusion disorder, multiple sclerosis, ulcerative colitis, acute respiratory distress syndrome, cytotoxic shock, diabetes, autoimmune disease, in transplanted organ rejection reactions, immunosuppression, cancer metastasis and acquired immune deficiency syndrome. Furthermore, in the specification, the inhibition effect on the binding of RANTES to CCR5 and the inhibition effect on the binding of MCP-1 to CCR2 had been found experimentally. However, the test which indicates that the compounds represented by formula (I) are used for actual HIV infection has never been described.

Furthermore, in the specification, a combination of chemokine/chemokine regulator with other drugs has never been described.

DISCLOSURE OF THE INVENTION

The present inventors have investigated, and consequently, the present inventors have found experimentally that triazaspiro[5.5]undecane derivatives represented by formula (I), quaternary salts thereof or N-oxides thereof, or non-toxic salts thereof have effect for HIV infection.

Furthermore, the present inventors have found that a combination of triazaspiro[5.5]undecane derivatives represented by formula (I), quaternary salts thereof or N-oxides thereof, or non-toxic salts thereof with at least one member of other preventive and/or treating agents for HIV infection has effect for HIV infection, too.

The present invention relates to (1) A pharmaceutical composition for prevention and/or treatment for HIV infection which comprises, as an active ingredient, at least one triazaspiro[5.5]undecane derivative represented by formula (I)

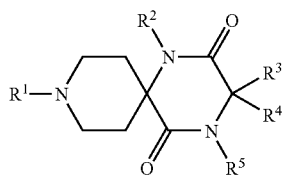

[wherein $R^1$ is
(1) hydrogen,
(2) C1-18 alkyl,
(3) C2-18 alkenyl,
(4) C2-18 alkynyl,
(5) —$COR^6$,
(6) —$CONR^7R^8$,
(7) —$COOR^9$,
(8) —$SO_2R^{10}$,
(9) —$COCOOR^{11}$,
(10) —$CONR^{12}COR^{13}$,
(11) Cyc1 or
(12) C1-18 alkyl, C2-18 alkenyl or C2-18 alkynyl substituted by 1-5 substituents optionally selected from (a) halogen, (b) —$CONR^7R^8$, (c) —$COOR^9$, (d) —$OR^{14}$, (e) —$SR^{15}$, (f) —$NR^{16}R^{17}$, (g) —$NR^{18}COR^{19}$, (h) —$SO_2NR^{20}R^{21}$, (i) —$OCOR^{22}$, (j) —$NR^{23}SO_2R^{24}$, (k) —$NR^{25}COOR^{26}$, (l) —$NR^{27}CONR^{28}R^{29}$, (m) Cyc1, (n) keto and (o) —$N(SO_2R^{24})_2$, $R^6$-$R^9$, $R^{11}$-$R^{21}$, $R^{23}$, $R^{25}$ and $R^{27}$-$R^{29}$ are each independently
(1) hydrogen,
(2) C1-8 alkyl,
(3) C2-8 alkenyl,
(4) C2-8 alkynyl,
(5) Cyc1 or
(6) C1-8 alkyl, C2-8 alkenyl or C2-8 alkynyl substituted by 1-5 substituents optionally selected from (a) Cyc1, (b) halogen, (c) —$OR^{30}$, (d) —$SR^{31}$, (e) —$NR^{32}R^{33}$, (f) —$COOR^{34}$, (g) —$CONR^{35}R^{36}$, (h) —$NR^{37}COR^{38}$, (i) —$NR^{39}SO_2R^{40}$ and (j) —$N(SO_2R^{40})_2$, $R^7$ and $R^8$, $R^{20}$ and $R^{21}$, or $R^{28}$ and $R^{29}$, taken together, are
1) C2-6 alkylene,
2) —(C2-6 alkylene)-O—(C2-6 alkylene)-,
3) —(C2-6 alkylene)-S—(C2-6 alkylene)- or
4) —(C2-6 alkylene)-$NR^{195}$—(C2-6 alkylene)- (wherein $R^{195}$ is hydrogen, C1-8 alkyl, phenyl, or C1-8 alkyl substituted by phenyl.), $R^{10}$, $R^{22}$, $R^{24}$ and $R^{26}$ are each independently
(1) C1-8 alkyl,
(2) C2-8 alkenyl,
(3) C2-8 alkynyl,
(4) Cyc1 or
(5) C1-8 alkyl, C2-8 alkenyl or C2-8 alkynyl substituted by 1-5 substituents optionally selected from (a) Cyc1, (b) halogen, (c) —$OR^{30}$, (d) —$SR^{31}$, (e) —$NR^{32}R^{33}$, (f) —$COOR^{34}$, (g) —$CONR^{35}R^{36}$, (h) —$NR^{37}COR^{38}$, (i) —$NR^{39}SO_2R^{40}$ and (j) —$N(SO_2R^{40})_2$, $R^{30}$—$R^{37}$ and $R^{39}$ are each independently hydrogen, C1-8 alkyl, Cyc1 or C1-8 alkyl substituted by Cyc1, $R^{35}$ and $R^{36}$, taken together, are
1) C2-6 alkylene,
2) —(C2-6 alkylene)-O—(C2-6 alkylene)-,
3) —(C2-6 alkylene)-S—(C2-6 alkylene)- or
4) —(C2-6 alkylene)-$NR^{196}$—(C2-6 alkylene)- (wherein $R^{196}$ is hydrogen, C1-8 alkyl, phenyl or C1-8 alkyl substituted by phenyl.), $R^{38}$ and $R^{40}$ are each independently C1-8 alkyl, Cyc1 or C1-8 alkyl substituted by Cyc1, Cyc1 is C3-15 mono-, bi- or tri-(fused or spiro)carbocyclic ring or 3-15 membered mono-, bi- or tri-(fused or spiro)cyclic hetero ring containing 1-4 nitrogen atoms, 1-3 oxygen atoms and/or 1-3 sulfur atoms, wherein Cyc1 may be optionally substituted by 1-5 of $R^{51}$, $R^{51}$ is
(1) C1-8 alkyl,
(2) C2-8 alkenyl,
(3) C2-8 alkynyl,
(4) halogen,
(5) nitro,
(6) trifluoromethyl,
(7) trifluoromethoxy,
(8) nitrile,
(9) keto,
(10) Cyc2,
(11) —$OR^{52}$,
(12) —$SR^{53}$,
(13) —$NR^{54}R^{55}$,
(14) —$COOR^{56}$,
(15) —$CONR^{57}R^{58}$,
(16) —$NR^{59}COR^{60}$,
(17) —$SO_2NR^{61}R^{62}$,
(18) —$OCOR^{63}$,
(19) —$NR^{64}SO_2R^{65}$,
(20) —$NR^{66}COOR^{67}$,
(21) —$NR^{68}CONR^{69}R^{70}$,
(22) —$B(OR^{71})_2$,
(23) —$SO_2R^{72}$,
(24) —$N(SO_2R^{72})_2$,
(25) —$S(O)R^{72}$ or
(26) C1-8 alkyl, C2-8 alkenyl or C2-8 alkynyl substituted by 1-5 substituents optionally selected from (a) halogen, (b) Cyc2, (c) —$OR^{52}$, (d) —$SR^{53}$, (e) —$NR^{54}R^{55}$, (f) —$COOR^{56}$, (g) —$CONR^{57}R^{58}$, (h) —$NR^{59}COR^{60}$, (i) —$SO_2NR^{61}R^{62}$, (j) —$OCOR^{63}$, (k) —$NR^{64}SO_2R^{65}$, (l) —$NR^{66}COOR^{67}$, (m) —$NR^{68}CONR^{69}R^{70}$, (n) —$B(OR^{71})_2$, (o) —$SO_2R^{72}$, (p) —$N(SO_2R^{72})_2$, (q) —$S(O)R^{72}$ and (r) keto, $R^{52}$-$R^{62}$, $R^{64}$, $R^{66}$ and $R^{68}$-$R^{71}$ are each independently
1) hydrogen,
2) C1-8 alkyl,
3) C2-8 alkenyl,
4) C2-8 alkynyl,
5) Cyc2 or 6) C1-8 alkyl, C2-8 alkenyl or C2-8 alkynyl substituted by Cyc2, —$OR^{73}$, —$COOR^{74}$ or —$NR^{75}R^{76}$, $R^{57}$ and $R^{58}$, $R^{61}$ and $R^{62}$, or $R^{69}$ and $R^{70}$, taken together, are
1) C2-6 alkylene,
2) —(C2-6 alkylene)-O—(C2-6 alkylene)-,
3) —(C2-6 alkylene)-S—(C2-6 alkylene)- or
4) —(C2-6 alkylene)-$NR^{197}$—(C2-6 alkylene)- (wherein $R^{197}$ is hydrogen, C1-8 alkyl, phenyl or C1-8 alkyl substituted by phenyl.), $R^{63}$, $R^{65}$, $R^{67}$ and $R^{72}$ are each independently
1) C1-8 alkyl,
2) C2-8 alkenyl,
3) C2-8 alkynyl,
4) Cyc2 or
5) C1-8 alkyl, C2-8 alkenyl or C2-8 alkynyl substituted by Cyc2, —$OR^{73}$, —$COOR^{74}$ or —$NR^{75}R^{76}$, $R^{73}$-$R^{76}$ are each independently hydrogen, C1-8 alkyl, Cyc2 or C1-8 alkyl substituted by Cyc2, Cyc2 has the same meaning as Cyc1, wherein Cyc2 may be optionally substituted by 1-5 of $R^{77}$, $R^{77}$ is
1) C1-8 alkyl,
2) halogen,
3) nitro,
4) trifluoromethyl,
5) trifluoromethoxy,
6) nitrile,
7) —$OR^{78}$,
8) —$NR^{79}R^{80}$,
9) —$COOR^{81}$,
10) —$SR^{82}$,
11) —$CONR^{83}R^{84}$,
12) C2-8 alkenyl,
13) C2-8 alkynyl,
14) keto,
15) Cyc6,
16) —$NR^{161}COR^{162}$,
17) —$SO_2NR^{163}R^{164}$,
18) —$OCOR^{165}$,
19) —$NR^{166}SO_2R^{167}$,
20) —$NR^{168}COOR^{169}$,
21) —$NR^{170}CONR^{171}R^{172}$,
22) —$SO_2R^{173}$,
23) —$N(SO_2R^{167})_2$,
24) —$S(O)R^{173}$ or
25) C1-8 alkyl, C2-8 alkenyl or C2-8 alkynyl substituted by 1-5 substituents optionally selected from (a) halogen, (b) —$OR^{78}$, (c) —$NR^{79}R^{80}$, (d) —$COOR^{81}$, (e) —$SR^{82}$, (f) —$CONR^{83}R^{84}$, (g) keto, (h) Cyc6, (i) —$NR^{161}COR^{162}$, (j) —$SO_2NR^{163}R^{164}$, (k) —$OCOR^{165}$, (l) —$NR^{166}SO_2R^{167}$, (m) —$NR^{168}COOR^{169}$, (n) —$NR^{170}CONR^{171}R^{172}$, (o) —$SO_2R^{173}$, (p) —$N(SO_2R^{167})_2$ and (q) —$S(O)R^{173}$, $R^{78}$-$R^{84}$, $R^{161}$-$R^{164}$, $R^{166}$, $R^{168}$ and $R^{170}$-$R^{172}$ are each independently, (a) hydrogen, (b) C1-8 alkyl, (c) C2-8 alkenyl, (d) C2-8 alkynyl, (e) Cyc6, (f) C1-8 alkyl, C2-8 alkenyl or C2-8 alkynyl substituted by Cyc6, —$OR^{174}$, —$COOR^{175}$, —$NR^{176}R^{177}$ or —$CONR^{178}R^{179}$, $R^{83}$ and $R^{84}$, $R^{163}$ and $R^{64}$, or $R^{171}$ and $R^{172}$, taken together, are
1) C2-6 alkylene,
2) —(C2-6 alkylene)-O—(C2-6 alkylene)-,
3) —(C2-6 alkylene)-S—(C2-6 alkylene)- or
4) —(C2-6 alkylene)-$NR^{198}$—(C2-6 alkylene)- (wherein $R^{198}$ is hydrogen, C1-8 alkyl, phenyl or C1-8 alkyl substituted by phenyl.), $R^{165}$, $R^{167}$, $R^{169}$ and $R^{173}$ are each independently (a) C1-8 alkyl, (b) C2-8 alkenyl, (c) C2-8 alkynyl, (d) Cyc6 or (e) C1-8 alkyl, C2-8 alkenyl or C2-8 alkynyl substituted by Cyc6, —OR$^{174}$, —COOR$^{175}$, —NR$^{176}$R$^{177}$ or —CONR$^{178}$R$^{179}$, $R^{174}$-$R^{177}$ are each independently
1) hydrogen,
2) C1-8 alkyl,
3) Cyc6 or
4) C1-8 alkyl substituted by Cyc6, $R^{178}$ and $R^{179}$, taken together, are
1) C2-6 alkylene,
2) —(C2-6 alkylene)-O—(C2-6 alkylene)-,
3) —(C2-6 alkylene)-S—(C2-6 alkylene)- or
4) —(C2-6 alkylene)-NR$^{199}$—(C2-6 alkylene)- (wherein $R^{199}$ is hydrogen, C1-8 alkyl, phenyl or C1-8 alkyl substituted by phenyl.), Cyc6 is C3-8 mono-carbocyclic ring or 3-8 membered mono-cyclic hetero ring containing 1-4 nitrogen atoms, 1-2 oxygen atoms and/or 1-2 sulfur atoms, wherein Cyc6 may be optionally substituted by 1-5 of $R^{180}$, $R^{180}$ is
(1) C1-8 alkyl,
(2) halogen,
(3) nitro,
(4) trifluoromethyl,
(5) trifluoromethoxy,
(6) nitrile,
(7) —OR$^{181}$,
(8) —NR$^{182}$R$^{183}$,
(9) —COOR$^{184}$,
(10) —SR$^{185}$ or
(11) —CONR$^{186}$R$^{187}$, $R^{181}$-$R^{187}$ are each independently
1) hydrogen,
2) C1-8 alkyl,
3) phenyl or
4) C1-8 alkyl substituted by phenyl, $R^{182}$ and $R^{183}$, or $R^{185}$ and $R^{187}$, taken together, are
1) C2-6 alkylene,
2) —(C2-6 alkylene)-O—(C2-6 alkylene)-,
3) —(C2-6 alkylene)-S—(C2-6 alkylene)- or
4) —(C2-6 alkylene)-NR$^{200}$—(C2-6 alkylene)- (wherein $R^{200}$ is hydrogen, C1-8 alkyl, phenyl, C1-8 alkyl substituted by phenyl.), $R^2$ is
(1) hydrogen,
(2) C1-8 alkyl,
(3) C2-8 alkenyl,
(4) C2-8 alkynyl,
(5) —OR$^{90}$,
(6) Cyc3 or
(7) C1-8 alkyl, C2-8 alkenyl or C2-8 alkynyl substituted by 1-5 substituents optionally selected from (a) halogen, (b) —OR$^{90}$, (c) —SR$^{91}$, (d) —NR$^{92}$R$^{93}$, (e) —COOR$^{94}$, (f) —CONR$^{95}$R$^{96}$, (g) —NR$^{97}$COR$^{98}$, (h) —SO$_2$NR$^{99}$R$^{100}$, (i) —OCOR$^{101}$, (j) —NR$^{102}$SO$_2$R$^{103}$, (k) —NR$^{104}$COOR$^{105}$, (l) —NR$^{106}$CONR$^{107}$R$^{108}$, (m) Cyc3, (n) keto and (o) —N(SO$_2$R$^{103}$)$_2$, $R^{90}$-$R^{100}$, $R^{102}$, $R^{104}$ and $R^{106}$-$R^{108}$ are each independently
1) hydrogen,
2) C1-8 alkyl,
3) C2-8 alkenyl,
4) C2-8 alkynyl,
5) Cyc3 or
6) C1-8 alkyl, C2-8 alkenyl or C2-8 alkynyl substituted by Cyc3, $R^{95}$ and $R^{96}$, $R^{99}$ and $R^{100}$, or $R^{107}$ and $R^{108}$, taken together, are
1) C2-6 alkylene,
2) —(C2-6 alkylene)-O—(C2-6 alkylene)-,
3) —(C2-6 alkylene)-S—(C2-6 alkylene)- or
4) —(C2-6 alkylene)-NR$^{201}$—(C2-6 alkylene)-, $R^{201}$ is hydrogen, C1-8 alkyl, phenyl or C1-8 alkyl substituted by phenyl, $R^{101}$, $R^{103}$ and $R^{105}$ are each independently
1) C1-8 alkyl,
2) C2-8 alkenyl,
3) C2-8 alkynyl or
4) Cyc3, or C1-8 alkyl, C2-8 alkenyl or C2-8 alkynyl substituted by Cyc3, Cyc3 has the same meaning as Cyc1, wherein Cyc3 may be optionally substituted by 1-5 of $R^{109}$, $R^{109}$ has the same meaning as $R^{51}$, $R^3$ and $R^4$ are each independently
(1) hydrogen,
(2) C1-8 alkyl,
(3) C2-8 alkenyl,
(4) C2-8 alkynyl,
(5) —COOR$^{120}$,
(6) —CONR$^{121}$R$^{122}$,
(7) Cyc4 or
(8) C1-8 alkyl, C2-8 alkenyl or C2-8 alkynyl substituted by 1-5 substituents selected from (a) halogen, (b) nitrile, (c) Cyc4, (d) —COOR$^{120}$, (e) —CONR$^{121}$R$^{122}$, (f) —OR$^{123}$, (g) —SR$^{124}$, (h) —NR$^{125}$R$^{126}$, (i) —NR$^{127}$COR$^{128}$, (j) —SO$_2$NR$^{129}$R$^{130}$, (k) —OCOR$^{131}$, (l) —NR$^{132}$SO$_2$R$^{133}$, (m) —NR$^{134}$COOR$^{135}$, (n) —NR$^{136}$CONR$^{137}$R$^{138}$, (o) —S—SR$^{139}$, (p) —NHC(=NH)NHR$^{140}$, (q) keto, (r) —NR$^{145}$CONR$^{146}$COR$^{147}$ and (s) —N(SO$_2$R$^{133}$)$_2$, $R^{120}$-$R^{130}$, $R^{132}$, $R^{134}$, $R^{136}$-$R^{138}$, $R^{145}$ and $R^{146}$ are each independently
1) hydrogen,
2) C1-8 alkyl,
3) C2-8 alkenyl,
4) C2-8 alkynyl,
5) Cyc4 or
6) C1-8 alkyl, C2-8 alkenyl or C2-8 alkynyl substituted by Cyc4, halogen, —OR$^{148}$, —SR$^{149}$, —COOR$^{150}$ or —NHCOR$^{141}$, $R^{121}$ and $R^{122}$, $R^{129}$ and $R^{130}$, or $R^{137}$ and $R^{138}$, taken together, are
1) C2-6 alkylene,
2) —(C2-6 alkylene)-O—(C2-6 alkylene)-,
3) —(C2-6 alkylene)-S—(C2-6 alkylene)- or
4) —(C2-6 alkylene)-NR$^{202}$—(C2-6 alkylene)- (wherein $R^{202}$ is hydrogen, C1-8 alkyl, phenyl, C1-8 alkyl substituted by phenyl.), $R^{131}$, $R^{133}$, $R^{135}$, $R^{139}$ and $R^{147}$ are each independently
1) C1-8 alkyl,
2) C2-8 alkenyl,
3) C2-8 alkynyl,
4) Cyc4 or
5) C1-8 alkyl, C2-8 alkenyl or C2-8 alkynyl substituted by Cyc4, halogen, —OR$^{148}$, —SR$^{149}$, —COOR$^{150}$ or —NHCOR$^{141}$, $R^{140}$ is hydrogen, —COOR$^{142}$ or —SO$_2$R$^{143}$, $R^{141}$-$R^{143}$ are each independently
1) C1-8 alkyl,
2) C2-8 alkenyl,
3) C2-8 alkynyl,
4) Cyc4 or 5) C1-8 alkyl, C2-8 alkenyl or C2-8 alkynyl substituted by Cyc4, $R^{148}$-$R^{150}$ are each independently
1) hydrogen,
2) C1-8 alkyl,
3) C2-8 alkenyl,
4) C2-8 alkynyl,
5) Cyc4 or
6) C1-8 alkyl, C2-8 alkenyl or C2-8 alkynyl substituted by Cyc4, Cyc4 has the same meaning as Cyc1, wherein Cyc4 may be optionally substituted by 1-5 of $R^{144}$, and $R^{144}$ has the same meaning as $R^{51}$, $R^3$ and $R^4$, taken together, are

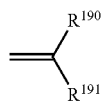

(wherein $R^{190}$ and $R^{191}$ are each independently the same meaning as $R^3$ or $R^4$.), $R^5$ is
(1) hydrogen,
(2) C1-8 alkyl,
(3) Cyc5 or
(4) C1-8 alkyl substituted by Cyc5.

(wherein Cyc5 has the same meaning as Cyc1, and Cyc5 may be optionally substituted by 1-5 of $R^{160}$, $R^{160}$ has the same meaning as $R^{51}$.)], a quaternary ammonium salt thereof, an N-oxide thereof, or a non-toxic salt thereof, (2) A pharmaceutical composition for prevention and/or treatment for AIDS, which comprises, as an active ingredient, at least one triazaspiro[5.5]undecane derivative represented by formula (I) according to above 1, a quaternary ammonium salt thereof, an N-oxide thereof, or a non-toxic salt thereof, (3) A pharmaceutical composition for prevention and/or treatment for HIV infection acquiring multidrug resistance, which comprises, as an active ingredient, at least one triazaspiro[5.5]undecane derivative represented by formula (I) according to above 1, a quaternary ammonium salt thereof, an N-oxide thereof, or a non-toxic salt thereof, (4) A pharmaceutical composition for prevention and/or treatment for HIV infection, which comprises a combination of at least one triazaspiro[5.5]undecane derivative represented by formula (I) according to above 1, a quaternary ammonium salt thereof, an N-oxide thereof, or a non-toxic salt thereof with at least one other preventive and/or treating agent for HIV infection, (5) A pharmaceutical composition for prevention and/or treatment for AIDS, which comprises a combination of at least one triazaspiro[5.5]undecane derivative represented by formula (I) according to above 1, a quaternary ammonium salt thereof, an N-oxide thereof, or a non-toxic salt thereof with at least one other preventive and/or treating agent for HIV infection, (6) A pharmaceutical composition for prevention and/or treatment for HIV infection acquiring multidrug resistance, which comprises a combination of at least one triazaspiro[5.5]undecane derivative represented by formula (I) according to above 1, a quaternary ammonium salt thereof, an N-oxide thereof, or a non-toxic salt thereof with at least one other preventive and/or treating agents for HIV infection, (7) The pharmaceutical composition according to any one of above 4, 5 and 6, wherein the other preventive and/or treating agent for HIV infection is a protease inhibitor, a reverse transcriptase inhibitor, a fusion inhibitor and/or a chemokine regulator, (8) A pharmaceutical composition for prevention and/or treatment for HIV infection having more enhanced treating effect than a single preparation, which comprises a combination of at least one triazaspiro[5.5]undecane derivative represented by formula (I) according to above 1, a quaternary ammonium salt thereof, an N-oxide thereof, or a non-toxic salt thereof with a drug which does not inhibit HIV infection.

DISCLOSURE OF THE INVENTION

In the present invention, C1-18 alkyl means methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl or isomeric groups thereof.

C2-18 alkenyl means C2-18 alkylene optionally having 1-9 double bond(s) (preferably 1-4 double bond(s)), concretely, vinyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, butadienyl, pentadienyl, hexadienyl, heptadienyl, octadienyl, nonadienyl, decadienyl, undecadienyl, dodecadienyl, tridecadienyl, tetradecadienyl, pentadecadienyl, hexadecadienyl, heptadecadienyl, octadecadienyl, hexatrienyl, heptatrienyl, octatrienyl, nonatrienyl, decatrienyl, undecatrienyl, dodecatrienyl, tridecatrienyl, tetradecatrienyl, pentadecatrienyl, hexadecatrienyl, heptadecatrienyl, octadecatrienyl or isomeric groups thereof.

C2-18 alkynyl means C2-18 alkylene optionally having 1-9 triple bond(s) (preferably 1-4 triple bond(s)), concretely, ethynyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, butadiynyl, pentadiynyl, hexadiynyl, heptadiynyl, octadiynyl, nonadiynyl, decadiynyl, undecadiynyl, dodecadiynyl, tridecadiynyl, tetradecadiynyl, pentadecadiynyl, hexadecadiynyl, heptadecadiynyl, octadecadiynyl, hexatriynyl, heptatriynyl, octatriynyl, nonatriynyl, decatriynyl, undecatriynyl, dodecatriynyl, tridecatriynyl, tetradecatriynyl, pentadecatriynyl, hexadecatriynyl, heptadecatriynyl, octadecatriynyl or isomeric groups thereof.

Halogen is chlorine, bromine, fluorine or iodine.

C1-8 alkyl means methyl, ethyl, propyl, butyl, pentyl, hexyl, heptyl, octyl or isomeric groups thereof.

C2-8 alkenyl means C2-8 alkylene optionally having 1-4 double bond(s), concretely, vinyl, propenyl, butenyl, pentenyl, hexenyl, heptenyl, octenyl, butadienyl, pentadienyl, hexadienyl, heptadienyl, octadienyl, hexatrienyl, heptatrienyl, octatrienyl or isomeric groups thereof.

C2-8 alkynyl means C2-8 alkylene optionally having 1-4 triple bond(s), concretely, ethynyl, propynyl, butynyl, pentynyl, hexynyl, heptynyl, octynyl, butadiynyl, pentadiynyl, hexadiynyl, heptadiynyl, octadiynyl, hexatriynyl, heptatriynyl, octatriynyl or isomeric groups thereof.

C2-6 alkylene means methylene, ethylene, trimethylene, tetramethylene, pentamethylene, hexamethylene or isomeric groups thereof.

C3-15 mono-, bi- or tri-(fused or spiro)carbocyclic ring means concretely, cyclopropane, cyclobutane, cyclopentane, cyclohexane, cycloheptane, cyclooctane, cyclopentene, cyclohexene, cycloheptene, cyclooctene, cyclopentadiene, cyclohexadiene, cycloheptadiene, cyclooctadiene, benzene, indene, naphthalene, indan, tetrahydronaphthalene, bicyclo[3.3.0]octane, bicyclo[4.3.0]nonane, bicyclo[4.4.0]decane, spiro[4.4]nonane, spiro[4.5]decane, spiro[5.5]undecane, bicyclo[3.1.1]heptane, bicyclo[3.3.1]hept-2-ene, fluorene or anthracene etc.

3-15 membered mono-, bi- or tri-(fused or spiro)cyclic hetero ring containing 1-4 nitrogen atom(s), 1-3 oxygen atom(s) and/or 1-3 sulfur atom(s) means 3-15 membered mono-, bi- or tri-(fused or spiro)cyclic hetero aryl containing 1-4 nitrogen atom(s), 1-3 oxygen atom(s) and/or 1-3 sulfur atom(s), and partially or fully saturated one.

3-15 membered mono-, bi- or tri-(fused or spiro)cyclic hetero aryl containing 1-4 nitrogen atom(s), 1-3 oxygen atom(s) and/or 1-3 sulfur atom(s) is pyrrole, imidazole, triazole, tetrazole, pyrazole, pyridine, pyrazine, pyrimidine, pyridazine, azepine, diazepine, furan, pyran, oxepine, thiophene, thiain (thiopyran), thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzimidazole, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, acridine, dibenzofuran or dibenzothiophene etc.

In above 3-15 membered mono-, bi- or tri-(fused or spiro)cyclic hetero ring containing 1-4 nitrogen atom(s), 1-3 oxygen atom(s) and/or 1-3 sulfur atom(s), partially or fully saturated one is pyrroline, pyrrolidine, imidazoline, imidazolidine, pyrazoline, pyrazolidine, triazoline, triazolidine, tetrazoline, tetrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrothiophene, tetrahydrothiophene, dihydrothiain (dihydrothiopyran), tetrahydrothiain (tetrahydrothiopyran), dihydrooxazole, tetrahydrooxazole, dihydroisoxazole, tetrahydroisoxazole, dihydrothiazole, tetrahydrothiazole, dihydroisothiazole, tetrahydroisothiazole, dihydrooxadiazole, tetrahydrooxadiazole, dihydrothiodiazole, tetrahydrothiodiazole, tetrahydrooxadiazine, tetrahydrothiadiazine, tetrahydrooxazepine, tetrahydrooxadiazepine, perhydrooxazepine, perhydrooxadiazepine, tetrahydrothiazepine, tetrahydrothiadiazepine, perhydrothiazepine, perhydrothiadiazepine, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzimidazole, perhydrobenzimidazole, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, benzodioxalane, benzodioxane, benzodithiolane, benzodithiane, 2,4,6-trioxaspiro[bicyclo[3.3.0]octane-3,1'-cyclohexane], 1,3-dioxolano[4,5-g]chromene or 2-oxabicyclo[2.2.1]heptane etc.

C3-8 mono-carbocyclic ring is concretely, cyclopropane, cyclobutane, cyclopentane, cyclohexane, cycloheptane, cyclooctane, cyclopentene, cyclohexene, cycloheptene, cyclooctene, cyclopentadiene, cyclohexadiene, cycloheptadiene, cyclooctadiene or benzene etc.

3-8 membered mono-cyclic hetero ring containing 1-4 nitrogen atom(s), 1-2 oxygen atom(s) and/or 1-2 sulfur atom(s) means 3-8 membered mono-cyclic hetero aryl containing 1-4 nitrogen atom(s), 1-2 oxygen atom and/or 1-2 sulfur atom(s) and partially or fully saturated one.

3-8 membered mono-cyclic hetero aryl containing 1-4 nitrogen atom(s), 1-2 oxygen atom(s) and/or 1-2 sulfur atom(s) is pyrrole, imidazole, triazole, tetrazole, pyrazole, pyridine, pyrazine, pyrimidine, pyridazine, azepine, diazepine, furan, pyran, oxepine, thiophene, thiain (thiopyran), thiepine, oxazole, isoxazole, thiazole, isothiazole, furazan, oxadiazole, oxazine, oxadiazine, oxazepine, oxadiazepine, thiadiazole, thiazine, thiadiazine, thiazepine or thiadiazepine etc.

In above 3-8 membered mono-cyclic hetero ring containing 1-4 nitrogen atom(s), 1-2 oxygen atom(s) and/or 1-2 sulfur atom(s), partially or fully saturated one is pyrroline, pyrrolidine, imidazoline, imidazolidine, pyrazoline, pyrazolidine, triazoline, triazolidine, tetrazoline, tetrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrothiophene, tetrahydrothiophene, dihydrothiain (dihydrothiopyran), tetrahydrothiain (tetrahydrothiopyran), dihydrooxazole, tetrahydrooxazole, dihydroisoxazole, tetrahydroisoxazole, dihydrothiazole, tetrahydrothiazole, dihydroisothiazole, tetrahydroisothiazole, dihydrooxadiazole, tetrahydrooxadiazole, dihydrothiodiazole, tetrahydrothiodiazole, tetrahydrooxadiazine, tetrahydrothiadiazine, tetrahydrooxazepine, tetrahydrooxadiazepine, perhydrooxazepine, perhydrooxadiazepine, tetrahydrothiazepine, tetrahydrothiadiazepine, perhydrothiazepine, perhydrothiadiazepine, morpholine, thiomorpholine, dioxolane, dioxane, dithiolane or dithiane etc.

In the present invention, each group represented by $R^1$, $R^2$, $R^3$, $R^4$ or $R^5$ is all preferable.

Preferred $R^1$ is C1-18 alkyl substituted by Cyc 1, C2-18 alkenyl substituted by Cyc 1 or C2-18 alkynyl substituted by Cyc 1, and more preferred $R^1$ is C1-6 alkyl substituted by Cyc 1.

Preferred Cyc 1 is C3-10 mono- or bi-(fused or spiro) carbocyclic ring or 3-10 membered mono- or bi-(fused or spiro)cyclic hetero ring containing 1-4 nitrogen atom(s), 1-2 oxygen atom(s) and/or 1-2 sulfur atom(s), and more preferred Cyc 1 is C5-7 mono-carbocyclic aryl or 5-10 membered mono-cyclic hetero ring containing 1-4 nitrogen atom(s), 2 oxygen atoms and/or 1 sulfur atom.

Preferred Cyc 1 concretely is benzene, pyrazole, imidazole, furan, thiophene, benzodioxane, thiazole or quinoline.

Preferred $R^{51}$ which is a substituent of Cyc 1 is Cyc 2, $-OR^{52}$, $-SR^{53}$ or $-NR^{54}R^{55}$. Preferred $R^{52}$, $R^{53}$, $R^{54}$ and $R^{55}$ are C1-8 alkyl or Cyc 2, and more preferred $R^{52}$, $R^{53}$, $R^{54}$ and $R^{55}$ are methyl, ethyl, propyl or phenyl.

Preferred Cyc 2 is C5-7 mono-carbocyclic aryl or 5-7 membered mono-cyclic hetero aryl containing 1-4 nitrogen atom(s), 1 oxygen atom and/or 1 sulfur atom, and more preferred Cyc 2 is benzene.

Preferred $R^{77}$ which is a substituent of Cyc 2 is $-CONR^{83}R^{84}$, $-NR^{161}COR^{162}$, $-SO_2NR^{163}R^{164}$, $-NR^{166}SO_2R^{167}$, C1-8 alkyl substituted by $-CONR^{83}R^{84}$, C1-8 alkyl substituted by $-NR^{161}COR^{162}$, C1-8 alkyl substituted by $-SO_2NR^{163}R^{164}$ or C1-8 alkyl substituted by $-NR^{166}SO_2R^{167}$. Preferred $R^{83}$, $R^{84}$, $R^{161}$, $R^{162}$, $R^{163}$, $R^{164}$, $R^{166}$ and $R^{167}$ are C1-8 alkyl, Cyc6, C1-8 alkyl substituted by $-NR^{176}R^{177}$, and more preferred $R^{83}$, $R^{84}$, $R^{161}$, $R^{162}$, $R^{163}$, $R^{164}$, $R^{166}$ and $R^{167}$ are methyl, ethyl, propyl, phenyl or dimethylaminoethyl etc.

Most preferred $R^1$ is phenylethyl, phenylpropyl, phenylbutyl, phenylpentyl, phenylhexyl, 4-methoxyphenylmethyl, 4-propyloxyphenylmethyl, 4-phenyloxyphenylmethyl, 3,5-dimethyl-1-phenylpyrazol-4-ylmethyl, 2-phenylimidazol-4-ylmethyl, 5-ethylfuran-2-ylmethyl, 5-ethylthiophen-2-ylmethyl, 3-chloro-5-methyl-1-phenylpyrazol-4-ylmethyl, 1,4-benzodioxan-6-ylmethyl, 4-(4-methylsulfonylaminophenyloxy)phenylmethyl, 4-(4-(2-dimethylaminoethylsulfonylamino)phenyloxy) phenylmethyl, 4-(4-dimethylaminosulfonylphenyloxy) phenylmethyl, 4-(4-methylcarbonylaminophenyloxy) phenylmethyl, 4-(4-(2-dimethylaminoethylcarbonylamino) phenyloxy)phenylmethyl or 4-(4-dimethylaminocarbonylphenyloxy)phenylmethyl etc.

Preferred $R^2$ is C1-8 alkyl, C2-8 alkenyl, C2-8 alkynyl, C1-8 alkyl substituted by Cyc 3. Most preferred $R^2$ is C1-4 alkyl, C2-4 alkenyl or C2-4 alkynyl.

Most preferred $R^2$ is ethyl, propyl, butyl, 2-propenyl, 2-butenyl, 2-propynyl, phenylmethyl, thiophen-2-ylmethyl or 2-butynyl etc.

Preferred $R^3$ or $R^4$ is hydrogen, C1-8 alkyl, C1-8 alkyl substituted by Cyc4, C1-8alkyl substituted by $-OR^{123}$, C1-8 alkyl substituted by Cyc4 and $-OR^{123}$, C1-8 alkyl substituted by $-NR^{127}COR^{128}$, C1-8 alkyl substituted by $-NR^{132}SO_2R^{133}$, C1-8 alkyl substituted by $-NR^{134}COOR^{135}$ or C1-8 alkyl substituted by $-NR^{136}CONR^{137}R^{138}$. Most preferred $R^3$ or $R^4$ is C1-4 alkyl, C1-4 alkyl substituted by Cyc4, C1-4 alkyl substituted by $-OR^{123}$, C1-4 alkyl substituted by Cyc4 and $-OR^{123}$, C1-4 alkyl substituted by $-NR^{127}COR^{128}$, C1-4 alkyl substituted by $-NR^{132}SO_2R^{133}$, C1-4 alkyl substituted by $-NR^{134}COOR^{135}$ or C1-4 alkyl substituted by $-NR^{136}CONR^{137}R^{138}$.

Preferred Cyc 4 is benzene or cyclohexane.

Preferred $R^{123}$ is hydrogen, C1-4 alkyl, Cyc 4 or C1-4 alkyl substituted by Cyc 4, and more preferred $R^{123}$ is hydrogen, methyl, ethyl, phenyl or phenylmethyl.

Preferred $R^{127}$, $R^{132}$, $R^{134}$, $R^{136}$ and $R^{138}$ are hydrogen or methyl.

Preferred $R^{128}$, $R^{133}$, $R^{135}$ and $R^{137}$ are Cyc 4 or C1-4 alkyl substituted by Cyc 4, and more preferred $R^{128}$, $R^{133}$, $R^{135}$ and $R^{137}$ are phenyl, phenylmethyl or phenylethyl.

Preferred $R^{144}$ which is a substitute of Cyc 4 is C1-4 alkyl, halogen, phenyl or phenyloxy, and more preferred $R^{144}$ is methyl, fluorine, chlorine, phenyl or phenyloxy.

Most preferred $R^3$ or $R^4$ is propyl, 1-methylpropyl, 2-methylpropyl, cyclohexylmethyl, 1-hydroxy-2-methylpropyl, 1-hydroxy-1-cyclohexylmethyl, 3-(cyclopentylethylcarbonyl)aminobutyl, 3-(benzyloxycarbonyl)aminopropyl, 3-(phenylcarbonyl)aminobutyl, 3-(phenylmethylcarbonyl) aminobutyl, 3-(phenylethylcarbonyl)aminobutyl, 3-(phenylethenylcarbonyl)aminobutyl, 3-(4-phenylphenylcarbonyl)aminobutyl, 3-(4-phenyloxyphenylaminocarbonyl) aminobutyl, 3-(4-chlorophenylaminocarbonyl)aminobutyl, 3-(4-fluorophenylaminocarbonyl)aminobutyl, 3-(phenylmethylaminocarbonyl)aminobutyl, 3-(4-trifluoromethylsulfonyl)aminobutyl, 4-(cyclopentylethylcarbonyl)aminobutyl, 4-(benzyloxycarbonyl)aminobutyl, 4-(phenylcarbonyl)aminobutyl, 4-(phenylmethylcarbonyl)aminobutyl, 4-(phenylethylcarbonyl)aminobutyl, 4-(phenylethenylcarbonyl)aminobutyl, 4-(4-phenylphenylcarbonyl)aminobutyl, 4-(4-phenyloxyphenylaminocarbonyl)aminobutyl, 4-(4-chlorophenylaminocarbonyl)aminobutyl, 4-(4-fluorophenylaminocarbonyl)aminobutyl, 4-(phenylmethylaminocarbonyl)aminobutyl or 4-(4-trifluoromethylsulfonyl)aminobutyl.

Preferred $R^5$ is hydrogen or methyl.

In the compounds of the present invention of formula (I), the compound represented by formula (Ia)

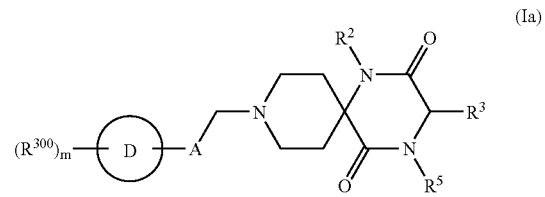

(wherein $R^2$ is C1-8 alkyl,
$R^3$ is C1-8 alkyl or C3-7 cycloalkyl(C1-4)alkyl,
$R^5$ is hydrogen or C1-8 alkyl,
A is a bond or C1-10 alkylene,
D ring is C3-10 mono- or bi-(fused or spiro)carbocyclic ring or 3-10 membered mono- or bi-(fused or spiro)cyclic hetero ring,
m is 0 or an integer of 1-4,
$R^{300}$ is C1-4 alkyl, C1-4 alkoxy, phenyl, phenoxy or benzyloxy.)

is preferable.

Preferred C3-10 carbocyclic ring represented by D ring is C3-10 mono- or bi-carbocyclic ring, and more preferred C3-10 carbocyclic ring is C3-7 mono-carbocyclic ring or C8-10 bi-carbocyclic ring.

Preferred 3-10 membered cyclic hetero ring represented by D ring is 3-10 membered mono- or bi-cyclic hetero aryl containing 1-4 nitrogen atom(s), 1-2 oxygen atom(s) and/or 1 sulfur atom, or partially or fully saturated one. More preferred 3-10 membered cyclic hetero ring is 5-7 membered mono- or 8-10 membered bi-cyclic hetero aryl containing 1-4 nitrogen atom(s), 1-2 oxygen atom(s) and/or 1 sulfur atom, or partially or fully saturated one.

Unless otherwise specified, all isomers are included in the present invention. For example, alkyl, alkoxy and alkylene groups include straight or branched ones. In addition, isomers on double bond, ring, fused ring (E-, Z-, cis-, trans-isomer), isomers generated from asymmetric carbon atom(s) (R-, S-, α-, β-isomer, enantiomer, diastereomer), optically active isomer (D-, L-, d-, l-isomer), polar compounds generated by chromatographic separation (more polar compound, less polar compound), equilibrium compounds, mixtures thereof at voluntary ratios and racemic mixtures are also included in the present invention.

[Salts]

The salts of the present invention include all non-toxic salts, for example, general salts or acid addition salts etc.

The compounds of the present invention represented by formula (I) may be converted into the corresponding salts by conventional means. Non-toxic salts or water-soluble salts are preferred. Suitable salts, for example, include: salts of alkali metals (e.g. potassium, sodium), salts of alkaline earth metals (e.g. calcium, magnesium), ammonium salts, salts of pharmaceutically acceptable organic amines (e.g. tetramethylammonium, triethylamine, methylamine, dimethylamine, cyclopentylamine, benzylamine, phenethylamine, piperidine, monoethanolamine, diethanolamine, tris(hydroxymethyl)amine, lysine, arginine, N-methyl-D-glucamine).

The compounds of the present invention represented by formula (I) may be converted into the corresponding acid addition salts by conventional means. Water-soluble salts are preferred. Suitable salts, for example, include: salts of inorganic acids e.g. hydrochloride, hydrobromide, sulfate, phosphate, nitrate; salts of organic acids e.g. acetate, trifluoroacetate, lactate, tartrate, oxalate, fumarate, maleate, citrate, benzoate, methanesulfonate, ethanesulfonate, benzenesulfonate, toluenesulfonate, isethionate, glucuronate, gluconate.

The compounds of the present invention represented by formula (I) and salts thereof may be converted into the corresponding hydrates by conventional means.

All of the compounds of formula (I) or non-toxic salts thereof are preferable, concretely, the compounds described in the example or non-toxic salts thereof.

Quaternary ammonium salts of the compounds represented by formula (I) are the compounds where nitrogen of the compounds represented by formula (I) is quarternalized by $R^0$.

$R^0$ is C1-8 alkyl or C1-8 alkyl substituted by phenyl.

N-oxides of the compounds represented by formula (I) are the compounds where nitrogen of the compounds represented by formula (I) is oxidized.

[Methods for Preparation of the Compounds the Present Invention]

The compounds of the present invention of formula (I) may be prepared by the following methods or the methods described in examples.

Among the compounds of the present invention of formula (I), the compounds where nitrogens are not quaternary ammonium salts or N-oxides, i.e., the compounds of formula (I-1)

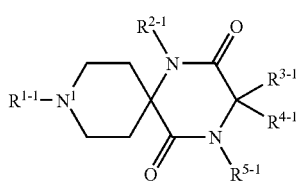

(wherein $R^{1-1}$, $R^{2-1}$, $R^{3-1}$, $R^{4-1}$ and $R^{5-1}$ have the same meaning as $R^1$, $R^2$, $R^3$, $R^4$ and $R^5$ respectively, and $N^1$ is nitrogen, wherein any nitrogen are not quaternary ammonium salts or N-oxides.)

may be prepared by the following methods.

Among the compounds of the present invention represented by formula (I-1), the compounds in which any $R^{1-1}$, $R^{2-1}$, $R^{3-1}$, $R^{4-1}$ and $R^{5-1}$ are not a group containing carboxyl, hydroxy, amino or thiol, i.e., the compounds of formula (I-1A)

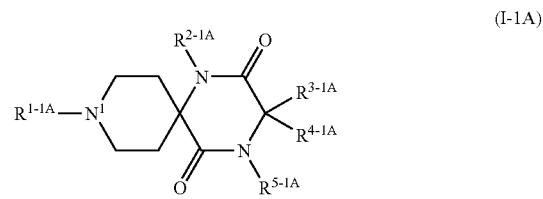

(wherein $R^{1-1A}$, $R^{2-1A}$, $R^{3-1A}$, $R^{4-1A}$ and $R^{5-1A}$ have the same meaning as $R^{1-1}$, $R^{2-1}$, $R^{3-1}$, $R^{4-1}$ and $R^{5-1}$ respectively, wherein all of them are not a group containing carboxyl, hydroxy, amino or thiol, and the other symbol have the same meanings as defined hereinbefore.)

may be prepared by the following methods.

Among the compounds of formula (I-1A), the compounds in which $R^1$ does not represent hydrogen, i.e., the compounds of formula (I-1A-1)

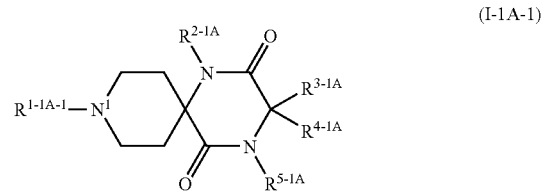

(wherein $R^{1-1A-1}$ have the same meaning as $R^{1-1A}$, $R^{1-1A-1}$ is not hydrogen, and the other symbols have the same meanings as defined hereinbefore.)

may be prepared by cyclization of the compounds of formula (II-1)

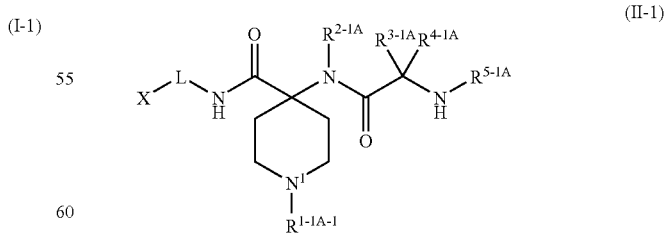

(wherein X-L—NH— is an amino terminus of aminated polystyrene resin, and the other symbols have the same meaning as defined hereinbefore.), or the compounds of formula (II-2)

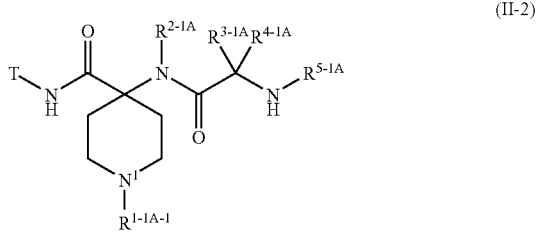

(II-2)

(wherein T is C1-8 alkyl, C3-8 mono-carbocyclic ring or C1-8 alkyl substituted by C3-8 mono-carbocyclic ring.).

The cyclization of compounds of formula (II-1) is well known. For example, it may be carried out by heating in an organic solvent (toluene etc.) in the presence of acid (acetic acid, trifluoroacetic acid or hydrochloric acid etc.) at 60-120° C. This cyclization reaction is carried out with the cleavage from polystyrene resin.

If necessary, the conversion to desired non-toxic salts may be carried out by the conventional method in succession to this reaction.

The cyclization of compounds of formula (II-2) is well known. For example, it may be carried out by heating in an organic solvent (dichroloethane or toluene etc.), with tertiary amine (triethylamine or diisopropylethylamine etc.) at 60-120° C. This cyclization reaction is carried out with the cleavage of T group.

Among the compounds of formula (I-1A), the compounds in which $R^1$ is hydrogen, i.e., the compounds of formula (I-1A-2)

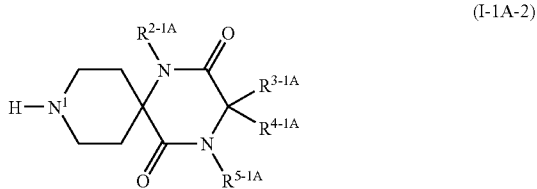

(I-1A-2)

(wherein all of the symbols have the same meanings as defined hereinbefore.)

may be prepared by the removal of an amino-protecting group of the compounds in which $R^{1.4-1}$ is an amino-protecting group, i.e., the compounds of formula (I-1A-1-1)

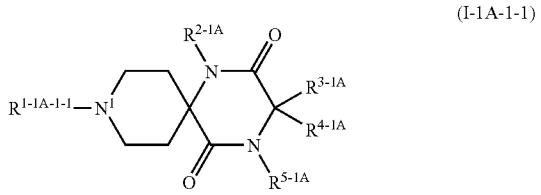

(I-1A-1-1)

(wherein $R^{1-1.4-1-1}$ is an amino-protecting group, and the other symbols have the same meaning as defined hereinbefore.).

A protecting group of amino includes, for example, benzyl, benzyloxycarbonyl, allyloxycarbonyl, t-butoxycarbonyl or trifluoroacetyl etc.

The protecting group of amino includes the above one, in addition, the other protecting group which is removable selectively and easily, for example, one described in T. W. Greene et. al., Protective Groups in Organic Synthesis, Third Edition, Wiley-Interscience, New York, 1999.

The removal of a protecting group of amino is well known. For example, it is (1) the alkaline hydrolysis, (2) the removal of a protecting group in an acidic condition, (3) the removal of a protecting group by hydrogenolysis or (4) the removal of a protecting group using metal complex etc.

Concrete descriptions of these methods are as follows:

(1) The removal of protecting group in an alkaline condition (e.g. trifluoroacethyl group) may be carried out, for example, in an organic solvent (methanol, tetrahydrofuran or dioxane etc.) with hydroxide of alkaline metal (sodium hydroxide, potassium hydroxide or lithium hydroxide etc.), hydroxide of alkaline earth metal (barium hydroxide or calcium hydroxide etc.), carbonate (sodium carbonate or potassium carbonate etc.), or an aqueous solution thereof or a mixture thereof at 0-40° C.

(2) The removal of protecting group in an acidic condition (e.g. t-butoxycarbonyl group) may be carried out, for example, in an organic solvent (dichloromethane, chloroform, dioxane, ethyl acetate or anisole etc.), organic acid (acetic acid, trifluoroacetic acid or methanesulfonic acid etc.) or inorganic acid (hydrochloric acid or sulfuric acid etc.), or a mixture thereof (hydrogen bromide/acetic acid etc.) at 0-100° C.

(3) The removal of a protecting group by hydrogenolysis (e.g. benzyl, benzyloxycarbonyl or allyloxycarbonyl) may be carried out, for example, in a solvent (ether (tetrahydrofuran, dioxane, dimethoxyethane or diethylether etc.), alcohol (methanol or ethanol etc.), benzene (benzene or toluene etc.), ketone (acetone or methylethylketone etc.), nitrile (acetonitrile etc.), amide (dimethylformamide etc.), water, ethyl acetate, acetic acid or a mixture thereof etc.) in the presence of a catalyst (palladium on carbon, palladium black, palladium hydroxide, platinum oxide, Raney nickel etc.), at atmospheric or positive pressure under an atmosphere of hydrogen or in the presence of ammonium formate at 0-200° C.

(4) The removal of a protecting group using metal complex may be carried out, for example, in an organic solvent (dichloromethane, dimethylformamide or tetrahydrofuran etc.) in the presence of a trap reagent (tributyltin hydride or dimedone etc.) and/or an organic acid (acetic acid etc.) with metal complex (tetrakis(triphenylphosphine)palladium(0) complex etc.) at 0-40° C.

Moreover, the compounds of formula (I-1A-1) may be prepared with the compounds of formula (I-1A-2) by the following methods of (a)-(g).

(a) Among the compounds of formula (I-1A-1), the compounds, in which $R^{1.4-1}$ is C1-18 alkyl, C2-18 alkenyl, C2-18 alkynyl, or C1-18 alkyl, C2-18 alkenyl or C2-18 alkynyl substituted by various substituents, and in which $R^{1.4-1}$ bonds with $N^1$ through —$CH_2$—, i.e., the compounds of formula (I-1A-1a)

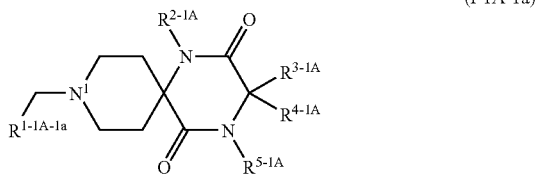

(I-1A-1a)

(wherein $R^{1\text{-}1A\text{-}1a}$ is C1-17 alkyl, C2-17 alkenyl, C2-17 alkynyl, or C1-17 alkyl, C2-17 alkenyl or C2-17 alkynyl substituted by 1-5 of optionally selected from (a) halogen, (b) —$CONR^7R^8$, (c) —$COOR^9$, (d) —$OR^{14}$, (e) —$SR^{15}$, (f) —$NR^{16}R^{17}$, (g) —$NR^{18}COR^{19}$, (h) —$SO_2NR^{20}R^{21}$, (i) —$OCOR^{22}$, (j) —$NR^{23}SO_2R^{24}$, (k) —$NR^{25}COOR^{26}$, (l) —$NR^{27}CONR^{28}R^{29}$, (m) Cyc 1, (n) keto, (o) —$N(SO_2R^{24})_2$, wherein $R^{1\text{-}1A\text{-}1a}$ is not a group containing carboxyl, hydroxy, amino or thiol, and the other symbols have the same meaning as defined hereinbefore.)

may be prepared by the reductive amination of the compounds of formula (I-1A-2) with the compounds of formula (III)

$$R^{1\text{-}1A\text{-}1a}\text{—CHO} \quad \quad (III)$$

(wherein all of the symbols have the same meanings as defined hereinbefore.).

The reductive amination is well known. For example, it may be carried out in an organic solvent (dichloroethane, dichloromethane, dimethylformamide, acetic acid or a mixture thereof etc.) in the presence of a reducing agent (sodium triacetoxyborohydride or sodium cyanoborohydride etc.) at 0-40° C.

Moreover, the reductive amination may be carried out with the compounds in which nitrogen of $R^1$ is oxidized to N-oxide.

(b) Among the compounds of formula (I-1A-1), the compounds, in which $R^{1A\text{-}1}$ is C1-18 alkyl, C2-18 alkenyl, C2-18 alkynyl, or C1-18 alkyl, C2-18 alkenyl or C2-18 alkynyl substituted by various substituents, and in which $R^{1A\text{-}1}$ bonds with $N^1$ through —$CHR^{A\text{-}1b}$— (wherein $R^{A\text{-}1b}$ is C1-17 alkyl, C2-17 alkenyl or C2-17 alkynyl.), i.e., the compounds of formula (I-1A-1b)

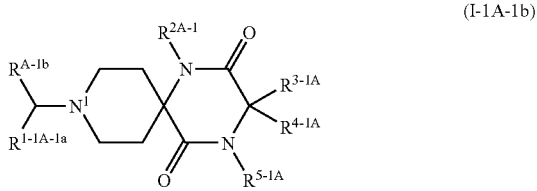

(I-1A-1b)

(wherein $R^{A\text{-}1b}$ is C1-17 alkyl, C2-17 alkenyl or C2-17 alkynyl, and the other symbols have the same meanings as defined hereinbefore.)

may be prepared by reductive amination of the compounds of formula (I-1A-2) with the compounds of formula (IV)

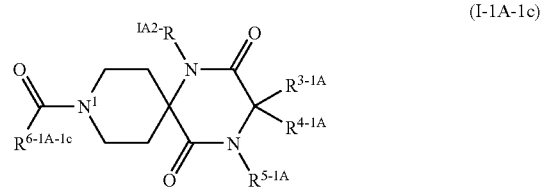

(IV)

(wherein all of the symbols have the same meanings as defined hereinbefore.).

The reductive amination is well known. For example, it may be carried out in an organic solvent (dichloroethane or dichloromethane etc.) in the presence of tertiary amine (triethylamine or diisopropylethylamine etc.) with Lewis acid (titanium tetrachloride etc.), at 0-40° C., and subsequently by the addition of a reducing agent (sodium triacetoxyborohydride or sodium cyanoborohydride etc.) at 0-40° C.

(c) Among the compounds of formula (I-1A-1), the compounds in which $R^{1A\text{-}1}$ is $COR^6$, i.e., the compounds of formula (I-1A-1c)

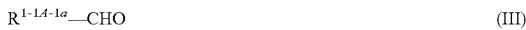

(I-1A-1c)

(wherein $R^{6\text{-}1A\text{-}1c}$ has the same meaning as $R^6$, wherein $R^{6\text{-}1A\text{-}1c}$ is not a group containing carboxyl, hydroxy, amino or thiol, and any nitrogen atoms are not quaternary ammonium salt nor N-oxide, and the other symbols have the same meaning as defined hereinbefore.)

may be prepared by the amidation of the compounds of formula (I-1A-2) with the compounds of formula (V)

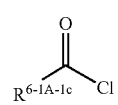

(V)

(wherein all of the symbols have the same meanings as defined hereinbefore.).

The amidation is well known. For example, it may be carried out in an organic solvent (chloroform, dichloromethane, diethylether, tetrahydrofuran, dioxane or dimethylformamide etc.) in the presence of tertiary amine (isopropylethylamine, pyridine, triethylamine, dimethylaniline or dimethylaminopyridine etc.) or an aqueous alkali solution (solution of bicarbonate or solution of sodium hydroxide etc.) at 0-40° C.

(d) Among the compounds of formula (I-1A-1), the compounds in which $R^{1\text{-}1A\text{-}1}$ is $SO_2R^{10}$, i.e., the compounds of formula (I-1A-1d)

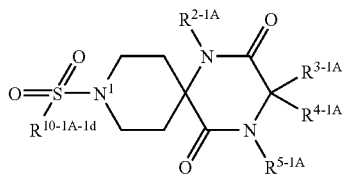

(I-1A-1d)

(wherein $R^{10-1A-1d}$ has the same meaning as $R^{10}$, wherein $R^{10-1A-1d}$ is not a group containing carboxyl, hydroxy, amino or thiol, and any nitrogen atoms are not quaternary ammonium salt nor N-oxide, and the other symbols have the same meaning as defined hereinbefore.)

may be prepared by the sulfonamidation of the compounds of formula (I-1A-2) with the compounds of formula (VI)

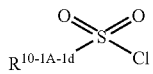

(VI)

(wherein all of the symbols have the same meanings as defined hereinbefore.).

The sulfonamidation is well known. For example, it may be carried out in an inert organic solvent (chloroform, dichloromethane, dichloroethane, diethylether or tetrahydrofuran etc.) in the presence of tertiary amine (diisopropylethylamine, pyridine, triethylamine, dimethylaniline or dimethylaminopyridine etc.) at 0-40° C.

(e) Among the compounds of formula (I-1A-1), the compounds in which $R^{1-1A-1}$ is $CONR^7R^8$, i.e., the compounds of formula (I-1A-1e)

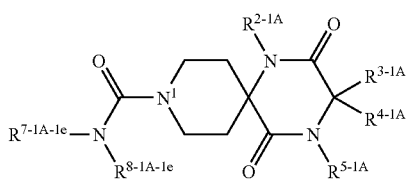

(I-1A-1e)

(wherein $R^{7-1A-1e}$ has the same meaning as $R^7$, $R^{10-1A-1d}$ is not a group containing carboxyl, hydroxy, amino or thiol, any nitrogen atoms are not quaternary ammonium salt nor N-oxide, and the other symbols have the same meaning as defined hereinbefore.)

may be prepared by the reaction of the compounds of formula (I-1A-2) with the compounds of formula (VII-1)

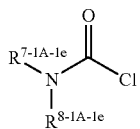

(VII-1)

(wherein all of the symbols have the same meanings as defined hereinbefore.)

or with the compounds of formula (VII-2)

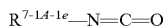

$R^{7-1A-1e}$—N=C=O  (VII-2)

(wherein all of the symbols have the same meanings as defined hereinbefore.).

The reaction with the compounds of formula (VII-1) is well known. For example, it may be carried out in an organic solvent (chloroform, dichloromethane, diethylether or tetrahydrofuran etc.), in the presence of a tertiary amine (isopropylethylamine, pyridine, triethylamine, dimethylaniline or dimethylaminopyridine etc.) at 0-40° C.

The reaction with the compounds of formula (VII-2) is well known. For example, it may be carried out in an inert organic solvent (chloroform, dichloromethane, dichloroethane, dimethylformamide, diethylether or tetrahydrofuran etc.) at 0-40° C.

(f) Among the compounds of formula (I-1A-1), the compounds in which $R^{1-1A-1}$ is —CH$_2$—CH(OH)—$R^{4-1f}$ ($R^{4-1f}$ is C1-16 alkyl, C2-16 alkenyl, C2-16 alkynyl, or C1-16 alkyl, C2-16 alkenyl or C2-16 alkynyl substituted by various substituents.), i.e., the compounds of formula (I-1A-1f)

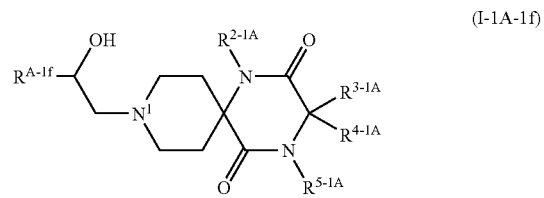

(I-1A-1f)

(wherein $R^{4-1f}$ is C1-16alkyl, C2-16 alkenyl, C2-16 alkynyl, or C1-16 alkyl, C2-16 alkenyl or C2-16 alkynyl substituted by 1-4 of optionally selected from (a) halogen, (b) —CONR$^7$R$^8$, (c) —COOR$^9$, (d) —OR$^{14}$, (e) —SR$^{15}$, (f) —NR$^{16}$R$^{17}$, (g) —NR$^{18}$COR$^{19}$, (h) —SO$_2$NR$^{20}$R$^{21}$, (i) —OCOR$^{22}$, (j) —NR$^{23}$SO$_2$R$^{24}$, (k) —NR$^{25}$COOR$^{26}$, (l) —NR$^{27}$CONR$^{28}$R$^{29}$, (m) Cyc 1, (n) keto, (o) —(SO$_2$R$^{24}$)$_2$, and any nitrogen atoms are not quaternary ammonium salt nor N-oxide and the other symbols have the same meaning as defined hereinbefore.)

may be prepared by the reaction of the compounds of formula (I-1A-2) with the compounds formula (VIII)

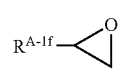

(VIII)

(wherein all of the symbols have the same meanings as defined hereinbefore.).

The reaction is well known, and it may be carried out in an organic solvent (methanol, ethanol, 2-propanol, tetrahydrofuran or acetonitlile etc.), in the presence or absence of a tertialy amine (triethylamine or N-methylmorpholine etc.) at 40-100° C.

(g) Among the compounds of formula (I-1A-1), the compounds in which $R^{1-1A-1}$ is —CH$_2$—C(=O)—$R^{4-1g}$ ($R^{4-1g}$ has the same meaning as $R^{4-1f}$), i.e., the compounds of formula (I-1A-1g)

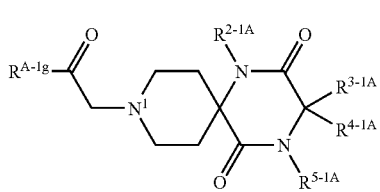

(I-1A-1g)

(wherein $R^{A-1g}$ has the same meaning as $R^{A-1f}$, and the other symbols have the same meanings as defined hereinbefore.)

may be prepared by the reaction of the compounds of formula (I-1A-2) with the compounds of formula (IX-1)

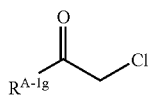

(IX-1)

(wherein all of the symbols have the same meanings as defined hereinbefore.)

or with the compounds of formula (IX-2)

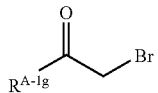

(IX-2)

(wherein all of the symbols have the same meanings as defined hereinbefore.).

The reaction is well known, and it may be carried out in an organic solvent (chloroform, dichloromethane, diethylether, tetrahydrofuran, dioxane or dimethylformamide etc.) in the presence of a tertiary amine (isopropylethylamine, pyridine, triethylamine, dimethylaniline or dimethylaminopyridine etc.) at 0-40° C.

Moreover, the compounds of formula (I-1A-1) may be prepared by the methods described in (h).

(h) Among the compounds of formula (I-1A-1), the compounds in which $R^{1-1A-1}$ is 2-propenyl ($-CH_2CH=CH_2$), i.e., the compounds of formula (I-1A-1h)

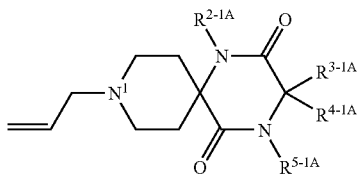

(I-1A-1h)

(wherein all of the symbols have the same meanings as defined hereinbefore.)

may be prepared by the reaction of the compounds in which $R^{1-1A-1}$ is 2-propenyloxycarbonyl ($-COO-CH_2CH=CH_2$) among the compounds of formula (I-1A-1) prepared by the above method, i.e., the compounds of formula (I-1A-1-2)

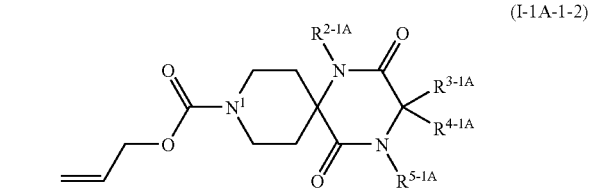

(I-1A-1-2)

(wherein all of the symbols have the same meanings as defined hereinbefore.) with a metal complex.

The reaction with a metal complex is well known, and it may be carried out, for example, in an organic solvent (tetrahydrofuran or acetic acid etc.), with a metal complex (tetrakis(triphenylphosphine)palladium(0) complex etc.), at 0-40° C.

Among the compounds of formula (I-1), the compounds in which at least one group of $R^1$, $R^2$, $R^3$, $R^4$ and $R^5$ represents a group containing carboxyl, hydroxy, amino or thiol, i.e., the compounds of formula (I-1B)

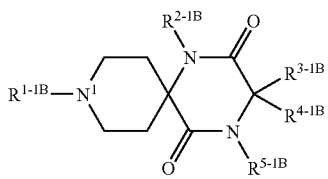

(I-1B)

(wherein $R^{1-1B}$, $R^{2-1B}$, $R^{3-1B}$, $R^{4-1B}$ and $R^{5-1B}$ have the same meanings as $R^{1-1}$, $R^{2-1}$, $R^{3-1}$, $R^{4-1}$ and $R^{5-1}$, respectively, at least one group represents a group containing carboxyl, hydroxy, amino or thiol, and the other symbols have the same meanings as defined hereinbefore.)

may be prepared by the removal of a protecting group of the compounds in which at least one group of $R^{1-1}$, $R^{2-1}$, $R^{3-1}$, $R^{4-1}$ or $R^{5-1}$ represents a group containing carboxyl, hydroxy, amino and thiol protected by a protecting group, i.e., the compounds of formula (I-1A-3)

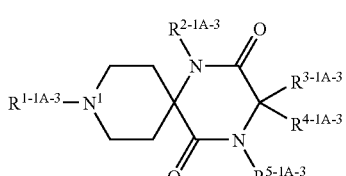

(I-1A-3)

(wherein $R^{1-1A-3}$, $R^{2-1A-3}$, $R^{3-1A-3}$, $R^{4-1A-3}$ and $R^{5-1A-3}$ have the same meanings of $R^{1-1}$, $R^{2-1}$, $R^{3-1}$, $R^{4-1}$ and $R^{5-1}$, respectively, at least one group represents a group containing carboxyl, hydroxy, amino or thiol protected by a protecting group, and the other symbols have the same meanings as defined hereinbefore.).

A protecting group of carboxyl includes, for example, methyl, ethyl, t-butyl, benzyl or allyl.

A protecting group of hydroxy includes, for example, methoxymethyl, 2-tetrahydropyranyl, t-butyldimethylsilyl, t-butyldiphenylsilyl, acetyl or benzyl.

A protecting group of amino includes, for example, benzyloxycarbonyl, allyloxycarbonyl, t-butoxycarbonyl, trifluoroacetyl or 9-fluorenylmethoxycarbonyl.

A protecting group of thiol includes, for example, benzyl, methoxybenzyl, acetoamidomethyl, triphenylmethyl or acetyl.

The protecting group of carboxyl, hydroxy, amino or thiol includes the above one, and in addition the other protecting group which is removable selectively and easily, for example, one described in T. W. Greene et. al., Protective Groups in Organic Synthesis, Third Edition, Wiley-Interscience, New York, 1999.

The removal of a protecting group of amino may be carried out by the method described hereinbefore.

The removal of a protecting group of carboxyl, hydroxy or thiol is well known. For example, it is
(1) the alkaline hydrolysis,
(2) the removal of a protecting group in an acidic condition,
(3) the removal of a protecting group by hydrogenolysis, or
(4) the removal of a protecting group containing silyl or
(5) the removal of a protecting group using metal complex etc.

Among these methods, (1), (2), (3) and (5) may be carried out by the same methods of the removal of a protecting group of amino.

Concretely describing (4), the removal of a protecting group containing silyl may be carried out, for example, in an organic solvent (tetrahydrofuran or acetonitrile etc.), with tetrabutylammoniumfluoride at 0-40° C.

As well known to the person in the art, the aimed compounds of the present invention may be prepared easily by choice of these removal of a protecting group.

Moreover, the compounds of formula (I-1A-1) may be prepared by the methods described in (j)-(m) with the compounds of formula (I-1B-1)

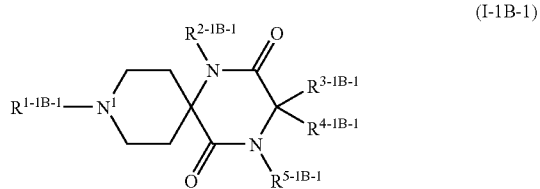

(wherein $R^{1-1B-1}$, $R^{2-1B-1}$, $R^{3-1B-1}$, $R^{4-1B-1}$ and $R^{5-1B-1}$ have the same meanings of $R^{1-1}$, $R^{2-1}$, $R^{3-1}$, $R^{4-1}$ and $R^{5-1}$, respectively, at least one group represents a group containing amino, and the other symbols have the same meanings as defined hereinbefore.).

(j) Among the compounds of formula (I-1A-1), the compounds in which at least one group of $R^{1-1A-1}$, $R^{2-1A-1}$, $R^{3-1A-1}$, $R^{4-1A-1}$ and $R^{5-1A-1}$ represent a group containing amide, i.e., the compounds of formula (I-1A-1j)

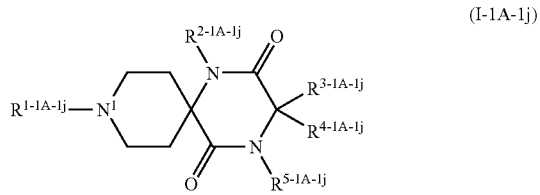

(wherein $R^{1-1A-1j}$, $R^{2-1A-1j}$, $R^{3-1A-1j}$, $R^{4-1A-1j}$ and $R^{5-1A-1j}$ have the same meanings as $R^{1-1}$, $R^{2-1}$, $R^{3-1}$, $R^{4-1}$ and $R^{5-1}$, respectively, at least one group represents a group containing amide, and the other symbols have the same meanings as defined hereinbefore.)

may be prepared by the amidation of the compounds of formula (I-1B-1).

The amidation may be carried out by the method described hereinbefore.

(k) Among the compounds of formula (I-1A-1), the compounds in which at least one group of $R^{1-1A-1}$, $R^{2-1A}$, $R^{3-1A}$, $R^{4-1A}$ and $R^{5-1A}$ represents a group containing sulfonamide, i.e., the compounds of formula (I-1A-1k)

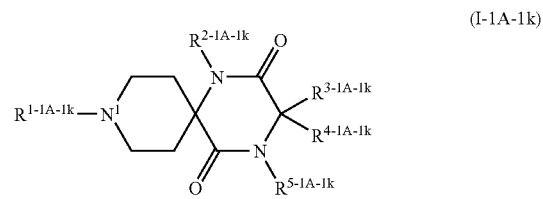

(wherein $R^{1-1A-1k}$, $R^{2-1A-1k}$, $R^{3-1A-1k}$, $R^{4-1A-1k}$ and $R^{5-1A-1k}$ have the same meanings as $R^{1-1}$, $R^{2-1}$, $R^{3-1}$, $R^{4-1}$ and $R^{5-1}$, respectively, at least one group represents a group containing sulfonamide, and the other symbols have the same meanings as defined hereinbefore.)

may be prepared by the sulfonamidation of the compounds of formula (I-1B-1).

The sulfonamidation may be carried out the method described hereinbefore.

(m) Among the compounds of formula (I-1A-1), the compounds in which at least one group of $R^{1-1A-1}$, $R^{2-1A}$, $R^{3-1A}$, $R^{4-1A}$ and $R^{5-1A}$ represents a group containing urea, i.e., the compounds of formula (I-1A-1m)

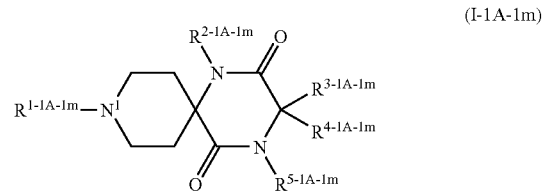

(wherein, $R^{1-1A-1m}$, $R^{2-1A-1m}$, $R^{3-1A-1m}$, $R^{4-1A-1m}$ and $R^{5-1A-1m}$ have the same meanings as $R^{1-1}$, $R^{2-1}$, $R^{3-1}$, $R^{4-1}$ and $R^{5-1}$, respectively, at least one group represents a group containing urea, and the other symbols have the same meanings as defined hereinbefore.)

may be prepared by the urea formation of the compounds of formula (I-1B-1).

The urea formation may be carried out the method described hereinbefore.

Among the compounds of formula (I-1), the compounds in which at least one group of $R^{1-1}$, $R^{2-1}$, $R^{3-1}$, $R^{4-1}$ and $R^{5-1}$ represents a group containing hydroxy, and/or $R^1$ represents a group containing carboxyl, i.e., the compounds of formula (I-1B-2)

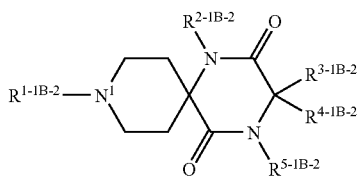

(I-1B-2)

(wherein, $R^{1\text{-}1B\text{-}2}$, $R^{2\text{-}1B\text{-}2}$, $R^{3\text{-}1B\text{-}2}$, $R^{4\text{-}1B\text{-}2}$ and $R^{5\text{-}1B\text{-}2}$ have the same meanings as $R^{1\text{-}1}$, $R^{2\text{-}1}$, $R^{3\text{-}1}$, $R^{4\text{-}1}$ and $R^{5\text{-}1}$, respectively, at least one group of $R^{1\text{-}1B\text{-}2}$, $R^{2\text{-}1B\text{-}2}$, $R^{3\text{-}1B\text{-}2}$, $R^{4\text{-}1B\text{-}2}$ and $R^{5\text{-}1B\text{-}2}$ represents a group containing hydroxy and/or $R^{1B\text{-}2}$ includes carboxyl, and the other symbols have the same meanings as defined hereinbefore.)

may be prepared by the method described in (n).

(n) Among the compounds of formula (I-1B-2), the compounds in which $R^{1\text{-}1B\text{-}2}$ is C1-18 alkyl, C2-18 alkenyl, C2-18 alkynyl or C1-18 alkyl, C2-18 alkenyl or C2-18 alkynyl substituted by various substituent, and in which that $R^{1\text{-}1B\text{-}2}$ bonds to $N^1$ atom through —$CH_2$—, i.e., the compounds of formula (I-1B-1n)

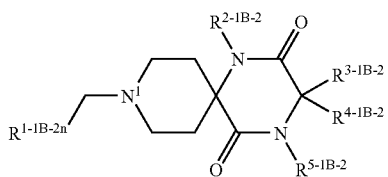

(I-1B-1n)

(wherein $R^{1\text{-}1B\text{-}2n}$ is C1-17alkyl, C2-17 alkenyl, C2-17 alkynyl, or C1-17 alkyl, C2-17 alkenyl or C2-17 alkynyl substituted by 1-5 substituents optionally selected from (a) halogen, (b) —$CONR^7R^8$, (c) —$COOR^9$, (d) —$OR^{14}$, (e) —$SR^{15}$, (f) —$NR^{16}R^{17}$, (g) —$NR^{18}COR^{19}$, (h) —$SO_2NR^{20}R^{21}$, (i) —$OCOR^{22}$, (j) —$NR^{23}SO_2R^{24}$, (k) —$NR^{25}COOR^{26}$, (l) —$NR^{27}CONR^{28}R^{29}$, (m) Cyc 1, (n) keto, (o) —$N(SO_2R^{24})_2$, at least one group of $R^{1\text{-}1B\text{-}2n}$, $R^{2\text{-}1B\text{-}2n}$, $R^{3\text{-}1B\text{-}2n}$, $R^{4\text{-}1B\text{-}2n}$ and $R^{5\text{-}1B\text{-}2n}$ represents a group containing hydroxy, and/or $R^{1B\text{-}2n}$ represents a group containing carboxyl, and any nitrogen atoms are not quaternary ammonium salt nor N-oxide and the other symbols have the same meaning as defined hereinbefore.)

may be prepared by the reductive amination of the compounds in which $R^1$ is hydrogen, and at least one group of $R^{2\text{-}1}$, $R^{3\text{-}1}$, $R^{4\text{-}1}$ and $R^{5\text{-}1}$ represents a group containing hydroxy among the compounds of formula (I-1B) prepared by the above method, i.e., the compounds of formula (I-1B-3)

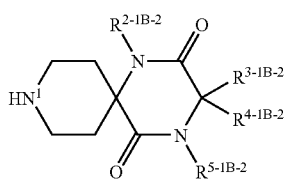

(I-1B-3)

(wherein, all of the symbols have the same meanings as defined hereinbefore.)

with the compounds of formula (X)

$$R^{1\text{-}1B\text{-}2n}\text{—CHO} \quad (X)$$

(wherein, all of the symbols have the same meanings as defined hereinbefore.).

The reductive amination may be carried out by the method described hereinbefore.

Moreover, the reductive amination may be carried out in the compounds in which nitrogen in $R^1$ represents N-oxide.

Among the compounds of the present invention of formula (I), the compounds in which at least one nitrogen is quaternary ammonium salt, i.e., the compounds of formula (I-2)

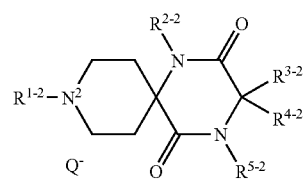

(I-2)

(wherein $R^{1\text{-}2}$, $R^{2\text{-}2}$, $R^{3\text{-}2}$, $R^{4\text{-}2}$ and $R^{5\text{-}2}$ have the same meanings as $R^1$, $R^2$, $R^3$, $R^4$ and $R^5$, respectively, and $N^2$ is nitrogen, at least one nitrogen is quaternary ammonium salt, and Q is halogen.)

may be prepared by the reaction of the compounds of formula (I-1) with the compounds of formula (XI)

$$R^0\text{-Q} \quad (XI)$$

(wherein, $R^0$ is C1-8 alkyl or C1-8 alkyl substituted by phenyl and Q is halogen.).

The reaction is well known and it may be carried out, for example, in an organic solvent (acetone, dimethylformamide or methyl ethyl ketone etc.) at 0-40° C.

Among the compounds of formula (I), the compounds in which at least one nitrogen represents N-oxide, i.e. the compounds of formula (I-3)

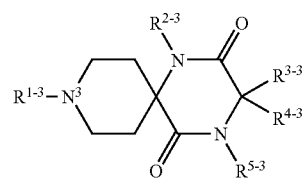

(I-3)

(wherein $R^{1\text{-}3}$, $R^{2\text{-}3}$, $R^{3\text{-}3}$, $R^{4\text{-}3}$ and $R^{5\text{-}3}$ have the same meanings of $R^1$, $R^2$, $R^3$, $R^4$ and $R^5$, respectively, and $N^3$ is nitrogen, and at least one nitrogen represents N-oxide.)

may be prepared by the oxidation of the compounds of formula (I-1).

The oxidation is well known and it may be carried out, for example, in a suitable organic solvent (dichloromethane, chloroform, benzene, hexane or t-butylalcohol etc.) in the presence of a excessive oxidizing reagent (hydrogen peroxide, sodium periodate, acyl nitrite, sodium perborate, peroxidized acid (for example, 3-chloroperbenzoic acid, per-acetic acid etc.), OXONE (brand name, Potassium peroxymonosulfate is abbreviated as OXONE.), potassium permanganate or chromic acid etc.) at 20-60° C.
The compounds of the (II-1) may be prepared according to the following Reaction Schemes 1-3.
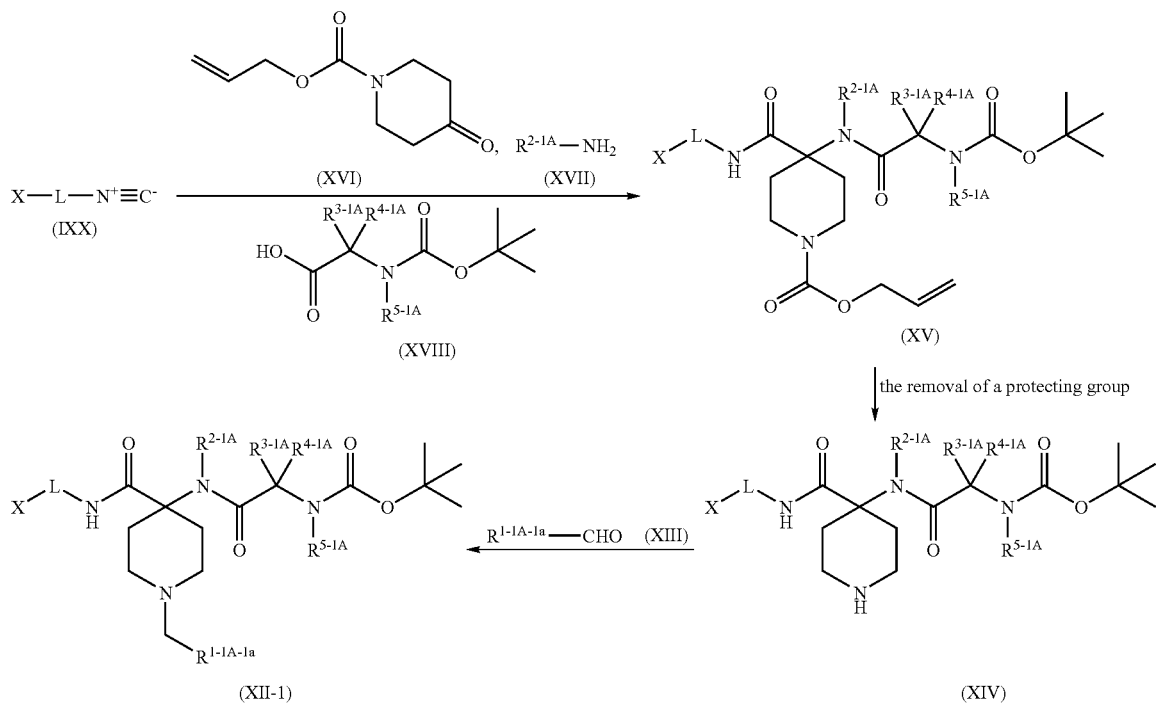
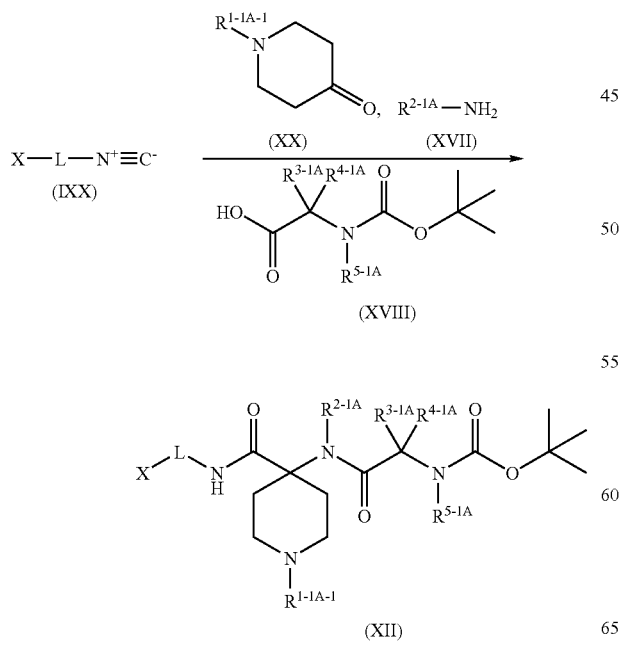
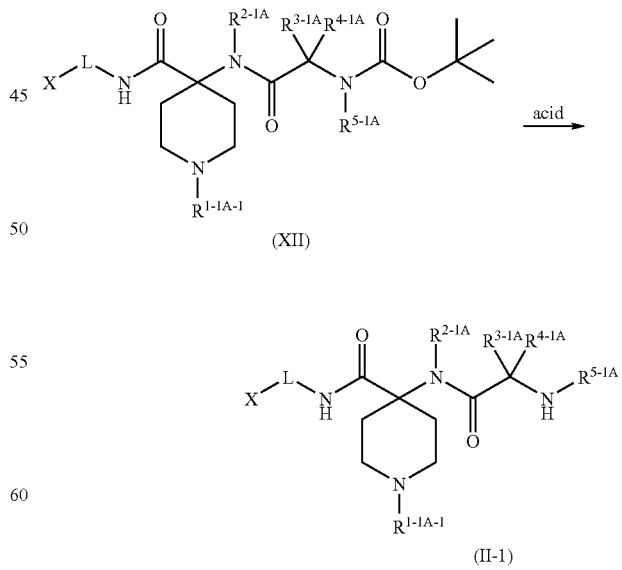
In Reaction Schemes, X is polystyrene resin, L is bivalent group, and the other symbols have the same meanings as defined hereinbefore.

Bivalent group represented by L is, though it depends on the type of the used resin, e.g. methylene or Rink. Rink is 4-(2,4-dimethoxybenzyl)phenoxymethyl.

In the present invention, e.g. aminomethylated polystyrene resin or 9-fluorenylmethyloxycarbonylamino-Rink resin etc. can be used as terminal amino polystyrene resin.

As shown the following Reaction Scheme 4, the resin of formula (XVI) may be prepared from aminomethylated polystyrene resin or 9-fluorenylmethyloxycarbonylamino-Rink resin.

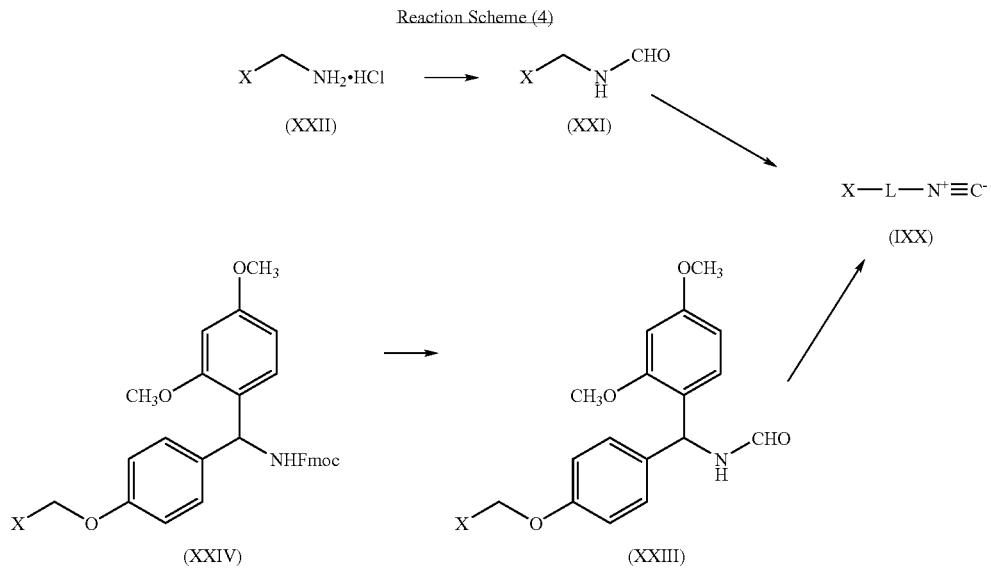

In the reaction using polystyrene resin in the present invention, the reaction products may be purified by the conventional methods, for example, washing with a solvent (dimethylformamide, dichloromethane, methanol, tetrahydrofuran, toluene or acetic acid/toluene etc.) at several times. Moreover the obtained products may be purified by conventional techniques. For example, purification may be carried out by distillation at atmospheric or reduced pressure, by high performance liquid chromatography, by thin layer chromatography or by column chromatography using silica gel or magnesium silicate, by washing or by recrystallization.

The compounds of formula (II-2) may be prepared according to the following Reaction Scheme 5.

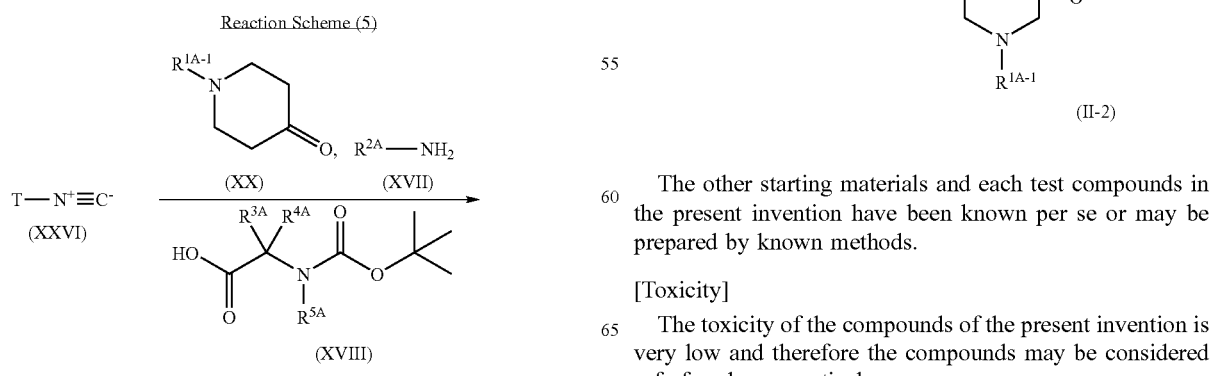

The other starting materials and each test compounds in the present invention have been known per se or may be prepared by known methods.

[Toxicity]

The toxicity of the compounds of the present invention is very low and therefore the compounds may be considered safe for pharmaceutical use.

INDUSTRIAL APPLICABILITY

[Application for Pharmaceuticals]

In animal included human, especially human, the compounds of the present invention of formula (I) are used for prevention and/or treatment for HIV infection or AIDS induced by the infection.

For the purpose above described, the compounds of the present invention of formula (I), the quaternary ammonium salts thereof or the N-oxides thereof, or the non-toxic salts thereof may be normally administered systemically or locally, usually by oral or parenteral administration.

The doses to be administered are determined depending upon, for example, age, body weight, symptom, the desired therapeutic effect, the route of administration, and the duration of the treatment. In the human adult, the doses per person are generally from 1 mg to 1000 mg, by oral administration, up to several times per day, and from 1 mg to 100 mg, by parenteral administration (preferably intravenous administration), up to several times per day, or continuous administration from 1 to 24 hours per day from vein.

As mentioned above, the doses to be used depend upon various conditions.

Therefore, there are cases in which doses lower than or greater than the ranges specified above may be used.

The compounds of the present invention may be administered for example, in the form of solid for oral administration, liquid forms for oral administration, injections, liniments or suppositories for parenteral administration.

Solid forms for oral administration include compressed tablets, pills, capsules, dispersible powders, and granules. Capsules include hard capsules and soft capsules.

In such solid forms, one or more of the active compound(s) may be admixed with vehicles (such as lactose, mannitol, glucose, microcrystalline cellulose or starch), binders (such as hydroxypropyl cellulose, polyvinylpyrrolidone or magnesium metasilicate aluminate), disintegrants (such as cellulose calcium glycolate), lubricants (such as magnesium stearate), stabilizing agents, and solution adjuvants (such as glutamic acid or aspartic acid) and prepared according to methods well known in normal pharmaceutical practice. The solid forms may, if desired, be coated with coating agents (such as sugar, gelatin, hydroxypropyl cellulose or hydroxypropylmethyl cellulose phthalate), or be coated with two or more films. And further, coating may include containment within capsules of absorbable materials such as gelatin.

Liquid forms for oral administration include pharmaceutically acceptable solutions, suspensions, emulsions, syrups and elixirs. In such forms, one or more of the active compound(s) may be dissolved, suspended or emulsified into diluent(s) commonly used in the art (such as purified water, ethanol or a mixture thereof). Besides such liquid forms may also comprise some additives, such as wetting agents, suspending agents, emulsifying agents, sweetening agents, flavoring agents, aroma, preservative or buffering agent.

Injections for parenteral administration include sterile aqueous, suspensions, emulsions and solid forms which are dissolved or suspended into solvent(s) for injection immediately before use. In injections, one or more of the active compound(s) may be dissolved, suspended or emulsified into solvent(s). The solvents may include distilled water for injection, saline, vegetable oil, propylene glycol, polyethylene glycol, alcohol, e.g. ethanol, or a mixture thereof. Injections may comprise some additives, such as stabilizing agents, solution adjuvants (such as glutamic acid, aspartic acid or POLYSORBATE80 (registered trade mark)), suspending agents, emulsifying agents, soothing agent, buffering agents, preservative. They may be sterilized at a final step, or may be prepared and compensated according to sterile methods. They may also be manufactured in the form of sterile solid forms such as freeze-dried products, which may be dissolved in sterile water or some other sterile diluent(s) for injection immediately before use.

Other forms for parenteral administration include liquids for external use, ointments and endermic liniments, inhalations, sprays, suppositories and pessaries for vaginal administration which comprise one or more of the active compound(s) and may be prepared by methods known per se.

Sprays may comprise additional substances other than diluents, such as stabilizing agents, such as sodium sulfate, isotonic buffers, such as sodium chloride, sodium citrate or citric acid. For preparation of such sprays, for example, the method described in the U.S. Pat. No. 2,868,691 or 3,095,355 may be used.

The compound of the present invention represented by formula (I), a quaternary ammonium salt thereof, an N-oxide thereof or a non-toxic salt thereof may be used together with at least one member of other preventive and/or treating agent(s) for HIV infection (particularly an agent for preventive and/or treating agent AIDS). In that case, the drug as such may be mixed with pharmacologically acceptable excipient, binder, disintegrating agent, lubricant, stabilizer, solubilizer, diluent, etc. either separately or simultaneously to make into a pharmaceutical preparation and that can be administered either orally or parenterally as a pharmaceutical composition for prevention and/or treatment of HIV infection.

The compound of the present invention represented by formula (I), a quaternary ammonium salt thereof, an N-oxide thereof or a non-toxic salt thereof has an infection inhibiting activity to HIV-I which acquired resistance to other agent for preventive and/or treating HIV infection (particularly, an agent for preventive and/or treating agent AIDS). Therefore, it is also able to be used for HIV-infected patients to whom other agent for preventive and/or treating HIV infection is no longer effective. In that case, although the compound of the present invention may be used solely, it may be also used together with an agent for preventive and/or treating HIV infection where infected HIV-1 strain acquired resistance or with other drugs.

The present invention covers the case where the compound represented by formula (I), a quaternary ammonium salt thereof, an N-oxide thereof or a non-toxic salt thereof is combined with a drug which does not inhibit the HIV infection whereby preventive and/or treating effect for HIV infection is enhanced as compared with a single preparation.

Examples of other agent for preventive and/or treating HIV infection used for a combination with the compound of the present invention represented by formula (I), a quaternary ammonium salt thereof, an N-oxide thereof or a non-toxic salt thereof are reverse transcriptase inhibitor, protease inhibitor, chemokine antagonist (such as CCR2 antagonist, CCR3 antagonist, CCR4 antagonist, CCR5 antagonist and CXCR4 antagonist), fusion inhibitor, antibody to surface antigen of HIV-1 and vaccine of HIV-1.

Reverse transcriptase inhibitors are concretely (1) nucleoside/nucleotide reverse transcriptase inhibitors: zidovudine (brand name: Retrovir), didanosine (brand name: Videx), zalcitabine (brand name: HIVID), stavudine (brand name: Zerit), lamivudine (brand name: Epivir), abacavir (brand name: Ziagen), adefovir, adefovir dipivoxil, emtricitabine (brand name: Coviracil) or PMPA (brand name: Tenofovir) etc. and (2) nonnucleoside reverse transcriptase inhibitors: nevirapine (brand name: Viramune), delavirdine (brand name: Rescriptor), efavirenz (brand name: Sustiva, Stocklin) or capravirine (AG1549) etc.

Protease inhibitors are concretely indinavir (brand name: Crixivan), ritonavir (brand name: Norvir), nelfinavir (brand name: Viracept), saquinavir (brand name: Invirase, Fortovase), amprenavir (brand name: Agenerase), lopinavir (brand name: Kaletra) or tipranavir etc.

As chemokine antagonists, internal ligand of chemokine receptor, its derivatives, its non-peptide low molecular compound or antibody of chemokine receptor are included.

The examples of internal ligand of chemokine receptor are concretely, MIP-1α, MIP-1β, RANTES, SDF-1α, SDF-1β, MCP-1, MCP-2, MCP-4, Eotaxin and MDC etc.

The derivatives of internal ligand are concretely, AOP-RANTES, Met-SDF-1α, Met-SDF-1β etc.

Antibodies of chemokine receptor are concretely, Pro-140 etc.

CCR2 antagonists are concretely written in specification of WO99/07351, WO99/40913, WO00/46195, WO00/46196, WO00/46197, WO00/46198, WO00/46199, WO00/69432 or WO00/69815 or in Bioorg. Med. Chem. Lett., 10, 1803 (2000) etc.

CCR3 antagonists are concretely written in specification of DE19837386, WO99/55324, WO99/55330, WO00/04003, WO00/27800, WO00/27835, WO00/27843, WO00/29377, WO00/31032, WO00/31033, WO00/34278, WO00/35449, WO00/35451, WO00/35452, WO00/35453, WO00/35454, WO00/35876, WO00/35877, WO00/41685, WO00/51607, WO00/51608, WO00/51609, WO00/51610, WO00/53172, WO00/53600, WO00/58305, WO00/59497, WO00/59498, WO00/59502, WO00/59503, WO00/62814, WO00/73327 or WO01/09088 etc.

CCR5 antagonists are concretely written in specification of WO99/17773, WO99/32100, WO00/06085, WO00/06146, WO00/10965, WO00/06153, WO00/21916, WO00/37455, EP1013276, WO00/38680, WO00/39125, WO00/40239, WO00/42045, WO00/53175, WO00/42852, WO00/66551, WO00/66558, WO00/66559, WO00/66141, WO00/68203, JP2000309598, WO00/51607, WO00/51608, WO00/51609, WO00/51610, WO00/56729, WO00/59497, WO00/59498, WO00/59502, WO00/59503, WO00/76933, WO98/25605 or WO99/04794, WO99/38514 or in Bioorg. Med. Chem. Lett., 10, 1803 (2000) etc.

CXCR4 antagonists are concretely AMD-3100, T-22, KRH-1120 or the compounds written in specification of WO00/66112 etc.

Fusion Inhibitors are concretely, T-20(Pentafuside) and T-1249 etc.

The examples of combination agents written above are intended to illustrate the present invention, but do not limit them.

The typical examples of the usual the dosage level in clinical trials of reverse transcriptase inhibitors or protease inhibitors written below are intended to illustrate the present invention, but do not limit them.

Zidovudine: 100 mg capsule, 200 mg per dose, 3 times per day;
300 mg tablet, 300 mg per dose, twice per day;
didanosine: 25-200 mg tablet, 125-200 mg per dose, twice per day;
zalcitabine: 0.375-0.75 mg tablet, 0.75 mg per dose, 3 times per day;
stavudine: 15-40 mg capsule, 30-40 mg per dose, twice per day;
lamivudine: 150 mg tablet, 150 mg per dose, twice per day;
abacavir: 300 mg tablet, 300 mg per dose, twice per day;
nevirapine: 200 mg tablet, 200 mg per dose, once per day for 14 days and then twice per day;
delavirdine: 100 mg tablet, 400 mg per dose, 3 times per day;
efavirenz: 50-200 mg capsule, 600 mg per dose, once per day;
indinavir: 200-400 mg capsule, 800 mg per dose, 3 times per day;
ritonavir: 100 mg capsule, 600 mg per dose, twice per day;
nelfinavir: 250 mg tablet, 750 mg per dose, 3 times per day;
saquinavir: 200 mg capsule, 100 or 200 mg per dose, 3 times per day;
amprenavir: 50-150 mg tablet, 100 or 200 mg per dose, twice per day.

BEST MODE FOR CARRYING OUT THE INVENTION

The following Reference Examples and Examples are intended to illustrate the present invention, but do not limit them.

In chromatographic separations and TLC, the solvents in parenthesis show the eluting and developing solvents and the ratios of the solvents used are by volume.

The solvents in parenthesis in NMR show the solvents used for measurement.

R* and S* do not represent the absolute position but the relative position.

REFERENCE EXAMPLE 1

Preparation of Resin (2)

Resin (1)    Resin (2)

Aminomethylpolystyrene resin hydrochloride (Resin (1); X is polystyrene resin.) (30.0 g) (1% divinylbenzene copolymer, Watanabe Kagaku, Catalog No A00062) was washed with dimethylformamide (300 ml), 10% diisopropylethylamine-dimethylformamide solution (300 ml) and dimethylformamide (300 ml) successively, and was suspended in dimethylformamide (200 ml). To the suspension were added formic acid (10.2 ml) and diisopropylcarbodiimide (42.3 ml) under cooling with ice, and it was stirred for 1 hour at room temperature. The resin was collected by filtration from the reaction solution, and was washed with dimethylformamide (250 ml×3), dichloromethane (250 ml×4), methanol (250 ml×2) and dichloromethane (250 ml×4) to give Resin (2).

IR (KBr): ν 1682 cm$^{-1}$.

REFERENCE EXAMPLE 2

Preparation of Resin (3)

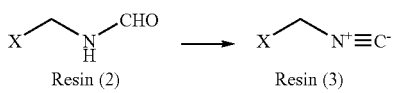

To a suspension of Resin (2) prepared in Reference Example 1 in dichloromethane (300 ml) were added triethylamine (18.8 ml), carbon tetrachloride (13.0 ml) and triphenylphosphine (35.4 g), and it was refluxed for 1 hour. The reaction solution was cooled to room temperature, and the resin was collected by filtration. The resin was washed with dichloromethane (250 ml×3), methanol (250 ml×1) and dichloromethane (250 ml×2) and dried under reduced pressure to give Resin (3) (28.2 g).

IR (KBr): ν 2147 cm$^{-1}$.

REFERENCE EXAMPLE 3

Preparation of Compound (1)

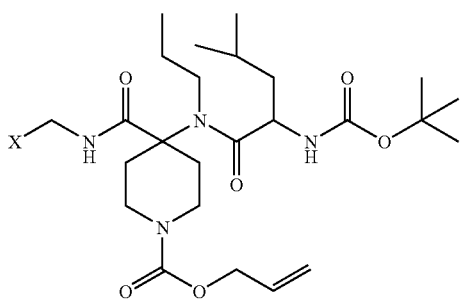

To a suspension of Resin (3) prepared in Reference Example 2 (2.5 g) in tetrahydrofuran/methanol (1:1; 25 ml) were added N-allyloxycarbonyl-4-piperidone (2.15 g), n-propylamine (0.97 ml) and N-(t-butyloxycarbonyl)leucine (2.93 g), and it was stirred for 16 hours at 65° C. The reaction solution was cooled to room temperature, and the resin was collected by filtration. The obtained resin was washed with tetrahydrofuran (25 ml×2), methanol (25 ml×2) and dichloromethane (25 ml×2) to give compound (1).

REFERENCE EXAMPLE 4

Preparation of Compound (2)

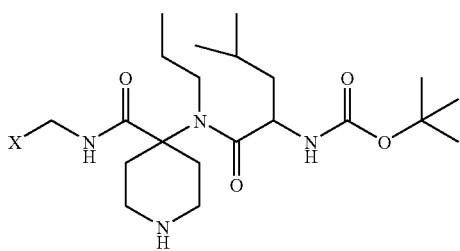

To a suspension of the compound (1) prepared in Reference Example 3 in dichloromethane (25 ml) were added acetic acid (0.81 ml), tributyltin hydride (1.90 ml) and tetrakis(triphenylphosphine)palladium (0) complex (270 mg), and it was stirred for 6 hours at room temperature. The resin was collected by filtration from the reaction solution, and was washed with dichloromethane (25 ml×3), methanol (25 ml×2), dichloromethane (25 ml×2) and dimethylformamide (25 ml×3) to give compound (2).

REFERENCE EXAMPLE 5

Preparation of Compound (3)

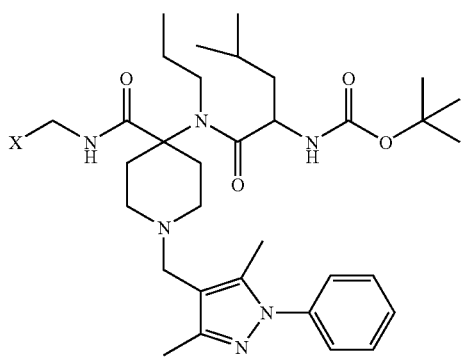

To a suspension of the compound (2) prepared in Reference Example 4 in dimethylformamide (25 ml) were added 3,5-dimethyl-1-phenyl-4-formylpyrazole (1.41 g), sodium triacetoxyborohydride (1.50 g) and acetic acid (0.2 ml), and it was stirred for 16 hours at room temperature. The resin was collected by filtration from the reaction solution, and was washed with dimethylformamide (20 ml×2), dichloromethane (20 ml×2), methanol (20 ml×2) and dichloromethane (20 ml×4) to give compound (3).

REFERENCE EXAMPLE 6

Preparation of Compound (4)

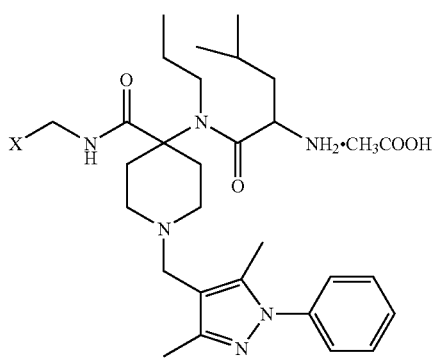

The compound (3) prepared in Reference Example 5 was suspended in 50% trifluoroacetic acid-dichloromethane solution (25 ml), and the suspension was stirred for 5 minutes at room temperature. The reaction solution was filtrated. The obtained resin was suspended in 50% trifluoroacetic acid-dichloromethane solution (25 ml), and it was stirred for 30 minutes at room temperature. The resin was collected by filtration from the reaction solution and was washed with dichloromethane (25 ml×4), toluene (25 ml×4), and 1.25 M acetic acid-toluene solution (25 ml×1) to give compound (4).

REFERENCE EXAMPLE 7

Preparation of Resin (5)

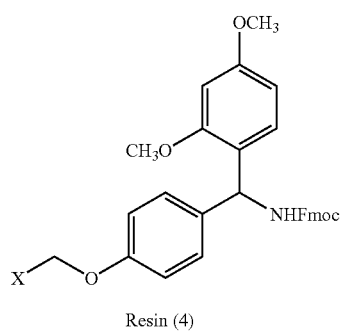

Resin (4)

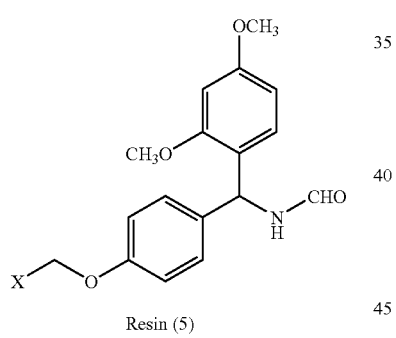

Resin (5)

9-fluorenylmethyloxycarbonylamino-Rink resin (Resin (4)) (5.0 g) (1% divinylbenzene copolymer, Watanabe Kagaku, Catalog No A00102) was washed with dimethylformamide (50 ml×3), and 20% piperidine-dimethylformamide solution (50 ml×2). The washed resin was suspended in 20% piperidine-dimethylformamide solution (50 ml), and the suspension was stirred for 30 minutes at room temperature. The reaction solution was filtrated. The obtained resin was washed with dimethylformamide (50 ml×5). To a suspension of the washed resin in dimethylformamide (20 ml) was added ethyl formate (30 ml), and it was refluxed for 6 hours. The reaction solution was cooled to room temperature and was filtrated. The filtrated resin was washed with dimethylformamide (50 ml×2), dichloromethane (50 ml×4), methanol (50 ml×4) and dichloromethane (50 ml×4), and dried under reduced pressure to give Resin (5) (4.34 g).

IR (KBr): ν 1693 cm$^{-1}$.

REFERENCE EXAMPLE 8

Preparation of Resin (6)

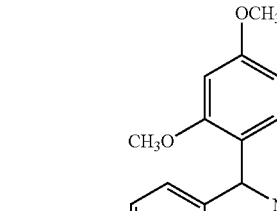

Resin (5)

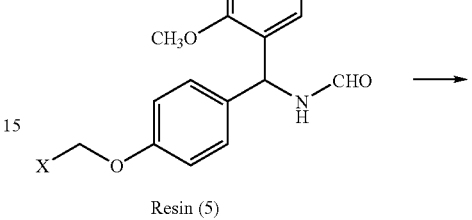

Resin (6)

By the same procedure as described in Reference Example 2 using Resin (4) prepared in Reference Example 7 (4.0 g), Resin (6) (3.56 g) was obtained.

IR (KBr): ν 2136 cm$^{-1}$.

REFERENCE EXAMPLE 9

Preparation of Compound (5)

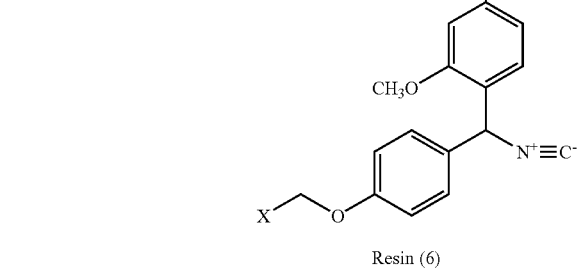

By the same procedure as described in Reference Example 3 using Resin (6) prepared in Reference Example 8 (1.0 g), N-(6-phenylhexyl)-4-piperidone (0.44 g), n-propylamine (0.14 ml) and N-(t-butyloxycarbonyl)-L-leucine (0.42 g), compound (5) was obtained.

REFERENCE EXAMPLE 10

Preparation of Compound (6)

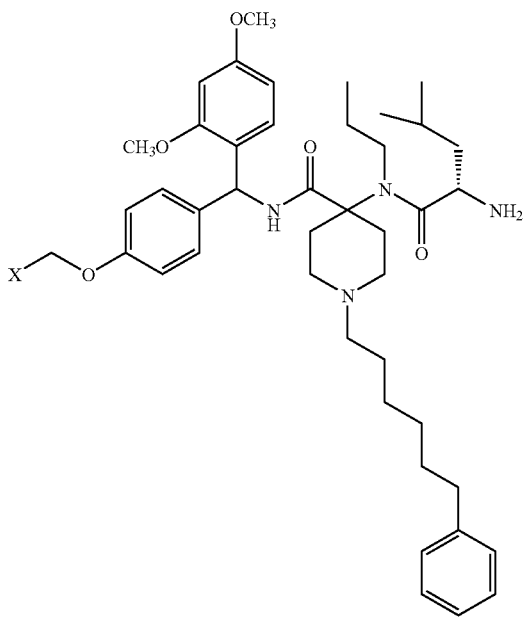

To a suspension of the compound (5) prepared in Reference Example 9 in 1.5 M 2,6-lutidine-dichloromethane (4 ml) was added 1M trimethylsilyl trifluoromethanesulfonate-dichloromethane solution (4 ml), and it was stirred for 30 minutes at room temperature. The resin was collected by filtration from the reaction solution. The obtained resin was again suspended in 1.5 M 2,6-lutidine-dichloromethane solution (4 ml), and 1M trimethylsilyl trifluoromethane-sulfonate-dichloromethane solution (4 ml) was added thereto. It was stirred for 30 minutes at room temperature. The resin was collected by filtration from the reaction solution. The resin was washed with dichloromethane (6 ml×4), methanol (6 ml×4), and toluene (6 ml×5) to give compound (6).

EXAMPLE 1

9-(3,5-dimethyl-1-phenylpyrazol-4-ylmethyl)-2,5-dioxo-3-(2-methyl-1-propyl)-1-propyl-1,4,9-triazaspiro[5.5]undecane.2 hydrochloride

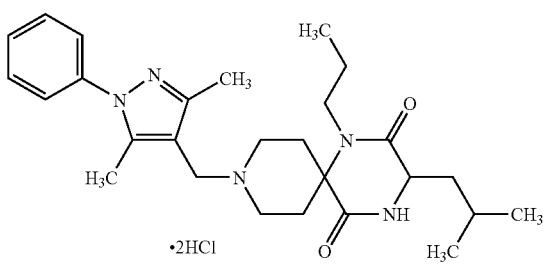

The compound (4) prepared in Reference Example 6 was suspended in 1.25 M acetic acid-toluene solution (25 ml), and the suspension was stirred for 24 hours at 90° C., and was stirred for 16 hours at room temperature. The reaction solution was filtrated. The obtained resin was washed with chloroform-methanol (1:1; 20 ml×2). The filtrate and the washings were concentrated. The residue was purified by column chromatography on silica gel (Fuji Silysia Chemical Ltd., FL60D; chloroform:methanol=30:1). A solution of the obtained residue in methanol was acidified by adding 1N hydrochloric acid, and was concentrated to give the title compound (703 mg) having the following physical data.

TLC: Rf 0.50 (chloroform:methanol=10:1); NMR (CD$_3$OD): δ 7.68-7.50 (m, 5H), 4.36 (s, 2H), 4.03 (dd, J=7.8, 5.2 Hz, 1H), 3.83 (m, 2H), 3.64 (m, 2H), 3.47 (m, 2H), 2.64 (m, 2H), 2.49 (s, 3H), 2.44 (s, 3H), 2.20 (m, 2H), 1.81 (m, 1H), 1.68 (m, 2H), 1.60 (m, 2H), 1.05-0.90 (m, 9H); IR (KBr): ν 3424, 3215, 2960, 2873, 2492, 1671, 1645, 1554, 1501, 1468, 1418, 1370, 1330, 1297, 1243, 1148, 958, 928, 754, 698 cm$^{-1}$; MS (MALDI, Pos., α-CHCA): 488 (M+Na)$^+$, 466 (M+H)$^+$, 185. elemental analysis: calculated (C$_{27}$H$_{39}$N$_5$O$_2$.2HCl) C, 60.22%; H, 7.67%; N, 13.00%. Found C, 59.89%; H, 7.67%; N, 12.79%.

EXAMPLE 2(1) TO 2(3)

By the same procedure as described in Reference Example 3→Reference Example 4 using Resin (3) prepared in Reference Example 2 and N-allyloxycarbonyl-4-piperidone, using the corresponding compounds respectively instead of n-propylamine and N-(t-butyloxycarbonyl)leucine, and furthermore by the same procedure as described in Reference Example 5→Reference Example 6→Example 1 using the corresponding compound instead of 3,5-dimethyl-1-phenyl-4-formylpyrazole, the following compounds of the present invention were obtained.

EXAMPLE 2(1)

9-(1,4-benzodioxan-6-ylmethyl)-1-butyl-3-cyclohexylmethyl-2,5-dioxo-1,4,9-triazaspiro[5.5]undecane.hydrochloride

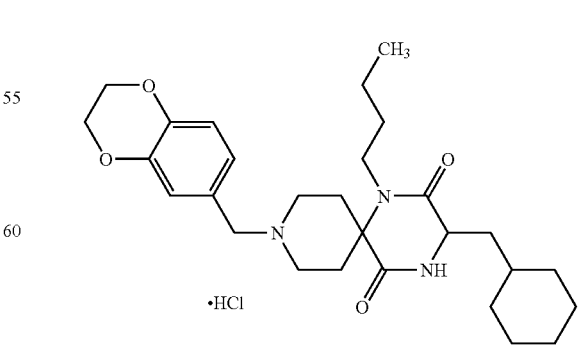

TLC: Rf 0.63 (chloroform:methanol=10:1); NMR (CD$_3$OD): δ 7.08 (d, J=2.2 Hz, 1H), 6.99 (dd, J=8.0, 2.2 Hz, 1H), 6.92 (d, J=8.0 Hz, 1H), 4.27 (s, 4H), 4.23 (s, 2H), 4.04 (dd, J=7.6, 4.8 Hz, 1H), 3.74 (m, 2H), 3.60-3.35 (m, 4H), 2.43 (m, 2H), 2.15 (m, 2H), 1.90-1.60 (m, 7H), 1.60-1.45 (m, 2H), 1.45-1.30 (m, 2H), 1.30-1.10 (m, 4H), 1.10-0.80 (m, 5H); IR (KBr): ν 3436, 2926, 2852, 2511, 1675, 1645, 1591, 1511, 1418, 1374, 1294, 1261, 1068, 1050, 930, 888 cm$^{-1}$; MS (MALDI, Pos., α-CHCA): 484 (M+H)$^+$, 149. elemental analysis: calculated (C$_{28}$H$_{41}$N$_3$O$_4$.HCl) C, 64.66%; H, 8.14%; N, 8.08%. Found C, 64.00%; H, 7.94%; N, 7.90%.

EXAMPLE 2(2)

1-butyl-3-cyclohexylmethyl-2,5-dioxo-9-(2-phenylimidazol-4-ylmethyl)-1,4,9-triazaspiro[5.5]undecane.2 hydrochloride

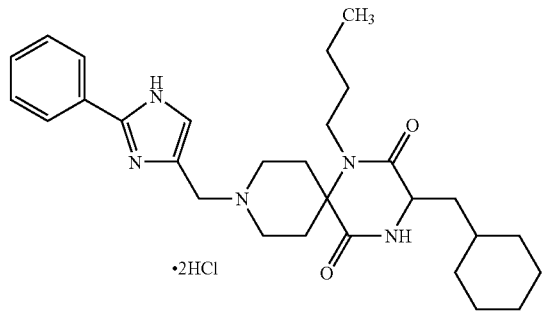

TLC: Rf 0.25 (chloroform:methanol=10:1); NMR (CD$_3$OD): δ 8.05-7.94 (m, 3H), 7.75-7.60 (m, 3H), 4.59 (s, 2H), 4.05 (dd, J=7.4, 4.8 Hz, 1H), 3.88 (m, 2H), 3.65 (m, 2H), 3.51 (m, 2H), 2.68 (m, 2H), 2.19 (m, 2H), 1.90-1.60 (m, 6H), 1.60-1.45 (m, 3H), 1.45-1.30 (m, 3H), 1.30-1.10 (m, 3H), 1.10-0.80 (m, 5H); IR (KBr): ν 3423, 2927, 2854, 2664, 1672, 1644, 1421, 1373, 1177, 775, 709, 688 cm$^{-1}$; MS (MALDI, Pos., α-CHCA): δ 492 (M+H)$^+$. elemental analysis: calculated (C$_{29}$H$_{41}$N$_5$O$_2$.2HCl.2.8H$_2$O) C, 56.63%; H, 7.96%, N, 11.39%. Found C, 56.90%; H, 7.23%; N, 10.78%.

EXAMPLE 2(3)

1-butyl-3-(2-methyl-1-propyl)-2,5-dioxo-9-(4-phenyloxyphenylmethyl)-1,4,9-triazaspiro[5.5]undecane.hydrochloride

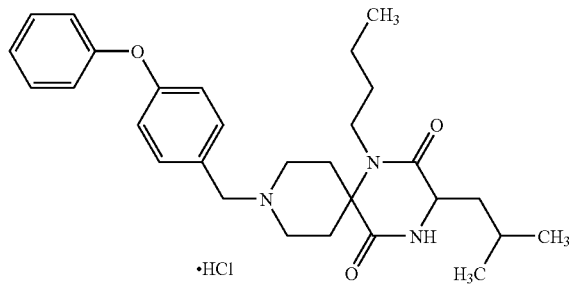

TLC: Rf 0.63 (chloroform:methanol=10:1); NMR (CD$_3$OD): δ 7.54 (d, J=8.8 Hz, 2H), 7.40 (m, 2H), 7.18 (m, 1H), 7.11-7.00 (m, 4H), 4.33 (s, 2H), 4.01 (dd, J=7.6, 4.8 Hz, 1H), 3.80 (m, 2H), 3.60-3.35 (m, 4H), 2.46 (m, 2H), 2.18 (m, 2H), 1.80 (m, 1H), 1.70 (m, 1H), 1.54 (m, 2H), 1.37 (m, 3H), 1.00-0.90 (m, 9H); IR (KBr): ν 3440, 3221, 3066, 2957, 2871, 2559, 1673, 1590, 1509, 1489, 1419, 1371, 1329, 1242, 1172, 873, 693 cm$^{-1}$; MS (MALDI, Pos., α-CHCA): 478 (M+H)$^+$, 183. elemental analysis: calculated (C$_{29}$H$_{39}$N$_3$O$_3$.HCl) C, 67.75%; H, 7.84%; N, 8.17%. Found C, 67.29%; H, 7.70%; N, 8.06%.

EXAMPLE 2(4)

(3S)-2,5-dioxo-3-(2-methylpropyl)-9-(6-phenylhexyl)-1-propyl-1,4,9-triazaspiro[5.5]undecane.hydrochloride

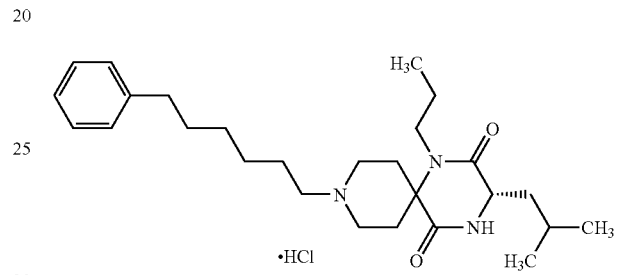

By the same procedure as described in Example 1 using the compound (6) prepared in Reference Example 10, the title compound (69 mg) having the following physical data was obtained.

TLC: Rf 0.46 (chloroform:methanol=10:1); NMR (CD$_3$OD): δ 7.18 (m, 5H), 4.02 (dd, J=7.6, 4.8 Hz, 1H), 3.70 (m, 2H), 3.56 (m, 2H), 3.39 (m, 2H), 3.11 (m, 2H), 2.63 (dd, J=7.8, 7.2 Hz, 2H), 2.48 (m, 2H), 2.17 (m, 2H), 1.95-1.50 (m, 9H), 1.42 (m, 4H), 1.00-0.89 (m, 9H); IR (KBr): ν 3435, 3205, 3082, 3026, 2935, 2870, 2493, 2361, 1674, 1454, 1417, 1370, 1331, 1155, 1071, 1004, 961, 750, 700 cm$^{-1}$; MS (FAB, Pos., glycerin-m-nitrobenzyl alcohol): 442 (M+H)$^+$, 232, 171, 79 (base peak). elemental analysis: calculated (C$_{27}$H$_{43}$N$_3$O$_2$.HCl) C, 67.83%; H, 9.28%; N, 8.79%. Found C, 67.56%; H, 9.50%; N, 8.71%.

EXAMPLE 2(5)

(3R)-2,5-dioxo-3-(2-methylpropyl)-9-(6-phenylhexyl)-1-propyl-1,4,9-triazaspiro[5.5]undecane.hydrochloride

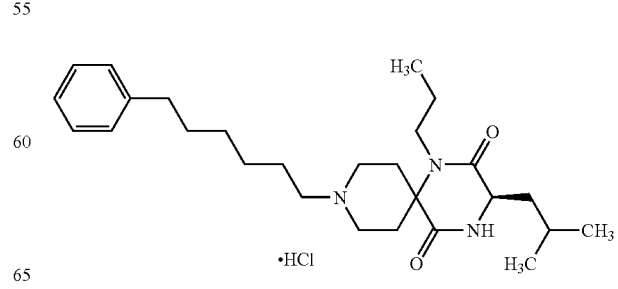

By the same procedure as described in Reference Example 9→Reference Example 10→Example 1 using Resin (6) prepared in Reference Example 8 (1.0 g), N-(6-phenylhexyl)-4-piperidone (0.44 g), n-propylamine (0.14 ml) and N-(t-butyloxycarbonyl)-D-leucine (0.42 g), the title compound (63 mg) having the following physical data was obtained.

TLC: Rf 0.46 (chloroform:methanol=10:1); NMR (CD$_3$OD): δ 7.18 (m, 5H), 4.02 (dd, J=7.6, 4.6 Hz, 1H), 3.70 (m, 2H), 3.56 (m, 2H), 3.39 (m, 2H), 3.11 (m, 2H), 2.63 (dd, J=7.8, 7.2 Hz, 2H), 2.48 (m, 2H), 2.17 (m, 2H), 1.95-1.50 (m, 9H), 1.42 (m, 4H), 1.00-0.89 (m, 9H); IR (KBr): ν 3441, 3204, 3082, 3026, 2935, 2870, 2660, 2499, 2413, 2361, 1674, 1455, 1417, 1370, 1330, 1267, 1205, 1154, 1070, 1003, 960, 928, 899, 750, 700 cm$^{-1}$;

MS (FAB, Pos., glycerin-m-nitrobenzyl alcohol): 442 (M+H)$^+$ (base peak), 294, 232, 202, 171, 79. elemental analysis: calculated (C$_{27}$H$_{43}$N$_3$O$_2$.HCl) C, 67.83%; H, 9.28%; N, 8.79%. Found C, 67.52%; H, 9.51%; N, 8.70%.

EXAMPLE 3(1) TO 3(4)

By the same procedure as described in Reference Example 3→Reference Example 4 using Resin (3) prepared in Reference Example 2 and N-allyloxycarbonyl-4-piperidone, using the corresponding compounds respectively instead of n-propylamine and N-(t-butyloxycarbonyl)leucine, and furthermore by the same procedure as described in Reference Example 5→Reference Example 6→Example 1 using the corresponding compound instead of 3,5-dimethyl-1-phenyl-4-formylpyrazole, the following compounds of the present invention were obtained.

EXAMPLE 3(1)

1-butyl-9-((3,5-dimethyl-1-phenyl)-4-pyrazolyl)methyl)-2,5-dioxo-3-(2-methyl-1-propyl)-1,4,9-triazaspiro[5.5]undecane.2 hydrochlorie

EXAMPLE 3(2)

1-butyl-3-cyclohexylmethyl-2,5-dioxo-9-(4-phenyloxyphenylmethyl)-1,4,9-triazaspiro[5.5]undecane.hydrochloride

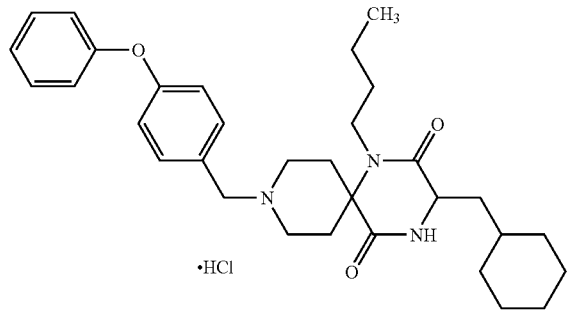

TLC: Rf 0.73 (chloroform:methanol=10:1); NMR (CD$_3$OD): δ 7.74-7.56 (m, 1H), 7.53 (d, J=8.8 Hz, 2H), 7.40 (m, 2H), 7.18 (m, 1H), 7.10-7.00 (m, 3H), 4.33 (s, 2H), 4.04 (dd, J=7.4, 4.8 Hz, 1H), 3.80 (m, 2H), 3.60-3.35 (m, 4H), 2.43 (m, 2H), 2.17 (m, 2H), 1.90-1.60 (m, 7H), 1.60-1.45 (m, 2H), 1.45-1.30 (m, 2H), 1.30-1.15 (m, 4H), 1.10-0.80 (m, 5H).

EXAMPLE 3(3)

9-(1,4-benzodioxan-6-ylmethyl)-1-butyl-3-(2-methyl-1-propyl)-2,5-dioxo-1,4,9-triazaspiro[5.5]undecane.hydrochloride

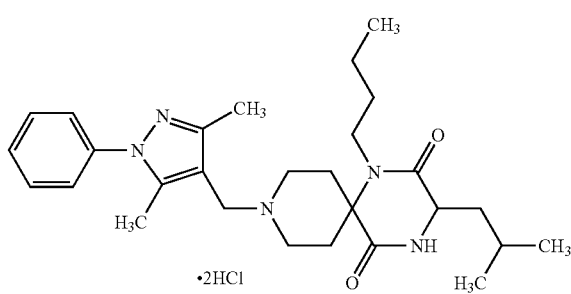

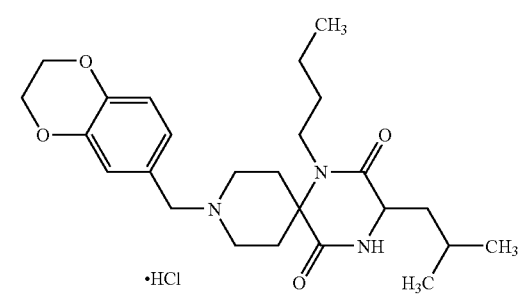

TLC: Rf 0.52 (chloroform:methanol=10:1); NMR (CD$_3$OD): δ 7.70-7.48 (m, 5H), 4.35 (s, 2H), 4.03 (dd, J=7.8, 4.8 Hz, 1H), 3.83 (m, 2H), 3.63 (m, 2H), 3.51 (m, 2H), 2.64 (m, 2H), 2.48 (s, 3H), 2.43 (s, 3H), 2.20 (m, 2H), 1.81 (m, 2H), 1.71 (m, 2H), 1.55 (m, 2H), 1.50-1.35 (m, 4H), 1.05-0.90 (m, 6H).

TLC: Rf 0.53 (chloroform:methanol=10:1); NMR (CD$_3$OD): δ 7.08 (d, J=2.2 Hz, 1H), 7.01 (dd, J=8.2, 2.2 Hz, 1H), 6.93 (d, J=8.2 Hz, 1H), 4.27 (s, 4H), 4.23 (s, 2H), 4.01 (dd, J=7.8, 4.8 Hz, 1H), 3.72 (m, 2H), 3.55-3.35 (m, 4H), 2.43 (m, 2H), 2.16 (m, 2H), 1.80 (m, 1H), 1.67 (m, 2H), 1.55 (m, 2H), 1.37 (m, 2H), 1.00-0.90 (m, 9H).

EXAMPLE 3(4)

9-(4-benzyloxyphenylmethyl)-1-butyl-2,5-dioxo-3-(2-methyl-1-propyl)-1,4,9-triazaspiro[5.5]undecane.hydrochloride

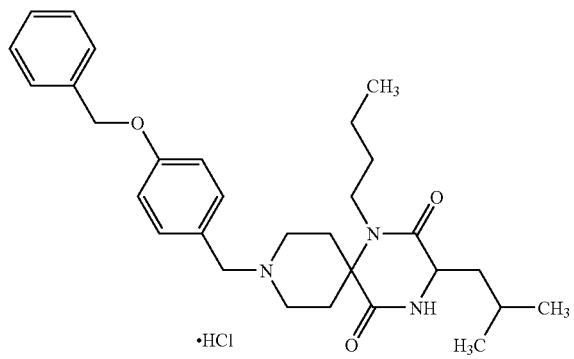

TLC: Rf 0.59 (chloroform:methanol=10:1); NMR (CD$_3$OD): δ 7.54-7.25 (m, 7H), 7.10 (m, 2H), 5.13 (s, 2H), 4.27 (s, 2H), 4.00 (dd, J=8.2, 4.8 Hz, 1H), 3.72 (m, 2H), 3.55-3.35 (m, 4H), 2.42 (m, 2H), 2.16 (m, 2H), 1.90-1.25 (m, 7H), 1.00-0.90 (m, 9H).

EXAMPLE 4

1-butyl-2,5-dioxo-3-(2-methylpropyl)-9-(6-phenylhexyl)-1,4,9-triazaspiro[5.5]undecane.hydrochloide

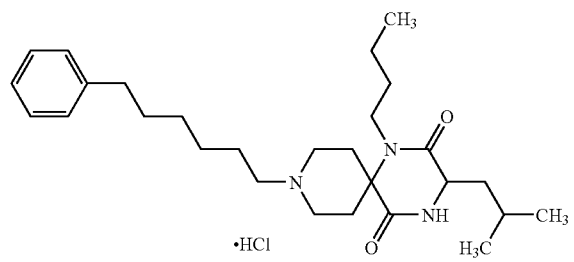

By the same procedure as described in Reference Example 3→Reference Example 6→Example 1 using Resin (3) prepared in Reference Example 2, N-(6-phenylhexyl)-4-piperidone, n-butylamine and N-(t-butyloxycarbonyl)leucine, the compound of the present invention having the following physical data was obtained.

TLC: Rf 0.62 (chloroform:methanol=10:1); NMR (CD$_3$OD): δ 7.30-7.06 (m, 5H), 4.02 (dd, J=7.8, 4.8 Hz, 1H), 3.70 (m, 2H), 3.56 (m, 2H), 3.43 (m, 2H), 3.11 (m, 2H), 2.63 (t, J=7.8 Hz, 2H), 2.46 (m, 2H), 2.18 (m, 2H), 1.95-1.50 (m, 9H), 1.50-1.25 (m, 6H), 0.97 (m, 9H).

EXAMPLE 5(1) TO 5(12)

By the same procedure as described in Reference Example 9→Reference Example 10→Example 1 using the corresponding compounds respectively instead of N-(6-phenylhexyl)-4-piperidone, n-propylamine and N-(t-butyloxycarbonyl)-L-leucine, using Resin (6) prepared in Reference Example 8, the following compounds of the present invention were obtained.

EXAMPLE 5(1)

(3S)-1-(2-methylpropyl)-2,5-dioxo-3-(4-(N-benzyloxycarbonyl)aminobutyl)-9-(2-phenylethyl)-1,4,9-triazaspiro[5.5]undecane.hydrochloride

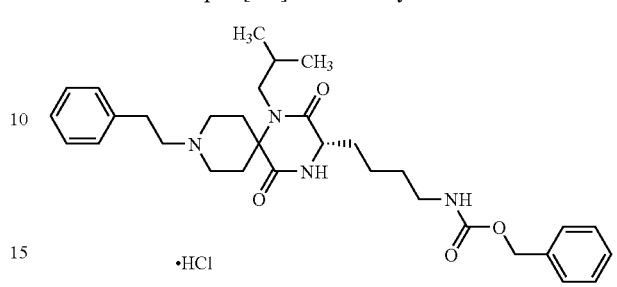

TLC: Rf 0.52 (chloroform:methanol=10:1); NMR (CD$_3$OD): δ 7.33 (m, 10H), 5.07 (s, 2H), 4.12 (m, 1H), 3.94 (m, 1H), 3.61 (m, 5H), 3.39 (m, 2H), 3.13 (m, 4H), 2.31 (m, 4H), 1.92 (m, 3H), 1.51 (m, 2H), 1.39 (m, 2H), 0.93 (t, J=6.4 Hz, 6H).

EXAMPLE 5(2)

(3S)-1-propyl-2,5-dioxo-3-(4-(N-benzyloxycarbonyl)aminobutyl)-9-(2-phenylethyl)-1,4,9-triazaspiro[5.5]undecane.hydrochloride

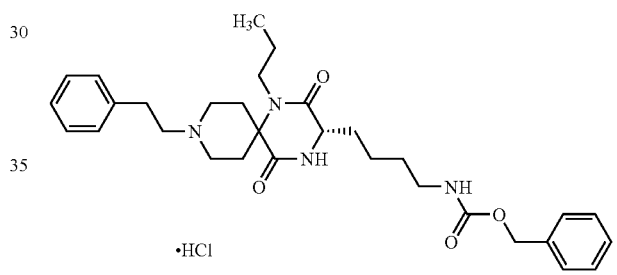

TLC: Rf 0.41 (chloroform:methanol=10:1); NMR (CD$_3$OD): δ 7.33 (m, 10H), 5.06 (m, 2H), 4.07 (m, 1H), 3.86 (m, 1H), 3.76 (m, 1H), 3.63 (m, 2H), 3.37 (m, 4H), 3.12 (m, 4H), 2.43 (m, 2H), 2.21 (m, 2H), 1.86 (m, 2H), δ 1.55 (m, 4H), 1.37 (m, 2H), 0.95 (t, J=7.2 Hz, 3H).

EXAMPLE 5(3)

(3R)-1-propyl-2,5-dioxo-3-(4-(N-benzyloxycarbonyl)aminobutyl)-9-(2-phenylethyl)-1,4,9-triazaspiro[5.5]undecane.hydrochloride

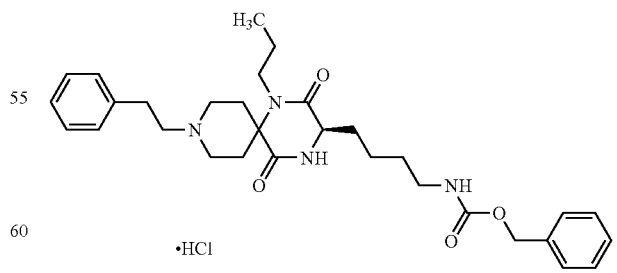

TLC: Rf 0.41 (chloroform:methanol=10:1); NMR (CD$_3$OD): δ 7.33 (m, 10H), 5.06 (s, 2H), 4.07 (m, 1H), 3.86 (m, 1H), 3.76 (m, 1H), 3.63 (m, 2H), 3.37 (m, 4H), 3.12 (m, 4H), 2.43 (m, 2H), 2.21 (m, 2H), 1.86 (m, 2H), 1.55 (m, 4H), 1.37 (m, 2H), 0.95 (t, J=7.2 Hz, 3H).

EXAMPLE 5(4)
(3S)-1-propyl-2,5-dioxo-3-(4-(N-benzyloxycarbonyl)aminobutyl)-9-(3-phenylpropyl)-1,4,9-triazaspiro[5.5]undecane.hydrochloride
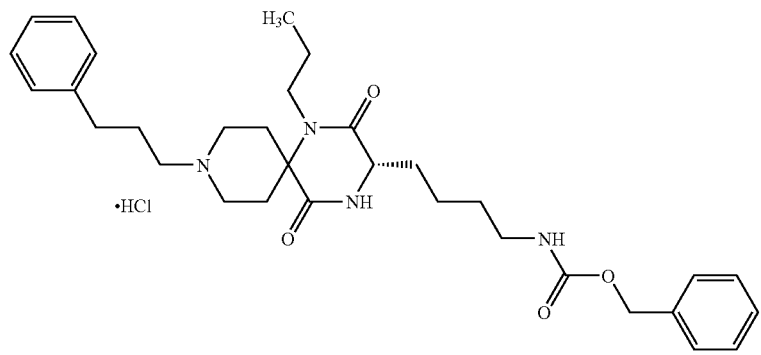
TLC: Rf 0.43 (chloroform:methanol=10:1); NMR (CD$_3$OD): δ 7.33 (m, 5H), 7.26 (m, 5H), 5.05 (s, 2H), 4.05(m, 1H), 3.85-3.30 (m, 6H), 3.12 (m, 4H), 2.73 (t, J=7.6 Hz, 2H), 2.44 (m, 2H), 2.13 (m, 4H), 1.85 (m, 2H), 1.54 (m, 4H), 1.38 (m, 2H), 0.94 (t, J=7.2 Hz, 3H).
EXAMPLE 5(5)
(3R)-1-propyl-2,5-dioxo-3-(4-(N-benzyloxycarbonyl)aminobutyl)-9-(3-phenylpropyl)-1,4,9-triazaspiro[5.5]undecane.hydrochloride
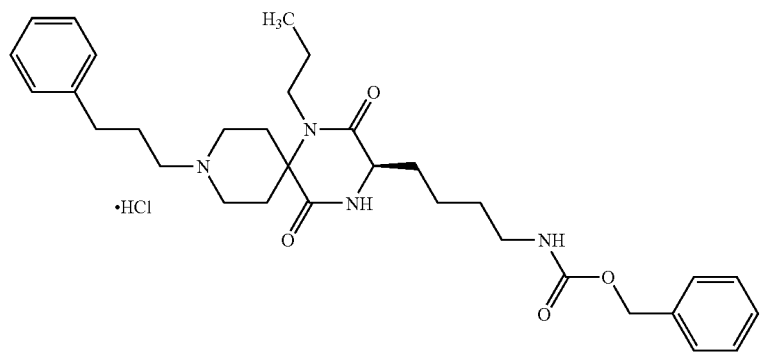

TLC: Rf 0.43 (chloroform:methanol=10:1); NMR (CD$_3$OD): δ 7.33 (m, 5H), 7.26 (m, 5H), 5.05 (s, 2H), 4.05 (m, 1H), 3.85-3.30 (m, 6H), 3.12 (m, 4H), 2.73 (t, J=7.2 Hz, 2H), 2.44 (m, 2H), 2.13 (m, 4H), 1.85 (m, 2H), 1.54 (m, 4H), 1.38 (m, 2H), 0.94 (t, J=7.2 Hz, 3H).

EXAMPLE 5(6)

(3S)-1-propyl-2,5-dioxo-3-(4-(N-benzyloxyarbonyl)aminobutyl)-9-(4-phenylbutyl)-1,4,9-triazaspiro[5.5]undecane.hydrochloride

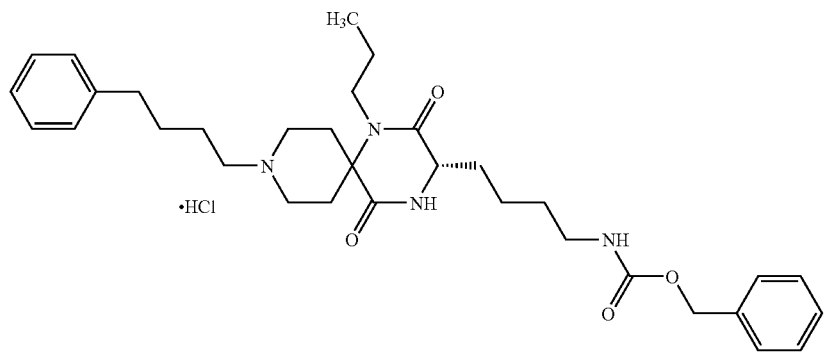

TLC: Rf 0.44 (chloroform:methanol=10:1); NMR (CD$_3$OD): δ 7.33 (m, 5H), 7.22 (m, 5H), 5.06 (s, 2H), 4.05(m, 1H), 3.85-3.38 (m, 6H), 3.12 (m, 4H), 2.70 (m, 2H), 2.40 (m, 2H), 2.18 (m, 2H), 1.74 (m, 6H), 1.54 (m, 4H), 1.38 (m, 2H), 0.94 (t, J=7.0 Hz, 3H).

EXAMPLE 5(7)

(3R)-1-propyl-2,5-dioxo-3-(4-(N-benzyloxycarbonyl)aminobutyl)-9-(4-phenylbutyl)-1,4,9-triazaspiro[5.5]undecane.hydrochloride

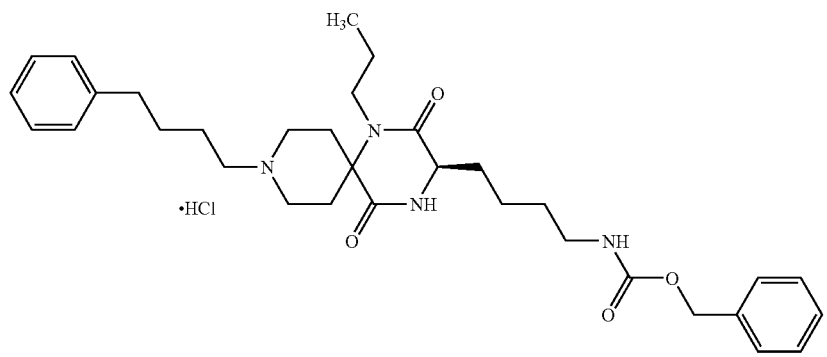

TLC: Rf 0.44 (chloroform:methanol=10:1); NMR (CD$_3$OD): δ 7.33 (m, 5H), 7.22 (m, 5H), 5.06 (s, 2H), 4.05(m, 1H), 3.85-3.38 (m, 6H), 3.12 (m, 4H), 2.70 (m, 2H), 2.40 (m, 2H), 2.18 (m, 2H), 1.74 (m, 6H), 1.54 (m, 4H), 1.38 (m, 2H), 0.94 (t, J=7.0 Hz, 3H).

EXAMPLE 5(8)

(3S)-1-benzyl-2,5-dioxo-3-(2-methylpropyl)-9-benzyl-1,4,9-triazaspiro[5.5]undecane.hydrochloride

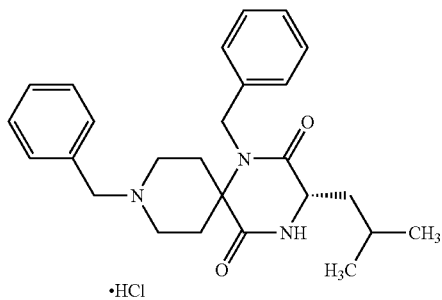

TLC: Rf 0.57 (chloroform:methanol=10:1); NMR (CD$_3$OD): δ 7.48 (m, 5H), 7.23 (m, 5H), 4.82 (m, 2H), 4.31 (s, 2H), 4.17 (dd, J=8.0, 4.6 Hz, 1H), 3.72 (m, 2H), 3.40 (m, 2H), 2.52 (m, 2H), 2.08 (m, 2H), 2.00-1.60 (m, 3H), 0.98 (d, J=6.0 Hz, 6H).

EXAMPLE 5(9)

(3R)-1-benzyl-2,5-dioxo-3-(2-methylpropyl)-9-benzyl-1,4,9-triazaspiro[5.5]undecane.hydrochloride

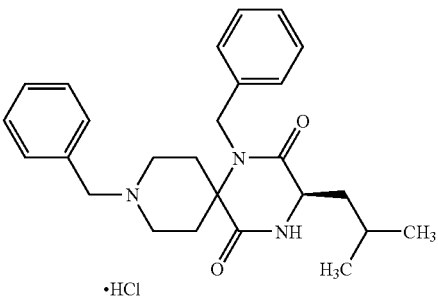

TLC: Rf 0.57 (chloroform:methanol=10:1); NMR (CD$_3$OD): δ 7.48 (m, 5H), 7.23 (m, 5H), 4.82 (m, 2H), 4.31 (s, 2H), 4.17 (dd, J=8.0, 4.6 Hz, 1H), 3.72 (m, 2H), 3.40 (m, 2H), 2.52 (m, 2H), 2.08 (m, 2H), 2.00-1.60 (m, 3H), 0.98 (d, J=6.0 Hz, 6H).

EXAMPLE 5(10)

(3S)-1-propyl-2,5-dioxo-3-(4-(N-benzyloxycarbonyl)aminobutyl)-9-(2-(2-phenyl-5-methyloxazol-4-yl)ethyl)-1,4,9-triazaspiro[5.5]undecane.hydrochloride

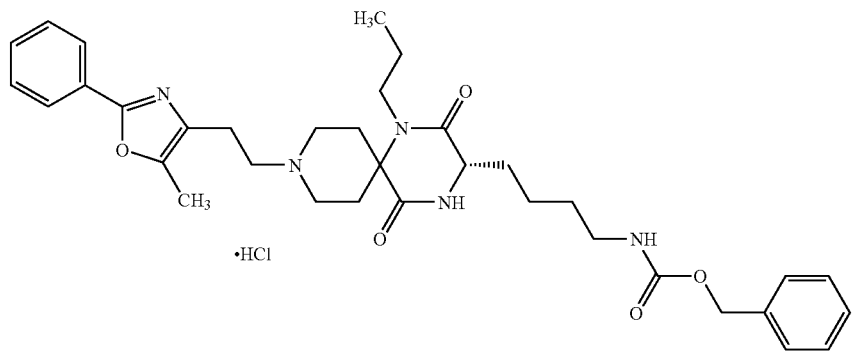

TLC: Rf 0.45 (chloroform:methanol=10:1); NMR (CD₃OD): δ 8.01 (m, 2H), 7.53 (m, 3H), 7.34 (m, 5H), 5.07 (s, 2H), 4.08 (dd, J=5.4, 4.4 Hz, 1H), 4.00-3.60 (m, 4H), 3.47 (m, 4H), 3.13 (m, 4H), 2.56 (m, 2H), 2.46 (s, 3H), 2.25 (m, 2H), 1.87 (m, 2H), 1.75-1.25 (m, 6H), 0.94 (t, J=7.2 Hz, 3H).

EXAMPLE 5(11)

(3S)-1-propyl-2,5-dioxo-3-(4-(N-(2-chlorophenylmethyl)oxycarbonyl)aminobutyl)-9-(2-phenylethyl)-1,4,9-triazaspiro[5.5]undecane.hydrochloride

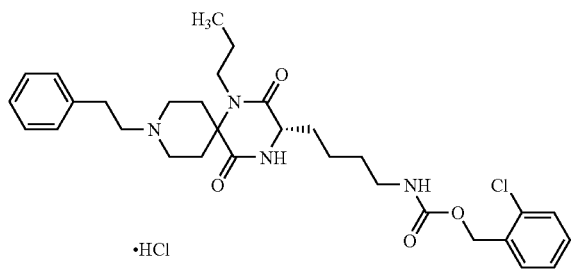

TLC: Rf 0.33 (chloroform:methanol=10:1); NMR (CD₃OD): δ 7.33 (m, 9H), 5.17 (s, 2H), 4.08 (dd, J=5.2, 4.8 Hz, 1H), 3.80 (m, 2H), 3.65 (m, 3H), 3.39 (m, 3H), 3.14 (m, 4H), 2.50 (m, 2H), 2.22 (m, 2H), 1.85 (m, 2H), 1.70-1.20 (m, 6H), 0.95 (t, J=7.2 Hz, 3H).

EXAMPLE 5(12)

(3S)-1-propyl-2,5-dioxo-3-[3-(3-(2,4,6-trimethylphenylsulfonyl)guanidino)propyl]-9-(2-phenylethyl)-1,4,9-triazaspiro[5.5]undecane.hydrochloride

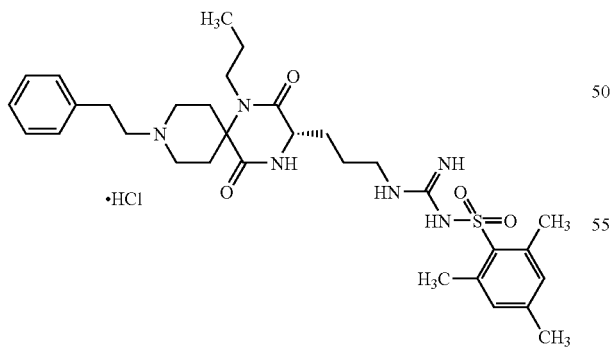

TLC: Rf 0.39 (chloroform:methanol=10:1); NMR (CD₃OD): δ 7.32 (m, 5H), 7.05 (s, 2H), 4.10 (m, 1H), 3.88 (m, 1H), 3.67 (m, 3H), 3.40 (m, 4H), 3.18 (m, 4H), 2.66 (s, 6H), 2.51 (m, 2H), 2.31 (s, 3H), 2.21 (m, 2H), 1.82 (m, 2H), 1.60 (m, 4H), 0.96 (t, J=7.2 Hz, 3H).

EXAMPLE 6(1) TO 6(32)

By the same procedure as described in Reference Example 3→Reference Example 4 using Resin (3) prepared in Reference Example 2, N-allyloxycarbonyl-4-piperidone, the corresponding amine derivatives and the corresponding amino acid derivatives, and furthermore by the same procedure as described in Reference Example 5→Reference Example 6→Example 1 using the corresponding aldehyde derivatives, the following compounds of the present invention were obtained.

EXAMPLE 6(1)

1-propyl-2,5-dioxo-3-(2-methylpropyl)-9-(4-phenyloxyphenylmethyl)-1,4,9-triazaspiro[5.5]undecane.hydrochloride

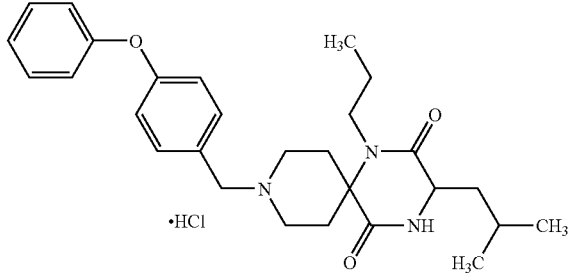

TLC: Rf 0.61 (chloroform:methanol=10:1); NMR (CD₃OD): δ 7.55 (m, 2H), 7.40 (m, 2H), 7.18 (m, 1H), 7.05 (m, 4H), 4.33 (s, 2H), 4.01 (dd, J=7.6, 4.8 Hz, 1H), 3.79 (m, 2H), 3.60-3.30 (m, 4H), 2.46 (m, 2H), 2.17 (m, 2H), 1.95-1.40 (m, 5H), 0.94 (m, 9H).

EXAMPLE 6(2)

1-butyl-2,5-dioxo-3-cyclohexylmethyl-9-(4-methoxyphenylmethyl)-1,4,9-triazaspiro[5.5]undecane.hydrochloride

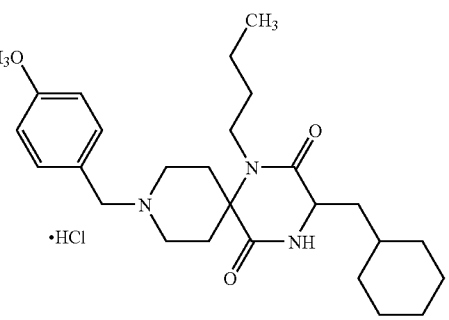

TLC: Rf 0.63 (chloroform:methanol=10:1); NMR (CD₃OD): δ 7.47 (d, J=8.8 Hz, 2H), 7.03 (d, J=8.8 Hz, 2H), 4.29 (s, 2H), 4.04 (dd, J=7.6, 4.8 Hz, 1H), 3.83 (s, 3H), 3.74 (m, 2H), 3.55-3.35 (m, 4H), 2.41 (m, 2H), 2.15 (m, 2H), 1.85-1.55 (m, 7H), 1.55-1.42 (m, 3H), 1.42-1.30 (m, 3H), 1.30-1.10 (m, 2H), 1.08-0.80 (m, 5H).

EXAMPLE 6(3)

1-butyl-2,5-dioxo-3-cyclohexylmethyl-9-(4-allyloxyphenylmethyl)-1,4,9-triazaspiro[5.5]undecane.hydrochloride

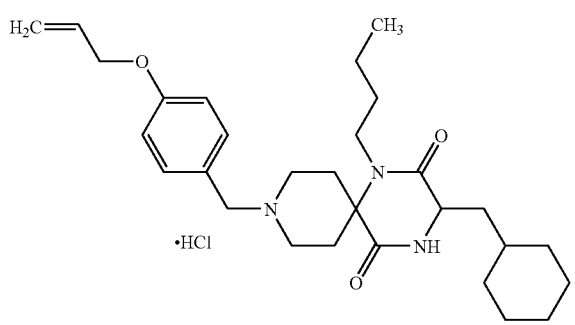

TLC: Rf 0.57 (chloroform:methanol=10:1); NMR (CD$_3$OD): δ 7.46 (d, J=8.4 Hz, 2H), 7.04 (d, J=8.4 Hz, 2H), 6.06 (m, 1H), 5.41 (m, 1H), 5.28 (m, 2H), 4.59 (m, 2H), 4.28 (s, 2H), 4.04 (dd, J=7.2, 4.8 Hz, 1H), 3.77 (m, 2H), 3.55-3.35 (m, 4H), 2.39 (m, 2H), 2.16 (m, 2H), 1.90-1.60 (m, 7H), 1.60-1.45 (m, 2H), 1.45-1.30 (m, 2H), 1.30-1.10 (m, 3H), 1.10-0.80 (m, 5H).

EXAMPLE 6(4)

(3S)-1-propyl-9-(3,5-dimethyl-1-phenylpyrazol-4-ylmethyl)-2,5-dioxo-3-(2-methyl-1-propyl)-1,4,9-triazaspiro[5.5]undecane.2 hydrochloride

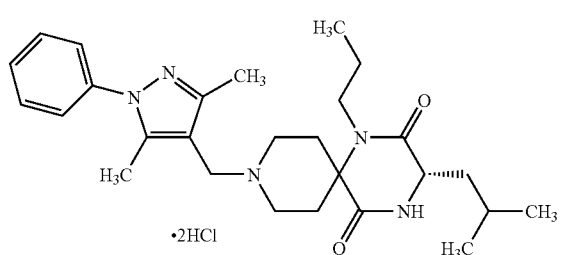

TLC: Rf 0.50 (chloroform:methanol=10:1); NMR (CD$_3$OD): δ 7.65-7.45 (m, 5H), 4.33 (s, 2H), 4.03 (dd, J=7.8, 5.2 Hz, 1H), 3.85 (m, 2H), 3.62 (m, 2H), 3.44 (m, 2H), 2.59 (m, 2H), 2.43 (s, 3H), 2.41 (s, 3H), 2.20 (m, 2H), 1.81 (m, 1H), 1.71 (m, 2H), 1.64 (m, 2H), 1.00-0.90 (m, 9H).

EXAMPLE 6(5)

(3R)-1-propyl-9-(3,5-dimethyl-1-phenylpyrazol-4-ylmethyl)-2,5-dioxo-3-(2-methyl-1-propyl)-1,4,9-triazaspiro[5.5]undecane.2 hydrochloride

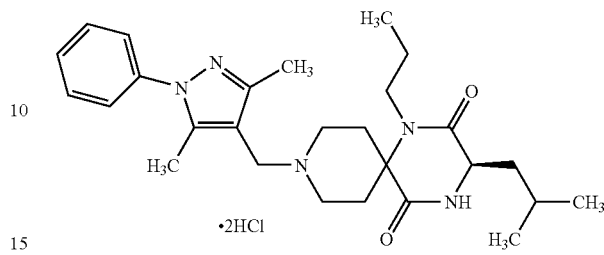

TLC: Rf 0.50 (chloroform:methanol=10:1); NMR (CD$_3$OD): δ 7.65-7.45 (m, 5H), 4.33 (s, 2H), 4.03 (dd, J=7.8, 5.2 Hz, 1H), 3.85 (m, 2H), 3.62 (m, 2H), 3.44 (m, 2H), 2.59 (m, 2H), 2.43 (s, 3H), 2.41 (s, 3H), 2.20 (m, 2H), 1.81 (m, 1H), 1.71 (m, 2H), 1.64 (m, 2H), 1.00-0.90 (m, 9H).

EXAMPLE 6(6)

1-butyl-2,5-dioxo-3-(2-methylpropyl)-9-phenylmethyl-1,4,9-triazaspiro[5.5]undecane.hydrochloride

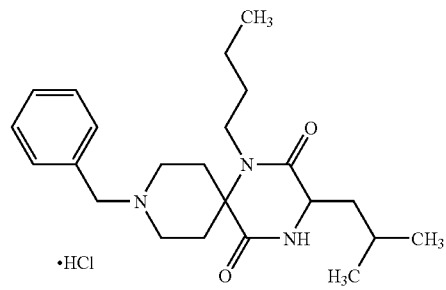

TLC: Rf 0.54 (chloroform:methanol=10:1); NMR (CD$_3$OD): δ 7.64-7.44 (m, 5H), 4.36 (s, 2H), 4.01 (dd, J=7.8, 4.8 Hz, 1H), 3.77 (m, 2H), 3.55-3.35 (m, 4H), 2.60-2.30 (m, 2H), 2.17 (m, 2H), 1.95-1.75 (m, 1H), 1.75-1.60 (m, 2H), 1.60-1.45 (m, 2H), 1.45-1.20 (m, 2H), 1.10-0.80 (m, 9H).

EXAMPLE 6(7)

1-butyl-2,5-dioxo-3-(2-methylpropyl)-9-benzyloxycarbonyl-1,4,9-triazaspiro[5.5]undecane

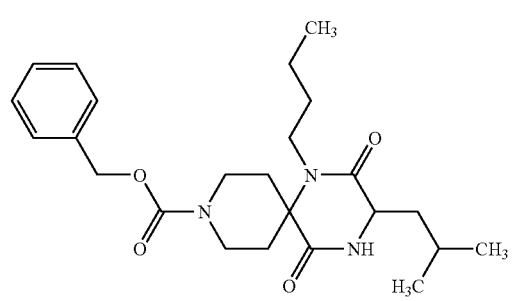

TLC: Rf 0.41 (chloroform:methanol=20:1); NMR (CDCl$_3$): δ 7.45-7.28 (m, 5H), 6.31 (m, 1H), 5.15 (s, 2H), 4.14 (m, 2H), 3.96 (m, 1H), 3.63 (m, 1H), 3.44 (m, 1H), 3.26 (m, 2H), 1.99-1.14 (m, 11H), 1.02-0.88 (m, 9H).

EXAMPLE 6(8)

1-butyl-2,5-dioxo-3-cyclohexylmethyl-9-benzyloxycarbonyl-1,4,9-triazaspiro[5.5]undecane

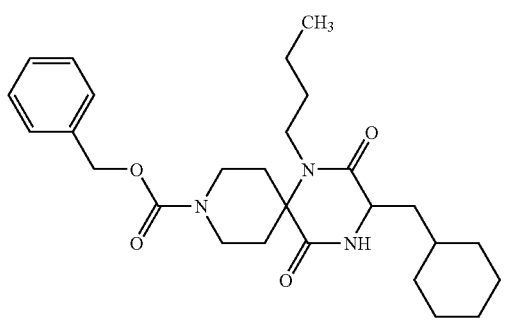

TLC: Rf 0.46 (chloroform:methanol=20:1); NMR (CDCl$_3$): δ 7.40-7.29 (m, 5H), 5.98 (m, 1H), 5.15 (s, 2H), 4.14 (m, 2H), 4.00 (m, 1H), 3.65 (m, 1H), 3.43 (m, 1H), 3.26 (m, 2H), 2.03-1.81 (m, 4H), 1.80-1.60 (m, 5H), 1.60-1.10 (m, 10H), 1.10-0.85 (m, 5H).

EXAMPLE 6(9)

1-benzyl-2,5-dioxo-3-(2-methylpropyl)-9-(4-phenyloxyphenylmethyl)-1,4,9-triazaspiro[5.5]undecane-.hydrochloride

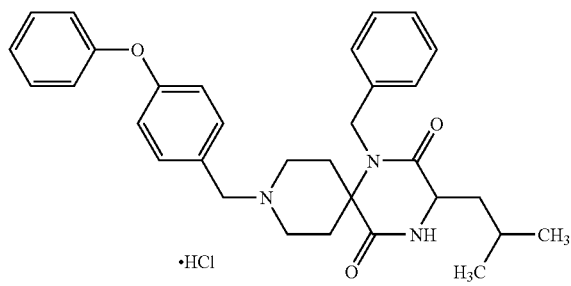

TLC: Rf 0.66 (chloroform:methanol=10:1); NMR (CD$_3$OD): δ 7.50 (d, J=8.4 Hz, 2H), 7.45-7.12 (m, 8H), 7.10-6.98 (m, 4H), 4.82 (m, 2H), 4.29 (s, 2H), 4.18 (dd, J=8.0, 4.6 Hz, 1H), 3.73 (m, 2H), 3.42 (m, 2H), 2.65-2.30 (m, 2H), 2.20-2.05 (m, 2H), 2.00-1.60 (m, 3H), 0.98 (d, J=6.2 Hz, 6H).

EXAMPLE 6(10)

1-butyl-2,5-dioxo-3-propyl-9-(4-phenyloxyphenylmethyl)-1,4,9-triazaspiro[5.5]undecane.hydrochloride

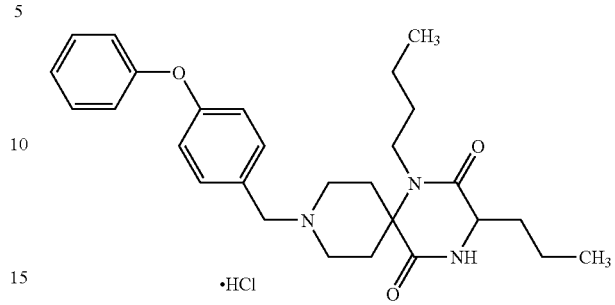

TLC: Rf 0.36 (chloroform:methanol=10:1); NMR (CD$_3$OD): δ 7.51 (d, J=8.7 Hz, 2H), 7.39 (dd, J=8.7, 7.5 Hz, 2H), 7.18 (t, J=7.5 Hz, 1H), 7.10-7.00 (m, 4H), 4.33 (s, 2H), 4.04 (dd, J=5.7, 4.5 Hz, 1H), 3.93-3.66 (m, 2H), 3.55-3.31 (m, 4H), 2.47-2.09 (m, 4H), 1.92-1.68 (m, 2H), 1.61-1.21 (m, 6H), 1.01-0.90 (m, 6H).

EXAMPLE 6(11)

1-butyl-2,5-dioxo-3-methoxymethyl-9-(4-phenyloxyphenylmethyl)-1,4,9-triazaspiro[5.5]undecane.hydrochlori

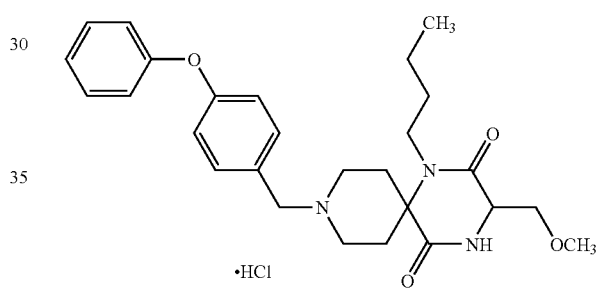

TLC: Rf 0.48 (chloroform:methanol=10:1); NMR (CD$_3$OD): δ 7.51 (d, J=8.7 Hz, 2H), 7.39 (dd, J=8.7, 7.2 Hz, 2H), 7.17 (t, J=7.2 Hz, 1H), 7.09-6.99 (m, 4H), 4.30 (s, 2H), 4.07 (t, J=3.0 Hz, 1H), 3.91 (m, 1H), 3.77 (dd, J=9.0, 3.0 Hz, 1H), 3.67 (m, 1H), 3.58-3.39 (m, 4H), 3.31 (s, 3H), 3.26 (m, 1H), 2.48-2.13 (m, 4H), 1.65 (m, 1H), 1.53-1.28 (m, 3H), 0.95 (t, J=7.5 Hz, 3H).

EXAMPLE 6(12)

1-(1-methylpropyl)-2,5-dioxo-3-(2-methylpropyl)-9-(4-phenyloxyphenylmethyl)-1,4,9-triazaspiro[5.5]undecane.hydrochloride

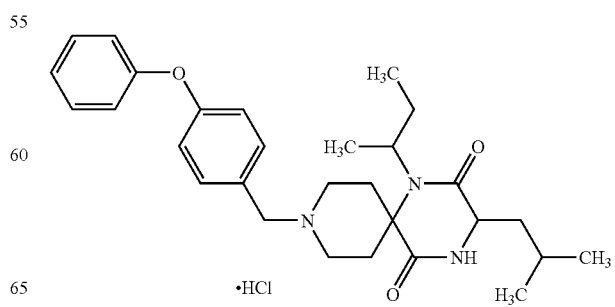

TLC: Rf 0.43 (chloroform:methanol=10:1); NMR (CD₃OD): δ 7.46 (d, J=8.4 Hz, 2H), 7.38 (dd, J=8.4, 7.5 Hz, 2H), 7.16 (t, J=7.5 Hz, 1H), 7.08-6.99 (m, 4H), 4.15 (s, 2H), 3.91-3.82 (m, 1H), 3.81-3.65 (m, 1H), 3.64-3.44 (m, 1H), 3.44-3.15 (m, 3H), 2.42-2.00 (m, 4H), 1.88-1.56 (m, 5H), 1.46-1.37 (m, 3H), 0.99-0.85 (m, 9H).

EXAMPLE 6(13)

1-(2-methylbutyl)-2,5-dioxo-3-(2-methylpropyl)-9-(4-phenyloxyphenylmethyl)-1,4,9-triazaspiro[5.5]undecane.hydrochloride

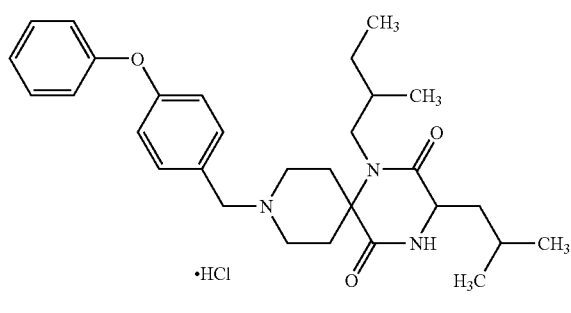

TLC: Rf 0.49 (chloroform:methanol=10:1); NMR (CD₃OD): δ 7.49 (d, J=8.7 Hz, 2H), 7.39 (dd, J=8.7, 7.2 Hz, 2H), 7.17 (t, J=7.2 Hz, 1H), 7.08-6.94 (m, 4H), 4.27 (s, 2H), 4.04 (dd, J=8.4, 4.5 Hz, 1H), 3.83-3.21 (m, 6H), 2.45-2.12 (m, 4H), 1.92-1.56 (m, 4H), 1.42 (m, 1H), 1.14 (m, 1H), 1.00-0.83 (m, 12H).

EXAMPLE 6(14)

1-(2-methylpropyl)-2,5-dioxo-3-(2-methylpropyl)-9-(4-phenyloxyphenylmethyl)-1,4,9-triazaspiro[5.5]undecane.hydrochloride

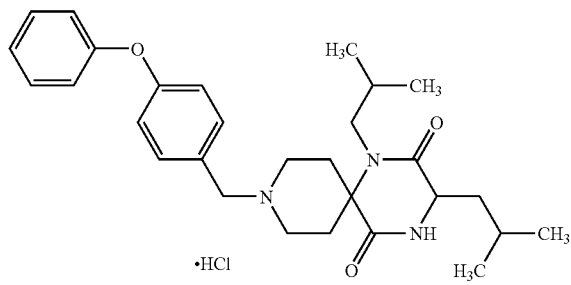

TLC: Rf 0.50 (chloroform:methanol=10:1); NMR (CD₃OD): δ 7.50 (d, J=8.7 Hz, 2H), 7.39 (dd, J=8.7, 7.5 Hz, 2H), 7.17 (t, J=7.5 Hz, 1H), 7.13-7.04 (m, 4H), 4.28 (s, 2H), 4.04 (dd, J=8.1, 4.2 Hz, 1H), 3.81-3.54 (m, 2H), 3.52-3.21 (m, 4H), 2.46-2.11 (m, 4H), 2.00-1.57 (m, 4H), 0.94 (d, J=6.3 Hz, 6H), 0.90 (d, J=6.3 Hz, 3H), 0.90 (d, J=6.3 Hz, 3H).

EXAMPLE 6(15)

1-(2-dimethylaminoethyl)-2,5-dioxo-3-(2-methylpropyl)-9-(4-phenyloxyphenylmethyl)-1,4,9-triazaspiro[5.5]undecane.2 hydrochloride

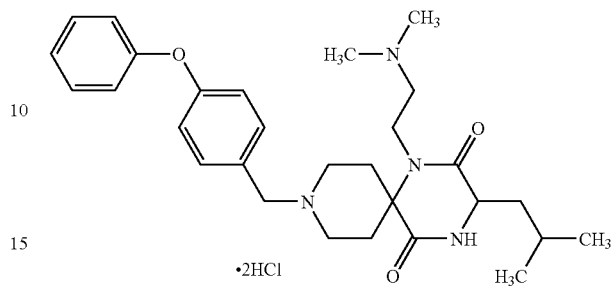

TLC: Rf 0.87 (chloroform:methanol:28% NH₄OH=80:10:1); NMR (CD₃OD): δ 7.60 (d, J=8.7 Hz, 2H), 7.39 (dd, J=8.7, 7.5 Hz, 2H), 7.17 (t, J=7.5 Hz, 1H), 7.07-6.99 (m, 4H), 4.33 (s, 2H), 4.07 (dd, J=8.4, 4.8 Hz, 1H), 3.99-3.63 (m, 4H), 3.53-3.42 (m, 2H), 3.32-3.21 (m, 2H), 2.99 (s, 3H), 2.96 (s, 3H), 2.70-2.49 (m, 2H), 2.30-2.10 (m, 2H), 1.93-1.56 (m, 3H), 0.94 (d, J=6.6 Hz, 6H).

EXAMPLE 6(16)

1-(2-methoxyethyl)-2,5-dioxo-3-(2-methylpropyl)-9-(4-phenyloxyphenylmethyl)-1,4,9-triazaspiro[5.5]undecane.hydrochloride

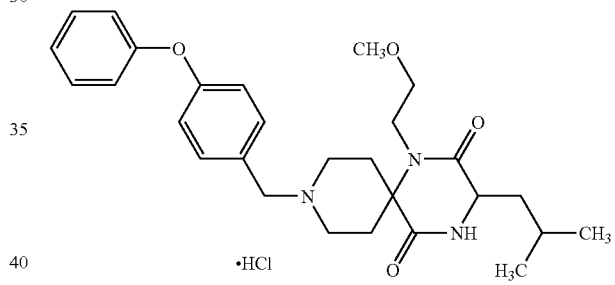

TLC: Rf 0.40 (chloroform:methanol=10:1); NMR (CD₃OD): δ 7.47 (d, J=8.7 Hz, 2H), 7.39 (dd, J=8.7, 7.5 Hz, 2H), 7.17 (t, J=7.5 Hz, 1H), 7.09-6.99 (m, 4H), 4.25 (s, 2H), 4.03 (dd, J=7.8, 4.8 Hz, 1H), 3.75-3.34 (m, 8H), 3.31 (s, 3H), 2.48-2.28 (m, 2H), 2.25-2.06 (m, 2H), 1.90-1.57 (m, 3H), 0.94 (d, J=6.3 Hz, 3H), 0.93 (d, J=6.3 Hz, 3H).

EXAMPLE 6(17)

1-(2-methylthioethyl)-2,5-dioxo-3-(2-methylpropyl)-9-(4-phenyloxyphenylmethyl)-1,4,9-triazaspiro[5.5]undecane.hydrochloride

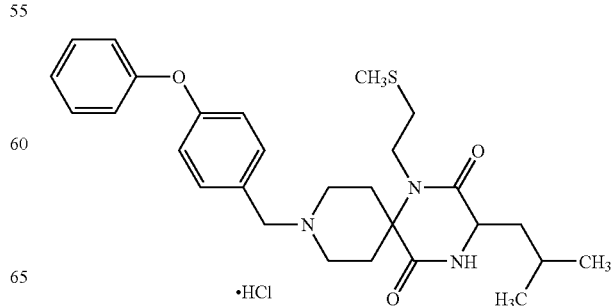

TLC: Rf 0.43 (chloroform:methanol=10:1); NMR (CD₃OD): δ 7.48 (d, J=8.7 Hz, 2H), 7.39 (dd, J=8.7, 7.8 Hz, 2H), 7.17 (t, J=7.8 Hz, 1H), 7.08-6.99 (m, 4H), 4.25 (s, 2H), 4.02 (dd, J=7.8, 4.5 Hz, 1H), 3.81-3.49 (m, 4H), 3.48-3.33 (m, 2H), 2.74-2.51 (m, 2H), 2.39-2.10 (m, 7H), 1.90-1.56 (m, 3H), 0.94 (d, J=6.6 Hz, 3H), 0.93 (d, J=6.6 Hz, 3H).

EXAMPLE 6(18)

1-benzyl-2,5-dioxo-3-(2-methylpropyl)-9-(1,4-benzodioxan-6-ylmethyl)-1,4,9-triazaspiro[5.5]undecane.hydrochloride

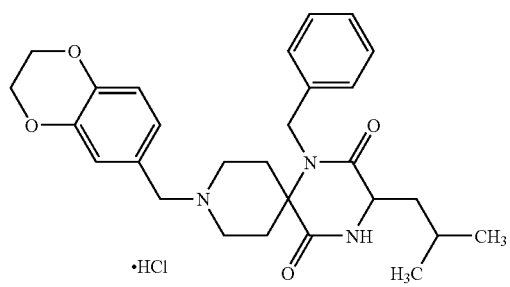

TLC: Rf 0.55 (chloroform:methanol=10:1); NMR (CD₃OD): δ 7.40-7.15 (m, 5H), 7.03 (d, J=2.0 Hz, 1H), 6.96 (dd, J=8.2, 2.0 Hz, 1H), 6.90 (d, J=8.2 Hz, 1H), 4.80 (m, 2H), 4.25 (s, 4H), 4.21-4.10 (m, 3H), 3.80-3.55 (m, 2H), 3.50-3.30 (m, 2H), 2.60-2.25 (m, 2H), 2.20-2.00 (m, 2H), 2.00-1.60 (m, 3H), 0.98 (d, J=6.4 Hz, 6H).

EXAMPLE 6(19)

1-benzyl-2,5-dioxo-3-(2-methylpropyl)-9-(4-benzyloxyphenylmethyl)-1,4,9-triazaspiro[5.5]undecane.hydrochloride

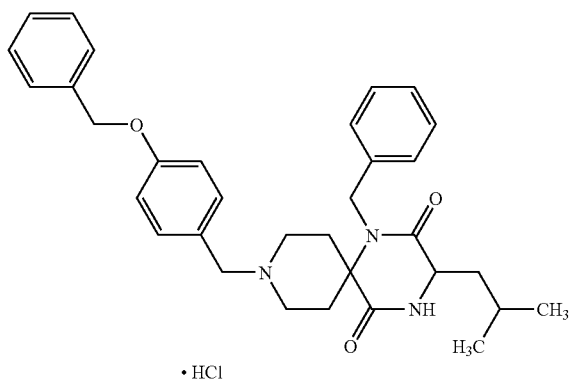

TLC: Rf 0.53 (chloroform:methanol=10:1); NMR (CD₃OD): δ 7.50-7.15 (m, 12H), 7.07 (d, J=8.8 Hz, 2H), 5.12 (s, 2H), 4.81 (m, 2H), 4.24 (s, 2H), 4.17 (dd, J=8.4, 4.8 Hz, 1H), 3.70-3.55 (m, 2H), 3.50-3.35 (m, 2H), 2.60-2.25 (m, 2H), 2.20-2.00 (m, 2H), 2.00-1.60 (m, 3H), 0.98 (d, J=6.0 Hz, 6H).

EXAMPLE 6(20)

1-benzyl-2,5-dioxo-3-(2-methylpropyl)-9-(3,5-dimethyl-1-phenylpyrazol-4-ylmethyl)-1,4,9-triazaspiro[5.5]undecane.2 hydrochloride

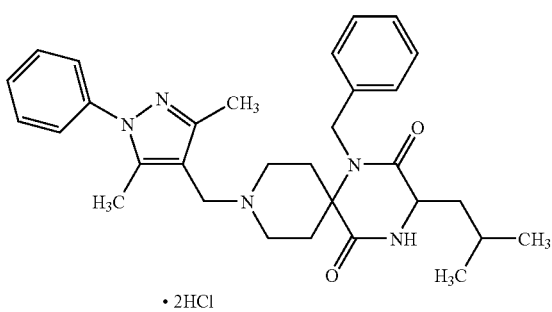

TLC: Rf 0.50 (chloroform:methanol=10:1); NMR (CD₃OD): δ 7.70-7.45 (m, 5H), 7.40-7.15 (m, 5H), 4.92 (m, 2H), 4.29 (s, 2H), 4.20 (dd, J=8.4, 4.8 Hz, 1H), 3.90-3.65 (m, 2H), 3.65-3.45 (m, 2H), 2.85-2.50 (m, 2H), 2.44 (s, 3H), 2.39 (s, 3H), 2.20-2.00 (m, 2H), 2.00-1.60 (m, 3H), 1.00 (d, J=5.4 Hz, 6H).

EXAMPLE 6(21)

1-(3-methylphenylmethyl)-2,5-dioxo-3-(2-methylpropyl)-9-(1,4-benzodioxan-6-ylmethyl)-1,4,9-triazaspiro[5.5]undecane.hydrochloride

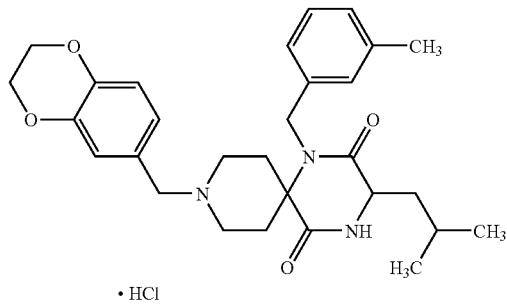

TLC: Rf 0.56 (chloroform:methanol=10:1); NMR (CD₃OD): δ 7.18 (t, J=7.8 Hz, 1H), 7.10-6.85 (m, 6H), 4.77 (m, 2H), 4.25 (s, 4H), 4.19 (m, 3H), 3.68 (m, 2H), 3.40 (m, 2H), 2.60-2.30 (m, 2H), 2.29 (s, 3H), 2.20-2.00 (m, 2H), 2.00-1.60 (m, 3H), 0.99 (d, J=6.2 Hz, 6H).

EXAMPLE 6(22)

1-(3-methylphenylmethyl)-2,5-dioxo-3-(2-methylpropyl)-9-(3,5-dimethyl-1-phenylpyrazol-4-ylmethyl)-1,4,9-triazaspiro[5.5]undecane.2 hydrochloride

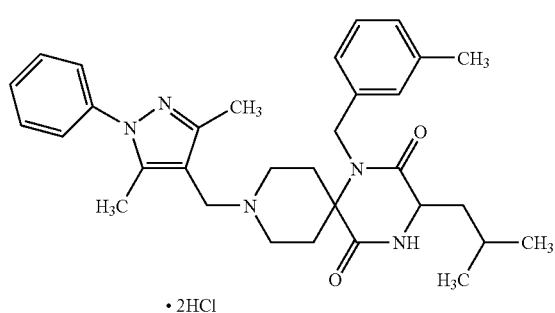

TLC: Rf 0.59 (chloroform:methanol=10:1); NMR (CD$_3$OD): δ 7.70-7.45 (m, 5H), 7.18 (t, J=7.4 Hz, 1H), 7.10-7.00 (m, 3H), 4.88 (s, 2H), 4.31 (s, 2H), 4.20 (dd, J=8.2, 4.8 Hz, 1H), 3.76 (m, 2H), 3.60 (m, 2H), 2.90-2.50 (m, 2H), 2.47 (s, 3H), 2.41 (s, 3H), 2.30 (s, 3H), 2.10 (m, 2H), 1.88 (m, 1H), 1.85-1.65 (m, 2H), 1.00 (d, J=5.8 Hz, 6H).

EXAMPLE 6(23)

1-(1-methylbutyl)-2,5-dioxo-3-(2-methylpropyl)-9-(4-phenyloxyphenylmethyl)-1,4,9-triazaspiro[5.5]undecane.hydrochloride

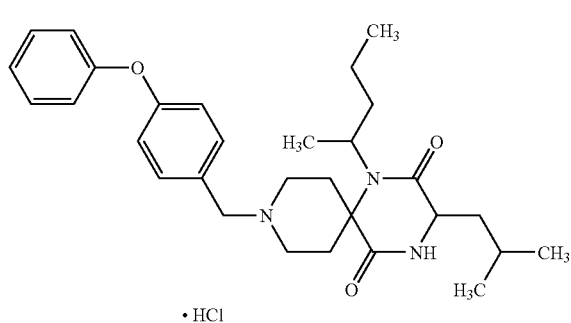

TLC: Rf 0.49, 0.56 (chloroform:methanol=10:1); NMR (CD$_3$OD): δ 7.49 (d, J=8.7 Hz, 2H), 7.39 (dd, J=8.7, 7.5 Hz, 2H), 7.17 (t, J=7.5 Hz, 1H), 7.08-6.99 (m, 4H), 4.26 (s, 2H), 3.97-3.79 (m, 2H), 3.78-3.60 (m, 1H), 3.54-3.33 (m, 3H), 2.47-2.29 (m, 2H), 2.26-2.03 (m, 3H), 1.87-1.71 (m, 1H), 1.70-1.53 (m, 3H), 1.48-1.16 (m, 5H), 1.02-0.90 (m, 9H).

EXAMPLE 6(24)

1-(3-methylbutyl)-2,5-dioxo-3-(2-methylpropyl)-9-(4-phenyloxyphenylmethyl)-1,4,9-triazaspiro[5.5]undecane.hydrochloride

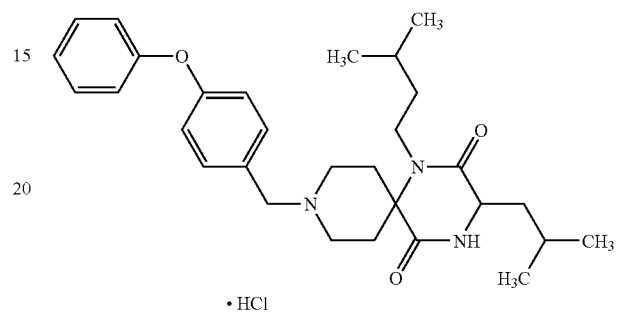

TLC: Rf 0.54 (chloroform:methanol=10:1); NMR (CD$_3$OD): δ 7.51 (d, J=8.7 Hz, 2H), 7.39 (dd, J=8.7, 7.5 Hz, 2H), 7.18 (t, J=7.5 Hz, 1H), 7.10-7.00 (m, 4H), 4.33 (s, 2H), 4.00 (dd, J=8.1, 4.8 Hz, 1H), 3.90-3.71 (m, 2H), 3.56-3.34 (m, 4H), 2.46-2.29 (m, 2H), 2.28-2.10 (m, 2H), 1.90-1.56 (m, 4H), 1.55-1.32 (m, 2H), 1.04-0.85 (m, 12H).

EXAMPLE 6(25)

1-(2-methoxyphenylmethyl)-2,5-dioxo-3-(2-methylpropyl)-9-((3,5-dimethyl-phenyl)-4-pyrazolyl)methyl)-1,4,9-triazaspiro[5.5]undecane.2 hydrochloride

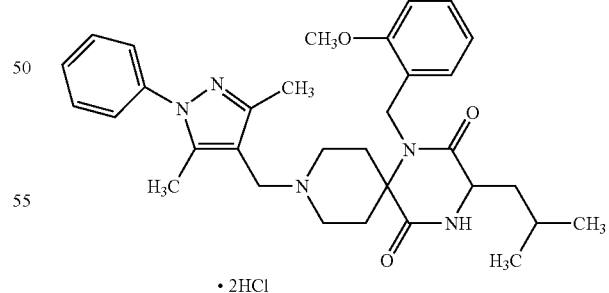

TLC: Rf 0.38 (chloroform:methanol=20:1); NMR (CD$_3$OD): δ 7.59-7.41 (m, 5H), 7.26-7.17 (m, 1H), 6.99-6.84 (m, 3H), 4.74 (brs, 2H), 4.27 (s, 2H), 4.19 (dd, J=8.4, 4.5 Hz, 1H), 3.88 (s, 3H), 3.90-3.68 (m, 2H), 3.62-3.45 (m, 2H), 2.60-2.14 (m, 4H), 2.35 (s, 3H), 2.33 (s, 3H), 2.00-1.63 (m, 3H), 0.99 (d, J=6.3 Hz, 6H).

EXAMPLE 6(26)

1-(3-methoxyphenylmethyl)-2,5-dioxo-3-(2-methyl-propyl)-9-((3,5-dimethyl-1-phenyl)-4-pyrazolyl)methyl)-1,4,9-triazaspiro[5.5]undecane.2 hydrochloride

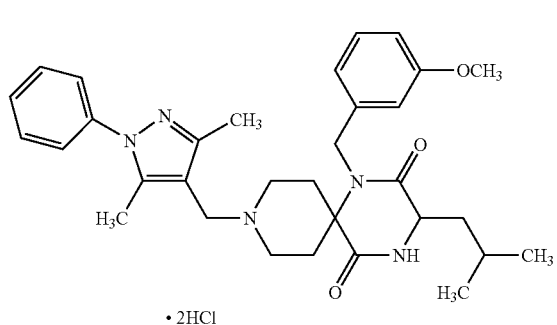

TLC: Rf 0.33 (chloroform:methanol=20:1); NMR (CD$_3$OD): δ 7.65-7.48 (m, 5H), 7.20 (t, J=8.1 Hz, 1H), 6.85-6.80 (m, 2H), 6.77 (dd, J=7.8, 2.1 Hz, 1H), 4.90 (brs, 2H), 4.31 (s, 2H), 4.20 (dd, J=8.1, 4.8 Hz, 1H), 3.84-3.65 (m, 2H), 3.75 (s, 3H), 3.65-3.48 (m, 2H), 2.84-2.56 (m, 2H), 2.47 (s, 3H), 2.40 (s, 3H), 2.19-2.03 (m, 2H), 2.00-1.65 (m, 3H), 0.99 (d, J=6.3 Hz, 6H).

EXAMPLE 6(27)

1-(2-methylphenylmethyl)-2,5-dioxo-3-(2-methyl-propyl)-9-(3,5-dimethyl-1-phenylpyrazol-4-ylmethyl)-1,4,9-triazaspiro[5.5]undecane.2 hydrochloride

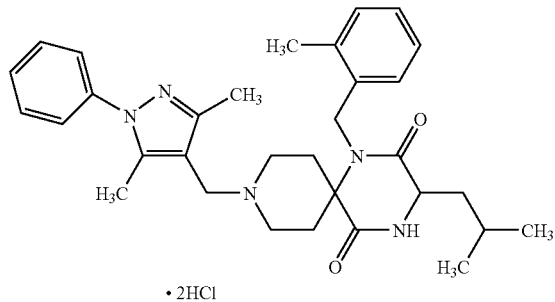

TLC: Rf 0.35 (chloroform:methanol=20:1); NMR (CD$_3$OD): δ 7.63-7.46 (m, 5H), 7.18-7.06 (m, 3H), 6.99-6.91 (m, 1H), 4.81 (brs, 2H), 4.29 (s, 2H), 4.20 (dd, J=8.4, 4.5 Hz, 1H), 3.90-3.66 (m, 2H), 3.63-3.57 (m, 2H), 2.75-2.40 (m, 2H), 2.44 (s, 3H), 2.40 (s, 3H), 2.38 (s, 3H), 2.30-2.10 (m, 2H), 2.00-1.65 (m, 3H), 0.99 (d, J=6.3 Hz, 6H).

EXAMPLE 6(28)

1-(3-methylphenylmethyl)-2,5-dioxo-3-(2-methyl-propyl)-9-(4-phenyloxyphenylmethyl)-1,4,9-triazaspiro[5.5]undecane.hydrochloride

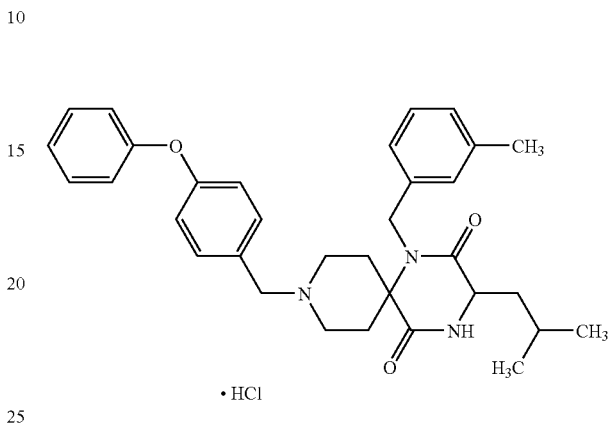

TLC: Rf 0.48 (chloroform:methanol=20:1); NMR (CD$_3$OD): δ 7.53-7.46 (m, 2H), 7.42-7.36 (m, 2H), 7.22-7.14 (m, 2H), 7.06-6.96 (m, 7H), 4.85-4.65 (m, 2H), 4.28 (s, 2H), 4.18 (dd, J=8.1, 4.5 Hz, 1H), 3.80-3.62 (m, 2H), 3.50-3.30 (m, 2H), 2.58-2.25 (m, 2H), 2.29 (s, 3H), 2.18-2.04 (m, 2H), 1.95-1.62 (m, 3H), 0.98 (d, J=6.3 Hz, 6H).

EXAMPLE 6(29)

1-butyl-2,5-dioxo-3-cyclohexylmethyl-9-(5-ethylthiophen-2-ylmethyl)-1,4,9-triazaspiro[5.5]undecane.hydrochloride

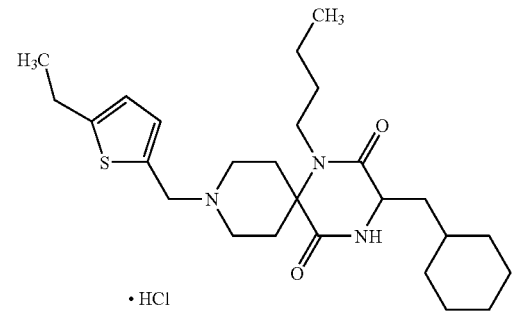

TLC: Rf 0.62 (chloroform:methanol=20:1); NMR (CD$_3$OD): δ 7.17 (d, J=3.6 Hz, 1H), 6.85 (d, J=3.6 Hz, 1H), 4.53 (s, 2H), 4.04 (dd, J=7.8, 4.5 Hz, 1H), 3.88-3.72 (m, 2H), 3.58-3.45 (m, 2H), 3.43-3.33 (m, 2H), 2.87 (q, J=7.5 Hz, 2H), 2.50-2.30 (m, 2H), 2.30-2.08 (m, 2H), 1.83-1.10 (m, 17H), 1.31 (t, J=7.5 Hz, 3H), 1.05-0.85 (m, 2H), 0.95 (t, J=7.5 Hz, 3H).

EXAMPLE 6(30)

1-butyl-2,5-dioxo-3-cyclohexylmethyl-9-(5-ethylfuran-2-ylmethyl)-1,4,9-triazaspiro[5.5]undecane.hydrochloride

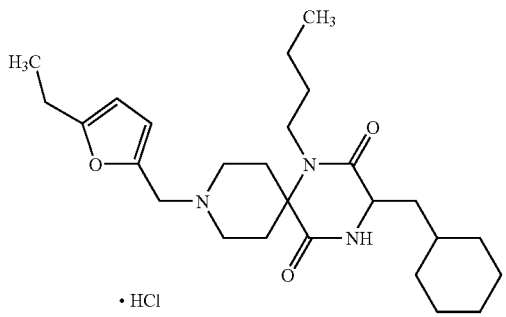

TLC: Rf 0.62 (chloroform:methanol=20:1); NMR (CD$_3$OD): δ 6.63 (d, J=3.0 Hz, 1H), 6.14 (d, J=3.0 Hz, 1H), 4.39 (s, 2H), 4.04 (dd, J=7.5, 4.5 Hz, 1H), 3.90-3.70 (m, 2H), 3.55-3.40 (m, 2H), 3.40-3.35 (m, 2H), 2.69 (q, J=7.5 Hz, 2H), 2.50-2.30 (m, 2H), 2.30-2.10 (m, 2H), 1.85-1.05 (m, 17H), 1.25 (t, J=7.5 Hz, 3H), 1.05-0.85 (m, 2H), 0.96 (t, J=7.5 Hz, 3H).

EXAMPLE 6(31)

(3S)-1-butyl-2,5-dioxo-3-((1R)-1-hydroxy-2-methylpropyl)-9-(4-phenyloxyphenylmethyl)-1,4,9-triazaspiro[5.5]undecane.hydrochloride

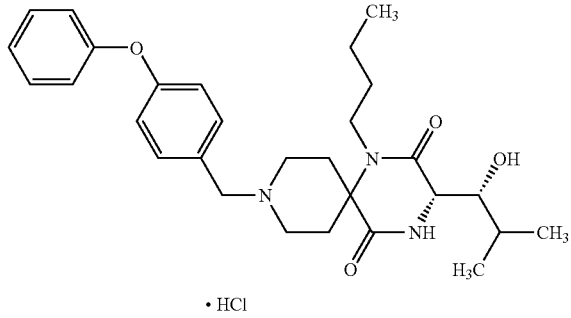

TLC: Rf 0.47 (chloroform:methanol=10:1); NMR (CD$_3$OD): δ 7.52 (d, J=9.0 Hz, 2H), 7.44-7.35 (m, 2H), 7.18 (t, J=7.5 Hz, 1H), 7.10-7.00 (m, 4H), 4.33(s, 2H), 4.16-4.00 (m, 2H), 3.75-3.40 (m, 5H), 3.26-3.09 (m, 1H), 2.56-2.08 (m, 4H), 1.82-1.60 (m, 2H), 1.50-1.30 (m, 3H), 1.05-0.89 (m, 9H).

EXAMPLE 6(32)

(3R)-1-butyl-2,5-dioxo-3-((1S)-1-hydroxy-2-methylpropyl)-9-(4-phenyloxyphenylmethyl)-1,4,9-triazaspiro[5.5]undecane.hydrochloride

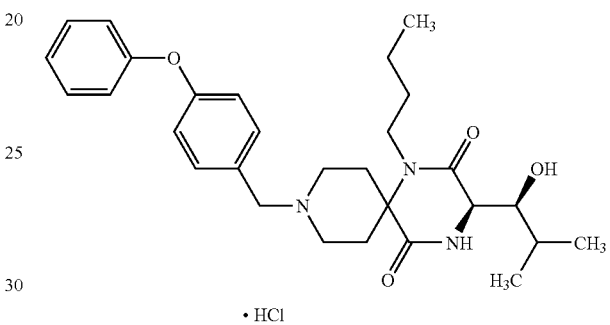

TLC: Rf 0.47 (chloroform:methanol=10:1); NMR (CD$_3$OD): δ 7.52 (d, J=9.0 Hz, 2H), 7.44-7.35 (m, 2H), 7.18 (t, J=7.5 Hz, 1H), 7.10-7.00 (m, 4H), 4.33(s, 2H), 4.16-4.00 (m, 2H), 3.75-3.40 (m, 5H), 3.26-3.09 (m, 1H), 2.56-2.08 (m, 4H), 1.82-1.60 (m, 2H), 1.50-1.30 (m, 3H), 1.05-0.89 (m, 9H).

EXAMPLE 7

(3S)-1-propyl-2,5-dioxo-3-(4-(N-benzyloxycarbonyl)aminobutyl)-9-allyloxycarbonyl-1,4,9-triazaspiro[5.5]undecane

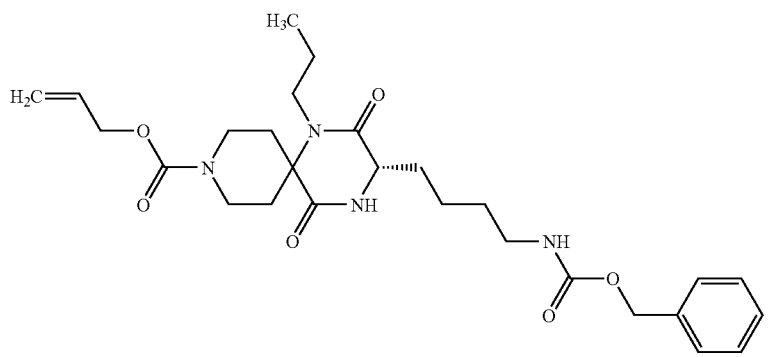

By the same procedure as described in Reference Example 9→Reference Example 10→Example 1 using Resin (6) prepared in Reference Example 8, N-allyloxycarbonyl-4-piperidone, n-propylamine and N-(t-butyloxycarbonyl)-N'-(benzyloxycarbonyl)-L-lysine, the compound of the present invention having the following physical data was obtained.

TLC: Rf 0.24 (ethyl acetate:hexane=4:1); NMR (CD$_3$OD): δ 7.35 (m, 5H), 6.40 (m, 1H), 5.96 (ddt, J=17.2, 10.2, 5.6 Hz, 1H), 5.34 (m, 1H), 5.24 (m, 1H), 5.12 (s, 2H), 4.88 (m, 1H), 4.62 (m, 2H), 4.10 (m, 2H), 4.00 (m, 1H), 3.75 (m, 1H), 3.36 (m, 2H), 3.18 (m, 3H), 1.94 (m, 6H), 1.51 (m, 6H), 0.90 (t, J=7.2 Hz, 3H).

EXAMPLE 8

(3S)-1-propyl-2,5-dioxo-3-(4-(N-benzyloxycarbonyl)aminobutyl)-1,4,9-triazaspiro[5.5]undecane

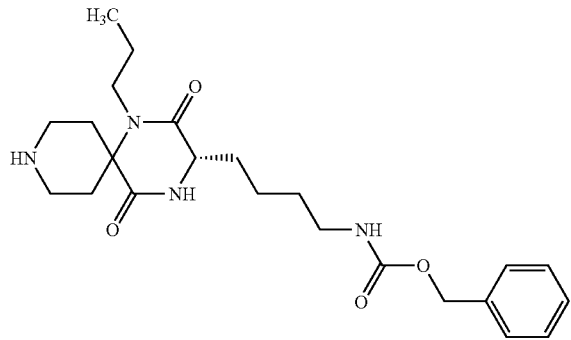

By the same procedure as described in Reference Example 4 using the compound prepared in Example 7, and furthermore, purification by cation-exchange resin and column chromatography on silica gel, the compound of the present invention having the following physical data was obtained.

TLC: Rf 0.56 (chloroform:methanol:28% NH$_4$OH=20:5:1); NMR (CD$_3$OD): δ 7.40-7.20 (m, 10H), 5.06 (s, 2H), 4.03 (t, J=5.0 Hz, 1H), 3.55-3.18 (m, 4H), 3.12 (t, J=6.6 Hz, 2H), 3.08-2.98 (m, 2H), 2.20-1.70 (m, 6H), 1.70-1.20 (m, 6H), 0.93 (t, J=7.2 Hz, 3H).

EXAMPLE 8(1)

1-propyl-2,5-dioxo-3-(2-methylpropyl)-1,4,9-triazaspiro[5.5]undecane

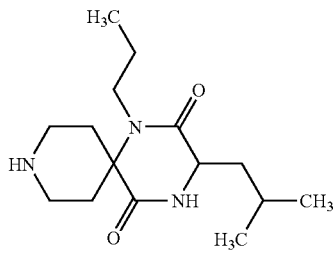

By the same procedure as described in Example 7→Example 8 using N-(t-butyloxycarbonyl)leucine instead of N-(t-butyloxycarbonyl)-N'-(benzyloxycarbonyl)-L-lysine, the compound of the present invention having the following physical data was obtained.

TLC: Rf 0.44 (chloroform:methanol:triethylamine=18:2:1); NMR (CD$_3$OD): δ 3.99 (d, J=7.8, 4.4 Hz, 1H), 3.50-3.20 (m, 4H), 3.05-2.85 (m, 2H), 2.10-1.75 (m, 5H), 1.75-1.40 (m, 4H), 1.00-0.85 (m, 9H).

EXAMPLE 9

1-butyl-2,5-dioxo-3-(2-methylpropyl)-1,4,9-triazaspiro[5.5]undecane

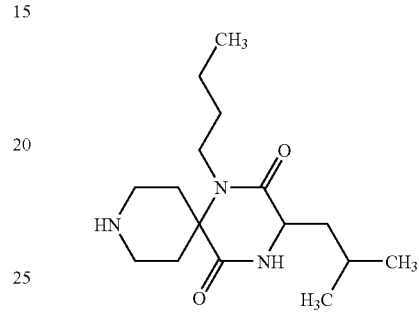

To a solution of the compound prepared in Example 6(7) (202 mg) in methanol (5 ml) was added 5% palladium on carbon (20 mg). Under an atmosphere of hydrogen, the reaction mixture was stirred for 3 hours at room temperature. The reaction mixture was filtrated through Celite (brand name). The filtrate was concentrated to give the compound of the present invention (127 mg) having the following physical data.

TLC: Rf 0.61 (chloroform:methanol:28% NH$_4$OH=20:5:1); NMR (CD$_3$OD): δ 3.97 (dd, J=7.8 Hz, 4.5 Hz, 1H), 3.48-3.22 (m, 4H), 3.00-2.90 (m, 2H), 2.12-1.60 (m, 11H), 0.95 (t, J=7.2 Hz, 3H), 0.94 (d, J=6.6 Hz, 3H), 0.93 (d, J=6.6 Hz, 3H).

EXAMPLE 9(1)

1-butyl-2,5-dioxo-3-cyclohexylmethyl-1,4,9-triazaspiro[5.5]undecane

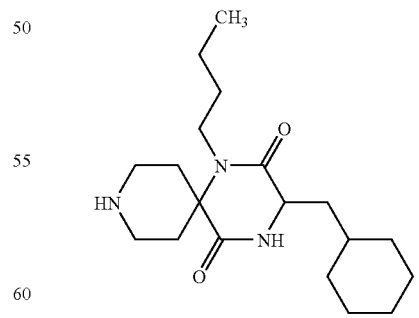

By the same procedure as described in Example 9 using the compound prepared in Example 6(8) instead of the compound prepared in Example 6(7), the compound of the present invention having the following physical data was obtained.

TLC: Rf 0.65 (chloroform:methanol:28% NH$_4$OH=20:5:1); NMR (CD$_3$OD): δ 4.00 (dd, J=7.8 Hz, 4.5 Hz, 1H), 3.46-3.24 (m, 4H), 3.03-2.92 (m, 2H), 2.08-1.08 (m, 19H), 1.05-0.84 (m, 5H).

EXAMPLE 10

(3S)-1-propyl-2,5-dioxo-3-(4-(N-benzyloxycarbonyl)aminobutyl)-9-(4-dihydroxyboranephenylmethyl)-1,4,9-triazaspiro[5.5]undecane.hydrochloride

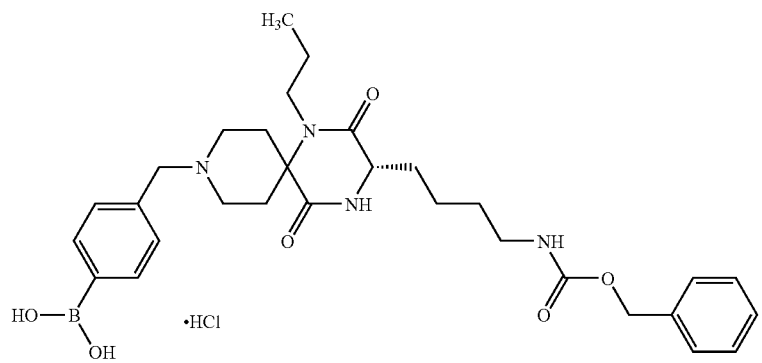

The compound prepared in Example 8 (70 mg) was dissolved in 1% acetic acid-dimethylformamide solution (2 ml). To this solution were added sodium triacetoxyborohydride (46 mg) and 4-formylphenylboronic acid (30 mg). The reaction mixture was stirred for 46 hours at room temperature. To the reaction mixture was added 10% acetic acid-methanol solution. This solution was loaded on cation-exchange resin (BondElut-SCX, Varian Co. Ltd., 0.6 mmol/g, 500 mg/3 ml), and the resin was washed with methanol, and furthermore, was eluted with 10% triethylamine-methanol solution. Only solution which was eluted with 10% triethylamine-methanol solution, was concentrated. The obtained residue was purified by column chromatography on silica gel (chloroform:methanol=1:0→30:1→10:1) to give the compound of the present invention (45 mg) having the following physical data.

TLC: Rf 0.24 (chloroform:methanol=10:1); NMR (CD$_3$OD): δ 7.73 (br, 2H), 7.52 (br, 2H), 7.32 (m, 5H), 5.03 (s, 2H), 4.36 (s, 2H), 4.05 (t, J=4.8 Hz, 1H), 3.81 (m, 2H), 3.46 (m, 3H), 3.10 (t, J=6.6 Hz, 2H), 2.37 (br, 2H), 2.22 (br, 2H), 1.92-1.66 (m, 2H), 1.60-1.28 (m, 7H), 0.91 (t, J=7.5 Hz, 3H).

EXAMPLE 10(1)

(3S)-1-propyl-2,5-dioxo-3-(4-(N-benzyloxycarbonyl)aminobutyl)-9-(1,3-benzodioxalan-4-ylmethyl)-1,4,9-triazaspiro[5.5]undecane.hydrochloride

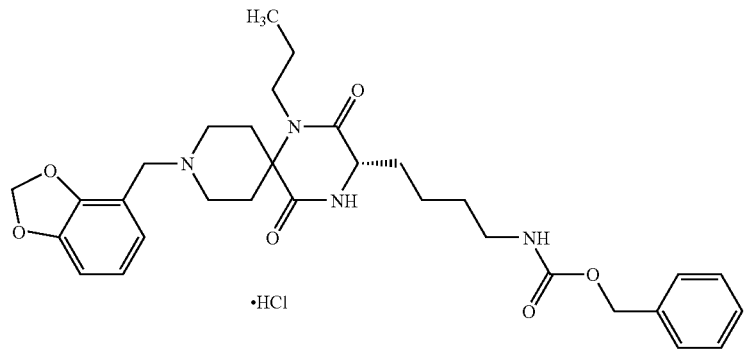

By the same procedure as described in Example 10 using 2,3-(methylenedioxy)benzaldehyde instead of 4-formylphenylboronic acid, the compound of the present invention having the following physical data was obtained.

TLC: Rf 0.25 (chloroform:methanol=10:1); NMR (CD$_3$OD): δ 7.32 (m, 5H), 6.96 (m, 3H), 6.05 (s, 2H), 5.04 (s, 2H), 4.33 (s, 2H), 4.05 (t, J=4.5 Hz, 1H), 3.98-3.54 (m, 2H), 3.53 (m, 2H), 3.38 (m, 3H), 3.11 (t, J=6.6 Hz, 2H), 2.37 (br, 2H), 2.22 (br, 2H), 1.98-1.76 (m, 2H), 1.61-1.28 (m, 5H), 0.92 (t, J=7.2 Hz, 3H).

EXAMPLE 11

1-butyl-2,5-dioxo-3-(2-methylpropyl)-9-(1-(1,4-benzodioxan-6-yl)ethyl)-1,4,9-triazaspiro[5.5]undecane.hydrochloride

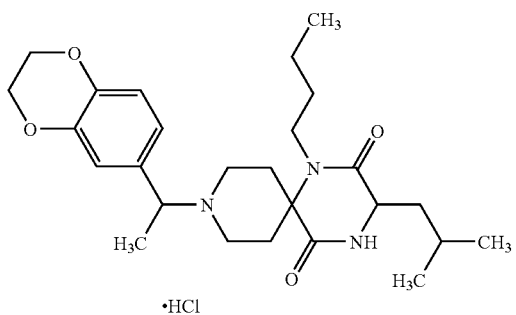

Under an atmosphere of argon, to a solution of the compound prepared in Example 9 (315 mg) in dichloromethane (5 ml) were added 1,4-benzodioxan-6-yl methyl ketone (285 mg), triethylamine (0.354 ml) and a solution of titanium tetrachloride in dichloromethane (1.0 M, 0.63 ml). The reaction mixture was stirred for 16 hours at room temperature. To the reaction mixture was added a solution of sodium cyanoborohydride (133 mg) in methanol (2 ml). The reaction mixture was stirred for 1 hour at room temperature. To the reaction mixture was added 2N aqueous solution of sodium hydroxide, and was extracted with ethyl acetate. The extract was dried over anhydrous magnesium sulfate and concentrated. The obtained residue was purified by column chromatography on silica gel (Fuji Silysia Chemical Ltd., BW235; chloroform:methanol=50:1). The obtained residue was dissolved in methanol. The solution was acidified by adding 1N hydrochloric acid, and was concentrated to give the compound of the present invention (176 mg) having the following physical data.

TLC: Rf 0.46 (chloroform:methanol=10:1); NMR (CD$_3$OD): δ 7.04 (d, J=2.1 Hz, 1H), 6.98 (dd, J=8.4, 2.1 Hz, 1H), 6.92 (d, J=8.4 Hz, 1H), 4.40 (q, J=6.9 Hz, 1H), 4.26 (s, 4H), 3.98 (dd, J=8.1, 4.5 Hz, 1H), 3.82-3.17 (m, 6H), 2.55-2.04 (m, 4H), 1.87-1.28 (m, 10H), 1.04-0.85 (m, 9H).

EXAMPLE 11(1)

1-butyl-2,5-dioxo-3-(2-methylpropyl)-9-(1-(4-phenyloxyphenyl)ethyl)-1,4,9-triazaspiro[5.5]undecane.hydrochloride

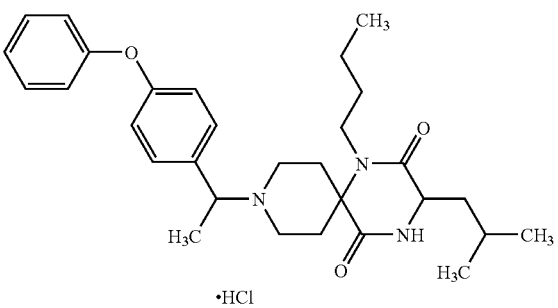

By the same procedure as described in Example 11 using 4-phenoxyacetophenone instead of 1,4-benzodioxan-6-yl methyl ketone, the compound of the present invention having the following physical data was obtained.

TLC: Rf 0.58, 0.62 (chloroform:methanol=10:1); NMR (CD$_3$OD): δ 7.51 (d, J=8.7 Hz, 2H), 7.39 (dd, J=8.7, 7.5 Hz, 2H), 7.17 (t, J=7.5 Hz, 1H), 7.09-7.01 (m, 4H), 4.48 (m, 1H), 3.98 (dd, J=7.8, 4.8 Hz, 1H), 3.80-3.17 (m, 6H), 2.56-2.28 (m, 2H), 2.28-2.03 (m, 2H), 1.88-1.24 (m, 7H), 1.76 (d, J=6.9 Hz, 3H), 1.04-0.86 (m, 9H).

EXAMPLE 12

1-butyl-2,5-dioxo-3-cyclohexylmethyl-9-(1-(1,4-benzodioxan-6-yl)ethyl)-1,4,9-triazaspiro[5.5]undecane.hydrochloride

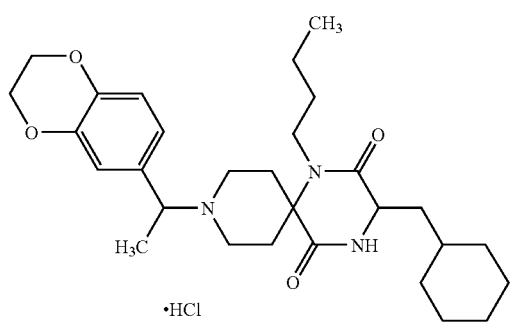

By the same procedure as described in Example 11 using the compound prepared in Example 9(1) instead of the compound prepared in Example 9, the compound of the present invention having the following physical data was obtained.

TLC: Rf 0.50 (chloroform:methanol=10:1); NMR (CD₃OD): δ 7.02 (d, J=1.8 Hz, 1H), 6.96 (dd, J=8.4, 1.8 Hz, 1H), 6.92 (d, J=8.4 Hz, 1H), 4.39 (m, 1H), 4.26 (s, 4H), 4.01 (dd, J=7.5, 4.5 Hz, 1H), 3.80-3.20 (m, 6H), 2.50-2.02 (m, 4H), 1.82-1.13 (m, 18H), 1.04-0.83 (m, 5H).

EXAMPLE 13

(3S)-1-propyl-2,5-dioxo-3-(4-(N-benzyloxycarbonyl)aminobutyl)-9-allyl-1,4,9-triazaspiro[5.5]undecane.hydrochloride

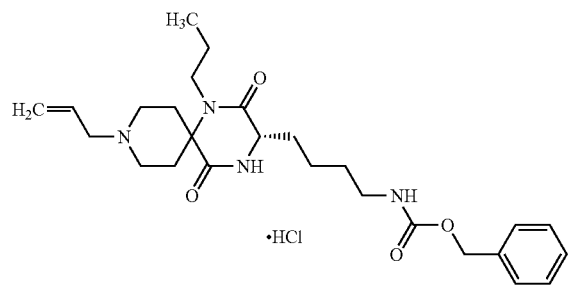

Under an atmosphere of argon, to a solution of the compound prepared in Example 7 (225 mg) in tetrahydrofuran (5 ml) was added tetrakis(triphenylphosphine)palladium (0) (51 mg) at room temperature. The reaction mixture was stirred for 16 hours at room temperature. The reaction mixture was loaded on cation-exchange resin (BondElut-SCX, Varian Co. Ltd., 0.6 mmol/g, 500 mg/3 ml), and the resin was washed with methanol, and furthermore, was eluted with 10% triethylamine-methanol solution (20 ml). Only solution which was eluted with 10% triethylamine-methanol solution, was concentrated. The obtained residue was purified by column chromatography on silica gel (chloroform:methanol=20:1) to give the compound of the present invention (122 mg) having the following physical data.

TLC: Rf 0.34 (chloroform:methanol=10:1); NMR (CD₃OD): δ 7.34 (m, 5H), 6.00 (m, 1H), 5.62 (m, 1H), 5.61 (m, 1H), 5.06 (s, 2H), 4.07 (t, J=5.2 Hz, 1H), 3.77 (m, 4H), 3.44 (m, 4H), 3.12 (t, J=6.6 Hz, 2H), 2.39 (m, 2H), 2.20 (m, 2H), 1.84 (m, 2H), 1.54 (m, 4H), 1.37 (m, 2H), 0.94 (t, J=7.2 Hz, 3H).

EXAMPLE 14

(3S)-1-propyl-2,5-dioxo-3-(4-aminobutyl)-9-phenylethyl-1,4,9-triazaspiro[5.5]undecane

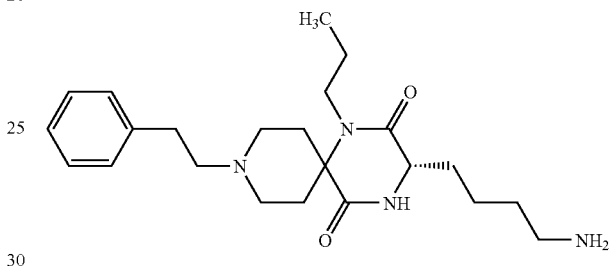

By the same procedure as described in Example 9 using the compound prepared in Example 5(11) instead of the compound prepared in Example 6(7), the compound of the present invention having the following physical data was obtained.

TLC: Rf 0.66 (chloroform:methanol:28% NH₄OH=20:5:1); NMR (CD₃OD): δ 7.23 (m, 5H), 4.05 (t, J=5.2 Hz, 1H), 3.42 (m, 2H), 2.98 (m, 3H), 2.81 (m, 3H), 2.65 (m, 4H), 2.16 (m, 2H), 1.99 (m, 1H), 1.89 (m, 3H), 1.53 (m, 3H), 1.48 (m, 3H), 0.94 (t, J=7.2 Hz, 3H).

EXAMPLE 15

(3S)-1-propyl-2,5-dioxo-3-(4-(N-(4-phenyl)phenylcarbonyl)aminobutyl)-9-phenylethyl-1,4,9-triazaspiro[5.5]undecane.hydrochloride

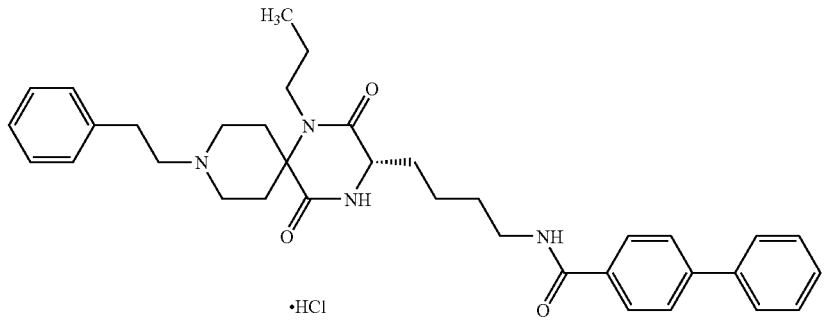

To a solution of the compound prepared in Example 14 (42 mg) in dichloroethane (2 ml) were added diisopropylethylamine (35 μl) and 4-phenylbenzoyl chloride (33 mg). The reaction mixture was stirred for 3 hours at room temperature. The reaction mixture was loaded on cation-exchange resin (BondElut-SCX, Varian Co. Ltd., 0.6 mmol/g, 500 mg/3 ml), and the resin was washed with methanol, and furthermore, was eluted with 10% triethylamine-methanol solution (20 ml). Only solution which was eluted with 10% triethylamine-methanol solution, was concentrated. The obtained residue was purified by column chromatography on silica gel (chloroform:methanol=10:0→10:1). To the obtained compound was added 4N hydrogen chloride-ethyl acetate solution to give the compound of the present invention (66 mg) having the following physical data.

TLC: Rf 0.50 (chloroform:methanol=10:1); NMR (CD$_3$OD): δ 7.89 (d, J=8.1 Hz, 2H), 7.72 (d, J=8.1 Hz, 2H), 7.65 (d, J=7.2 Hz, 2H), 7.45 (t, J=7.2 Hz, 2H), 7.39-7.26 (m, 6H), 4.11 (m, 1H), 3.86-3.71 (m, 2H), 3.63-3.53 (m, 2H), 3.45-3.30 (m, 4H), 3.07 (m, 2H), 2.42 (br, 2H), 2.19 (m, 2H), 1.99-1.78 (m, 2H), 1.68-1.28 (m, 7H), 0.86 (t, J=7.5 Hz, 3H).

To a solution of the compound prepared in Example 2(1) (50 mg) in chloroform (2 ml) was added 1N aqueous solution of sodium hydroxide (2 ml). The reaction mixture was stirred for 10 minutes at room temperature. The aqueous layer of the reaction mixture was removed. The organic layer was washed with water, dried over anhydrous magnesium sulfate and concentrated. To a solution of the obtained residue in acetone (2 ml) was added methyl iodide (118 μl). The reaction mixture was stirred for 18 hours at room temperature. The reaction mixture was concentrated. The obtained residue was solidified by diethyl ether to give the compound of the present invention (58 mg) having the following physical data.

TLC: Rf 0.23(ethyl acetate:acetic acid:water=8:1:1); NMR (CD$_3$OD): δ 7.10-6.90 (m, 3H), 4.60+4.49 (s+s, 2H), 4.29 (s, 4H), 4.20-4.00 (m, 3H), 3.70-3.35 (m, 4H), 3.11+2.99 (s+s, 3H), 2.80-2.30 (m, 2H), 2.30-2.00 (m, 2H), 1.90-1.10 (m, 15H), 1.10-0.80 (m, 5H).

EXAMPLE 17

(3S)-3-(4-(N-benzyloxycarbonyl)aminobutyl)-2,5-dioxo-9-(2-hydroxy-2-phenylethyl)-1-propyl-1,4,9-triazaspiro[5.5]undecane

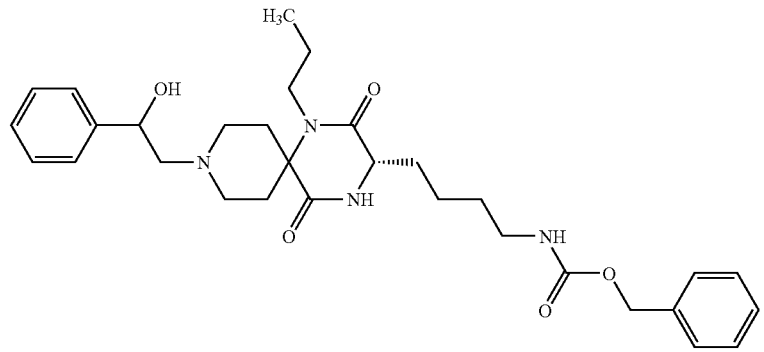

EXAMPLE 16

1-butyl-2,5-dioxo-3-cyclohexylmethyl-9-methyl-9-(1-(1,4-benzodioxan-6-yl)ethyl)-1,4,-diaza-9-azoniaspiro[5.5]undecane iodide

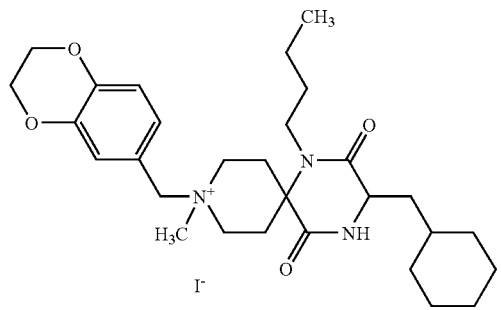

To a solution of the compound prepared in Example 8 (0.01 g) in 2-propanol (0.4 ml) was added styrene oxide (10 μl). The reaction mixture was refluxed for 4 hours. The reaction mixture was cooled to room temperature, and was loaded on ion exchange resin (OASIS MCX, Waters, 60 mg) washed with methanol (3 ml) prior to use. The resin was washed with methanol (2 ml), and was eluted with 10% triethylamine-methanol solution (2 ml). The elution was concentrated to give the compound of the present invention (13 mg) having the following physical data.

TLC: Rf 0.34 (chloroform:methanol=10:1); NMR (CD$_3$OD): δ 7.40-7.20 (m, 10H), 5.06 (s, 2H), 4.03 (m, 1H), 3.40 (m, 2H), 3.12 (m, 2H), 3.10-2.60 (m, 6H), 2.50 (m, 1H), 2.40-2.00 (m, 2H), 2.00-1.70 (m, 4H), 1.70-1.20 (m, 6H), 0.93 (t, J=7.2 Hz, 3H).

EXAMPLE 18

(3S)-3-(4-(N-benzyloxycarbonyl)aminobutyl)-2,5-dioxo-9-(2-oxo2-phenylethyl)-1-propyl-1,4,9-triazaspiro[5.5]undecane

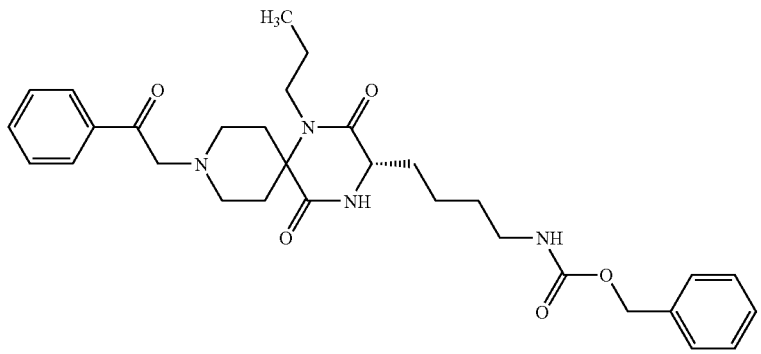

To a solution of the compound prepared in Example 8 (0.01 g) in dimethylformamide (0.4 ml) were added triethylamine (6 µl), and phenacyl bromide (9 mg). The reaction mixture was allowed to stand for 24 hours at room temperature. The reaction mixture was acidified by adding acetic acid (0.4 ml). The reaction mixture was loaded on ion exchange resin (OASIS MCX, Waters, 120 mg) washed with methanol (6 ml) prior to use. The resin was washed with methanol (2 ml), and was eluted with 10% triethylamine-methanol solution (4 ml). The elution was concentrated to give the compound of the present invention (12 mg) having the following physical data.

TLC: Rf 0.33 (chloroform:methanol=10:1); NMR (CD$_3$OD): δ 8.01 (m, 2H), 7.54 (m, 3H), 7.33 (m, 5H), 5.05 (s, 2H), 4.02 (m, 1H), 4.00 (s, 2H), 3.44 (m, 2H), 3.12 (t, J=6.6 Hz, 2H), 2.95 (m, 2H), 2.40-2.10 (m, 2H), 2.00-1.70 (m, 5H), 1.68-1.20 (m, 7H), 0.94 (t, J=7.2 Hz, 3H).

EXAMPLE 19

(3S)-1-(2-methylpropyl)-2,5-dioxo-3-methyl-9-allyloxycarbonyl-1,4,9-triazaspiro[5.5]undecane

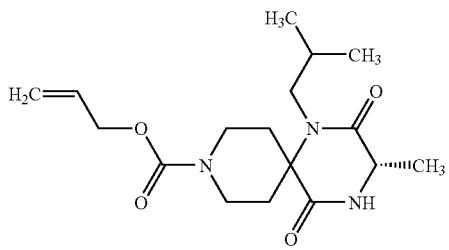

To a suspension of Resin (6) prepared in Reference Example 8 (300 mg) in tetrahydrofuran (1.5 ml) and methanol (1.5 ml) were added N-allyloxycarbonyl-4-piperidone (403 mg), isobutylamine (0.22 ml) and N-(t-butyloxycarbonyl)-L-alanine (381 mg) at room temperature. The reaction mixture was stirred for 20 hours at 65° C. The reaction mixture was cooled to room temperature and the resin was collected by filtration. The obtained resin was washed with tetrahydrofuran (3 ml×4) and dichloromethane (3 ml×5), and dried. The resin (384 mg) was obtained. To a suspension of the obtained resin (146 mg) in 1.5 M 2,6-lutidine-dichloromethane (2 ml) was added 1M trimethylsilyl trifluoromethanesulfonate-dichloromethane solution (2 ml). It was stirred for 30 minutes at room temperature. The reaction mixture was filtrated, and the resin was washed with dichloromethane (2 ml×3). The obtained resin was suspended in 1.5 M 2,6-lutidine-dichloromethane solution (2 ml) and 1M trimethylsilyl trifluoromethanesulfonate-dichloromethane solution (2 ml) was added thereto. The reaction mixture was stirred for 30 minutes at room temperature. The resin was collected by filtration from the reaction solution, and was washed with dichloromethane (2 ml×4), methanol (2 ml×4) and dichloromethane (2 ml×4), dried and the resin was obtained. The obtained resin was suspended in 1.25M acetic acid-toluene solution (2 ml). The reaction mixture was stirred for 20 hours at 90° C. The reaction mixture was filtrated, and the resin was washed with toluene (2 ml×3) and methanol (2 ml×4). The filtrate was concentrated to give the compound of the present invention (19 mg) having the following physical data.

TLC: Rf 0.39 (chloroform:methanol=10:1); MS (ESI, Pos., 20 V): 388 (M+H)$^+$; HPLC condition: F; HPLC retention time: 3.40 min; NMR (CD$_3$OD): δ 5.98 (ddt, J=15.8, 10.4, 5.4 Hz, 1H), 5.30 (m, 1H), 5.21 (m, 1H), 4.59 (m, 2H), 4.20-4.00 (m, 3H), 3.85-3.60 (m, 2H), 3.41 (dd, J=14.2, 8.0 Hz, 1H), 3.18 (dd, J=14.2, 7.2 Hz, 1H), 2.10-1.70 (m, 5H), 1.43 (d, J=6.8 Hz, 3H), 0.89 (t, J=6.2 Hz, 6H).

EXAMPLE 19(1)

(3S)-1-(2-methylpropyl)-2,5-dioxo-3-methyl-9-(2-phenylethyl)-1,4,9-triazaspiro[5.5]undecane.acetate By the same procedure as described in Example 19 using Resin (6) prepared in Reference Example 8 (200 mg), N-(2-phenylethyl)-4-piperidone (252 mg), isobutylamine (0.123 ml) and N-(t-butyloxycarbonyl)-L-alanine (235 mg), the compound of the present invention (50 mg) having the following physical data was obtained.

TLC: Rf 0.46 (chloroform:methanol=10:1); MS (ESI, Pos., 20 V): 358 (M+H)$^+$; HPLC condition: F; HPLC retention time: 3.14 min; NMR (CD$_3$OD): δ 7.40-7.20 (m, 5H), 4.15 (q, J=6.8 Hz, 1H), 3.65 (m, 1H), 3.55-3.35 (m, 3H), 3.25-3.05 (m, 3H), 3.05-2.90 (m, 3H), 2.50-2.05 (m, 4H), 1.98 (s, 3H), 1.92 (m, 1H), 1.43 (d, J=6.8 Hz, 3H), 0.92 (t, J=6.4 Hz, 6H).

EXAMPLE 19(2)

(3S)-1-(2-methylpropyl)-2,5-dioxo-3-(4-(N-benzyloxycarbonyl)aminobutyl)-9-(2-phenylethyl)-1,4,9-triazaspiro[5.5]undecane.acetate

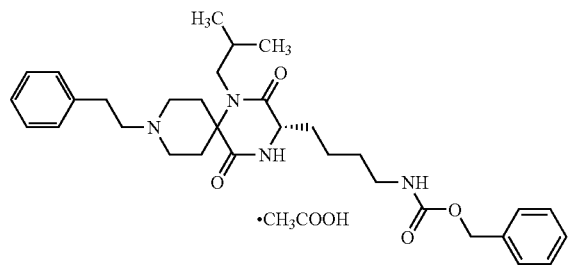

By the same procedure as described in Example 19 using Resin (6) prepared in Reference Example 8 (200 mg), N-(2-phenylethyl)-4-piperidone (252 mg), isobutylamine (0.123 ml) and N-(t-butyloxycarbonyl)-N'-(benzyloxycarbonyl)-L-lysine (472 mg), the compound of the present invention (71 mg) having the following physical data was obtained.

TLC: Rf 0.44 (chloroform:methanol=10:1); MS (ESI, Pos., 20 V): 549 (M+H)$^+$; HPLC condition: F; HPLC retention time: 3.49 min; NMR (CD$_3$OD): δ 7.40-7.20 (m, 10H), 5.06 (s, 2H), 4.10 (m, 1H), 3.67 (m, 1H), 3.60-3.40 (m, 3H), 3.28-3.05 (m, 5H), 3.05-2.90 (m, 3H), 2.50-2.10 (m, 4H), 1.98 (s, 3H), 2.05-1.70 (m, 3H), 1.65-1.20 (m, 4H), 0.92 (t, J=6.2 Hz, 6H).

EXAMPLE 19(3)

(3S)-1-(1-benzylpiperidin-4-yl)-2,5-dioxo-3-methyl-9-(2-phenylethyl)-1,4,9-triazaspiro[5.5]undecane.2 acetat

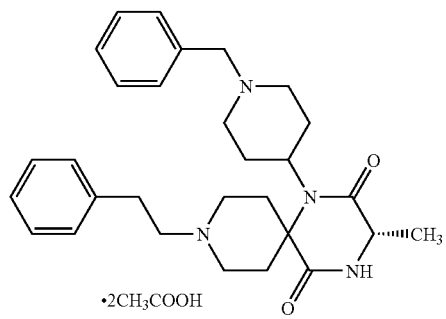

By the same procedure as described in Example 19 using Resin (6) prepared in Reference Example 8 (200 mg), N-(2-phenylethyl)-4-piperidone (252 mg), 4-amino-1-benzylpiperidine (0.253 ml) and N-(t-butyloxycarbonyl)-L-alanine (235 mg), the compound of the present invention (41 mg) having the following physical data was obtained.

TLC: Rf 0.10 (chloroform:methanol=10:1); MS (ESI, Pos., 20 V): 475 (M+H)$^+$; HPLC condition: F; HPLC retention time: 3.09 min; NMR (CD$_3$OD): δ 7.47 (m, 5H), 7.40-7.20 (m, 5H), 4.19 (s, 2H), 4.00 (q, J=6.8 Hz, 1H), 3.80-3.53 (m, 4H), 3.53-3.35 (m, 4H), 3.30-3.15 (m, 2H), 3.15-2.90 (m, 3H), 2.55-2.30 (m, 3H), 2.30-2.00 (m, 2H), 1.98 (s, 6H), 1.85-1.70 (m, 3H), 1.42 (d, J=7.0 Hz, 3H).

EXAMPLE 19(4)

(3S)-1-(1-benzylpiperidin-4-yl)-2,5-dioxo-3-(4-(N-benzyloxycarbonyl)aminobutyl)-9-(2-phenylethyl)-1,4,9-triazaspiro[5.5]undecane.2 acetate

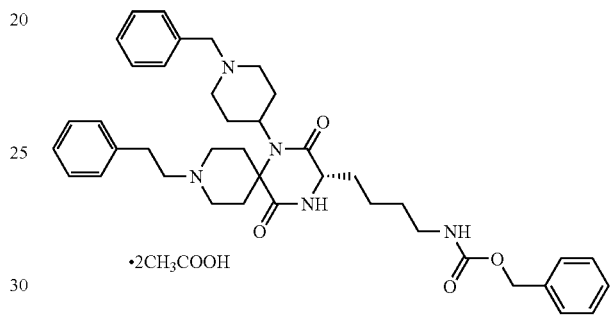

By the same procedure as described in Example 19 using Resin (6) prepared in Reference Example 8 (200 mg), N-(2-phenylethyl)-4-piperidone (252 mg), 4-amino-1-benzylpiperidine (0.253 ml) and N-(t-butyloxycarbonyl)-N'-(benzyloxycarbonyl)-L-lysine (472 mg), the compound of the present invention (33 mg) having the following physical data was obtained.

TLC: Rf 0.12 (chloroform:methanol=10:1); MS (ESI, Pos., 20 V): 666 (M+H)$^+$; HPLC condition: F; HPLC retention time: 3.36 min; NMR (CD$_3$OD): δ 7.46 (m, 5H), 7.40-7.20 (m, 10H), 5.03 (s, 2H), 4.19 (s, 2H), 3.99 (m, 1H), 3.80-3.40 (m, 6H), 3.30-2.85 (m, 9H), 2.50-2.10 (m, 6H), 1.98 (s, 6H), 1.95-1.60 (m, 4H), 1.60-1.40 (m, 4H).

EXAMPLE 19(5)

(3S)-1-(2,2-diphenylpropyl)-2,5-dioxo-3-methyl-9-(2-phenylethyl)-1,4,9-triazaspiro[5.5]undecane.acetate

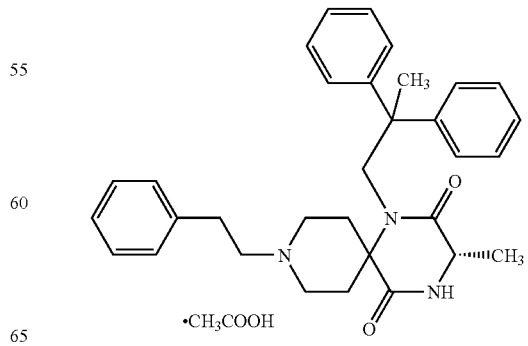

By the same procedure as described in Example 19 using Resin (6) prepared in Reference Example 8 (200 mg), N-(2-phenylethyl)-4-piperidone (252 mg), 2,2-diphenylpropylamine (307 mg) and N-(t-butyloxycarbonyl)-L-alanine (235 mg), the compound of the present invention (22 mg) having the following physical data was obtained.

TLC: Rf 0.42 (chloroform:methanol=10:1); MS (ESI, Pos., 20 V): 496 (M+H)$^+$; HPLC condition: F; HPLC retention time: 3.58 min; NMR (CD$_3$OD): δ 7.40-7.10 (m, 15H), 4.79 (m, 1H), 4.16 (m, 1H), 3.93 (m, 1H), 3.71 (s, 2H), 3.23 (m, 1H), 3.10-2.80 (m, 5H), 1.98 (s, 3H), 1.95-1.82 (m, 2H), 1.70-1.15 (m, 1H), 1.58 (s, 3H), 1.49 (d, J=6.8 Hz, 3H), 0.70 (m, 1H).

EXAMPLE 19(6)

(3S)-1-(2,2-diphenylpropyl)-2,5-dioxo-3-(4-(N-benzyloxycarbonyl)aminobutyl)-9-(2-phenylethyl)-1,4,9-triazaspiro[5.5]undecane.acetate

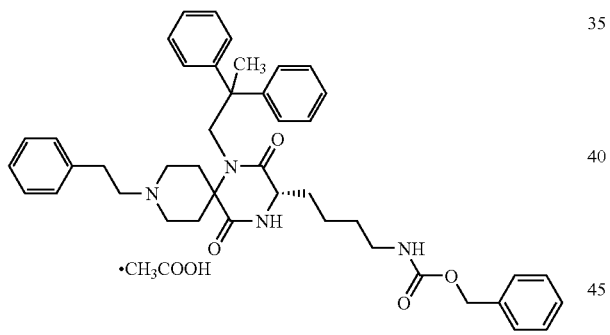

By the same procedure as described in Example 19 using Resin (6) prepared in Reference Example 8 (200 mg), N-(2-phenylethyl)-4-piperidone (252 mg), 2,2-diphenylpropylamine (307 mg) and N-(t-butyloxycarbonyl)-N'-(benzyloxycarbonyl)-L-lysine (472 mg), the compound of the present invention (18 mg) having the following physical data was obtained.

MS (ESI, Pos., 20 V): 687 (M+H)$^+$; HPLC condition: F; HPLC retention time: 3.80 min;

TLC: Rf 0.46 (chloroform:methanol=10:1); NMR (CD$_3$OD): δ 7.40-7.00 (m, 20H), 5.06 (s, 2.H), 4.16 (m, 1H), 3.93 (m, 1H), 3.70 (s, 2H), 3.55 (m, 1H), 3.30-3.10 (m, 2H), 3.10-2.80 (m, 6H), 1.98 (s, 3H), 1.95-1.85 (m, 2H), 1.80 (s, 3H), 1.70-1.30 (m, 8H).

EXAMPLE 19(7)

(3S)-1-propyl-2,5-dioxo-3-(4-benzyloxyphenylmethyl)-9-(2-phenylethyl)-1,4,9-triazaspiro[5.5]undecane.acetate

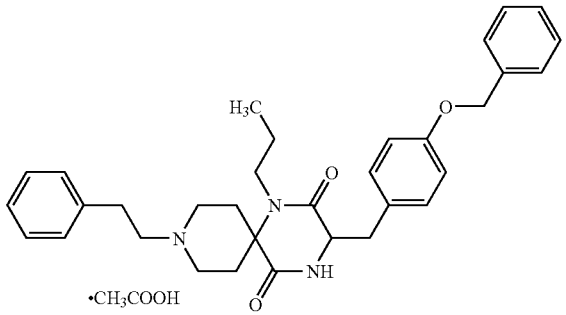

By the same procedure as described in Example 19 using Resin (6) prepared in Reference Example 8 (0.5 g), N-(2-phenylethyl)-4-piperidone (0.32 g), n-propylamine (0.13 ml) and N-(t-butyloxycarbonyl)-O-benzyl-L-tyrosine (0.58 g), the compound of the present invention (68 mg) having the following physical data was obtained.

TLC: Rf 0.51 (chloroform:methanol=10:1); NMR (CD$_3$OD): δ 7.50-7.10 (m, 10H), 7.06 (d, J=8.8 Hz, 2H), 6.92 (d, J=8.8 Hz, 2H), 5.07 (s, 2H), 4.31 (m, 1H), 3.68 (m, 1H), 3.40 (m, 1H), 3.28-3.13 (m, 4H), 3.13-2.80 (m, 6H), 2.30-2.00 (m, 2H), 1.80-1.35 (m, 4H), 0.91 (t, J=7.2 Hz, 3H).

EXAMPLE 20

(3S)-1-propyl-2,5-dioxo-3-(4-(benzylcarbonylamino)butyl)-9-(2,4,6-trimethoxybenzyl)-1,4,9-triazaspiro[5.5]undecane

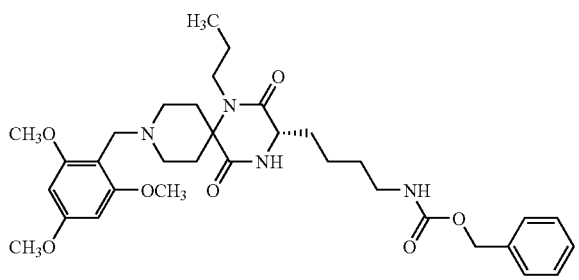

To a solution of the compound prepared in Example 8 (0.01 g) in dichloroethane (0.2 ml) were added 2,4,6-trimethoxybenzaldehyde (0.013 g), sodium triacetoxyborohydride (0.015 g) and dimethylformamide (0.2 ml). The reaction mixture was stirred for 50 hours at room temperature. The reaction mixture was loaded on ion exchange resin (OASIS MCX, Waters, 60 mg) washed with methanol (3 ml) prior to use. The resin was washed with methanol (2 ml), and was eluted with 10% triethylamine-methanol solution (2 ml). The elution was concentrated to give the compound of the present invention (4.4 mg) having the following physical data.

TLC: Rf 0.33 (chloroform:methanol=10:1); NMR (CD$_3$OD): δ 7.33 (m, 5H), 6.21 (s, 2H), 5.05 (s, 2H), 4.00 (m, 1H), 3.80 (s, 9H), 3.59 (s, 2H), 3.40 (m, 2H), 3.11 (t, J=6.6 Hz, 2H), 3.05-2.75 (m, 4H), 2.40-2.00 (m, 2H), 2.00-1.70 (m, 4H), 1.65-1.25 (m, 6H), 0.90 (t, J=7.2 Hz, 3H).

EXAMPLE 20(1)

(3S)-1-propyl-2,5-dioxo-3-(4-(benzylcarbonylamino)butyl)-9-(2,2-dimethylpropyl)-1,4,9-triazaspiro[5.5]undecane

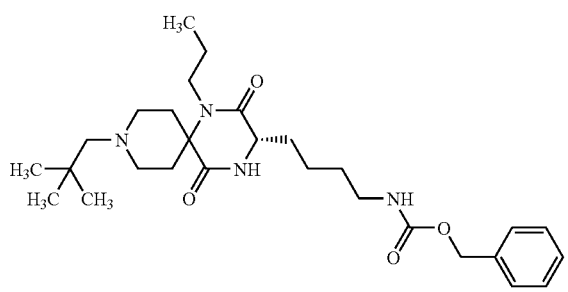

By the same procedure as described in Example 20 using the compound prepared in Example 8 (0.01 g) and pivalaldehyde (8 μl), the compound of the present invention (2.5 mg) having the following physical data was obtained.

TLC: Rf 0.53 (chloroform:methanol=10:1); NMR (CD$_3$OD): δ 7.33 (m, 5H), 5.06 (s, 2H), 4.02 (m, 1H), 3.50-3.30 (m, 2H), 3.20-3.00 (m, 4H), 3.00-2.60 (m, 4H), 2.20-2.00 (m, 2H), 1.90-1.70 (m, 3H), 1.70-1.20 (m, 7H), 0.92 (t, J=7.4 Hz, 3H), 0.90 (s, 9H).

EXAMPLE 21

(3S)-1-propyl-2,5-dioxo-3-(4-(benzylcarbonylamino)butyl)-9-(3-phenylpropanoyl)-1,4,9-triazaspiro[5.5]undecane

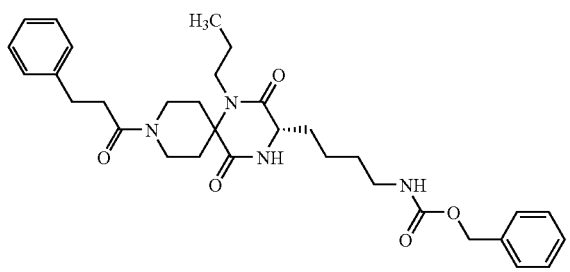

To a solution of the compound prepared in Example 8 (0.01 g) in dichloroethane (0.2 ml) were added diisopropylethylamine (6 μl), 3-phenylpropanoyl chloride (5 μl). The reaction mixture was stirred for 1 hour at room temperature. The reaction mixture was passed through the column with aminomethylated polystyrene-2% divinylbenzene copolymer resin (NovaBiochem, AM Resin, 50 mg). The resin was washed with dichloroethane and filtrated. The filtrate was concentrated to give the compound of the present invention (14 mg) having the following physical data.

TLC: Rf 0.55 (chloroform:methanol=10:1); NMR (CD$_3$OD): δ 7.40-7.10 (m, 10H), 5.06 (s, 2H), 4.03 (m, 1H), 3.70-3.55 (m, 2H), 3.28-3.00 (m, 5H), 3.00-2.80 (m, 3H), 2.80-2.60 (m, 2H), 2.00-1.65 (m, 6H), 1.65-1.40 (m, 6H), 0.90 (t, J=7.2 Hz, 3H).

EXAMPLE 21(1)

(3S)-1-propyl-2,5-dioxo-3-(4-(benzylcarbonylamino)butyl)-9-benzenesulfonyl-1,4,9-triazaspiro[5.5]undecane

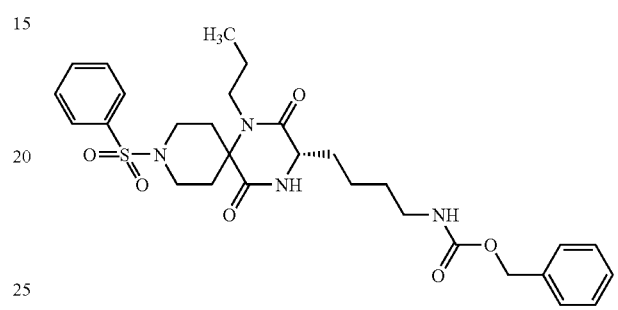

By the same procedure as described in Example 21 using the compound prepared in Example 8 (0.01 g), diisopropylethylamine (6 μl) and benzenesulfonyl chloride (4.5 μl), the compound of the present invention (16 mg) having the following physical data was obtained.

TLC: Rf 0.58 (chloroform:methanol=10:1); NMR (CD$_3$OD): δ 7.80 (m, 2H), 7.63 (m, 3H), 7.33 (m, 5H), 5.04 (s, 2H), 3.98 (t, J=4.8 Hz, 1H), 3.60-3.35 (m, 2H), 3.28-2.90 (m, 6H), 2.20-1.65 (m, 6H), 1.65-1.20 (m, 6H), 0.89 (t, J=7.2 Hz, 3H).

EXAMPLE 21(2)

(3S)-1-propyl-2,5-dioxo-3-(4-(benzylcarbonylamino)butyl)-9-benzylaminocarbonyl-1,4,9-triazaspiro[5.5]undecane

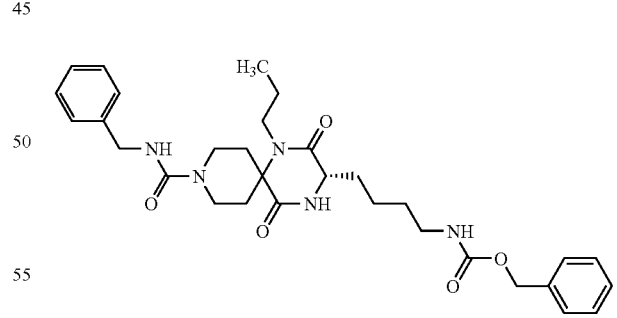

By the same procedure as described in Example 21 using the compound prepared in Example 8 (0.01 g) and benzyl isocyanate (4 μl), the compound of the present invention (16 mg) having the following physical data was obtained.

TLC: Rf 0.45 (chloroform:methanol=10:1); NMR (CD$_3$OD): δ 7.40-7.10 (m, 10H), 5.05 (s, 2H), 4.37 (s, 2H), 4.10-3.90 (m, 3H), 3.60-3.45 (m, 2H), 3.30-3.00 (m, 4H), 2.10-1.70 (m, 6H), 1.65-1.20 (m, 6H), 0.87 (t, J=7.4 Hz, 3H).

EXAMPLE 22

(3S)-1-propyl-2,5-dioxo-3-(4-(3-phenylpropanoyl)
aminobutyl)-9-(2-phenylethyl)-1,4,9-triazaspiro[5.5]
undecane

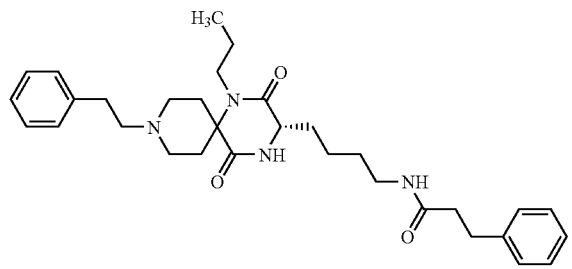

To a solution of the compound prepared in Example 14 (5 mg) in dichloroethane (0.5 ml) were added pyridine (2 μl), 3-phenylpropanoyl chloride (4 μl). The reaction mixture was stirred for 3 hours at room temperature. To the reaction mixture was added methanol, and it was loaded on ion exchange resin (OASIS MCX, Waters, 60 mg) washed with methanol (3 ml) prior to use. The resin was washed with methanol (2 ml), and was eluted with 10% triethylamine-methanol solution (2 ml). The elution was concentrated to give the compound of the present invention (1.6 mg) having the following physical data.

TLC: Rf 0.49 (chloroform:methanol=10:1); NMR (CD$_3$OD): δ 7.40-7.10 (m, 10H), 4.03 (m, 1H), 3.60-3.30 (m, 2H), 3.14 (m, 2H), 3.06-2.90 (m, 3H), 2.90-2.75 (m, 4H), 2.75-2.60 (m, 3H), 2.45 (t, J=7.4 Hz, 2H), 2.30-2.00 (m, 2H), 2.00-1.70 (m, 4H), 1.70-1.20 (m, 6H), 0.93 (t, J=7.2 Hz, 3H).

EXAMPLE 22(1)

(3S)-1-propyl-2,5-dioxo-3-(4-benzenesulfonylami-
nobutyl)-9-(2-phenylethyl)-1,4,9-triazaspiro[5.5]
undecane

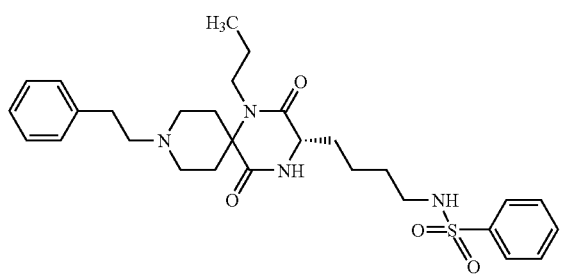

By the same procedure as described in Example 22 using the compound prepared in Example 14 (5 mg), pyridine (2 μl), benzenesulfonyl chloride (3 μl), the compound of the present invention (4.4 mg) having the following physical data was obtained.

TLC: Rf 0.49 (chloroform:methanol=10:1); NMR (CD$_3$OD): δ 7.84 (m, 2H), 7.59 (m, 3H), 7.34-7.10 (m, 5H), 4.01 (t, J=5.0 Hz, 1H), 3.55-3.30 (m, 2H), 3.05-2.90 (m, 3H), 2.90-2.75 (m, 4H), 2.75-2.60 (m, 3H), 2.30-2.00 (m, 2H), 1.96 (m, 2H), 1.88-1.70 (m, 2H), 1.70-1.20 (m, 6H), 0.94 (t, J=7.4 Hz, 3H).

EXAMPLE 22(2)

(3S)-1-propyl-2,5-dioxo-3-(4-(N-benzylcarbamoyl)
aminobutyl)-9-(2-phenylethyl)-1,4,9-triazaspiro[5.5]
undecane

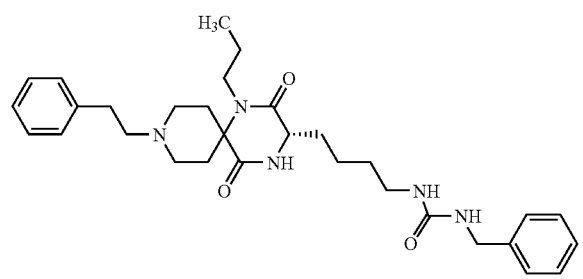

By the same procedure as described in Example 22 using the compound prepared in Example 14 (5 mg), and benzyl isocyanate (3 μl), the compound of the present invention (7 mg) having the following physical data was obtained.

TLC: Rf 0.46 (chloroform:methanol=10:1); NMR (CD$_3$OD): δ 7.40-7.10 (m, 10H), 4.30 (s, 2H), 4.04 (t, J=5.0 Hz, 1H), 3.55-3.30 (m, 2H), 3.15 (t, J=6.6 Hz, 3H), 3.05-2.90 (m, 3H), 2.90-2.75 (m, 3H), 2.75-2.60 (m, 2H), 2.35-2.05 (m, 2H), 2.02-1.70 (m, 4H), 1.70-1.20 (m, 6H), 0.93 (t, J=7.4 Hz, 3H).

EXAMPLE 23

1-cyclopropylmethyl-2,5-dioxo-3-(2-methylpropyl)-
9-(4-phenoxyphenyl)-1,3,9-triazaspiro[5.5]undeca-
ne.acetate

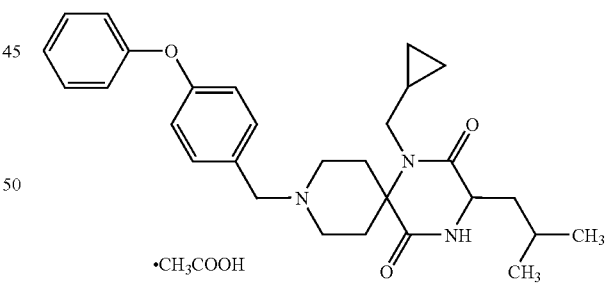

To a suspension of Resin (3) prepared in Reference Example 2 (0.5 g) in tetrahydrofuran/methanol (1:1; 5 ml) were added N-allyloxycarbonyl-4-piperidone (0.396 g), cyclopropylmethylamine (0.189 ml) and N-(t-butyloxycarbonyl)leucine (0.542 g), and it was stirred for 18 hours at 65° C. The reaction solution was cooled to room temperature and the resin was collected by filtration. The obtained resin was washed with dimethylformamide (5 ml×2), dichloromethane (5 ml×2), methanol (5 ml×2) and dichloromethane (5 ml×2). To a suspension of the obtained resin in dichloromethane (5 ml) were added acetic acid (0.149 ml), tributyltin hydride (0.351 ml) and tetrakis(triphenylphosphine)palladium (0) complex (50 mg), and it was stirred for 6 hours at room temperature. The resin was collected by filtration from the reaction solution, and was washed with dichloromethane (5 ml×4) and dimethylformamide (5 ml×3). The obtained resin was suspended in 1% acetic acid-dimethylformamide solution (5 ml), and 4-phenyloxybenzaldehyde (0.252 g), and sodium triacetoxyborohydride (0.277 g) were added thereto. It was stirred for 15 hours at room temperature. The resin was collected by filtration from reaction mixture, and was washed with methanol (5 ml×1), dimethylformamide (5 ml×3), methanol (5 ml×4) and dichloromethane (5 ml×4). The obtained resin was suspended in 50% trifluoroacetic acid-dichloromethane solution (5 ml), and it was stirred for 5 minutes at room temperature. The reaction solution was filtrated, and the obtained resin was suspended in 50% trifluoroacetic acid-dichloromethane solution (5 ml), and it was stirred for 30 minutes at room temperature. The obtained resin by filtration from the reaction solution was washed with dichloromethane (5 ml×3) and 1.25M acetic acid-toluene solution (5 ml×3). The obtained resin was suspended in 1.25M acetic acid-toluene solution (5 ml), and it was stirred for 23 hours at 90° C. The reaction solution was filtrated. The obtained resin was washed with chloroform-methanol (1:1; 2 ml×2). The filtrate and the washings were concentrated to give the compound of the present invention (274 mg) having the following physical data.

TLC: Rf 0.40 (chloroform:methanol=20:1); NMR (CD$_3$OD): δ 7.49 (m, 2H), 7.40 (m, 2H), 7.18 (m, 2H), 7.04 (m, 3H), 4.33 (s, 2H), 4.04 (dd, J=8.1, 4.8 Hz, 1H), 3.78 (m, 2H), 3.52 (m, 2H), 3.35 (m, 2H), 2.45-2.10 (m, 4H), 1.98 (s, 3H, CH3COOH), 1.97-1.58 (m, 4H), 0.94 (d, J=6.0 Hz, 6H), 0.51 (m, 2H), 0.36 (m, 2H).

EXAMPLE 23(1)

1-(thiophen-2-ylmethyl)-2,5-dioxo-3-(2-methylpropyl)-9-(4-phenoxyphenyl)-1,3,9-triazaspiro[5.5]undecane.acetate

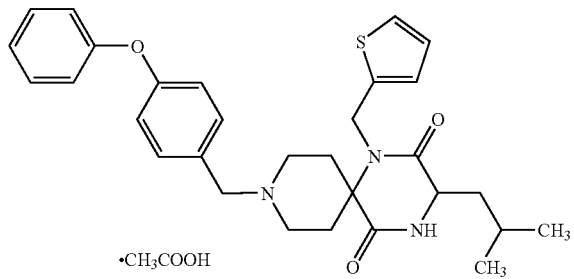

By the same procedure as described in Example 23 using Resin (3) prepared in Reference Example 2 (0.5 g), N-allyloxycarbonyl-4-piperidone (0.396 g), thiophen-2-ylmethylamine (0.205 ml) and N-(t-butyloxycarbonyl)leucine (0.542 g), 4-phenoxybenzaldehyde (0.252 g), the compound of the present invention (274 mg) having the following physical data was obtained.

TLC: Rf 0.39 (chloroform:methanol=20:1); NMR (CD$_3$OD): δ 7.48 (m, 2H), 7.39 (m, 2H), 7.28 (m, 1H), 7.18 (m, 2H), 7.04 (m, 4H), 6.91 (m, 1H), 4.86 (s, 2H), 4.32 (s, 2H), 4.12 (dd, J=8.1, 4.5 Hz, 1H), 3.77 (m, 2H), 3.49 (m, 2H), 2.60-2.30 (m, 2H), 2.19 (m, 2H), 1.98 (s, 3H), 1.97-1.58 (m, 3H), 0.94 (d, J=6.0 Hz, 6H).

EXAMPLE 24(1) TO 24(119)

By the same procedure as described in Reference Example 3→Reference Example 4 using Resin (3) prepared in Reference Example 2 and N-allyloxycarbonyl-4-piperidone, using the corresponding compounds respectively instead of n-propylamine and N-(t-butyloxycarbonyl)leucine, and furthermore by the same procedure as described in Reference Example 5→Reference Example 6→Example 1 using the corresponding compound instead of 3,5-dimethyl-1-phenyl-4-formylpyrazole, the following compounds of the present invention were obtained.

EXAMPLE 24(1)

(3S)-1-butyl-2,5-dioxo-3-(4-methoxyphenylmethyl)-9-cyclohexylmethyl-1,4,9-triazaspiro[5.5]undecane-.hydrochloride

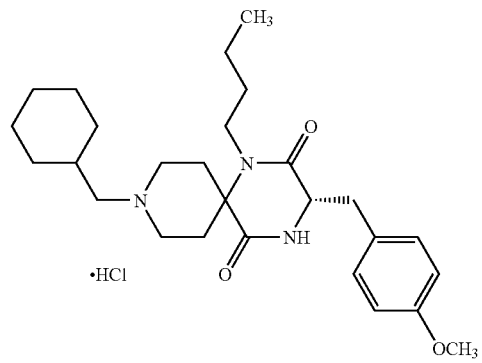

TLC: Rf 0.44 (chloroform:methanol=10:1); NMR (CD$_3$OD): δ 7.06 (d, J=9.0 Hz, 2H), 6.84 (d, J=9.0 Hz, 2H), 4.31 (dd, J=4.5, 3.6 Hz, 1H), 3.82-3.67 (m, 4H), 3.49-3.30 (m, 3H), 3.25 (dd, J=13.8, 3.6 Hz, 1H), 3.23-3.10 (m, 2H), 2.95-2.87 (m, 2H), 2.87 (dd, J=13.8, 4.5 Hz, 1H), 2.31 (m, 1H), 2.05 (m, 1H), 1.91-1.64 (m, 7H), 1.56-1.14 (m, 7H), 1.09-0.91 (m, 5H), 0.26 (m, 1H).

EXAMPLE 24(2)

1-butyl-2,5-dioxo-3-(2-methylpropyl)-9-(2-(4-chlorophenyl)thiophen-5-ylmethyl)-1,4,9-triazaspiro[5.5]undecane.hydrochloride

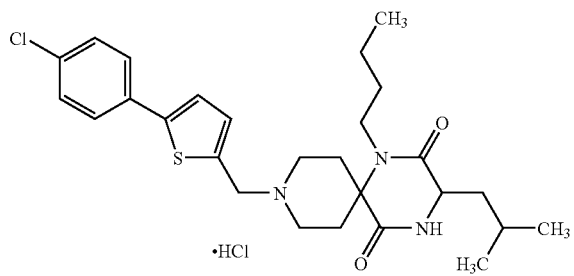

TLC: Rf 0.60 (chloroform:methanol=10:1); NMR (CD$_3$OD): δ 7.65 (d, J=8.7 Hz, 2H), 7.42 (d, J=8.7 Hz, 2H), 7.42 (d, J=3.6 Hz, 1H), 7.34 (d, J=3.6 Hz, 1H), 4.61 (brs, 2H), 4.01 (dd, J=7.8, 4.5 Hz, 1H), 3.95-3.72 (m, 2H), 3.65-3.50 (m, 2H), 3.44-3.34 (m, 2H), 2.50-2.12 (m, 4H), 1.89-1.45 (m, 5H), 1.45-1.28 (m, 2H), 1.13-0.89 (m, 9H).

EXAMPLE 24(3)

1-butyl-2,5-dioxo-3-(2-methylpropyl)-9-(2-(4-methoxyphenyl)thiophen-5-ylmethyl)-1,4,9-triazaspiro[5.5]undecane.hydrochloride

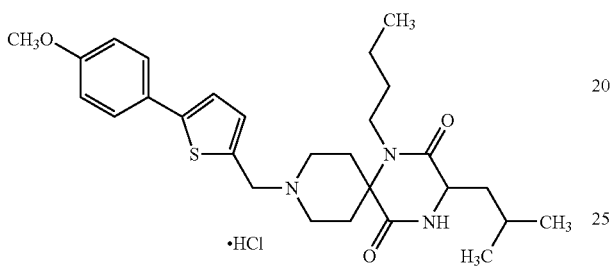

TLC: Rf 0.60 (chloroform:methanol=10:1); NMR (CD$_3$OD): δ 7.57 (d, J=9.0 Hz, 2H), 7.33-7.26 (m, 2H), 6.97 (d, J=9.0 Hz, 2H), 4.58 (brs, 2H), 4.01 (dd, J=7.5, 4.5 Hz, 1H), 3.93-3.71 (m, 5H), 3.64-3.50 (m, 2H), 3.44-3.34 (m, 2H), 2.49-2.12 (m, 4H), 1.90-1.45 (m, 5H), 1.45-1.28 (m, 2H), 1.03-0.88 (m, 9H).

EXAMPLE 24(4)

1-((2E)-2-butenyl)-2,5-dioxo-3-(2-methylpropyl)-9-(4-phenyloxyphenylmethyl)-1,4,9-triazaspiro[5.5]undecane.hydrochloride

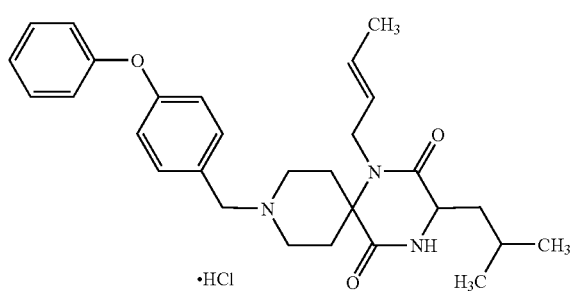

TLC: Rf 0.32 (chloroform:methanol=20:1); NMR (CD$_3$OD): δ 7.52 (d, J=8.7 Hz, 2H), 7.44-7.35 (m, 2H), 7.22-7.14 (m, 1H), 7.06 (d, J=8.7 Hz, 2H), 7.10-7.00 (m, 2H), 5.75-5.60 (m, 1H), 5.52-5.38 (m, 1H), 4.33 (s, 2H), 4.15-3.93 (m, 2H), 4.03 (dd, J=7.8, 4.5 Hz, 1H), 3.88-3.66 (m, 2H), 3.55-3.42 (m, 2H), 2.52-2.35 (m, 2H), 2.28-2.08 (m, 2H), 1.90-1.57 (m, 3H), 1.65 (dd, J=6.3, 1.5 Hz, 3H), 0.95 (d, J=6.6 Hz, 3H), 0.94 (d, J=6.6 Hz, 3H).

EXAMPLE 24(5)

1-(furan-2-ylmethyl)-2,5-dioxo-3-(2-methylpropyl)-9-(4-phenyloxyphenylmethyl)-1,4,9-triazaspiro[5.5]undecane.hydrochloride

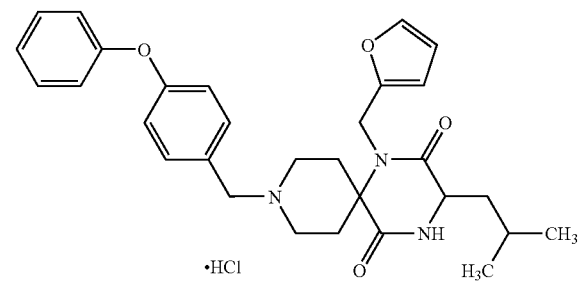

TLC: Rf 0.33 (chloroform:methanol=20:1); NMR (CD$_3$OD): δ 7.52 (d, J=8.7 Hz, 2H), 7.43-7.36 (m, 3H), 7.18 (t, J=7.2 Hz, 1H), 7.09-6.99 (m, 4H), 6.33 (m, 1H), 6.28 (d, J=3.0 Hz, 1H), 4.69 (s, 2H), 4.33 (s, 2H), 4.08 (dd, J=7.8, 4.5 Hz, 1H), 3.87-3.72 (m, 2H), 3.57-3.42 (m, 2H), 2.65-2.38 (m, 2H), 2.30-2.12 (m, 2H), 1.90-1.56 (m, 3H), 0.93 (d, J=6.6 Hz, 3H), 0.91 (d, J=6.6 Hz, 3H).

EXAMPLE 24(6)

1-(thiophen-2-ylmethyl)-2,5-dioxo-3-(2-methylpropyl)-9-(4-phenyloxyphenylmethyl)-1,4,9-triazaspiro[5.5]undecane.hydrochloride

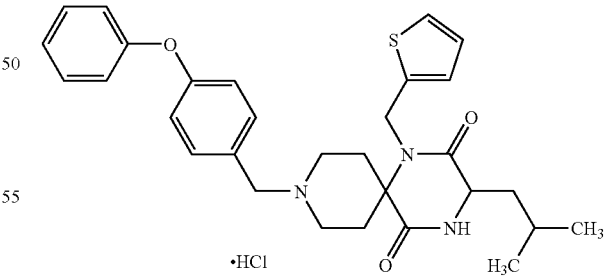

TLC: Rf 0.39 (chloroform:methanol=20:1); NMR (CD$_3$OD): δ 7.53 (d, J=8.7 Hz, 2H), 7.43-7.34 (m, 2H), 7.27 (dd, J=5.1, 1.2 Hz, 1H), 7.18 (t, J=7.2 Hz, 1H), 7.09-7.00 (m, 5H), 6.91 (dd, J=5.1, 3.3 Hz, 1H), 4.92 (brs, 2H), 4.32 (s, 2H), 4.11 (dd, J=7.8, 4.5 Hz, 1H), 3.84-3.66 (m, 2H), 3.53-3.41 (m, 2H), 2.68-2.46 (m, 2H), 2.23-2.06 (m, 2H), 1.95-1.59 (m, 3H), 0.95 (d, J=6.6 Hz, 6H).

EXAMPLE 24(7)

1-cyclopropylmethyl-2,5-dioxo-3-(2-methylpropyl)-9-(4-phenyloxyphenylmethyl)-1,4,9-triazaspiro[5.5]undecane.hydrochloride

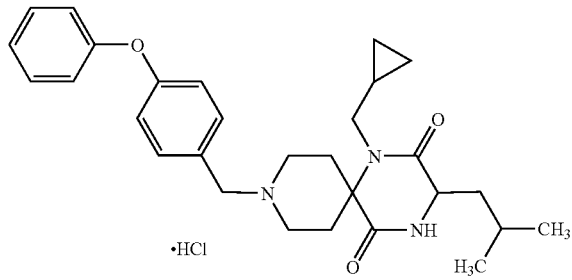

TLC: Rf 0.40 (chloroform:methanol=20:1); NMR (CD$_3$OD): δ 7.53 (d, J=8.7 Hz, 2H), 7.43-7.35 (m, 2H), 7.18 (t, J=7.2 Hz, 1H), 7.08-7.00 (m, 4H), 4.33 (s, 2H), 4.04 (dd, J=7.8, 4.5 Hz, 1H), 3.87-3.68 (m, 2H), 3.56-3.43 (m, 2H), 3.46-3.35 (m 2H), 2.56-2.35 (m, 2H), 2.23-2.12 (m, 2H), 1.95-1.58 (m, 3H), 1.10-0.95 (m, 1H), 0.95 (d, J=6.6 Hz, 6H), 0.56-0.45 (m, 2H), 0.42-0.34 (m, 2H).

EXAMPLE 24(8)

1-(2-fluorophenylmethyl)-2,5-dioxo-3-(2-methylpropyl)-9-(4-phenyloxyphenylmethyl)-1,4,9-triazaspiro[5.5]undecane.hydrochloride

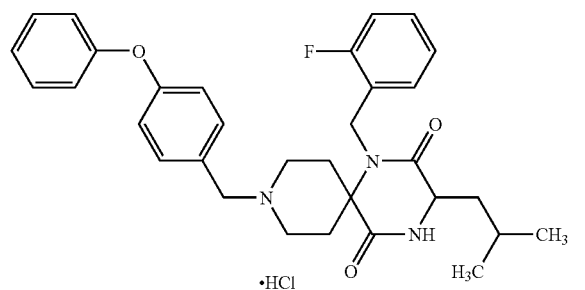

TLC: Rf 0.43 (chloroform:methanol=20:1); NMR (CD$_3$OD): δ 7.48 (d, J=9.0 Hz, 2H), 7.42-7.34 (m, 2H), 7.32-7.21 (m, 1H), 7.17 (t, J=7.5 Hz, 1H), 7.14-7.06 (m, 3H), 7.06-6.98 (m, 4H), 4.80 (brs, 2H), 4.30 (s, 2H), 4.18 (dd, J=8.1, 4.8 Hz, 1H), 3.86-3.68 (m, 2H), 3.50-3.35 (m, 2H), 2.50-2.30 (m, 1H), 2.30-2.14 (m, 3H), 1.94-1.62 (m, 3H), 0.97 (d, J=6.3 Hz, 6H).

EXAMPLE 24(9)

1-(3-methyl-2-butenyl)-2,5-dioxo-3-(2-methylpropyl)-9-(4-phenyloxyphenylmethyl)-1,4,9-triazaspiro[5.5]undecane.hydrochloride

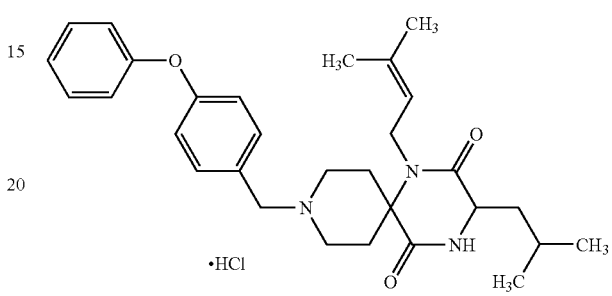

TLC: Rf 0.29 (chloroform:methanol=20:1); NMR (CD$_3$OD): δ 7.52 (d, J=8.4 Hz, 2H), 7.43-7.35 (m, 2H), 7.18 (t, J=7.5 Hz, 1H), 7.09-7.00 (m, 4H), 4.97 (br, 1H), 4.32 (s, 2H), 4.20-4.00 (m, 2H), 4.02 (dd, J=7.8, 4.5 Hz, 1H), 3.90-3.68 (m, 2H), 3.55-3.45 (m, 2H), 2.52-2.32 (m, 2H), 2.30-2.08 (m, 2H), 1.90-1.56 (m, 3H), 1.74 (s, 3H), 1.69 (s, 3H), 0.94 (d, J=6.3 Hz, 3H), 0.94 (d, J=6.3 Hz, 3H).

EXAMPLE 24(10)

1-butyl-2,5-dioxo-3-(2-methylpropyl)-9-(quinolin-3-ylmethyl)-1,4,9-triazaspiro[5.5]undecane.2 hydrochloride

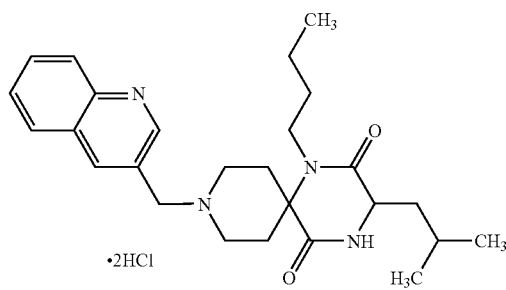

TLC: Rf 0.25 (chloroform:methanol=20:1); NMR (CD$_3$OD): δ 9.52 (d, J=1.5 Hz, 1H), 9.35 (d, J=1.5 Hz, 1H), 8.35 (d, J=8.7 Hz, 1H), 8.27 (d, J=8.7 Hz, 1H), 8.24-8.16 (m, 1H), 8.04-7.96 (m, 1H), 4.76 (s, 2H), 4.03 (dd, J=7.5, 4.5 Hz, 1H), 4.00-3.85 (m, 2H), 3.68-3.55 (m, 2H), 3.55-3.43 (m, 2H), 2.76-2.56 (m, 2H), 2.27-2.05 (m, 2H), 1.82-1.10 (m, 15H), 1.05-0.83 (m, 2H), 0.92 (t, J=7.2 Hz, 3H).

EXAMPLE 24(11)

1-butyl-2,5-dioxo-3-(benzyloxycarbonylmethyl)-9-(4-phenyloxyphenylmethyl)-1,4,9-triazaspiro[5.5]undecane.hydrochloride

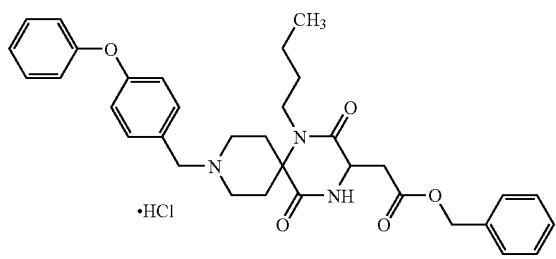

TLC: Rf 0.74 (chloroform:methanol=9:1); NMR (CD$_3$OD): δ 7.52 (d, J=7.0 Hz, 2H), 7.40 (t, J=7.5 Hz, 2H), 7.33 (m, 5H), 7.18 (t, J=7.5 Hz, 1H), 7.05 (m, 4H), 5.12 (s, 2H), 4.33 (s, 2H), 4.31 (m, 1H), 3.88 (m, 1H), 3.66 (m, 1H), 3.50-3.35 (m, 4H), 3.08 (dd, J=17.7, 4.8 Hz, 1H), 2.86 (dd, J=17.7, 3.0 Hz, 1H), 2.34 (m, 2H), 2.25 (m, 2H), 1.50 (m, 2H), 1.36 (m, 2H), 0.94 (t, J=7.5 Hz, 3H).

EXAMPLE 24(12)

1-(3-methyl-2-butenyl)-2,5-dioxo-3-cyclohexylmethyl-9-(1,4-benzodioxan-6-ylmethyl)-1,4,9-triazaspiro[5.5]undecane.hydrochloride

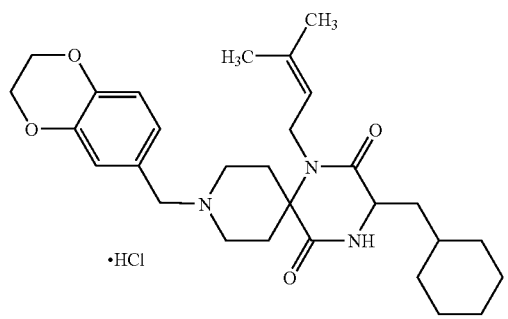

TLC: Rf 0.63 (chloroform:methanol=10:1); NMR (CD$_3$OD): δ 7.04 (d, J=2.1 Hz, 1H), 6.96 (dd, J=8.1, 2.1 Hz, 1H), 6.92 (d, J=8.1 Hz, 1H), 4.96 (m, 1H), 4.26 (s, 4H), 4.22 (s, 2H), 4.10-4.00 (m, 3H), 3.84-3.68 (m, 2H), 3.52-3.40 (m, 2H), 2.43-2.08 (m, 4H), 1.84-1.42 (m, 13H), 1.38-1.12 (m, 4H), 1.04-0.85 (m, 2H).

EXAMPLE 24(13)

1-butyl-2,5-dioxo-3-cyclohexylmethyl-9-((2E)-3-phenyl-2-propenyl)-1,4,9-triazaspiro[5.5]undecane-.hydrochloride

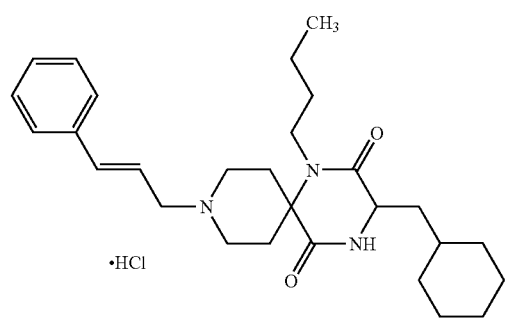

TLC: Rf 0.28 (chloroform:methanol=20:1); NMR (CD$_3$OD): δ 7.53-7.48 (m, 2H), 7.30-7.40 (m, 3H), 6.95 (d, J=16.2 Hz, 1H), 6.36 (dd, J=16.2, 8.1 Hz, 1H), 4.07 (dd, J=7.5, 4.5 Hz, 1H), 3.96 (d, J=8.1 Hz, 2H), 3.86-3.75 (m, 2H), 3.60-3.52 (m, 2H), 3.42-3.34 (m, 2H), 2.42-2.18 (m, 4H), 1.82-1.14 (m, 15H), 0.96 (t, J=7.2 Hz, 3H), 0.96 (m, 2H).

EXAMPLE 24(14)

(3S)-1-butyl-2,5-dioxo-3-(1,1-dimethylethyl)-9-(4-phenyloxyphenylmethyl)-1,4,9-triazaspiro[5.5]undecane.hydrochloride

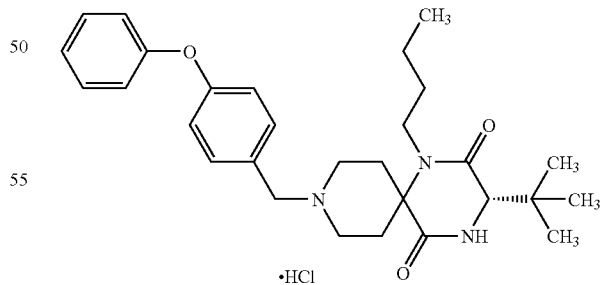

TLC: Rf 0.50 (chloroform:methanol=10:1); NMR (CD$_3$OD): δ 7.54 (d, J=8.5 Hz, 2H), 7.39 (m, 2H), 7.18 (t, J=7.5 Hz, 1H), 7.08-7.02 (m, 4H), 4.34 (s, 2H), 3.88 (m, 2H), 3.62 (s, 1H), 3.46 (m, 4H), 2.45 (m, 2H), 2.13 (m, 2H), 1.66-1.47 (m, 2H), 1.36 (m, 2H), 1.02 (s, 9H), 0.95 (t, J=7.0 Hz, 3H).

EXAMPLE 24(15)

(3S)-1-butyl-2,5-dioxo-3-(1,1-dimethylethyl)-9-(1,4-benzodioxan-6-ylmethyl)-1,4,9-triazaspiro[5.5]undecane.hydrochloride

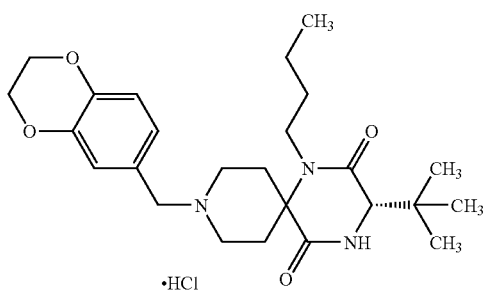

TLC: Rf 0.47 (chloroform:methanol=10:1); NMR (CD$_3$OD): δ 7.07 (m, 1H), 6.99 (d, J=8.0 Hz, 1H), 6.91 (d, J=8.0 Hz, 1H), 4.26 (m, 4H), 4.24 (s, 2H), 3.83 (m, 2H), 3.62 (s, 1H), 3.45 (m, 4H), 2.42 (m, 2H), 2.11 (m, 2H), 1.64-1.5 (m, 2H), 1.38 (m, 2H), 1.01 (s, 9H), 0.95 (t, J=7.0 Hz, 3H).

EXAMPLE 24(16)

1-butyl-2,5-dioxo-3-(2-methylpropyl)-9-(4-methylthiazol-2-ylmethyl)-1,4,9-triazaspiro[5.5]undecane.hydrochloride

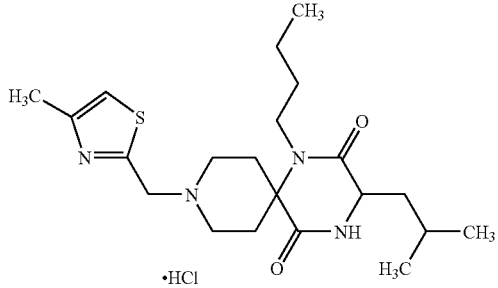

TLC: Rf 0.67 (chloroform:methanol=10:1); NMR (CD$_3$OD): δ 7.34 (s, 1H), 4.73 (s, 2H), 4.01 (dd, J=8.0, 4.5 Hz, 1H), 3.93 (m, 2H), 3.65 (m, 2H), 3.41 (m, 2H), 2.53-2.41 (m, 2H), 2.48 (s, 3H), 2.23 (m, 2H), 1.85-1.52 (m, 5H), 1.38 (m, 2H), 0.96 (t, J=7.0 Hz, 3H), 0.94 (d, J=6.5 Hz, 3H), 0.93 (d, J=6.5 Hz, 3H).

EXAMPLE 24(17)

1-butyl-2,5-dioxo-3-cyclohexylmethyl-9-(5-methylthiazol-2-ylmethyl)-1,4,9-triazaspiro[5.5]undecane.hydrochloride

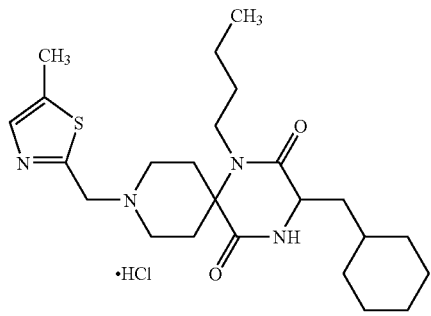

TLC: Rf 0.66 (chloroform:methanol=10:1); NMR (CD$_3$OD): δ 7.34 (s, 1H), 4.72 (s, 2H), 4.04 (dd, J=7.5, 4.5 Hz, 1H), 3.98-3.86 (m, 2H), 3.67-3.63 (m, 2H), 3.44-3.38 (m, 2H), 2.56-2.42 (m, 2H), 2.48 (s, 3H), 2.30-2.14 (m, 2H), 1.84-1.18 (m, 15H), 0.96 (t, J=7.2 Hz, 3H), 0.96 (m, 2H).

EXAMPLE 24(18)

1-butyl-2,5-dioxo-3-cyclohexylmethyl-9-(4-methylthiazol-2-ylmethyl)-1,4,9-triazaspiro[5.5]undecane.hydrochloride

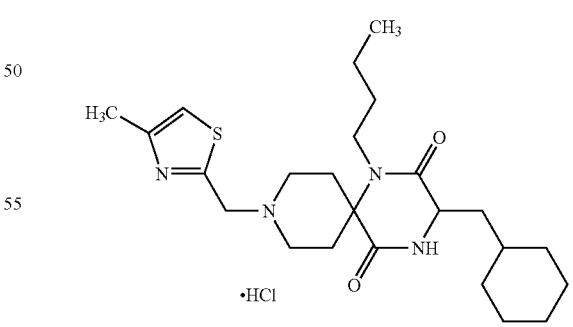

TLC: Rf 0.63 (chloroform:methanol=10:1); NMR (CD$_3$OD): δ 7.63 (s, 1H), 4.69 (s, 2H), 4.03 (dd, J=7.3, 4.5 Hz, 1H), 3.96-3.82 (m, 2H), 3.72-3.58 (m, 2H), 3.42-3.37 (m, 2H), 2.52 (s, 3H), 2.56-2.36 (m, 2H), 2.28-2.12 (m, 2H), 1.80-1.12 (m, 15H), 0.96 (t, J=7.5 Hz, 3H), 0.96 (m, 2H).

EXAMPLE 24(19)

1-butyl-2,5-dioxo-3-(2-methylpropyl)-9-(5-methylthiazol-2-ylmethyl)-1,4,9-triazaspiro[5.5]undecane.hydrochloride

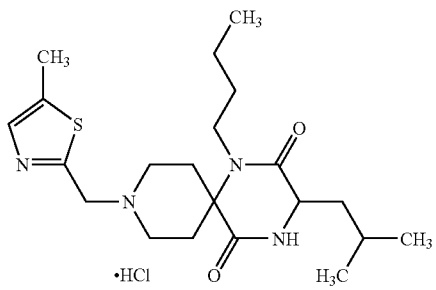

TLC: Rf 0.70 (chloroform:methanol=10:1); NMR (CD$_3$OD): δ 7.63 (s, 1H), 4.69 (brs, 2H), 4.01 (dd, J=7.8, 4.5 Hz, 1H), 3.99-3.83 (m, 2H), 3.70-3.58 (m, 2H), 3.44-3.34 (m, 2H), 2.53 (s, 3H), 2.50-2.33 (m, 2H), 2.32-2.12 (m, 2H), 1.88-1.46 (m, 5H), 1.45-1.31 (m, 2H), 1.01-0.90 (m, 9H).

EXAMPLE 24(20)

(3R)-1-butyl-2,5-dioxo-3-cyclohexylmethyl-9-(1,4-benzodioxan-6-ylmethyl)-1,4,9-triazaspiro[5.5]undecane.hydrochloride

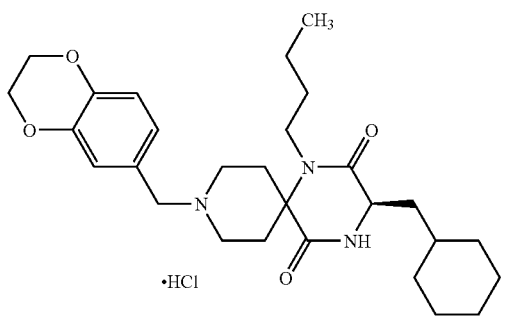

TLC: Rf 0.59 (chloroform:methanol=10:1); NMR (CD$_3$OD): δ 7.04 (d, J=2.0 Hz, 1H), 6.97 (dd, J=8.5, 2.0 Hz, 1H), 6.93 (d, J=8.5 Hz, 1H), 4.26 (s, 4H), 4.24 (s, 2H), 4.04 (dd, J=7.5, 5.0 Hz, 1H), 3.76 (m, 2H), 3.46 (m, 4H), 2.39-2.11 (m, 4H), 1.78-1.17 (m, 15H), 0.95 (t, J=7.0 Hz, 3H), 0.95 (m, 2H). HPLC condition Column: YMC CHIRAL-CD BR, 0.46×25 cm, YMC, DB12S05-2546WTI; Flow rate: 0.5 mL/min; eluent Component A: 0.1M potassium dihydrogenphosphate aqueous solution Component B: acetonitrile A:B=84:16; UV: 235 nm; Retention time: 18 min.

EXAMPLE 24(21)

(3S)-1-butyl-2,5-dioxo-3-cyclohexylmethyl-9-(1,4-benzodioxan-6-ylmethyl)-1,4,9-triazaspiro[5.5]undecane.hydrochlori

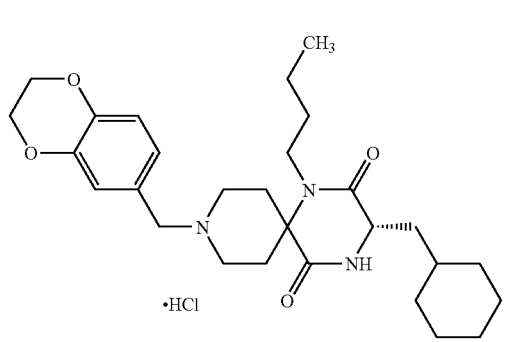

TLC: Rf 0.59 (chloroform:methanol=10:1); NMR (CD$_3$OD): δ 7.04 (d, J=2.0 Hz, 1H), 6.97 (dd, J=8.5, 2.0 Hz, 1H), 6.93 (d, J=8.5 Hz, 1H), 4.26 (s, 4H), 4.24 (s, 2H), 4.04 (dd, J=7.5, 5.0 Hz, 1H), 3.76 (m, 2H), 3.46 (m, 4H), 2.39-2.11 (m, 4H), 1.78-1.17 (m, 15H), 0.95 (t, J=7.0 Hz, 3H), 0.95 (m, 2H). HPLC condition Column: YMC CHIRAL-CD BR, 0.46×25 cm, YMC, DB12S05-2546WTI; Flow rate: 0.5 mL/min; Eluent Component A: 0.1M potassium dihydrogenphosphate aqueous solution Component B: acetonitrile A:B=84:16; UV: 235 nm; Retention time: 20 min.

EXAMPLE 24(22)

(3R)-1-butyl-2,5-dioxo-3-((1R)-1-methylpropyl)-9-(4-phenyloxyphenylmethyl)-1,4,9-triazaspiro[5.5]undecane.hydrochloride

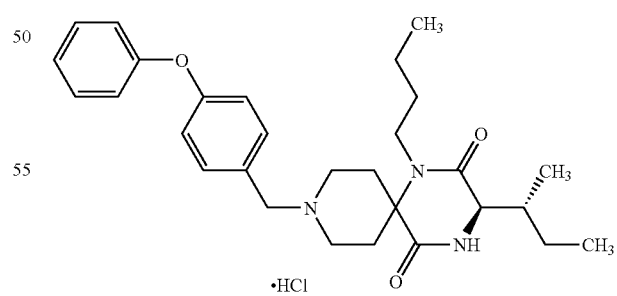

TLC: Rf 0.59 (chloroform:methanol=10:1); NMR (CD$_3$OD): δ 7.53 (d, J=8.5 Hz, 2H), 7.39 (m, 2H), 7.18 (t, J=7.5 Hz, 1H), 7.08-7.01 (m, 4H), 4.33 (s, 2H), 3.96 (d, J=2.5 Hz, 1H), 3.92 (m, 1H), 3.75 (m, 1H), 3.53-3.44 (m, 4H), 2.49-2.32 (m, 2H), 2.16 (m, 2H), 2.06-1.98 (m, 1H), 1.61-1.21 (m, 6H), 1.00-0.89 (m, 9H).

EXAMPLE 24(23)

(3S)-1-butyl-2,5-dioxo-3-((1S)-1-methylpropyl)-9-(4-phenyloxyphenylmethyl)-1,4,9-triazaspiro[5.5]undecane.hydrchloride

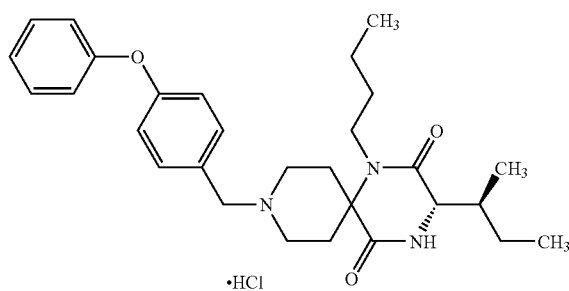

TLC: Rf 0.59 (chloroform:methanol=10:1); NMR (CD$_3$OD): δ 7.53 (d, J=8.5 Hz, 2H), 7.39 (m, 2H), 7.18 (t, J=7.5 Hz, 1H), 7.08-7.01 (m, 4H), 4.33 (s, 2H), 3.96 (d, J=2.5 Hz, 1H), 3.92 (m, 1H), 3.75 (m, 1H), 3.53-3.44 (m, 4H), 2.49-2.32 (m, 2H), 2.16 (m, 2H), 2.06-1.98 (m, 1H), 1.61-1.21 (m, 6H), 1.00-0.89 (m, 9H).

EXAMPLE 24(24)

1-(2-butynyl)-2,5-dioxo-3-(2-methylpropyl)-9-(4-phenyloxyphenylmethyl)-1,4,9-triazaspiro[5.5]undecane.hydrochloride

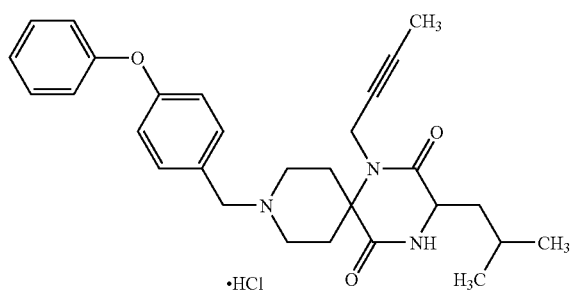

TLC: Rf 0.70 (chloroform:methanol=10:1); NMR (CD$_3$OD): δ 7.51 (d, J=8.7 Hz, 2H), 7.39 (dd, J=8.7, 7.2 Hz, 2H), 7.18 (t, J=7.2 Hz, 1H), 7.09-7.00 (m, 4H), 4.33 (brs, 2H), 4.28-4.10 (m, 2H), 4.05 (dd, J=7.8, 4.5 Hz, 1H), 3.86-3.70 (m, 2H), 3.56-3.43 (m, 2H), 2.59-2.40 (m, 2H), 2.34-2.15 (m, 2H), 1.89-1.57 (m, 6H), 0.94 (d, J=6.6 Hz, 3H), 0.93 (d, J=6.6 Hz, 3H).

EXAMPLE 24(25)

1-(2-butynyl)-2,5-dioxo-3-cyclohexylmethyl-9-(1,4-benzodioxan-6-ylmethyl)-1,4,9-triazaspiro[5.5]undecane.hydrochloride

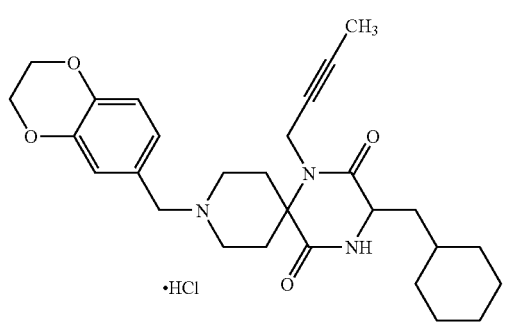

TLC: Rf 0.52 (chloroform:methanol=10:1); NMR (CD$_3$OD): δ 7.04 (d, J=2.1 Hz, 1H), 6.97 (dd, J=8.4, 2.1 Hz, 1H), 6.93 (d, J=8.4 Hz, 1H), 4.26 (s, 4H), 4.23 (s, 2H), 4.18 (brs, 2H), 4.07 (dd, J=6.9, 4.8 Hz, 1H), 3.84-3.68 (m, 2H), 3.55-3.42 (m, 2H), 2.57-2.40 (m, 2H), 2.32-2.12 (m, 2H), 1.85-1.42 (m, 11H), 1.38-1.13 (m, 3H), 1.04-0.85 (m, 2H).

EXAMPLE 24(26)

1-pentyl-2,5-dioxo-3-cyclohexylmethyl-9-(1,4-benzodioxan-6-ylmethyl)-1,4,9-triazaspiro[5.5]undecane.hydrochloride

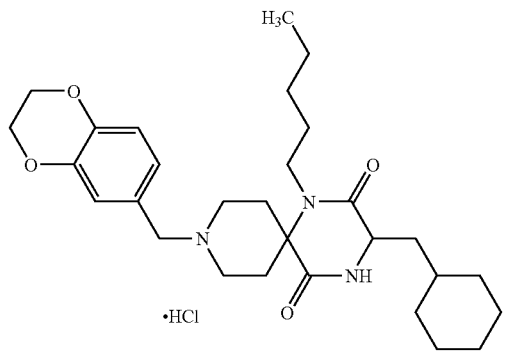

TLC: Rf 0.61 (chloroform:methanol=10:1); NMR (CD$_3$OD): δ 7.04 (d, J=2.1 Hz, 1H), 6.97 (dd, J=8.4, 2.1 Hz, 1H), 6.92 (d, J=8.4 Hz, 1H), 4.26 (s, 4H), 4.22 (brs, 2H), 4.03 (dd, J=7.2, 4.5 Hz, 1H), 3.84-3.67 (m, 2H), 3.52-3.33 (m, 4H), 2.43-2.07 (m, 4H), 1.83-1.42 (m, 9H), 1.41-1.13 (m, 8H), 1.04-0.85 (m, 5H).

EXAMPLE 24(27)

1-(3-methoxyphenylmethyl)-2,5-dioxo-3-(benzyloxymethyl)-9-(3,5-dimethyl-1-phenylpyrazol-4-ylmethyl)-1,4,9-triazaspiro[5.5]undecane.2 hydrochlride

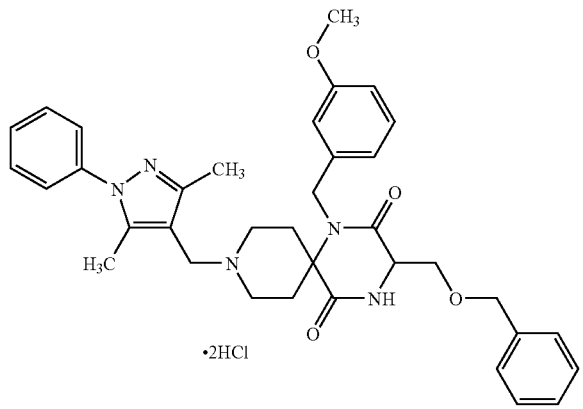

TLC: Rf 0.45 (chloroform:methanol=10:1); NMR (CD$_3$OD): δ 7.60-7.43 (m, 5H), 7.38-7.24 (m, 5H), 7.14 (t, J=8.4 Hz, 1H), 6.83-6.72 (m, 3H), 4.96-4.70 (m, 2H), 4.60 (d, J=11.4 Hz, 1H), 4.50 (d, J=11.4 Hz, 1H), 4.29 (t, J=2.4 Hz, 1H), 4.24 (s, 2H), 4.02 (dd, J=9.6, 2.4 Hz, 1H), 3.93-3.79 (m, 1H), 3.72 (s, 3H), 3.70 (dd, J=9.6, 2.4 Hz, 1H), 3.70-3.60 (m, 1H), 3.55-3.44 (m, 1H), 3.35-3.23 (m, 1H), 2.58-2.05 (m, 10H).

EXAMPLE 24(28)

(3R)-1-butyl-2,5-dioxo-3-(2-methylpropyl)-9-(4-phenyloxyphenylmethyl)-1,4,9-triazaspiro[5.5]undecane.hydrochloride

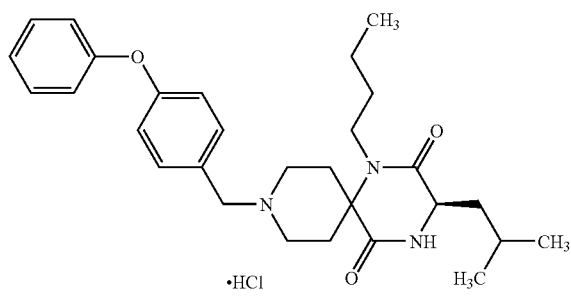

TLC: Rf 0.29 (chloroform:methanol=10:1); NMR (CD$_3$OD): δ 7.54 (d, J=8.7 Hz, 2H), 7.42-7.36 (m, 2H), 7.18 (m, 1H), 7.05 (d, J=8.7 Hz, 2H), 7.05-7.02 (m, 2H), 4.32 (s, 2H), 4.01 (dd, J=7.8, 4.8 Hz, 1H), 3.85-3.72 (m, 2H), 3.50-3.39 (m, 4H), 2.52-2.38 (m, 2H), 2.24-2.11 (m, 2H), 1.84-1.20 (m, 7H), 0.95 (t, J=7.2 Hz, 3H), 0.95 (d, J=6.3 Hz, 3H), 0.93 (d, J=6.3 Hz, 3H). HPLC condition Column: CHIRALCEL OD-R, 0.46×25 cm, DAICEL, ODR0CE-HD028; Flow rate: 0.4 mL/min; Eluent Component A: 0.2M potassium dihydrogenphosphate aqueous solution Component B: acetonitrile A:B=64:36; UV: 235 nm; Retention time: 30 min.

EXAMPLE 24(29)

(3S)-1-butyl-2,5-dioxo-3-(2-methylpropyl)-9-(4-phenyloxyphenylmethyl)-1,4,9-triazaspiro[5.5]undecane.hydrochloride

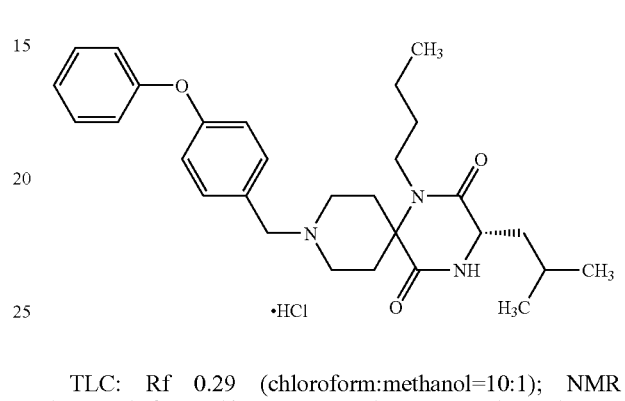

TLC: Rf 0.29 (chloroform:methanol=10:1); NMR (CD$_3$OD): δ 7.54 (d, J=8.7 Hz, 2H), 7.42-7.36 (m, 2H), 7.18 (m, 1H), 7.05 (d, J=8.7 Hz, 2H), 7.05-7.02 (m, 2H), 4.33 (s, 2H), 3.98 (dd, J=8.1, 4.5 Hz, 1H), 3.86-3.72 (m, 2H), 3.53-3.37 (m, 4H), 2.47-2.36 (m, 2H), 2.24-2.12 (m, 2H), 1.80-1.30 (m, 7H), 0.95 (t, J=7.2 Hz, 3H), 0.95 (d, J=6.3 Hz, 3H), 0.93 (d, J=6.3 Hz, 3H). HPLC condition Column: CHIRALCEL OD-R, 0.46×25 cm, DAICEL, ODR0CE-HD028; Flow rate: 0.4 mL/min; Eluent Component A: 0.2M potassium dihydrogenphosphate aqueous solution Component B: acetonitrile A:B=64:36; UV: 235 nm; Retention time: 28 min.

EXAMPLE 24(30)

1-butyl-2,5-dioxo-3-cyclopentylmethyl-9-(1,4-benzodioxan-6-ylmethyl)-1,4,9-triazaspiro[5.5]undecane.hydrochloride

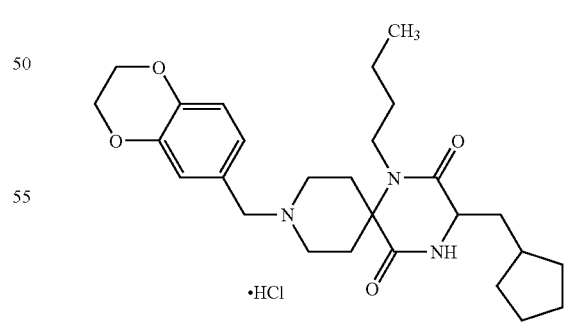

TLC: Rf 0.53 (chloroform:methanol=10:1); NMR (CD$_3$OD): δ 7.05 (d, J=2.0 Hz, 1H), 6.98 (dd, J=8.5, 2.0 Hz, 1H), 6.93 (d, J=8.5 Hz, 1H), 4.26 (s, 4H), 4.23 (s, 2H), 3.99 (t, J=6.0 Hz, 1H), 3.77 (m, 2H), 3.46 (m, 2H), 3.37 (m, 2H), 2.36 (m, 2H), 2.15 (m, 2H), 1.96 (m, 1H), 1.81 (m, 4H), 1.59 (m, 6H), 1.36 (m, 2H), 1.15 (m, 2H), 0.95 (t, J=7.0 Hz, 3H).

EXAMPLE 24(31)

1-propyl-2,5-dioxo-3-(cyclohexylmethyloxymethyl)-9-(3,5-dimethyl-1-phenylpyrazol-4-ylmethyl)-1,4,9-triazaspiro[5.5]undecane.2 hydrochloride

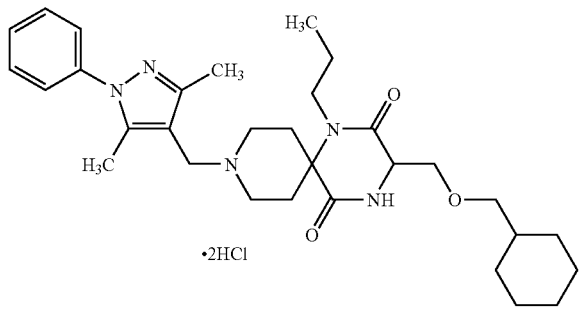

TLC: Rf 0.63 (chloroform:methanol=10:1); NMR (CD$_3$OD): δ 7.59-7.46 (m, 5H), 4.33 (s, 2H), 4.08 (m, 1H), 4.00 (m, 1H), 3.83 (m, 1H), 3.77 (m, 1H), 3.59 (m, 2H), 3.52 (m, 1H), 3.25 (d, J=6.5 Hz, 2H), 2.53 (m, 2H), 2.42 (m, 1H), 2.40 (s, 3H), 2.39 (s, 3H), 2.21 (m, 2H), 1.69 (m, 6H), 1.52 (m, 2H), 1.21 (m, 4H), 0.95 (t, J=7.0 Hz, 3H), 0.88 (m, 2H).

EXAMPLE 24(32)

(3S)-1-butyl-2,5-dioxo-3-(1-methylpropyl)-9-(1,4-benzodioxan-6-ylmethyl)-1,4,9-triazaspiro[5.5]undecane.hydrochloride

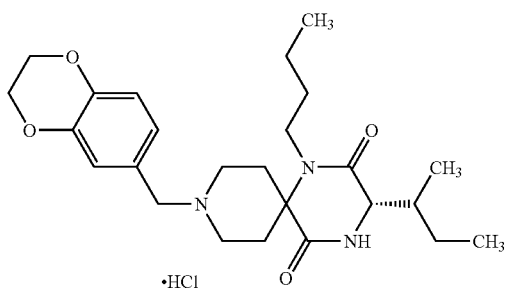

TLC: Rf 0.47 (chloroform:methanol=10:1); NMR (CD$_3$OD): δ 7.06-6.90 (m, 3H), 4.26 (s, 4H), 4.23 (s, 2H), 3.95 (d, J=3.3 Hz, 1H), 3.87 (m, 1H), 3.70 (m, 1H), 3.58-3.42 (m, 4H), 2.56-2.30 (m, 2H), 2.20-1.98 (m, 2H), 1.54-1.00 (m, 7H), 0.99 (d, J=7.2 Hz, 3H), 0.95 (t, J=7.5 Hz, 3H), 0.91 (t, J=7.5 Hz, 3H).

EXAMPLE 24(33)

(3R)-1-butyl-2,5-dioxo-3-(1-methylpropyl)-9-(1,4-benzodioxan-6-ylmethyl)-1,4,9-triazaspiro[5.5]undecane.hydrochloride

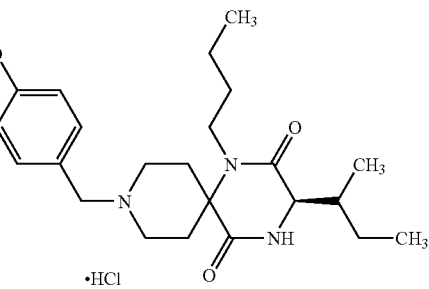

TLC: Rf 0.47 (chloroform:methanol=10:1); NMR (CD$_3$OD): δ 7.06-6.91 (m, 3H), 4.26 (s, 4H), 4.23 (s, 2H), 3.95 (d, J=3.3 Hz, 1H), 3.87 (m, 1H), 3.70 (m, 1H), 3.56-3.40 (m, 4H), 2.50-2.32 (m, 2H), 2.18-1.96 (m, 2H), 1.62-1.17 (m, 7H), 0.99 (d, J=7.2 Hz, 3H), 0.95 (t, J=7.2 Hz, 3H), 0.91 (t, J=7.5 Hz, 3H).

EXAMPLE 24(34)

1-butyl-2,5-dioxo-3-(2-methylpropyl)-9-(5-phenylmethylthiophen-2-ylmethyl)-1,4,9-triazaspiro[5.5]undecane.hydrochloride

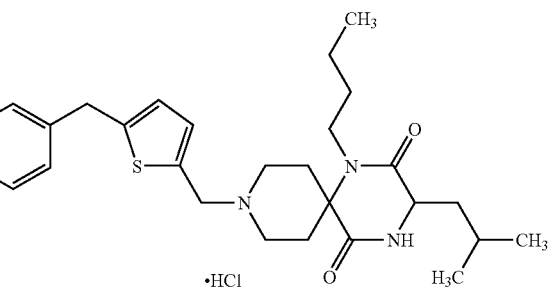

TLC: Rf 0.56 (chloroform:methanol=10:1); NMR (CD$_3$OD): δ 7.32-7.21 (m, 5H), 7.17 (d, J=3.6 Hz, 1H), 6.89 (d, J=3.6 Hz, 1H), 4.51 (s, 2H), 4.17 (s, 2H), 4.00 (dd, J=7.8 Hz, 4.5 Hz, 1H), 3.84-3.72 (m, 2H), 3.56-3.44 (m, 2H), 3.38-3.32 (m, 2H), 2.42-2.14 (m, 4H), 1.84-1.30 (m, 7H), 0.95 (t, J=6.9 Hz, 3H), 0.94 (d, J=6.3 Hz, 3H), 0.92 (d, J=6.3 Hz, 3H).

EXAMPLE 24(35)

1-butyl-2,5-dioxo-3-cyclohexylmethyl-9-(2-phenyl-methylthiophen-5-ylmethyl)-1,4,9-triazaspiro[5.5]undecane.hydrochloride

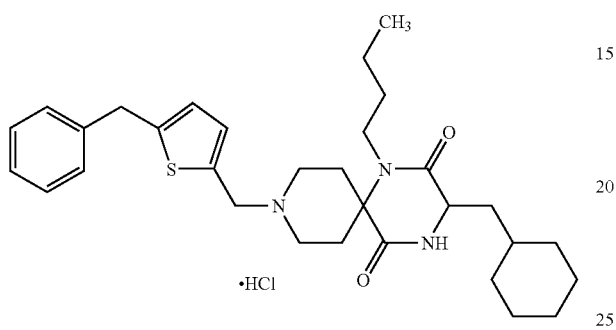

TLC: Rf 0.59 (chloroform:methanol=10:1); NMR (CD$_3$OD): δ 7.32-7.21 (m, 5H), 7.18 (d, J=3.6 Hz, 1H), 6.89 (d, J=3.6 Hz, 1H), 4.51 (s, 2H), 4.17 (s, 2H), 4.03 (dd, J=7.8, 4.8 Hz, 1H), 3.84-3.72 (m, 2H), 3.58-3.44 (m, 2H), 3.40-3.36 (m, 2H), 2.44-2.08 (m, 4H), 1.81-1.07 (m, 15H), 0.95 (t, J=7.2 Hz, 3H), 0.95 (m, 2H).

EXAMPLE 24(36)

(3R)-1-butyl-2,5-dioxo-3-(2,2-dimethylpropyl)-9-(1,4-benzodioxan-6-ylmethyl)-1,4,9-triazaspiro[5.5]undecane.hydrochloride

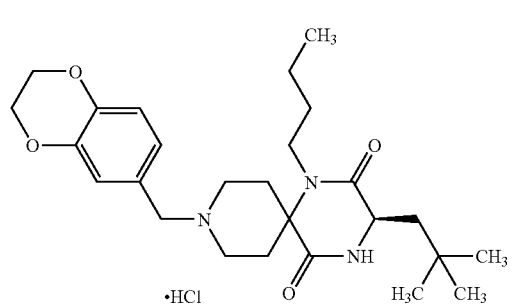

TLC: Rf 0.41 (chloroform:methanol=20:1); NMR (CD$_3$OD): δ 7.05 (s, 1H), 6.98 (d, J=8.4 Hz, 1H), 6.92 (d, J=8.4 Hz, 1H), 4.26 (s, 4H), 4.23 (s, 2H), 4.00 (dd, J=7.0, 3.0 Hz, 1H), 3.83-3.64 (m, 2H), 3.50 (m, 2H), 3.38 (m, 2H), 2.35 (m, 2H), 2.25 (m, 2H), 1.99 (m, 1H), 1.55 (m, 1H), 1.50 (m, 2H), 1.35 (m, 2H), 0.99 (s, 9H), 0.95 (t, J=7.0 Hz, 3H).

EXAMPLE 24(37)

(3S)-1-butyl-2,5-dioxo-3-(2,2-dimethylpropyl)-9-(1,4-benzodioxan-6-ylmethyl)-1,4,9-triazaspiro[5.5]undecane.hydrochloride

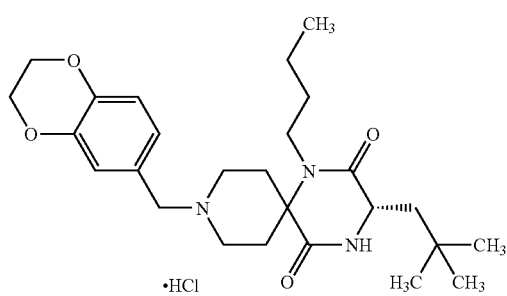

TLC: Rf 0.41 (chloroform:methanol=20:1); NMR (CD$_3$OD): δ 7.05 (s, 1H), 6.98 (d, J=8.4 Hz, 1H), 6.92 (d, J=8.4 Hz, 1H), 4.26 (s, 4H), 4.23 (s, 2H), 4.00 (dd, J=7.0, 3.0 Hz, 1H), 3.83-3.63 (m, 2H), 3.50 (m, 2H), 3.38 (m, 2H), 2.35 (m, 2H), 2.25 (m, 2H), 1.99 (dd, J=14.0, 3.0 Hz, 1H), 1.55 (dd, J=14.0, 7.0 Hz, 1H), 1.50 (m, 2H), 1.35 (m, 2H), 0.99 (s, 9H), 0.95 (t, J=7.0 Hz, 3H).

EXAMPLE 24(38)

(3R)-1-(2-butynyl)-2,5-dioxo-3-(2,2-dimethylpropyl)-9-(4-phenyloxyphenylmethyl)-1,4,9-triazaspiro[5.5]undecane.hydrochloride

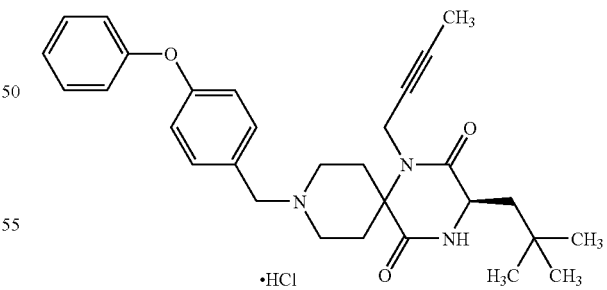

TLC: Rf 0.60 (chloroform:methanol=10:1); NMR (CD$_3$OD): δ 7.51 (d, J=8.7 Hz, 2H), 7.39 (dd, J=8.7, 7.5 Hz, 2H), 7.18 (t, J=7.5 Hz, 1H), 7.10-7.00 (m, 4H), 4.33 (brs, 2H), 4.33-4.09 (m, 2H), 4.03 (dd, J=6.9, 3.3 Hz, 1H), 3.85-3.68 (m, 2H), 3.58-3.43 (m, 2H), 2.59-2.41 (m, 2H), 2.40-2.20 (m, 2H), 2.03 (dd, J=14.4, 3.3 Hz, 1H), 1.75 (brs, 3H), 1.56 (dd, J=14.4, 6.9 Hz, 1H), 0.99 (s, 9H).

EXAMPLE 24(39)

(3S)-1-(2-butynyl)-2,5-dioxo-3-(2,2-dimethylpropyl)-9-(4-phenyloxyphenylmethyl)-1,4,9-triazaspiro[5.5]undecane.hydrochloride

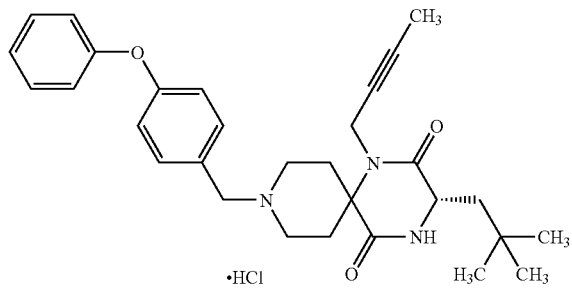

TLC: Rf 0.60 (chloroform:methanol=10:1); NMR (CD$_3$OD): δ 7.51 (d, J=8.7 Hz, 2H), 7.39 (dd, J=8.7, 7.5 Hz, 2H), 7.18 (t, J=7.5 Hz, 1H), 7.10-7.00 (m, 4H), 4.33 (brs, 2H), 4.33-4.09 (m, 2H), 4.03 (dd, J=6.9, 3.3 Hz, 1H), 3.85-3.68 (m, 2H), 3.58-3.43 (m, 2H), 2.59-2.41 (m, 2H), 2.40-2.20 (m, 2H), 2.03 (dd, J=14.4, 3.3 Hz, 1H), 1.75 (brs, 3H), 1.56 (dd, J=14.4, 6.9 Hz, 1H), 0.99 (s, 9H).

EXAMPLE 24(40)

1-butyl-2,5-dioxo-3-cycloheptylmethyl-9-(1,4-benzodioxan-6-ylmethyl)-1,4,9-triazaspiro[5.5]undecane.hydrochloride

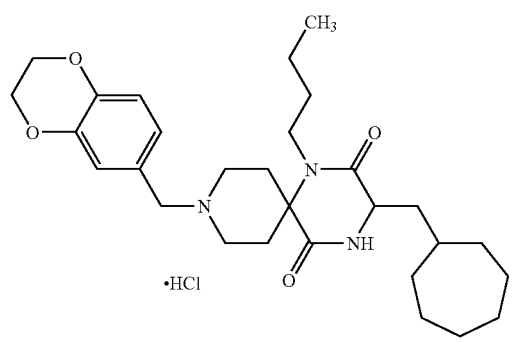

TLC: Rf 0.70 (chloroform:methanol=10:1); NMR (CD$_3$OD): δ 7.04 (d, J=2.1 Hz, 1H), 6.97 (dd, J=8.4, 2.1 Hz, 1H), 6.93 (d, J=8.4 Hz, 1H), 4.26 (s, 4H), 4.24 (s, 2H), 3.99 (dd, J=8.1, 4.2 Hz, 1H), 3.84-3.70 (m, 2H), 3.45 (m, 2H), 3.36 (m, 2H), 2.37-2.11(m, 4H), 1.80-1.49 (m, 15H), 1.36 (m, 2H), 1.22 (m, 2H), 0.95 (t, J=7.5 Hz, 3H).

EXAMPLE 24(41)

1-butyl-2,5-dioxo-3-cyclohexylmethyl-9-(2,4,6-trimethoxyphenylmethyl)-1,4,9-triazaspiro[5.5]undecane.hydrochloride

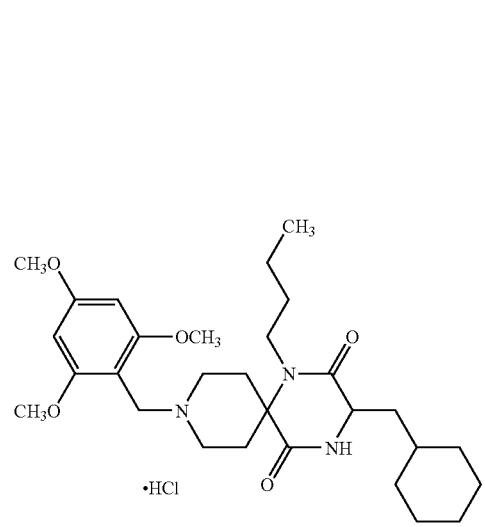

TLC: Rf 0.55 (chloroform:methanol=10:1); NMR (CD$_3$OD): δ 6.31 (s, 2H), 4.26 (s, 2H), 4.03 (dd, J=7.8, 4.5 Hz, 1H), 3.89 (s, 6H), 3.84 (s, 3H), 3.84-3.73 (m, 2H), 3.54-3.33 (m, 4H), 2.44-2.25 (m, 2H), 2.24-2.03 (m, 2H), 1.84-1.12 (m, 15H), 1.06-0.85 (m, 5H).

EXAMPLE 24(42)

1-butyl-2,5-dioxo-3-(3-cyclohexylpropyl)-9-(1,4-benzodioxan-6-ylmethyl)-1,4,9-triazaspiro[5.5]undecane.hydrochloride

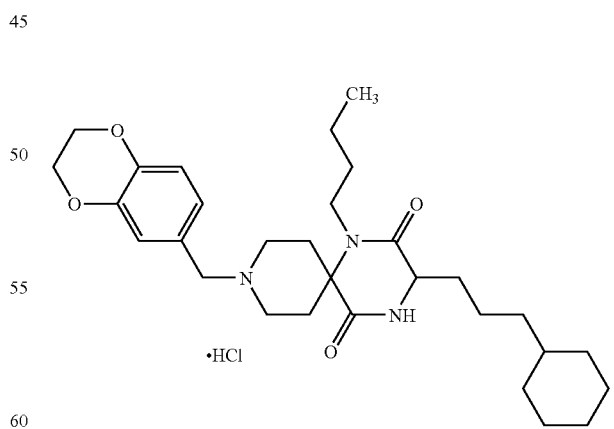

TLC: Rf 0.71 (chloroform:methanol=10:1); NMR (CD$_3$OD): δ 7.05-6.91 (m, 3H), 4.26 (s, 4H), 4.22 (s, 2H), 4.04 (t, J=5.4 Hz, 1H), 3.84 (m, 1H), 3.67 (m, 1H), 3.54-3.40 (m, 3H), 3.35 (m, 1H), 2.44-2.08 (m, 4H), 1.90-1.16 (m, 19H), 0.95 (t, J=7.5 Hz, 3H), 0.95 (m, 2H).

EXAMPLE 24(43)

1-butyl-2,5-dioxo-3-(3-cyclohexylpropyl)-9-(4-phenyloxyphenylmethyl)-1,4,9-triazaspiro[5.5]undecane.hydrochloride

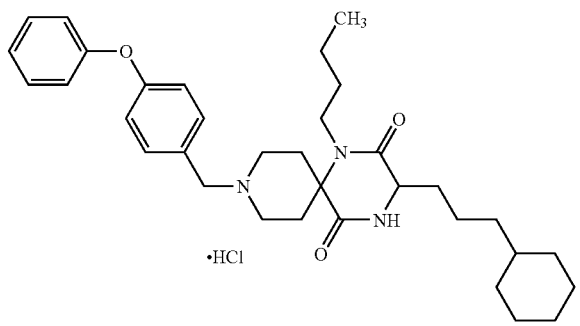

TLC: Rf 0.76 (chloroform:methanol=10:1); NMR (CD$_3$OD): δ 7.53-7.49 (m, 2H), 7.42-7.36 (m, 2H), 7.18 (m, 1H), 7.10-7.02 (m, 4H), 4.32 (s, 2H), 4.04 (t, J=4.8 Hz, 1H), 3.87 (m, 1H), 3.71 (m, 1H), 3.56-3.40 (m, 3H), 3.35 (m, 1H), 2.48-2.12 (m, 4H), 1.86-1.10 (m, 19H), 0.95 (t, J=7.5 Hz, 3H), 0.95 (m, 2H).

EXAMPLE 24(44)

1-butyl-2,5-dioxo-3-(3-cyclohexylpropyl)-9-(3,5-dimethyl-1-phenylpyrazol-4-ylmethyl)-1,4,9-triazaspiro[5.5]undecane.2 hydrochloride

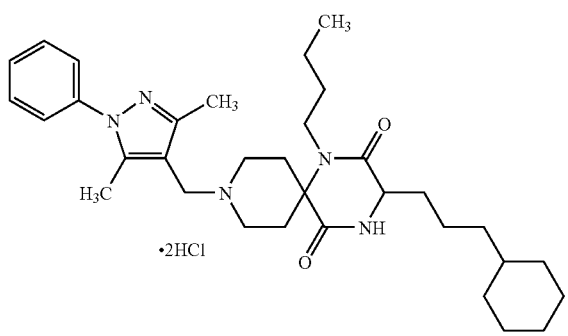

TLC: Rf 0.64 (chloroform:methanol=10:1); NMR (CD$_3$OD): δ 7.59-7.45 (m, 5H), 4.31 (s, 2H), 4.06 (t, J=5.0 Hz, 1H), 3.92 (m, 1H), 3.77 (m, 1H), 3.63-3.37 (m, 4H), 2.44 (m, 2H), 2.39 (s, 3H), 2.38 (s, 3H), 2.21 (m, 2H), 1.85-1.68 (m, 7H), 1.54 (m, 2H), 1.39 (m, 4H), 1.23 (m, 6H), 0.96 (t, J=7.5 Hz, 3H), 0.89 (m, 2H).

EXAMPLE 24(45)

1-butyl-2,5-dioxo-3-(2-hydroxy-2-methylpropyl)-9-(4-phenyloxyphenylmethyl)-1,4,9-triazaspiro[5.5]undecane.hydrochloride

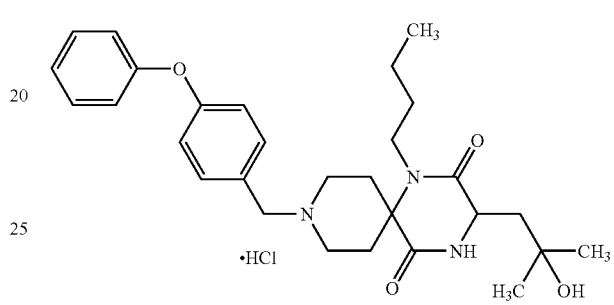

TLC: Rf 0.52 (chloroform:methanol=10:1); NMR (CD$_3$OD): δ 7.50 (d, J=8.7 Hz, 2H), 7.39 (dd, J=8.7, 7.5 Hz, 2H), 7.18 (t, J=7.5 Hz, 1H), 7.09-7.00 (m, 4H), 4.32 (brs, 2H), 4.29 (dd, J=9.9, 3.0 Hz, 1H), 4.04-3.88 (m, 2H), 3.59-3.40 (m, 4H), 2.46-2.21 (m, 4H), 2.18 (dd, J=14.4, 3.0 Hz, 1H), 1.75 (dd, J=14.4, 9.9 Hz, 1H), 1.61-1.43 (m, 2H), 1.42-1.29 (m, 2H), 1.28 (s, 6H), 0.95 (t, J=7.5 Hz, 3H).

EXAMPLE 24(46)

1-(2-butynyl)-2,5-dioxo-3-(2-methylpropyl)-9-(3,5-dimethyl-1-phenylpyrazol-4-ylmethyl)-1,4,9-triazaspiro[5.5]undecane.2 hydrochloride

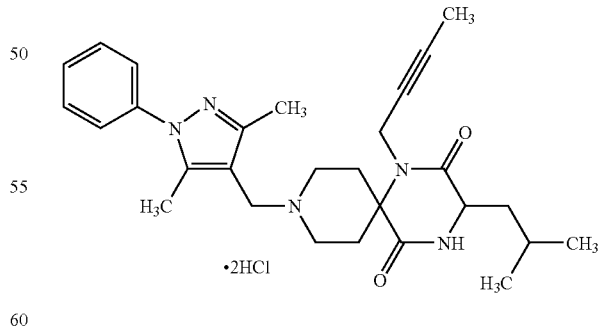

TLC: Rf 0.41 (chloroform:methanol=10:1); NMR (CD$_3$OD): δ 7.61-7.45 (m, 5H), 4.32 (s, 2H), 4.31-4.18 (m, 2H), 4.06 (dd, J=7.8, 4.5 Hz, 1H), 3.93-3.77 (m, 2H), 3.68-3.57 (m, 2H), 2.72-2.57 (m, 2H), 2.40 (s, 3H), 2.38 (s, 3H), 2.36-2.16 (m, 2H), 1.92-1.59 (m, 6H), 0.95 (d, J=6.6 Hz, 3H), 0.94 (d, J=6.6 Hz, 3H).

EXAMPLE 24(47)

1-(2-butynyl)-2,5-dioxo-3-cyclohexylmethyl-9-(3,5-dimethyl-1-phenylpyrazol-4-ylmethyl)-1,4,9-triazaspiro[5.5]undecane.2 hydrochloride

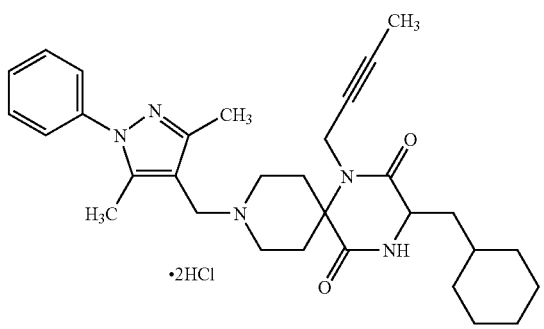

TLC: Rf 0.37 (chloroform:methanol=10:1); NMR (CD$_3$OD): 7.60-7.43 (m, 5H), 4.32 (s, 2H), 4.23 (d, J=2.1 Hz, 2H), 4.09 (dd, J=7.2, 4.8 Hz, 1H), 3.92-3.78 (m, 2H), 3.68-3.56 (m, 2H), 2.66-2.51 (m, 2H), 2.38 (s, 3H), 2.36 (s, 3H), 2.36-2.16 (m, 2H), 1.83-1.60 (m, 10H), 1.59-1.43 (m, 1H), 1.38-1.12 (m, 3H), 1.06-0.87 (m, 2H).

EXAMPLE 24(48)

1-butyl-2,5-dioxo-3-cyclohexylmethyl-9-(3,5-dimethyl-1-phenylpyrazol-4-ylmethyl)-1,4,9-triazaspiro[5.5]undecane.2 hydrochloride

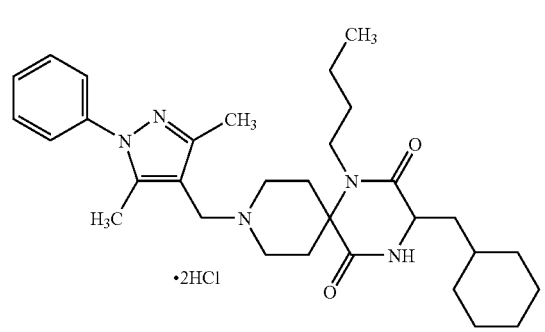

TLC: Rf 0.35 (chloroform:methanol=20:1); NMR (CD$_3$OD): δ 7.63-7.48 (m, 5H), 4.33 (s, 2H), 4.05 (dd, J=7.8, 4.5 Hz, 1H), 3.95-3.74 (m, 2H), 3.67-3.56 (m, 2H), 3.48 (m, 2H), 2.72-2.58 (m, 2H), 2.45 (s, 3H), 2.41 (s, 3H), 2.30-2.07 (m, 2H), 1.84-1.10 (m, 15H), 1.02-0.92 (m, 2H), 0.96 (t, J=7.2 Hz, 3H).

EXAMPLE 24(49)

1-butyl-2,5-dioxo-3-(2-methylpropyl)-9-(2-phenyloxypyridin-3-ylmethyl)-1,4,9-triazaspiro[5.5]undecane.2 hydrochloride

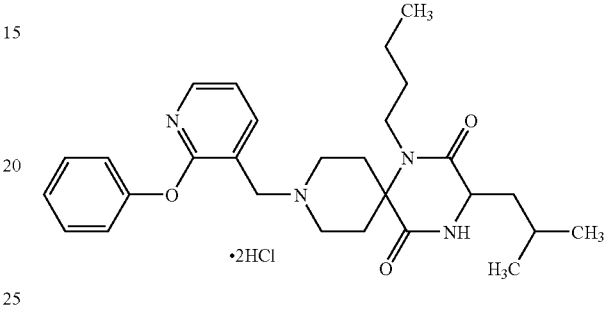

TLC: Rf 0.23 (chloroform:methanol=10:1); NMR (CD$_3$OD): δ 8.19 (m, 1H), 8.07 (m, 1H), 7.47-7.42 (m, 2H), 7.29-7.19 (m, 4H), 4.55 (s, 2H), 4.03 (dd, J=7.8, 4.5 Hz, 1H), 3.94 (m, 2H), 3.64 (m, 2H), 3.38 (m, 2H), 2.54-2.16 (m, 4H), 1.90-1.28 (m, 7H), 0.96 (t, J=6.9 Hz, 3H), 0.96 (d, J=6.3 Hz, 3H), 0.94 (d, J=6.3 Hz, 3H).

EXAMPLE 24(50)

1-butyl-2,5-dioxo-3-cyclohexylmethyl-9-(2-phenyloxypyridin-3-ylmethyl)-1,4,9-triazaspiro[5.5]undecane.2 hydrochloride

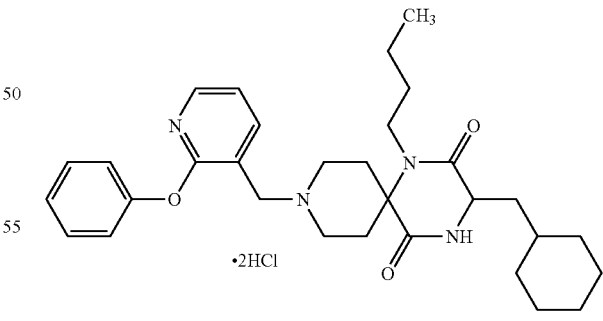

TLC: Rf 0.62 (chloroform:methanol=10:1); NMR (CD$_3$OD): δ 8.19 (m, 1H), 8.09 (m, 1H), 7.47-7.42 (m, 2H), 7.29-7.19 (m, 4H), 4.55 (s, 2H), 4.05 (dd, J=7.8, 4.8 Hz, 1H), 3.96 (m, 2H), 3.64 (m, 2H), 3.42 (m, 2H), 2.48 (m, 2H), 2.36-2.16 (m, 2H), 1.82-1.14 (m, 15H), 0.96 (t, J=7.5 Hz, 3H), 0.95-0.84 (m, 2H).

EXAMPLE 24(51)

1-butyl-2,5-dioxo-3-cyclohexylmethyl-9-(4-methyl-benzomorpholin-7-ylmethyl)-1,4,9-triazaspiro[5.5]undecane.2 hydrochloride

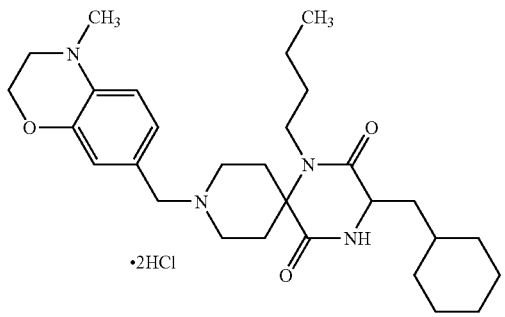

TLC: Rf 0.69 (chloroform:methanol=10:1); NMR (CDCl₃): δ 6.93 (d, J=8.7 Hz, 1H), 6.86 (s, 1H), 6.75 (d, J=8.7 Hz, 1H), 4.28-4.25 (m, 2H), 4.17 (s, 2H), 4.03 (dd, J=7.5, 4.5 Hz, 1H), 3.80-3.65 (m, 2H), 3.50-3.40 (m, 2H), 3.40-3.30 (m, 2H), 2.91 (s, 3H), 2.38-2.06 (m, 4H), 1.78-1.63 (m, 8H), 1.63-1.42 (m, 3H), 1.40-1.18 (m, 6H), 1.05-0.90 (m, 2H), 0.95 (t, J=7.2 Hz, 3H).

EXAMPLE 24(52)

1-butyl-2,5-dioxo-3-(2-methylpropyl)-9-(4-methyl-benzomorpholin-7-ylmethyl)-1,4,9-triazaspiro[5.5]undecane.2 hydrochloride

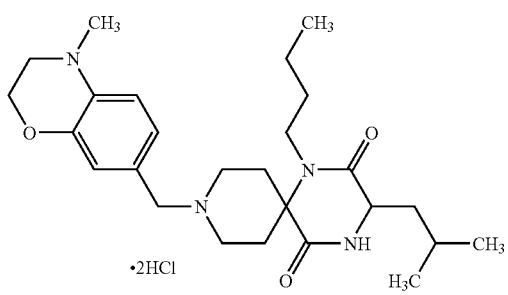

TLC: Rf 0.56 (chloroform:methanol=10:1); NMR (CDCl₃): δ 7.00 (d, J=7.2 Hz, 1H), 6.94 (s, 1H), 6.85 (d, J=7.2 Hz, 1H), 4.31-4.29 (m, 2H), 4.19 (s, 2H), 4.00 (dd, J=7.8, 4.5 Hz, 1H), 3.79-3.66 (m, 2H), 3.47-3.34 (m, 6H), 2.97 (s, 3H), 2.45-2.34 (m, 2H), 2.22-2.10 (m, 2H), 1.84-1.75 (m, 1H), 1.71-1.46 (m, 4H), 1.42-1.32 (m, 2H), 0.97-0.92 (m, 9H).

EXAMPLE 24(53)

1-butyl-2,5-dioxo-3-(2-methylpropyl)-9-(4-(N-methyl-N-phenylamino)phenylmethyl)-1,4,9-triazaspiro[5.5]undecane.2 hydrochloride

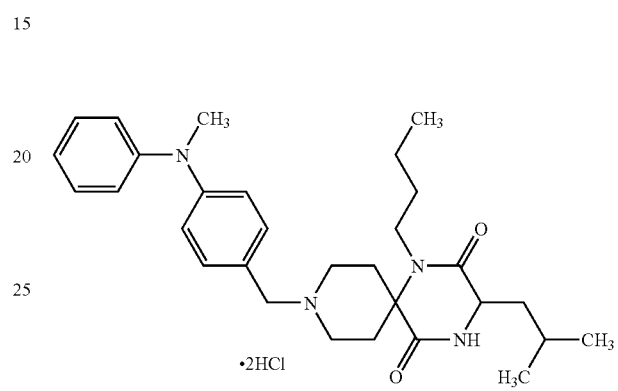

TLC: Rf 0.40 (chloroform:methanol=20:1); NMR (CD₃OD): δ 7.40-7.28 (m, 4H), 7.19-7.10 (m, 3H), 6.94-6.86 (m, 2H), 4.23 (s, 2H), 4.00 (dd, J=7.8, 4.5 Hz, 1H), 3.86-3.63 (m, 2H), 3.55-3.30 (m, 4H), 3.31 (s, 3H), 2.46-2.27 (m, 2H), 2.26-2.06 (m, 2H), 1.90-1.42 (m, 5H), 1.44-1.26 (m, 2H), 0.98-0.91 (m, 9H).

EXAMPLE 24(54)

1-butyl-2,5-dioxo-3-cyclohexylmethyl-9-(4-(N-methyl-N-phenylamino)phenylmethyl)-1,4,9-triazaspiro[5.5]undecane.2 hydrochloride

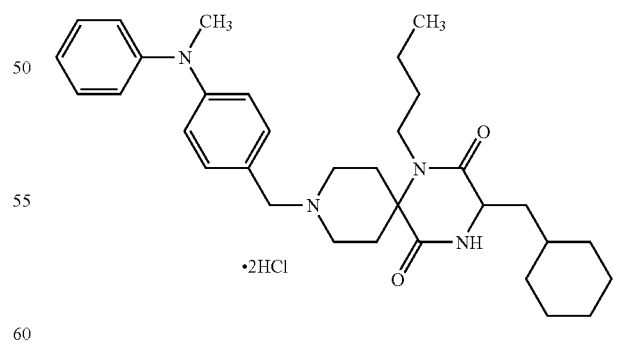

TLC: Rf 0.52 (chloroform:methanol=20:1); NMR (CD₃OD): δ 7.40-7.28 (m, 4H), 7.20-7.12 (m, 3H), 6.93-6.86 (m, 2H), 4.24 (s, 2H), 4.03 (dd, J=7.5, 4.8 Hz, 1H), 3.85-3.66 (m, 2H), 3.55-3.40 (m, 2H), 3.40-3.30 (m, 2H), 3.32 (s, 3H), 2.44-2.07 (m, 4H), 1.84-1.40 (m, 10H), 1.40-1.10 (m, 5H), 1.06-0.85 (m, 2H), 0.95 (t, J=7.5 Hz, 3H).

EXAMPLE 24(55)

1-butyl-2,5-dioxo-3-(2-methylpropyl)-9-(2-(3,5-dimethylpyrazol-1-yl)-5-methoxyphenylmethyl)-1,4,9-triazaspiro[5.5]undecane.2 hydrochloride

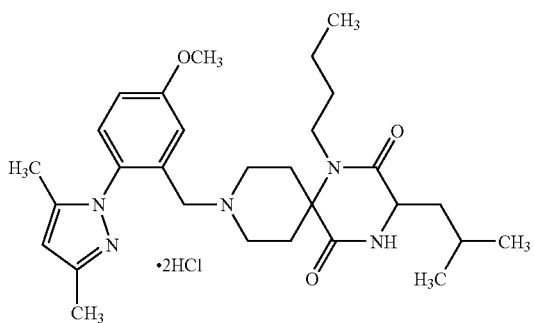

TLC: Rf 0.58 (chloroform:methanol=10:1); NMR (CD$_3$OD): δ 7.53 (d, J=3.0 Hz, 1H), 7.44 (d, J=8.7 Hz, 1H), 7.22 (dd, J=8.7, 3.0 Hz, 1H), 6.29 (s, 1H), 4.09 (s, 2H), 4.02 (dd, J=7.5, 4.5 Hz, 1H), 3.94 (s, 3H), 3.74 (m, 2H), 3.42 (m, 4H), 2.44 (m, 2H), 2.37 (s, 3H), 2.22 (s, 3H), 2.22 (m, 2H), 1.86-1.30 (m, 7H), 0.96 (t, J=7.8 Hz, 3H), 0.95 (d, J=6.3 Hz, 3H), 0.94 (d, J=6.3 Hz, 3H).

EXAMPLE 24(56)

1-butyl-2,5-dioxo-3-cyclohexylmethyl-9-(2-(3,5-dimethylpyrazol-1-yl)-5-methoxyphenylmethyl)-1,4,9-triazaspiro[5.5]undecane.2 hydrochloride

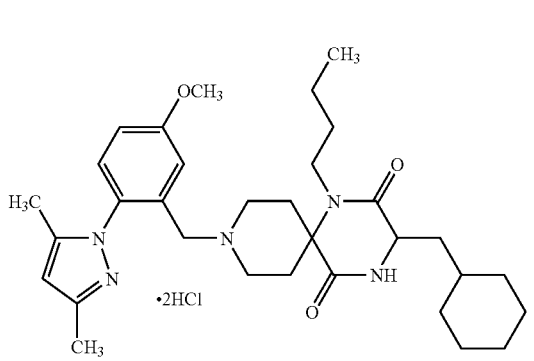

TLC: Rf 0.61 (chloroform:methanol=10:1); NMR (CD$_3$OD): δ 7.43 (d, J=8.7 Hz, 1H), 7.40 (d, J=2.7 Hz, 1H), 7.22 (dd, J=8.7, 2.7 Hz, 1H), 6.22 (s, 1H), 4.09 (s, 2H), 4.06 (dd, J=7.5, 4.2 Hz, 1H), 3.93 (s, 3H), 3.80 (m, 2H), 3.42 (m, 4H), 2.38 (m, 2H), 2.34 (s, 3H), 2.22 (s, 3H), 2.20 (m, 2H), 1.80-1.16 (m, 15H), 0.96 (t, J=7.2 Hz, 3H), 0.96 (m, 2H).

EXAMPLE 24(57)

1-butyl-2,5-dioxo-3-(2-methylpropyl)-9-(3,5-diethyl-1-(4-chlorophenyl)pyrazol-4-ylmethyl)-1,4,9-triazaspiro[5.5]undecane.2 hydrochloride

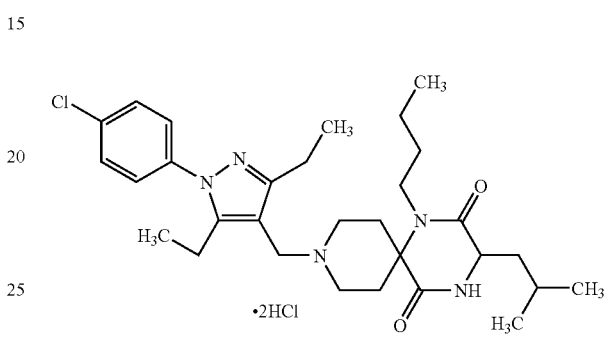

TLC: Rf 0.47 (chloroform:methanol=20:1); NMR (CD$_3$OD): δ 7.53 (d, J=9.0 Hz, 2H), 7.49 (d, J=9.0 Hz, 2H), 4.31 (s, 2H), 4.02 (dd, J=7.8, 4.5 Hz, 1H), 3.94-3.73 (m, 2H), 3.65-3.54 (m, 2H), 3.49-3.38 (m, 2H), 2.88 (q, J=7.5 Hz, 2H), 2.77 (q, J=7.5 Hz, 2H), 2.58-2.38 (m, 2H), 2.30-2.12 (m, 2H), 1.90-1.56 (m, 5H), 1.55-1.30 (m, 2H), 1.31 (t, J=7.5 Hz, 3H), 0.99-0.94 (m, 12H).

EXAMPLE 24(58)

1-butyl-2,5-dioxo-3-cyclohexylmethyl-9-(3,5-diethyl-1-(4-chlorophenyl)pyrazol-4-ylmethyl)-1,4,9-triazaspiro[5.5]undecane.2 hydrochloride

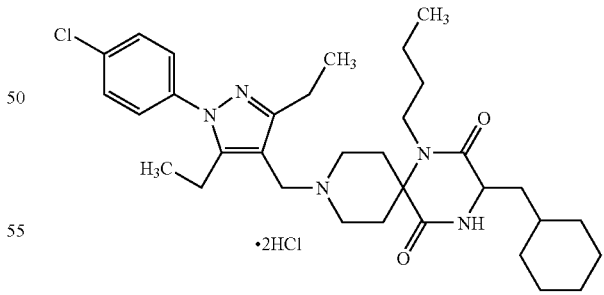

TLC: Rf 0.51 (chloroform:methanol=20:1); NMR (CD$_3$OD): δ 7.58 (d, J=9.0 Hz, 2H), 7.48 (d, J=9.0 Hz, 2H), 4.31 (s, 2H), 4.05 (dd, J=7.5, 4.5 Hz, 1H), 3.94-3.73 (m, 2H), 3.65-3.54 (m, 2H), 3.50-3.38 (m, 2H), 2.88 (q, J=7.5 Hz, 2H), 2.77 (q, J=7.5 Hz, 2H), 2.60-2.40 (m, 2H), 2.28-2.09 (m, 2H), 1.85-1.10 (m, 15H), 1.31 (t, J=7.5 Hz, 3H), 1.04-0.85 (m, 2H), 0.96 (t, J=7.5 Hz, 3H), 0.94 (t, J=7.5 Hz, 3H).

EXAMPLE 24(59)

1-butyl-2,5-dioxo-3-(2-methylpropyl)-9-(6-phenyloxypyridin-3-ylmethyl)-1,4,9-triazaspiro[5.5]undecane.2 hydrochloride

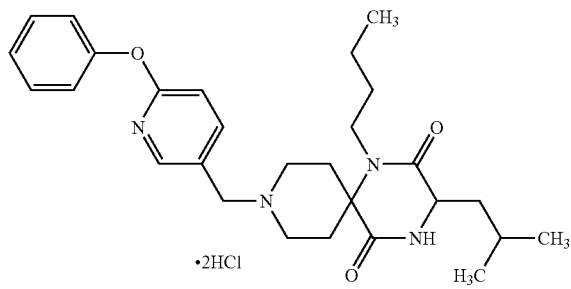

TLC: Rf 0.65 (chloroform:methanol=10:1); NMR (CD$_3$OD): δ 8.32 (s, 1H), 8.06 (m, 1H), 7.44 (t, J=7.5 Hz, 2H), 7.26 (t, J=7.5 Hz, 1H), 7.14 (d, J=7.5 Hz, 2H), 7.06 (d, J=8.7 Hz, 1H), 4.39 (s, 2H), 4.01 (dd, J=7.5, 4.5 Hz, 1H), 3.90-3.70 (m, 2H), 3.53-3.41 (m, 4H), 2.45 (m, 2H), 2.25-2.12 (m, 2H), 1.78 (m, 1H), 1.72-1.50 (m, 4H), 1.36 (m, 2H), 0.97-0.93 (m, 9H).

EXAMPLE 24(60)

1-butyl-2,5-dioxo-3-cyclohexylmethyl-9-(6-phenyloxypyridin-3-ylmethyl)-1,4,9-triazaspiro[5.5]undecane.2 hydrochloride

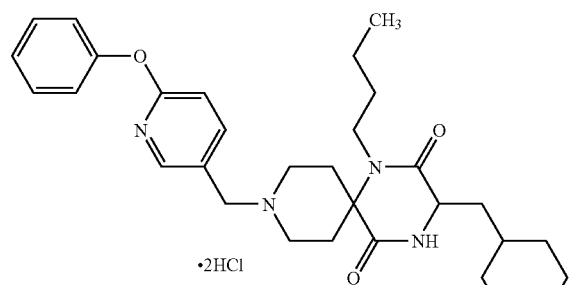

TLC: Rf 0.67 (chloroform:methanol=10:1); NMR (CD$_3$OD): δ 8.31 (s, 1H), 8.07 (d, J=8.3 Hz, 1H), 7.44 (t, J=7.5 Hz, 2H), 7.26 (t, J=7.5 Hz, 1H), 7.14 (d, J=7.5 Hz, 2H), 7.06 (d, J=8.3 Hz, 1H), 4.39 (s, 2H), 4.04 (dd, J=7.8, 4.6 Hz, 1H), 3.90-3.76 (m, 2H), 3.52-3.38 (m, 4H), 2.58-2.36 (m, 2H), 2.25-2.11 (m, 2H), 1.80-1.42 (m, 10H), 1.42-1.17 (m, 5H), 1.05-0.85 (m, 2H), 0.95 (t, J=7.2 Hz, 3H).

EXAMPLE 24(61)

1-butyl-2,5-dioxo-3-(2-methylpropyl)-9-(1,3-benzodioxolan-5-ylmethyl)-1,4,9-triazaspiro[5.5]undecane.hydrochloride

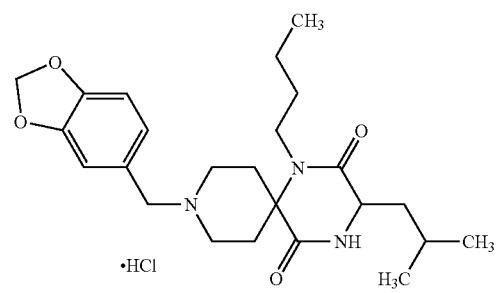

TLC: Rf 0.38 (chloroform:methanol=10:1); NMR (CD$_3$OD): δ 7.05-7.00 (m, 2H), 6.92 (m, 1H), 6.03 (s, 2H), 4.26 (s, 2H), 4.02 (dd, J=7.5, 4.5 Hz, 1H), 3.84-3.68 (m, 2H), 3.52-3.36 (m, 4H), 2.42-2.10 (m, 4H), 1.88-1.32 (m, 7H), 0.96 (t, J=6.9 Hz, 3H), 0.95 (d, J=6.3 Hz, 3H), 0.94 (d, J=6.3 Hz, 3H).

EXAMPLE 24(62)

1-butyl-2,5-dioxo-3-cyclohexylmethyl-9-(1,3-benzodioxolan-5-ylmethyl)-1,4,9-triazaspiro[5.5]undecane.hydrochloride

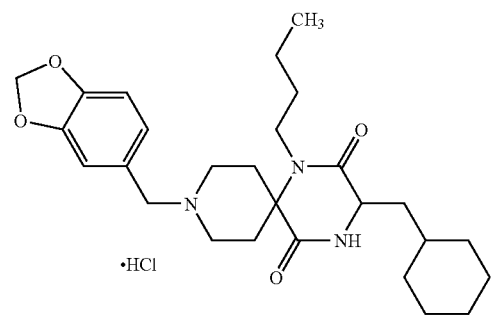

TLC: Rf 0.42 (chloroform:methanol=10:1); NMR (CD$_3$OD): δ 7.06-7.01 (m, 2H), 6.92 (m, 1H), 6.03 (s, 2H), 4.27 (s, 2H), 4.04 (dd, J=7.5, 4.5 Hz, 1H), 3.82-3.70 (m, 2H), 3.56-3.36 (m, 4H), 2.48-2.10 (m, 4H), 1.82-1.16 (m, 15H), 0.96 (t, J=7.5 Hz, 3H), 0.96 (m, 2H).

EXAMPLE 24(63)

1-butyl-2,5-dioxo-3-cyclohexylmethyl-9-(2-hydroxy-4-methoxyphenylmethyl)-1,4,9-triazaspiro[5.5]undecane.hydrochloride

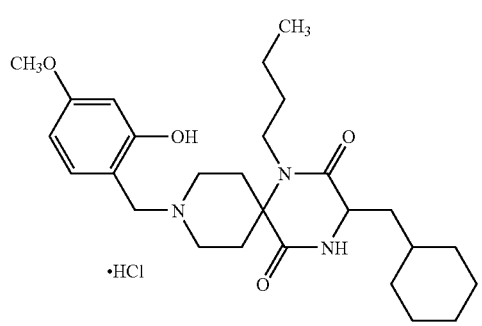

TLC: Rf 0.88 (chloroform:methanol=10:1); NMR (CD$_3$OD): δ 7.26 (d, J=8.5 Hz, 1H), 6.51 (dd, J=8.5, 2.5 Hz, 1H), 6.48 (d, J=2.5 Hz, 1H), 4.26 (s, 2H), 4.03 (m, 1H), 3.77 (m, 5H), 3.47 (m, 2H), 3.37 (m, 2H), 2.34 (m, 2H), 2.15 (m, 2H), 1.69 (m, 6H), 1.52 (m, 4H), 1.31 (m, 5H), 0.95 (m, 5H).

EXAMPLE 24(64)

1-butyl-2,5-dioxo-3-cyclohexylmethyl-9-(4-methylthiophenylmethyl)-1,4,9-triazaspiro[5.5]undecane.hydrochloride TLC: Rf 0.83 (chloroform:methanol=10:1); NMR (CD$_3$OD): δ 7.44 (d, J=8.7 Hz, 2H), 7.36 (d, J=8.7 Hz, 2H), 4.32 (s, 2H), 4.03 (dd, J=7.5, 4.5 Hz, 1H), 3.80 (m, 2H), 3.49 (m, 2H), 3.34 (m, 2H), 2.50 (s, 3H), 2.36-2.11 (m, 4H), 1.69 (m, 10H), 1.39-1.23 (m, 5H), 0.95 (m, 5H).

EXAMPLE 24(65)

1-butyl-2,5-dioxo-3-(2-methylpropyl)-9-(4-(N,N-diphenylamino)phenylmethyl)-1,4,9-triazaspiro[5.5]undecane.hydrochloride

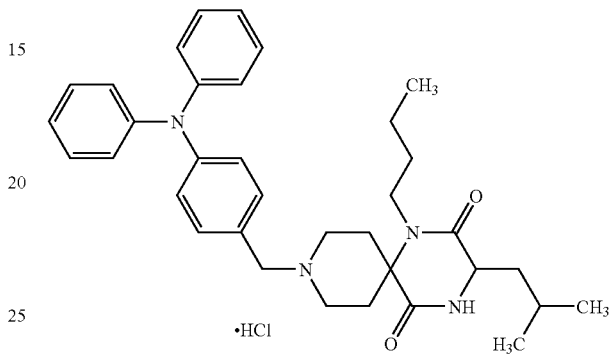

TLC: Rf 0.48 (chloroform:methanol=20:1); NMR (CD$_3$OD): δ 7.40-7.25 (m, 6H), 7.13-7.01 (m, 8H), 4.27 (s, 2H), 4.01 (dd, J=7.8, 4.5 Hz, 1H), 3.87-3.68 (m, 2H), 3.56-3.44 (m, 2H), 3.44-3.32 (m, 2H), 2.48-2.32 (m, 2H), 2.29-2.10 (m, 2H), 1.90-1.44 (m, 5H), 1.44-1.30 (m, 2H), 0.96 (t, J=6.9 Hz, 3H), 0.94 (d, J=6.3 Hz, 3H), 0.94 (d, J=6.3 Hz, 3H).

EXAMPLE 24(66)

1-butyl-2,5-dioxo-3-cyclohexylmethyl-9-(4-(N,N-diphenylamino)phenylmethyl)-1,4,9-triazaspiro[5.5]undecane.hydrochloride

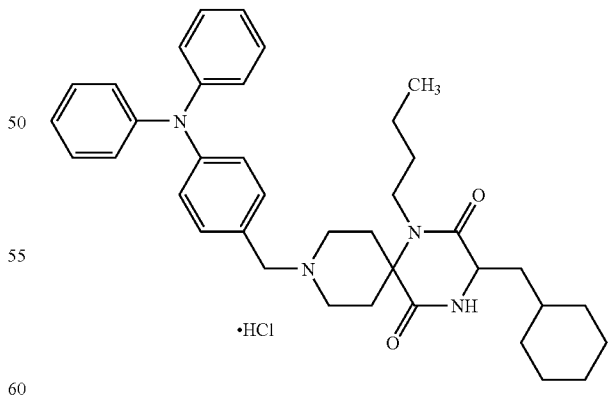

TLC: Rf 0.53 (chloroform:methanol=20:1); NMR (CD$_3$OD): δ 7.41-7.26 (m, 6H), 7.14-7.00 (m, 8H), 4.27 (s, 2H), 4.04 (dd, J=7.5, 4.5 Hz, 1H), 3.88-3.68 (m, 2H), 3.57-3.45 (m, 2H), 3.44-3.36 (m, 2H), 2.48-2.32 (m, 2H), 2.28-2.07 (m, 2H), 1.84-1.44 (m, 10H), 1.44-1.14 (m, 5H), 1.00-0.90 (m, 2H), 0.96 (t, J=6.9 Hz, 3H).

EXAMPLE 24(67)

(3S)-1-(2-butynyl)-2,5-dioxo-3-cyclohexylmethyl-9-(3,5-dimethyl-1-phenylpyrazol-4-ylmethyl)-1,4,9-triazaspiro[5.5]undecane.2 hydrochloride

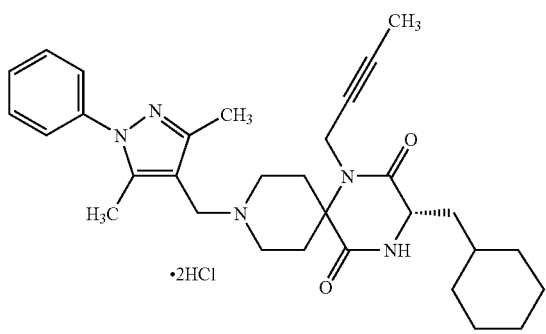

TLC: Rf 0.32 (chloroform:methanol=20:1); NMR (CD$_3$OD): δ 7.59-7.46 (m, 5H), 4.32 (s, 2H), 4.24 (s, 2H), 4.09 (dd, J=7.5, 4.5 Hz, 1H), 3.86 (m, 2H), 3.65 (m, 2H), 2.60 (m, 2H), 2.39 (s, 3H), 2.38 (s, 3H), 2.26 (m, 2H), 1.88-1.66 (m, 10H), 1.53 (m, 1H), 1.25 (m, 3H), 0.96 (m, 2H).

EXAMPLE 24(68)

(3S)-1-(2-butynyl)-2,5-dioxo-3-(2-methylpropyl)-9-(3,5-dimethyl-1-phenylpyrazol-4-ylmethyl)-1,4,9-triazaspiro[5.5]undecane.2 hydrochloride

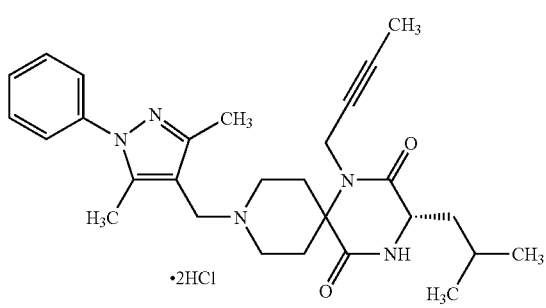

TLC: Rf 0.43 (chloroform:methanol=20:1); NMR (CD$_3$OD): δ 7.60-7.46 (m, 5H), 4.32 (s, 2H), 4.26 (m, 2H), 4.06 (dd, J=7.5, 4.5 Hz, 1H), 3.85 (m, 2H), 3.62 (m, 2H), 2.60 (m, 2H), 2.39 (s, 3H), 2.38 (s, 3H), 2.27 (m, 2H), 1.89-1.61 (m, 6H), 0.95 (d, J=6.5 Hz, 3H), 0.94 (d, J=6.5 Hz, 3H).

EXAMPLE 24(69)

(3S)-1-butyl-2,5-dioxo-3-cyclohexylmethyl-9-(3,5-dimethyl-1-phenylpyrazol-4-ylmethyl)-1,4,9-triazaspiro[5.5]undecane.2 hydrochloride

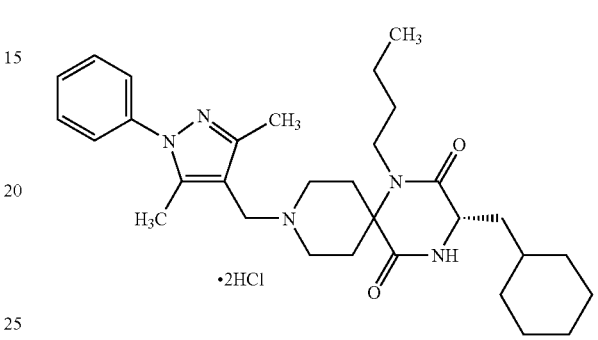

TLC: Rf 0.57 (chloroform:methanol=20:1); NMR (CD$_3$OD): δ 7.59-7.45 (m, 5H), 4.32 (s, 2H), 4.06 (dd, J=7.8, 4.5 Hz, 1H), 3.85 (m, 2H), 3.60 (m, 2H), 3.43 (m, 2H), 2.53-2.44 (m, 2H), 2.45 (s, 3H), 2.41 (s, 3H), 2.32-2.16 (m, 2H), 1.80-1.17 (m, 15H), 1.02-0.93 (m, 2H), 0.96 (d, J=7.0 Hz, 3H).

EXAMPLE 24(70)

1-butyl-2,5-dioxo-3-(2-methylpropyl)-9-(3,5-dimethyl-1-(4-methylphenyl)pyrazol-4-ylmethyl)-1,4,9-triazaspiro[5.5]undecane.2 hydrochloide

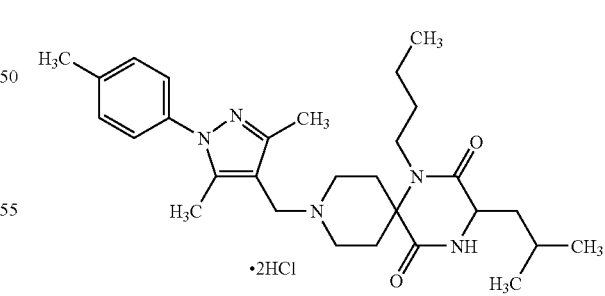

TLC: Rf 0.46 (chloroform:methanol=10:1); NMR (CD$_3$OD): δ 7.36 (d, J=8.4 Hz, 2H), 7.31 (d, J=8.4 Hz, 2H), 4.30 (s, 2H), 4.02 (dd, J=7.8, 4.8 Hz, 1H), 3.84 (m, 2H), 3.60 (m, 2H), 3.38 (m, 2H), 2.42 (s, 3H), 2.37 (s, 3H), 2.35 (s, 3H), 2.52-2.18 (m, 4H), 1.90-1.32 (m, 7H), 0.96 (t, J=7.8 Hz, 3H), 0.95 (d, J=6.3 Hz, 3H), 0.94 (d, J=6.3 Hz, 3H).

EXAMPLE 24(71)

1-butyl-2,5-dioxo-3-cyclohexylmethyl-9-(3,5-dimethyl-1-(4-methylphenyl)pyrazol-4-ylmethyl)-1,4,9-triazaspiro[5.5]undecane.2 hydrochloride

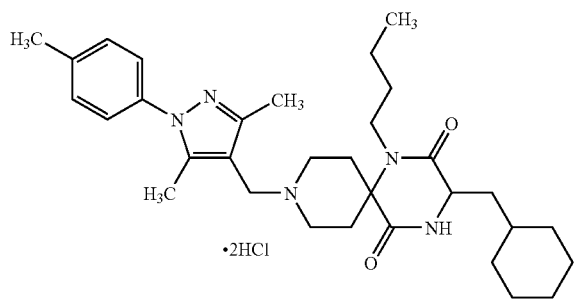

TLC: Rf 0.51 (chloroform:methanol=10:1); NMR (CD$_3$OD): δ 7.38 (d, J=8.4 Hz, 2H), 7.33 (d, J=8.4 Hz, 2H), 4.31 (s, 2H), 4.06 (dd, J=7.5, 4.5 Hz, 1H), 3.82 (m, 2H), 3.60 (m, 2H), 3.42 (m, 2H), 2.43 (s, 3H), 2.38 (s, 3H), 2.36 (s, 3H), 2.56-2.14 (m, 3H), 1.84-1.16 (m, 15H), 0.97 (t, J=7.2 Hz, 3H), 0.97 (m, 2H).

EXAMPLE 24(72)

1-butyl-2,5-dioxo-3-(2-methylpropyl)-9-(3,5-dimethyl-1-(4-chlorophenyl)pyrazol-4-ylmethyl)-1,4,9-triazaspiro[5.5]undecane.2 hydrochloride

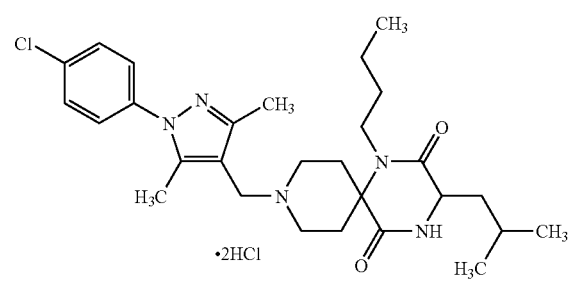

TLC: Rf 0.30 (chloroform:methanol=20:1); NMR (CD$_3$OD): δ 7.57 (d, J=9.0 Hz, 2H), 7.49 (d, J=9.0 Hz, 2H), 4.31 (s, 2H), 4.02 (dd, J=7.8, 4.5 Hz, 1H), 3.91-3.80 (m, 2H), 3.60 (m, 2H), 3.46 (m, 2H), 2.52 (m, 2H), 2.40 (s, 3H), 2.39 (s, 3H), 2.27-2.15 (m, 2H), 1.86-1.81 (m, 1H), 1.76-1.51 (m, 4H), 1.44-1.32 (m, 2H), 0.96 (t, J=7.0 Hz, 3H), 0.95 (d, J=6.0 Hz, 3H), 0.94 (d, J=6.0 Hz, 3H).

EXAMPLE 24(73)

1-butyl-2,5-dioxo-3-cyclohexylmethyl-9-(3,5-dimethyl-1-(4-chlorophenyl)pyrazol-4-ylmethyl)-1,4,9-triazaspiro[5.5]undecane.2 hydrochloride

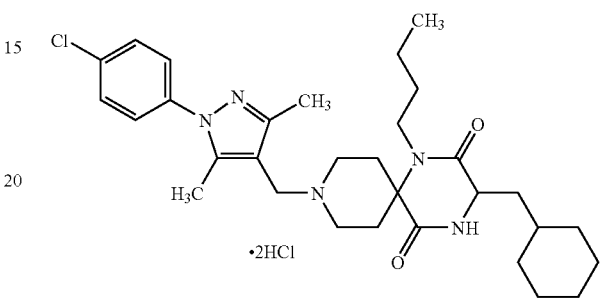

TLC: Rf 0.27 (chloroform:methanol=20:1); NMR (CD$_3$OD): δ 7.57 (d, J=8.5 Hz, 2H), 7.48 (d, J=8.5 Hz, 2H), 4.31 (s, 2H), 4.04 (dd, J=7.8, 4.5 Hz, 1H), 3.91-3.77 (m, 2H), 3.60 (m, 2H), 3.45 (m, 2H), 2.50 (m, 2H), 2.39 (s, 6H), 2.27-2.14 (m, 2H), 1.80-1.51 (m, 9H), 1.44-1.17 (m, 6H), 1.03-0.89 (m, 5H).

EXAMPLE 24(74)

1-butyl-2,5-dioxo-3-(2-methylpropyl)-9-(3,5-dimethyl-1-(4-trifluoromethylphenyl)pyrazol-4-ylmethyl)-1,4,9-triazaspiro[5.5]undecane.2 hydrochloride

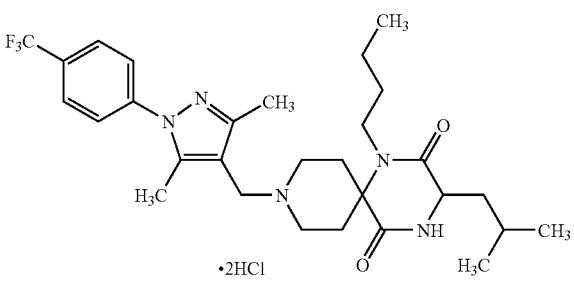

TLC: Rf 0.23 (chloroform:methanol=20:1); NMR (CD$_3$OD): δ 7.87 (d, J=8.7 Hz, 2H), 7.72 (d, J=8.7 Hz, 2H), 4.32 (s, 2H), 4.02 (dd, J=7.8, 4.5 Hz, 1H), 3.93-3.78 (m, 2H), 3.60 (m, 2H), 3.43 (m, 2H), 2.50 (m, 2H), 2.45 (s, 3H), 2.40 (s, 3H), 2.29-2.16 (m, 2H), 1.86-1.77 (m, 1H), 1.74-1.54 (m, 4H), 1.44-1.34 (m, 2H), 0.96 (t, J=7.0 Hz, 3H), 0.95 (d, J=6.0 Hz, 3H), 0.94 (d, J=6.0 Hz, 3H).

EXAMPLE 24(75)

1-butyl-2,5-dioxo-3-cyclohexylmethyl-9-(3,5-dimethyl-1-(4-trifluoromethylphenyl)pyrazol-4-ylmethyl)-1,4,9-triazaspiro[5.5]undecane.2 hydrochloride

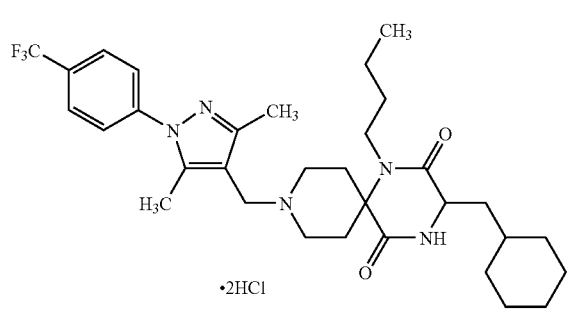

TLC: Rf 0.37 (chloroform:methanol=20:1); NMR (CD$_3$OD): δ 7.87 (d, J=8.4 Hz, 2H), 7.72 (d, J=8.4 Hz, 2H), 4.32 (s, 2H), 4.05 (dd, J=7.8, 4.5 Hz, 1H), 3.92-3.78 (m, 2H), 3.60 (m, 2H), 3.45 (m, 2H), 2.50 (m, 2H), 2.45 (s, 3H), 2.40 (s, 3H), 2.28-2.15 (m, 2H), 1.80-1.51 (m, 9H), 1.44-1.21 (m, 6H), 1.03-0.93 (m, 5H).

EXAMPLE 24(76)

1-butyl-2,5-dioxo-3-(2-methylpropyl)-9-(3,5-diethyl-1-phenylpyrazol-4-ylmethyl)-1,4,9-triazaspiro[5.5]undecane.2 hydrochloride

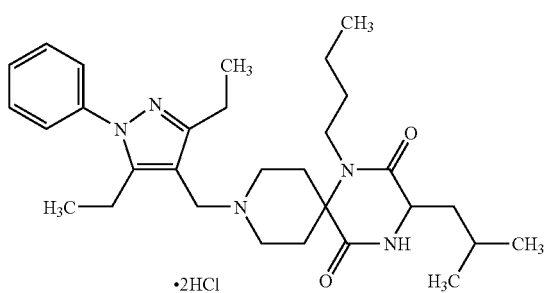

TLC: Rf 0.70 (chloroform:methanol=10:1); NMR (CD$_3$OD): δ 7.61-7.53 (m, 3H), 7.53-7.46 (m, 2H), 4.32 (s, 2H), 4.03 (dd, J=7.5, 4.5 Hz, 1H), 3.95-3.79 (m, 2H), 3.65-3.58 (m, 2H), 3.50-3.38 (m, 2H), 2.85-2.75 (m, 4H), 2.47 (br, 2H), 2.28-2.16 (m, 2H), 1.83-1.46 (m, 3H), 1.41-1.29 (m, 4H), 0.98-0.91 (m, 15H).

EXAMPLE 24(77)

1-butyl-2,5-dioxo-3-cyclohexylmethyl-9-(3,5-diethyl-1-phenylpyrazol-4-ylmethyl)-1,4,9-triazaspiro[5.5]undecane.2 hydrochloride

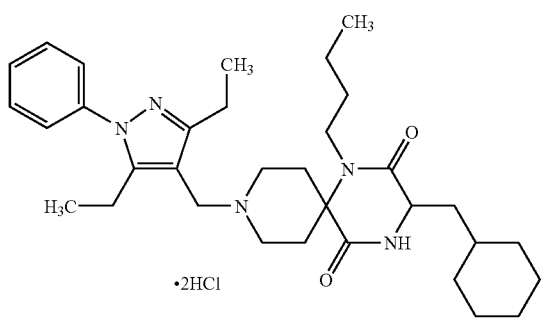

TLC: Rf 0.67 (chloroform:methanol=10:1); NMR (CD$_3$OD): δ 7.61-7.53 (m, 3H), 7.53-7.46 (m, 2H), 4.32 (s, 2H), 4.05 (dd, J=7.5, 4.5 Hz, 1H), 3.95-3.79 (m, 2H), 3.70-3.55 (m, 2H), 3.47-3.31 (m, 2H), 2.91-2.75 (m, 4H), 2.60-2.45 (m, 2H), 2.30-2.14 (m, 2H), 1.80-1.43 (m, 9H), 1.43-1.15 (m, 8H), 0.98-0.91 (m, 9H).

EXAMPLE 24(78)

1-butyl-2,5-dioxo-3-cyclohexylmethyl-9-(2-phenylthiazol-4-ylmethyl)-1,4,9-triazaspiro[5.5]undecane.hydrochloride

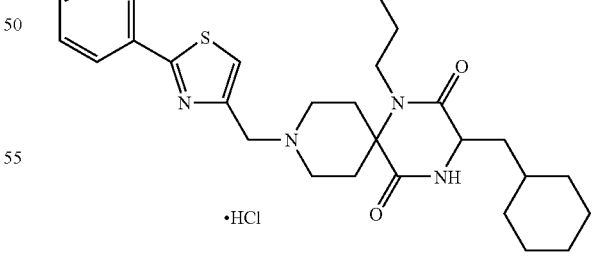

TLC: Rf 0.62 (chloroform:methanol=10:1); NMR (CD$_3$OD): δ 8.03-8.00 (m, 2H), 7.87 (s, 1H), 7.52-7.49 (m, 3H), 4.54 (s, 2H), 4.04 (dd, J=7.6, 4.8 Hz, 1H), 4.04-3.87 (m, 2H), 3.70-3.58 (m, 2H), 3.51-3.39 (m, 2H), 2.58-2.38 (m, 2H), 2.26-2.13 (m, 2H), 1.78-1.43 (m, 9H), 1.40-1.15 (m, 6H), 1.10-0.90 (m, 5H).

EXAMPLE 24(79)

1-butyl-2,5-dioxo-3-(2-methylpropyl)-9-(2-phenylthiazol-4-ylmethyl)-1,4,9-triazaspiro[5.5]undecane.hydrochloride

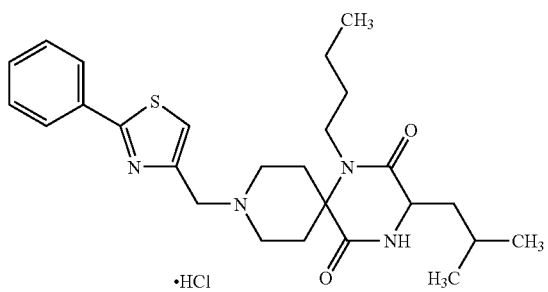

TLC: Rf 0.38 (chloroform:methanol=10:1); NMR (CD$_3$OD): δ 8.02-8.01 (m, 2H), 7.85 (s, 1H), 7.51-7.50 (m, 3H), 4.55 (s, 2H), 4.03-3.86 (m, 3H), 3.68-3.59 (m, 2H), 3.45-3.36 (m, 2H), 2.50-2.34 (m, 2H), 2.29-2.16 (m, 2H), 1.88-1.45 (m, 5H), 1.36 (q, J=7.2 Hz, 2H), 0.97-0.93 (m, 9H).

EXAMPLE 24(80)

1-butyl-2,5-dioxo-3-(2-methylpropyl)-9-(2-(1,4-benzodioxan-2-yl)thiazol-4-ylmethyl)-1,4,9-triazaspiro[5.5]undecane.hydrochloride

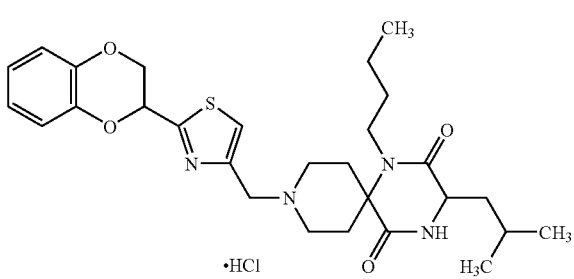

TLC: Rf 0.36 (chloroform:methanol=10:1); NMR (CD$_3$OD): δ 7.88 (s, 1H), 7.00 (m, 1H), 6.94-6.87 (m, 3H), 5.66 (dd, J=6.0, 2.7 Hz, 1H), 4.62 (dd, J=11.7, 2.7 Hz, 1H), 4.51 (s, 2H), 4.42 (dd, J=11.7, 6.0 Hz, 1H), 4.02 (dd, J=7.5, 4.5 Hz, 1H), 3.88 (m, 2H), 3.58 (m, 2H), 3.40 (m, 2H), 2.48-2.16 (m, 4H), 1.90-1.28 (m, 7H), 0.97 (t, J=7.5 Hz, 3H), 0.95 (d, J=6.3 Hz, 3H), 0.94 (d, J=6.3 Hz, 3H).

EXAMPLE 24(81)

1-butyl-2,5-dioxo-3-(2-methylpropyl)-9-(4-trifluoromethyl-2-(morpholin-1-yl)thiazol-5-ylmethyl)-1,4,9-triazaspiro[5.5]undecane.2 hydrochloride

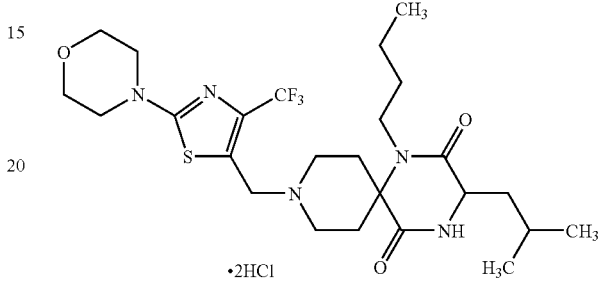

TLC: Rf 0.78 (chloroform:methanol=10:1); NMR (CD$_3$OD): δ 4.63 (s, 2H), 4.03 (dd, J=7.8, 4.8 Hz, 1H), 3.86-3.78 (m, 6H), 3.58 (m, 6H), 3.40 (m, 2H), 2.44 (m, 2H), 2.22 (m, 2H), 1.88-1.32 (m, 8H), 0.97 (t, J=7.2 Hz, 3H), 0.95 (d, J=6.6 Hz, 3H), 0.94 (d, J=6.6 Hz, 3H).

EXAMPLE 24(82)

1-butyl-2,5-dioxo-3-(tetrahydropyran-4-ylmethyl)-9-(3,5-dimethyl-1-phenylpyrazol-4-ylmethyl)-1,4,9-triazaspiro[5.5]undecane.2 hydrochloride

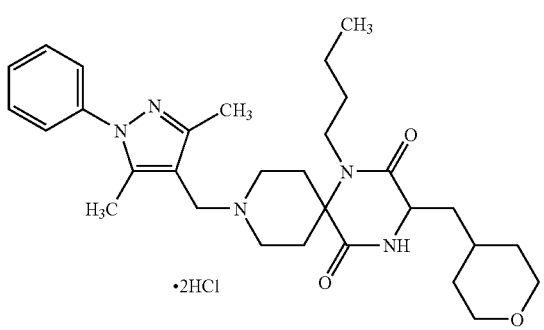

TLC: Rf 0.31 (chloroform:methanol=10:1); NMR (CD$_3$OD): δ 7.60-7.46 (m, 5H), 4.33 (s, 2H), 4.09 (dd, J=7.5, 4.5 Hz, 1H), 3.98-3.78 (m, 4H), 3.68-3.56 (m, 2H), 3.50-3.36 (m, 4H), 2.58-2.16 (m, 4H), 2.40 (s, 3H), 2.39 (s, 3H), 1.84-1.20 (m, 11H), 0.97 (t, J=7.2 Hz, 3H).

EXAMPLE 24(83)

1-butyl-2,5-dioxo-3-(tetrahydropyran-4-ylmethyl)-9-(1,4-benzodioxan-6-ylmethyl)-1,4,9-triazaspiro[5.5]undecane.hydrochloride

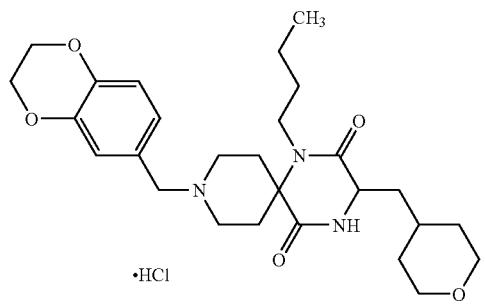

TLC: Rf 0.34 (chloroform:methanol=10:1); NMR (CD$_3$OD): δ 7.06-6.92 (m, 3H), 4.27 (s, 4H), 4.24 (s, 2H), 4.07 (dd, J=7.5, 4.5 Hz, 1H), 3.96-3.86 (m, 2H), 3.84-3.68 (m, 2H), 3.52-3.36 (m, 6H), 2.44-2.10 (m, 4H), 1.82-1.22 (m, 11H), 0.96 (t, J=7.2 Hz, 3H).

EXAMPLE 24(84)

1-butyl-2,5-dioxo-3-cyclohexylmethyl-9-(4-carboxyphenylmethyl)-1,4,9-triazaspiro[5.5]undecane.hydrochloride

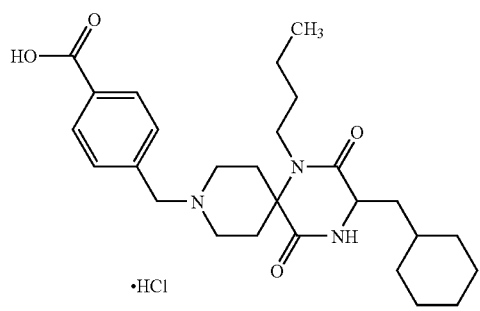

TLC: Rf 0.58 (chloroform:methanol:acetic acid=20:2:1); NMR (CD$_3$OD): δ 8.14 (d, J=8.4 Hz, 2H), 7.68 (d, J=8.4 Hz, 2H), 4.45 (s, 2H), 4.04 (dd, J=7.5, 4.5 Hz, 1H), 3.94-3.76 (m, 2H), 3.56-3.43 (m, 2H), 3.43-3.34 (m, 2H), 2.50-2.31 (m, 2H), 2.28-2.08 (m, 2H), 1.84-1.12 (m, 15H), 1.06-0.90 (m, 2H), 0.95 (t, J=7.2 Hz, 3H).

EXAMPLE 24(85)

1-butyl-2,5-dioxo-3-(2-cyclohexylethyl)-9-(3,5-dimethyl-1-phenylpyrazol-4-ylmethyl)-1,4,9-triazaspiro[5.5]undecane.2 hydrochloride

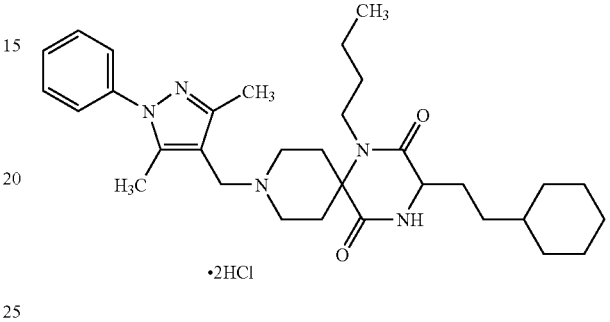

TLC: Rf 0.47 (chloroform:methanol=10:1); NMR (CD$_3$OD): δ 7.56-7.45 (m, 5H), 4.32 (s, 2H), 4.02 (t, J=4.8 Hz, 1H), 3.98-3.85 (m, 1H), 3.85-3.70 (m, 1H), 3.65-3.56 (m, 2H), 3.56-3.42 (m, 1H), 3.42-3.30 (m, 1H), 2.55-2.37 (m, 2H), 2.38 (s, 3H), 2.37 (s, 3H), 2.30-2.13 (m, 2H), 1.92-1.78 (m, 2H), 1.78-1.60 (m, 5H), 1.60-1.48 (m, 2H), 1.48-1.32 (m, 2H), 1.32-1.08 (m, 6H), 0.96 (t, J=7.2 Hz, 3H), 0.96-0.85 (m, 2H).

EXAMPLE 24(86)

1-butyl-2,5-dioxo-3-(2-cyclohexylethyl)-9-(1,4-benzodioxan-6-ylmethyl)-1,4,9-triazaspiro[5.5]undecane.hydrochloride

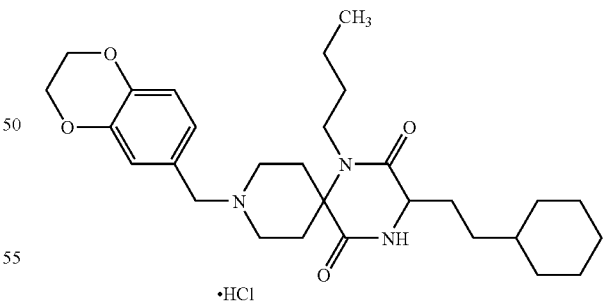

TLC: Rf 0.50 (chloroform:methanol=10:1); NMR (CD$_3$OD): δ 7.05 (d, J=2.1 Hz, 1H), 6.98 (dd, J=8.1, 2.1 Hz, 1H), 6.92 (d, J=8.1 Hz, 1H), 4.26 (s, 4H), 4.23 (s, 2H), 4.03 (t, J=4.8 Hz, 1H), 3.90-3.79 (m, 1H), 3.76-3.62 (m, 1H), 3.50-3.38 (m, 3H), 3.38-3.30 (m, 1H), 2.43-2.06 (m, 4H), 1.92-1.78 (m, 2H), 1.78-1.60 (m, 5H), 1.60-1.45 (m, 2H), 1.42-1.30 (m, 2H), 1.30-1.08 (m, 6H), 0.95 (t, J=7.2 Hz, 3H), 0.97-0.88 (m, 2H).

EXAMPLE 24(87)

(3R)-1-butyl-2,5-dioxo-3-cyclohexylmethyl-9-(3,5-dimethyl-1-phenylpyrazol-4-ylmethyl)-1,4,9-triazaspiro[5.5]undecane.2 hydrochloride

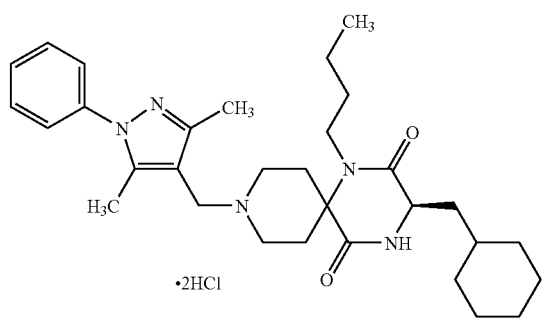

TLC: Rf 0.43 (chloroform:methanol=10:1); NMR (CD$_3$OD): δ 7.61-7.48 (m, 5H), 4.33 (s, 2H), 4.06 (dd, J=7.5, 4.5 Hz, 1H), 3.95-3.78 (m, 2H), 3.68-3.58 (m, 2H), 3.50-3.40 (m, 2H), 2.62-2.45 (m, 2H), 2.42 (s, 3H), 2.40 (s, 3H), 2.30-2.12 (m, 2H), 1.82-1.12 (m, 15H), 0.97 (t, J=7.2 Hz, 3H), 0.97 (m, 2H).

EXAMPLE 24(88)

1-butyl-2,5-dioxo-3-(2-methylpropyl)-9-(4-methyl-2-phenylthiazol-5-ylmethyl)-1,4,9-triazaspiro[5.5]undecane.hydrochloride

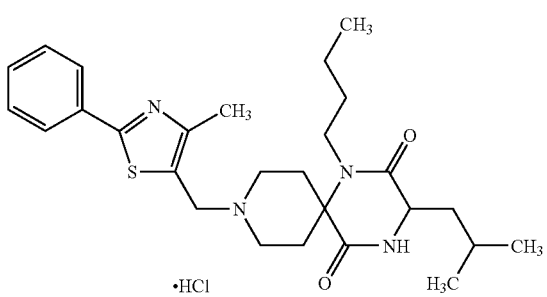

TLC: Rf 0.75 (chloroform:methanol=10:1); NMR (CD$_3$OD): δ 7.98-7.95 (m, 2H), 7.55-7.50 (m, 3H), 4.69 (s, 2H), 4.01 (dd, J=7.5, 4.5 Hz, 1H), 3.98-3.78 (m, 2H), 3.65-3.56 (m, 2H), 3.50-3.40 (m, 2H), 2.58 (s, 3H), 2.60-2.48 (m, 2H), 2.27-2.14 (m, 2H), 1.88-1.48 (m, 5H), 1.48-1.30 (m, 2H), 0.97-0.93 (m, 9H).

EXAMPLE 24(89)

1-butyl-2,5-dioxo-3-(2-methylpropyl)-9-(2-(thiophen-1-yl)thiazol-4-ylmethyl)-1,4,9-triazaspiro[5.5]undecane.hydrochloride

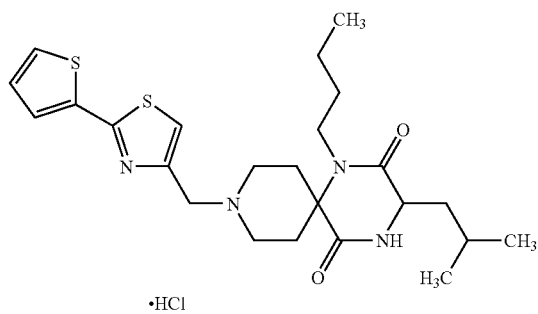

TLC: Rf 0.60 (chloroform:methanol=10:1); NMR (CD$_3$OD): δ 7.81 (s, 1H), 7.67 (d, J=3.9 Hz, 1H), 7.60 (d, J=5.4 Hz, 1H), 7.14 (dd, J=5.4, 3.9 Hz, 1H), 4.49 (s, 2H), 4.00 (dd, J=7.8, 4.5 Hz, 1H), 3.98-3.82 (m, 2H), 3.62-3.55 (m, 2H), 3.42 (t, J=7.5 Hz, 2H), 2.58-2.40 (m, 2H), 2.28-2.10 (m, 2H), 1.86-1.42 (m, 5H), 1.46-1.30 (m, 2H), 0.97-0.93 (m, 9H).

EXAMPLE 24(90)

1-butyl-2,5-dioxo-3-(2-methylpropyl)-9-(2-(pyridin-4-yl)thiazol-4-ylmethyl)-1,4,9-triazaspiro[5.5]undecane.2 hydrochloride

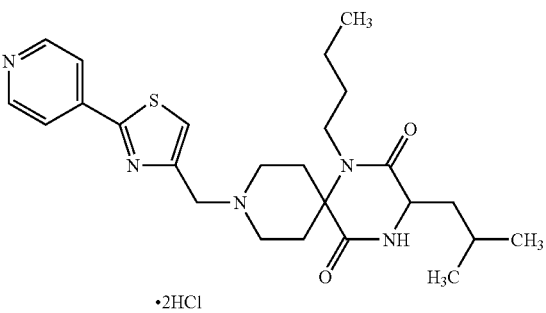

TLC: Rf 0.51 (chloroform:methanol=10:1); NMR (CD$_3$OD): δ 8.98 (d, J=6.9 Hz, 2H), 8.71 (d, J=6.9 Hz, 2H), 8.37 (s, 1H), 4.66 (s, 2H), 4.01 (dd, J=7.8, 4.8 Hz, 1H), 4.00-3.87 (m, 2H), 3.70-3.59 (m, 2H), 3.50 (t, J=7.8 Hz, 2H), 2.72-2.58 (m, 2H), 2.25-2.08 (m, 2H), 1.88-1.46 (m, 5H), 1.46-1.35 (m, 2H), 0.97-0.92 (m, 9H).

EXAMPLE 24(91)

1-butyl-2,5-dioxo-3-cyclohexylmethyl-9-(3,4-dimethoxyphenylmethyl)-1,4,9-triazaspiro[5.5]undecane.hydrochlorie

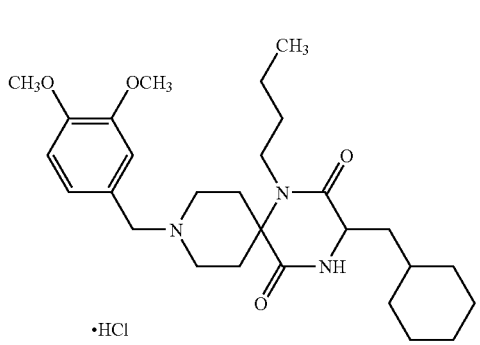

TLC: Rf 0.28 (chloroform:methanol=10:1); NMR (CD$_3$OD): δ 7.23 (s, 1H), 7.09 (d, J=8.4 Hz, 1H), 7.03 (d, J=8.4 Hz, 1H), 4.29 (s, 2H), 4.04 (dd, J=7.5, 4.8 Hz, 1H), 3.90 (s, 3H), 3.86 (s, 3H), 3.88-3.64 (m, 2H), 3.56-3.38 (m, 4H), 2.58-2.37 (m, 2H), 2.24-2.08 (m, 2H), 1.82-1.10 (m, 15H), 0.96 (t, J=7.2 Hz, 3H), 0.96 (m, 2H).

EXAMPLE 24(92)

1-butyl-2,5-dioxo-3-cyclohexylmethyl-9-(3,5-dimethoxyphenylmethyl)-1,4,9-triazaspiro[5.5]undecane.hydrochloride

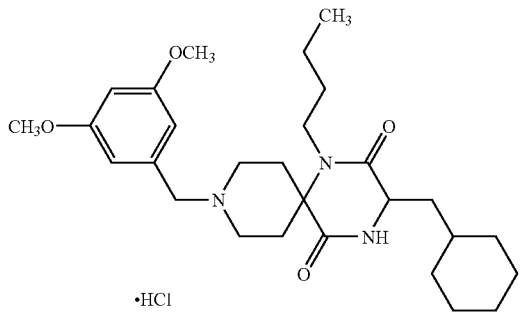

TLC: Rf 0.31 (chloroform:methanol=10:1); NMR (CD$_3$OD): δ 6.74 (d, J=1.8 Hz, 2H), 6.60 (t, J=1.8 Hz, 1H), 4.28 (s, 2H), 4.04 (dd, J=7.8, 4.8 Hz, 1H), 3.86-3.70 (m, 2H), 3.83 (s, 6H), 3.58-3.36 (m, 4H), 2.52-2.36 (m, 2H), 2.24-2.08 (m, 2H), 1.82-1.10 (m, 15H), 0.96 (t, J=7.2 Hz, 3H), 0.96 (m, 2H).

EXAMPLE 24(93)

1-butyl-2,5-dioxo-3-(2-methylpropyl)-9-(5-(pyridin-2-yl)furan-2-ylmethyl)-1,4,9-triazaspiro[5.5]undecane.2 hydrochloride

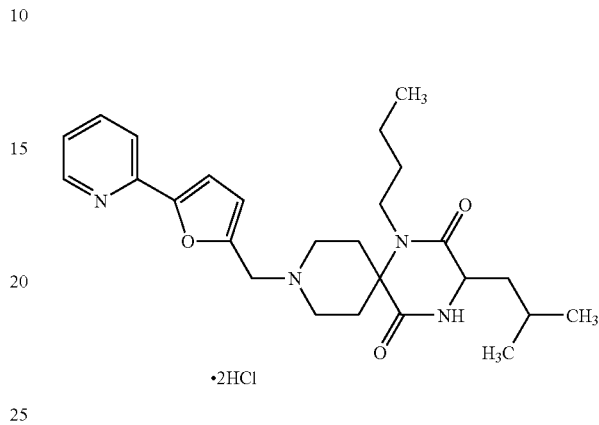

TLC: Rf 0.39 (chloroform:methanol=10:1); NMR (CD$_3$OD): δ 8.76 (dd, J=5.4, 1.5 Hz, 1H), 8.51 (ddd, J=8.1, 7.5, 1.5 Hz, 1H), 8.39 (d, J=7.5 Hz, 1H), 7.85 (dd, J=8.1, 5.4 Hz, 1H), 7.61 (d, J=3.6 Hz, 1H), 7.08 (d, J=3.6 Hz, 1H), 4.63 (s, 2H), 4.00 (dd, J=7.8, 4.5 Hz, 1H), 3.98-3.81 (m, 2H), 3.65-3.55 (m, 2H), 3.49 (t, J=8.1 Hz, 2H), 2.72-2.55 (m, 2H), 2.28-2.10 (m, 2H), 1.90-1.27 (m, 7H), 1.00-0.89 (m, 9H).

EXAMPLE 24(94)

1-butyl-2,5-dioxo-3-(2-methylpropyl)-9-(5-(pyridin-3-yl)furan-2-ylmethyl)-1,4,9-triazaspiro[5.5]undecane.2 hydrochloride

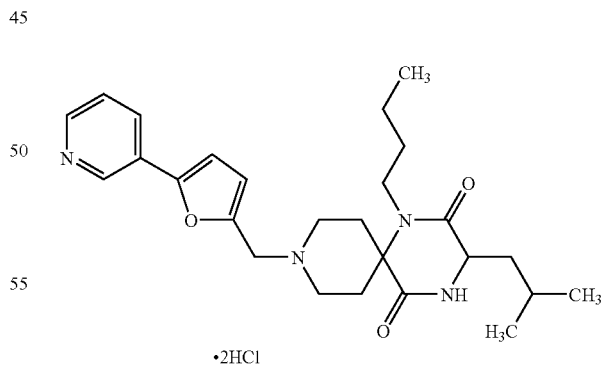

TLC: Rf 0.45 (chloroform:methanol=10:1); NMR (CD$_3$OD): δ 9.34 (d, J=1.8 Hz, 1H), 8.94 (dd, J=8.1, 1.8 Hz, 1H), 8.75 (d, J=5.4 Hz, 1H), 8.10 (dd, J=8.1, 5.4 Hz, 1H), 7.34 (d, J=3.6 Hz, 1H), 6.98 (d, J=3.6 Hz, 1H), 4.57 (s, 2H), 4.00 (dd, J=7.8, 4.5 Hz, 1H), 3.98-3.77 (m, 2H), 3.63-3.43 (m, 4H), 2.73-2.55 (m, 2H), 2.28-2.09 (m, 2H), 1.89-1.27 (m, 7H), 1.00-0.89 (m, 9H).

EXAMPLE 24(95)

1-butyl-2,5-dioxo-3-(2-methylpropyl)-9-(4-(3,5-dimethylpyrazol-1-yl)phenylmethyl)-1,4,9-triazaspiro[5.5]undecane.2 hydrochloride

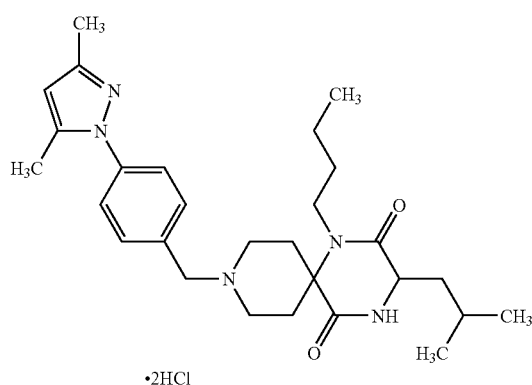

TLC: Rf 0.52 (chloroform:methanol=10:1); NMR (CD$_3$OD): δ 7.94 (d, J=8.1 Hz, 2H), 7.71 (d, J=8.1 Hz, 2H), 6.51 (s, 1H), 4.49 (s, 2H), 4.01 (dd, J=7.8, 4.5 Hz, 1H), 3.85-3.76 (m, 2H), 3.58-3.48 (m, 4H), 2.72-2.58 (m, 2H), 2.45 (s, 3H), 2.39 (s, 3H), 2.23-2.06 (m, 2H), 1.88-1.45 (m, 5H), 1.45-1.34 (m, 2H), 0.97-0.92 (m, 9H).

EXAMPLE 24(96)

1-butyl-2,5-dioxo-3-(2-methylpropyl)-9-(4-(5-chloropyridin-3-yloxy)phenylmethyl)-1,4,9-triazaspiro[5.5]undecane.2 hydrochloride

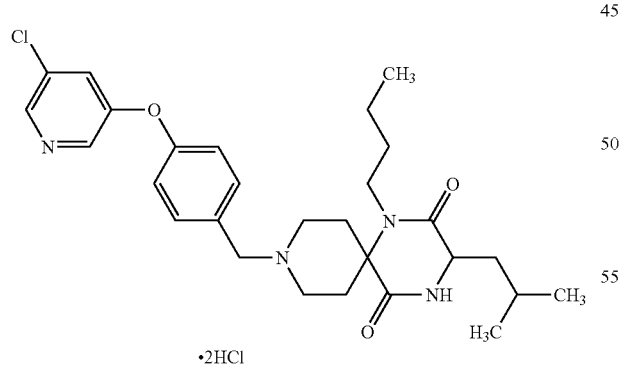

TLC: Rf 0.57 (chloroform:methanol=10:1); NMR (CD$_3$OD): δ 8.54 (bs, 1H), 8.45 (bs, 1H), 7.87 (bs, 1H), 7.71 (d, J=8.4 Hz, 2H), 7.26 (d, J=8.4 Hz, 2H), 4.39 (s, 2H), 4.01 (dd, J=7.8, 4.8 Hz, 1H), 3.90-3.73 (m, 2H), 3.56-3.40 (m, 4H), 2.64-2.46 (m, 2H), 2.24-2.09 (m, 2H), 1.86-1.42 (m, 5H), 1.42-1.30 (m, 2H), 0.97-0.92 (m, 9H).

EXAMPLE 24(97)

1-butyl-2,5-dioxo-3-(2-methylpropyl)-9-(4-(pyrimidin-2-yloxy)phenylmethyl)-1,4,9-triazaspiro[5.5]undecane.2 hydrochloide

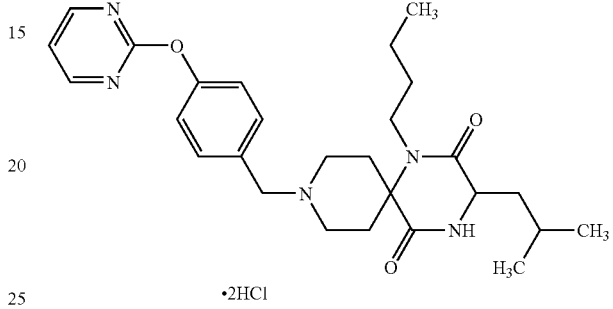

TLC: Rf 0.61 (chloroform:methanol=10:1); NMR (CD$_3$OD): δ 8.62 (d, J=4.8 Hz, 2H), 7.68 (d, J=8.4 Hz, 2H), 7.32 (d, J=8.4 Hz, 2H), 7.26 (t, J=4.8 Hz, 1H), 4.40 (s, 2H), 4.02 (dd, J=7.5, 4.5 Hz, 1H), 3.93-3.72 (m, 2H), 3.60-3.35 (m, 4H), 2.58-2.40 (m, 2H), 2.28-2.07 (m, 2H), 1.90-1.45 (m, 5H), 1.45-1.36 (m, 2H), 0.98-0.90 (m, 9H).

EXAMPLE 24(98)

1-butyl-2,5-dioxo-3-(2-methylpropyl)-9-(4-(pyridin-3-yloxy)phenylmethyl)-1,4,9-triazaspiro[5.5]undecane.2 hydrochloride

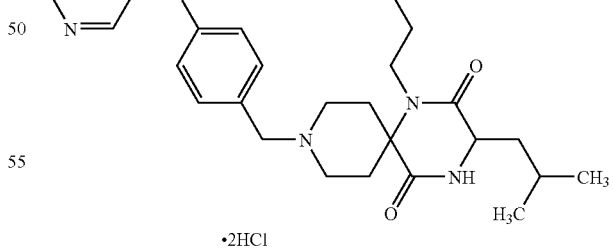

TLC: Rf 0.61 (chloroform:methanol=10:1); NMR (CD$_3$OD): δ 8.76 (d, J=2.7 Hz, 1H), 8.63 (d, J=5.7 Hz, 1H), 8.28 (dd, J=8.7, 2.7 Hz, 1H), 8.07 (dd, J=8.7, 5.7 Hz, 1H), 7.78 (d, J=8.4 Hz, 2H), 7.35 (d, J=8.4 Hz, 2H), 4.41 (s, 2H), 4.02 (dd, J=7.8, 4.5 Hz, 1H), 3.93-3.72 (m, 2H), 3.58-3.40 (m, 4H), 2.68-2.48 (m, 2H), 2.26-2.06 (m, 2H), 1.90-1.46 (m, 5H), 1.46-1.30 (m, 2H), 0.98-0.91 (m, 9H).

EXAMPLE 24(99)

1-(2-butynyl)-2,5-dioxo-3-(2-methylpropyl)-9-(3,5-dimethyl-1-(4-methylphenyl)pyrazol-4-ylmethyl)-1,4,9-triazaspiro[5.5]undecane.2 hydrochloride

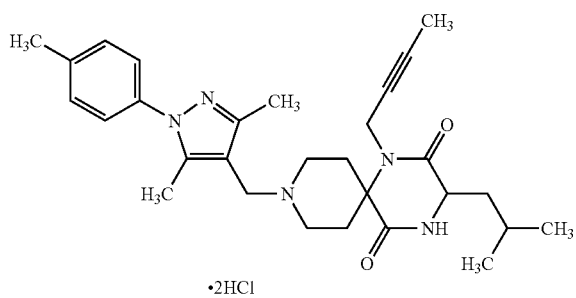

TLC: Rf 0.28 (chloroform:methanol=19:1); NMR (CD$_3$OD): δ 7.39-7.29 (m, 4H), 4.31 (s, 2H), 4.27-4.20 (m, 2H), 4.06 (dd, J=7.5, 4.8 Hz, 1H), 3.84 (m, 2H), 3.62 (m, 2H), 2.59 (m, 2H), 2.42 (s, 3H), 2.37 (s, 3H), 2.34 (s, 3H), 2.28 (m, 2H), 1.92-1.60 (m, 6H), 0.96 (d, J=6.3 Hz, 3H), 0.95 (d, J=6.3 Hz, 3H).

EXAMPLE 24(100)

(3R)-1-(2-butynyl)-2,5-dioxo-3-cyclohexylmethyl-9-(3,5-dimethyl-1-phenylpyrazol-4-ylmethyl)-1,4,9-triazaspiro[5.5]undecane.2 hydrochloride

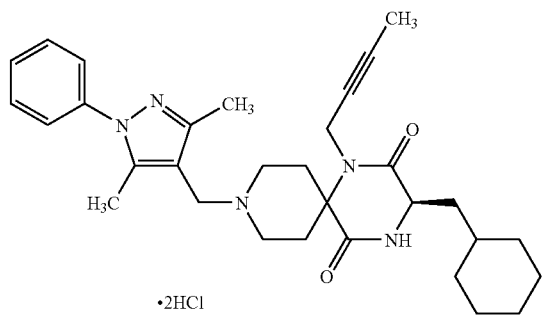

TLC: Rf 0.29 (chloroform:methanol=19:1); NMR (CD$_3$OD): δ 7.59-7.43 (m, 5H), 4.31 (s, 2H), 4.25 (q, J=2.1 Hz, 2H), 4.09 (dd, J=7.2, 4.8 Hz, 1H), 3.85 (dt, J=3.0, 12.3 Hz, 2H), 3.68-3.56 (m, 2H), 2.61 (m, 2H), 2.38 (s, 3H), 2.37 (s, 3H), 2.26 (m, 2H), 1.83-1.43 (m, 8H), 1.75 (t, J=2.1 Hz, 3H), 1.38-1.12 (m, 3H), 0.96 (m, 2H).

EXAMPLE 24(101)

1-butyl-2,5-dioxo-3-(2-methylpropyl)-9-(4-(4-hydroxyphenyloxy)phenylmethyl)-1,4,9-triazaspiro[5.5]undecane.hydrochloride

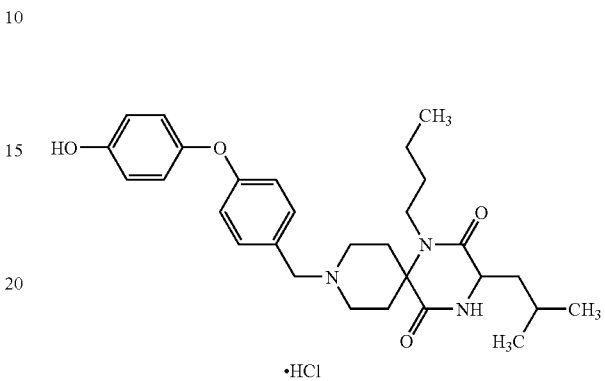

TLC: Rf 0.46 (chloroform:methanol=10:1); NMR (CD$_3$OD): δ 7.47 (d, J=9.0 Hz, 2H), 6.97 (d, J=9.0 Hz, 2H), 6.88 (d, J=9.0 Hz, 2H), 6.80 (d, J=9.0 Hz, 2H), 4.30 (s, 2H), 4.00 (dd, J=7.5, 4.8 Hz, 1H), 3.86-3.70 (m, 2H), 3.52-3.34 (m, 4H), 2.48-2.30 (m, 2H), 2.28-2.10 (m, 2H), 1.88-1.44 (m, 5H), 1.44-1.28 (m, 2H), 0.97-0.92 (m, 9H).

EXAMPLE 24(102)

1-butyl-2,5-dioxo-3-(2-methylpropyl)-9-(4-(pyridin-2-yl)phenylmethyl)-1,4,9-triazaspiro[5.5]undecane.2 hydrochloride

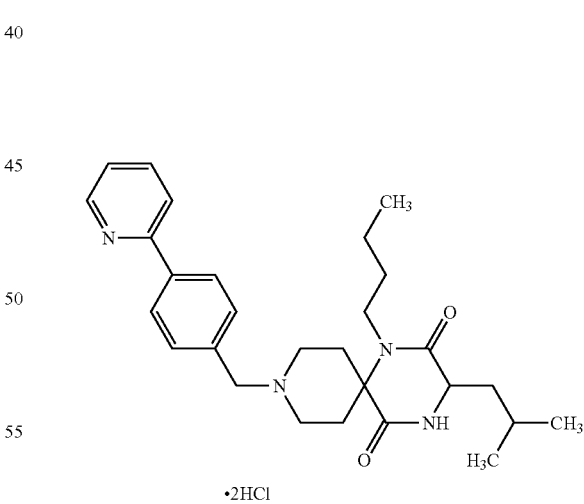

TLC: Rf 0.50 (chloroform:methanol=10:1); NMR (CD$_3$OD): δ 8.89 (d, J=7.8 Hz, 1H), 8.70 (t, J=7.8 Hz, 1H), 8.43 (d, J=8.4 Hz, 1H), 8.10-8.06 (m, 3H), 7.98 (d, J=8.7 Hz, 2H), 4.51 (s, 2H), 4.01 (dd, J=7.8, 4.8 Hz, 1H), 3.96-3.78 (m, 2H), 3.56-3.45 (m, 4H), 2.72-2.58 (m, 2H), 2.24-2.08 (m, 2H), 1.84-1.44 (m, 5H), 1.44-1.34 (m, 2H), 0.97-0.92 (m, 9H).

EXAMPLE 24(103)

1-butyl-2,5-dioxo-3-(2-methylpropyl)-9-(4-(pyridin-3-yl)phenylmethyl)-1,4,9-triazaspiro[5.5]undecane.2 hydrochloride

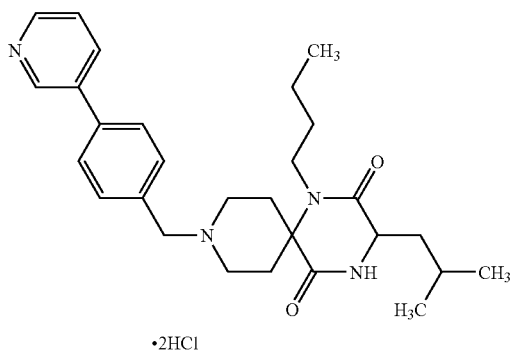

TLC: Rf 0.47 (chloroform:methanol=10:1); NMR (CD$_3$OD): δ 9.24 (s, 1H), 8.98 (d, J=8.4 Hz, 1H), 8.88 (d, J=8.4 Hz, 1H), 8.21 (dd, J=8.4, 5.7 Hz, 1H), 7.96 (d, J=8.4 Hz, 2H), 7.87 (d, J=8.4 Hz, 2H), 4.47 (s, 2H), 4.01 (dd, J=7.5, 4.8 Hz, 1H), 3.96-3.75 (m, 2H), 3.58-3.44 (m, 4H), 2.64-2.50 (m, 2H), 2.25-2.08 (m, 2H), 1.88-1.48 (m, 5H), 1.48-1.32 (m, 2H), 0.97-0.92 (m, 9H).

EXAMPLE 24(104)

1-butyl-2,5-dioxo-3-(2-methylpropyl)-9-(3,5-dimethyl-1-(4-carboxyphenyl)pyrazol-4-ylmethyl)-1,4,9-triazaspiro[5.5]undecane.2 hydrochloride

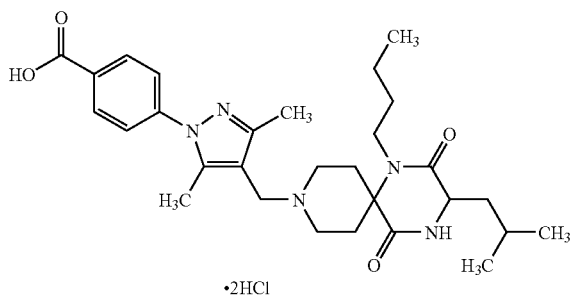

TLC: Rf 0.27 (chloroform:methanol=10:1); NMR (CD$_3$OD): δ 8.19 (d, J=8.4 Hz, 2H), 7.61 (d, J=8.4 Hz, 2H), 4.32 (s, 2H), 4.03 (dd, J=7.5, 4.5 Hz, 1H), 3.96-3.74 (m, 2H), 3.66-3.55 (m, 2H), 3.48-3.36 (m, 2H), 2.58-2.40 (m, 2H), 2.45 (s, 3H), 2.40 (s, 3H), 2.32-2.14 (m, 2H), 1.90-1.46 (m, 5H), 1.46-1.30 (m, 2H), 0.99-0.95 (m, 9H).

EXAMPLE 24(105)

1-butyl-2,5-dioxo-3-(2-methylpropyl)-9-(4-(pyrazin-2-yloxy)phenylmethyl)-1,4,9-triazaspiro[5.5]undecane.2 hydrochloride

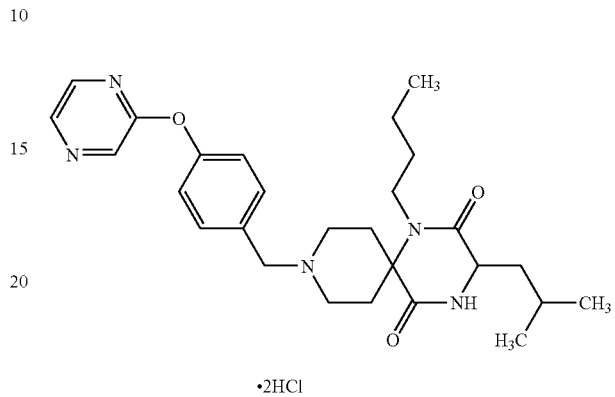

TLC: Rf 0.48 (chloroform:methanol=20:1); NMR (CD$_3$OD): δ 8.47 (d, J=1.5 Hz, 1H), 8.32 (d, J=2.7 Hz, 1H), 8.13 (dd, J=2.7, 1.5 Hz, 1H), 7.65 (d, J=8.4 Hz, 2H), 7.32 (d, J=8.4 Hz, 2H), 4.40 (s, 2H), 4.02 (dd, J=7.5, 4.5 Hz, 1H), 3.94-3.73 (m, 2H), 3.58-3.46 (m, 2H), 3.44-3.34 (m, 2H), 2.52-2.34 (m, 2H), 2.30-2.10 (m, 2H), 1.90-1.43 (m, 5H), 1.43-1.26 (m, 2H), 0.99-0.90 (m, 9H).

EXAMPLE 24(106)

1-butyl-2,5-dioxo-3-(2-methylpropyl)-9-(4-(4-carboxyphenyl)phenylmethyl)-1,4,9-triazaspiro[5.5]undecane.hydrochloride

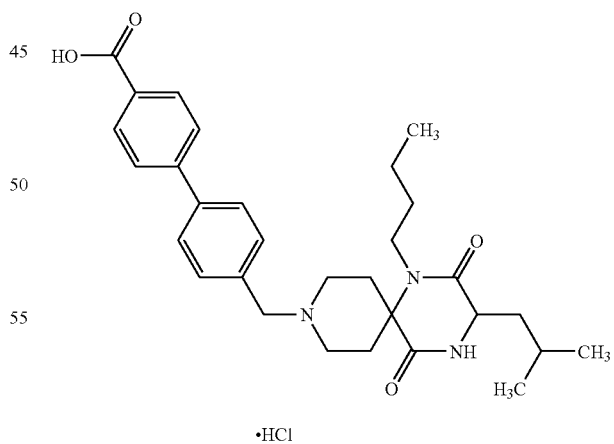

TLC: Rf 0.20 (chloroform:methanol=10:1); NMR (CD$_3$OD): δ 8.11 (d, J=8.4 Hz, 2H), 7.83 (d, J=8.4 Hz, 2H), 7.77 (d, J=8.4 Hz, 2H), 7.69 (d, J=8.4 Hz, 2H), 4.43 (s, 2H), 4.01 (dd, J=7.8, 4.5 Hz, 1H), 3.96-3.74 (m, 2H), 3.58-3.36 (m, 4H), 2.55-2.38 (m, 2H), 2.28-2.10 (m, 2H), 1.88-1.44 (m, 5H), 1.44-1.30 (m, 2H), 0.97-0.92 (m, 9H).

EXAMPLE 24(107)

1-butyl-2,5-dioxo-3-(2-methylpropyl)-9-(4-(pyridin-4-yl)phenylmethyl)-1,4,9-triazaspiro[5.5]undecane.2 hydrochloride

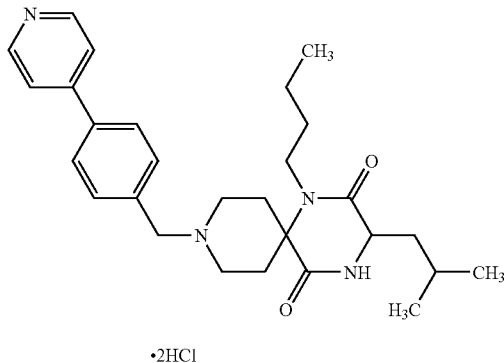

TLC: Rf 0.50 (chloroform:methanol=10:1); NMR (CD$_3$OD): δ 8.91 (d, J=6.9 Hz, 2H), 8.45 (d, J=6.9 Hz, 2H), 8.11 (d, J=7.8 Hz, 2H), 7.91 (d, J=7.8 Hz, 2H), 4.49 (s, 2H), 4.01 (dd, J=7.8, 4.8 Hz, 1H), 3.96-3.78 (m, 2H), 3.58-3.40 (m, 4H), 2.64-2.48 (m, 2H), 2.26-2.08 (m, 2H), 1.90-1.28 (m, 7H), 0.96-0.93 (m, 9H).

EXAMPLE 24(108)

1-butyl-2,5-dioxo-3-(2-methylpropyl)-9-(4-(pyridin-2-yloxy)phenylmethyl)-1,4,9-triazaspiro[5.5]undecane.2 hydrochloride

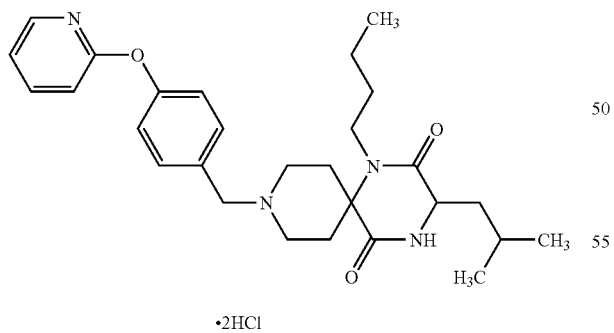

TLC: Rf 0.46 (chloroform:methanol=10:1); NMR (CD$_3$OD): δ 8.44-8.15 (m, 2H), 7.82 (d, J=7.2 Hz, 2H), 7.60-7.40 (m, 1H), 7.42 (d, J=7.2 Hz, 2H), 7.27-7.24 (m, 1H), 4.43 (s, 2H), 4.02 (dd, J=7.5, 4.5 Hz, 1H), 3.92-3.70 (m, 2H), 3.58-3.40 (m, 4H), 2.64-2.42 (m, 2H), 2.28-2.06 (m, 2H), 1.92-1.28 (m, 7H), 0.97-0.94 (m, 9H).

EXAMPLE 24(109)

1-butyl-2,5-dioxo-3-cyclohexylmethyl-9-(naphthalen-2-ylmethyl)-1,4,9-triazaspiro[5.5]undecane.hydrochloride

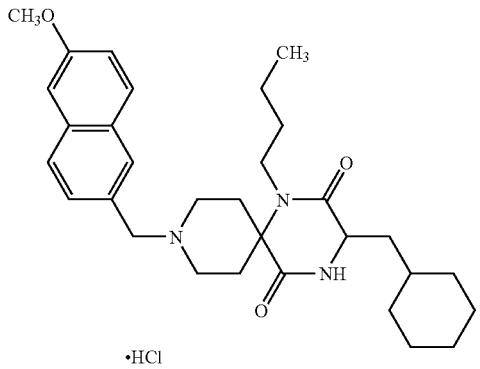

TLC: Rf 0.71 (chloroform:methanol=10:1); NMR (CD$_3$OD): δ 8.08-7.93 (m, 4H), 7.64-7.57 (m, 3H), 4.54 (s, 2H), 4.04 (dd, J=7.5, 4.8 Hz, 1H), 3.96-3.80 (m, 2H), 3.60-3.44 (m, 2H), 3.42-3.36 (m, 2H), 2.42-2.08 (m, 4H), 1.82-1.16 (m, 15H), 0.95 (t, J=7.5 Hz, 3H), 0.95 (m, 2H).

EXAMPLE 24(110)

1-butyl-2,5-dioxo-3-cyclohexylmethyl-9-(6-methoxynaphthalen-2-ylmethyl)-1,4,9-triazaspiro[5.5]undecane.hydrochloride TLC: Rf 0.75 (chloroform:methanol=10:1); NMR (CD$_3$OD): δ 7.98 (s, 1H), 7.91 (d, J=8.7 Hz, 1H), 7.85 (d, J=8.7 Hz, 1H), 7.58 (d, J=8.7 Hz, 1H), 7.31 (d, J=2.4 Hz, 1H), 7.22 (dd, J=8.7, 2.4 Hz, 1H), 4.48 (s, 2H), 4.04 (dd, J=7.8, 4.8 Hz, 1H), 3.94-3.78 (m, 2H), 3.93 (s, 3H), 3.58-3.44 (m, 2H), 3.42-3.36 (m, 2H), 2.48-2.30 (m, 2H), 2.24-2.08 (m, 2H), 1.82-1.10 (m, 15H), 0.95 (t, J=7.2 Hz, 3H), 0.95 (m, 2H).

EXAMPLE 24(111)

1-butyl-2,5-dioxo-3-(2-methylpropyl)-9-(4-(4-carboxyphenyloxy)phenylmethyl)-1,4,9-triazaspiro[5.5]undecane.hydochloride

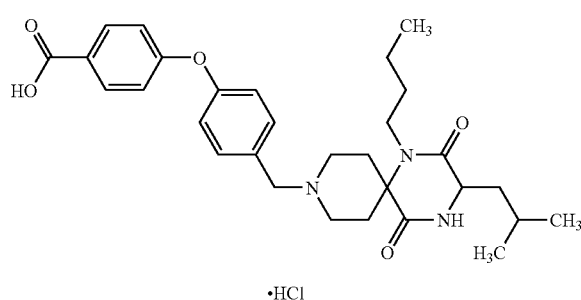

TLC: Rf 0.27 (chloroform:methanol=10:1); NMR (CD$_3$OD): δ 8.03 (d, J=8.7 Hz, 2H), 7.63 (d, J=8.4 Hz, 2H), 7.17 (d, J=8.4 Hz, 2H), 7.07 (d, J=8.7 Hz, 2H), 4.37 (s, 2H), 4.01 (dd, J=7.5, 4.5 Hz, 1H), 3.90-3.70 (m, 2H), 3.56-3.36 (m, 4H), 2.56-2.38 (m, 2H), 2.25-2.10 (m, 2H), 1.84-1.44 (m, 5H), 1.44-1.39 (m, 2H), 0.98-0.93 (m, 9H).

EXAMPLE 24(112)

1-butyl-2,5-dioxo-3-(2-methylpropyl)-9-(5-(pyridin-4-yl)furan-2-ylmethyl)-1,4,9-triazaspiro[5.5]undecane.2 hydrochloride

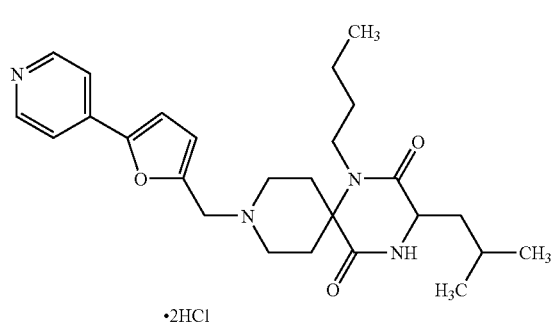

TLC: Rf 0.39 (chloroform:methanol=10:1); NMR (CD$_3$OD): δ 8.80 (d, J=6.9 Hz, 2H), 8.39 (d, J=6.9 Hz, 2H), 7.69 (d, J=3.6 Hz, 1H), 7.08 (d, J=3.6 Hz, 1H), 4.62 (s, 2H), 4.00 (dd, J=7.8, 4.5, Hz, 1H), 3.99-3.79 (m, 2H), 3.65-3.43 (m, 4H), 2.72-2.54 (m, 2H), 2.30-2.10 (m, 2H), 1.88-1.26 (m, 7H), 1.00-0.84 (m, 9H).

EXAMPLE 24(113)

1-butyl-2,5-dioxo-3-cyclopentylmethyl-9-(4-phenyloxyphenylmethyl)-1,4,9-triazaspiro[5.5]undecane-.hydrocloride

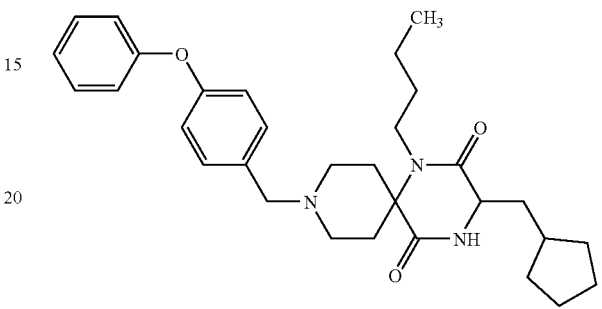

TLC: Rf 0.66 (chloroform:methanol=10:1); NMR (CD$_3$OD): δ 7.52 (d, J=8.5 Hz, 2H), 7.40 (t, J=7.5 Hz, 2H), 7.18 (t, J=7.5 Hz, 1H), 7.05 (m, 4H), 4.34 (s, 2H), 4.00 (t, J=6.0 Hz, 1H), 3.82 (m, 2H), 3.49 (m, 2H), 3.39 (m, 2H), 2.37 (m, 2H), 2.17 (m, 2H), 1.96 (m, 1H), 1.81 (m, 4H), 1.58 (m, 6H), 1.38 (m, 2H), 1.17 (m, 2H), 0.95 (t, J=7.0 Hz, 3H).

EXAMPLE 24(114)

(3R)-1-butyl-2,5-dioxo-3-(2,2-dimethylpropyl)-9-(4-phenyloxyphenylmethyl)-1,4,9-triazaspiro[5.5]undecane.hydrochloride

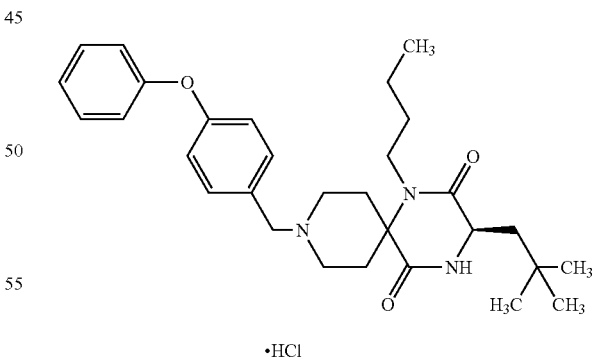

TLC: Rf 0.52 (chloroform:methanol=20:1); NMR (CD$_3$OD): δ 7.52 (d, J=9.0 Hz, 2H), 7.40 (t, J=7.5 Hz, 2H), 7.18 (t, J=7.5 Hz, 1H), 7.04 (m, 4H), 4.33 (s, 2H), 4.01 (dd, J=7.2, 3.3 Hz, 1H), 3.82 (m, 1H), 3.71 (m, 1H), 3.50 (m, 2H), 3.43 (m, 2H), 2.38 (m, 2H), 2.24 (m, 2H), 2.00 (dd, J=14.0, 3.3 Hz, 1H), 1.55 (dd, J=14.0, 7.2 Hz, 1H), 1.50 (m, 2H), 1.36 (m, 2H), 0.99 (s, 9H), 0.95 (t, J=7.0 Hz, 3H).

EXAMPLE 24(115)

(3S)-1-butyl-2,5-dioxo-3-(2,2-dimethylpropyl)-9-(4-phenyloxyphenylmethyl)-1,4,9-triazaspiro[5.5]undecane.hydrochloride

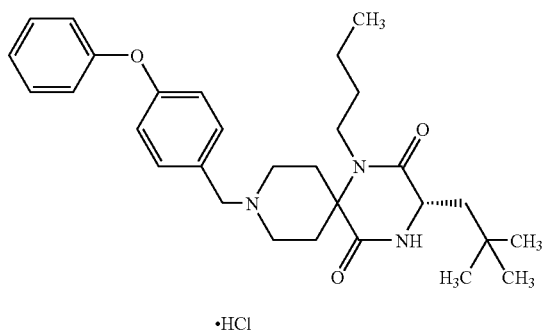

·HCl

TLC: Rf 0.52 (chloroform:methanol=20:1); NMR (CD$_3$OD): δ 7.52 (d, J=9.0 Hz, 2H), 7.40 (t, J=7.5 Hz, 2H), 7.18 (t, J=7.5 Hz, 1H), 7.04 (m, 4H), 4.33 (s, 2H), 4.01 (dd, J=7.2, 3.3 Hz, 1H), 3.82 (m, 1H), 3.71 (m, 1H), 3.50 (m, 2H), 3.43 (m, 2H), 2.38 (m, 2H), 2.24 (m, 2H), 2.00 (dd, J=14.0, 3.3 Hz, 1H), 1.55 (dd, J=14.0, 7.2 Hz, 1H), 1.50 (m, 2H), 1.36 (m, 2H), 0.99 (s, 9H), 0.95 (t, J=7.0 Hz, 3H).

EXAMPLE 24(116)

1-butyl-2,5-dioxo-3-cyclohexylmethyl-9-(4-nitrophenylmethyl)-1,4,9-triazaspiro[5.5]undecane.hydrochloride

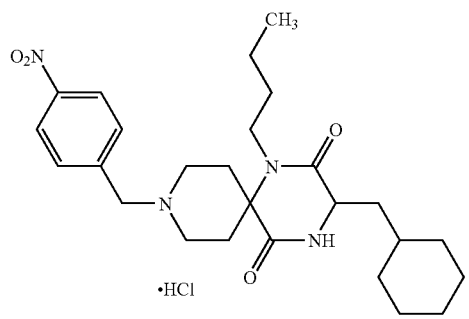

·HCl

TLC: Rf 0.68 (chloroform:methanol=10:1); NMR (CD$_3$OD): δ 8.33 (d, J=8.7Hz, 2H), 7.78 (d, J=8.7Hz, 2H), 4.49 (s, 2H), 4.03 (dd, J=7.5, 4.5Hz, 1H), 3.93-3.76 (m, 2H), 3.55-3.43 (m, 2H), 3.40-3.31 (m, 2H), 2.45-2.28 (m, 2H), 2.27-2.08 (m, 2H), 1.83-1.14 (m, 15H), 1.04-0.86 (m, 5H).

EXAMPLE 24(117)

(3R)-1-(tetrahydrofuran-2-ylmethyl)-2,5-dioxo-3-phenylmethyl-9-(4-phenylbutyl)-1,4,9-triazaspiro[5.5]undecane.hydrocoride

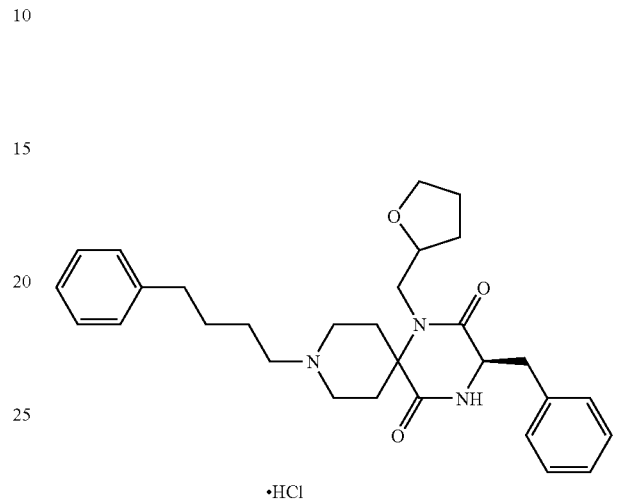

·HCl

TLC: Rf 0.55 (chloroform:methanol=10:1); NMR (CDCl$_3$): δ 7.38-7.14 (m, 10H), 6.00-5.75 (m, 1H), 4.40-4.15 (m, 2H), 3.92-3.58 (m, 3H), 3.58-2.25 (m, 13H), 2.18-1.45 (m, 10H).

EXAMPLE 24(118)

(3S)-1-(tetrahydrofuran-2-ylmethyl)-2,5-dioxo-3-phenylmethyl-9-(4-phenylbutyl)-1,4,9-triazaspiro[5.5]undecane.hydrochloride

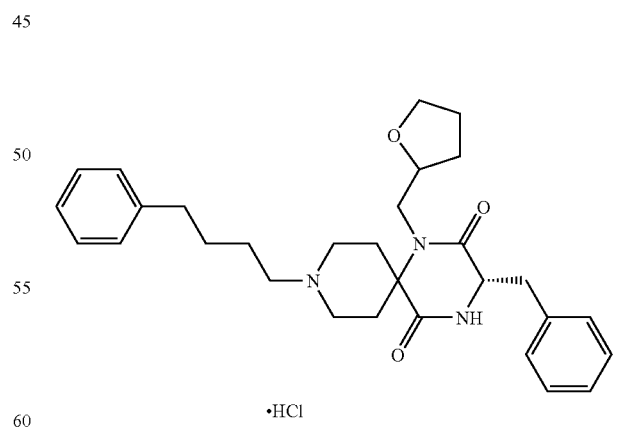

·HCl

TLC: Rf 0.55 (chloroform:methanol=10:1); NMR (CDCl$_3$): δ 7.40-7.15 (m, 10H), 6.05-5.80 (m, 1H), 4.40-4.10 (m, 2H), 3.90-3.55 (m, 3H), 3.55-2.20 (m, 13H), 2.18-1.45 (m, 10H).

EXAMPLE 24(119)

(3S)-1-propyl-2,5-dioxo-3-(3-(benzyloxycarbonylamino)propyl)-9-(2-phenylethyl)-1,4,9-triazaspiro[5.5]undecane.hydrochloride

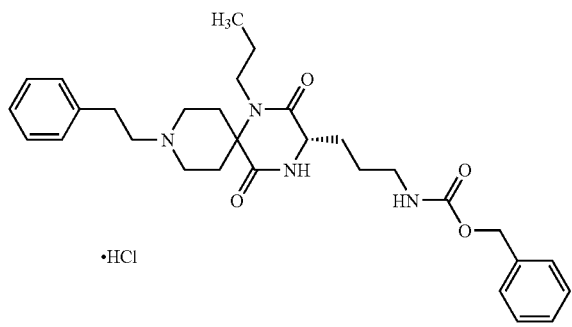

TLC: Rf 0.32 (chloroform:methanol=10:1); NMR (CD₃OD): δ 7.40-7.20 (m, 10H), 5.06 (s, 2H), 4.09 (dd, J=5.2, 4.6 Hz, 1H), 4.00-3.70 (m, 2H), 3.70-3.55 (m, 2H), 3.50-3.30 (m, 4H), 3.20-3.00 (m, 4H), 2.65-2.35 (m, 2H), 2.30-2.10 (m, 2H), 2.00-1.75 (m, 2H), 1.70-1.40 (m, 4H), 0.96 (t, J=7.4 Hz, 3H).

EXAMPLE 25

1-butyl-2,5-dioxo-3-(carboxymethyl)-9-(4-phenyloxyphenylmethyl)-1,4,9-triazaspiro[5.5]undecane.hydrochloride

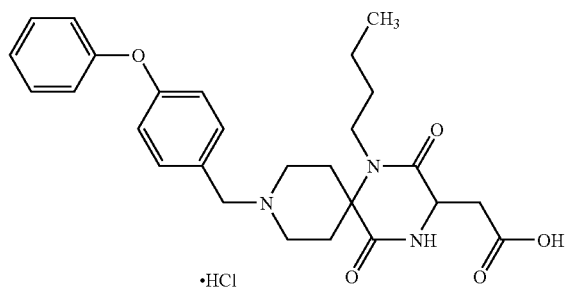

To a solution of the compound prepared in Example 24(11) (173 mg) in methanol (5 mL) was added 2N aqueous solution of sodium hydroxide (2 ml). The reaction mixture was stirred for 3 hours at room temperature. The reaction mixture was acidified to pH 4 by adding 2N hydrochloric acid, and was extracted with ethyl acetate. The extract was washed with a saturated aqueous solution of sodium chloride, dried over anhydrous sodium sulfate and concentrated. The obtained residue was dissolved in 1,4-dioxane, and 4N hydrogen chloride-1,4-dioxane solution was added thereto. The reaction mixture was concentrated. The obtained residue was washed with diethyl ether and dried to give the compound of the present invention (127 mg) having the following physical data.

TLC: Rf 0.51 (chloroform:methanol:acetic acid=20:4:1); NMR (CD₃OD): δ 7.55-7.53 (m, 2H), 7.42-7.36 (m, 2H), 7.20-7.15 (m, 1H), 7.07-7.02 (m, 4H), 4.33 (s, 2H), 4.27 (t, J=4.5 Hz, 1H), 3.96-3.90 (m, 1H), 3.72-3.66 (m, 1H), 3.54-3.38 (m, 4H), 2.97 (dd, J=18.0, 4.8 Hz, 1H), 2.79 (dd, J=18.0, 4.8 Hz, 1H), 2.50-2.36 (m, 3H), 2.27-2.16 (m, 1H), 1.62-1.48 (m, 2H), 1.41-1.30 (m, 2H), 0.94 (t, J=7.2 Hz, 3H).

EXAMPLE 26(1) TO 26(3)

By the same procedure as described in Reference Example 3→Reference Example 4 using Resin (3) prepared in Reference Example 2 and N-allyloxycarbonyl-4-piperidone, using the corresponding compounds respectively instead of n-propylamine and N-(t-butyloxycarbonyl)leucine, and furthermore by the same procedure as described in Reference Example 5→Reference Example 6→Example 1 using the corresponding compound instead of 3,5-dimethyl-1-phenyl-4-formylpyrazole, and furthermore by the same procedure as described in Example 25 because of acetylation of a part of hydroxy group, the following compounds of the present invention were obtained.

EXAMPLE 26(1)

1-(3-hydroxybutyl)-2,5-dioxo-3-(2-methylpropyl)-9-(4-phenyloxyphenylmethyl)-1,4,9-triazaspiro[5.5]undecane.hydrochloride

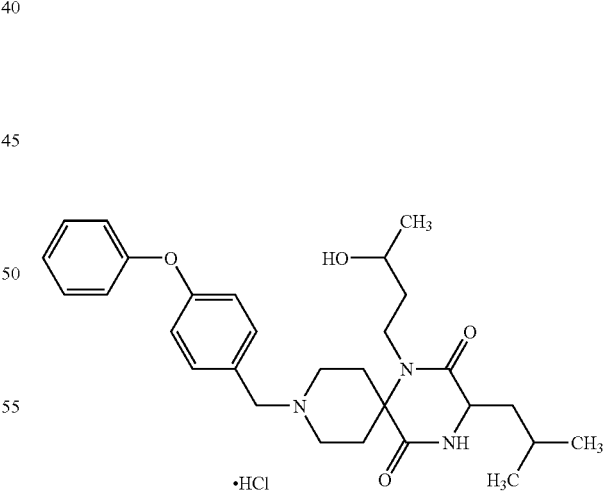

TLC: Rf 0.49 (chloroform:methanol=10:1); NMR (CD₃OD): δ 7.54 (d, J=8.5 Hz, 2H), 7.39 (t, J=7.5 Hz, 2H), 7.18 (t, J=7.5 Hz, 1H), 7.04 (m, 4H), 4.33 (s, 2H), 4.02 (m, 1H), 3.80 (m, 3H), 3.51 (m, 4H), 2.46 (m, 2H), 2.19 (m, 2H), 1.85-1.57 (m, 5H), 1.17 (d, J=6.0 Hz, 3H), 0.94 (d, J=9.0 Hz, 6H).

EXAMPLE 26(2)

1-(3-hydroxypropyl)-2,5-dioxo-3-(2-methylpropyl)-9-(4-phenyloxyphenylmethyl)-1,4,9-triazaspiro[5.5]undecane.hydrochloide

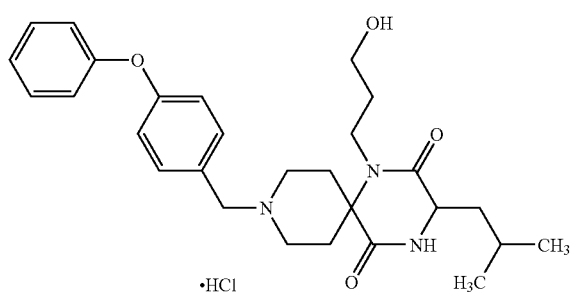

TLC: Rf 0.46 (chloroform:methanol=10:1); NMR (CD$_3$OD): δ 7.51 (d, J=8.5 Hz, 2H), 7.40 (t, J=7.5 Hz, 2H), 7.18 (t, J=7.5 Hz, 1H), 7.04 (m, 4H), 4.34 (s, 2H), 4.02 (dd, J=7.5, 4.0 Hz, 1H), 3.80 (m, 2H), 3.60 (t, J=6.0 Hz, 2H), 3.48 (m, 4H), 2.40 (m, 2H), 2.20 (m, 2H), 1.82-1.58 (m, 5H), 0.94 (d, J=6.0 Hz, 3H), 0.93 (d, J=6.0 Hz, 3H).

EXAMPLE 26(3)

1-(2-hydroxybutyl)-2,5-dioxo-3-(2-methylpropyl)-9-(4-phenyloxyphenylmethyl)-1,4,9-triazaspiro[5.5]undecane.hydrochloride

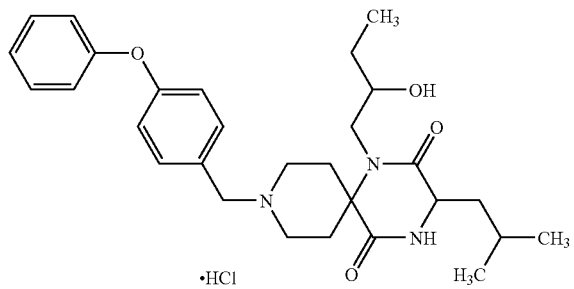

TLC: Rf 0.49 (chloroform:methanol=10:1); NMR (CD$_3$OD): δ 7.50 (d, J=8.7 Hz, 2H), 7.39 (dd, J=8.7, 7.5 Hz, 2H), 7.18 (t, J=7.5 Hz, 1H), 7.10-7.00 (m, 4H), 4.32 (s, 2H), 4.03 (dd, J=8.1, 4.8 Hz, 1H), 3.96-3.41 (m, 6H), 3.27-3.14 (m, 1H), 2.68-2.53 (m, 1H), 2.37-2.26 (m, 3H), 1.94-1.24 (m, 5H), 1.08-0.82 (m, 9H).

EXAMPLE 27

1-butyl-2,5-dioxo-3-cyclohexylmethyl-9-(4-aminophenylmethyl)-1,4,9-triazaspiro[5.5]undecane.2 hydrochloride

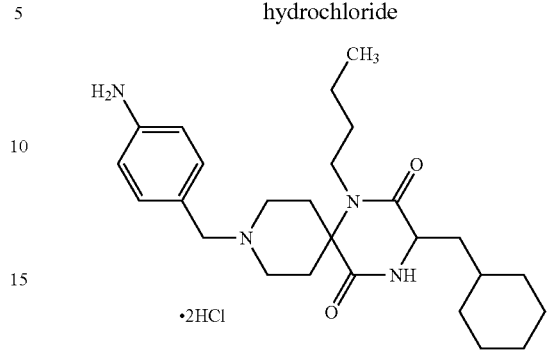

Under an atmosphere of argon, to a solution of the compound prepared in Example 24(116) (50 mg) in methanol was added 5% palladium on carbon (10 mg). Under an atmosphere of hydrogen, the reaction mixture was stirred for 20 minutes at room temperature. The reaction mixture was filtrated through Celite (brand name). The filtrate was concentrated. The residue was purified by column chromatography on silica gel (chloroform:methanol=50:1→30:1→20:1). The obtained compound was dissolved in methanol, and 4N-hydrogen chloride/ethyl acetate solution was added thereto. It was concentrated. The obtained residue was washed with diethyl ether and dried to give the compound of the present invention (34 mg) having the following physical data.

TLC: Rf 0.21 (chloroform:methanol=10:1); NMR (CD$_3$OD): δ 7.80 (d, J=8.4 Hz, 2H), 7.47 (d, J=8.4 Hz, 2H), 4.41 (s, 2H), 4.03 (dd, J=7.5, 4.5 Hz, 1H), 3.86-3.74 (m, 2H), 3.52-3.45 (m, 4H), 2.65-2.52 (m, 2H), 2.24-2.08 (m, 2H), 1.80-1.16 (m, 15H), 0.94 (t, J=7.5 Hz, 3H), 0.94 (m, 2H).

EXAMPLE 28

1-butyl-2,5-dioxo-3-cyclohexylmethyl-9-(4-((4-methylphenyl)sulfonylamino)phenylmethyl)-1,4,9-triazaspiro[5.5]undecane.hydrochloride

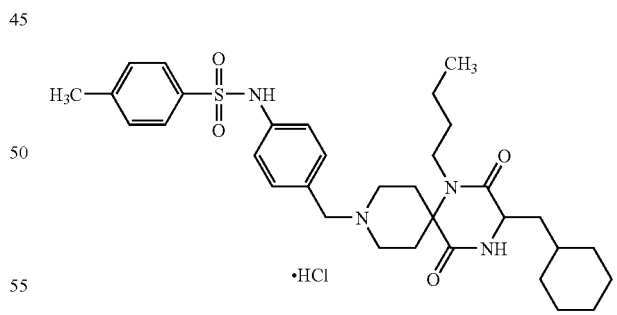

To a solution of the compound prepared in Example 28 (33 mg) in pyridine (2 ml) was added p-toluenesulfonyl chloride (21 mg). The reaction mixture was stirred for 27 hours at room temperature. The reaction mixture was concentrated, and saturated aqueous solution of sodium hydrogen carbonate was added thereto. It was extracted with ethyl acetate. The extract was washed with saturated aqueous solution of sodium chloride, dried over anhydrous sodium sulfate, and concentrated. The residue was purified by column chromatography on silica gel (chloroform:methanol=10:1). The obtained compound was dissolved in methanol, and 4N hydrogen chloride/ethyl acetate solution was added thereto, and it was concentrated. The residue was washed with diethyl ether and dried to give the compound of the present invention (27 mg) having the following physical data.

TLC: Rf 0.63 (chloroform:methanol=10:1); NMR (CD$_3$OD): δ 7.70 (d, J=8.4 Hz, 2H), 7.41 (d, J=8.4 Hz, 2H), 7.30 (d, J=8.4 Hz, 2H), 7.22 (d, J=8.4 Hz, 2H), 4.25 (s, 2H), 4.03 (dd, J=7.2, 4.5 Hz, 1H), 3.78 (m, 2H), 3.42 (m, 4H), 2.42-2.06 (m, 4H), 2.37 (s, 3H), 1.82-1.10 (m, 15H), 0.95 (t, J=7.2 Hz, 3H), 0.95 (m, 2H).

EXAMPLE 28(1)

1-butyl-2,5-dioxo-3-cyclohexylmethyl-9-(4-(phenylcarbonylamino)phenylmethyl)-1,4,9-triazaspiro[5.5]undecane.2 hydrochloride

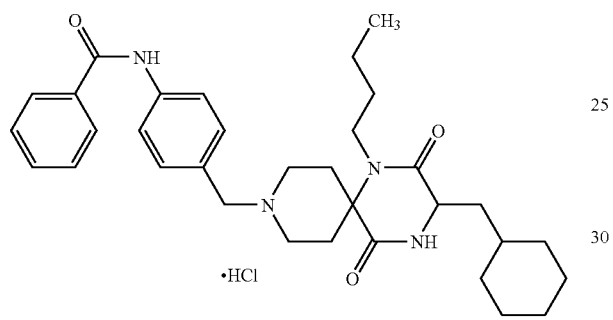

By the same procedure as described in Example 28 using benzoyl chloride instead of p-toluenesulfonyl chloride, the compound of the present invention having the following physical data was obtained.

TLC: Rf 0.43 (chloroform:methanol=10:1); NMR (CD$_3$OD): δ 7.93 (d, J=8.4 Hz, 2H), 7.88 (d, J=8.4 Hz, 2H), 7.61-7.50 (m, 5H), 4.34 (s, 2H), 4.05 (dd, J=7.8, 4.5 Hz, 1H), 3.80 (m, 2H), 3.42 (m, 4H), 2.24 (m, 4H), 1.82-1.16 (m, 15H), 0.96 (t, J=7.2 Hz, 3H), 0.96 (m, 2H).

EXAMPLE 29

(3S)-1-butyl-2,5-dioxo-3-benzyloxymethyl-9-benzyloxycarbonyl-1,4,9-triazaspiro[5.5]undecane

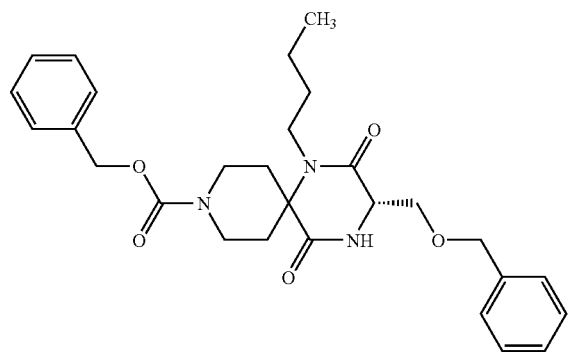

By the same procedure as described in Reference Example 3→Reference Example 6→Example 1 using Resin (3) prepared in Reference Example 2 and N-benzyloxycarbonyl-4-piperidone, O-benzyl-N-(t-butyloxycarbonyl)-L-serine, the compound of the present invention having the following physical data was obtained.

TLC: Rf 0.66 (chloroform:methanol=20:1); NMR (CDCl$_3$): δ 7.40-7.25 (m, 10H), 6.09 (brs, 1H), 5.15 (s, 2H), 4.54 (s, 2H), 4.20-3.98 (br, 2H), 4.18 (dd, J=8.4, 3.6 Hz, 1H), 3.93 (dd, J=9.3, 3.6 Hz, 1H), 3.80-3.56 (br, 1H), 3.66 (dd, J=9.3, 8.4, Hz, 1H), 3.45-3.12 (m, 3H), 2.02-1.75 (m, 4H), 1.57-1.39 (m, 2H), 1.38-1.20 (m, 2H), 0.91 (t, J=7.2 Hz, 3H).

EXAMPLE 30

(3S)-1-butyl-2,5-dioxo-3-hydroxymethyl-9-benzyloxycarbonyl-1,4,9-triazaspiro[5.5]undecane

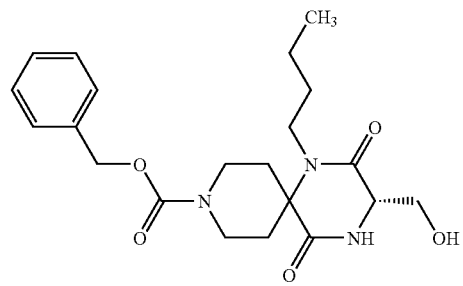

To a solution of the compound prepared in Example 29 (245 mg) in dichloromethane (5 ml) was added a 1M solution of tribromoborane in dichloromethane (1.4 ml) at −40° C., and it was stirred for 3 hours at −20° C. To the reaction mixture were added water and saturated aqueous solution of sodium hydrogen carbonate, and it was extracted with ethyl acetate. The extract was washed with water and saturated aqueous solution of sodium chloride, dried over anhydrous sodium sulfate, and concentrated. The residue was purified by column chromatography on silica gel (chloroform:methanol=30:1) to give the compound of the present invention (173 mg) having the following physical data.

TLC: Rf 0.29 (chloroform:methanol=20:1); NMR (CDCl$_3$): δ 7.42-7.27 (m, 5H), 6.26-6.15 (br, 1H), 5.16 (s, 2H), 4.26-4.00 (m, 2H), 3.98-3.82 (m, 2H), 3.84-3.60 (br, 1H), 3.43-3.13 (m, 4H), 2.80-2.68 (br, 1H), 2.05-1.75 (m, 4H), 1.58-1.40 (m, 2H), 1.40-1.20 (m, 2H), 0.92 (t, J=7.5 Hz, 3H).

EXAMPLE 31

(3S)-1-butyl-2,5-dioxo-3-hydroxymethyl-1,4,9-triazaspiro[5.5]undecane

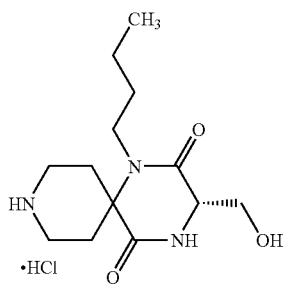

By the same procedure as described in Example 9 using the compound prepared in Example 30, the compound of the present invention having the following physical data was obtained.

TLC: Rf 0.21 (chloroform:methanol:acetic acid=20:4:1); NMR (d$_6$-DMSO): δ 7.83 (brs, 1H), 5.10-4.90 (br, 1H), 3.88-3.78 (m, 1H), 3.76-3.65 (m, 1H), 3.58-3.48 (m, 1H), 3.28-3.18 (m, 1H), 3.18-3.04 (m, 3H), 2.88-2.75 (m, 2H), 1.94-1.83 (m, 1H), 1.83-1.64 (m, 3H), 1.56-1.42 (m, 1H), 1.42-1.20 (m, 3H), 0.88 (t, J=7.2 Hz, 3H).

EXAMPLE 32(1)

(3S)-1-butyl-2,5-dioxo-3-hydroxymethyl-9-(4-phenyloxyphenylmethyl)-1,4,9-triazaspiro[5.5]undecane.hydrochloride

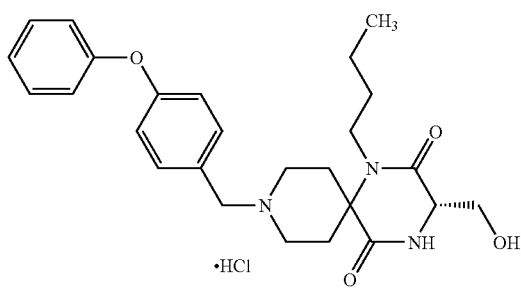

By the same procedure as described in Example 10 using 4-phenyloxybenzaldehyde and the compound prepared in Example 31, the compound of the present invention having the following physical data was obtained.

TLC: Rf 0.49 (chloroform:methanol=10:1); NMR (CD$_3$OD): δ 7.52 (d, J=8.7 Hz, 2H), 7.43-7.35 (m, 2H), 7.22-7.14 (m, 1H), 7.06 (d, J=8.7 Hz, 2H), 7.06-7.00 (m, 2H), 4.33 (s, 2H), 4.03-3.90 (m, 3H), 3.79-3.66 (m, 1H), 3.65 (dd, J=10.5, 2.4 Hz, 1H), 3.61-3.42 (m, 3H), 3.30-3.18 (m, 1H), 2.50-2.24 (m, 3H), 2.24-2.12 (m, 1H), 1.76-1.58 (m, 1H), 1.54-1.26 (m, 3H), 0.95 (t, J=7.5 Hz, 3H).

EXAMPLE 32(2)

(3S)-1-butyl-2,5-dioxo-3-hydroxymethyl-9-(3,5-dimethyl-1-phenylpyrazol-4-ylmethyl)-1,4,9-triazaspiro[5.5]undecane.2 hydrochlorie

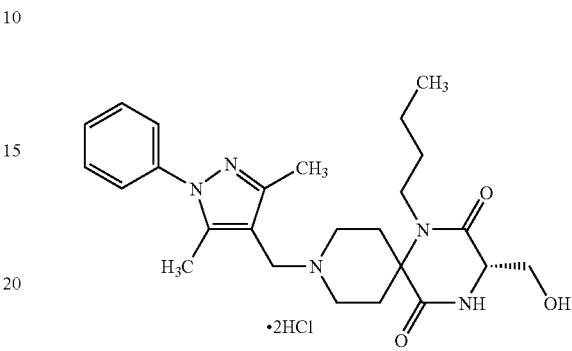

By the same procedure as described in Example 10 using 1-phenyl-3,5-dimethyl-4-formylpyrazole and the compound prepared in Example 31, the compound of the present invention having the following physical data was obtained.

TLC: Rf 0.47 (chloroform:methanol=10:1); NMR (CD$_3$OD): δ 7.61-7.46 (m, 5H), 4.32 (s, 2H), 4.08-3.92 (m, 3H), 3.83-3.70 (m, 1H), 3.66 (dd, J=10.5, 2.4 Hz, 1H), 3.66-3.52 (m, 3H), 3.40-3.25 (m, 1H), 2.64-2.50 (m, 1H), 2.50-2.40 (m, 2H), 2.41 (s, 3H), 2.39 (s, 3H), 2.28-2.15 (m, 1H), 1.80-1.58 (m, 1H), 1.58-1.30 (m, 3H), 0.96 (t, J=7.5 Hz, 3H).

REFERENCE EXAMPLE 11

Preparation of Compound (7)

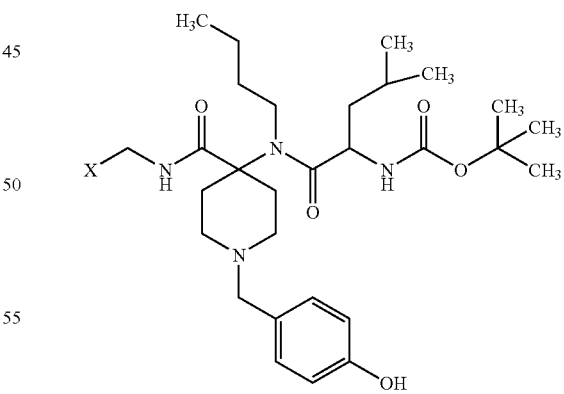

By the same procedure as described in Reference Example 3→Reference Example 4 using Resin (3) prepared in Reference Example 2 and N-allyloxycarbonyl-4-piperidone, n-butylamine and N-(t-butyloxycarbonyl)leucine, and furthermore by the same procedure as described in Reference Example 5 using 4-hydroxybenzaldehyde instead of 3,5-dimethyl-1-phenyl-4-formylpyrazole, compound (7) was obtained.

REFERENCE EXAMPLE 12

Preparation of Compound (8)

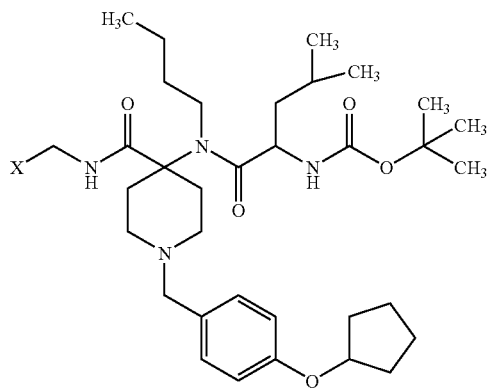

To a suspension of the compound prepared in Reference Example 11 (60 mg) in dichloromethane (2 ml) were added triphenylphosphine (80 mg), 1M cyclopentanol-dichloromethane solution (0.302 ml) and diethylazodicarboxylate (0.137 ml). The reaction mixture was stirred for 18 hours at room temperature. The reaction solution was filtrated. The obtained resin was washed with dichloromethane (2 ml×4), methanol (2 ml×3), and dichloromethane (3 ml×4) to give compound (8).

EXAMPLE 33

1-butyl-2,5-dioxo-3-(2-methylpropyl)-9-(4-cyclopentyloxyphenylmethyl)-1,4,9-triazaspiro[5.5]undecane.hydrochloride

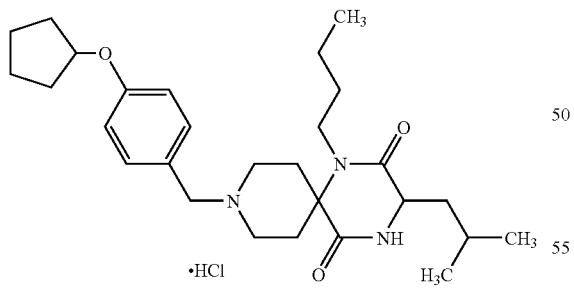

By the same procedure as described in Reference Example 6→Example 1 using the compound prepared in Reference Example 12, the compound of the present invention having the following physical data was obtained.

TLC: Rf 0.49 (chloroform:methanol=10:1); NMR (CD$_3$OD): δ 7.41 (d, J=8.7 Hz, 2H), 6.98 (d, J=8.7 Hz, 2H), 4.83 (m, 1H), 4.25 (brs, 2H), 4.00 (dd, J=7.8, 4.5 Hz, 1H), 3.86-3.65 (m, 2H), 3.53-3.27 (m, 4H), 2.40-2.06 (m, 4H), 2.02-1.43 (m, 13H), 1.43-1.24 (m, 2H), 1.01-0.90 (m, 9H).

EXAMPLE 33(1) TO 33(6)

By the same procedure as described in Reference Example 11 using the corresponding compounds instead of n-butylamine and N-(t-butyloxycarbonyl)leucine, and by the same procedure as described in Reference Example 12→Example 33 using the corresponding compounds instead of cyclopentanol, the following compounds of the present invention were obtained.

EXAMPLE 33(1)

1-butyl-2,5-dioxo-3-cyclohexylmethyl-9-(4-(2-diethylaminoethyloxy)phenylmethyl)-1,4,9-triazaspiro[5.5]undecane.2 hydrochloride

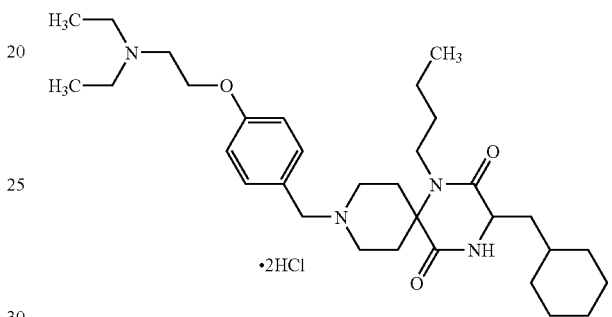

TLC: Rf 0.54 (chloroform:methanol:28% NH$_4$OH=80:10:1); NMR (CD$_3$OD): δ 7.57 (d, J=8.7 Hz, 2H), 7.12 (d, J=8.7 Hz, 2H), 4.40 (t, J=4.8 Hz, 2H), 4.30 (s, 2H), 4.03 (dd, J=7.5, 5.1 Hz, 1H), 3.84-3.67 (m, 2H), 3.63 (t, J=4.8 Hz, 2H), 3.50-3.40 (m, 4H), 3.40-3.31 (m, 4H), 2.58-2.41 (m, 2H), 2.23-2.04 (m, 2H), 1.82-1.42 (m, 10H), 1.41-1.12 (m, 11H), 1.04-0.87 (m, 5H).

EXAMPLE 33(2)

1-butyl-2,5-dioxo-3-cyclohexylmethyl-9-(4-(2-dimethylaminoethyloxy)phenylmethyl)-1,4,9-triazaspiro[5.5]undecane.2 hydrochloride

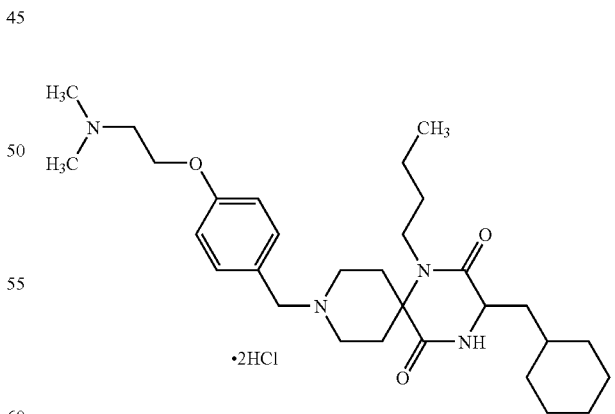

TLC: Rf 0.46 (chloroform:methanol:28% NH$_4$OH=80:10:1); NMR (CD$_3$OD): δ 7.57 (d, J=8.7 Hz, 2H), 7.13 (d, J=8.7 Hz, 2H), 4.39 (t, J=4.8 Hz, 2H), 4.30 (s, 2H), 4.02 (dd, J=7.5, 4.5 Hz, 1H), 3.84-3.67 (m, 2H), 3.61 (t, J=4.8 Hz, 2H), 3.50-3.38 (m, 4H), 2.98 (s, 6H), 2.59-2.42 (m, 2H), 2.24-2.03 (m, 2H), 1.83-1.12 (m, 15H), 1.04-0.86 (m, 5H).

EXAMPLE 33(3)

1-butyl-2,5-dioxo-3-cyclohexylmethyl-9-(4-propyloxyphenylmethyl)-1,4,9-triazaspiro[5.5]undecane.hydrochloride

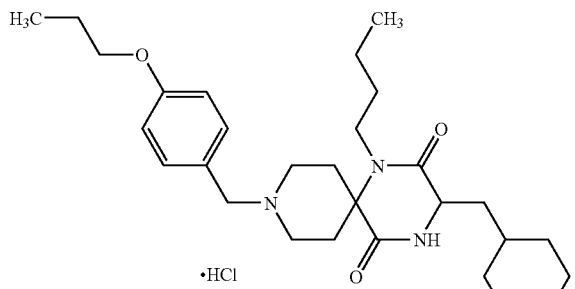

TLC: Rf 0.59 (chloroform:methanol=10:1); NMR (CD$_3$OD): δ 7.43 (d, J=8.7 Hz, 2H), 7.01 (d, J=8.7 Hz, 2H), 4.27 (brs, 2H), 4.03 (dd, J=7.5, 4.5 Hz, 1H), 3.96 (t, J=6.6 Hz, 2H), 3.85-3.67 (m, 2H), 3.53-3.33 (m, 4H), 2.45-2.27 (m, 2H), 2.26-2.07 (m, 2H), 1.86-1.14 (m, 17H), 1.03 (t, J=7.2 Hz, 3H), 1.00-0.89 (m, 5H).

EXAMPLE 33(4)

1-(thiophen-2-ylmethyl)-2,5-dioxo-3-cyclohexylmethyl-9-(4-cyclopropylmethyloxyphenylmethyl)-1,4,9-triazaspiro[5.5]undecane.hydrochloride

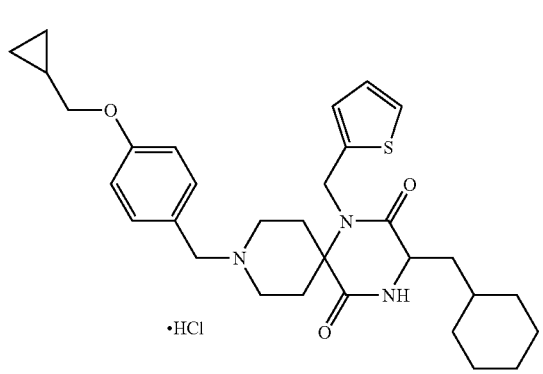

TLC: Rf 0.61 (chloroform:methanol=10:1); NMR (CD$_3$OD): δ 7.42 (d, J=8.7 Hz, 2H), 7.27 (dd, J=5.4, 0.9 Hz, 1H), 7.06-6.97 (m, 3H), 6.91 (dd, J=5.4, 3.6 Hz, 1H), 4.95-4.85 (m, 2H), 4.27 (brs, 2H), 4.14 (dd, J=7.5, 4.5 Hz, 1H), 3.84 (d, J=6.6 Hz, 2H), 3.84-3.66 (m, 2H), 3.51-3.39 (m, 2H), 2.59-2.36 (m, 2H), 2.24-2.07 (m, 2H), 1.84-1.44 (m, 8H), 1.35-1.12 (m, 4H), 1.04-0.85 (m, 2H), 0.66-0.57 (m, 2H), 0.38-0.31 (m, 2H).

EXAMPLE 33(5)

1-butyl-2,5-dioxo-3-cyclohexylmethyl-9-(4-cyclopropylmethyloxyphenylmethyl)-1,4,9-triazaspiro[5.5]undecane.hydrochloride

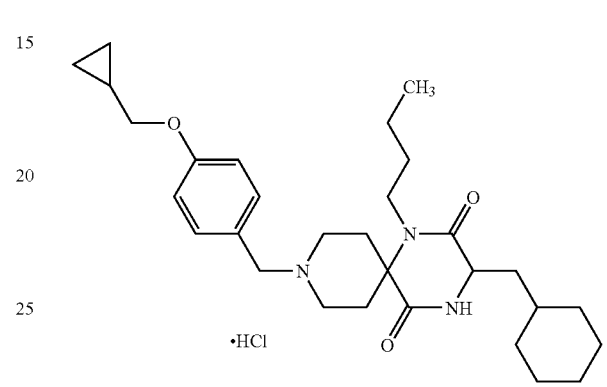

TLC: Rf 0.61 (chloroform:methanol=10:1); NMR (CD$_3$OD): δ 7.42 (d, J=8.4 Hz, 2H), 7.01 (d, J=8.4 Hz, 2H), 4.26 (brs, 2H), 4.03 (dd, J=7.8, 4.8 Hz, 1H), 3.84 (d, J=6.9 Hz, 2H), 3.83-3.66 (m, 2H), 3.51-3.33 (m, 4H), 2.44-2.26 (m, 2H), 2.25-2.06 (m, 2H), 1.82-1.12 (m, 16H), 1.04-0.86 (m, 5H), 0.66-0.57 (m, 2H), 0.38-0.31 (m, 2H).

EXAMPLE 33(6)

1-butyl-2,5-dioxo-3-(2-methylpropyl)-9-(4-cyclopropylmethyloxyphenylmethyl)-1,4,9-triazaspiro[5.5]undecane.hydrochloride

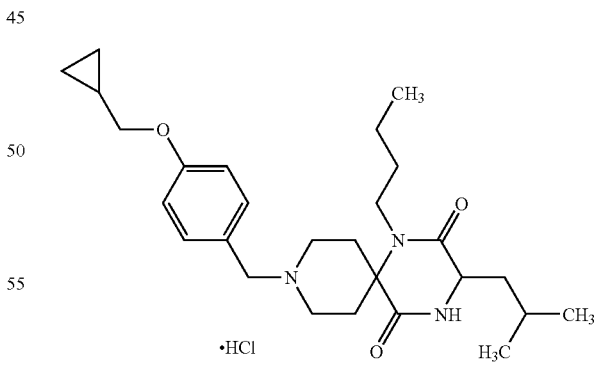

TLC: Rf 0.55 (chloroform:methanol=10:1); NMR (CD$_3$OD): δ 7.42 (d, J=8.7 Hz, 2H), 7.01 (d, J=8.7 Hz, 2H), 4.26 (brs, 2H), 4.00 (dd, J=7.8, 4.5 Hz, 1H), 3.84 (d, J=6.9 Hz, 2H), 3.84-3.66 (m, 2H), 3.50-3.33 (m, 4H), 2.43-2.26 (m, 2H), 2.26-2.08 (m, 2H), 1.89-1.43 (m, 5H), 1.43-1.17 (m, 3H), 1.00-0.88 (m, 9H), 0.66-0.58 (m, 2H), 0.38-0.31 (m, 2H).

EXAMPLE 34

1-butyl-2,5-dioxo-3-cyclohexylmethyl-9-(4-(dimethylamino)phenylmethyl)-1,4,9-triazaspiro[5.5]undecane.2 hydrochloride

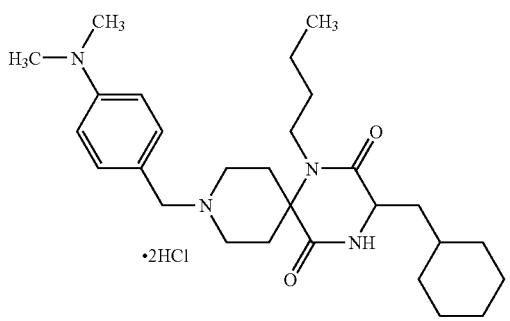

By the same procedure as described in Example 10 using 4-dimethylaminobenzaldehyde and the compound prepared in Example 9(1), the compound of the present invention having the following physical data was obtained.

TLC: Rf 0.26 (chloroform:methanol=10:1); NMR (CD$_3$OD): δ 7.78 (d, J=8.7 Hz, 2H), 7.59 (d, J=8.7 Hz, 2H), 4.39 (s, 2H), 4.03 (dd, J=7.5, 4.8, Hz, 1H), 3.90-3.70 (m, 2H), 3.52-3.40 (m, 4H), 3.26 (s, 6H), 2.64-2.47 (m, 2H), 2.24-2.04 (m, 2H), 1.82-1.12 (m, 15H), 1.04-0.88 (m, 5H).

EXAMPLE 34(1)

1-butyl-2,5-dioxo-3-cyclohexylmethyl-9-(4-(diethylamino)phenylmethyl)-1,4,9-triazaspiro[5.5]undecane.2 hydrochloride

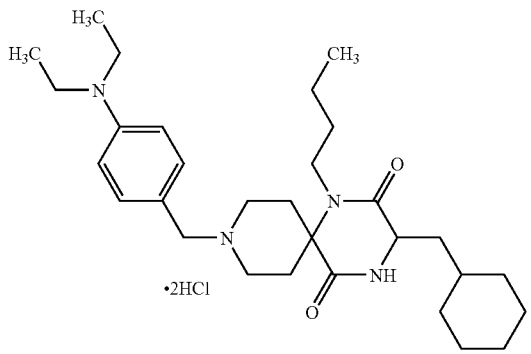

By the same procedure as described in Example 34 using 4-diethylaminobenzaldehyde instead of 4-dimethylaminobenzaldehyde, the compound of the present invention having the following physical data was obtained.

TLC: Rf 0.28 (chloroform:methanol:acetic acid=10:1); NMR (CD$_3$OD): δ 7.94-7.78 (m, 2H), 7.72-7.52 (m, 2H), 4.43 (s, 2H), 4.03 (dd, J=7.5, 4.8, Hz, 1H), 3.92-3.73 (m, 2H), 3.73-3.60 (m, 4H), 3.54-3.40 (m, 4H), 2.63-2.45 (m, 2H), 2.25-2.05 (m, 2H), 1.82-1.10 (m, 21H), 1.04-0.86 (m, 5H).

EXAMPLE 35

(3S)-1-butyl-2,5-dioxo-3-(2-methylpropyl)-9-benzyloxycarbonyl-1,4,9-triazaspiro[5.5]undecane

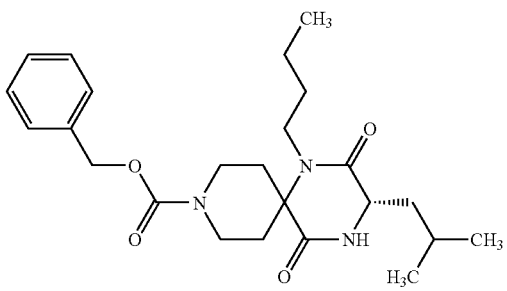

By the same procedure as described in Reference Example 3→Reference Example 6→Example 1 using Resin (3) prepared in Reference Example 2, N-benzyloxycarbonyl-4-piperidone, n-butylamine and N-(t-butyloxycarbonyl)-L-leucine, the compound of the present invention having the following physical data was obtained.

TLC: Rf 0.67 (chloroform:methanol=20:1); NMR (CD$_3$OD): δ 7.35 (m, 5H), 6.50 (brs, 1H), 5.15 (s, 2H), 4.08 (m, 2H), 3.96 (m, 1H), 3.62 (brs, 1H), 3.44 (brs, 1H), 3.26 (m, 2H), 1.95-1.76 (m, 4H), 1.61-1.45 (m, 5H), 1.31 (m, 2H), 0.96 (d, J=6.3 Hz, 3H), 0.93 (d, J=6.3 Hz, 3H), 0.91 (t, J=7.2 Hz, 3H).

EXAMPLE 36

(3S)-1-butyl-2,5-dioxo-3-(2-methylpropyl)-1,4,9-triazaspiro[5.5]undecane.hydrochloride

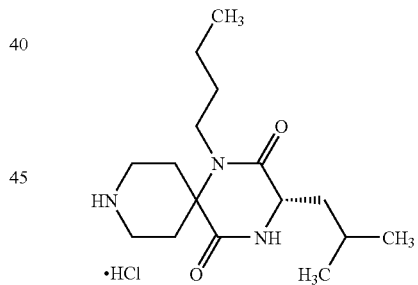

By the same procedure as described in Example 9 using the compound prepared in Example 35, the compound of the present invention having the following physical data was obtained.

TLC: Rf 0.18 (chloroform:methanol=4:1); NMR (CD$_3$OD): δ 4.02 (dd, J=7.8, 4.6 Hz, 1H), 3.80 (dd, J=12.5, 4.0 Hz, 1H), 3.72 (dd, J=12.5, 4.0 Hz, 1H), 3.39 (m, 4H), 2.34-2.09 (m, 4H), 1.88-1.50 (m, 5H), 1.37 (m, 2H), 0.96 (t, J=7.5 Hz, 3H), 0.95 (d, J=6.5 Hz, 3H), 0.94 (d, J=6.5 Hz, 3H).

EXAMPLE 37(1) TO 37(88)

By the same procedure as described in Example 10 using the compound prepared in Example 36 and the corresponding aldehyde derivatives, the following compounds of the present invention were obtained.

EXAMPLE 37(1)

(3S)-1-butyl-2,5-dioxo-3-(2-methylpropyl)-9-(5-(3-methyl-4-chlorophenyl)-1-(4-methylphenylmethyl)pyrazol-3-ylmethyl)-1,4,9-triazaspiro[5.5]undecane.2 hydrocloride

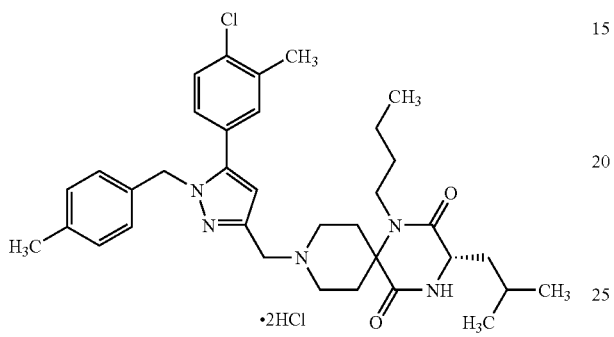

TLC: Rf 0.46 (chloroform:methanol=20:1); NMR (CD$_3$OD): δ 7.42 (d, J=8.1 Hz, 1H), 7.28 (d, J=1.5 Hz, 1H), 7.19 (dd, J=8.1, 1.5 Hz, 1H), 7.11 (d, J=8.1 Hz, 2H), 6.92 (d, J=8.1 Hz, 2H), 6.65 (s, 1H), 5.35 (s, 2H), 4.40 (s, 2H), 4.02 (dd, J=7.5, 4.5 Hz, 1H), 3.97-3.76 (m, 2H), 3.64-3.52 (m, 2H), 3.46-3.35 (m, 2H), 2.56-2.38 (m, 2H), 2.35 (s, 3H), 2.28 (s, 3H), 2.30-2.10 (m, 2H), 1.91-1.46 (m, 5H), 1.46-1.30 (m, 2H), 0.96 (t, J=6.9 Hz, 3H), 0.95 (d, J=6.3 Hz, 6H).

EXAMPLE 37(2)

(3S)-1-butyl-2,5-dioxo-3-(2-methylpropyl)-9-(4-dimethylaminophenylmethyl)-1,4,9-triazaspiro[5.5]undecane.2 hydrochloride

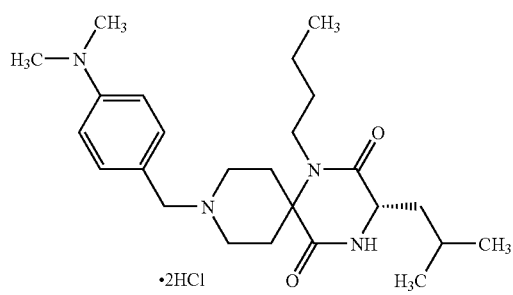

TLC: Rf 0.47 (chloroform:methanol=10:1); NMR (CD$_3$OD): δ 7.78 (d, J=8.7 Hz, 2H), 7.58 (d, J=8.7 Hz, 2H), 4.40 (s, 2H), 4.01 (dd, J=7.8, 4.5 Hz, 1H), 3.82 (m, 2H), 3.42 (m, 4H), 3.26 (s, 6H), 2.56 (m, 2H), 2.18 (m, 2H), 1.88-1.30 (m, 7H), 0.95 (t, J=7.2 Hz, 3H), 0.95 (d, J=6.3 Hz, 3H), 0.94 (d, J=6.3 Hz, 3H).

EXAMPLE 37(3)

(3S)-1-butyl-2,5-dioxo-3-(2-methylpropyl)-9-(4-diethylaminophenylmethyl)-1,4,9-triazaspiro[5.5]undecane.2 hydrochloride

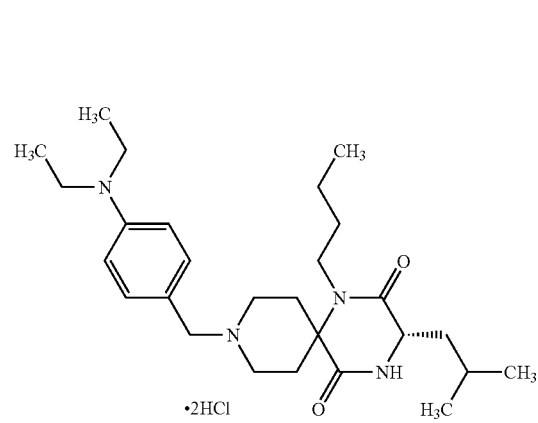

TLC: Rf 0.34 (chloroform:methanol=10:1); NMR (CD$_3$OD): δ 7.96-7.82 (m, 2H), 7.74-7.55 (m, 2H), 4.40 (s, 2H), 4.00 (dd, J=7.5, 4.5 Hz, 1H), 3.93-3.60 (m, 6H), 3.55-3.40 (m, 4H), 2.65-2.48 (m, 2H), 2.25-2.06 (m, 2H), 1.89-1.26 (m, 7H), 1.15 (t, J=7.2 Hz, 6H), 1.00-0.87 (m, 9H).

EXAMPLE 37(4)

(3S)-1-butyl-2,5-dioxo-3-(2-methylpropyl)-9-(4-cyclohexyloxyphenylmethyl)-1,4,9-triazaspiro[5.5]undecane.hydrochloride

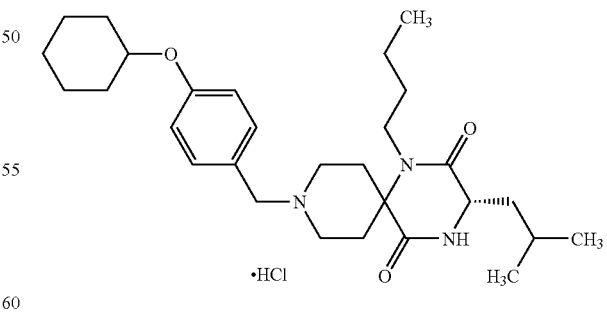

TLC: Rf 0.61 (chloroform:methanol=10:1); NMR (CD$_3$OD): δ 7.45-7.42 (m, 2H), 7.02-6.99 (m, 2H), 4.40-4.31 (m, 1H), 4.27 (s, 2H), 4.00 (dd, J=8.0, 4.5 Hz, 1H), 3.83-3.70 (m, 2H), 3.47 (brd, 2H), 3.42-3.35 (m, 2H), 2.43-2.32 (m, 2H), 2.24-2.11 (m, 2H), 2.00-1.93 (m, 2H), 1.86-1.32 (m, 15H), 0.97-0.92 (m, 9H).

EXAMPLE 37(5)

(3S)-1-butyl-2,5-dioxo-3-(2-methylpropyl)-9-(4-(4-methylphenyloxy)phenylmethyl)-1,4,9-triazaspiro[5.5]undecane.hydrochloride

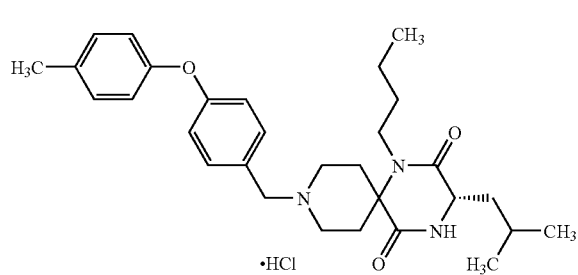

TLC: Rf 0.70 (chloroform:methanol=10:1); NMR (CD$_3$OD): δ 7.52-7.47 (m, 2H), 7.22-7.19 (m, 2H), 7.04-7.00 (m, 2H), 6.94-6.90 (m, 2H), 4.32 (s, 2H), 4.01 (dd, J=8.0, 4.5 Hz, 1H), 3.86-3.73 (m, 2H), 3.48 (brd, 2H), 3.42-3.34 (m, 2H), 2.45-2.33 (m, 5H), 2.25-2.12 (m, 2H), 1.85-1.48 (m, 5H), 1.41-1.31 (m, 2H), 0.97-0.92 (m, 9H).

EXAMPLE 37(6)

(3S)-1-butyl-2,5-dioxo-3-(2-methylpropyl)-9-(4-(4-methoxyphenyloxy)phenylmethyl)-1,4,9-triazaspiro[5.5]undecane.hydrochloride

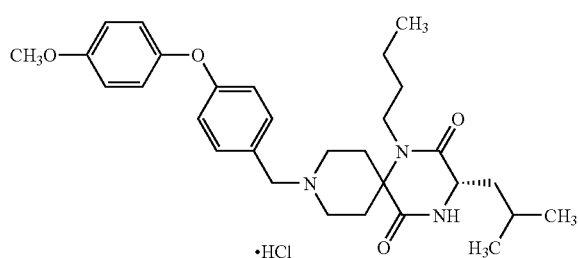

TLC: Rf 0.65 (chloroform:methanol=10:1); NMR (CD$_3$OD): δ 7.49-7.46 (m, 2H), 7.00-6.94 (m, 6H), 4.31 (s, 2H), 4.01 (dd, J=8.0, 4.5 Hz, 1H), 3.84-3.71 (m, 5H), 3.48 (brd, 2H), 3.40-3.31 (m, 2H), 2.42-2.30 (m, 2H), 2.25-2.12 (m, 2H), 1.83-1.48 (m, 5H), 1.41-1.30 (m, 2H), 0.97-0.92 (m, 9H).

EXAMPLE 37(7)

(3S)-1-butyl-2,5-dioxo-3-(2-methylpropyl)-9-(4-butylphenylmethyl)-1,4,9-triazaspiro[5.5]undecane-.hydrochloride

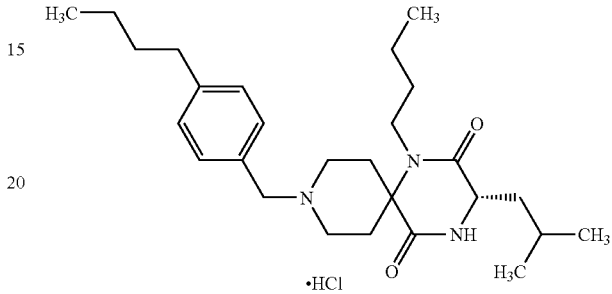

TLC: Rf 0.35 (chloroform:methanol=10:1); NMR (CD$_3$OD): δ 7.46 (d, J=8.1 Hz, 2H), 7.32 (d, J=8.1 Hz, 2H), 4.31 (s, 2H), 4.01 (dd, J=7.8, 4.5 Hz, 1H), 3.84-3.68 (m, 2H), 3.54-3.36 (m, 4H), 2.67 (t, J=7.8 Hz, 2H), 2.48-2.30 (m, 2H), 2.26-2.08 (m, 2H), 1.90-1.28 (m, 11H), 0.96 (t, J=7.2 Hz, 3H), 0.95 (d, J=6.3 Hz, 3H), 0.94 (d, J=6.3 Hz, 3H), 0.94 (t, J=7.2 Hz, 3H).

EXAMPLE 37(8)

(3S)-1-butyl-2,5-dioxo-3-(2-methylpropyl)-9-(4-(2-methylpropyl)phenylmethyl)-1,4,9-triazaspiro[5.5]undecane.hydrochloride

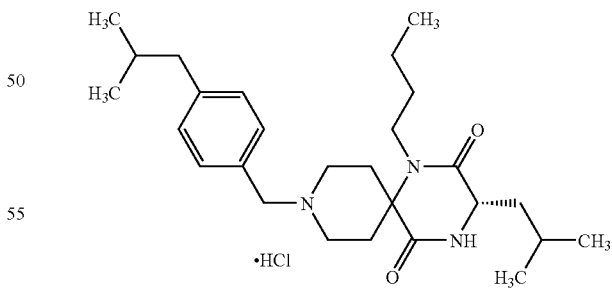

TLC: Rf 0.38 (chloroform:methanol=10:1); NMR (CD$_3$OD): δ 7.47 (d, J=6.9 Hz, 2H), 7.30 (d, J=6.9 Hz, 2H), 4.33 (s, 2H), 4.01 (dd, J=7.5, 4.5 Hz, 1H), 3.90-3.70 (m, 2H), 3.56-3.34 (m, 4H), 2.53 (d, J=7.2 Hz, 2H), 2.53-2.30 (m, 2H), 2.24-2.08 (m, 2H), 1.96-1.26 (m, 8H), 0.95 (t, J=7.8 Hz, 3H), 0.95 (d, J=6.6 Hz, 3H), 0.94 (d, J=6.6 Hz, 3H), 0.91 (d, J=6.6 Hz, 6H).

EXAMPLE 37(9)

(3S)-1-butyl-2,5-dioxo-3-(2-methylpropyl)-9-(4-(4-fluorophenyloxy)phenylmethyl)-1,4,9-triazaspiro[5.5]undecane.hydrochloride

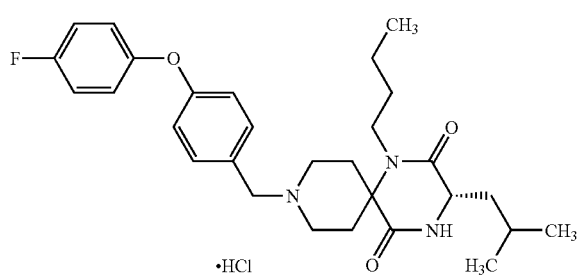

TLC: Rf 0.36 (chloroform:methanol=10:1); NMR (CD$_3$OD): δ 7.53 (d, J=8.4 Hz, 2H), 7.17 (d, J=8.4 Hz, 2H), 7.16-7.04 (m, 4H), 4.33 (s, 2H), 4.02 (dd, J=7.8, 4.8 Hz, 1H), 3.88-3.68 (m, 2H), 3.58-3.36 (m, 4H), 2.46-2.10 (m, 4H), 1.90-1.24 (m, 7H), 0.96 (t, J=6.9 Hz, 3H), 0.95 (d, J=6.6 Hz, 3H), 0.94 (d, J=6.6 Hz, 3H).

EXAMPLE 37(10)

(3S)-1-butyl-2,5-dioxo-3-(2-methylpropyl)-9-(3-hydroxy-4-methoxyphenylmethyl)-1,4,9-triazaspiro[5.5]undecane.hydrochloride

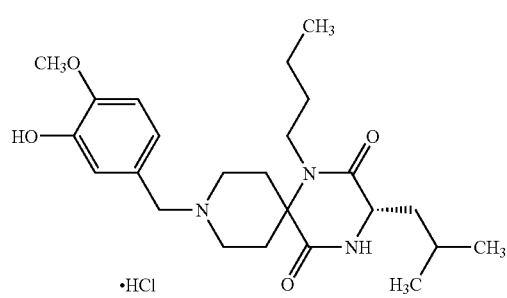

TLC: Rf 0.20 (chloroform:methanol=10:1); NMR (CD$_3$OD): δ 7.03-6.94 (m, 3H), 4.23 (s, 2H), 4.01 (dd, J=7.8, 4.5 Hz, 1H), 3.89 (s, 3H), 3.84-3.68 (m, 2H), 3.56-3.36 (m, 4H), 2.42-2.08 (m, 4H), 1.88-1.24 (m, 7H), 0.96 (t, J=7.2 Hz, 3H), 0.95 (d, J=6.3 Hz, 3H), 0.94 (d, J=6.3 Hz, 3H).

EXAMPLE 37(11)

(3S)-1-butyl-2,5-dioxo-3-(2-methylpropyl)-9-(2-fluorophenylmethyl)-1,4,9-triazaspiro[5.5]undecane-.hydrochloride

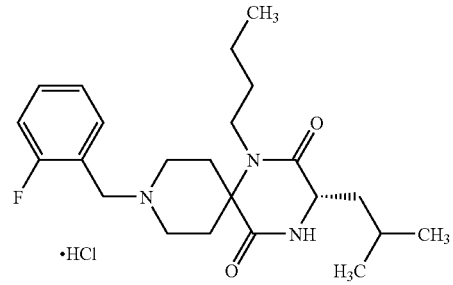

TLC: Rf 0.48 (hexane:ethyl acetate=1:1); NMR (CD$_3$OD): δ 7.64-7.54 (m, 2H), 7.37-7.27 (m, 2H), 4.45 (s, 2H), 4.01 (dd, J=7.5, 4.5 Hz, 1H), 3.94-3.81 (m, 2H), 3.54 (m, 2H), 3.36 (m, 2H), 2.38 (m, 2H), 2.19 (m, 2H), 1.82-1.49 (m, 5H), 1.35 (m, 2H), 0.95 (t, J=7.5 Hz, 3H), 0.94 (d, J=6.5 Hz, 3H), 0.93 (d, J=6.5 Hz, 3H).

EXAMPLE 37(12)

(3S)-1-butyl-2,5-dioxo-3-(2-methylpropyl)-9-(3-fluorophenylmethyl)-1,4,9-triazaspiro[5.5]undecane-.hydrochloride

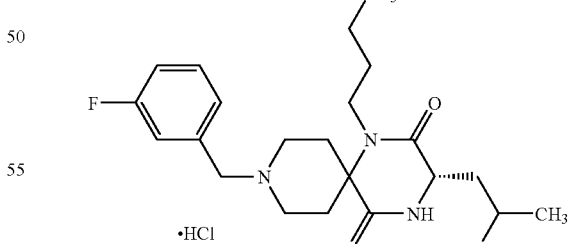

TLC: Rf 0.52 (hexane:ethyl acetate=1:1); NMR (CD$_3$OD): δ 7.52 (dt, J=8.3, 6.0 Hz, 1H), 7.41-7.37 (m, 2H), 7.26 (t, J=8.3 Hz, 1H), 4.39 (s, 2H), 4.01 (dd, J=7.5, 4.5 Hz, 1H), 3.89-3.76 (m, 2H), 3.50-3.38 (m, 4H), 2.48-2.38 (m, 2H), 2.25-2.12 (m, 2H), 1.84-1.75 (m, 1H), 1.72-1.46 (m, 4H), 1.42-1.28 (m, 2H), 0.99-0.92 (m, 9H).

EXAMPLE 37(13)

(3S)-1-butyl-2,5-dioxo-3-(2-methylpropyl)-9-(4-fluorophenylmethyl)-1,4,9-triazaspiro[5.5]undecane-.hydrochloride

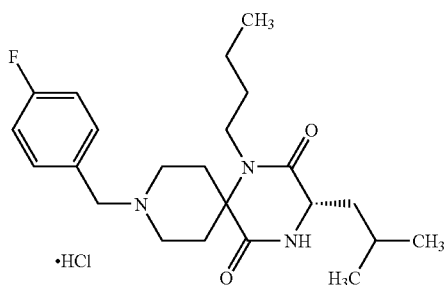

TLC: Rf 0.33 (hexane:ethyl acetate=1:1); NMR (CD₃OD): δ 7.60 (dd, J=8.7, 5.4 Hz, 2H), 7.24 (t, J=8.7 Hz, 2H), 4.36 (s, 2H), 3.99 (dd, J=7.5, 4.5 Hz, 1H), 3.78 (m, 2H), 3.49-3.35 (m, 4H), 2.44-2.13 (m, 4H), 1.84-1.46 (m, 5H), 1.37 (m, 2H), 0.99-0.95 (m, 9H).

EXAMPLE 37(14)

(3S)-1-butyl-2,5-dioxo-3-(2-methylpropyl)-9-(2-chlorophenylmethyl)-1,4,9-triazaspiro[5.5]undecane-.hydrochloride

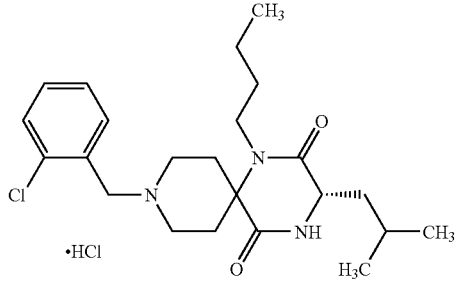

TLC: Rf 0.62 (hexane:ethyl acetate=1:1); NMR (CD₃OD): δ 7.72 (d, J=7.0 Hz, 1H), 7.60 (dd, J=8.0, 1.5 Hz, 1H), 7.56-7.45 (m, 2H), 4.55 (s, 2H), 4.00 (dd, J=7.5, 4.5 Hz, 1H), 3.94 (m, 2H), 3.55 (r, 2H), 3.42-3.32 (m, 2H), 2.43-2.37 (m, 2H), 2.26-2.13 (m, 2H), 1.85-1.46 (m, 5H), 1.35 (m, 2H), 0.97-0.92 (m, 9H).

EXAMPLE 37(15)

(3S)-1-butyl-2,5-dioxo-3-(2-methylpropyl)-9-(4-chlorophenylmethyl)-1,4,9-triazaspiro[5.5]undecane-.hydrochloride

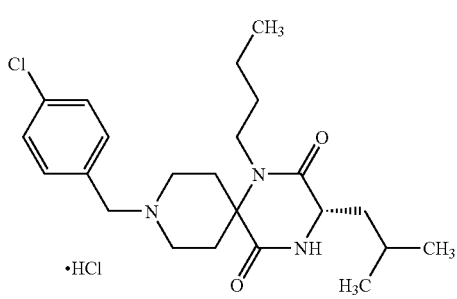

TLC: Rf 0.50 (chloroform:methanol=10:1); NMR (CD₃OD): δ 7.55 (d, J=8.7 Hz, 2H), 7.51 (d, J=8.7 Hz, 2H), 4.34 (s, 2H), 4.00 (dd, J=7.8, 4.5, Hz, 1H), 3.88-3.68 (m, 2H), 3.51-3.34 (m, 4H), 2.49-2.52 (m, 2H), 2.26-2.08 (m, 2H), 1.90-1.44 (m, 5H), 1.44-1.29 (m, 2H), 1.00-0.89 (m, 9H).

EXAMPLE 37(16)

(3S)-1-butyl-2,5-dioxo-3-(2-methylpropyl)-9-(3-chlorophenylmethyl)-1,4,9-triazaspiro[5.5]undecane-.hydrochloride

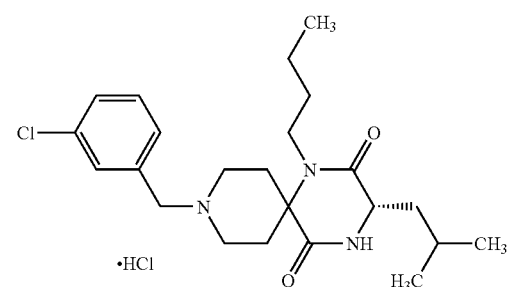

TLC: Rf 0.55 (chloroform:methanol=20:1); NMR (CD₃OD): δ 7.68-7.64 (m, 1H), 7.56-7.45 (m, 3H), 4.37 (s, 2H), 4.00 (dd, J=7.8, 4.5 Hz, 1H), 3.91-3.72 (m, 2H), 3.54-3.32 (m, 4H), 2.53-2.34 (m, 2H), 2.27-2.08 (m, 2H), 1.90-1.44 (m, 5H), 1.44-1.27 (m, 2H), 0.99-0.89 (m, 9H).

EXAMPLE 37(17)

(3S)-1-butyl-2,5-dioxo-3-(2-methylpropyl)-9-(3-methyl-4-methoxyphenylmethyl)-1,4,9-triazaspiro[5.5]undecane.hydrochloride

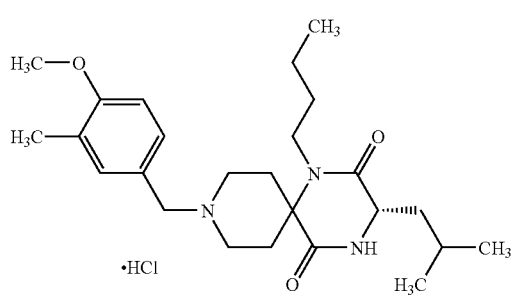

TLC: Rf 0.34 (chloroform:methanol=20:1); NMR (CD$_3$OD): δ 7.38-7.30 (m, 2H), 6.99 (d, J=8.1 Hz, 1H), 4.25 (s, 2H), 4.00 (dd, J=7.8, 4.5 Hz, 1H), 3.85 (s, 3H), 3.85-3.65 (m, 2H), 3.52-3.33 (m, 4H), 2.50-2.30 (m, 2H), 2.22 (s, 3H), 2.20-2.07 (m, 2H), 1.90-1.43 (m, 5H), 1.43-1.28 (m, 2H), 0.99-0.88 (m, 9H).

EXAMPLE 37(18)

(3S)-1-butyl-2,5-dioxo-3-(2-methylpropyl)-9-(7-methoxy-1,3-benzodioxolan-5-ylmethyl)-1,4,9-triazaspiro[5.5]undecane.hydrochloride

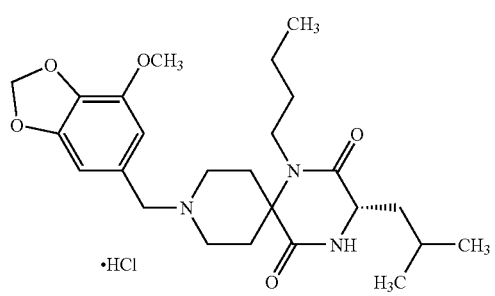

TLC: Rf 0.36 (chloroform:methanol=20:1); NMR (CD$_3$OD): δ 6.85 (d, J=1.8 Hz, 1H), 6.74 (d, J=1.8 Hz, 1H), 5.99 (s, 2H), 4.25 (s, 2H), 4.01 (dd, J=7.8, 4.5 Hz, 1H), 3.92 (s, 3H), 3.87-3.66 (m, 2H), 3.52-3.32 (m, 4H), 2.52-2.34 (m, 2H), 2.26-2.08 (m, 2H), 1.90-1.43 (m, 5H), 1.43-1.29 (m, 2H), 0.99-0.90 (m, 9H).

EXAMPLE 37(19)

(3S)-1-butyl-2,5-dioxo-3-(2-methylpropyl)-9-(4-phenylthiophenylmethyl)-1,4,9-triazaspiro[5.5]undecane.hydrochloride

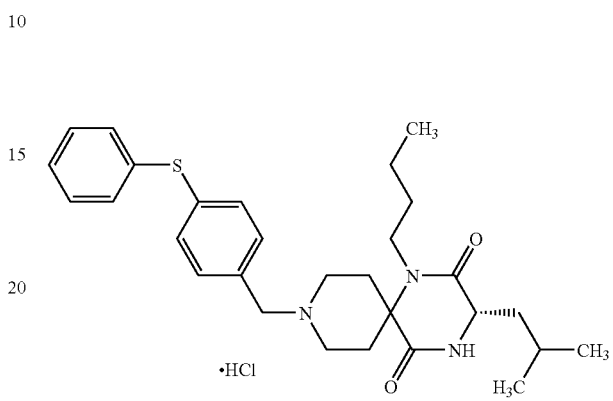

TLC: Rf 0.52 (chloroform:methanol=20:1); NMR (CD$_3$OD): δ 7.50-7.36 (m, 7H), 7.30 (d, J=8.7 Hz, 2H), 4.31 (s, 2H), 4.00 (dd, J=7.8, 4.5 Hz, 1H), 3.88-3.68 (m, 2H), 3.53-3.32 (m, 4H), 2.50-2.30 (m, 2H), 2.26-2.06 (m, 2H), 1.90-1.42 (m, 5H), 1.42-1.27 (m, 2H), 0.98-0.89 (m, 9H).

EXAMPLE 37(20)

(3S)-1-butyl-2,5-dioxo-3-(2-methylpropyl)-9-(2-methylphenylmethyl)-1,4,9-triazaspiro[5.5]undecane.hydrochloride

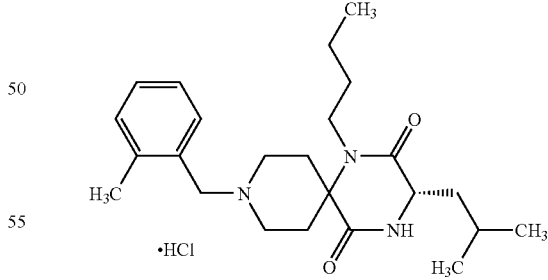

TLC: Rf 0.41 (chloroform:methanol=19:1); NMR (CD$_3$OD): δ 7.57 (d, J=7.8 Hz, 1H), 7.42-7.28 (m, 3H), 4.41 (s, 2H), 4.01 (dd, J=7.8, 4.8 Hz, 1H), 3.89 (m, 2H), 3.53 (m, 2H), 3.42 (m, 2H), 2.48 (s, 3H), 2.48 (m, 2H), 2.16 (m, 2H), 1.90-1.42 (m, 5H), 1.36 (sextet, J=7.2 Hz, 2H), 0.94 (d, J=6.6 Hz, 3H), 0.94 (t, J=7.2 Hz, 3H), 0.93 (d, J=6.6 Hz, 3H).

EXAMPLE 37(21)

(3S)-1-butyl-2,5-dioxo-3-(2-methylpropyl)-9-(3-methylphenylmethyl)-1,4,9-triazaspiro[5.5]undecane.hydrochloride

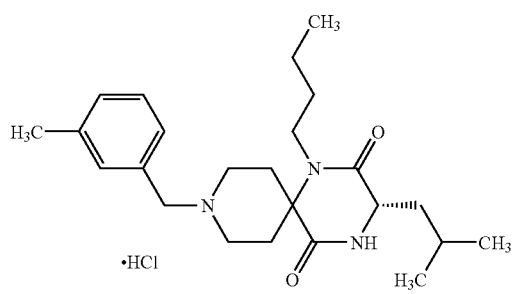

TLC: Rf 0.31 (chloroform:methanol=19:1); NMR (CD$_3$OD): δ 7.41-7.29 (m, 4H), 4.31 (s, 2H), 4.00 (dd, J=7.8, 4.8 Hz, 1H), 3.79 (m, 2H), 3.52-3.34 (m, 4H), 2.40 (m, 2H), 2.40 (s, 3H), 2.17 (m, 2H), 1.90-1.44 (m, 5H), 1.36 (sextet, J=7.5 Hz, 2H), 0.94 (t, J=7.5 Hz, 3H), 0.94 (d, J=6.6 Hz, 3H), 0.93 (d, J=6.6 Hz, 3H).

EXAMPLE 37(22)

(3S)-1-butyl-2,5-dioxo-3-(2-methylpropyl)-9-(4-methylphenylmethyl)-1,4,9-triazaspiro[5.5]undecane.hydrochloride

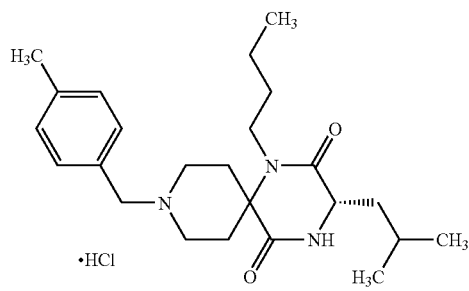

TLC: Rf 0.31 (chloroform:methanol=19:1); NMR (CD$_3$OD): δ 7.43 (d, J=7.8 Hz, 2H), 7.31 (d, J=7.8 Hz, 2H), 4.31 (s, 2H), 4.00 (dd, J=7.8, 4.8 Hz, 1H), 3.78 (m, 2H), 3.52-3.35 (m, 4H), 2.40 (m, 2H), 2.37 (s, 3H), 2.17 (m, 2H), 1.88-1.44 (m, 5H), 1.36 (sextet, J=7.5 Hz, 2H), 0.94 (t, J=7.5 Hz, 3H), 0.94 (d, J=6.6 Hz, 3H), 0.93 (d, J=6.6 Hz, 3H).

EXAMPLE 37(23)

(3S)-1-butyl-2,5-dioxo-3-(2-methylpropyl)-9-(4-(1-methylethyl)phenylmethyl)-1,4,9-triazaspiro[5.5]undecane.hydrochloride

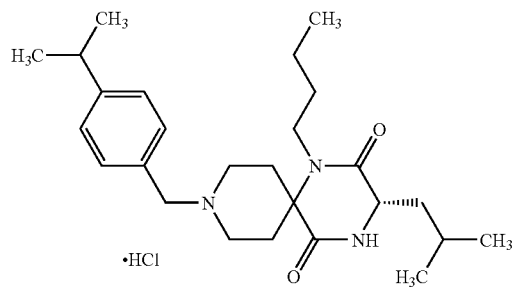

TLC: Rf 0.49 (chloroform:methanol=10:1); NMR (CD$_3$OD): δ 7.48 (d, J=8.4 Hz, 2H), 7.38 (d, J=8.4 Hz, 2H), 4.32 (s, 2H), 4.01 (dd, J=7.8, 4.5 Hz, 1H), 3.88-3.70 (m, 2H), 3.54-3.36 (m, 4H), 3.04-2.88 (m, 1H), 2.48-2.30 (m, 2H), 2.28-2.08 (m, 2H), 1.90-1.28 (m, 7H), 1.26 (d, J=6.9 Hz, 6H), 0.95 (t, J=7.2 Hz, 3H), 0.95 (d, J=6.9 Hz, 3H), 0.94 (d, J=6.9 Hz, 3H).

EXAMPLE 37(24)

(3S)-1-butyl-2,5-dioxo-3-(2-methylpropyl)-9-(3-fluoro-4-methoxyphenylmethyl)-1,4,9-triazaspiro[5.5]undecane.hydrochloride

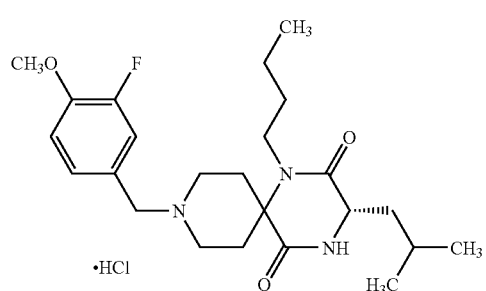

TLC: Rf 0.44 (chloroform:methanol=10:1); NMR (CD$_3$OD): δ 7.40-7.32 (m, 2H), 7.21 (m, 1H), 4.31 (s, 2H), 4.01 (dd, J=7.5, 4.5 Hz, 1H), 3.92 (s, 3H), 3.86-3.64 (m, 2H), 3.58-3.36 (m, 4H), 2.56-2.32 (m, 2H), 2.28-2.08 (m, 2H), 1.90-1.26 (m, 7H), 0.96 (t, J=7.2 Hz, 3H), 0.95 (d, J=6.6 Hz, 3H), 0.94 (d, J=6.6 Hz, 3H).

EXAMPLE 37(25)

(3S)-1-butyl-2,5-dioxo-3-(2-methylpropyl)-9-(4-(2-hydroxyethyloxy)phenylmethyl)-1,4,9-triazaspiro[5.5]undecane.hydrochloride

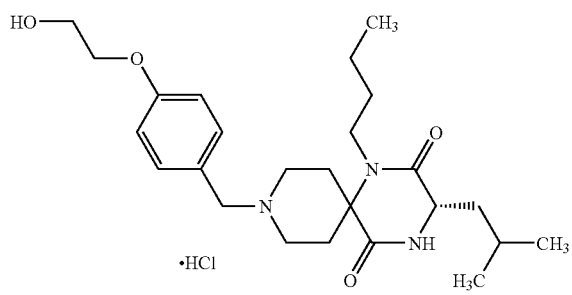

TLC: Rf 0.22 (chloroform:methanol=10:1); NMR (CD$_3$OD): δ 7.48 (d, J=8.7 Hz, 2H), 7.07 (d, J=8.7 Hz, 2H), 4.29 (s, 2H), 4.09 (t, J=5.1 Hz, 2H), 4.01 (dd, J=7.5, 4.5 Hz, 1H), 3.88 (t, J=5.1 Hz, 2H), 3.86-3.64 (m, 2H), 3.54-3.36 (m, 4H), 2.50-2.30 (m, 2H), 2.26-2.08 (m, 2H), 1.90-1.24 (m, 7H), 0.96 (t, J=7.2 Hz, 3H), 0.95 (d, J=6.6 Hz, 3H), 0.94 (d, J=6.6 Hz, 3H).

EXAMPLE 37(26)

(3S)-1-butyl-2,5-dioxo-3-(2-methylpropyl)-9-(2-hydroxy-3-methylphenylmethyl)-1,4,9-triazaspiro[5.5]undecane.hydrochloride

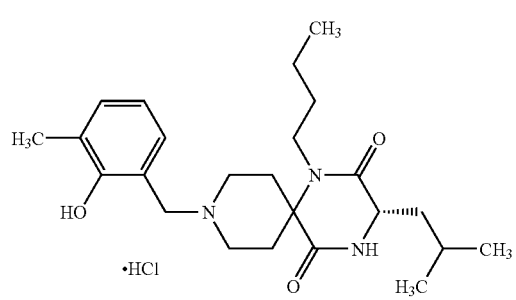

TLC: Rf 0.66 (chloroform:methanol=10:1); NMR (CD$_3$OD): δ 7.24 (d, J=7.7 Hz, 2H), 6.89 (t, J=7.7 Hz, 1H), 4.36 (s, 2H), 4.02 (dd, J=7.5, 4.5 Hz, 1H), 3.95-3.76 (m, 2H), 3.58-3.36 (m, 4H), 2.44-2.08 (m, 4H), 2.89 (s, 3H), 1.90-1.24 (m, 7H), 0.96 (t, J=7.2 Hz, 3H), 0.95 (d, J=6.6 Hz, 3H), 0.94 (d, J=6.6 Hz, 3H).

EXAMPLE 37(27)

(3S)-1-butyl-2,5-dioxo-3-(2-methylpropyl)-9-(4-trifluoromethyloxyphenylmethyl)-1,4,9-triazaspiro[5.5]undecane.hydrochloride

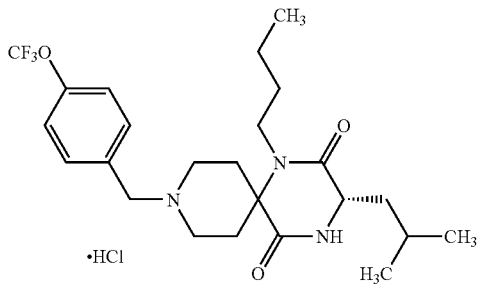

TLC: Rf 0.49 (chloroform:methanol=10:1); NMR (CD$_3$OD): δ 7.71 (d, J=7.8 Hz, 2H), 7.42 (d, J=7.8 Hz, 2H), 4.41 (s, 2H), 4.01 (dd, J=7.8, 4.8 Hz, 1H), 3.90-3.72 (m, 2H), 3.56-3.36 (m, 4H), 2.56-2.36 (m, 2H), 2.26-2.08 (m, 2H), 1.90-1.28 (m, 7H), 0.95 (t, J=7.5 Hz, 3H), 0.95 (d, J=6.3 Hz, 3H), 0.94 (d, J=6.3 Hz, 3H).

EXAMPLE 37(28)

(3S)-1-butyl-2,5-dioxo-3-(2-methylpropyl)-9-(3-methyl-5-chloro-1-phenylpyrazol-4-ylmethyl)-1,4,9-triazaspiro[5.5]undecane.2 hydrochloride

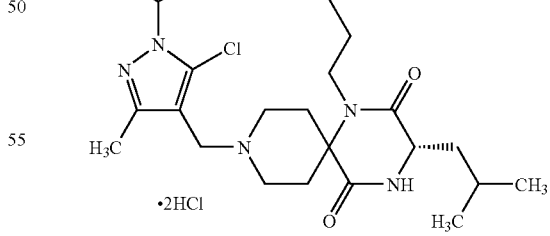

TLC: Rf 0.39 (chloroform:methanol=10:1); NMR (CD$_3$OD): δ 7.59-7.50 (m, 5H), 4.35 (s, 2H), 4.03 (dd, J=7.8, 4.5 Hz, 1H), 3.98-3.80 (m, 2H), 3.72-3.58 (m, 2H), 3.46-3.38 (m, 2H), 2.58-2.38 (m, 2H), 2.45 (s, 3H), 2.36-2.18 (m, 2H), 1.92-1.24 (m, 7H), 0.97 (t, J=7.5 Hz, 3H), 0.96 (d, J=6.6 Hz, 3H), 0.95 (d, J=6.6 Hz, 3H).

EXAMPLE 37(29)

(3S)-1-butyl-2,5-dioxo-3-(2-methylpropyl)-9-(6-phenylpyridin-3-ylmethyl)-1,4,9-triazaspiro[5.5]undecane.hydrochloride

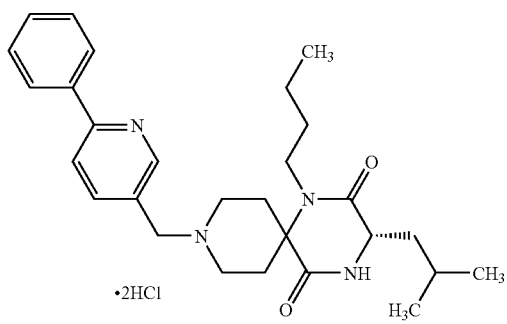

TLC: Rf 0.28 (chloroform:methanol=10:1); NMR (CD$_3$OD): δ 9.17 (s, 1H), 8.80 (m, 1H), 8.39 (m, 1H), 8.03-7.97 (m, 2H), 7.73-7.65 (m, 3H), 4.65 (s, 2H), 4.03 (dd, J=7.2, 4.2 Hz, 1H), 4.02-3.82 (m, 2H), 3.64-3.42 (m, 2H), 3.78-3.56 (m, 2H), 2.30-2.08 (m, 2H), 1.88-1.24 (m, 7H), 0.96 (d, J=6.3 Hz, 3H), 0.95 (t, J=7.2 Hz, 3H), 0.95 (d, J=6.3 Hz, 3H).

EXAMPLE 37(30)

(3S)-1-butyl-2,5-dioxo-3-(2-methylpropyl)-9-(4-(4-methylsulfonylaminophenyloxy)phenylmethyl)-1,4,9-triazaspiro[5.5]undecane.hydrochloride

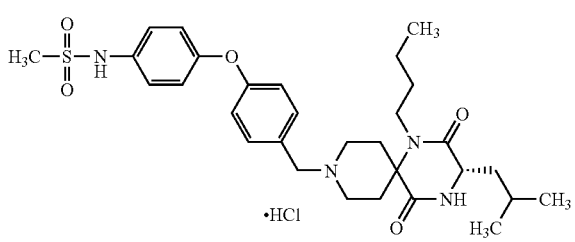

TLC: Rf 0.18 (chloroform:methanol=10:1); NMR (CD$_3$OD): δ 7.54 (d, J=8.7 Hz, 2H), 7.30 (d, J=9.0 Hz, 2H), 7.08 (d, J=8.7 Hz, 2H), 7.04 (d, J=9.0 Hz, 2H), 4.34 (s, 2H), 4.02 (dd, J=7.8, 4.5 Hz, 1H), 3.88-3.68 (m, 2H), 3.56-3.35 (m, 4H), 2.96 (s, 3H), 2.50-2.08 (m, 4H), 1.88-1.26 (m, 7H), 0.96 (t, J=6.9 Hz, 3H), 0.95 (d, J=6.6 Hz, 3H), 0.94 (d, J=6.6 Hz, 3H).

EXAMPLE 37(31)

(3S)-1-butyl-2,5-dioxo-3-(2-methylpropyl)-9-(3,5-dimethyl-1-(4-methylsulfonylaminophenyl)pyrazol-4-ylmethyl)-1,4,9-triazaspiro[5.5]undecane.2 hydrochloride

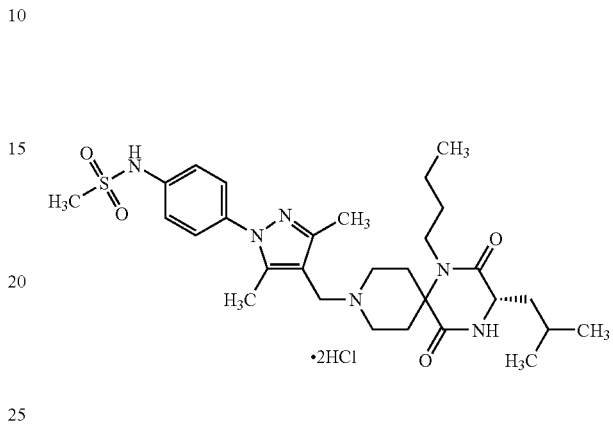

TLC: Rf 0.15 (chloroform:methanol=10:1); NMR (CD$_3$OD): δ 7.49 (d, J=8.7 Hz, 2H), 7.43 (d, J=8.7 Hz, 2H), 4.33 (s, 2H), 4.03 (dd, J=7.8, 4.8 Hz, 1H), 3.96-3.76 (m, 2H), 3.66-3.58 (m, 2H), 3.56-3.42 (m, 2H), 3.05 (s, 3H), 2.68-2.46 (m, 2H), 2.44 (s, 3H), 2.41 (s, 3H), 2.32-2.10 (m, 2H), 1.90-1.28 (m, 7H), 0.97 (t, J=6.6 Hz, 3H), 0.96 (d, J=6.3 Hz, 3H), 0.95 (d, J=6.3 Hz, 3H).

EXAMPLE 37(32)

(3S)-1-butyl-2,5-dioxo-3-(2-methylpropyl)-9-(4-(5-methylpyridin-2-yloxy)phenylmethyl)-1,4,9-triazaspiro[5.5]undecane.2 hydrochloride

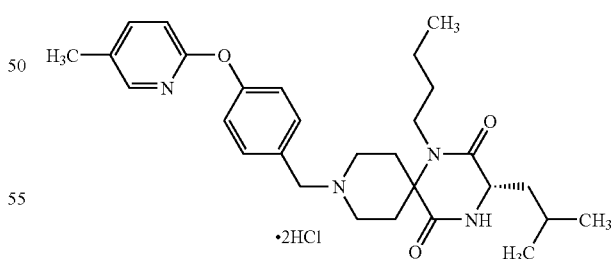

TLC: Rf 0.29 (chloroform:methanol=10:1); NMR (CD$_3$OD): δ 8.12 (s, 1H), 7.93 (d, J=8.4 Hz, 1H), 7.68 (d, J=8.7 Hz, 2H), 7.30 (d, J=8.7 Hz, 2H), 7.06 (d, J=8.4 Hz, 1H), 4.40 (s, 2H), 4.03 (dd, J=7.8, 4.8 Hz, 1H), 3.94-3.76 (m, 2H), 3.58-3.40 (m, 4H), 2.56-2.36 (m, 2H), 2.38 (s, 3H), 2.30-2.08 (m, 2H), 1.88-1.24 (m, 7H), 0.96 (t, J=7.8 Hz, 3H), 0.96 (d, J=6.6 Hz, 3H), 0.95 (d, J=6.6 Hz, 3H).

EXAMPLE 37(33)

(3S)-1-butyl-2,5-dioxo-3-(2-methylpropyl)-9-(4-(6-methylpyridin-1-oxido-3-yloxy)phenylmethyl)-1,4,9-triazaspiro[5.5]undecane.hydrochloride

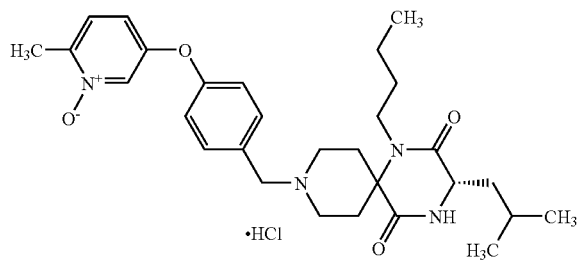

TLC: Rf 0.24 (chloroform:methanol=10:1); NMR (CD$_3$OD): δ 8.47 (s, 1H), 7.71 (d, J=8.7 Hz, 2H), 7.62-7.48 (m, 2H), 7.29 (d, J=8.7 Hz, 2H), 4.40 (s, 2H), 4.02 (dd, J=7.8, 4.5 Hz, 1H), 3.92-3.72 (m, 2H), 3.58-3.38 (m, 4H), 2.64-2.40 (m, 2H), 2.60 (s, 3H), 2.28-2.10 (m, 2H), 1.90-1.28 (m, 7H), 0.96 (t, J=7.8 Hz, 3H), 0.95 (d, J=6.6 Hz, 3H), 0.94 (d, J=6.6 Hz, 3H).

EXAMPLE 37(34)

(3S)-1-butyl-2,5-dioxo-3-(2-methylpropyl)-9-(1-(2-methylpropyloxycarbonyl)indol-5-ylmethyl)-1,4,9-triazaspiro[5.5]undecane.hydrochloride

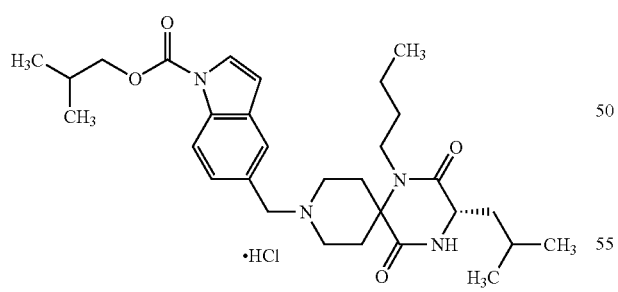

TLC: Rf 0.23 (chloroform:methanol=10:1); NMR (CD$_3$OD): δ 8.16 (d, J=8.4 Hz, 1H), 7.82 (d, J=1.5 Hz, 1H), 7.78 (d, J=3.6 Hz, 1H), 7.50 (dd, J=8.4, 1.5 Hz, 1H), 6.75 (d, J=3.6 Hz, 1H), 4.46 (s, 2H), 4.27 (d, J=6.6 Hz, 2H), 4.01 (dd, J=7.8, 4.5 Hz, 1H), 3.82-3.74 (m, 2H), 3.58-3.36 (m, 4H), 2.48-2.30 (m, 2H), 2.26-2.08 (m, 3H), 1.88-1.24 (m, 7H), 1.09 (s, 3H), 1.06 (s, 3H), 0.95 (t, J=7.2 Hz, 3H), 0.95 (d, J=6.3 Hz, 3H), 0.94 (d, J=6.3 Hz, 3H).

EXAMPLE 37(35)

(3S)-1-butyl-2,5-dioxo-3-(2-methylpropyl)-9-(2-phenyl-5-methyloxazol-4-ylmethyl)-1,4,9-triazaspiro[5.5]undecane.hydrochloride

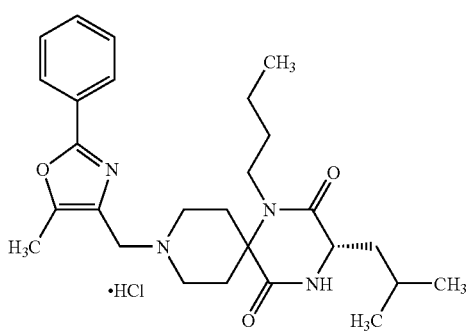

TLC: Rf 0.32 (chloroform:methanol=10:1); NMR (CD$_3$OD): δ 8.05-8.02 (m, 2H), 7.52-7.50 (m, 3H), 4.35 (s, 2H), 4.02 (dd, J=7.8, 4.5 Hz, 1H), 3.98-3.80 (m, 2H), 3.70-3.58 (m, 2H), 3.44-3.38 (m, 2H), 2.53 (s, 3H), 2.53-2.36 (m, 2H), 2.34-2.14 (m, 2H), 1.90-1.26 (m, 7H), 0.96 (t, J=7.2 Hz, 3H), 0.95 (d, J=6.3 Hz, 3H), 0.94 (d, J=6.3 Hz, 3H).

EXAMPLE 37(36)

(3S)-1-butyl-2,5-dioxo-3-(2-methylpropyl)-9-(4-(tetrahydropyran-4-yloxy)phenylmethyl)-1,4,9-triazaspiro[5.5]undecane.hydrochloride

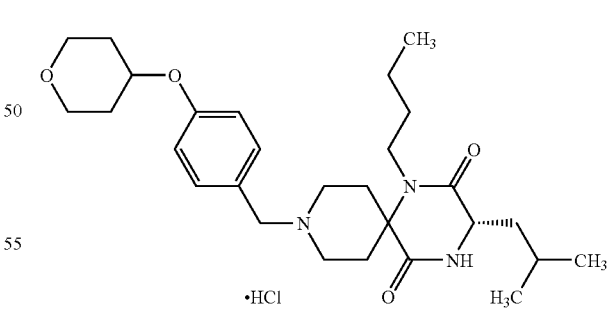

TLC: Rf 0.33 (chloroform:methanol=10:1); NMR (CD$_3$OD): δ 7.47 (d, J=8.4 Hz, 2H), 7.07 (d, J=8.4 Hz, 2H), 4.64 (m, 1H), 4.29 (s, 2H), 4.01 (dd, J=7.5, 4.5 Hz, 1H), 3.98-3.91 (m, 2H), 3.84-3.68 (m, 2H), 3.64-3.56 (m, 2H), 3.50-3.37 (m, 4H), 2.50-2.30 (m, 2H), 2.24-1.98 (m, 4H), 1.88-1.26 (m, 9H), 0.95 (t, J=7.2 Hz, 3H), 0.95 (d, J=6.3 Hz, 3H), 0.94 (d, J=6.3 Hz, 3H).

EXAMPLE 37(37)

(3S)-1-butyl-2,5-dioxo-3-(2-methylpropyl)-9-(4-(6-methylpyridin-3-yloxy)phenylmethyl)-1,4,9-triazaspiro[5.5]undecane.2 hydrochloride

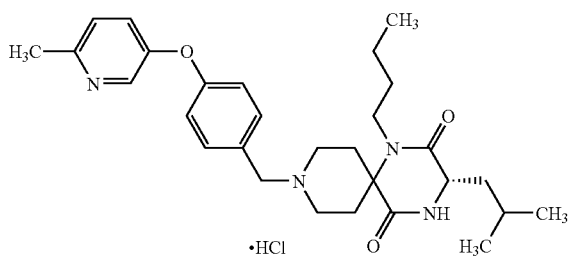

TLC: Rf 0.22 (chloroform:methanol=10:1); NMR (CD$_3$OD): δ 8.55 (d, J=2.7 Hz, 1H), 8.10 (dd, J=9.0, 2.7 Hz, 1H), 7.84 (d, J=9.0 Hz, 1H), 7.72 (d, J=8.7 Hz, 2H), 7.29 (d, J=8.7 Hz, 2H), 4.40 (s, 2H), 4.02 (dd, J=7.8, 4.5 Hz, 1H), 3.94-3.70 (m, 2H), 3.58-3.38 (m, 4H), 2.74 (s, 3H), 2.60-2.42 (m, 2H), 2.28-2.08 (m, 2H), 1.90-1.26 (m, 7H), 0.96 (t, J=7.5 Hz, 3H), 0.96 (d, J=6.6 Hz, 3H), 0.95 (d, J=6.6 Hz, 3H).

EXAMPLE 37(38)

(3S)-1-butyl-2,5-dioxo-3-(2-methylpropyl)-9-(3,5-dimethyl-1-(4-fluorophenyl)pyrazol-4-ylmethyl)-1,4,9-triazaspiro[5.5]undecane.2 hydrochloride

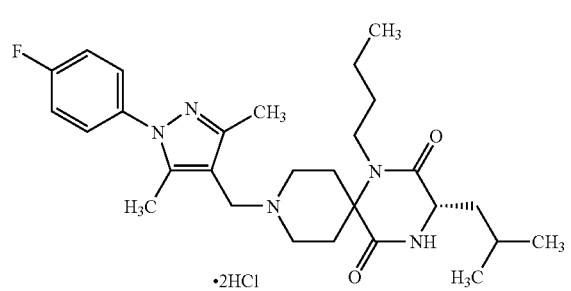

TLC: Rf 0.58 (chloroform:methanol=10:1); NMR (CD$_3$OD): δ 7.55-7.46 (m, 2H), 7.36-7.25 (m, 2H), 4.30 (s, 2H), 4.02 (dd, J=7.8, 4.5 Hz, 1H), 3.95-3.73 (m, 2H), 3.66-3.55 (m, 2H), 3.52-3.40 (m, 2H), 2.63-2.45 (m, 2H), 2.39 (s, 3H), 2.37 (s, 3H), 2.30-2.10 (m, 2H), 1.90-1.43 (m, 5H), 1.43-1.30 (m, 2H), 0.99-0.91 (m, 9H).

EXAMPLE 37(39)

(3S)-1-butyl-2,5-dioxo-3-(2-methylpropyl)-9-(3,5-dimethyl-1-(pyridin-2-yl)pyrazol-4-ylmethyl)-1,4,9-triazaspiro[5.5]undecane.2 hydrochloride

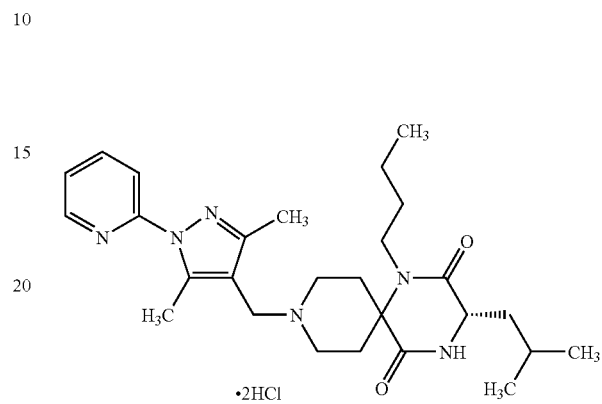

TLC: Rf 0.52 (chloroform:methanol=10:1); NMR (CD$_3$OD): δ 8.55 (d, J=4.8 Hz, 1H), 8.12 (dd, J=8.4, 7.2 Hz, 1H), 7.87 (d, J=8.4 Hz, 1H), 7.50 (dd, J=7.2, 4.8 Hz, 1H), 4.32 (s, 2H), 4.02 (dd, J=7.8, 4.5 Hz, 1H), 3.96-3.73 (m, 2H), 3.67-3.55 (m, 2H), 3.54-3.40 (m, 2H), 2.69 (s, 3H), 2.70-2.48 (m, 2H), 2.44 (s, 3H), 2.28-2.08 (m, 2H), 1.92-1.43 (m, 5H), 1.43-1.26 (m, 2H), 0.99-0.90 (m, 9H).

EXAMPLE 37(40)

(3S)-1-butyl-2,5-dioxo-3-(2-methylpropyl)-9-(3,5-dimethyl-1-(4-hydroxyphenyl)pyrazol-4-ylmethyl)-1,4,9-triazaspiro[5.5]undecane.2 hydrochloride

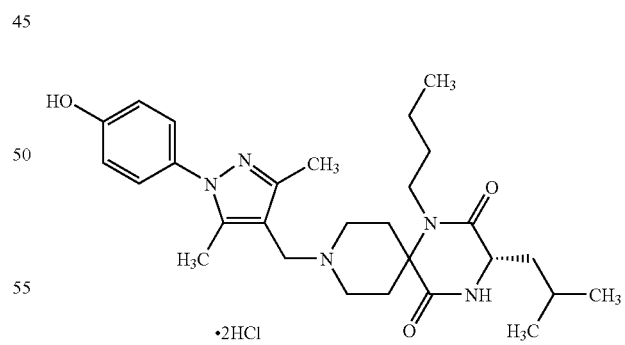

TLC: Rf 0.48 (chloroform:methanol=10:1); NMR (CD$_3$OD): δ 7.30 (d, J=9.0 Hz, 2H), 6.95 (d, J=9.0 Hz, 2H), 4.33 (s, 2H), 4.02 (dd, J=7.5, 4.5 Hz, 1H), 3.92-3.77 (m, 2H), 3.61 (m, 2H), 3.47 (m, 2H), 2.58 (m, 2H), 2.45 (s, 3H), 2.36 (s, 3H), 2.20 (m, 2H), 1.88-1.76 (m, 1H), 1.73-1.32 (m, 6H), 0.96 (t, J=7.5 Hz, 3H), 0.95 (d, J=6.5 Hz, 3H), 0.94 (d, J=6.5 Hz, 3H).

EXAMPLE 37(41)

(3S)-1-butyl-2,5-dioxo-3-(2-methylpropyl)-9-(4-(2-carboxyethyl)phenylmethyl)-1,4,9-triazaspiro[5.5]undecane.hydrochloride

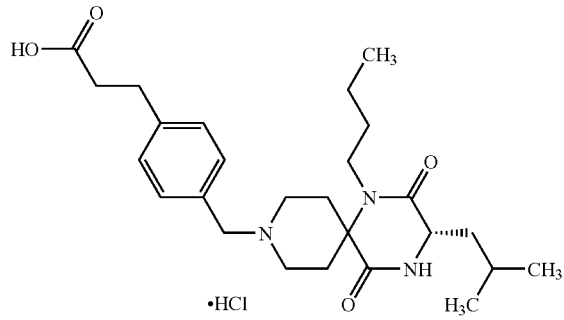

TLC: Rf 0.38 (chloroform:methanol=10:1); NMR (CD$_3$OD): δ 7.47 (d, J=8.0 Hz, 2H), 7.37 (d, J=8.0 Hz, 2H), 4.31 (s, 2H), 4.00 (dd, J=7.5, 4.5 Hz, 1H), 3.86-3.73 (m, 2H), 3.49-3.35 (m, 4H), 2.96 (t, J=7.5 Hz, 2H), 2.62 (t, J=7.5 Hz, 2H), 2.44-2.33 (m, 2H), 2.23-2.11 (m, 2H), 1.84-1.32 (m, 7H), 0.94 (t, J=7.5 Hz, 3H), 0.94 (d, J=6.5 Hz, 3H), 0.93 (d, J=6.5 Hz, 3H).

EXAMPLE 37(42)

(3S)-1-butyl-2,5-dioxo-3-(2-methylpropyl)-9-(3,5-dimethyl-1-(4-(dimethylaminosulfonyl)phenyl)pyrazol-4-ylmethyl)-1,4,9-triazaspiro[5.5]undecane.2 hydrochloride

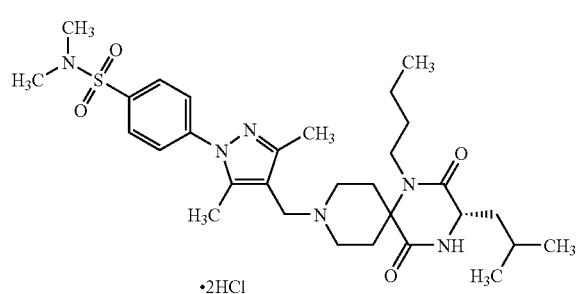

TLC: Rf 0.54 (chloroform:methanol=9:1); NMR (CD$_3$OD): δ 7.96 (d, J=8.7 Hz, 2H), 7.77 (d, J=8.7 Hz, 2H), 4.32 (s, 2H), 4.02 (dd, J=7.8, 4.8 Hz, 1H), 3.95-3.75 (m, 2H), 3.66-3.56 (m, 2H), 3.47 (m, 2H), 2.74 (s, 6H), 2.56 (m, 2H), 2.48 (s, 3H), 2.41 (s, 3H), 2.30-2.12 (m, 2H), 1.90-1.46 (m, 5H), 1.38 (sextet, J=7.2 Hz, 2H), 0.98-0.93 (m, 9H).

EXAMPLE 37(43)

(3S)-1-butyl-2,5-dioxo-3-(2-methylpropyl)-9-(4-(5-methylpyridin-1-oxido-2-yloxy)phenylmethyl)-1,4,9-triazaspiro[5.5]undecane.hydrochloride

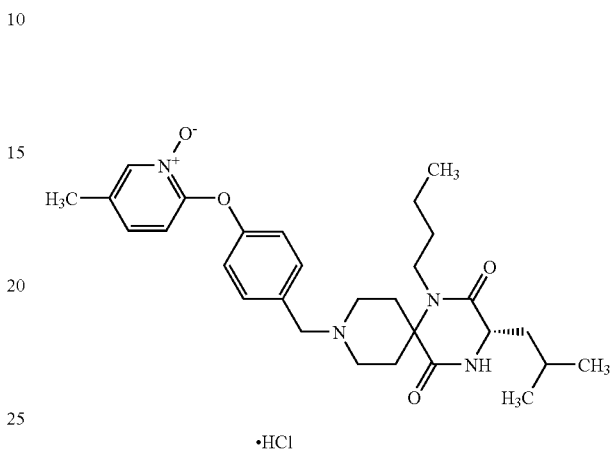

TLC: Rf 0.41 (chloroform:methanol=9:1); NMR (CD$_3$OD): δ 7.77 (brs, 1H), 7.65-7.59 (m, 2H), 7.56 (dd, J=9.3, 2.4 Hz, 1H), 7.03-6.97 (m, 2H), 6.73 (d, J=9.3 Hz, 1H), 4.33 (s, 2H), 4.00 (dd, J=7.8, 4.8 Hz, 1H), 3.86-3.68 (m, 2H), 3.51-3.36 (m, 4H), 2.46 (m, 2H), 2.25-2.07 (m, 2H), 2.18 (s, 3H), 1.90-1.44 (m, 5H), 1.36 (sextet, J=7.2 Hz, 2H), 0.97-0.91 (m, 9H).

EXAMPLE 37(44)

(3S)-1-butyl-2,5-dioxo-3-(2-methylpropyl)-9-(4-(2-carboxy-1-ethenyl)phenylmethyl)-1,4,9-triazaspiro[5.5]undecane.hydrochloride

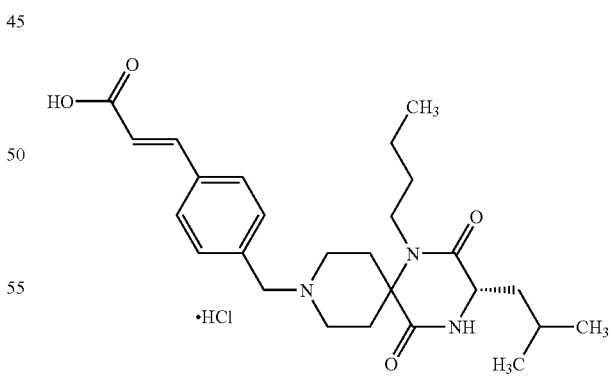

TLC: Rf 0.20 (chloroform:methanol=10:1); NMR (CD$_3$OD): δ 7.75 (d, J=8.4 Hz, 2H), 7.70 (d, J=16.2 Hz, 1H), 7.61 (d, J=8.4 Hz, 2H), 6.58 (d, J=16.2 Hz, 2H), 4.39 (s, 2H), 4.02 (dd, J=7.8, 4.5 Hz, 1H), 3.92-3.74 (m, 2H), 3.58-3.36 (m, 4H), 2.50-2.32 (m, 2H), 2.30-2.10 (m, 2H), 1.90-1.24 (m, 7H), 0.96 (t, J=7.2 Hz, 3H), 0.95 (d, J=6.3 Hz, 3H), 0.94 (d, J=6.3 Hz, 3H).

EXAMPLE 37(45)

(3S)-1-butyl-2,5-dioxo-3-(2-methylpropyl)-9-(4-(4-(2-carboxy-1-ethenyl)phenyloxy)phenylmethyl)-1,4,9-triazaspiro[5.5]undecane.hydrochloride

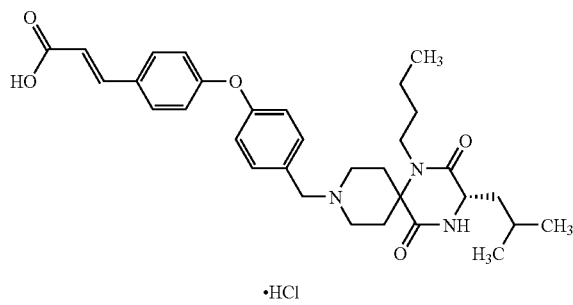

TLC: Rf 0.34 (chloroform:methanol=10:1); NMR (CD$_3$OD): δ 7.69-7.57 (m, 5H), 7.14 (d, J=8.4 Hz, 2H), 7.05 (d, J=8.7 Hz, 2H), 6.42 (d, J=15.9 Hz, 1H), 4.36 (s, 2H), 4.01 (dd, J=7.8, 4.5 Hz, 1H), 3.92-3.70 (m, 2H), 3.56-3.35 (m, 4H), 2.48-2.30 (m, 2H), 2.30-2.12 (m, 2H), 1.88-1.25 (m, 7H), 0.98-0.88 (m, 9H).

EXAMPLE 37(46)

(3S)-1-butyl-2,5-dioxo-3-(2-methylpropyl)-9-(4-(4-aminocarbonylphenyloxy)phenylmethyl)-1,4,9-triazaspiro[5.5]undecane.hydrochloride

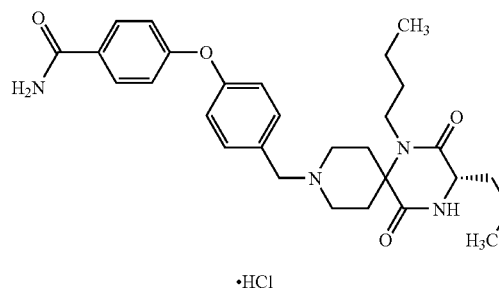

TLC: Rf 0.38 (chloroform:methanol=10:1); NMR (CD$_3$OD): δ 7.90 (d, J=8.7 Hz, 2H), 7.60 (d, J=8.7 Hz, 2H), 7.15 (d, J=8.7 Hz, 2H), 7.07 (d, J=8.7 Hz, 2H), 4.36 (s, 2H), 4.01 (dd, J=7.8, 4.5, Hz, 1H), 3.90-3.70 (m, 2H), 3.58-3.35 (m, 4H), 2.54-2.36 (m, 2H), 2.30-2.10 (m, 2H), 1.90-1.26 (m, 7H), 1.00-0.86 (m, 9H).

EXAMPLE 37(47)

(3S)-1-butyl-2,5-dioxo-3-(2-methylpropyl)-9-(4-(4-aminosulfonylphenyloxy)phenylmethyl)-1,4,9-triazaspiro[5.5]undecane.hydrochloride

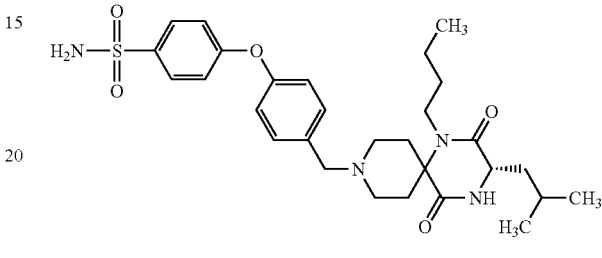

TLC: Rf 0.41 (chloroform:methanol=10:1); NMR (CD$_3$OD): 7.90 (d, J=8.7 Hz, 2H), 7.57 (d, J=8.7 Hz, 2H), 7.17 (d, J=8.7 Hz, 2H), 7.13 (d, J=8.7 Hz, 2H), 4.28 (brs, 2H), 4.01 (dd, J=7.8, 4.5, Hz, 1H), 3.83-3.60 (m, 2H), 3.49-3.34 (m, 4H), 2.44-2.26 (m, 2H), 2.26-2.09 (m, 2H), 1.89-1.26 (m, 7H), 1.00-0.88 (m, 9H).

EXAMPLE 37(48)

(3S)-1-butyl-2,5-dioxo-3-(2-methylpropyl)-9-(3,5-dimethyl-1-benzylpyrazol-4-ylmethyl)-1,4,9-triazaspiro[5.5]undecane.2 hydrochloride

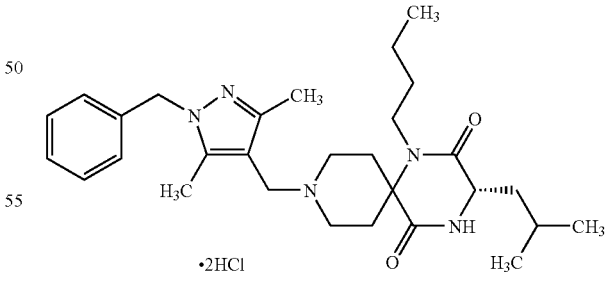

TLC: Rf 0.40 (chloroform:methanol=10:1); NMR (CD$_3$OD): δ 7.41-7.33 (m, 3H), 7.21-7.19 (m, 2H), 5.45 (s, 2H), 4.30 (s, 2H), 4.01 (dd, J=7.5, 4.5 Hz, 1H), 3.89-3.73 (m, 2H), 3.60-3.46 (m, 4H), 2.61 (m, 2H), 2.48 (s, 3H), 2.46 (s, 3H), 2.23-2.11 (m, 2H), 1.87-1.31 (m, 7H), 0.95 (t, J=7.0 Hz, 3H), 0.94 (d, J=6.5 Hz, 3H), 0.93 (d, J=6.5 Hz, 3H).

EXAMPLE 37(49)

(3S)-1-butyl-2,5-dioxo-3-(2-methylpropyl)-9-(3,5-dimethyl-1-(2,4-difluorophenyl)pyrazol-4-ylmethyl)-1,4,9-triazaspiro[5.5]undecane.2 hydrochoride

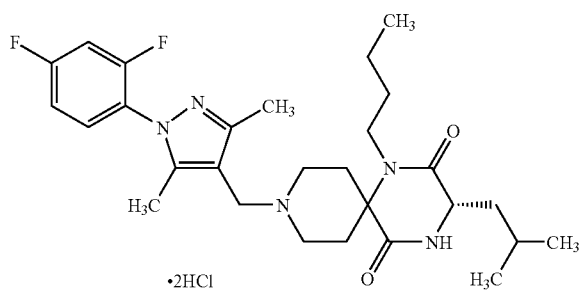

TLC: Rf 0.40 (chloroform:methanol=10:1); NMR (CD$_3$OD): δ 7.61-7.53 (m, 1H), 7.33-7.26 (m, 1H), 7.23-7.16 (m, 1H), 4.31 (s, 2H), 4.02 (dd, J=7.5, 4.5 Hz, 1H), 3.92-3.76 (m, 2H), 3.63-3.56 (m, 2H), 3.49-3.45 (m, 2H), 2.57 (m, 2H), 2.40 (s, 3H), 2.29 (s, 3H), 2.19 (m, 2H), 1.86-1.34 (m, 7H), 0.96 (t, J=7.0 Hz, 3H), 0.95 (d, J=6.5 Hz, 3H), 0.94 (d, J=6.5 Hz, 3H).

EXAMPLE 37(50)

(3S)-1-butyl-2,5-dioxo-3-(2-methylpropyl)-9-(4-(pyrrolidin-1-ylmethyl)phenylmethyl)-1,4,9-triaza-spiro[5.5]undecane.2 hydrochloride

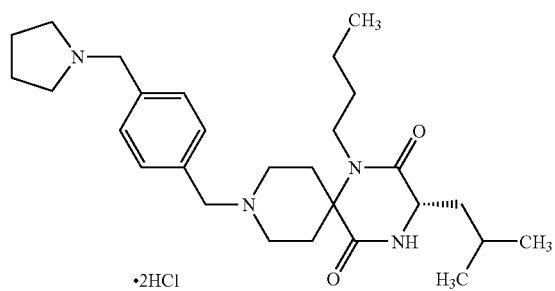

TLC: Rf 0.10 (chloroform:methanol=10:1); NMR (CD$_3$OD): δ 7.75 (d, J=8.4 Hz, 2H), 7.65 (d, J=8.4 Hz, 2H), 4.43 (s, 2H), 4.40 (s, 2H), 4.00 (dd, J=7.5, 4.5 Hz, 1H), 3.92-3.70 (m, 2H), 3.56-3.40 (m, 6H), 3.25-3.12 (m, 2H), 2.68-2.48 (m, 2H), 2.28-1.95 (m, 6H), 1.88-1.42 (m, 5H), 1.42-1.30 (m, 2H), 0.98-0.90 (m, 9H).

EXAMPLE 37(51)

(3S)-1-butyl-2,5-dioxo-3-(2-methylpropyl)-9-(3,5-dimethyl-1-(4-(morpholin-4-ylsulfonyl)phenyl)pyrazol-4-ylmethyl)-1,4,9-triazaspiro[5.5]undecane.2 hydrochloride

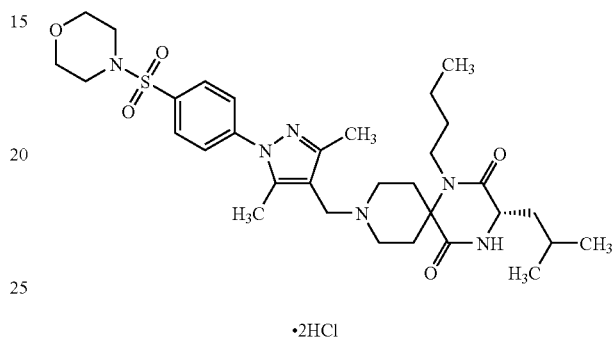

TLC: Rf 0.43 (chloroform:methanol=20:1); NMR (CD$_3$OD): δ 7.95 (d, J=8.7 Hz, 2H), 7.80 (d, J=8.7 Hz, 2H), 4.32 (s, 2H), 4.02 (dd, J=7.8, 4.8 Hz, 1H), 3.95-3.72 (m, 2H), 3.76-3.67 (m, 4H), 3.66-3.57 (m, 2H), 3.56-3.42 (m, 2H), 3.08-2.95 (m, 4H), 2.70-2.50 (m, 2H), 2.50 (s, 3H), 2.42 (s, 3H), 2.31-2.10 (m, 2H), 1.90-1.44 (m, 5H), 1.44-1.30 (m, 2H), 1.00-0.91 (m, 9H).

EXAMPLE 37(52)

(3S)-1-butyl-2,5-dioxo-3-(2-methylpropyl)-9-(3,5-dimethyl-1-(4-(methylaminosulfonyl)phenyl)pyrazol-4-ylmethyl)-1,4,9-triazaspiro[5.5]undecane.2 hydrochloride

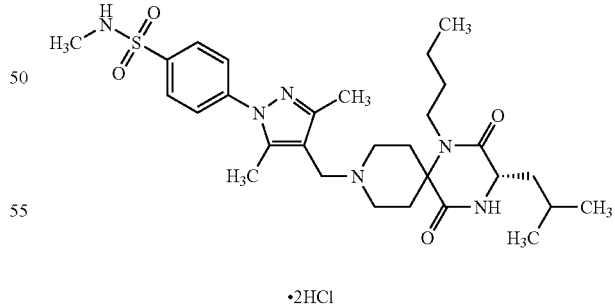

TLC: Rf 0.21 (chloroform:methanol=10:1); NMR (CD$_3$OD): δ 8.01 (d, J=8.4 Hz, 2H), 7.73 (d, J=8.4 Hz, 2H), 4.34 (s, 2H), 4.04 (dd, J=7.8, 4.8 Hz, 1H), 3.98-3.78 (m, 2H), 3.66-3.58 (m, 2H), 3.44-3.30 (m, 2H), 2.59 (s, 3H), 2.54-2.38 (m, 2H), 2.47 (s, 3H), 2.40 (s, 3H), 2.36-2.16 (m, 2H), 1.90-1.26 (m, 7H), 0.97 (t, J=7.5 Hz, 3H), 0.96 (d, J=6.6 Hz, 6H).

EXAMPLE 37(53)

(3S)-1-butyl-2,5-dioxo-3-(2-methylpropyl)-9-(4-(4-cyanophenyloxy)phenylmethyl)-1,4,9-triazaspiro[5.5]undecane.hydrochloride

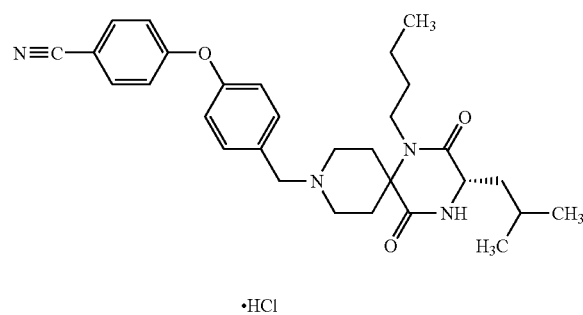

·HCl

TLC: Rf 0.30 (chloroform:methanol=10:1); NMR (CD$_3$OD): δ 7.75 (d, J=8.4 Hz, 2H), 7.66 (d, J=8.7 Hz, 2H), 7.21 (d, J=8.4 Hz, 2H), 7.14 (d, J=8.7 Hz, 2H), 4.39 (s, 2H), 4.02 (dd, J=7.8, 4.5 Hz, 1H), 3.94-3.72 (m, 2H), 3.58-3.36 (m, 4H), 2.58-2.38 (m, 2H), 2.28-2.08 (m, 2H), 1.88-1.24 (m, 7H), 0.96 (t, J=7.2 Hz, 3H), 0.95 (d, J=6.3 Hz, 3H), 0.94 (d, J=6.3 Hz, 3H).

EXAMPLE 37(54)

(3S)-1-butyl-2,5-dioxo-3-(2-methylpropyl)-9-(4-(dimethylaminomethyl)phenylmethyl)-1,4,9-triazaspiro[5.5]undecane.2 hydrochloride

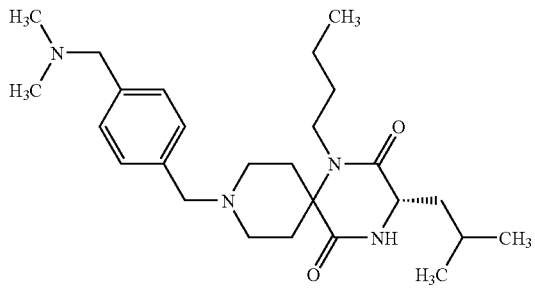

·2HCl

TLC: Rf 0.16 (chloroform:methanol=10:1); NMR (CD$_3$OD): δ 7.76 (d, J=8.1 Hz, 2H), 7.63 (d, J=8.1 Hz, 2H), 4.41 (s, 2H), 4.37 (s, 2H), 4.00 (dd, J=7.8, 4.8 Hz, 1H), 3.90-3.72 (m, 2H), 3.50-3.42 (m, 4H), 2.87 (s, 6H), 2.65-2.50 (m, 2H), 2.22-2.04 (m, 2H), 1.88-1.32 (m, 7H), 0.97-0.92 (m, 9H).

EXAMPLE 37(55)

(3S)-1-butyl-2,5-dioxo-3-(2-methylpropyl)-9-(3,5-dimethyl-1-(4-(2-dimethylaminoethylaminosulfonyl)phenyl)pyrazol-4-ylmethyl)-1,4,9-triazaspiro[5.5]undecane.3 hydrochloride

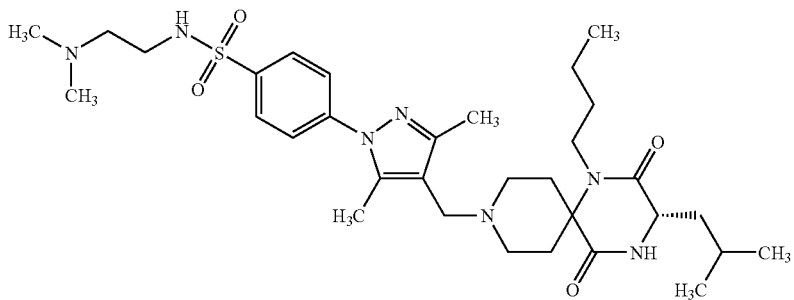

·3HCl

TLC: Rf 0.13 (chloroform:methanol=10:1); NMR (CD₃OD): δ 8.07 (d, J=8.7 Hz, 2H), 7.78 (d, J=8.7 Hz, 2H), 4.31 (s, 2H), 4.01 (dd, J=8.1, 5.1 Hz, 1H), 3.95-3.74 (m, 2H), 3.68-3.45 (m, 4H), 3.40-3.20 (m, 4H,), 2.95 (s, 6H), 2.70-2.50 (m, 2H), 2.49 (s, 3H), 2.41 (s, 3H), 2.28-2.12 (m, 2H), 1.88-1.34 (m, 7H), 0.98-0.92 (m, 9H).

EXAMPLE 37(56)

(3S)-1-butyl-2,5-dioxo-3-(2-methylpropyl)-9-(3-(4-hydroxyphenyl)phenylmethyl)-1,4,9-triazaspiro[5.5]undecane.hydrochloride

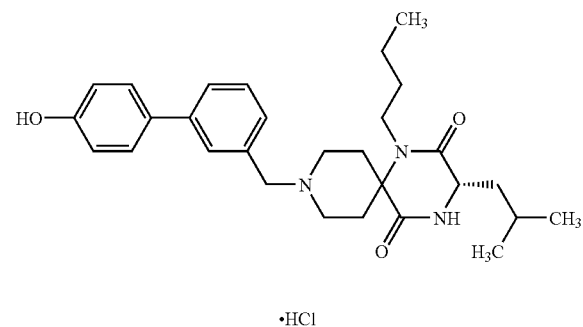

·HCl

TLC: Rf 0.53 (chloroform:methanol=10:1); NMR (CD₃OD): δ 7.81 (s, 1H), 7.69 (d, J=7.5 Hz, 1H), 7.53 (d, J=9.0 Hz, 2H), 7.55-7.48 (m, 1H), 7.45 (d, J=7.5 Hz, 1H), 6.87 (d, J=9.0 Hz, 2H), 4.40 (s, 2H), 4.00 (dd, J=7.5, 4.5 Hz, 1H), 3.94-3.73 (m, 2H), 3.56-3.44 (m, 2H), 3.44-3.30 (m, 2H), 2.53-2.33 (m, 2H), 2.26-2.08 (m, 2H), 1.90-1.40 (m, 5H), 1.43-1.25 (m, 2H), 0.94 (d, J=6.3 Hz, 3H), 0.94 (t, J=7.2 Hz, 3H), 0.93 (d, J=6.3 Hz, 3H).

EXAMPLE 37(57)

(3S)-1-butyl-2,5-dioxo-3-(2-methylpropyl)-9-(4-(3-methoxyphenyloxy)phenylmethyl)-1,4,9-triazaspiro[5.5]undecane.hydrochloride

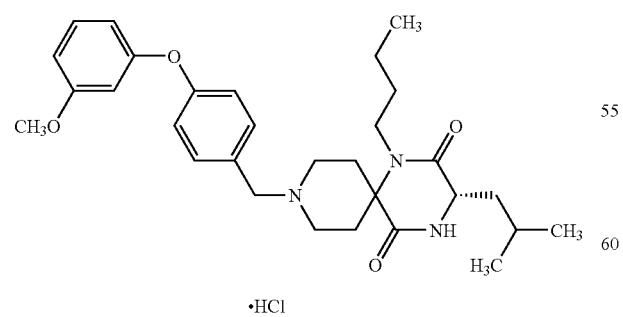

·HCl

TLC: Rf 0.54 (chloroform:methanol=10:1); NMR (CD₃OD): δ 7.53 (d, J=8.5 Hz, 2H), 7.28 (t, J=8.3 Hz, 1H), 7.07 (d, J=8.5 Hz, 2H), 6.75 (ddd, J=8.3, 2.3, 1.0 Hz, 1H), 6.60-6.57 (m, 2H), 4.33 (s, 2H), 4.01 (dd, J=7.5, 4.5 Hz, 1H), 3.86-3.73 (m, 2H), 3.77 (s, 3H), 3.51-3.34 (m, 4H), 2.41 (m, 2H), 2.42-2.12 (m, 2H), 1.84-1.33 (m, 7H), 0.95 (t, J=7.2 Hz, 3H), 0.94 (d, J=6.5 Hz, 3H), 0.93 (d, J=6.5 Hz, 3H).

EXAMPLE 37(58)

(3S)-1-butyl-2,5-dioxo-3-(2-methylpropyl)-9-(3,5-dimethyl-1-(quinoxalin-2-yl)pyrazol-4-ylmethyl)-1,4,9-triazaspiro[5.5]undecane.2 hydrochloride

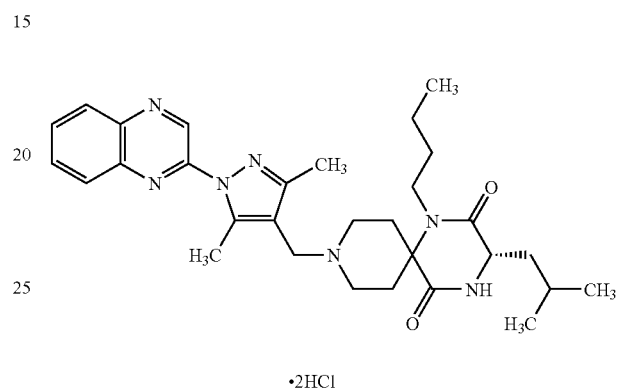

·2HCl

TLC: Rf 0.52 (chloroform:methanol=10:1); NMR (CD₃OD): δ 9.51 (s, 1H), 8.12 (d, J=8.0 Hz, 1H), 8.04 (d, J=8.0 Hz, 1H), 7.90-7.80 (m, 2H), 4.37 (s, 2H), 4.02 (dd, J=7.5, 4.5 Hz, 1H), 3.96-3.81 (m, 2H), 3.63 (m, 2H), 3.44 (m, 2H), 2.92 (s, 3H), 2.47 (s, 3H), 2.47 (m, 2H), 2.29-2.17 (m, 2H), 1.86-1.33 (m, 7H), 0.95 (t, J=7.2 Hz, 3H), 0.95 (d, J=6.5 Hz, 3H), 0.94 (d, J=6.5 Hz, 3H).

EXAMPLE 37(59)

(3S)-1-butyl-2,5-dioxo-3-(2-methylpropyl)-9-(4-phenylcarbonylphenylmethyl)-1,4,9-triazaspiro[5.5]undecane.hydrochloride

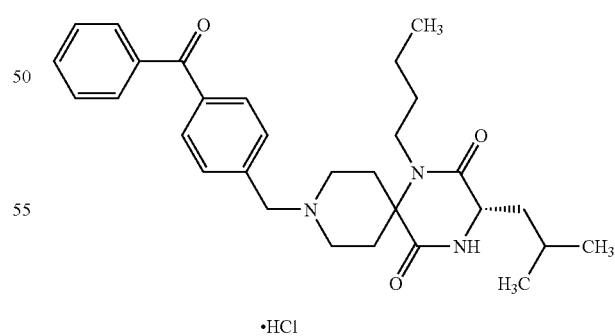

·HCl

TLC: Rf 0.76 (chloroform:methanol=10:1); NMR (CD₃OD): δ 7.88 (d, J=8.4 Hz, 2H), 7.81-7.67 (m, 5H), 7.57-7.52 (m, 2H), 4.49 (s, 2H), 4.01 (dd, J=8.1, 4.8 Hz, 1H), 4.00-3.78 (m, 2H), 3.59-3.48 (m, 2H), 3.44-3.35 (m, 2H), 2.50-2.32 (m, 2H), 2.32-2.14 (m, 2H), 1.88-1.24 (m, 7H), 1.02-0.88 (m, 9H).

EXAMPLE 37(60)

(3S)-1-butyl-2,5-dioxo-3-(2-methylpropyl)-9-(3,5-dimethyl-1-(4-(N-(2-hydroxyethyl)-N-methylaminosulfonyl)phenyl)pyrazol-4-ylmethyl)-1,4,9-triazaspiro[5.5]undecane.2 hydrochloride

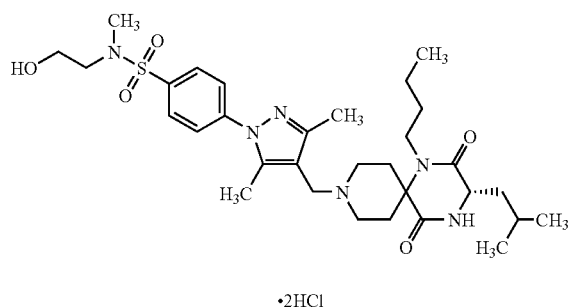

TLC: Rf 0.34 (chloroform:methanol=10:1); NMR (CD$_3$OD): δ 8.00 (d, J=8.7 Hz, 2H), 7.76 (d, J=8.7 Hz, 2H), 4.34 (s, 2H), 4.04 (dd, J=7.8, 4.5 Hz, 1H), 3.98-3.76 (m, 2H), 3.70 (t, J=5.7 Hz, 2H), 3.68-3.58 (m, 2H), 3.50-3.38 (m, 2H), 3.20 (t, J=5.7 Hz, 2H), 2.88 (s, 3H), 2.58-2.38 (m, 2H), 2.48 (s, 3H), 2.41 (s, 3H), 2.36-2.16 (m, 2H), 1.90-1.24 (m, 7H), 0.97 (t, J=6.9 Hz, 3H), 0.96 (d, J=6.3 Hz, 3H), 0.95 (d, J=6.3 Hz, 3H).

EXAMPLE 37(61)

(3S)-1-butyl-2,5-dioxo-3-(2-methylpropyl)-9-(3,5-dimethyl-1-(2-phenylethyl)pyrazol-4-ylmethyl)-1,4,9-triazaspiro[5.5]undecane.2 hydrochloride

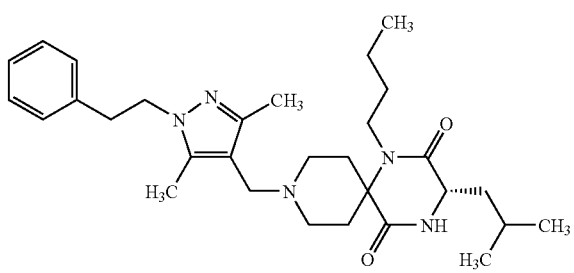

TLC: Rf 0.24 (chloroform:methanol=10:1); NMR (CD$_3$OD): δ 7.31-7.23 (m, 3H), 7.10 (d, J=6.6 Hz, 2H), 4.44 (t, J=6.3 Hz, 2H), 4.21 (s, 2H), 4.03 (dd, J=7.8, 4.8 Hz, 1H), 3.82-3.60 (m, 2H), 3.58-3.32 (m, 4H), 3.13 (t, J=6.3 Hz, 2H), 2.72-2.52 (m, 2H), 2.50 (s, 3H), 2.24-2.04 (m, 2H), 1.99 (s, 3H), 1.90-1.36 (m, 7H), 0.97 (t, J=7.2 Hz, 3H), 0.96 (d, J=6.6 Hz, 3H), 0.95 (d, J=6.6 Hz, 3H).

EXAMPLE 37(62)

(3S)-1-butyl-2,5-dioxo-3-(2-methylpropyl)-9-(1,3,5-trimethylpyrazol-4-ylmethyl)-1,4,9-triazaspiro[5.5]undecane.2 hydrochloride

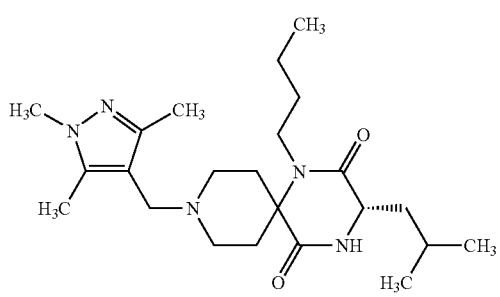

TLC: Rf 0.43 (chloroform:methanol=10:1); NMR (CD$_3$OD): δ 4.28 (s, 2H), 4.00 (dd, J=7.8, 4.8 Hz, 1H), 3.87 (s, 3H), 3.87-3.69 (m, 2H), 3.60-3.43 (m, 4H), 2.69-2.50 (m, 2H), 2.46 (s, 3H), 2.44 (s, 3H), 2.26-2.08 (m, 2H), 1.90-1.28 (m, 7H), 0.98-0.85 (m, 9H).

EXAMPLE 37(63)

(3S)-1-butyl-2,5-dioxo-3-(2-methylpropyl)-9-(4-(morpholin-4-ylmethyl)phenylmethyl)-1,4,9-triazaspiro[5.5]undecane.2 hydrochloride

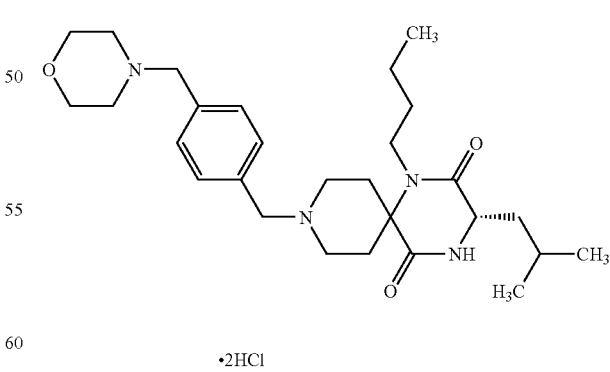

TLC: Rf 0.56 (chloroform:methanol=10:1); NMR (CD$_3$OD): δ 7.74 (d, J=8.4 Hz, 2H), 7.66 (d, J=8.4 Hz, 2H), 4.40 (s, 4H), 4.00 (dd, J=7.5, 4.5 Hz, 1H), 4.10-3.70 (m, 6H), 3.54-3.42 (m, 4H), 3.40-3.16 (m, 4H), 2.65-2.46 (m, 2H), 2.24-2.03 (m, 2H), 1.88-1.28 (m, 7H), 1.02-0.88 (m, 9H).

EXAMPLE 37(64)

(3S)-1-butyl-2,5-dioxo-3-(2-methylpropyl)-9-(4-(4-methylpiperazin-1-ylmethyl)phenylmethyl)-1,4,9-triazaspiro[5.5]undecane.3 hydrochloride

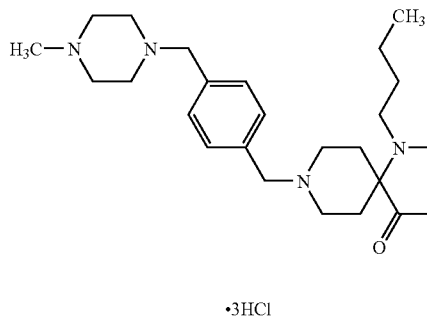

TLC: Rf 0.64 (chloroform:methanol=5:1); NMR (CD$_3$OD): δ 7.45 (m, 4H), 4.55 (s, 2H), 4.42 (s, 2H), 4.01 (dd, J=7.5, 4.5 Hz, 1H), 3.88-3.56 (m, 10H), 3.53-3.43 (m, 4H), 3.01 (s, 3H), 2.59-2.47 (m, 2H), 2.22-2.09 (m, 2H), 1.85-1.33 (m, 7H), 0.94 (t, J=7.2 Hz, 3H), 0.94 (d, J=6.5 Hz, 3H), 0.93 (d, J=6.5 Hz, 3H).

EXAMPLE 37(65)

(3S)-1-butyl-2,5-dioxo-3-(2-methylpropyl)-9-(4-phenylsulfonylphenylmethyl)-1,4,9-triazaspiro[5.5]undecane.hydrochloride

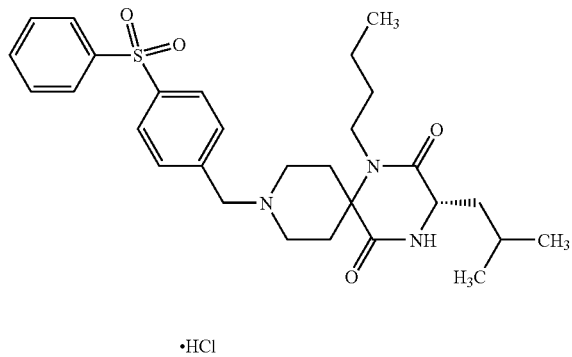

TLC: Rf 0.70 (ethyl acetate:methanol=9:1); NMR (CD$_3$OD): δ 8.08 (d, J=8.4 Hz, 2H), 8.02-7.96 (m, 2H), 7.80 (d, J=8.4 Hz, 2H), 7.70-7.55 (m, 3H), 4.43 (s, 2H), 3.99 (dd, J=7.8, 4.8 Hz, 1H), 3.91-3.72 (m, 2H), 3.48-3.34 (m, 4H), 2.48-2.32 (m, 2H), 2.23-2.06 (m, 2H), 1.88-1.43 (m, 5H), 1.34 (sextet, J=7.2 Hz, 2H), 0.96-0.90 (m, 9H).

EXAMPLE 37(66)

(3S)-1-butyl-2,5-dioxo-3-(2-methylpropyl)-9-(3,5-dimethyl-1-cyclohexylpyrazol-4-ylmethyl)-1,4,9-triazaspiro[5.5]undecane.2 hydrochloride

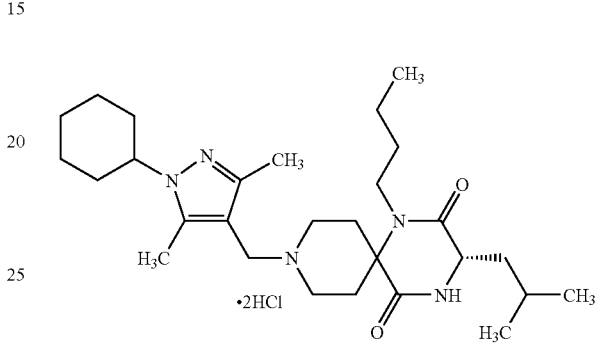

TLC: Rf 0.28 (ethyl acetate:methanol=9:1); NMR (CD$_3$OD): δ 4.35-4.20 (m, 3H), 4.01 (dd, J=7.8, 4.8 Hz, 1H), 3.90-3.68 (m, 2H), 3.58-3.41 (m, 4H), 2.60-2.46 (m, 2H), 2.45 (s, 3H), 2.40 (s, 3H), 2.26-2.08 (m, 2H), 1.98-1.26 (m, 17H), 0.98-0.91 (m, 9H).

EXAMPLE 37(67)

(3S)-1-butyl-2,5-dioxo-3-(2-methylpropyl)-9-(4-(3-carboxyphenyloxy)phenylmethyl)-1,4,9-triazaspiro[5.5]undecane.hydrochloride

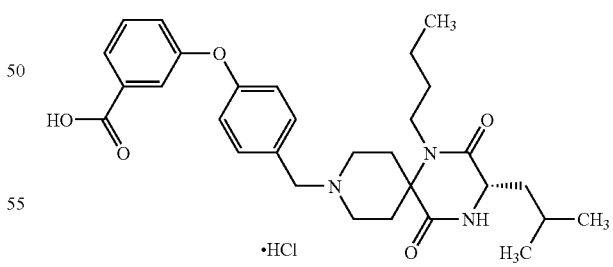

TLC: Rf 0.11 (ethyl acetate:methanol=9:1); NMR (CD$_3$OD): δ 7.83 (ddd, J=7.8, 1.5, 0.9 Hz, 1H), 7.61 (dd, J=2.4, 1.5 Hz, 1H), 7.58 (d, J=8.7 Hz, 2H), 7.51 (t, J=7.8 Hz, 1H), 7.29 (ddd, J=7.8, 2.4, 0.9 Hz, 1H), 7.11 (d, J=8.7 Hz, 2H), 4.35 (s, 2H), 4.01 (dd, J=7.8, 4.8 Hz, 1H), 3.90-3.72 (m, 2H), 3.57-3.36 (m, 4H), 2.50-2.34 (m, 2H), 2.28-2.09 (m, 2H), 1.89-1.44 (m, 5H), 1.36 (sextet, J=7.2 Hz, 2H), 0.98-0.91 (m, 9H).

EXAMPLE 37(68)

(3S)-1-butyl-2,5-dioxo-3-(2-methylpropyl)-9-(4-(piperidin-1-ylmethyl)phenylmethyl)-1,4,9-triaza-spiro[5.5]undecane.2 hydrochloride

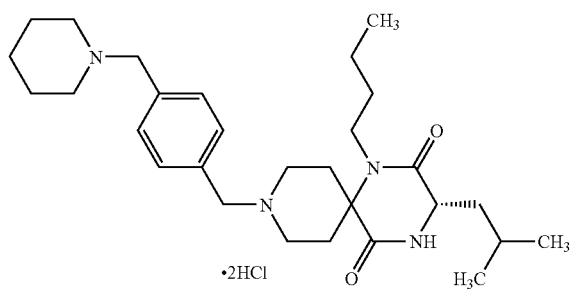

TLC: Rf 0.52 (chloroform:methanol=9:1); NMR (CD₃OD): δ 7.75 (d, J=8.4 Hz, 2H), 7.65 (d, J=8.4 Hz, 2H), 4.41 (s, 2H), 4.34 (s, 2H), 4.00 (dd, J=7.8, 4.5 Hz, 1H), 3.91-3.71 (m, 2H), 3.54-3.41 (m, 6H), 3.05-2.91 (m, 2H), 2.67-2.49 (m, 2H), 2.25-2.05 (m, 2H), 2.00-1.28 (m, 13H), 0.98-0.91 (m, 9H).

EXAMPLE 37(69)

(3S)-1-butyl-2,5-dioxo-3-(2-methylpropyl)-9-(3,5-dimethyl-1-(4-(pyrrolidin-1-ylsulfonyl)phenyl)pyrazol-4-ylmethyl)-1,4,9-triazaspiro[5.5]undecane.2 hydrochloride

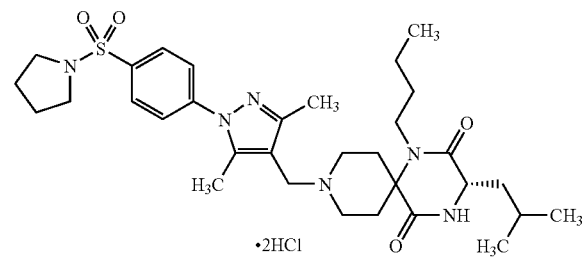

TLC: Rf 0.36 (ethyl acetate:methanol=9:1); NMR (CD₃OD): δ 8.01 (d, J=8.7 Hz, 2H), 7.76 (d, J=8.7 Hz, 2H), 4.32 (s, 2H), 4.02 (dd, J=7.8, 4.8 Hz, 1H), 3.95-3.74 (m, 2H), 3.66-3.55 (m, 2H), 3.50-3.40 (m, 2H), 3.34-3.24 (m, 4H), 2.62-2.47 (m, 2H), 2.48 (s, 3H), 2.40 (s, 3H), 2.30-2.11 (m, 2H), 1.90-1.45 (m, 9H), 1.38 (sextet, J=7.2 Hz, 2H), 1.00-0.90 (m, 9H).

EXAMPLE 37(70)

(3S)-1-butyl-2,5-dioxo-3-(2-methylpropyl)-9-(2,3-dihydrobenzofuran-5-ylmethyl)-1,4,9-triazaspiro[5.5]undecane.hydrochloride

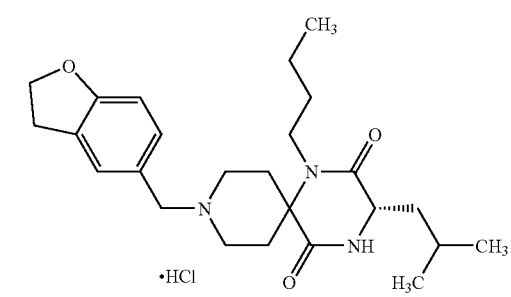

TLC: Rf 0.56 (ethyl acetate:methanol=9:1); NMR (CD₃OD): δ 7.40 (brs, 1H), 7.26 (dd, J=8.1, 1.8 Hz, 1H), 6.80 (d, J=8.1 Hz, 1H), 4.59 (t, J=8.7 Hz, 2H), 4.26 (s, 2H), 4.00 (dd, J=7.8, 4.8 Hz, 1H), 3.84-3.66 (m, 2H), 3.52-3.36 (m, 4H), 3.24 (t, J=8.7 Hz, 2H), 2.49-2.35 (m, 2H), 2.25-2.08 (m, 2H), 1.89-1.43 (m, 5H), 1.36 (sextet, J=7.2 Hz, 2H), 0.98-0.91 (m, 9H).

EXAMPLE 37(71)

(3S)-1-butyl-2,5-dioxo-3-(2-methylpropyl)-9-(3,5-dimethyl-1-(4-(2-hydroxyethylaminosulfonyl)phenyl)pyrazol-4-ylmethyl)-1,4,9-triazaspiro[5.5]undecane.2 hydrochloride

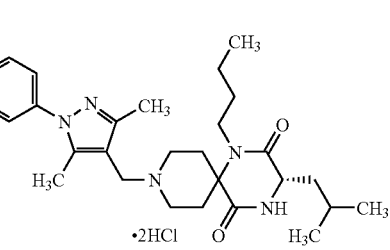

TLC: Rf 0.35 (chloroform:methanol=10:1); NMR (CD₃OD): δ 8.03 (d, J=8.7 Hz, 2H), 7.72 (d, J=8.7 Hz, 2H), 4.32 (s, 2H), 4.02 (dd, J=7.5, 4.5 Hz, 1H), 3.95-3.73 (m, 2H), 3.67-3.57 (m, 2H), 3.56 (t, J=5.7 Hz, 2H), 3.51-3.40 (m, 2H), 3.01 (t, J=5.7 Hz, 2H), 2.63-2.42 (m, 2H), 2.47 (s, 3H), 2.41 (s, 3H), 2.32-2.12 (m, 2H), 1.92-1.44 (m, 5H), 1.44-1.30 (m, 2H), 1.00-0.91 (m, 9H).

EXAMPLE 37(72)

(3S)-1-butyl-2,5-dioxo-3-(2-methylpropyl)-9-(4-(carboxymethyloxy)phenylmethyl)-1,4,9-triazaspiro[5.5]undecane.hydrochloride

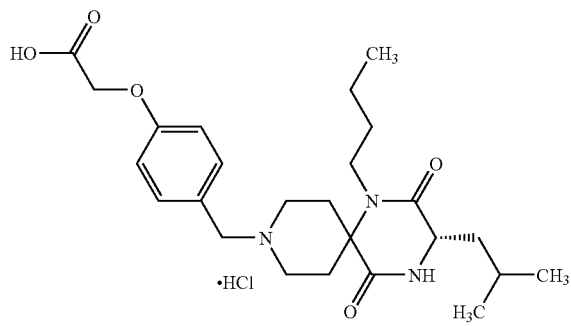

TLC: Rf 0.30 (chloroform:methanol=10:1); NMR (CD$_3$OD): δ 7.47 (d, J=8.7 Hz, 2H), 7.04 (d, J=8.7 Hz, 2H), 4.71 (s, 2H), 4.29 (s, 2H), 4.00 (dd, J=7.8, 4.5 Hz, 1H), 3.88-3.67 (m, 2H), 3.53-3.33 (m, 4H), 2.46-2.28 (m, 2H), 2.26-2.08 (m, 2H), 1.90-1.27 (m, 7H), 0.99-0.90 (m, 9H).

EXAMPLE 37(73)

(3S)-1-butyl-2,5-dioxo-3-(2-methylpropyl)-9-(4-(1-phenyl-1-hydroxymethyl)phenylmethyl)-1,4,9-triazaspiro[5.5]undecane.hydrochloride

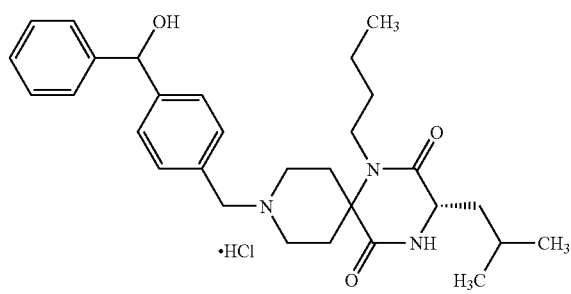

TLC: Rf 0.23 (chloroform:methanol=10:1); NMR (CD$_3$OD): δ 7.62-7.18 (m, 9H), 5.82 (s, 1H), 4.33 (s, 2H), 4.00 (dd, J=7.8, 4.8 Hz, 1H), 3.88-3.68 (m, 2H), 3.56-3.36 (m, 4H), 2.48-2.28 (m, 2H), 2.24-2.06 (m, 2H), 1.88-1.24 (m, 7H), 0.95 (t, J=6.6 Hz, 3H), 0.94 (d, J=6.3 Hz, 3H), 0.93 (d, J=6.3 Hz, 3H).

EXAMPLE 37(74)

(3S)-1-butyl-2,5-dioxo-3-(2-methylpropyl)-9-(4-(4-hydroxypiperidin-1-ylmethyl)phenylmethyl)-1,4,9-triazaspiro[5.5]undecane.2 hydrochloride

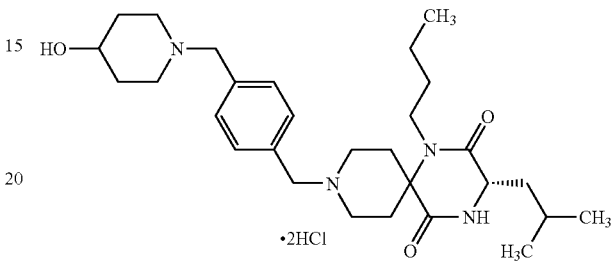

TLC: Rf 0.16 (chloroform:methanol=10:1); NMR (CD$_3$OD): δ 7.73 (d, J=7.8 Hz, 2H), 7.69-7.61 (m, 2H), 4.42 (s, 2H), 4.40-4.34 (m, 2H), 4.11-4.05 (m, 1H), 4.00 (dd, J=7.5, 4.5 Hz, 1H), 3.93-3.72 (m, 2H), 3.55-3.38 (m, 4H), 3.16-3.00 (m, 1H), 2.60-2.38 (m, 2H), 2.26-2.06 (m, 3H), 2.00-1.88 (m, 2H), 1.88-1.43 (m, 9H), 1.43-1.14 (m, 2H), 0.98-0.90 (m, 9H).

EXAMPLE 37(75)

(3S)-1-butyl-2,5-dioxo-3-(2-methylpropyl)-9-(4-(3-carboxyphenylmethyloxy)phenylmethyl)-1,4,9-triazaspiro[5.5]undecane.hydrochloride

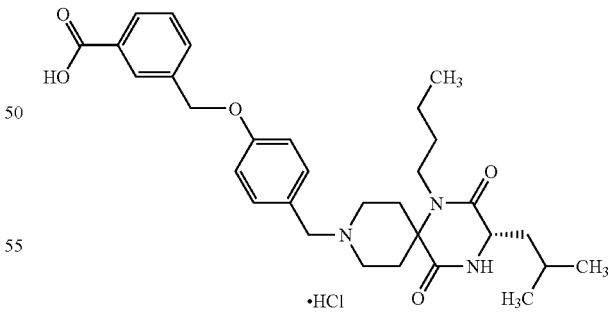

TLC: Rf 0.58 (chloroform:methanol=5:1); NMR (CD$_3$OD): δ 8.10 (s, 1H), 7.98 (d, J=8.1 Hz, 1H), 7.68 (d, J=8.7 Hz, 1H), 7.50 (t, J=8.1 Hz, 1H), 7.47 (d, J=8.7 Hz, 2H), 7.13 (d, J=8.7 Hz, 2H), 5.22 (s, 2H), 4.29 (s, 2H), 4.01 (dd, J=7.5, 4.5 Hz, 1H), 3.86-3.68 (m, 2H), 3.54-3.32 (m, 4H), 2.42-2.08 (m, 4H), 1.90-1.28 (m, 7H), 0.95 (t, J=6.9 Hz, 3H), 0.95 (d, J=6.3 Hz, 3H), 0.94 (d, J=6.3 Hz, 3H).

EXAMPLE 37(76)

(3S)-1-butyl-2,5-dioxo-3-(2-methylpropyl)-9-(4-(bis(methylsulfonyl)amino)phenylmethyl)-1,4,9-triazaspiro[5.5]undecane.hydrochloride

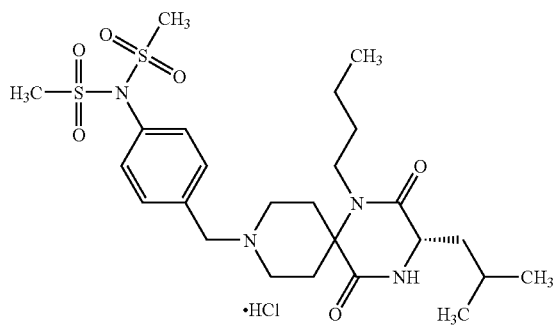

TLC: Rf 0.64 (chloroform:methanol=5:1); NMR (CD$_3$OD): δ 7.72 (d, J=8.4 Hz, 2H), 7.61 (d, J=8.4 Hz, 2H), 4.44 (s, 2H), 4.03 (dd, J=7.5, 4.5 Hz, 1H), 3.96-3.78 (m, 2H), 3.58-3.36 (m, 4H), 3.47 (s, 6H), 2.50-2.12 (m, 4H), 1.92-1.28 (m, 7H), 0.96 (t, J=6.9 Hz, 3H), 0.95 (d, J=6.3 Hz, 3H), 0.94 (d, J=6.3 Hz, 3H).

EXAMPLE 37(77)

(3S)-1-butyl-2,5-dioxo-3-(2-methylpropyl)-9-(4-(1,4-benzodioxan-6-yloxy)phenylmethyl)-1,4,9-triazaspiro[5.5]undecane.hydrochloride

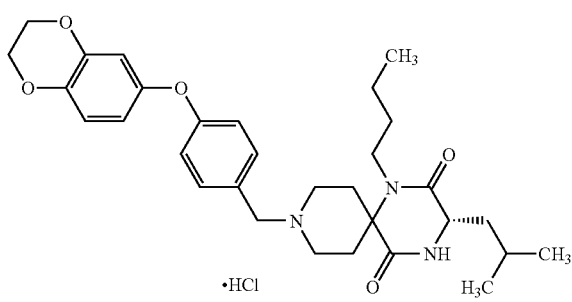

TLC: Rf 0.34 (chloroform:methanol=10:1); NMR (CD$_3$OD): δ 7.49 (d, J=8.7 Hz, 2H), 7.02 (d, J=8.7 Hz, 2H), 6.85 (m, 1H), 6.55-6.51 (m, 2H), 4.33 (s, 2H), 4.24 (s, 4H), 4.02 (dd, J=7.5, 4.8 Hz, 1H), 3.88-3.70 (m, 2H), 3.56-3.32 (m, 4H), 2.42-2.10 (m, 4H), 1.92-1.24 (m, 7H), 0.96 (t, J=7.2 Hz, 3H), 0.95 (d, J=6.6 Hz, 3H), 0.94 (d, J=6.6 Hz, 3H).

EXAMPLE 37(78)

(3S)-1-butyl-2,5-dioxo-3-(2-methylpropyl)-9-(3-(3-hydroxyphenyl)phenylmethyl)-1,4,9-triazaspiro[5.5]undecane.hydrochloride

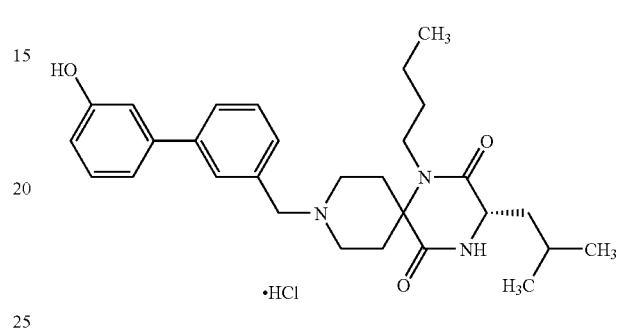

TLC: Rf 0.19 (chloroform:methanol=10:1); NMR (CD$_3$OD): δ 7.83 (s, 1H), 7.74 (m, 1H), 7.59-7.51 (m, 2H), 7.28 (m, 1H), 7.16-7.09 (m, 2H), 6.81 (m, 1H), 4.44 (s, 2H), 4.01 (dd, J=7.8, 4.5 Hz, 1H), 3.94-3.76 (m, 2H), 3.58-3.32 (m, 4H), 2.50-2.32 (m, 2H), 2.28-2.08 (m, 2H), 1.88-1.26 (m, 7H), 0.95 (t, J=7.2 Hz, 3H), 0.95 (d, J=6.3 Hz, 3H), 0.94 (d, J=6.3 Hz, 3H).

EXAMPLE 37(79)

(3S)-1-butyl-2,5-dioxo-3-(2-methylpropyl)-9-(4-(methylsulfonylamino)phenylmethyl)-1,4,9-triazaspiro[5.5]undecane.hydrochloride

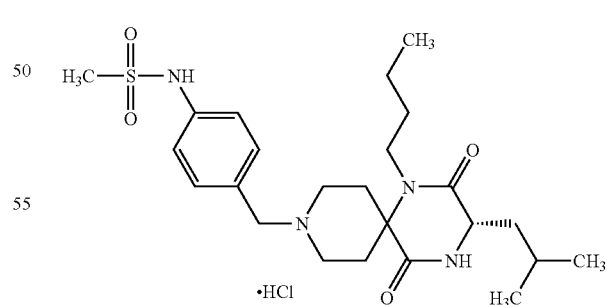

TLC: Rf 0.40 (chloroform:methanol=10:1); NMR (CD$_3$OD): δ 7.52 (d, J=8.4 Hz, 2H), 7.34 (d, J=8.4 Hz, 2H), 4.32 (s, 2H), 4.01 (dd, J=7.8, 4.8 Hz, 1H), 3.88-3.72 (m, 2H), 3.52-3.14 (m, 4H), 3.01 (s, 3H), 2.46-2.30 (m, 2H), 2.28-2.10 (m, 2H), 1.88-1.10 (m, 7H), 0.98-0.90 (m, 9H).

EXAMPLE 37(80)

(3S)-1-butyl-2,5-dioxo-3-(2-methylpropyl)-9-(6-(4-methoxyphenyloxy)pyridin-3-ylmethyl)-1,4,9-triazaspiro[5.5]undecane.2 hydrochloride

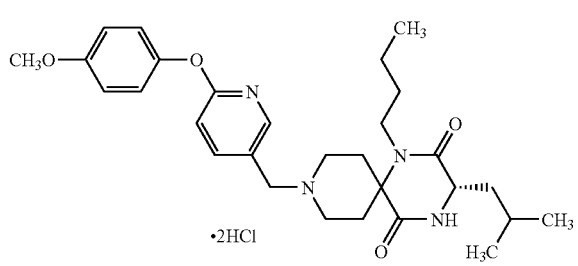

TLC: Rf 0.48 (chloroform:methanol=10:1); NMR (CD$_3$OD): δ 8.30 (m, 1H), 8.05 (m, 1H), 7.10-6.86 (m, 5H), 4.39 (s, 2H), 4.01 (dd, J=7.8, 4.8 Hz, 1H), 3.90-3.74 (m, 2H), 3.81 (s, 3H), 3.54-3.32 (m, 4H), 2.54-2.32 (m, 2H), 2.28-2.05 (m, 2H), 1.88-1.26 (m, 7H), 0.98-0.90 (m, 9H).

EXAMPLE 37(81)

(3S)-1-butyl-2,5-dioxo-3-(2-methylpropyl)-9-(4-(4-methylaminocarbonylphenyloxy)phenylmethyl)-1,4,9-triazaspiro[5.5]undecane.hydrochloride

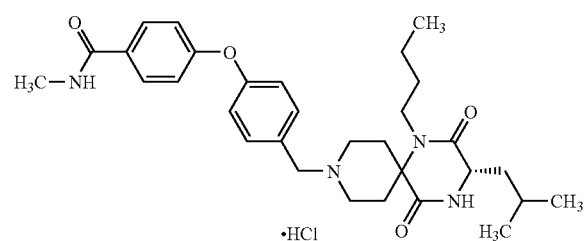

TLC: Rf 0.54 (chloroform:methanol=10:1); NMR (CD$_3$OD): δ 8.39 (brd, J=4.5 Hz, 1H), 7.84 (d, J=9.0 Hz, 2H), 7.59 (d, J=9.0 Hz, 2H), 7.15 (d, J=9.0 Hz, 2H), 7.07 (d, J=9.0 Hz, 2H), 4.35 (s, 2H), 4.01 (m, 1H), 3.86-3.73 (m, 2H), 3.53-3.41 (m, 4H), 2.91 (d, J=4.5 Hz, 3H), 2.55-2.30 (m, 2H), 2.30-2.10 (m, 2H), 1.90-1.30 (m, 7H), 0.95 (t, J=6.9 Hz, 3H), 0.94 (d, J=6.6 Hz, 3H), 0.93 (d, J=6.6 Hz, 3H).

EXAMPLE 37(82)

(3S)-1-butyl-2,5-dioxo-3-(2-methylpropyl)-9-(4-(4-chlorophenyloxy)phenylmethyl)-1,4,9-triazaspiro[5.5]undecane.hydrochloride

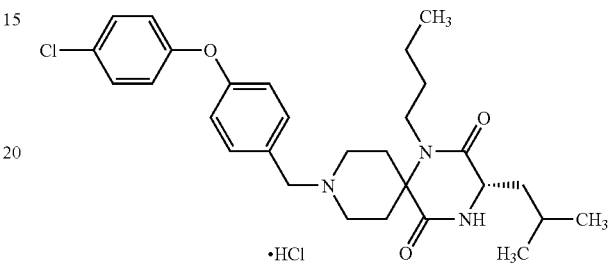

TLC: Rf 0.59 (chloroform:methanol=10:1); NMR (CD$_3$OD): δ 7.53 (d, J=8.4 Hz, 2H), 7.38 (d, J=9.0 Hz, 2H), 7.08 (d, J=8.4 Hz, 2H), 7.02 (d, J=9.0 Hz, 2H), 4.31 (s, 2H), 4.01 (m, 1H), 3.90-3.70 (m, 2H), 3.60-3.30 (m, 4H), 2.50-2.10 (m, 4H), 1.90-1.30 (m, 7H), 0.95 (t, J=7.2 Hz, 3H), 0.94 (d, J=6.6 Hz, 3H), 0.93 (d, J=6.6 Hz, 3H).

EXAMPLE 37(83)

(3S)-1-butyl-2,5-dioxo-3-(2-methylpropyl)-9-(3-(4-carboxyphenyl)phenylmethyl)-1,4,9-triazaspiro[5.5]undecane.hydrochloride

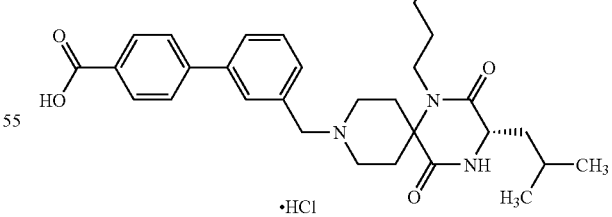

TLC: Rf 0.60 (chloroform:methanol=5:1); NMR (CD$_3$OD): δ 8.13 (d, J=9.0 Hz, 2H), 7.93 (s, 1H), 7.84 (m, 1H), 7.81 (d, J=9.0 Hz, 2H), 7.66-7.56 (m, 2H), 4.46 (s, 2H), 4.02 (dd, J=7.5, 4.8 Hz, 1H), 3.96-3.74 (m, 2H), 3.58-3.36 (m, 4H), 2.48-2.08 (m, 4H), 1.88-1.24 (m, 7H), 0.95 (t, J=6.9 Hz, 3H), 0.95 (d, J=6.3 Hz, 3H), 0.94 (d, J=6.3 Hz, 3H).

EXAMPLE 37(84)

(3S)-1-butyl-2,5-dioxo-3-(2-methylpropyl)-9-(4-(phenylaminocarbonyl)phenylmethyl)-1,4,9-triaza-spiro[5.5]undecane.hydrochloride

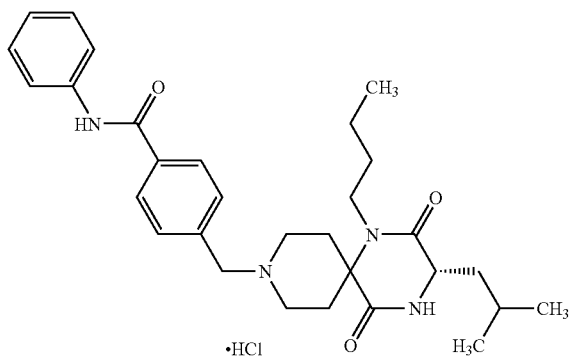

TLC: Rf 0.27 (chloroform:methanol=10:1); NMR (CD$_3$OD): δ 8.07 (d, J=8.4 Hz, 2H), 7.74 (d, J=8.4 Hz, 2H), 7.72-7.67 (m, 2H), 7.38 (t, J=7.5 Hz, 2H), 7.17 (t, J=7.5 Hz, 1H), 4.47 (s, 2H), 4.02 (dd, J=7.8, 4.5 Hz, 1H), 3.96-3.76 (m, 2H), 3.58-3.36 (m, 4H), 2.54-2.36 (m, 2H), 2.28-2.12 (m, 2H), 1.90-1.24 (m, 7H), 0.96 (t, J=7.2 Hz, 3H), 0.95 (d, J=6.3 Hz, 3H), 0.94 (d, J=6.3 Hz, 3H).

EXAMPLE 37(85)

(3S)-1-butyl-2,5-dioxo-3-(2-methylpropyl)-9-(4-(4-methylthiophenyloxy)phenylmethyl)-1,4,9-triaza-spiro[5.5]undecane.hydrochloride

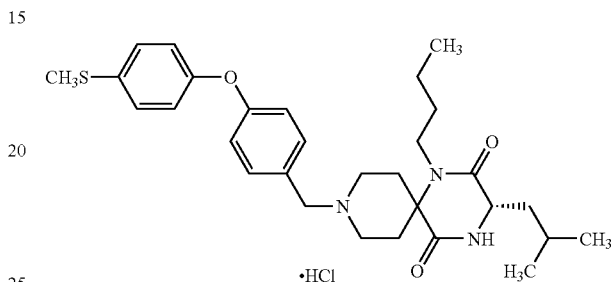

TLC: Rf 0.49 (chloroform:methanol=10:1); NMR (CD$_3$OD): δ 7.53 (d, J=8.7 Hz, 2H), 7.33 (d, J=8.7 Hz, 2H), 7.07 (d, J=8.7 Hz, 2H), 7.00 (d, J=8.7 Hz, 2H), 4.34 (s, 2H), 4.02 (dd, J=7.8, 4.5 Hz, 1H), 3.88-3.68 (m, 2H), 3.56-3.36 (m, 4H), 2.48 (s, 3H), 2.48-2.32 (m, 2H), 2.28-2.08 (m, 2H), 1.90-1.28 (m, 7H), 0.96 (t, J=7.2 Hz, 3H), 0.95 (d, J=6.3 Hz, 3H), 0.94 (d, J=6.3 Hz, 3H).

EXAMPLE 37(86)

(3S)-1-butyl-2,5-dioxo-3-(2-methylpropyl)-9-(4-(4-(2-dimethylaminoethylaminocarbonyl)phenyloxy)phenylmethyl)-1,4,9-triazaspiro[5.5]undecane.2 hydrochloride

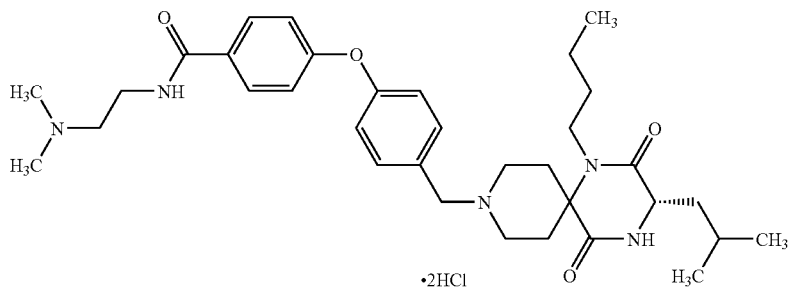

TLC: Rf 0.11 (chloroform:methanol=10:1); NMR (CD₃OD): δ 7.93 (d, J=9.0 Hz, 2H), 7.64 (d, J=8.7 Hz, 2H), 7.15 (d, J=8.7 Hz, 2H), 7.10 (d, J=9.0 Hz, 2H), 4.36 (s, 2H), 4.01 (dd, J=7.8, 4.8 Hz, 1H), 3.88-3.70 (m, 4H), 3.54-3.36 (m, 6H), 2.98 (s, 6H), 2.62-2.44 (m, 2H), 2.24-2.08 (m, 2H), 1.88-1.30 (m, 7H), 0.98-0.90 (m, 9H).

EXAMPLE 37(87)

(3S)-1-butyl-2,5-dioxo-3-(2-methylpropyl)-9-(4-aminocarbonylphenylmethyl)-1,4,9-triazaspiro[5.5]undecane.hydrochloride

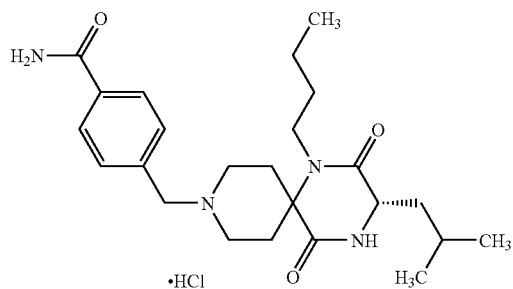

TLC: Rf 0.17 (chloroform:methanol=10:1); NMR (CD₃OD): δ 7.98 (d, J=8.7 Hz, 2H), 7.70 (d, J=8.7 Hz, 2H), 4.43 (s, 2H), 4.00 (dd, J=7.5, 4.5 Hz, 1H), 3.92-3.74 (m, 2H), 3.52-3.36 (m, 4H), 2.58-2.40 (m, 2H), 2.26-2.08 (m, 2H), 1.88-1.28 (m, 7H), 0.98-0.88 (m, 9H).

EXAMPLE 37(88)

(3S)-1-butyl-2,5-dioxo-3-(2-methylpropyl)-9-(4-dimethylaminocarbonylphenylmethyl)-1,4,9-triazaspiro[5.5]undecane.hydrochloride

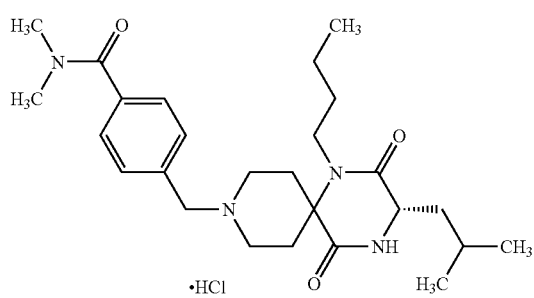

TLC: Rf 0.31 (chloroform:methanol=10:1); NMR (CD₃OD): δ 7.68 (d, J=8.1 Hz, 2H), 7.54 (d, J=8.1 Hz, 2H), 4.41 (s, 2H), 4.01 (dd, J=7.8, 4.8 Hz, 1H), 3.92-3.82 (m, 2H), 3.54-3.36 (m, 4H), 3.11 (s, 3H), 2.99 (s, 3H), 2.56-2.38 (m, 2H), 2.26-2.08 (m, 2H), 1.86-1.28 (m, 7H), 1.00-0.86 (m, 9H).

EXAMPLE 38

(3S)-1-butyl-2,5-dioxo-3-cyclohexylmethyl-9-benzyloxycarbonyl-1,4,9-triazaspiro[5.5]undecane

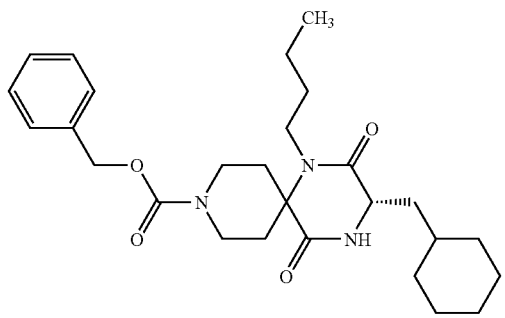

By the same procedure as described in Example 35 using N-(t-butyloxycarbonyl)-L-cyclohexylalanine instead of N-(t-butyloxycarbonyl-L-leucine, the compound of the present invention having the following physical data was obtained.

TLC: Rf 0.35 (hexane:ethyl acetate=1:1); NMR (CDCl₃): δ 7.39-7.31 (m, 5H), 6.48 (brs, 1H), 5.16 (s, 2H), 4.15 (brs, 2H), 4.00 (ddd, J=9.6, 4.8, 1.5 Hz, 1H), 3.76-3.16 (m, 4H), 2.02-1.12 (m, 19H), 1.08-0.88 (m, 2H), 0.92 (t, J=7.2 Hz, 3H).

EXAMPLE 39

(3S)-1-butyl-2,5-dioxo-3-cyclohexylmethyl-1,4,9-triazaspiro[5.5]undecane.hydrochloride

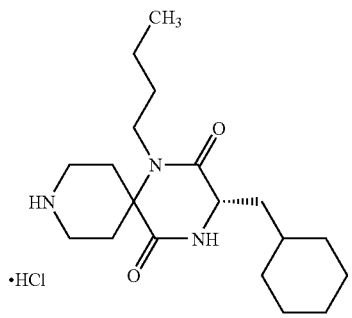

By the same procedure as described in Example 9 using the compound prepared in Example 38, the compound of the present invention having the following physical data was obtained.

TLC: Rf 0.08 (chloroform:methanol:acetic acid=90:10:1); NMR (CD₃OD): δ 4.05 (dd, J=7.8, 4.8 Hz, 1H), 3.84-3.68 (m, 2H), 3.46-3.34 (m, 4H), 2.40-2.04 (m, 4H), 1.83-1.46 (m, 10H), 1.39 (sextet, J=7.5 Hz, 2H), 1.33-1.15 (m, 3H), 1.05-0.86 (m, 2H), 0.97 (t, J=7.2 Hz, 3H).

EXAMPLE 40(1) TO 40(90)

By the same procedure as described in Example 10 using the compound prepared in Example 39 and the corresponding aldehyde derivatives, the following compounds of the present invention were obtained.

EXAMPLE 40(1)

(3S)-1-butyl-2,5-dioxo-3-cyclohexylmethyl-9-(4-(4-methylphenyloxy)phenylmethyl)-1,4,9-triazaspiro[5.5]undecane.hydrochloride

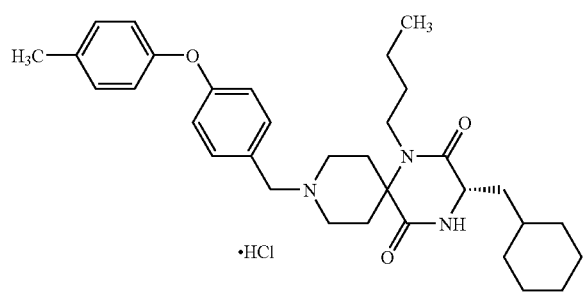

TLC: Rf 0.71 (ethyl acetate); NMR (CD$_3$OD): δ 7.50 (d, J=8.7 Hz, 2H), 7.19 (d, J=8.7 Hz, 2H), 7.02 (d, J=8.7 Hz, 2H), 6.92 (d, J=8.7 Hz, 2H), 4.32 (s, 2H), 4.04 (dd, J=7.5, 4.5 Hz, 1H), 3.87-3.69 (m, 2H), 3.55-3.42 (m, 2H), 3.42-3.34 (m, 2H), 2.49-2.30 (m, 2H), 2.33 (s, 3H), 2.30-2.08 (m, 2H), 1.82-1.10 (m, 15H), 1.05-0.85 (m, 2H), 0.95 (t, J=7.2 Hz, 3H).

EXAMPLE 40(2)

(3S)-1-butyl-2,5-dioxo-3-cyclohexylmethyl-9-(4-(4-methoxyphenyloxy)phenylmethyl)-1,4,9-triazaspiro[5.5]undecane.hydrochloride

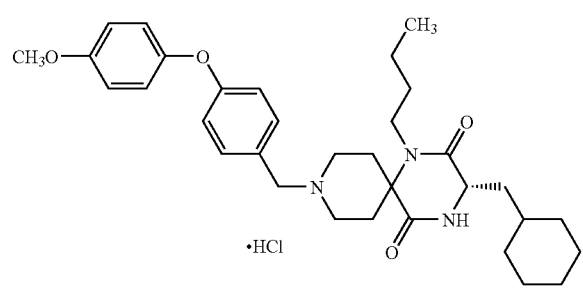

TLC: Rf 0.67 (ethyl acetate); NMR (CD$_3$OD): δ 7.49 (d, J=8.4 Hz, 2H), 7.02-6.92 (m, 6H), 4.31 (s, 2H), 4.03 (dd, J=7.5, 4.5 Hz, 1H), 3.86-3.69 (m, 2H), 3.79 (s, 3H), 3.54-3.30 (m, 4H), 2.50-2.30 (m, 2H), 2.28-2.06 (m, 2H), 1.83-1.10 (m, 15H), 1.05-0.83 (m, 2H), 0.95 (t, J=7.2 Hz, 3H).

EXAMPLE 40(3)

(3S)-1-butyl-2,5-dioxo-3-cyclohexylmethyl-9-(2-fluorophenylmethyl)-1,4,9-triazaspiro[5.5]undecane.hydrochloride

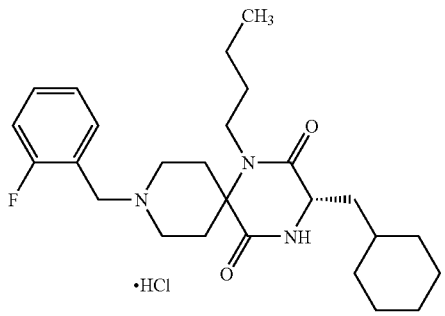

TLC: Rf 0.38 (hexane:ethyl acetate=1:1); NMR (CD$_3$OD): δ 7.70-7.53 (m, 2H), 7.38-7.23 (m, 2H), 4.44 (s, 2H), 4.03 (dd, J=7.5, 4.5 Hz, 1H), 3.95-3.77 (m, 2H), 3.60-3.45 (m, 2H), 3.45-3.30 (m, 2H), 2.53-2.34 (m, 2H), 2.28-2.08 (m, 2H), 1.83-1.10 (m, 15H), 1.05-0.82 (m, 2H), 0.94 (t, J=7.2 Hz, 3H).

EXAMPLE 40(4)

(3S)-1-butyl-2,5-dioxo-3-cyclohexylmethyl-9-(3-fluorophenylmethyl)-1,4,9-triazaspiro[5.5]undecane.hydrochloride

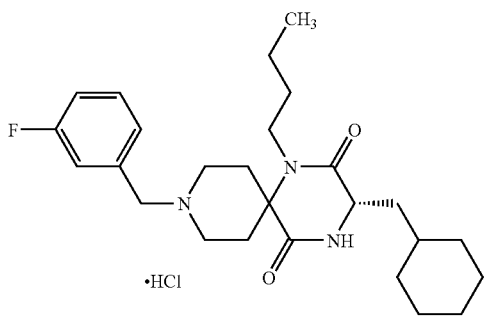

TLC: Rf 0.40 (hexane:ethyl acetate=1:1); NMR (CD$_3$OD): δ 7.57-7.48 (m, 1H), 7.44-7.37 (m, 2H), 7.30-7.21 (m, 1H), 4.38 (s, 2H), 4.03 (dd, J=7.8, 4.8 Hz, 1H), 3.90-3.72 (m, 2H), 3.55-3.33 (m, 4H), 2.56-2.37 (m, 2H), 2.25-2.04 (m, 2H), 1.82-1.08 (m, 15H), 1.06-0.83 (m, 2H), 0.95 (t, J=7.2 Hz, 3H).

EXAMPLE 40(5)

(3S)-1-butyl-2,5-dioxo-3-cyclohexylmethyl-9-(4-fluorophenylmethyl)-1,4,9-triazaspiro[5.5]undecane.hydrochloride

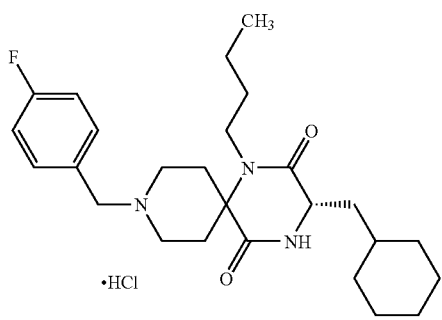

TLC: Rf 0.27 (hexane:ethyl acetate=1:1); NMR (CD$_3$OD): δ 7.62 (dd, J=8.7, 5.1 Hz, 2H), 7.23 (dd, J=8.7, 8.7 Hz, 2H), 4.36 (s, 2H), 4.03 (dd, J=7.8, 4.8 Hz, 1H), 3.88-3.71 (m, 2H), 3.53-3.33 (m, 4H), 2.53-2.35 (m, 2H), 2.27-2.04 (m, 2H), 1.82-1.10 (m, 15H), 1.05-0.82 (m, 2H), 0.94 (t, J=7.2 Hz, 3H).

EXAMPLE 40(6)

(3S)-1-butyl-2,5-dioxo-3-cyclohexylmethyl-9-(3-chlorophenylmethyl)-1,4,9-triazaspiro[5.5]undecane.hydrochloride

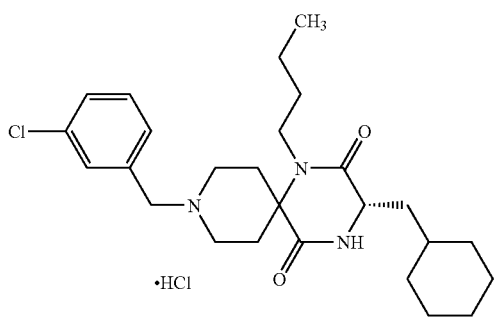

TLC: Rf 0.60 (hexane:ethyl acetate=1:1); NMR (CD$_3$OD): δ 7.65 (m, 1H), 7.55-7.49 (m, 3H), 4.37 (s, 2H), 4.04 (dd, J=7.0, 4.5 Hz, 1H), 3.83 (m, 2H), 3.54-3.47 (m, 2H), 3.41-3.35 (m, 2H), 2.38 (m, 2H), 2.18 (m, 2H), 1.78-1.47 (m, 9H), 1.42-1.17 (m, 6H), 0.95 (t, J=7.5 Hz, 3H), 0.97-0.92 (m, 2H).

EXAMPLE 40(7)

(3S)-1-butyl-2,5-dioxo-3-cyclohexylmethyl-9-(4-cyclohexyloxyphenylmethyl)-1,4,9-triazaspiro[5.5]undecane.hydrochloride

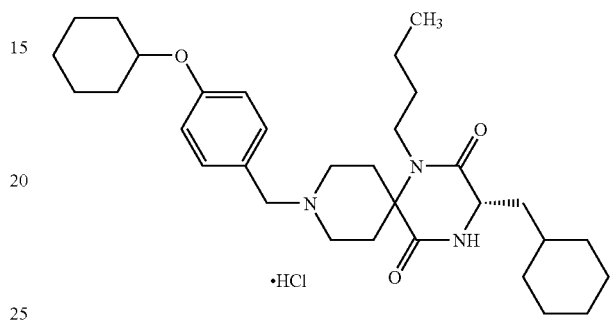

TLC: Rf 0.36 (chloroform:methanol=10:1); NMR (CD$_3$OD): δ 7.41 (d, J=8.7 Hz, 2H), 7.00 (d, J=8.7 Hz, 2H), 4.36 (m, 1H), 4.24 (s, 2H), 4.03 (dd, J=7.8, 4.5 Hz, 1H), 3.82-3.65 (m, 2H), 3.50-3.30 (m, 4H), 2.42-2.25 (m, 2H), 2.25-2.06 (m, 2H), 2.02-1.92 (m, 2H), 1.84-1.14 (m, 23H), 1.04-0.89 (m, 5H).

EXAMPLE 40(8)

(3S)-1-butyl-2,5-dioxo-3-cyclohexylmethyl-9-(4-methoxy-3-hydroxyphenylmethyl)-1,4,9-triazaspiro[5.5]undecane.hydrochloride

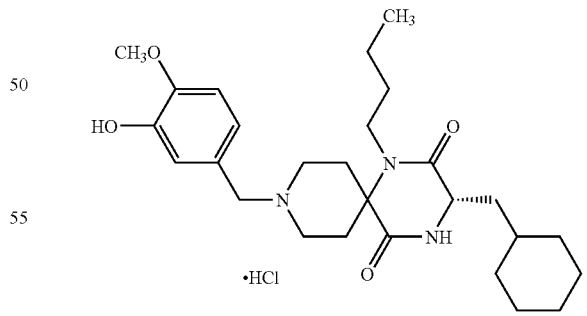

TLC: Rf 0.34 (chloroform:methanol=10:1); NMR (CD$_3$OD): δ 7.01 (d, J=7.8 Hz, 1H), 6.99-6.93 (m, 2H), 4.22 (s, 2H), 4.03 (dd, J=7.5, 4.8 Hz, 1H), 3.87 (s, 3H), 3.83-3.67 (m, 2H), 3.52-3.42 (m, 2H), 3.42-3.33 (m, 2H), 2.44-2.27 (m, 2H), 2.26-2.07 (m, 2H), 1.83-1.12 (m, 15H), 1.04-0.89 (m, 5H).

EXAMPLE 40(9)

(3S)-1-butyl-2,5-dioxo-3-cyclohexylmethyl-9-(2-chlorophenylmethyl)-1,4,9-triazaspiro[5.5]undecane.hydrochloride

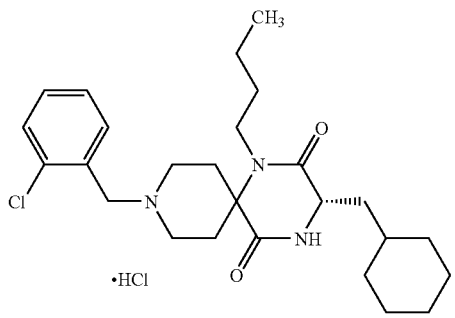

TLC: Rf 0.77 (chloroform:methanol=10:1); NMR (CD₃OD): δ 7.69 (dd, J=7.5, 2.1 Hz, 1H), 7.60 (dd, J=7.5, 2.1 Hz, 1H), 7.51 (dt, J=2.1, 7.5 Hz, 1H), 7.47 (dt, J=2.1, 7.5 Hz, 1H), 4.52 (s, 2H), 4.04 (dd, J=7.8, 4.8 Hz, 1H), 4.00-3.82 (m, 2H), 3.60-3.48 (m, 2H), 3.43-3.34 (m, 2H), 2.48-2.29 (m, 2H), 2.28-2.07 (m, 2H), 1.83-1.44 (m, 10H), 1.43-1.12 (m, 5H), 1.04-0.88 (m, 5H).

EXAMPLE 40(10)

(3S)-1-butyl-2,5-dioxo-3-cyclohexylmethyl-9-(2-methylphenylmethyl)-1,4,9-triazaspiro[5.5]undecane.hydrochloride

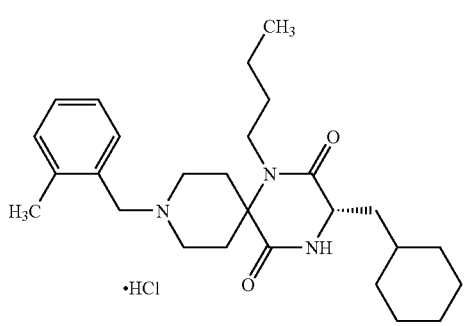

TLC: Rf 0.77 (chloroform:methanol=10:1); NMR (CD₃OD): δ 7.56 (d, J=7.2 Hz, 1H), 7.41-7.30 (m, 3H), 4.41 (s, 2H), 4.04 (dd, J=7.5, 4.5 Hz, 1H), 3.98-3.79 (m, 2H), 3.57-3.48 (m, 2H), 3.44-3.39 (m, 2H), 2.56-2.38 (m, 2H), 2.48 (s, 3H), 2.26-2.06 (m, 2H), 1.82-1.15 (m, 15H), 1.02-0.84 (m, 5H).

EXAMPLE 40(11)

(3S)-1-butyl-2,5-dioxo-3-cyclohexylmethyl-9-(3-methylphenylmethyl)-1,4,9-triazaspiro[5.5]undecane.hydrochloride

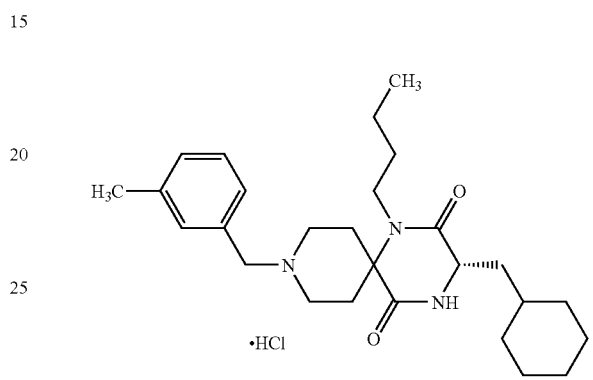

TLC: Rf 0.58 (chloroform:methanol=10:1); NMR (CD₃OD): δ 7.40-7.28 (m, 4H), 4.31 (s, 2H), 4.03 (dd, J=7.5, 4.5 Hz, 1H), 3.84-3.70 (m, 2H), 3.52-3.46 (m, 4H), 2.51-2.30 (m, 2H), 2.39 (s, 3H), 2.24-2.04 (m, 2H), 1.80-1.12 (m, 15H), 1.02-0.84 (m, 5H).

EXAMPLE 40(12)

(3S)-1-butyl-2,5-dioxo-3-cyclohexylmethyl-9-(4-methylphenylmethyl)-1,4,9-triazaspiro[5.5]undecane.hydrochloride

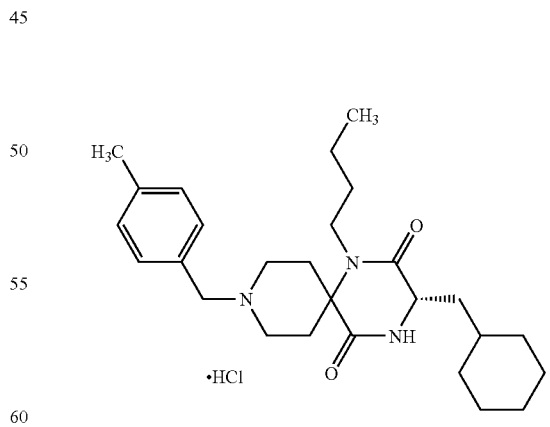

TLC: Rf 0.61 (chloroform:methanol=10:1); NMR (CD₃OD): δ 7.44 (d, J=8.4 Hz, 2H), 7.31 (d, J=8.4 Hz, 2H), 4.31 (s, 2H), 4.03 (dd, J=7.5, 4.5 Hz, 1H), 3.88-3.70 (m, 2H), 3.52-3.36 (m, 4H), 2.48-2.30 (m, 2H), 2.38 (s, 3H), 2.30-2.08 (m, 2H), 1.81-1.10 (m, 15H), 1.04-0.82 (m, 5H).

EXAMPLE 40(13)

(3S)-1-butyl-2,5-dioxo-3-cyclohexylmethyl-9-(4-phenylthiophenylmethyl)-1,4,9-triazaspiro[5.5]unde-cane.hydrochlorde

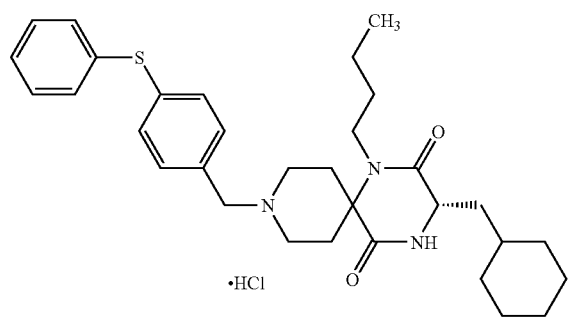

TLC: Rf 0.74 (chloroform:methanol=10:1); NMR (CD$_3$OD): δ 7.50-7.37 (m, 7H), 7.29 (d, J=8.4 Hz, 2H), 4.31 (s, 2H), 4.03 (dd, J=7.5, 4.8 Hz, 1H), 3.84-3.70 (m, 2H), 3.50-3.32 (m, 4H), 2.56-2.38 (m, 2H), 2.24-2.05 (m, 2H), 1.81-1.06 (m, 15H), 1.02-0.84 (m, 5H).

EXAMPLE 40(14)

(3S)-1-butyl-2,5-dioxo-3-cyclohexylmethyl-9-(3-(2-methylpropyl)phenylmethyl)-1,4,9-triazaspiro[5.5]undecane.hydrochloride

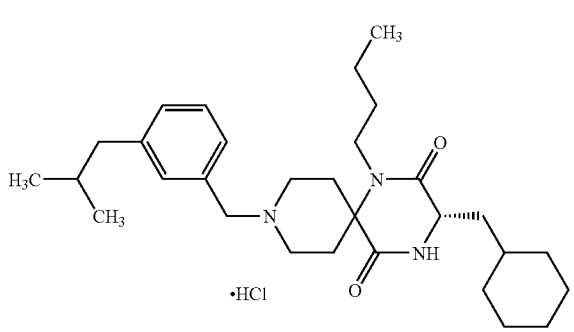

TLC: Rf 0.41 (chloroform:methanol=19:1); NMR (CD$_3$OD): δ 7.47 (d, J=7.5 Hz, 2H), 7.29 (d, J=7.5 Hz, 2H), 4.32 (s, 2H), 4.03 (dd, J=7.8, 4.8 Hz, 1H), 3.80 (m, 2H), 3.56-3.36 (m, 4H), 2.52 (d, J=7.2 Hz, 2H), 2.45 (m, 2H), 2.16 (m, 2H), 1.96-1.14 (m, 16H), 0.97-0.89 (m, 11H).

EXAMPLE 40(15)

(3S)-1-butyl-2,5-dioxo-3-cyclohexylmethyl-9-(3-butylphenylmethyl)-1,4,9-triazaspiro[5.5]undecane-.hydrochloride

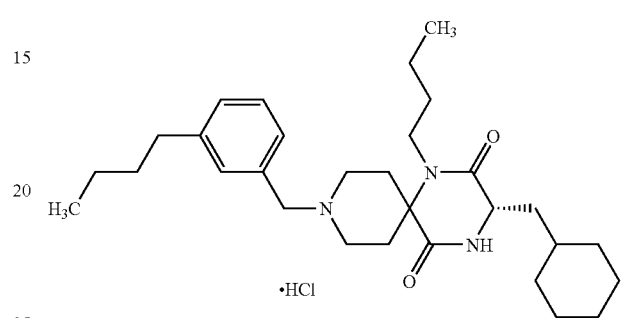

TLC: Rf 0.37 (chloroform:methanol=19:1); NMR (CD$_3$OD): δ 7.46 (d, J=8.4 Hz, 2H), 7.32 (d, J=8.4 Hz, 2H), 4.31 (s, 2H), 4.03 (dd, J=7.2, 4.8 Hz, 1H), 3.79 (m, 2H), 3.56-3.36 (m, 4H), 2.66 (t, J=7.5 Hz, 2H), 2.41 (m, 2H), 2.16 (m, 2H), 1.82-1.20 (m, 19H), 1.00-0.89 (m, 2H), 0.94 (t, J=7.2 Hz, 3H), 0.93 (t, J=7.2 Hz, 3H).

EXAMPLE 40(16)

(3S)-1-butyl-2,5-dioxo-3-cyclohexylmethyl-9-(4-isopropylphenylmethyl)-1,4,9-triazaspiro[5.5]unde-cane.hydrochloride

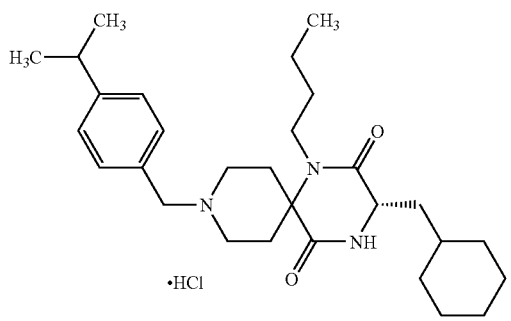

TLC: Rf 0.63 (chloroform:methanol=10:1); NMR (CD$_3$OD): δ 7.46 (d, J=8.4 Hz, 2H), 7.37 (d, J=8.4 Hz, 2H), 4.32 (s, 2H), 4.03 (dd, J=7.8, 4.8 Hz, 1H), 3.88-3.74 (m, 2H), 3.52-3.43 (m, 2H), 3.43-3.32 (m, 2H), 3.02-2.90 (m, 1H), 2.45-2.25 (m, 2H), 2.25-2.08 (m, 2H), 1.80-1.12 (m, 21H), 1.04-0.88 (m, 5H).

EXAMPLE 40(17)

(3S)-1-butyl-2,5-dioxo-3-cyclohexylmethyl-9-(4-methoxy-3-fluorophenylmethyl)-1,4,9-triazaspiro[5.5]undecane.hydrochloride

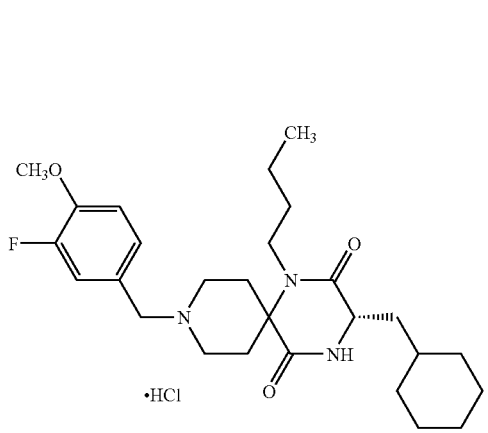

TLC: Rf 0.58 (chloroform:methanol=10:1); NMR (CD$_3$OD): δ 7.40-7.31 (m, 2H), 7.22-7.17 (m, 1H), 4.30 (s, 2H), 4.03 (dd, J=7.8, 4.8 Hz, 1H), 3.90 (s, 3H), 3.86-3.70 (m, 2H), 3.50-3.38 (m, 4H), 2.52-2.32 (m, 2H), 2.26-2.05 (m, 2H), 1.80-1.15 (m, 15H), 1.01-0.88 (m, 5H).

EXAMPLE 40(18)

(3S)-1-butyl-2,5-dioxo-3-cyclohexylmethyl-9-(4-(2-hydroxyethoxy)phenylmethyl)-1,4,9-triazaspiro[5.5]undecane.hydrochloride

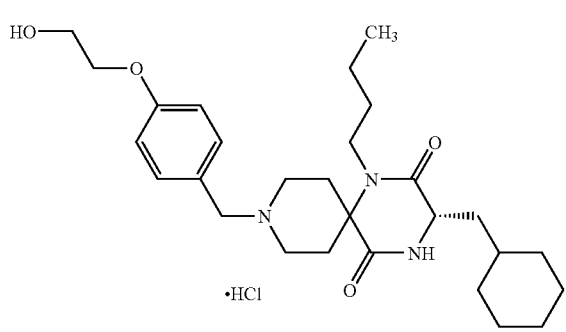

TLC: Rf 0.40 (chloroform:methanol=10:1); NMR (CD$_3$OD): δ 7.47 (d, J=8.7 Hz, 2H), 7.06 (d, J=8.7 Hz, 2H), 4.29 (s, 2H), 4.08-4.00 (m, 3H), 3.89-3.84 (m, 2H), 3.84-3.68 (m, 2H), 3.52-3.36 (m, 4H), 2.48-2.30 (m, 2H), 2.25-2.08 (m, 2H), 1.80-1.10 (m, 15H), 1.04-0.86 (m, 5H).

EXAMPLE 40(19)

(3S)-1-butyl-2,5-dioxo-3-cyclohexylmethyl-9-(2-hydroxy-3-methylphenylmethyl)-1,4,9-triazaspiro[5.5]undecane.hydrochloride

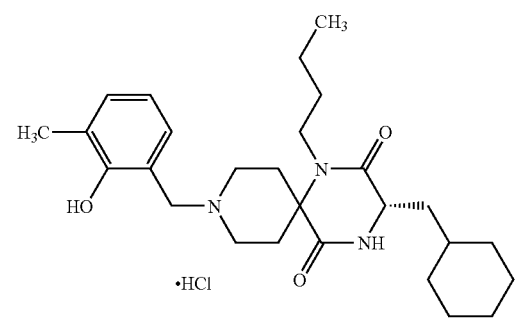

TLC: Rf 0.85 (chloroform:methanol=10:1); NMR (CD$_3$OD): δ 7.30-7.21 (m, 2H), 6.88 (t, J=7.5 Hz, 1H), 4.36 (s, 2H), 4.03 (dd, J 7.8, 4.2 Hz, 1H), 3.94-3.78 (m, 2H), 3.56-3.46 (m, 2H), 3.42-3.32 (m, 2H), 2.50-2.30 (m, 2H), 2.28 (s, 3H), 2.28-2.06 (m, 2H), 1.82-1.01 (m, 15H), 1.00-0.87 (m, 5H).

EXAMPLE 40(20)

(3S)-1-butyl-2,5-dioxo-3-cyclohexylmethyl-9-(4-chlorophenylmethyl)-1,4,9-triazaspiro[5.5]undecane.hydrochloride

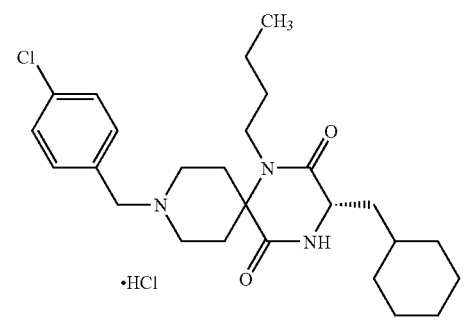

TLC: Rf 0.60 (chloroform:methanol=20:1); NMR (CD$_3$OD): δ 7.57 (d, J=8.7 Hz, 2H), 7.51 (d, J=8.7 Hz, 2H), 4.36 (s, 2H), 4.03 (dd, J=7.5, 4.8 Hz, 1H), 3.89-3.71 (m, 2H), 3.53-3.33 (m, 4H), 2.52-2.32 (m, 2H), 2.26-2.07 (m, 2H), 1.83-1.06 (m, 15H), 1.04-0.84 (m, 2H), 0.95 (t, J=6.9 Hz, 3H).

EXAMPLE 40(21)

(3S)-1-butyl-2,5-dioxo-3-cyclohexylmethyl-9-(7-methoxy-1,3-benzodioxolan-5-ylmethyl)-1,4,9-triazaspiro[5.5]undecane.hydrochloride

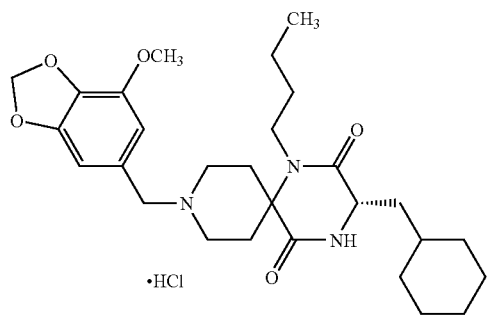

TLC: Rf 0.43 (chloroform:methanol=20:1); NMR (CD$_3$OD): δ 6.85 (s, 1H), 6.74 (s, 1H), 5.99 (s, 2H), 4.25 (s, 2H), 4.03 (dd, J=7.5, 4.5 Hz, 1H), 3.92 (s, 3H), 3.87-3.67 (m, 2H), 3.54-3.34 (m, 4H), 2.53-2.30 (m, 2H), 2.25-2.05 (m, 2H), 1.83-1.10 (m, 15H), 1.06-0.83 (m, 2H), 0.95 (t, J=7.2 Hz, 3H).

EXAMPLE 40(22)

(3S)-1-butyl-2,5-dioxo-3-cyclohexylmethyl-9-(3-methyl-4-methoxyphenylmethyl)-1,4,9-triazaspiro[5.5]undecane.hydrochloride

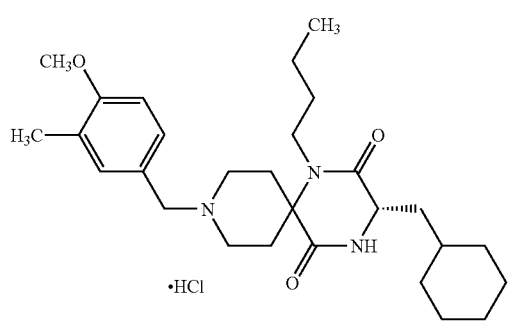

TLC: Rf 0.38 (chloroform:methanol=20:1); NMR (CD$_3$OD): δ 7.37-7.28 (m, 2H), 6.99 (d, J=8.1 Hz, 1H), 4.25 (s, 2H), 4.03 (dd, J=7.5, 4.5 Hz, 1H), 3.85 (s, 3H), 3.84-3.66 (m, 2H), 3.52-3.32 (m, 4H), 2.48-2.28 (m, 2H), 2.22 (s, 3H), 2.22-2.05 (m, 2H), 1.83-1.10 (m, 15H), 1.06-0.83 (m, 2H), 0.94 (t, J=6.9 Hz, 3H).

EXAMPLE 40(23)

(3S)-1-butyl-2,5-dioxo-3-cyclohexylmethyl-9-(4-(4-fluorophenyloxy)phenylmethyl)-1,4,9-triazaspiro[5.5]undecane.hydrochloride

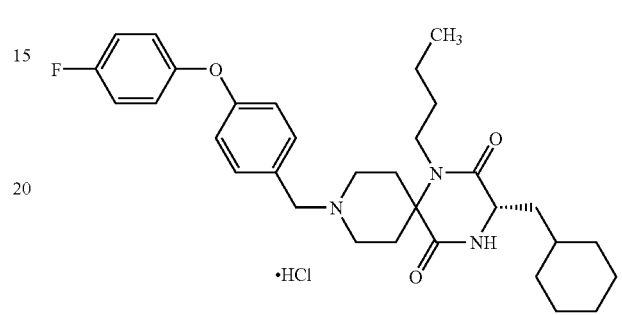

TLC: Rf 0.53 (chloroform:methanol=20:1); NMR (CD$_3$OD): δ 7.53 (d, J=8.7 Hz, 2H), 7.18-7.00 (m, 6H), 4.33 (s, 2H), 4.04 (dd, J=7.5, 4.5 Hz, 1H), 3.87-3.69 (m, 2H), 3.55-3.32 (m, 4H), 2.52-2.32 (m, 2H), 2.28-2.08 (m, 2H), 1.83-1.12 (m, 15H), 1.06-0.83 (m, 2H), 0.95 (t, J=7.2 Hz, 3H).

EXAMPLE 40(24)

(3S)-1-butyl-2,5-dioxo-3-cyclohexylmethyl-9-(4-trifluoromethoxyphenylmethyl)-1,4,9-triazaspiro[5.5]undecane.hydrochloride

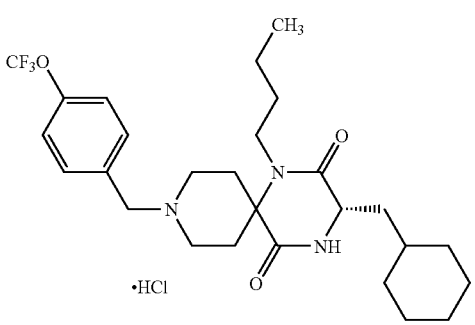

TLC: Rf 0.60 (chloroform:methanol=10:1); NMR (CD$_3$OD): δ 7.72-7.69 (m, 2H), 7.41 (d, J=7.8 Hz, 2H), 4.40 (s, 2H), 4.03 (dd, J=7.5, 4.5 Hz, 1H), 3.90-3.75 (m, 2H), 3.52-3.38 (m, 4H), 2.54-2.32 (m, 2H), 2.28-2.10 (m, 2H), 1.80-1.10 (m, 15H), 1.02-0.88 (m, 5H).

EXAMPLE 40(25)

(3S)-1-butyl-2,5-dioxo-3-cyclohexylmethyl-9-(3-methyl-5-chloro-1-phenylpyrazol-4-ylmethyl)-1,4,9-triazaspiro[5.5]undecane.2 hydrochloride

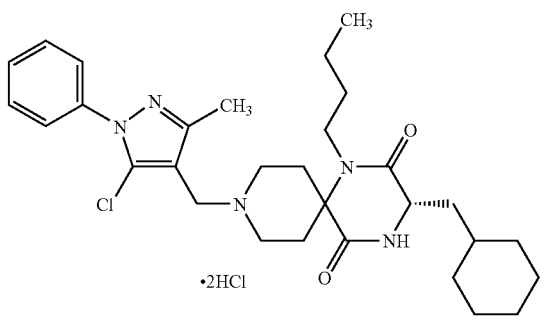

TLC: Rf 0.50 (chloroform:methanol=10:1); NMR (CD$_3$OD): δ 7.56-7.50 (m, 5H), 4.33 (s, 2H), 4.05 (dd, J=7.8, 4.5 Hz, 1H), 3.98-3.80 (m, 2H), 3.70-3.59 (m, 2H), 3.50-3.40 (m, 2H), 2.60-2.38 (m, 2H), 2.45 (s, 3H), δ 2.32-2.14 (m, 2H), 1.82-1.14 (m, 15H), 1.02-0.86 (m, 5H).

EXAMPLE 40(26)

(3S)-1-butyl-2,5-dioxo-3-cyclohexylmethyl-9-(2,3-dimethyl-5-oxo-1-phenylpyrazolin-4-ylmethyl)-1,4,9-triazaspiro[5.5]undecane.2 hydrochloride

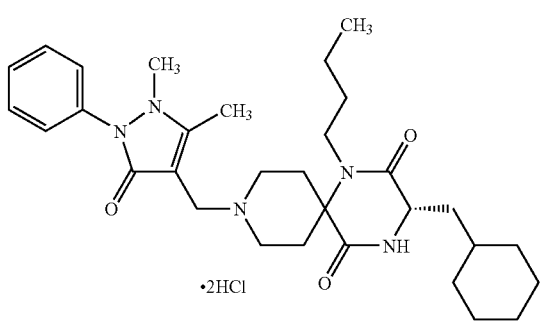

TLC: Rf 0.27 (chloroform:methanol=10:1); NMR (CD$_3$OD): δ 7.62-7.48 (m, 3H), 7.44-7.38 (m, 2H), 4.13 (s, 2H), 4.04 (dd, J=7.5, 4.5 Hz, 1H), 3.88-3.72 (m, 2H), 3.64-3.52 (m, 2H), 3.50-3.38 (m, 2H), 3.35 (s, 3H), 2.60-2.40 (m, 2H), 2.48 (s, 3H), 2.28-2.10 (m, 2H), 1.82-1.10 (m, 15H), 1.02-0.84 (m, 5H).

EXAMPLE 40(27)

(3S)-1-butyl-2,5-dioxo-3-cyclohexylmethyl-9-(1-(2-methylpropyloxycarbonyl)indol-5-ylmethyl)-1,4,9-triazaspiro[5.5]undecane.hydrochloride TLC: Rf 0.55 (chloroform:methanol=10:1); NMR (CD$_3$OD): δ 8.26 (d, J=8.4 Hz, 1H), 7.82 (s, 1H), 7.76 (d, J=3.6 Hz, 1H), 7.50 (dd, J=8.4, 1.8 Hz, 1H), 6.74 (d, J=3.6 Hz, 1H), 4.44 (s, 2H), 4.25 (d, J=6.6 Hz, 2H), 4.03 (dd, J=7.8, 4.8 Hz, 1H), 3.86-3.72 (m, 2H), 3.52-3.40 (m, 4H), 2.52-2.36 (m, 2H), 2.25-2.06 (m, 3H), 1.80-1.10 (m, 15H), 1.07 (d, J=9.0 Hz, 6H), 1.00-0.84 (m, 5H).

EXAMPLE 40(28)

(3S)-1-butyl-2,5-dioxo-3-cyclohexylmethyl-9-(5-methyl-2-phenyloxazol-4-ylmethyl)-1,4,9-triazaspiro[5.5]undecane.hydrochloride

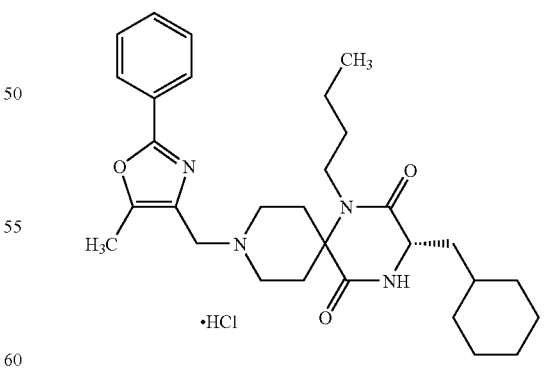

TLC: Rf 0.48 (chloroform:methanol=10:1); NMR (CD$_3$OD): δ 8.04-8.00 (m, 2H), 7.51-7.49 (m, 3H), 4.34 (s, 2H), 4.04 (dd, J=7.8, 4.8 Hz, 1H), 3.98-3.82 (m, 2H), 3.70-3.60 (m, 2H), 3.44-3.38 (m, 2H), 2.52 (s, 3H), 2.50-2.36 (m, 2H), 2.28-2.12 (m, 2H), 1.80-1.12 (m, 15H), 1.00-0.86 (m, 5H).

EXAMPLE 40(29)

(3S)-1-butyl-2,5-dioxo-3-cyclohexylmethyl-9-(3,5-dimethyl-1-(4-methylsulfonylaminophenyl)pyrazol-4-ylmethyl)-1,4,9-triazaspiro[5.5]undecane.2 hydrochloride

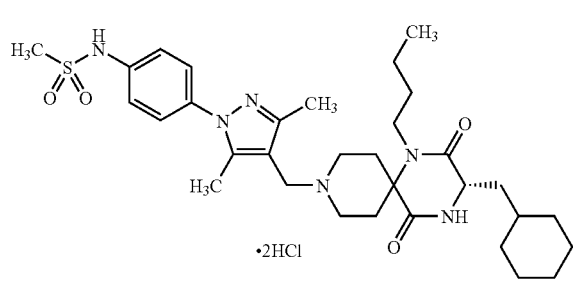

TLC: Rf 0.32 (chloroform:methanol=10:1); NMR (CD$_3$OD): δ 7.47 (d, J=9.0 Hz, 2H), 7.41 (d, J=9.0 Hz, 2H), 4.32 (s, 2H), 4.04 (dd, J=7.8, 4.8 Hz, 1H), 3.92-3.76 (m, 2H), 3.65-3.58 (m, 2H), 3.52-3.45 (m, 2H), 3.04 (s, 3H), 2.64-2.50 (m, 2H), 2.43 (s, 3H), 2.40 (s, 3H), 2.28-2.12 (m, 2H), 1.82-1.10 (m, 15H), 1.00-0.88 (m, 5H).

EXAMPLE 40(30)

(3S)-1-butyl-2,5-dioxo-3-cyclohexylmethyl-9-(4-(4-methylsulfonylaminophenyloxy)phenylmethyl)-1,4,9-triazaspiro[5.5]undecane.hydrochloride

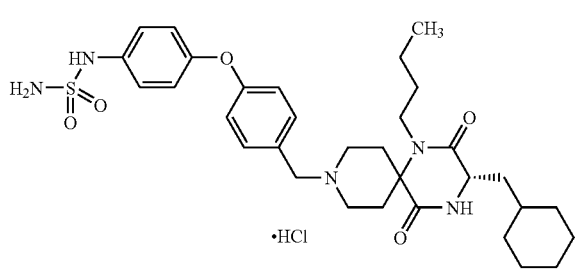

TLC: Rf 0.42 (chloroform:methanol=10:1); NMR (CD$_3$OD): δ 7.53 (d, J=9.0 Hz, 2H), 7.29 (d, J=9.0 Hz, 2H), 7.08-7.00 (m, 4H), 4.33 (s, 2H), 4.03 (dd, J=7.5, 4.8 Hz, 1H), 3.85-3.72 (m, 2H), 3.54-3.36 (m, 4H), 2.95 (s, 3H), 2.48-2.34 (m, 2H), 2.25-2.08 (m, 2H), 1.80-1.14 (m, 15H), 0.98-0.88 (m, 5H).

EXAMPLE 40(31)

(3S)-1-butyl-2,5-dioxo-3-cyclohexylmethyl-9-(4-(6-methylpyridin-3-yloxy)phenylmethyl)-1,4,9-triazaspiro[5.5]undecane.2 hydrochloride

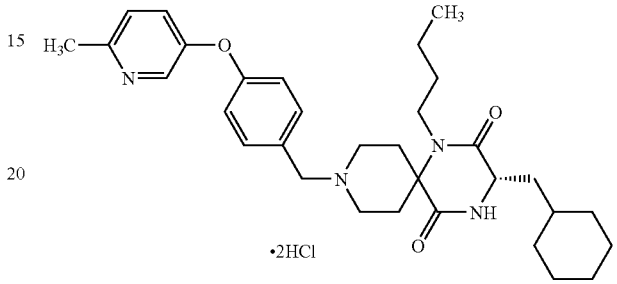

TLC: Rf 0.42 (chloroform:methanol=10:1); NMR (CD$_3$OD): δ 8.58 (d, J=2.7 Hz, 1H), 8.17 (m, 1H), 7.90 (d, J=8.4 Hz, 1H), 7.75 (d, J=9.0 Hz, 2H), 7.30 (d, J=9.0 Hz, 2H), 4.39 (s, 2H), 4.03 (dd, J=7.5, 4.8 Hz, 1H), 3.88-3.72 (m, 2H), 3.56-3.44 (m, 4H), 2.76 (s, 3H), 2.68-2.50 (m, 2H), 2.24-2.06 (m, 2H), 1.82-1.14 (m, 15H), 1.02-0.88 (m, 5H).

EXAMPLE 40(32)

(3S)-1-butyl-2,5-dioxo-3-cyclohexylmethyl-9-(4-(6-methylpyridin-1-oxido-3-yloxy)phenylmethyl)-1,4,9-triazaspiro[5.5]undecane.hydrochloride

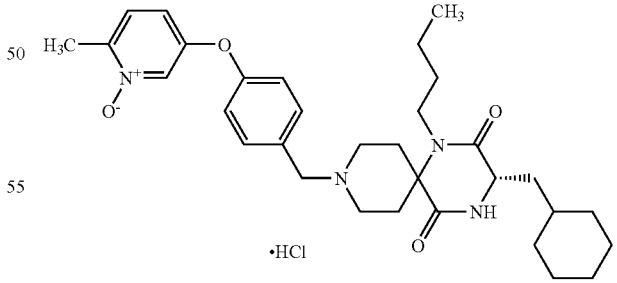

TLC: Rf 0.38 (chloroform:methanol=10:1); NMR (CD$_3$OD): δ 8.40 (m, 1H), 7.69 (d, J=8.4 Hz, 2H), 7.69 (m, 1H), 7.54 (m, 1H), 7.27 (d, J=8.4 Hz, 2H), 4.39 (s, 2H), 4.04 (dd, J=7.5, 4.8 Hz, 1H), 3.88-3.72 (m, 2H), 3.58-3.39 (m, 4H), 2.59 (s, 3H), 2.58-2.40 (m, 2H), 2.28-2.06 (m, 2H), 1.82-1.10 (m, 15H), 1.02-0.84 (m, 5H).

EXAMPLE 40(33)

(3S)-1-butyl-2,5-dioxo-3-cyclohexylmethyl-9-(4-(tetrahydropyran-4-yloxy)phenylmethyl)-1,4,9-triazaspiro[5.5]undecane.hydrochloride

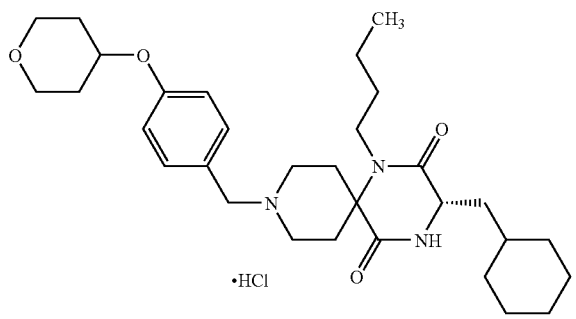

TLC: Rf 0.48 (chloroform:methanol=10:1); NMR (CD$_3$OD): δ 7.49 (d, J=8.4 Hz, 2H), 7.05 (d, J=8.4 Hz, 2H), 4.63 (m, 1H), 4.27 (s, 2H), 4.02 (dd, J=7.8, 4.8 Hz, 1H), 3.97-3.90 (m, 2H), 3.84-3.66 (m, 2H), 3.62-3.52 (m, 2H), 3.50-3.38 (m, 3H), 2.54-2.38 (m, 2H), 2.22-1.98 (m, 4H), 1.80-1.10 (m, 18H), 1.00-0.86 (m, 5H).

EXAMPLE 40(34)

(3S)-1-butyl-2,5-dioxo-3-cyclohexylmethyl-9-(6-phenylpyridin-3-ylmethyl)-1,4,9-triazaspiro[5.5]undecane.2 hydrochloride

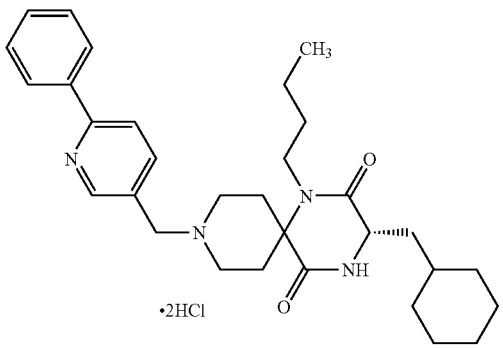

TLC: Rf 0.50 (chloroform:methanol=10:1); NMR (CD$_3$OD): δ 9.14 (m, 1H), 8.75 (m, 1H), 8.36 (m, 1H), 8.02-7.99 (m, 2H), 7.68-7.62 (m, 3H), 4.63 (s, 2H), 4.05 (dd, J=7.5, 4.5 Hz, 1H), 4.02-3.94 (m, 2H), 3.64-3.42 (m, 4H), 2.72-2.56 (m, 2H), 2.25-2.06 (m, 2H), 1.80-1.10 (m, 15H), 1.00-0.86 (m, 5H).

EXAMPLE 40(35)

(3S)-1-butyl-2,5-dioxo-3-cyclohexylmethyl-9-(3,5-dimethyl-1-(4-fluorophenyl)pyrazol-4-ylmethyl)-1,4,9-triazaspiro[5.5]undecane.2 hydrochloride

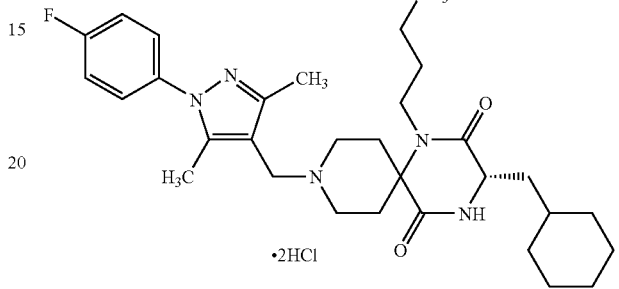

TLC: Rf 0.60 (chloroform:methanol=10:1); NMR (CD$_3$OD): δ 7.58-7.50 (m, 2H), 7.37-7.28 (m, 2H), 4.32 (s, 2H), 4.05 (dd, J=7.5, 4.5 Hz, 1H), 3.94-3.73 (m, 2H), 3.67-3.55 (m, 2H), 3.53-3.42 (m, 2H), 2.70-2.48 (m, 2H), 2.43 (s, 3H), 2.39 (s, 3H), 2.30-2.08 (m, 2H), 1.84-1.10 (m, 15H), 1.08-0.93 (m, 2H), 0.95 (t, J=7.2 Hz, 3H).

EXAMPLE 40(36)

(3S)-1-butyl-2,5-dioxo-3-cyclohexylmethyl-9-(3,5-dimethyl-1-(pyridin-2-yl)pyrazol-4-ylmethyl)-1,4,9-triazaspiro[5.5]undecane.2 hydrochloride

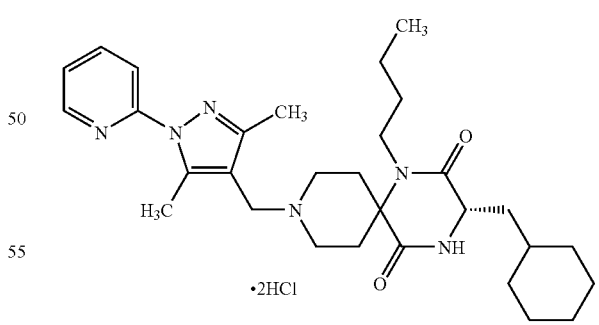

TLC: Rf 0.60 (chloroform:methanol=10:1); NMR (CD$_3$OD): δ 8.53 (dd, J=4.8, 1.5 Hz, 1H), 8.11-8.00 (m, 1H), 7.84 (d, J=8.4 Hz, 1H), 7.49-7.41 (m, 1H), 4.32 (s, 2H), 4.05 (dd, J=7.5, 4.5 Hz, 1H), 3.95-3.74 (m, 2H), 3.66-3.54 (m, 2H), 3.50-3.37 (m, 2H), 2.68 (s, 3H), 2.64-2.40 (m, 2H), 2.43 (s, 3H), 2.30-2.08 (m, 2H), 1.93-1.10 (m, 15H), 1.08-0.92 (m, 2H), 0.95 (t, J=7.2 Hz, 3H).

EXAMPLE 40(37)

(3S)-1-butyl-2,5-dioxo-3-cyclohexylmethyl-9-(3,5-dimethyl-1-(4-hydroxyphenyl)pyrazol-4-ylmethyl)-1,4,9-triazaspiro[5.5]undecane.2 hydrochloride

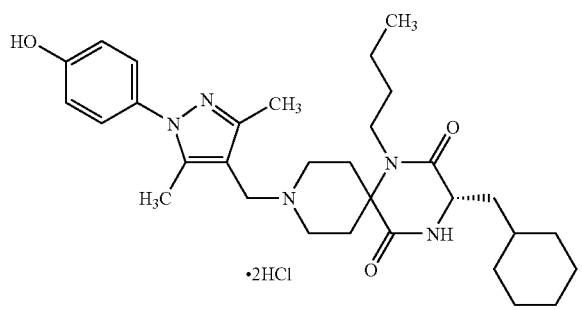

TLC: Rf 0.48 (chloroform:methanol=10:1); NMR (CD$_3$OD): δ 7.34 (d, J=9.0 Hz, 2H), 6.96 (d, J=9.0 Hz, 2H), 4.35 (s, 2H), 4.05 (dd, J=7.5, 4.5 Hz, 1H), 3.93-3.78 (m, 2H), 3.64-3.61 (m, 2H), 3.50 (t, J=8.0 Hz, 2H), 2.68-2.56 (m, 2H), 2.49 (s, 3H), 2.39 (s, 3H), 2.25-2.12 (m, 2H), 1.81-1.19 (m, 15H), 0.95 (t, J=7.5 Hz, 3H), 0.99-0.91 (m, 2H).

EXAMPLE 40(38)

(3S)-1-butyl-2,5-dioxo-3-cyclohexylmethyl-9-(4-(2-carboxyethyl)phenylmethyl)-1,4,9-triazaspiro[5.5]undecane.hydrochloride

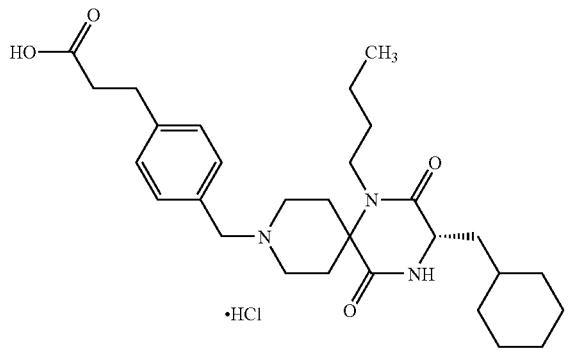

TLC: Rf 0.43 (chloroform:methanol=10:1); NMR (CD$_3$OD): δ 7.46 (d, J=8.3 Hz, 2H), 7.38 (d, J=8.3 Hz, 2H), 4.32 (s, 2H), 4.03 (dd, J=7.5, 4.5 Hz, 1H), 3.85-3.74 (m, 2H), 3.50-3.46 (m, 2H), 3.40-3.35 (m, 2H), 2.96 (t, J=7.2 Hz, 2H), 2.62 (t, J=7.2 Hz, 2H), 2.42-2.30 (m, 2H), 2.34-2.10 (m, 2H), 1.78-1.18 (m, 15H), 0.94 (t, J=7.2 Hz, 3H), 0.94 (m, 2H).

EXAMPLE 40(39)

(3S)-1-butyl-2,5-dioxo-3-cyclohexylmethyl-9-(4-(4-hydroxyphenyloxy)phenylmethyl)-1,4,9-triazaspiro[5.5]undecane.hydrochloride

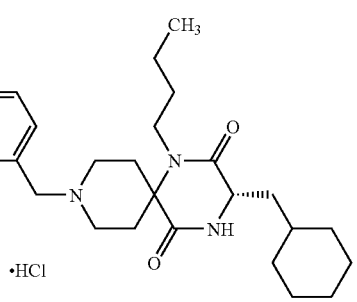

TLC: Rf 0.54 (chloroform:methanol=10:1); NMR (CD$_3$OD): δ 7.47 (d, J=8.4 Hz, 2H), 6.97 (d, J=8.4 Hz, 2H), 6.88 (d, J=9.0 Hz, 2H), 6.80 (d, J=9.0 Hz, 2H), 4.30 (s, 2H), 4.03 (dd, J=7.5, 4.5 Hz, 1H), 3.83-3.72 (m, 2H), 3.49-3.34 (m, 4H), 2.38 (m, 2H), 2.23-2.10 (m, 2H), 1.78-1.16 (m, 15H), 1.02-0.92 (m, 2H), 0.95 (t, J=7.2 Hz, 3H).

EXAMPLE 40(40)

(3S)-1-butyl-2,5-dioxo-3-cyclohexylmethyl-9-(3,5-dimethyl-1-(4-carboxyphenyl)pyrazol-4-ylmethyl)-1,4,9-triazaspiro[5.5]undecane.2 hydrochloride

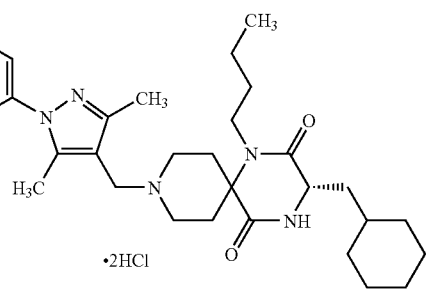

TLC: Rf 0.25 (chloroform:methanol=10:1); NMR (CD$_3$OD): δ 8.19 (d, J=8.4 Hz, 2H), 7.61 (d, J=8.4 Hz, 2H), 4.33 (s, 2H), 4.06 (dd, J=7.5, 4.5 Hz, 1H), 3.93-3.80 (m, 2H), 3.61 (m, 2H), 3.43-3.38 (m, 2H), 2.44 (s, 3H), 2.40 (m, 2H), 2.39 (s, 3H), 2.21 (m, 2H), 1.75-1.18 (m, 15H), 0.96 (m, 2H), 0.96 (t, J=7.2 Hz, 3H).

EXAMPLE 40(41)

(3S)-1-butyl-2,5-dioxo-3-cyclohexylmethyl-9-(3,5-dimethyl-1-(4-(dimethylaminosulfonyl)phenyl)pyrazol-4-ylmethyl)-1,4,9-triazaspiro[5.5]undecane.2 hydrochloride

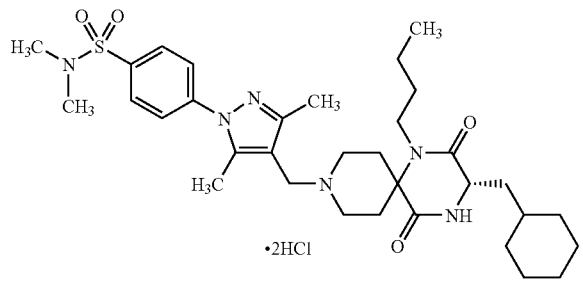

TLC: Rf 0.54 (chloroform:methanol=9:1); NMR (CD$_3$OD): δ 7.96 (d, J=8.7 Hz, 2H), 7.78 (d, J=8.7 Hz, 2H), 4.31 (s, 2H), 4.05 (dd, J=7.8, 4.5 Hz, 1H), 3.94-3.74 (m, 2H), 3.66-3.56 (m, 2H), 3.48 (m, 2H), 2.74 (s, 6H), 2.59 (m, 2H), 2.49 (s, 3H), 2.41 (s, 3H), 2.29-2.10 (m, 2H), 1.84-1.16 (m, 13H), 1.06-0.86 (m, 5H).

EXAMPLE 40(42)

(3S)-1-butyl-2,5-dioxo-3-cyclohexylmethyl-9-(4-(5-methylpyridin-1-oxido-2-yloxy)phenylmethyl)-1,4,9-triazaspiro[5.5]undecane.hydrochloride

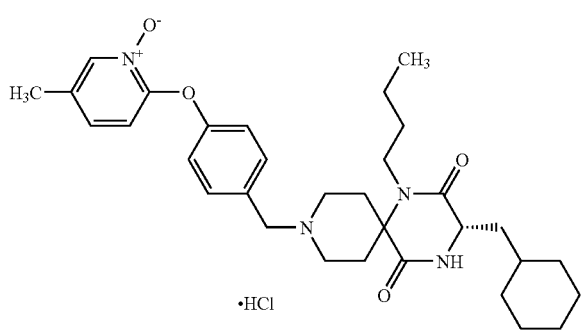

TLC: Rf 0.49 (chloroform:methanol=9:1); NMR (CD$_3$OD): δ 7.77 (brs, 1H), 7.61 (d, J=7.5 Hz, 2H), 7.56 (dd, J=9.3, 2.4 Hz, 1H), 7.00 (d, J=7.5 Hz, 2H), 6.73 (d, J=9.3 Hz, 1H), 4.34 (s, 2H), 4.03 (dd, J=7.8, 4.8 Hz, 1H), 3.86-3.69 (m, 2H), 3.52-3.35 (m, 4H), 2.44 (m, 2H), 2.25-2.06 (m, 2H), 2.18 (s, 3H), 1.84-1.14 (m, 15H), 1.04-0.96 (m, 5H).

EXAMPLE 40(43)

(3S)-1-butyl-2,5-dioxo-3-cyclohexylmethyl-9-(4-(2-carboxy-1-ethynyl)phenylmethyl)-1,4,9-triazaspiro[5.5]undecane.hydrochloride

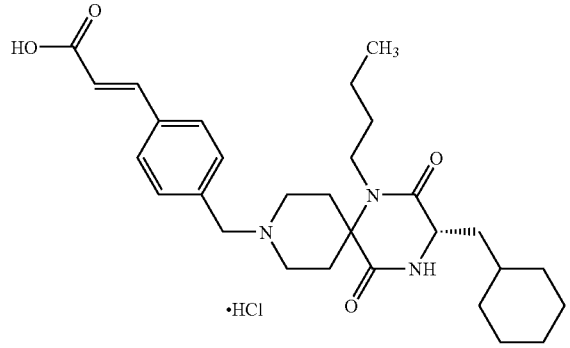

TLC: Rf 0.17 (chloroform:methanol=10:1); NMR (CD$_3$OD): δ 7.75 (d, J=8.4 Hz, 2H), 7.70 (d, J=15.9 Hz, 1H), 7.61 (d, J=8.4 Hz, 2H), 6.57 (d, J=15.9 Hz, 1H), 4.39 (s, 2H), 4.04 (dd, J=7.2, 4.8 Hz, 1H), 3.90-3.72 (m, 2H), 3.58-3.36 (m, 4H), 2.50-2.32 (m, 2H), 2.28-2.08 (m, 2H), 1.92-1.10 (m, 15H), 0.96 (t, J=7.2 Hz, 3H), 0.96 (m, 2H).

EXAMPLE 40(44)

(3S)-1-butyl-2,5-dioxo-3-cyclohexylmethyl-9-(4-(4-((1E)-2-carboxy-1-ethynyl)phenyloxy)phenylmethyl)-1,4,9-triazaspiro[5.5]undecane.hydrochloride

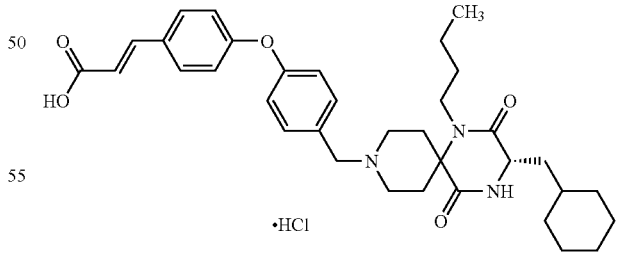

TLC: Rf 0.44 (chloroform:methanol=10:1); NMR (CD$_3$OD): δ 7.69-7.63 (m, 3H), 7.57 (d, J=8.7 Hz, 2H), 7.14 (d, J=8.7 Hz, 2H), 7.05 (d, J=8.4 Hz, 2H), 6.42 (d, J=15.9 Hz, 1H), 4.36 (s, 2H), 4.03 (dd, J=7.5, 4.5 Hz, 1H), 3.90-3.74 (m, 2H), 3.55-3.36 (m, 4H), 2.50-2.30 (m, 2H), 2.30-2.08 (m, 2H), 1.82-1.10 (m, 15H), 1.02-0.88 (m, 5H).

EXAMPLE 40(45)

(3S)-1-butyl-2,5-dioxo-3-cyclohexylmethyl-9-(4-(4-aminocarbonylphenyloxy)phenylmethyl)-1,4,9-triazaspiro[5.5]undecane.hydrochloride

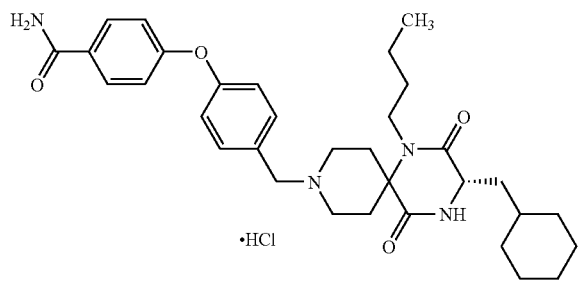

TLC: Rf 0.41 (chloroform:methanol=10:1); NMR (CD$_3$OD): δ 7.90 (d, J=9.0 Hz, 2H), 7.60 (d, J=9.0 Hz, 2H), 7.15 (d, J=9.0 Hz, 2H), 7.07 (d, J=9.0 Hz, 2H), 4.36 (s, 2H), 4.04 (dd, J=7.5, 4.5, Hz, 1H), 3.90-3.72 (m, 2H), 3.56-3.35 (m, 4H), 2.53-2.35 (m, 2H), 2.28-2.08 (m, 2H), 1.84-1.13 (m, 15H), 1.06-0.86 (m, 5H).

EXAMPLE 40(46)

(3S)-1-butyl-2,5-dioxo-3-cyclohexylmethyl-9-(4-(4-aminosulfonylphenyloxy)phenylmethyl)-1,4,9-triazaspiro[5.5]undecane.hydrochloride

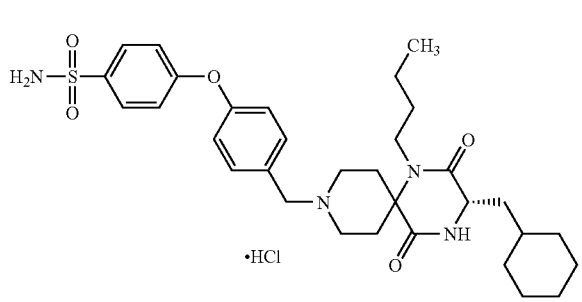

TLC: Rf 0.33 (chloroform:methanol=10:1); NMR (d$_6$-DMSO): δ 11.03 (brs, 1H), 8.42 (brs, 1H), 7.82 (d, J=8.7 Hz, 2H), 7.71 (d, J=8.7 Hz, 2H), 7.33 (brs, 2H), 7.16 (d, J=8.7 Hz, 4H), 4.38-4.23 (m, 2H), 3.91 (m, 1H), 3.61-3.23 (m, 6H), 2.58-2.30 (m, 2H), 2.18-1.91 (m, 2H), 1.76-1.00 (m, 15H), 0.98-0.71 (m, 5H).

EXAMPLE 40(47)

(3S)-1-butyl-2,5-dioxo-3-cyclohexylmethyl-9-(3,5-dimethyl-1-benzylpyrazol-4-ylmethyl)-1,4,9-triazaspiro[5.5]undecane.2 hydrochloride

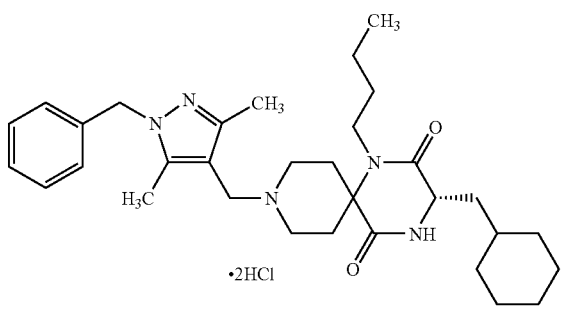

TLC: Rf 0.40 (chloroform:methanol=10:1); NMR (CD$_3$OD): δ 7.41-7.33 (m, 3H), 7.22-7.20 (m, 2H), 5.46 (s, 2H), 4.31 (s, 2H), 4.04 (dd, J=7.5, 4.5 Hz, 1H), 3.88-3.74 (m, 2H), 3.58-3.48 (m, 4H), 2.61 (m, 2H), 2.47 (s, 6H), 2.24-2.09 (m, 2H), 1.80-1.16 (m, 15H), 0.95 (t, J=7.2 Hz, 3H), 0.95 (m, 2H).

EXAMPLE 40(48)

(3S)-1-butyl-2,5-dioxo-3-cyclohexylmethyl-9-(3,5-dimethyl-1-(2,4-difluorophenyl)pyrazol-4-ylmethyl)-1,4,9-triazaspiro[5.5]undecane.2 hydrochloride

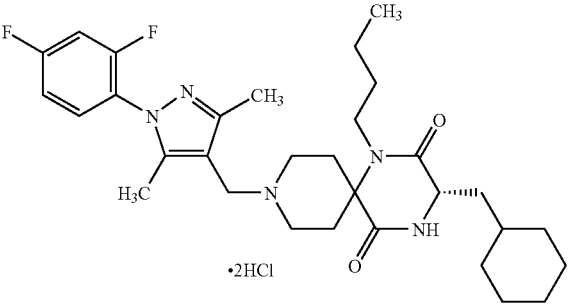

TLC: Rf 0.48 (chloroform:methanol=10:1); NMR (CD$_3$OD): δ 7.58-7.51 (m, 1H), 7.33-7.25 (m, 1H), 7.22-7.16 (m, 1H), 4.31 (s, 2H), 4.05 (dd, J=7.5, 4.5 Hz, 1H), 3.91-3.78 (m, 2H), 3.59 (m, 2H), 3.44 (m, 2H), 2.49 (m, 2H), 2.38 (s, 3H), 2.28 (s, 3H), 2.27-2.15 (m, 2H), 1.81-1.16 (m, 15H), 0.96 (t, J=7.0 Hz, 3H), 0.96 (m, 2H).

EXAMPLE 40(49)

(3S)-1-butyl-2,5-dioxo-3-cyclohexylmethyl-9-(4-(pyrrolidin-1-ylmethyl)phenylmethyl)-1,4,9-triazaspiro[5.5]undecane.2 hydrochloride

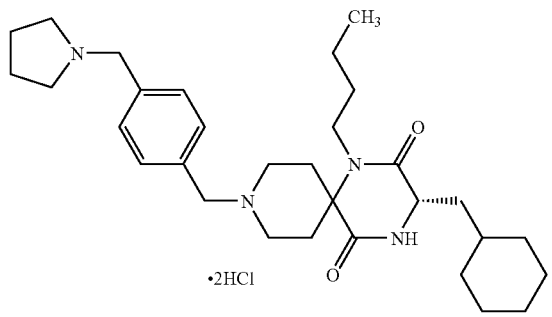

TLC: Rf 0.14 (chloroform:methanol=10:1); NMR (CD$_3$OD): δ 7.74 (d, J=8.4 Hz, 2H), 7.65 (d, J=8.4 Hz, 2H), 4.43 (s, 2H), 4.40 (s, 2H), 4.03 (dd, J=7.5, 4.5 Hz, 1H), 3.90-3.70 (m, 2H), 3.56-3.38 (m, 6H), 3.28-3.10 (m, 2H), 2.66-2.48 (m, 2H), 2.26-1.92 (m, 6H), 1.83-1.10 (m, 15H), 1.06-0.83 (m, 2H), 0.94 (t, J=7.2 Hz, 3H).

EXAMPLE 40(50)

(3S)-1-butyl-2,5-dioxo-3-cyclohexylmethyl-9-(3,5-dimethyl-1-(4-(morpholin-4-ylsulfonyl)phenyl)pyrazol-4-ylmethyl)-1,4,9-triazaspiro[5.5]undecane.2 hydrochloride

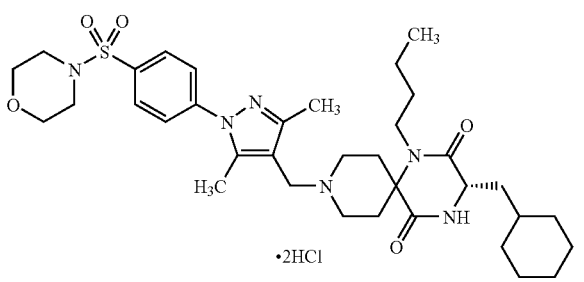

TLC: Rf 0.46 (chloroform:methanol=20:1); NMR (CD$_3$OD): δ 7.95 (d, J=8.7 Hz, 2H), 7.80 (d, J=8.7 Hz, 2H), 4.32 (s, 2H), 4.05 (dd, J=7.8, 4.5 Hz, 1H), 3.94-3.74 (m, 2H), 3.76-3.67 (m, 4H), 3.66-3.56 (m, 2H), 3.56-3.42 (m, 2H), 3.10-2.92 (m, 4H), 2.68-2.50 (m, 2H), 2.50 (s, 3H), 2.42 (s, 3H), 2.30-2.08 (m, 2H), 1.84-1.08 (m, 15H), 1.08-0.83 (m, 2H), 0.95 (t, J=7.2 Hz, 3H).

EXAMPLE 40(51)

(3S)-1-butyl-2,5-dioxo-3-cyclohexylmethyl-9-(4-(4-cyanophenyloxy)phenylmethyl)-1,4,9-triazaspiro[5.5]undecane.hydrochloride

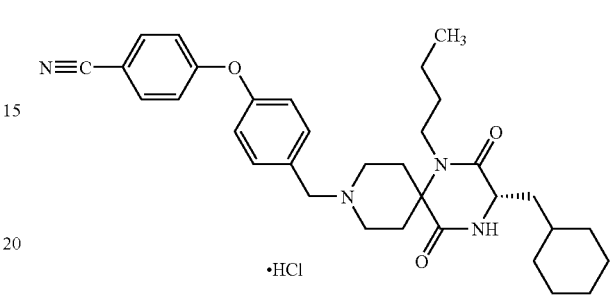

TLC: Rf 0.33 (chloroform:methanol=10:1); NMR (CD$_3$OD): δ 7.75 (d, J=9.3 Hz, 2H), 7.64 (d, J=9.0 Hz, 2H), 7.22 (d, J=9.0 Hz, 2H), 7.14 (d, J=9.3 Hz, 2H), 4.40 (s, 2H), 4.05 (dd, J=7.5, 4.8 Hz, 1H), 3.92-3.74 (m, 2H), 3.58-3.36 (m, 4H), 2.52-2.36 (m, 2H), 2.32-2.08 (m, 2H), 1.84-1.12 (m, 15H), 0.96 (t, J=7.2 Hz, 3H), 0.96 (m, 2H).

EXAMPLE 40(52)

(3S)-1-butyl-2,5-dioxo-3-cyclohexylmethyl-9-(3,5-dimethyl-1-(4-(N-(2-hydroxyethyl)-N-methylaminosulfonyl)phenyl)pyrazol-4-ylmethyl)-1,4,9-triazaspiro[5.5]undecane.2 hydrochloride

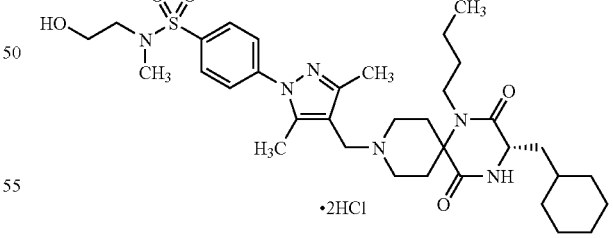

TLC: Rf 0.68 (chloroform:methanol=5:1); NMR (CD$_3$OD): δ 8.00 (d, J=8.7 Hz, 2H), 7.78 (d, J=8.7 Hz, 2H), 4.33 (s, 2H), 4.06 (dd, J=7.5, 4.5 Hz, 1H), 3.86-3.76 (m, 2H), 3.70 (t, J=5.7 Hz, 2H), 3.68-3.60 (m, 2H), 3.58-3.42 (m, 2H), 3.20 (t, J=5.7 Hz, 2H), 2.88 (s, 3H), 2.72-2.58 (m, 2H), 2.50 (s, 3H), 2.44 (s, 3H), 2.28-2.06 (m, 2H), 1.82-1.10 (m, 15H), 0.96 (t, J=7.2 Hz, 3H), 0.96 (m, 2H).

EXAMPLE 40(53)

(3S)-1-butyl-2,5-dioxo-3-cyclohexylmethyl-9-(3,5-dimethyl-1-(2-phenylethyl)pyrazol-4-ylmethyl)-1,4,9-triazaspiro[5.5]undecane.2 hydrochloride

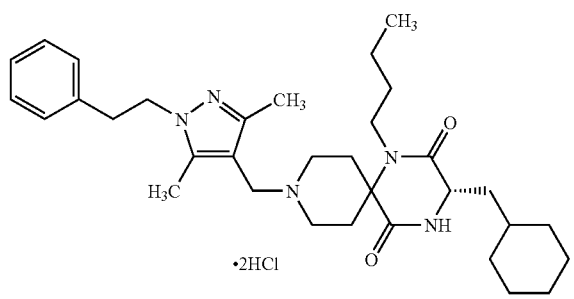

TLC: Rf 0.24 (chloroform:methanol=10:1); NMR (CD$_3$OD): δ 7.28-7.23 (m, 3H), 7.10-7.07 (m, 2H), 4.40 (t, J=6.6 Hz, 2H), 4.19 (s, 2H), 4.06 (dd, J=7.2, 4.8 Hz, 1H), 3.80-3.60 (m, 2H), 3.58-3.36 (m, 4H), 3.12 (t, J=6.6 Hz, 2H), 2.64-2.45 (m, 2H), 2.45 (s, 3H), 2.26-2.04 (m, 2H), 1.95 (s, 3H), 1.84-1.14 (m, 15H), 0.97 (t, J=7.5 Hz, 3H), 0.97 (m, 2H).

EXAMPLE 40(54)

(3S)-1-butyl-2,5-dioxo-3-cyclohexylmethyl-9-(4-(dimethylaminomethyl)phenylmethyl)-1,4,9-triazaspiro[5.5]undecane.2 hydrochloride

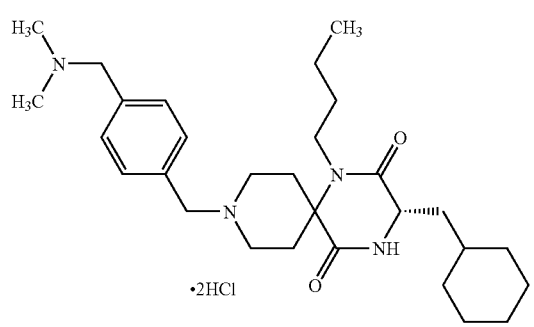

TLC: Rf 0.16 (chloroform:methanol=10:1); NMR (CD$_3$OD): δ 7.76 (d, J=8.1 Hz, 2H), 7.63 (d, J=8.1 Hz, 2H), 4.41 (s, 2H), 4.37 (s, 2H), 4.03 (dd, J=7.8, 5.1 Hz, 1H), 3.90-3.75 (m, 2H), 3.52-3.38 (m, 4H), 2.87 (s, 6H), 2.64-2.48 (m, 2H), 2.22-2.04 (m, 2H), 1.80-1.15 (m, 15H), 1.00-0.86 (m, 5H).

EXAMPLE 40(55)

(3S)-1-butyl-2,5-dioxo-3-cyclohexylmethyl-9-(3-(4-hydroxyphenyl)phenylmethyl)-1,4,9-triazaspiro[5.5]undecane.hydrochloride

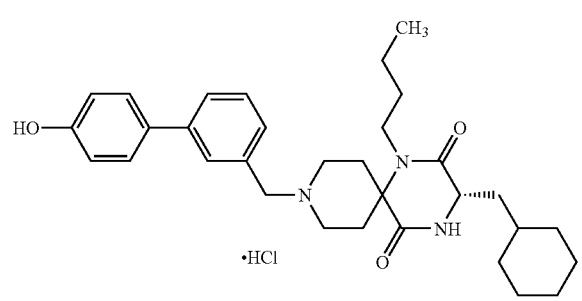

TLC: Rf 0.58 (chloroform:methanol=10:1); NMR (CD$_3$OD): δ 7.81 (s, 1H), 7.69 (d, J=7.5 Hz, 1H), 7.54 (d, J=9.0 Hz, 2H), 7.55-7.48 (m, 1H), 7.45 (d, J=7.5 Hz, 1H), 6.87 (d, J=9.0 Hz, 2H), 4.40 (s, 2H), 4.03 (dd, J=7.5, 4.5 Hz, 1H), 3.92-3.73 (m, 2H), 3.58-3.43 (m, 2H), 3.43-3.32 (m, 2H), 2.55-2.35 (m, 2H), 2.28-2.06 (m, 2H), 1.82-1.10 (m, 15H), 1.08-0.83 (m, 2H), 0.94 (t, J=7.2 Hz, 3H).

EXAMPLE 40(56)

(3S)-1-butyl-2,5-dioxo-3-cyclohexylmethyl-9-(3,5-dimethyl-1-(quinoxalin-2-yl)pyrazol-4-ylmethyl)-1,4,9-triazaspiro[5.5]undecane.2 hydrochloride

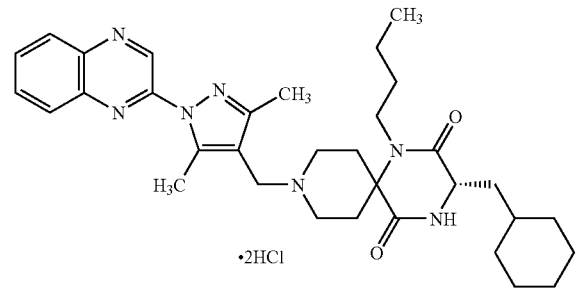

TLC: Rf 0.67 (chloroform:methanol=10:1); NMR (CD$_3$OD): δ 9.51 (s, 1H), 8.13 (d, J=8.0 Hz, 1H), 8.05 (d, J=8.0 Hz, 1H), 7.91-7.80 (m, 2H), 4.38 (s, 2H), 4.05 (dd, J=7.5, 4.5 Hz, 1H), 3.96-3.82 (m, 2H), 3.63 (m, 2H), 3.42 (m, 2H), 2.92 (s, 3H), 2.47 (s, 3H), 2.47 (m, 2H), 2.29-2.16 (m, 2H), 1.80-1.18 (m, 15H), 0.95 (t, J=7.2 Hz, 3H), 0.95 (m, 2H).

EXAMPLE 40(57)

(3S)-1-butyl-2,5-dioxo-3-cyclohexylmethyl-9-(4-(phenylcarbonyl)phenylmethyl)-1,4,9-triazaspiro[5.5]undecane.hydrochloride

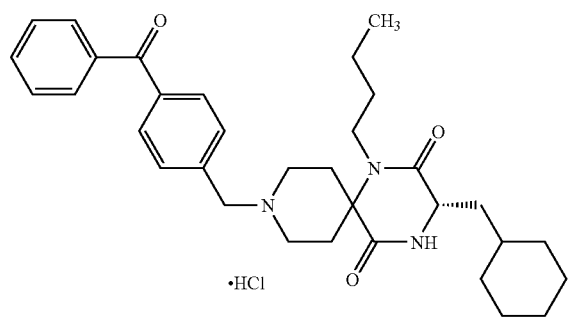

TLC: Rf 0.68 (chloroform:methanol=10:1); NMR (CD$_3$OD): δ 7.87 (d, J=8.4 Hz, 2H), 7.82-7.74 (m, 4H), 7.67 (t, J=8.4 Hz, 1H), 7.57-7.51 (m, 2H), 4.48 (s, 2H), 4.04 (dd, J=7.8, 4.8 Hz, 1H), 3.84-3.78 (m, 2H), 3.58-3.38 (m, 4H), 2.58-2.40 (m, 2H), 2.30-2.10 (m, 2H), 1.82-1.14 (m, 15H), 1.02-0.86 (m, 5H).

EXAMPLE 40(58)

(3S)-1-butyl-2,5-dioxo-3-cyclohexylmethyl-9-(3,5-dimethyl-1-(4-methylaminosulfonylphenyl)pyrazol-4-ylmethyl)-1,4,9-triazaspiro[5.5]undecane.2 hydrochloride

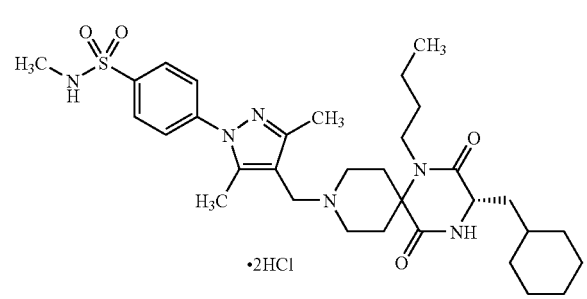

TLC: Rf 0.30 (chloroform:methanol=10:1); NMR (CD$_3$OD): δ 8.01 (d, J=8.7 Hz, 2H), 7.74 (d, J=8.7 Hz, 2H), 4.33 (s, 2H), 4.06 (dd, J=7.8, 4.5 Hz, 1H), 3.86-3.78 (m, 2H), 3.68-3.58 (m, 2H), 3.52-3.36 (m, 4H), 2.59 (s, 3H), 2.59-2.38 (m, 2H), 2.48 (s, 3H), 2.41 (s, 3H), 2.34-2.10 (m, 2H), 1.84-1.16 (m, 15H), 0.97 (t, J=7.2 Hz, 3H), 0.97 (m, 2H).

EXAMPLE 40(59)

(3S)-1-butyl-2,5-dioxo-3-cyclohexylmethyl-9-(1,3,5-trimethylpyrazol-4-ylmethyl)-1,4,9-triazaspiro[5.5]undecane.2 hydrochloride

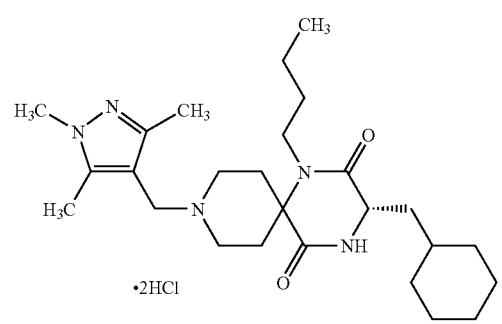

TLC: Rf 0.43 (chloroform:methanol=10:1); NMR (CD$_3$OD): δ 4.28 (s, 2H), 4.03 (dd, J=7.8, 4.5 Hz, 1H), 3.87 (s, 3H), 3.87-3.69 (m, 2H), 3.61-3.43 (m, 4H), 2.69-2.50 (m, 2H), 2.46 (s, 3H), 2.44 (s, 3H), 2.25-2.06 (m, 2H), 1.83-1.12 (m, 15H), 1.05-0.86 (m, 5H).

EXAMPLE 40(60)

(3S)-1-butyl-2,5-dioxo-3-cyclohexylmethyl-9-(4-(morpholin-4-ylmethyl)phenylmethyl)-1,4,9-triazaspiro[5.5]undecane.2 hydrochloride

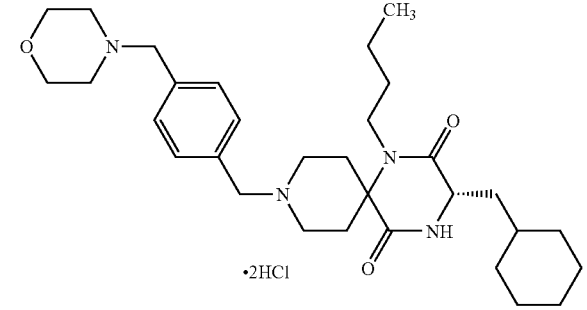

TLC: Rf 0.56 (chloroform:methanol=10:1); NMR (CD$_3$OD): δ 7.74 (d, J=8.4 Hz, 2H), 7.66 (d, J=8.4 Hz, 2H), 4.40 (s, 4H), 4.03 (dd, J=7.5, 4.5 Hz, 1H), 4.00-3.70 (m, 6H), 3.54-3.40 (m, 4H), 3.35-3.18 (m, 4H), 2.63-2.47 (m, 2H), 2.24-2.02 (m, 2H), 1.83-1.12 (m, 15H), 1.06-0.85 (m, 5H).

EXAMPLE 40(61)

(3S)-1-butyl-2,5-dioxo-3-cyclohexylmethyl-9-(4-(3-methoxyphenyloxy)phenylmethyl)-1,4,9-triazaspiro[5.5]undecane.hydrochloride

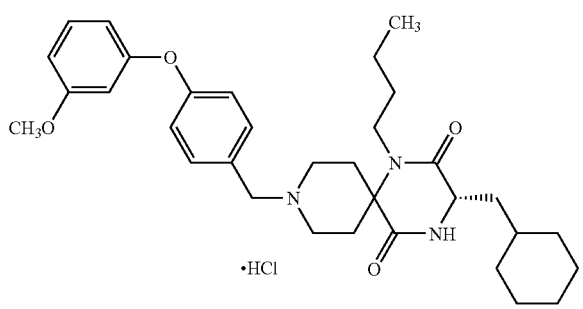

TLC: Rf 0.57 (chloroform:methanol=10:1); NMR (CD$_3$OD): δ 7.53 (d, J=8.7 Hz, 2H), 7.28 (t, J=8.4 Hz, 1H), 7.07 (d, J=8.7 Hz, 2H), 6.75 (ddd, J=8.4, 2.4, 1.0 Hz, 1H), 6.61-6.57 (m, 2H), 4.34 (s, 2H), 4.04 (dd, J=7.5, 4.5 Hz, 1H), 3.85-3.55 (m, 2H), 3.77 (s, 3H), 3.53-3.47 (m, 2H), 3.40 (m, 2H), 2.50-2.35 (m, 2H), 2.25-2.11 (m, 2H), 1.80-1.23 (m, 15H), 0.95 (t, J=7.2 Hz, 3H), 0.95 (m, 2H).

EXAMPLE 40(62)

(3S)-1-butyl-2,5-dioxo-3-cyclohexylmethyl-9-(4-(4-methylpiperazin-1-ylmethyl)phenylmethyl)-1,4,9-triazaspiro[5.5]undecane.3 hydrochloride

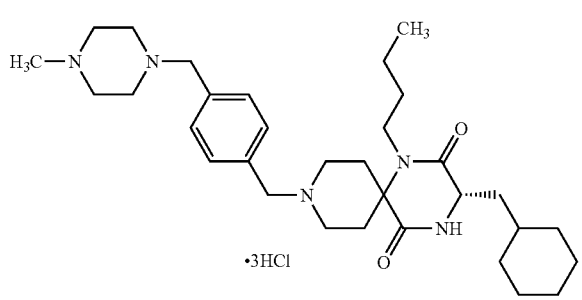

TLC: Rf 0.69 (chloroform:methanol=5:1); NMR (CD$_3$OD): δ 7.74 (s, 4H), 4.54 (s, 2H), 4.41 (s, 2H), 4.03 (dd, J=7.5, 4.5 Hz, 1H), 3.87-3.42 (m, 14H), 3.00 (s, 3H), 2.61-2.46 (m, 2H), 2.21-2.07 (m, 2H), 1.79-1.15 (m, 15H), 1.02-0.92 (m, 2H), 0.94 (t, J=7.2 Hz, 3H).

EXAMPLE 40(63)

(3S)-1-butyl-2,5-dioxo-3-cyclohexylmethyl-9-(4-(pyridin-1-oxido-3-yloxy)phenylmethyl)-1,4,9-triazaspiro[5.5]undecane.hydrochloride

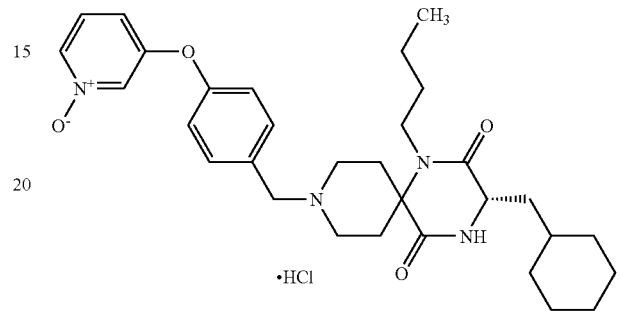

TLC: Rf 0.42 (chloroform:methanol=9:1); NMR (CD$_3$OD): δ 8.45 (t, J=1.8 Hz, 1H), 8.37 (brd, J=6.3 Hz, 1H), 7.71 (dd, J=8.4, 6.3 Hz, 1H), 7.72 (d, J=8.7 Hz, 2H), 7.59 (brdd, J=8.4, 1.8 Hz, 1H), 7.31 (d, J=8.7 Hz, 2H), 4.40 (s, 2H), 4.04 (dd, J=7.8 Hz, 1H), 3.90-3.74 (m, 2H), 3.57-3.40 (m, 4H), 2.58-2.40 (m, 2H), 2.28-2.08 (m, 2H), 1.82-1.14 (m, 15H), 1.04-0.90 (m, 5H).

EXAMPLE 40(64)

(3S)-1-butyl-2,5-dioxo-3-cyclohexylmethyl-9-(4-phenylsulfonylphenylmethyl)-1,4,9-triazaspiro[5.5]undecane.hydrochloride

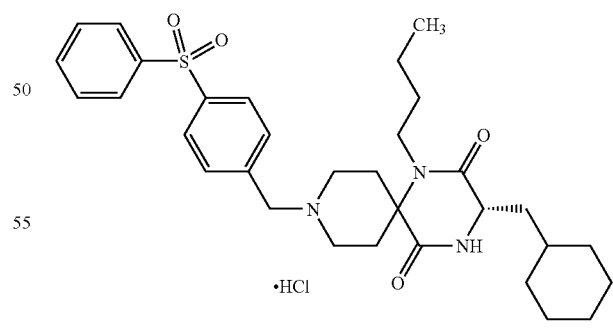

TLC: Rf 0.77 (ethyl acetate:methanol=9:1); NMR (CD$_3$OD): δ 8.08 (d, J=8.4 Hz, 2H), 8.02-7.96 (m, 2H), 7.80 (d, J=8.4 Hz, 2H), 7.70-7.55 (m, 3H), 4.43 (s, 2H), 4.02 (dd, J=7.8, 4.8 Hz, 1H), 3.89-3.73 (m, 2H), 3.49-3.34 (m, 4H), 2.48-2.33 (m, 2H), 2.23-2.04 (m, 2H), 1.82-1.14 (m, 15H), 1.03-0.85 (m, 5H).

EXAMPLE 40(65)

(3S)-1-butyl-2,5-dioxo-3-cyclohexylmethyl-9-(3,5-dimethyl-1-cyclohexylpyrazol-4-ylmethyl)-1,4,9-triazaspiro[5.5]undecane.2 hydrochloide

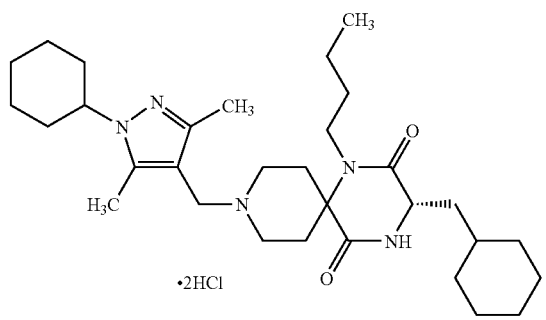

TLC: Rf 0.32 (ethyl acetate:methanol=9:1); NMR (CD$_3$OD): δ 4.42-4.28 (m, 1H), 4.28 (s, 2H), 4.04 (dd, J=7.5, 4.5 Hz, 1H), 3.90-3.72 (m, 2H), 3.60-3.43 (m, 4H), 2.68-2.50 (m, 2H), 2.50 (s, 3H), 2.46 (s, 3H), 2.25-2.06 (m, 2H), 2.04-1.15 (m, 25H), 1.05-0.89 (m, 5H).

EXAMPLE 40(66)

(3S)-1-butyl-2,5-dioxo-3-cyclohexylmethyl-9-(4-(3-carboxyphenyloxy)phenylmethyl)-1,4,9-triazaspiro[5.5]undecane.hydrochloride

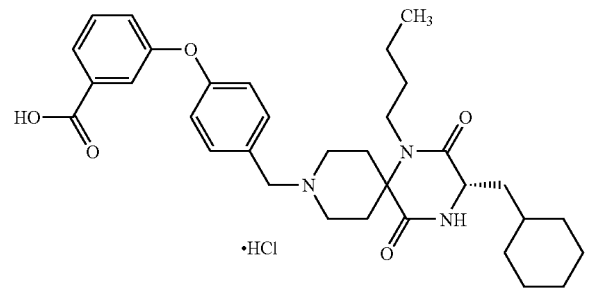

TLC: Rf 0.16 (ethyl acetate:methanol=9:1); NMR (CD$_3$OD): δ 7.83 (ddd, J=7.8, 1.5, 1.2 Hz, 1H), 7.60 (dd, J=2.4, 1.5 Hz, 1H), 7.57 (d, J=8.7 Hz, 2H), 7.51 (t, J=7.8 Hz, 1H), 7.29 (ddd, J=7.8, 2.4, 1.2 Hz, 1H), 7.12 (d, J=8.7 Hz, 2H), 4.35 (s, 2H), 4.04 (dd, J=7.5, 4.5 Hz, 1H), 3.90-3.74 (m, 2H), 3.58-3.35 (m, 4H), 2.49-2.34 (m, 2H), 2.28-2.09 (m, 2H), 1.93-1.10 (m, 15H), 1.07-0.85 (m, 5H).

EXAMPLE 40(67)

(3S)-1-butyl-2,5-dioxo-3-cyclohexylmethyl-9-(4-(piperidin-1-ylmethyl)phenylmethyl)-1,4,9-triazaspiro[5.5]undecane.2 hydrochloride

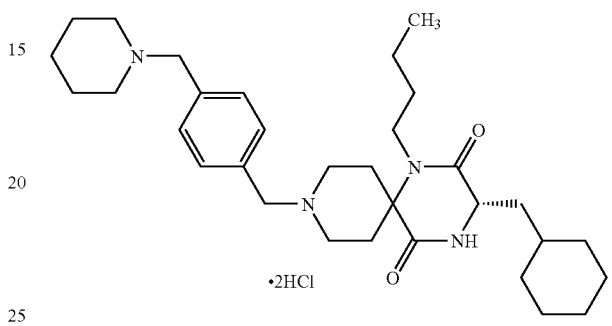

TLC: Rf 0.56 (chloroform:methanol=9:1); NMR (CD$_3$OD): δ 7.75 (d, J=8.4 Hz, 2H), 7.64 (d, J=8.4 Hz, 2H), 4.40 (s, 2H), 4.34 (s, 2H), 4.03 (dd, J=7.8, 4.8 Hz, 1H), 3.90-3.72 (m, 2H), 3.53-3.38 (m, 6H), 3.05-2.91 (m, 2H), 2.66-2.49 (m, 2H), 2.24-2.04 (m, 2H), 2.00-1.13 (m, 21H), 1.04-0.86 (m, 5H).

EXAMPLE 40(68)

(3S)-1-butyl-2,5-dioxo-3-cyclohexylmethyl-9-(3,5-dimethyl-1-(4-(pyrrolidin-1-ylsulfonyl)phenyl)pyrazol-4-ylmethyl)-1,4,9-triazaspiro[5.5]undecane.2 hydrochloride

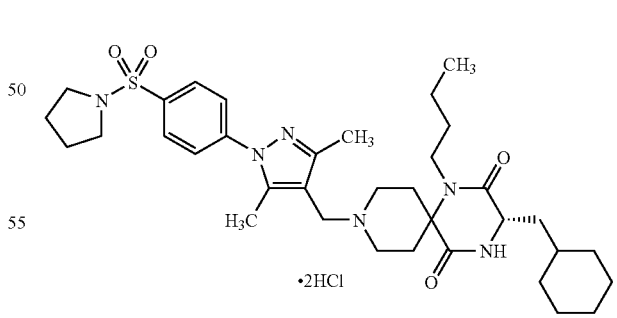

TLC: Rf 0.40 (ethyl acetate:methanol=9:1); NMR (CD$_3$OD): δ 8.01 (d, J=8.7 Hz, 2H), 7.76 (d, J=8.7 Hz, 2H), 4.32 (s, 2H), 4.05 (dd, J=7.5, 4.5 Hz, 1H), 3.94-3.75 (m, 2H), 3.66-3.56 (m, 2H), 3.49-3.41 (m, 2H), 3.32-3.25 (m, 4H), 2.60-2.46 (m, 2H), 2.48 (s, 3H), 2.40 (s, 3H), 2.30-2.11 (m, 2H), 1.83-1.14 (m, 19H), 1.05-0.87 (m, 5H).

EXAMPLE 40(69)

(3S)-1-butyl-2,5-dioxo-3-cyclohexylmethyl-9-(2,3-dihydrobenzofuran-5-ylmethyl)-1,4,9-triazaspiro[5.5]undecane.hydrochloride

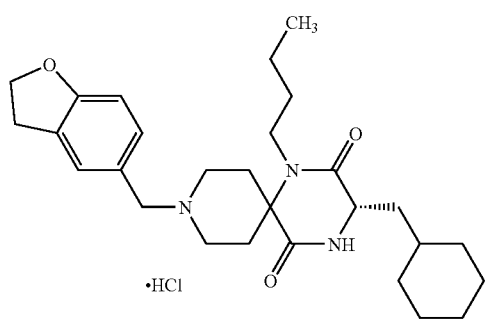

TLC: Rf 0.61 (ethyl acetate:methanol=9:1); NMR (CD₃OD): δ 7.39 (d, J=1.8 Hz, 1H), 7.26 (dd, J=8.4, 1.8 Hz, 1H), 6.81 (d, J=8.4 Hz, 1H), 4.59 (t, J=8.7 Hz, 2H), 4.26 (s, 2H), 4.04 (dd, J=7.8, 4.8 Hz, 1H), 3.84-3.67 (m, 2H), 3.54-3.34 (m, 4H), 3.25 (t, J=8.7 Hz, 2H), 2.48-2.31 (m, 2H), 2.26-2.07 (m, 2H), 1.83-1.14 (m, 15H), 1.04-0.87 (m, 5H).

EXAMPLE 40(70)

(3S)-1-butyl-2,5-dioxo-3-cyclohexylmethyl-9-(4-(4-carboxyphenyloxy)phenylmethyl)-1,4,9-triazaspiro[5.5]undecane.hydrochloride

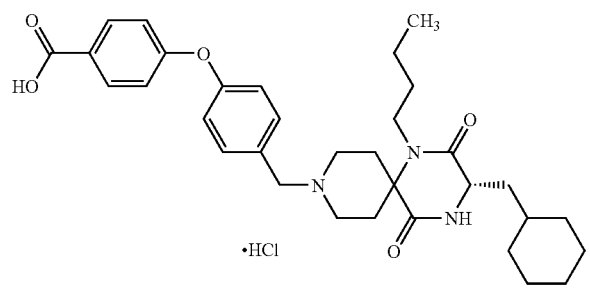

TLC: Rf 0.55 (ethyl acetate:methanol=9:1); NMR (CD₃OD): δ 8.04 (d, J=8.7 Hz, 2H), 7.61 (d, J=8.7 Hz, 2H), 7.18 (d, J=8.7 Hz, 2H), 7.07 (d, J=8.7 Hz, 2H), 4.38 (s, 2H), 4.05 (dd, J=7.8, 4.8 Hz, 1H), 3.91-3.74 (m, 2H), 3.57-3.35 (m, 4H), 2.50-2.33 (m, 2H), 2.29-2.09 (m, 2H), 1.84-1.14 (m, 15H), 1.05-0.86 (m, 5H).

EXAMPLE 40(71)

(3S)-1-butyl-2,5-dioxo-3-cyclohexylmethyl-9-(3,5-dimethyl-1-(4-(2-hydroxyethylaminosulfonyl)phenyl)pyrazol-4-ylmethyl)-1,4,9-triazaspiro[5.5]undecane.2 hydrochloride

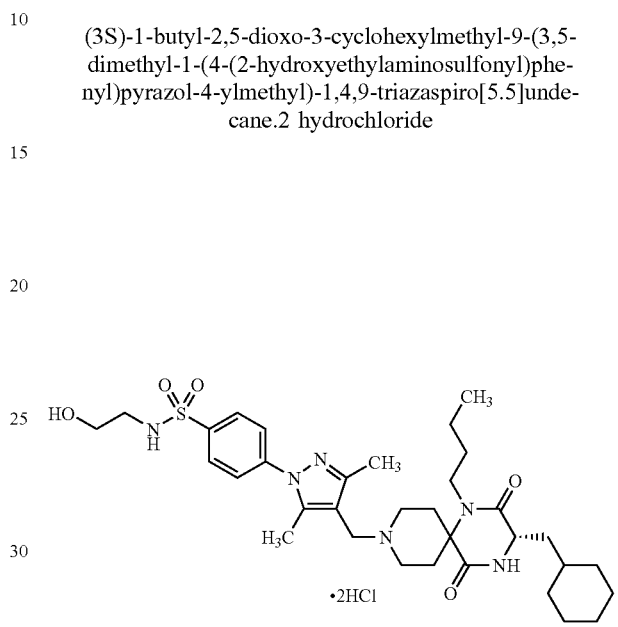

TLC: Rf 0.38 (chloroform:methanol=10:1); NMR (CD₃OD): δ 8.03 (d, J=8.7 Hz, 2H), 7.72 (d, J=8.7 Hz, 2H), 4.31 (s, 2H), 4.05 (dd, J=7.5, 4.5 Hz, 1H), 3.94-3.74 (m, 2H), 3.66-3.56 (m, 2H), 3.56 (t, J=5.7 Hz, 2H), 3.51-3.41 (m, 2H), 3.01 (t, J=5.7 Hz, 2H), 2.63-2.43 (m, 2H), 2.47 (s, 3H), 2.40 (s, 3H), 2.32-2.10 (m, 2H), 1.93-1.10 (m, 15H), 1.06-0.93 (m, 2H), 0.96 (t, J=7.2 Hz, 3H).

EXAMPLE 40(72)

(3S)-1-butyl-2,5-dioxo-3-cyclohexylmethyl-9-(3,5-dimethyl-1-(4-(2-dimethylaminoethylaminosulfonyl)phenyl)pyrazol-4-ylmethyl)-1,4,9-triazaspiro[5.5]undecane. 3 hydrochloride

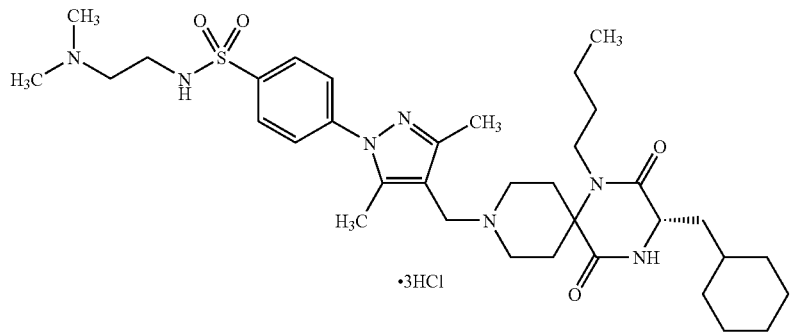

TLC: Rf 0.13 (chloroform:methanol=10:1); NMR (CD₃OD): δ 8.07 (d, J=8.7 Hz, 2H), 7.79 (d, J=8.7 Hz, 2H), 4.31 (s, 2H), 4.04 (dd, J=7.5, 4.2 Hz, 1H), 3.82-3.76 (m, 2H), 3.68-3.48 (m, 4H), 3.34-3.24 (m, 4H), 2.95 (s, 6H), 2.76-2.52 (m, 2H), 2.50 (s, 3H), 2.43 (s, 3H), 2.25-2.08 (m, 2H), 1.82-1.14 (m, 15H), 1.02-0.88 (m, 5H).

EXAMPLE 40(73)

(3S)-1-butyl-2,5-dioxo-3-cyclohexylmethyl-9-(4-(1-hydroxy-1-phenylmethyl)phenylmethyl)-1,4,9-triazaspiro[5.5]undecane.hydrochloride

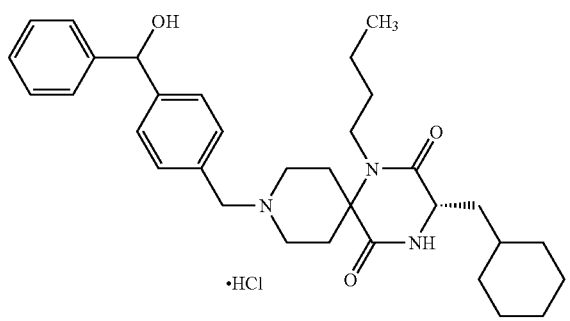

TLC: Rf 0.30 (chloroform:methanol=10:1); NMR (CD₃OD): δ 7.62-7.18 (m, 9H), 5.82 (s, 1H), 4.34 (s, 2H), 4.03 (dd, J=7.5, 4.5 Hz, 1H), 3.88-3.72 (m, 2H), 3.58-3.30 (m, 4H), 2.42-2.04 (m, 4H), 1.82-1.24 (m, 15H), 0.94 (t, J=7.2 Hz, 3H), 0.94 (m, 2H).

EXAMPLE 40(74)

(3S)-1-butyl-2,5-dioxo-3-cyclohexylmethyl-9-(4-(carboxymethyloxy)phenylmethyl)-1,4,9-triazaspiro[5.5]undecane.hydrochloride

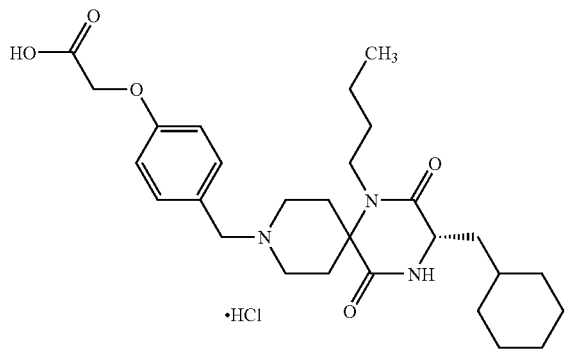

TLC: Rf 0.30 (chloroform:methanol=10:1); NMR (CD₃OD): δ 7.47 (d, J=8.7 Hz, 2H), 7.04 (d, J=8.7 Hz, 2H), 4.70 (s, 2H), 4.29 (s, 2H), 4.03 (dd, J=7.5, 4.5 Hz, 1H), 3.86-3.69 (m, 2H), 3.54-3.33 (m, 4H), 2.44-2.28 (m, 2H), 2.26-2.06 (m, 2H), 1.83-1.12 (m, 15H), 1.04-0.85 (m, 5H).

EXAMPLE 40(75)

(3S)-1-butyl-2,5-dioxo-3-cyclohexylmethyl-9-(4-(4-hydroxypiperidin-1-ylmethyl)phenylmethyl)-1,4,9-triazaspiro[5.5]undecane.2 hydrochlride

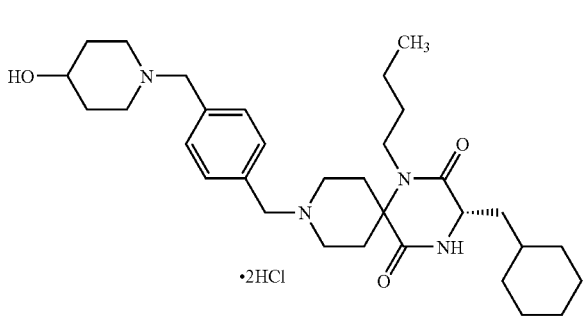

TLC: Rf 0.17 (chloroform:methanol=10:1); NMR (CD₃OD): δ 7.76 (d, J=7.8 Hz, 2H), 7.70-7.61 (m, 2H), 4.40 (s, 2H), 4.38-4.32 (m, 2H), 4.10-4.05 (m, 1H), 4.03 (dd, J=7.5, 4.5 Hz, 1H), 3.90-3.68 (m, 2H), 3.56-3.40 (m, 4H), 3.18-3.00 (m, 1H), 2.70-2.48 (m, 2H), 2.23-1.82 (m, 5H), 1.82-1.10 (m, 19H), 1.06-0.83 (m, 2H), 0.94 (t, J=7.2 Hz, 3H).

EXAMPLE 40(76)

(3S)-1-butyl-2,5-dioxo-3-cyclohexylmethyl-9-(4-(3-carboxyphenylmethyloxy)phenylmethyl)-1,4,9-triazaspiro[5.5]undecane.hydrochloride

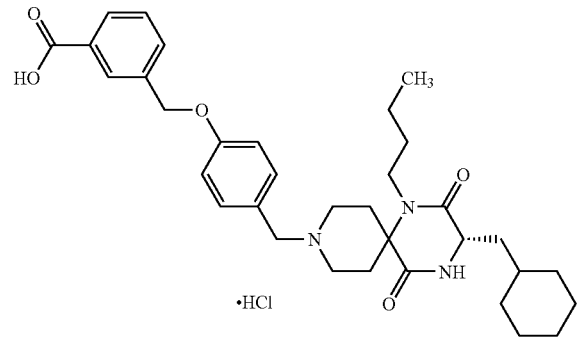

TLC: Rf 0.57 (chloroform:methanol=5:1); NMR (CD₃OD): δ 8.10 (s, 1H), 7.98 (d, J=7.8 Hz, 1H), 7.68 (d, J=7.8 Hz, 1H), 7.50 (t, J=7.8 Hz, 1H), 7.46 (d, J=8.7 Hz, 2H), 7.13 (d, J=8.7 Hz, 2H), 5.22 (s, 2H), 4.28 (s, 2H), 4.04 (dd, J=7.8, 4.8 Hz, 1H), 3.84-3.68 (m, 2H), 3.52-3.32 (m, 4H), 2.42-2.08 (m, 4H), 1.82-1.16 (m, 15H), 0.95 (t, J=7.8 Hz, 3H), 0.95 (m, 2H).

EXAMPLE 40(77)

(3S)-1-butyl-2,5-dioxo-3-cyclohexylmethyl-9-(4-(1,4-benzodioxan-6-yloxy)phenylmethyl)-1,4,9-triazaspiro[5.5]undecane.hydrochloride

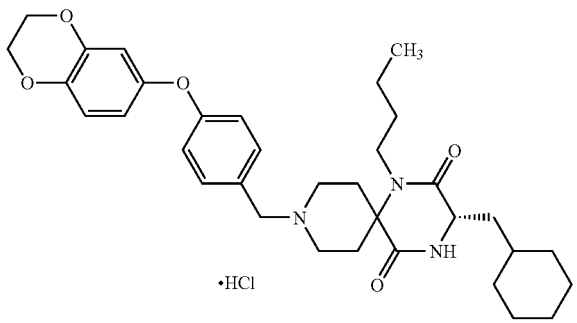

TLC: Rf 0.41 (chloroform:methanol=10:1); NMR (CD$_3$OD): δ 7.48 (d, J=9.0 Hz, 2H), 7.02 (d, J=9.0 Hz, 2H), 6.86 (m, 1H), 6.55-6.51 (m, 2H), 4.31 (s, 2H), 4.24 (s, 4H), 4.05 (dd, J=7.5, 4.5 Hz, 1H), 3.86-3.70 (m, 2H), 3.58-3.36 (m, 4H), 2.42-2.08 (m, 4H), 1.82-1.12 (m, 15H), 0.96 (t, J=7.2 Hz, 3H), 0.96 (m, 2H).

EXAMPLE 40(78)

(3S)-1-butyl-2,5-dioxo-3-cyclohexylmethyl-9-(3-(3-hydroxyphenyl)phenylmethyl)-1,4,9-triazaspiro[5.5]undecane.hydrochloride

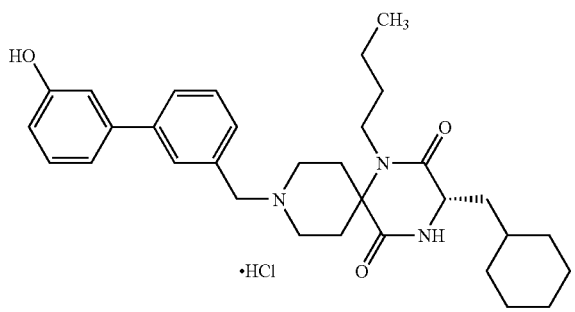

TLC: Rf 0.24 (chloroform:methanol=10:1); NMR (CD$_3$OD): δ 7.81 (s, 1H), 7.74 (m, 1H), 7.60-7.50 (m, 2H), 7.28 (m, 1H), 7.15-7.08 (m, 2H), 6.82 (m, 1H), 4.43 (s, 2H), 4.04 (dd, J=7.5, 4.5 Hz, 1H), 3.86-3.78 (m, 2H), 3.58-3.34 (m, 4H), 2.48-2.08 (m, 4H), 1.84-1.12 (m, 15H), 0.95 (t, J=7.2 Hz, 3H), 0.95 (m, 2H).

EXAMPLE 40(79)

(3S)-1-butyl-2,5-dioxo-3-cyclohexylmethyl-9-(4-(methylsulfonylamino)phenylmethyl)-1,4,9-triazaspiro[5.5]undecane.hydrochloride

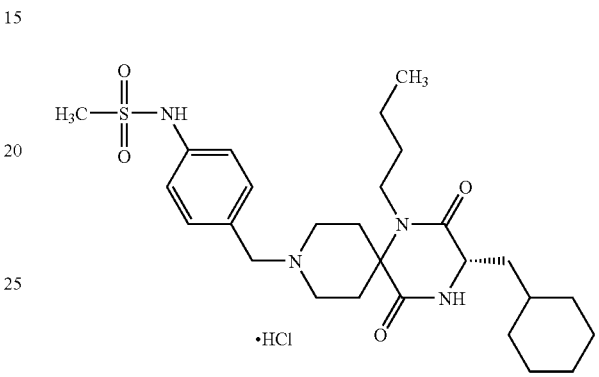

TLC: Rf 0.40 (chloroform:methanol=10:1); NMR (CD$_3$OD): δ 7.53 (d, J=8.4 Hz, 2H), 7.34 (d, J=8.4 Hz, 2H), 4.32 (s, 2H), 4.03 (dd, J=7.8, 4.8 Hz, 1H), 3.86-3.72 (m, 2H), 3.52-3.34 (m, 4H), 3.01 (s, 3H), 2.50-2.32 (m, 2H), 2.24-2.06 (m, 2H), 1.82-1.10 (m, 15H), 1.02-0.86 (m, 5H).

EXAMPLE 40(80)

(3S)-1-butyl-2,5-dioxo-3-cyclohexylmethyl-9-(6-(4-methoxyphenyl)pyridin-3-ylmethyl)-1,4,9-triazaspiro[5.5]undecane.2 hydrochloride

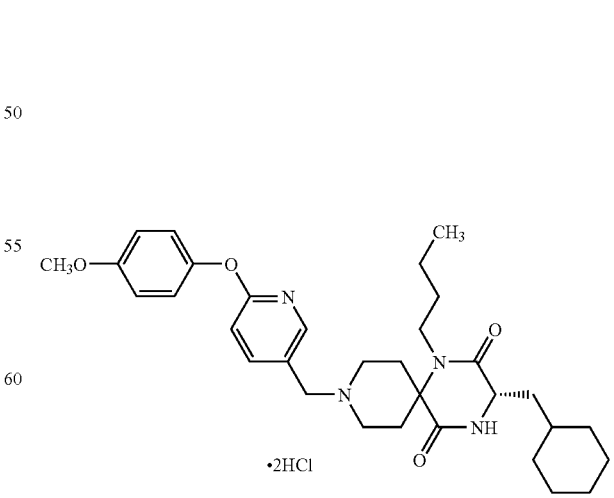

EXAMPLE 40(81)

(3S)-1-butyl-2,5-dioxo-3-cyclohexylmethyl-9-(4-(4-methylaminocarbonylphenyloxy)phenylmethyl)-1,4,9-triazaspiro[5.5]undecane.hydrochloride

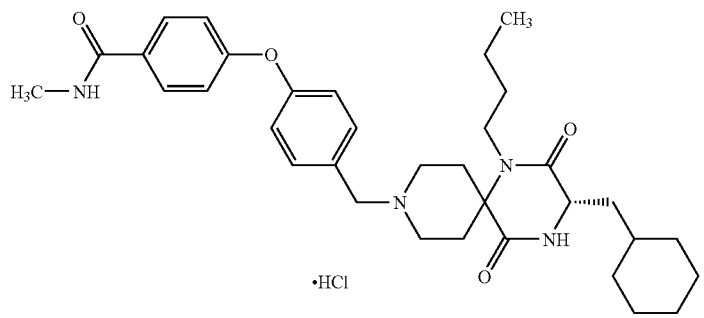

TLC: Rf 0.46 (chloroform:methanol=10:1); NMR (CD$_3$OD): δ 8.39 (br d, J=4.5 Hz, 1H), 7.84 (d, J=9.0 Hz, 2H), 7.58 (d, J=8.4 Hz, 2H), 7.15 (d, J=8.4 Hz, 2H), 7.07 (d, J=9.0 Hz, 2H), 4.35 (s, 2H), 4.04 (m, 1H), 3.85-3.74 (m, 2H), 3.53-3.38 (m, 4H), 2.91 (d, J=4.5 Hz, 3H), 2.55-2.30 (m, 2H), 2.30-2.10 (m, 2H), 1.80-1.10 (m, 15H), 1.10-0.90 (m, 2H), 0.95 (t, J=7.2 Hz, 3H).

EXAMPLE 40(82)

(3S)-1-butyl-2,5-dioxo-3-cyclohexylmethyl-9-(4-(4-chlorophenyloxy)phenylmethyl)-1,4,9-triazaspiro[5.5]undecane.hydrochloride

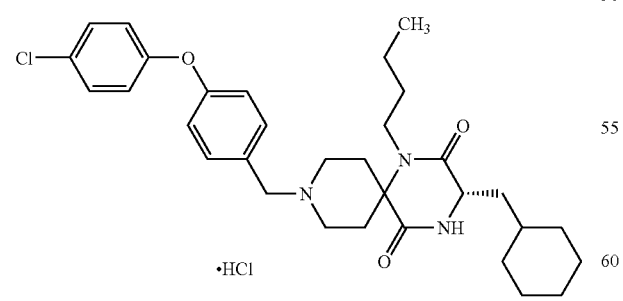

TLC: Rf 0.76 (chloroform:methanol=10:1); NMR (CD$_3$OD): δ 7.52 (d, J=9.0 Hz, 2H), 7.38 (d, J=9.0 Hz, 2H), 7.09 (d, J=9.0 Hz, 2H), 7.02 (d, J=9.0 Hz, 2H), 4.32 (s, 2H), 4.04 (m, 1H), 3.90-3.70 (m, 2H), 3.60-3.30 (m, 4H), 2.50-2.10 (m, 4H), 1.90-1.10 (m, 15H), 1.10-0.90 (m, 2H), 0.95 (t, J=7.5 Hz, 3H).

EXAMPLE 40(83)

(3S)-1-butyl-2,5-dioxo-3-cyclohexylmethyl-9-(4-bis(methylsulfonyl)aminophenylmethyl)-1,4,9-triazaspiro[5.5]undecane.hydrochloride

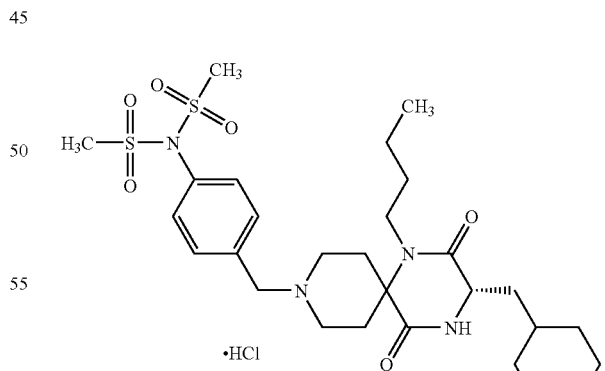

TLC: Rf 0.60 (chloroform:methanol=5:1); NMR (CD$_3$OD): δ 7.69 (d, J=8.4 Hz, 2H), 7.60 (d, J=8.4 Hz, 2H), 4.41 (s, 2H), 4.05 (dd, J=7.8, 4.8 Hz, 1H), 3.92-3.70 (m, 2H), 3.56-3.36 (m, 4H), 3.47 (s, 6H), 2.46-2.08 (m, 4H), 1.84-1.16 (m, 15H), 0.96 (t, J=7.5 Hz, 3H), 0.96 (m, 2H).

EXAMPLE 40(84)

(3S)-1-butyl-2,5-dioxo-3-cyclohexylmethyl-9-(3-(4-carboxyphenyl)phenylmethyl)-1,4,9-triazaspiro[5.5]undecane.hydrochloride

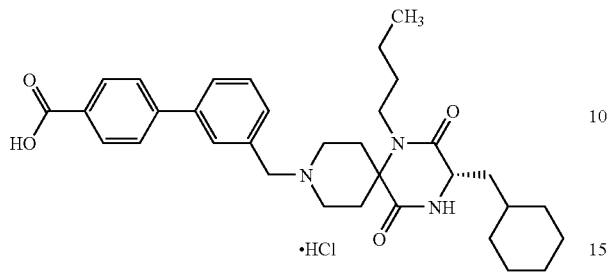

TLC: Rf 0.60 (chloroform:methanol=5:1); NMR (CD$_3$OD): δ 8.13 (d, J=9.0 Hz, 2H), 7.95 (s, 1H), 7.84 (m, 1H), 7.82 (d, J=9.0 Hz, 2H), 7.66-7.61 (m, 2H), 4.46 (s, 2H), 4.04 (dd, J=7.5, 4.5 Hz, 1H), 3.96-3.78 (m, 2H), 3.62-3.36 (m, 4H), 2.54-2.32 (m, 2H), 2.28-2.08 (m, 2H), 1.82-1.08 (m, 15H), 0.95 (t, J=7.2 Hz, 3H), 0.95 (m, 2H).

EXAMPLE 40(85)

(3S)-1-butyl-2,5-dioxo-3-cyclohexylmethyl-9-(4-(phenylaminocarbonyl)phenylmethyl)-1,4,9-triaza-spiro[5.5]undecane.hydrochloride

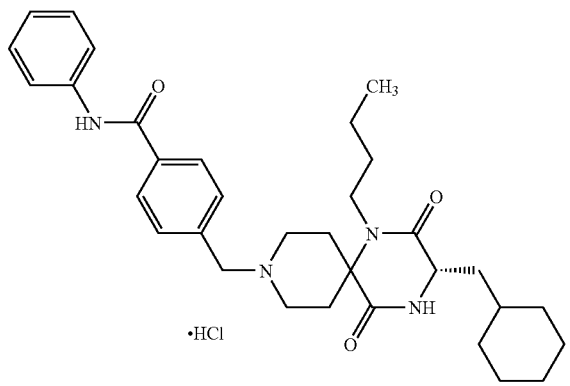

TLC: Rf 0.25 (chloroform:methanol=10:1); NMR (CD$_3$OD): δ 8.07 (d, J=8.1 Hz, 2H), 7.73-7.67 (m, 2H), 7.71 (d, J=8.1 Hz, 2H), 7.38 (t, J=7.5 Hz, 2H), 7.17 (t, J=7.5 Hz, 1H), 4.45 (s, 2H), 4.05 (dd, J=7.8, 4.8 Hz, 1H), 3.92-3.72 (m, 2H), 3.58-3.36 (m, 4H), 2.50-2.08 (m, 4H), 1.84-1.08 (m, 15H), 0.96 (t, J=7.8 Hz, 3H), 0.96 (m, 2H).

EXAMPLE 40(86)

(3S)-1-butyl-2,5-dioxo-3-cyclohexylmethyl-9-(4-(4-methylthiophenyloxy)phenylmethyl)-1,4,9-triaza-spiro[5.5]undecane.hydrochloride

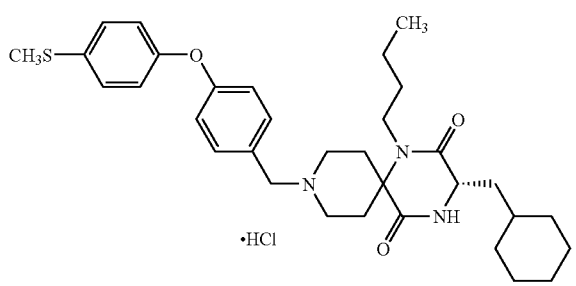

TLC: Rf 0.48 (chloroform:methanol=10:1); NMR (CD$_3$OD): δ 7.54 (d, J=8.7 Hz, 2H), 7.33 (d, J=8.7 Hz, 2H), 7.06 (d, J=8.7 Hz, 2H), 7.00 (d, J=8.7 Hz, 2H), 4.34 (s, 2H), 4.05 (dd, J=7.5, 4.5 Hz, 1H), 3.86-3.70 (m, 2H), 3.56-3.36 (m, 4H), 2.48 (s, 3H), 2.48-2.32 (m, 2H), 2.28-2.08 (m, 2H), 1.82-1.14 (m, 15H), 0.96 (t, J=7.2 Hz, 3H), 0.96 (m, 2H).

EXAMPLE 40(87)

(3S)-1-butyl-2,5-dioxo-3-cyclohexylmethyl-9-(4-(4-(2-dimethylaminoethylaminocarbonyl)phenyloxy)phenylmethyl)-1,4,9-triazaspiro[5.5]undecane.hydrochloride

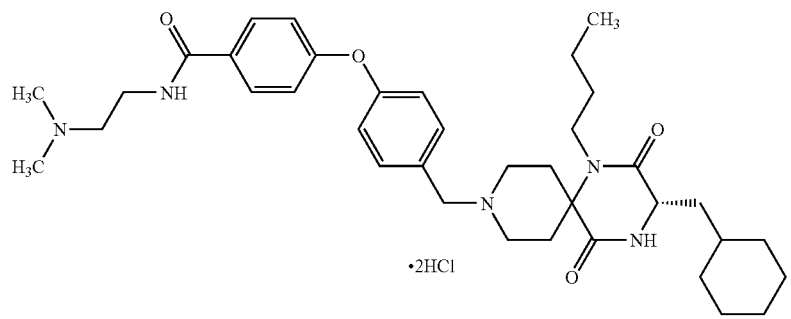

TLC: Rf 0.11 (chloroform:methanol=10:1); NMR (CD$_3$OD): δ 7.94 (d, J=9.0 Hz, 2H), 7.64 (d, J=8.7 Hz, 2H), 7.15 (d, J=8.7 Hz, 2H), 7.10 (d, J=9.0 Hz, 2H), 4.36 (s, 2H), 4.04 (dd, J=7.8, 4.8 Hz, 1H), 3.88-3.72 (m, 4H), 3.52-3.36 (m, 6H), 2.98 (s, 6H), 2.62-2.44 (m, 2H), 2.24-2.08 (m, 2H), 1.80-1.10 (m, 15H), 1.00-0.88 (m, 5H).

EXAMPLE 40(88)

(3S)-1-butyl-2,5-dioxo-3-cyclohexylmethyl-9-(4-aminocarbonylphenylmethyl)-1,4,9-triazaspiro[5.5]undecane.hydrochloride

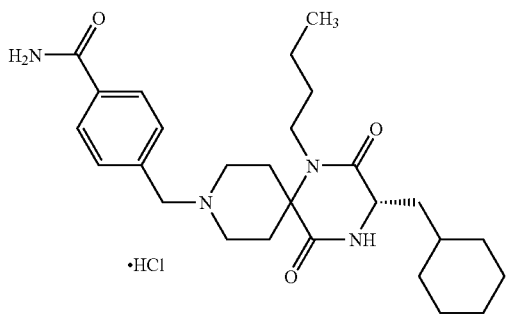

TLC: Rf 0.19 (chloroform:methanol=10:1); NMR (CD$_3$OD): δ 7.98 (d, J=8.4 Hz, 2H), 7.68 (d, J=8.4 Hz, 2H), 4.43 (s, 2H), 4.03 (dd, J=7.5, 4.8 Hz, 1H), 3.92-3.76 (m, 2H), 3.54-3.28 (m, 4H), 2.52-2.36 (m, 2H), 2.24-2.08 (m, 2H), 1.82-1.10 (m, 15H), 1.02-0.88 (m, 5H).

EXAMPLE 40(89)

(3S)-1-butyl-2,5-dioxo-3-cyclohexylmethyl-9-(4-(dimethylaminocarbonyl)phenylmethyl)-1,4,9-triazaspiro[5.5]undecane.hydrochloride

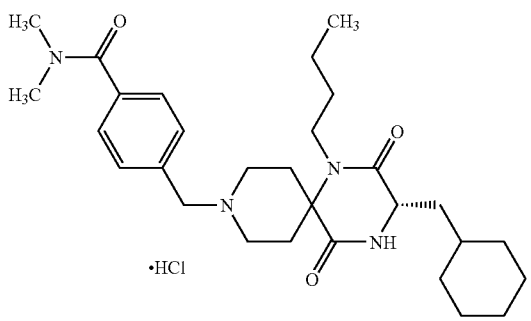

TLC: Rf 0.33 (chloroform:methanol=10:1); NMR (CD$_3$OD): δ 7.67 (d, J=8.1 Hz, 2H), 7.54 (d, J=8.1 Hz, 2H), 4.41 (s, 2H), 4.04 (dd, J=7.5, 4.2 Hz, 1H), 3.92-3.76 (m, 2H), 3.54-3.32 (m, 4H), 3.11 (s, 3H), 2.99 (s, 3H), 2.52-2.32 (m, 2H), 2.26-2.08 (m, 2H), 1.82-1.10 (m, 15H), 1.02-0.86 (m, 5H).

EXAMPLE 40(90)

(3S)-1-butyl-2,5-dioxo-3-cyclohexylmethyl-9-(4-phenyloxyphenylmethyl)-1,4,9-triazaspiro[5.5]undecane

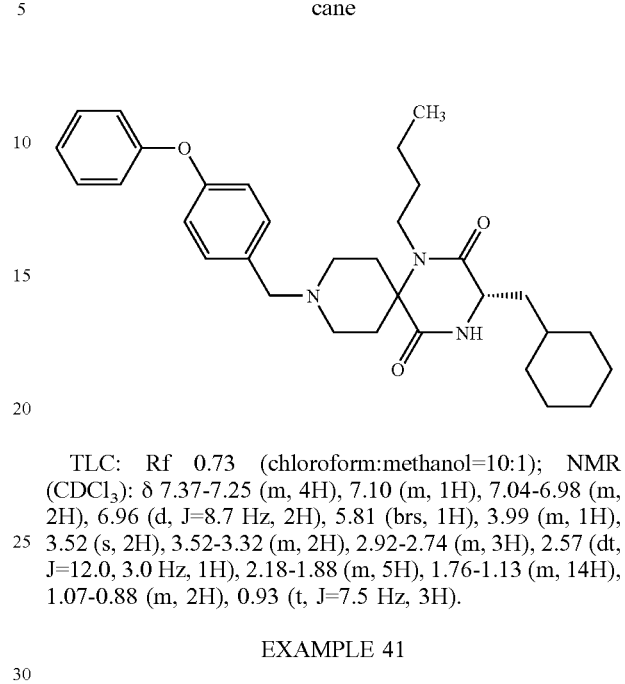

TLC: Rf 0.73 (chloroform:methanol=10:1); NMR (CDCl$_3$): δ 7.37-7.25 (m, 4H), 7.10 (m, 1H), 7.04-6.98 (m, 2H), 6.96 (d, J=8.7 Hz, 2H), 5.81 (brs, 1H), 3.99 (m, 1H), 3.52 (s, 2H), 3.52-3.32 (m, 2H), 2.92-2.74 (m, 3H), 2.57 (dt, J=12.0, 3.0 Hz, 1H), 2.18-1.88 (m, 5H), 1.76-1.13 (m, 14H), 1.07-0.88 (m, 2H), 0.93 (t, J=7.5 Hz, 3H).

EXAMPLE 41

By the same procedure as described in Reference Example 3→Reference Example 4 using Resin (3) prepared in Reference Example 2, N-allyloxycarbonyl-4-piperidone, n-butylamine and (2R*,3R*)-N-(t-butyloxycarbonyl)-2-amino-3-hydroxy-4-methylpentanoic acid, and furthermore by the same procedure as described in Reference Example 5→Reference Example 6→Example 1 using 1,4-benzodioxan-6-carboxyaldehyde, the following compounds (1) and (2) of the present invention were obtained respectively.

EXAMPLE 41(1)

1-butyl-2,5-dioxo-3-(1-hydroxy-2-methylpropyl)-9-(1,4-benzodioxan-6-ylmethyl)-1,4,9-triazaspiro[5.5]undecane.hydrochloride

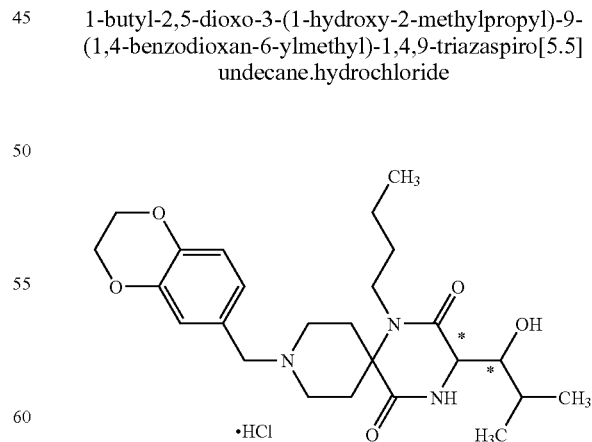

(Symbol * means the mixture of syn form and anti form (syn:anti=2:3.)

TLC: Rf 0.47 (chloroform:methanol=10:1); NMR (CD$_3$OD): δ 7.04 (d, J=2.1 Hz, 1H), 6.97 (dd, J=8.4, 2.1 Hz, 1H), 6.93 (d, J=8.4 Hz, 1H), 4.26 (s, 4H), 4.23 (s, 2H), 4.13 (d, J=2.1 Hz, 0.6H), 4.08 (d, J=1.2 Hz, 0.4H), 4.05-3.90 (m, 1H), 3.76-3.63 (m, 1H), 3.62-3.35 (m, 3.4H), 3.19 (dd, J=9.6, 2.1 Hz, 0.6H), 3.20-3.10 (m, 1H), 2.55-2.33 (m, 2H), 2.30-1.95 (m, 3H), 1.80-1.60 (m, 1H), 1.55-1.25 (m, 3H), 1.05-0.89 (m, 9H).

EXAMPLE 41(2)

(Z)-1-butyl-2,5-dioxo-3-(2-methylpropylidene)-9-(1,4-benzodioxan-6-ylmethyl)-1,4,9-triazaspiro[5.5]undecane.drochloride

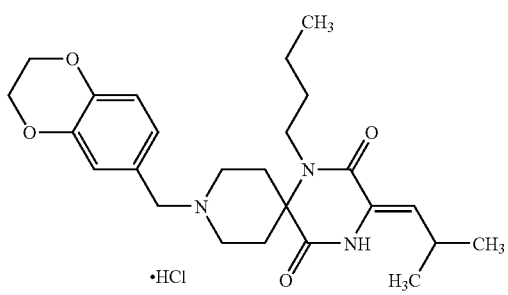

TLC: Rf 0.52 (chloroform:methanol=20:1); NMR (CD$_3$OD): δ 7.04 (d, J=2.1 Hz, 1H), 6.97 (dd, J=8.4, 2.1 Hz, 1H), 6.93 (d, J=8.4 Hz, 1H), 5.84 (d, J=10.5 Hz, 1H), 4.26 (s, 4H), 4.23 (s, 2H), 3.72-3.55 (m, 2H), 3.53-3.35 (m, 4H), 2.80-2.60 (m, 1H), 2.43-2.26 (m, 2H), 2.25-2.15 (m, 2H), 1.62-1.48 (m, 2H), 1.45-1.30 (m, 2H), 1.04 (d, J=6.6 Hz, 6H), 0.95 (t, J=7.5 Hz, 3H).

EXAMPLE 41(3) TO 41(5)

By the same procedure as described in Example 41 using the corresponding compounds instead of (2R*,3R*)-N-(t-butyloxycarbonyl)-2-amino-3-hydroxy-4-methylpentanoic acid, and the corresponding compounds instead of 1,4-benzodioxan-6-carboxaldehyde, the following compounds of the present invention were obtained.

EXAMPLE 41(3)

(3S)-1-butyl-2,5-dioxo-3-((1R)-1-hydroxyethyl)-9-(4-phenyloxyphenylmethyl)-1,4,9-triazaspiro[5.5]undecane.hydrochloride

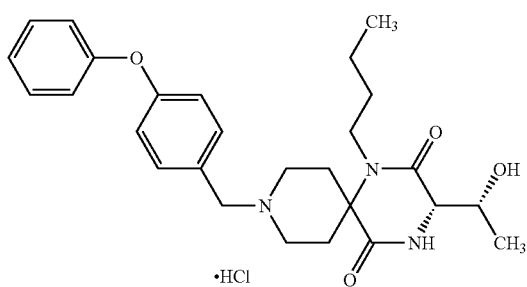

TLC: Rf 0.39 (chloroform:methanol=10:1); NMR (CD$_3$OD): δ 7.54 (d, J=8.7 Hz, 2H), 7.43-7.35 (m, 2H), 7.21-7.14 (m, 1H), 7.08-7.00 (m, 4H), 4.32 (s, 2H), 4.19 (dq, J=1.5, 6.9 Hz, 1H), 4.10-3.97 (m, 1H), 3.78 (d, J=1.5 Hz, 1H), 3.72-3.51 (m, 2H), 3.51-3.40 (m, 2H), 3.28-3.14 (m, 1H), 2.57-2.42 (m, 2H), 2.40-2.25 (m, 1H), 2.21-2.10 (m, 1H), 1.81-1.60 (m, 1H), 1.50-1.30 (m, 3H), 1.22 (d, J=6.9 Hz, 3H), 0.95 (t, J=7.2 Hz, 3H).

EXAMPLE 41(4)

(Z)-1-butyl-2,5-dioxo-3-ethylidene-9-(4-phenyloxyphenylmethyl)-1,4,9-triazaspiro[5.5]undecane.hydrochloride

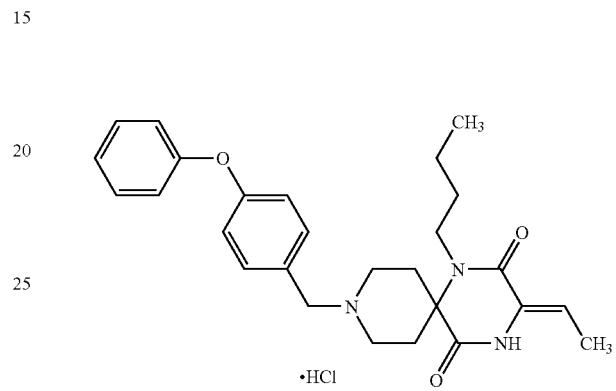

TLC: Rf 0.29 (chloroform:methanol=20:1); NMR (CD$_3$OD): δ 7.53 (d, J=9.0 Hz, 2H), 7.43-7.35 (m, 2H), 7.18 (t, J=7.5 Hz, 1H), 7.09-7.00 (m, 4H), 6.08 (q, J=7.5 Hz, 1H), 4.33 (s, 2H), 3.76-3.61 (m, 2H), 3.57-3.40 (m, 4H), 2.45-2.30 (m, 2H), 2.28-2.15 (m, 2H), 1.77 (d, J=7.5 Hz, 3H), 1.62-1.46 (m, 2H), 1.44-1.28 (m, 2H), 0.96 (t, J=7.5 Hz, 3H).

EXAMPLE 41(5)

(Z)-1-butyl-2,5-dioxo-3-(2-methylpropylidene)-9-(4-phenyloxyphenylmethyl)-1,4,9-triazaspiro[5.5]undecane.hydrochloride

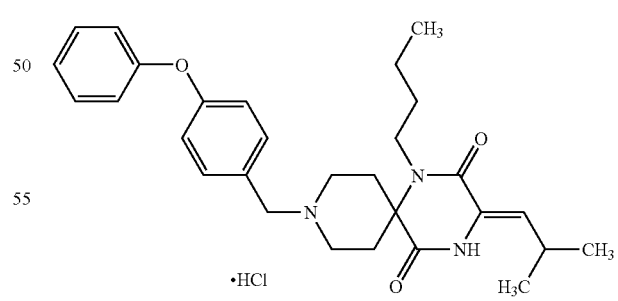

TLC: Rf 0.42 (chloroform:methanol=20:1); NMR (CD$_3$OD): δ 7.51 (d, J=8.7 Hz, 2H), 7.43-7.35 (m, 2H), 7.18 (t, J=7.5 Hz, 1H), 7.06 (d, J=8.7 Hz, 2H), 7.08-7.01 (m, 2H), 5.85 (d, J=10.5 Hz, 1H), 4.34 (s, 2H), 3.78-3.64 (m, 2H), 3.57-3.40 (m, 4H), 2.78-2.62 (m, 1H), 2.43-2.18 (m, 4H), 1.62-1.48 (m, 2H), 1.46-1.30 (m, 2H), 1.04 (d, J=6.6 Hz, 6H), 0.96 (t, J=7.5 Hz, 3H).

EXAMPLE 42

(3R*)-1-butyl-2,5-dioxo-3-((1R*)-1-hydroxy-2-methylpropyl)-9-benzyloxycarbonyl-1,4,9-triazaspiro[5.5]undecane

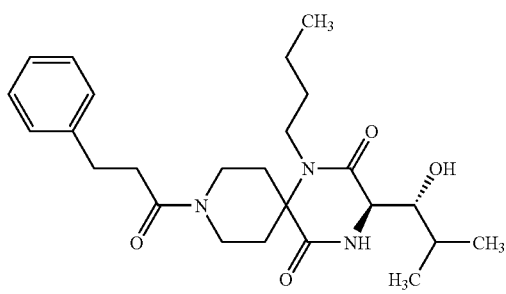

By the same procedure as described in Example 35 using (2R*,3R*)-N-(t-butyloxycarbonyl)-2-amino-3-hydroxy-4-methylpentanoic acid instead of N-(t-butyloxycarbonyl)-L-leucine, the compound of the present invention having the following physical data was obtained.

TLC: Rf 0.43 (chloroform:methanol=10:1); NMR (CD$_3$OD): δ 7.39-7.30 (m, 5H), 5.13 (br, 2H), 4.12 (d, J=2.5 Hz, 1H), 4.10-4.00 (m, 2H), 3.76-3.50 (m, 2H), 3.39-3.25 (m, 2H), 3.10-2.94 (m, 1H), 2.18 (m, 1H), 2.08-1.83 (m, 4H), 1.70-1.56 (m, 1H), 1.45-1.15 (m, 3H), 1.01-0.89 (m, 9H).

EXAMPLE 43

(3R*)-1-butyl-2,5-dioxo-3-((1R*)-1-hydroxy-2-methylpropyl)-1,4,9-triazaspiro[5.5]undecane.hydrochloride

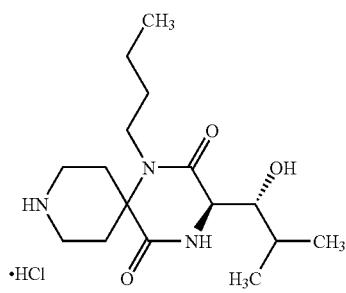

By the same procedure as described in Example 9 using the compound prepared in Example 42, the compound of the present invention having the following physical data was obtained.

TLC: Rf 0.08 (chloroform:methanol=10:1); NMR (CD$_3$OD): δ 4.15 (d, J=2.0 Hz, 1H), 3.96 (dt, J=13.0, 4.0 Hz, 1H), 3.71 (dt, J=13.0, 4.0 Hz, 1H), 3.57-3.47 (m, 1H), 3.40-3.34 (m, 2H), 3.23-3.12 (m, 2H), 2.47-2.30 (m, 2H), 2.25-1.98 (m, 3H), 1.79-1.66 (m, 1H), 1.52-1.28 (m, 3H), 1.07-0.94 (m, 9H).

EXAMPLE 44(1) TO 44(13)

By the same procedure as described in Example 10 using the compound prepared in Example 43 and the corresponding aldehyde derivatives, the following compounds were obtained.

EXAMPLE 44(1)

(3R*)-1-butyl-2,5-dioxo-3-((1R*)-1-hydroxy-2-methylpropyl)-9-(4-phenyloxyphenylmethyl)-1,4,9-triazaspiro[5.5]undecane.hydrochloride

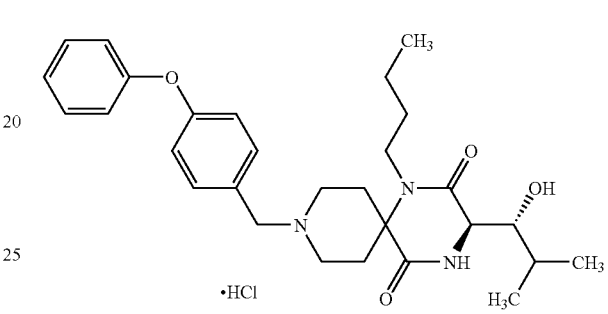

TLC: Rf 0.51 (chloroform:methanol=10:1); NMR (CD$_3$OD): δ 7.52 (d, J=8.7 Hz, 2H), 7.44-7.35 (m, 2H), 7.18 (t, J=7.5 Hz, 1H), 7.10-7.00 (m, 4H), 4.33 (s, 2H), 4.14 (d, J=2.1 Hz, 1H), 4.06-3.93 (m, 1H), 3.80-3.67 (m, 1H), 3.56-3.40 (m, 3H), 3.19 (dd, J=9.3, 2.1 Hz, 1H), 3.20-3.10 (m, 1H), 2.53-2.35 (m, 2H), 2.35-2.20 (m, 1H), 2.19-2.08 (m, 1H), 2.07-1.91 (m, 1H), 1.80-1.70 (m, 1H), 1.50-1.25 (m, 3H), 0.99 (d, J=6.6 Hz, 3H), 0.97 (d, J=6.6 Hz, 3H), 0.95 (t, J=7.2 Hz, 3H).

EXAMPLE 44(2)

(3R*)-1-butyl-2,5-dioxo-3-((1R*)-1-hydroxy-2-methylpropyl)-9-(3,5-dimethyl-1-phenylpyrazol-4-ylmethyl)-1,4,9-triazaspiro[5.5]undecane.2 hydrochloride

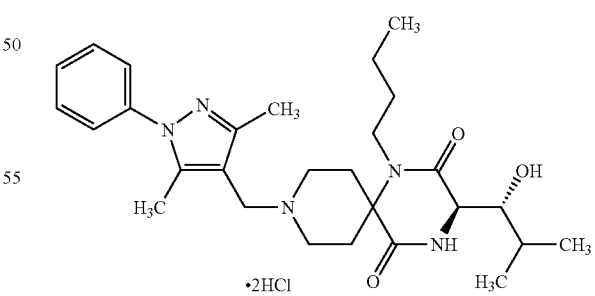

TLC: Rf 0.38 (chloroform:methanol=10:1); NMR (CD$_3$OD): δ 7.60-7.45 (m, 5H), 4.30 (s, 2H), 4.15 (d, J=2.4 Hz, 1H), 4.05 (m, 1H), 3.79 (m, 1H), 3.62-3.48 (m, 3H), 3.29-3.16 (m, 2H), 2.60-2.45 (m, 2H), 2.44-2.30 (m, 7H), 2.17 (m, 1H), 2.01 (m, 1H), 1.70 (m, 1H), 1.51-1.31 (m, 3H), 1.03-0.91 (m, 9H).

EXAMPLE 44(3)

(3R*)-1-butyl-2,5-dioxo-3-((1R*)-1-hydroxy-2-methylpropyl)-9-(6-phenyloxypyridin-3-ylmethyl)-1,4,9-triazaspiro[5.5]undecane.2 hydrochloride

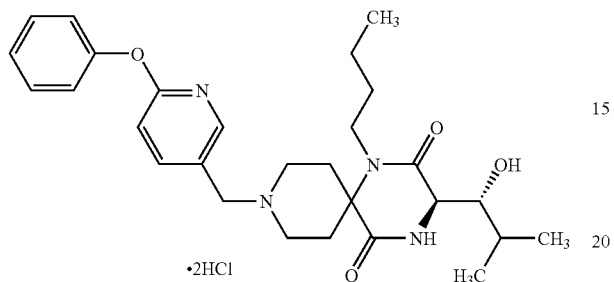

TLC: Rf 0.51 (chloroform:methanol=10:1); NMR (CD$_3$OD): δ 8.39 (d, J=2.1 Hz, 1H), 8.16 (dd, J=8.4, 2.1 Hz, 1H), 7.46 (t, J=7.8 Hz, 2H), 7.29 (t, J=7.8 Hz, 1H), 7.17 (d, J=7.8 Hz, 2H), 7.08 (d, J=8.4 Hz, 1H), 4.40 (s, 2H), 4.13 (d, J=2.1 Hz, 1H), 4.07-3.94 (m, 1H), 3.83-3.69 (m, 1H), 3.60-3.42 (m, 3H), 3.29-3.22 (m, 1H), 3.19 (dd, J=9.6, 2.1 Hz, 1H), 2.62-2.32 (m, 3H), 2.18-2.07 (m, 1H), 2.06-1.94 (m, 1H), 1.78-1.60 (m, 1H), 1.50-1.31 (m, 3H), 1.07-0.87 (m, 9H).

EXAMPLE 44(4)

(3R*)-1-butyl-2,5-dioxo-3-((1R*)-1-hydroxy-2-methylpropyl)-9-(4-(4-methylphenyloxy)phenylmethyl)-1,4,9-triazaspiro[5.5]undecane.hydrochloride

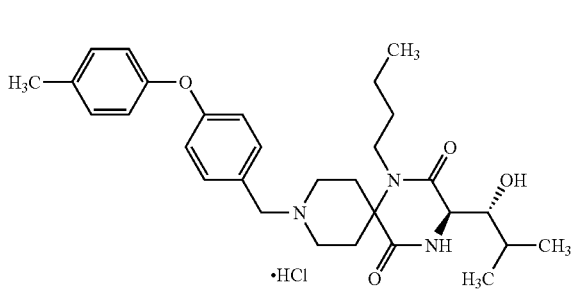

TLC: Rf 0.46 (chloroform:methanol=10:1); NMR (CD$_3$OD): δ 7.47 (d, J=8.7 Hz, 2H), 7.20 (d, J=8.7 Hz, 2H), 7.02 (d, J=8.7 Hz, 2H), 6.92 (d, J=8.7 Hz, 2H), 4.29 (s, 2H), 4.14 (d, J=2.1 Hz, 1H), 3.97 (m, 1H), 3.72 (m, 1H), 3.56-3.39 (m, 2H), 3.25-3.09 (m, 3H), 2.53-2.08 (m, 7H), 2.01 (m, 1H), 1.70 (m, 1H), 1.48-1.28 (m, 3H), 1.05-0.88 (m, 9H).

EXAMPLE 44(5)

(3R*)-1-butyl-2,5-dioxo-3-((1R*)-1-hydroxy-2-methylpropyl)-9-(4-cyclohexyloxyphenylmethyl)-1,4,9-triazaspiro[5.5]undecane.hydrochloride

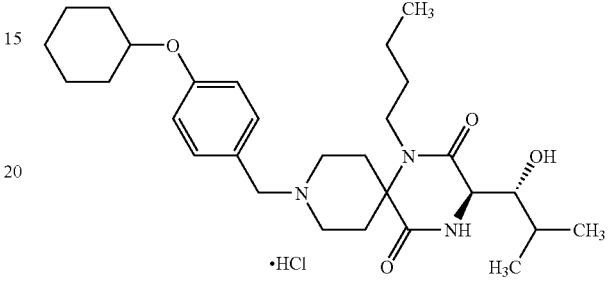

TLC: Rf 0.43 (chloroform:methanol=10:1); NMR (CD$_3$OD): δ 7.40 (d, J=8.7 Hz, 2H), 7.00 (d, J=8.7 Hz, 2H), 4.37 (m, 1H), 4.24 (brs, 2H), 4.13 (d, J=2.1 Hz, 1H), 3.94 (m, 1H), 3.68 (m, 1H), 3.52-3.34 (m, 2H), 3.29-3.07 (m, 3H), 2.52-1.92 (m, 7H), 1.85-1.27 (m, 12H), 1.04-0.89 (m, 9H).

EXAMPLE 44(6)

(3R*)-1-butyl-2,5-dioxo-3-((1R*)-1-hydroxy-2-methylpropyl)-9-(4-(tetrahydropyran-4-yloxy)phenylmethyl)-1,4,9-triazaspiro[5.5]undecane.hydrochloride

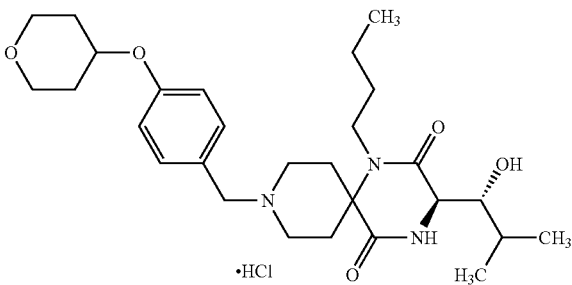

TLC: Rf 0.20 (ethyl acetate:methanol=10:1); NMR (CD$_3$OD): δ 7.45 (d, J=8.7 Hz, 2H), 7.06 (d, J=8.7 Hz, 2H), 4.67-4.59 (m, 1H), 4.28 (s, 2H), 4.13 (d, J=2.5 Hz, 1H), 4.00-3.90 (m, 3H), 3.75-3.67 (m, 1H), 3.63-3.53 (m, 2H), 3.50-3.41 (m, 3H), 3.18 (dd, J=9.0, 2.0 Hz, 1H), 3.18 (m, 1H), 2.49-1.96 (m, 7H), 1.77-1.65 (m, 3H), 1.44-1.30 (m, 3H), 0.98 □ (d, J=6.5 Hz, 3H), 0.96 (d, J=6.5 Hz, 3H), 0.94 (t, J=7.2 Hz, 3H).

EXAMPLE 44(7)

(3R*)-1-butyl-2,5-dioxo-3-((1R*)-1-hydroxy-2-methylpropyl)-9-(4-(pyridin-3-yloxy)phenylmethyl)-1,4,9-triazaspiro[5.5]undecane.2 hydrochloride

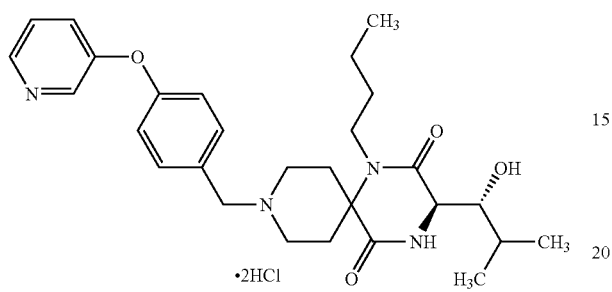

TLC: Rf 0.22 (ethyl acetate:methanol=10:1); NMR (CD₃OD): δ 8.76 (d, J=2.5 Hz, 1H), 8.63 (d, J=6.0 Hz, 1H), 8.29 (dd, J=9.0, 2.5 Hz, 1H), 8.08 (dd, J=9.0, 6.0 Hz, 1H), 7.77 (d, J=9.0 Hz, 2H), 7.35 (d, J=9.0 Hz, 2H), 4.41 (s, 2H), 4.14 (d, J=2.0 Hz, 1H), 4.00 (m, 1H), 3.76 (m, 1H), 3.61-3.47 (m, 3H), 3.20 (dd, J=9.5, 2.0 Hz, 1H), 3.20 (m, 1H), 2.62 (m, 1H), 2.46 (m, 2H), 2.10 (m, 1H), 2.05-1.95 (m, 1H), 1.69 (m, 1H), 1.41-1.35 (m, 3H), 0.99 (d, J=6.5 Hz, 3H), 0.97 (d, J=6.5 Hz, 3H), 0.95 (t, J=7.5 Hz, 3H).

EXAMPLE 44(8)

(3R*)-1-butyl-2,5-dioxo-3-((1R*)-1-hydroxy-2-methylpropyl)-9-(4-isopropylphenylmethyl)-1,4,9-triazaspiro[5.5]undecane.hydrochloride

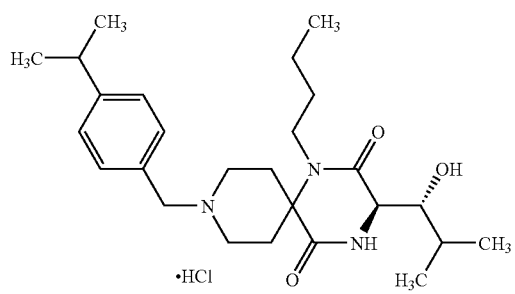

TLC: Rf 0.55 (chloroform:methanol=10:1); NMR (CD₃OD): δ 7.47 (d, J=8.1 Hz, 2H), 7.37 (d, J=8.1 Hz, 2H), 4.31 (s, 2H), 4.13 (d, J=2.1 Hz, 1H), 4.05-3.91 (m, 1H), 3.80-3.65 (m, 1H), 3.57-3.38 (m, 3H), 3.26-3.13 (m, 1H), 3.19 (dd, J=9.3, 2.1 Hz, 1H), 3.03-2.86 (m, 1H), 2.53-2.38 (m, 2H), 2.38-2.23 (m, 1H), 2.16-2.05 (m, 1H), 2.06-1.92 (m, 1H), 1.77-1.56 (m, 1H), 1.49-1.26 (m, 3H), 1.25 (d, J=6.9 Hz, 6H), 0.98 (d, J=6.6 Hz, 3H), 0.97 (d, J=6.6 Hz, 3H), 0.94 (t, J=7.2 Hz, 3H).

EXAMPLE 44(9)

(3R*)-1-butyl-2,5-dioxo-3-((1R*)-1-hydroxy-2-methylpropyl)-9-(3,5-dimethyl-1-(4-methylphenyl)pyrazol-4-ylmethyl)-1,4,9-triazaspiro[5.5]undecane.2 hydrochloride

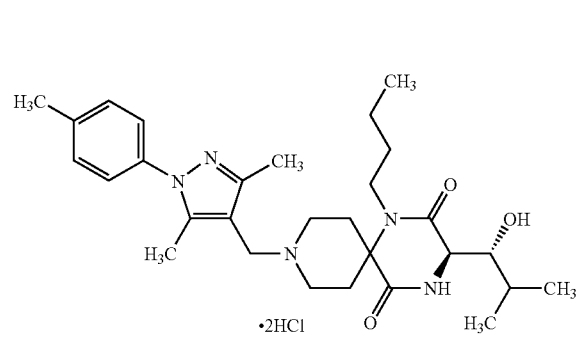

TLC: Rf 0.49 (chloroform:methanol=10:1); NMR (CD₃OD): δ 7.40 (s, 4H), 4.33 (s, 2H), 4.15 (d, J=2.1 Hz, 1H), 4.11-3.97 (m, 1H), 3.86-3.72 (m, 1H), 3.64-3.50 (m, 3H), 3.39-3.30 (m, 1H), 3.21 (dd, J=9.3, 2.1 Hz, 1H), 2.72-2.55 (m, 1H), 2.53-2.40 (m, 2H), 2.46 (s, 3H), 2.44 (s, 3H), 2.40 (s, 3H), 2.18-2.07 (m, 1H), 2.07-1.96 (m, 1H), 1.78-1.60 (m, 1H), 1.50-1.30 (m, 3H), 1.00 (d, J=6.6 Hz, 3H), 0.98 (d, J=6.6 Hz, 3H), 0.95 (t, J=7.2 Hz, 3H).

EXAMPLE 44(10)

(3R*)-1-butyl-2,5-dioxo-3-((1R*)-1-hydroxy-2-methylpropyl)-9-(3-methyl-5-chloro-1-phenylpyrazol-4-ylmethyl)-1,4,9-triazaspiro[5.5]undecane.2 hydrochloride

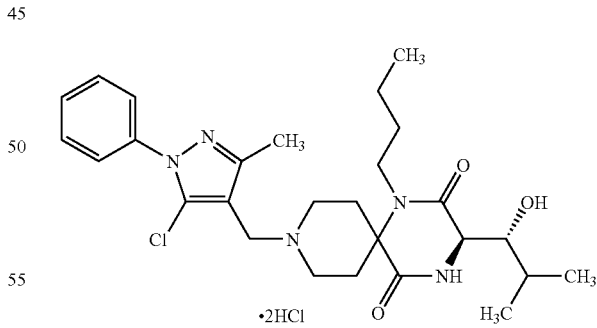

TLC: Rf 0.56 (chloroform:methanol=10:1); NMR (CD₃OD): δ 7.58-7.47 (m, 5H), 4.33 (s, 2H), 4.15 (d, J=2.1 Hz, 1H), 4.15-4.02 (m, 1H), 3.89-3.75 (m, 1H), 3.65-3.48 (m, 3H), 3.30-3.20 (m, 1H), 3.20 (dd, J=9.6, 2.1 Hz, 1H), 2.64-2.46 (m, 2H), 2.44 (s, 3H), 2.44-2.32 (m, 1H), 2.21-2.10 (m, 1H), 2.08-1.93 (m, 1H), 1.80-1.60 (m, 1H), 1.52-1.30 (m, 3H), 0.99 (d, J=6.6 Hz, 3H), 0.98 (d, J=6.6 Hz, 3H), 0.96 (t, J=7.2 Hz, 3H).

EXAMPLE 44(11)

(3R*)-1-butyl-2,5-dioxo-3-((1R*)-1-hydroxy-2-methylpropyl)-9-(4-(4-carboxyphenyloxy)phenylmethyl)-1,4,9-triazaspiro[5.5]undecane.hydrochloride

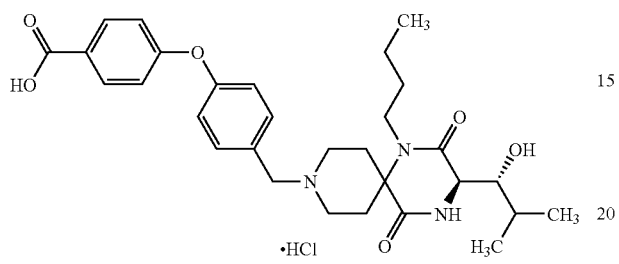

TLC: Rf 0.29 (chloroform:methanol=10:1); NMR (CD$_3$OD): δ 8.04 (d, J=9.0 Hz, 2H), 7.60 (d, J=8.7 Hz, 2H), 7.18 (d, J=8.7 Hz, 2H), 7.07 (d, J=9.0 Hz, 2H), 4.37 (s, 2H), 4.14 (d, J=2.1 Hz, 1H), 4.10-3.94 (m, 1H), 3.83-3.69 (m, 1H), 3.59-3.40 (m, 3H), 3.25-3.12 (m, 1H), 3.19 (dd, J=9.3, 2.1 Hz, 1H), 2.55-2.37 (m, 2H), 2.37-2.22 (m, 1H), 2.19-2.08 (m, 1H), 2.08-1.94 (m, 1H), 1.79-1.60 (m, 1H), 1.52-1.26 (m, 3H), 0.99 (d, J=6.6 Hz, 3H), 0.97 (d, J=6.6 Hz, 3H), 0.95 (t, J=7.2 Hz, 3H).

EXAMPLE 44(12)

(3R*)-1-butyl-2,5-dioxo-3-((1R*)-1-hydroxy-2-methylpropyl)-9-(3,5-dimethyl-1-(pyridin-2-yl)pyrazol-4-ylmethyl)-1,4,9-triazaspiro[5.5]undecane.2 hydrochloride

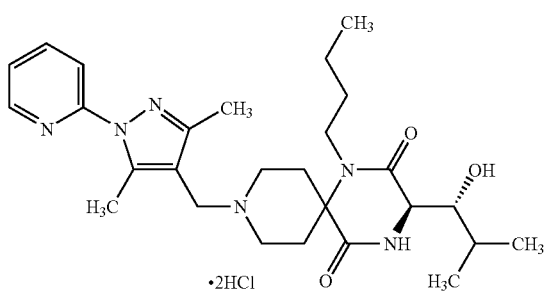

TLC: Rf 0.28 (chloroform:methanol=10:1); NMR (CD$_3$OD): δ 8.53 (d, J=5.1 Hz, 1H), 8.05 (t, J=7.8 Hz, 1H), 7.81 (d, J=7.8 Hz, 1H), 7.44 (dd, J=7.8, 5.1 Hz, 1H), 4.33 (s, 2H), 4.16 (d, J=2.1 Hz, 1H), 4.06 (m, 1H), 3.78 (m, 1H), 3.62-3.44 (m, 3H), 3.26 (m, 1H), 3.21 (dd, J=9.6, 2.1 Hz, 1H), 2.68 (s, 3H), 2.60-2.30 (m, 3H), 2.42 (s, 3H), 2.16 (m, 1H), 2.02 (m, 1H), 1.72 (m, 1H), 1.50-1.26 (m, 3H), 1.00 (d, J=6.6 Hz, 3H), 0.99 (d, J=6.6 Hz, 3H), 0.96 (t, J=7.2 Hz, 3H).

EXAMPLE 44(13)

(3R*)-1-butyl-2,5-dioxo-3-((1R*)-1-hydroxy-2-methylpropyl)-9-(3,5-dimethyl-1-(4-carboxyphenyl)pyrazol-4-ylmethyl)-1,4,9-triazaspiro[5.5]undecane.2 hydrochloride

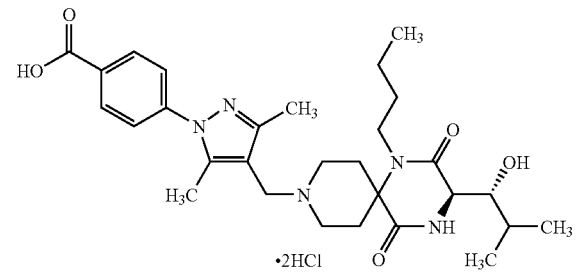

TLC: Rf 0.25 (chloroform:methanol:acetic acid=20:2:1); NMR (CD$_3$OD): δ 8.19 (d, J=8.7 Hz, 2H), 7.62 (d, J=8.7 Hz, 2H), 4.32 (s, 2H), 4.16 (d, J=2.1 Hz, 1H), 4.12-3.98 (m, 1H), 3.87-3.74 (m, 1H), 3.63-3.45 (m, 3H), 3.30-3.10 (m, 1H), 3.20 (dd, J=9.3, 2.1 Hz, 1H), 2.59-2.48 (m, 2H), 2.44 (s, 3H), 2.40-2.23 (m, 1H), 2.39 (s, 3H), 2.23-2.10 (m, 1H), 2.10-1.96 (m, 1H), 1.80-1.62 (m, 1H), 1.52-1.24 (m, 3H), 1.00 (d, J=6.6 Hz, 3H), 0.98 (d, J=6.6 Hz, 3H), 0.96 (t, J=7.2 Hz, 3H).

EXAMPLE 45

(3R*)-1-butyl-2,5-dioxo-3-((1R*)-1-hydroxy-1-cyclohexylmethyl)-9-benzyloxycarbonyl-1,4,9-triazaspiro[5.5]undecane

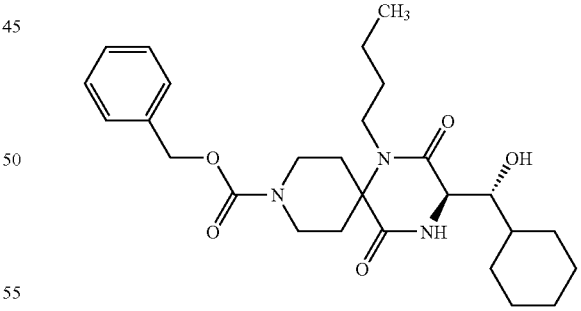

By the same procedure as described in Example 35 using (2R*,3R*)-N-(t-butyloxycarbonyl)-2-amino-3-hydroxy-3-cyclohexylpropanoic acid instead of N-(t-butyloxycarbonyl)-L-leucine, the compound of the present invention having the following physical data was obtained.

TLC: Rf 0.53 (chloroform:methanol=10:1); NMR (CD$_3$OD): δ 7.39-7.27 (m, 5H), 5.13 (m, 2H), 4.13 (d, J=2.5 Hz, 1H), 4.06-4.02 (m, 2H), 3.78-3.48 (m, 2H), 3.36-3.29 (m, 2H), 3.02 (br, 1H), 2.17 (m, 1H), 2.03-1.58 (m, 10H), 1.47-1.13 (m, 6H), 1.02-0.89 (m, 5H).

EXAMPLE 46

(3R*)-1-butyl-2,5-dioxo-3-((1R*)-1-hydroxy-1-cyclohexylmethyl)-1,4,9-triazaspiro[5.5]undecane

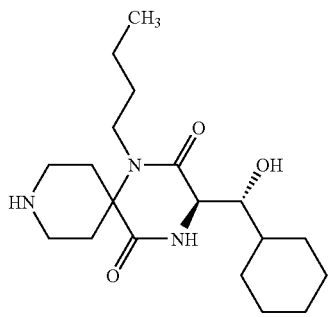

By the same procedure as described in Example 9 using the compound prepared in Example 45, the compound of the present invention having the following physical data was obtained.

TLC: Rf 0.33 (chloroform:methanol:acetic acid=20:6:1); NMR (CD$_3$OD): δ 4.13 (d, J=2.5 Hz, 1H), 3.48-3.22 (m, 5H), 2.97-2.89 (m, 2H), 2.12-1.65 (m, 10H), 1.56-1.16 (m, 7H), 1.03-0.85 (m, 5H).

EXAMPLE 47(1) TO 47(8)

By the same procedure as described in Example 10 using the compound prepared in Example 46 and the corresponding aldehyde compounds, the following compounds of the present invention were obtained.

EXAMPLE 47(1)

(3R*)-1-butyl-2,5-dioxo-3-((1R*)-1-hydroxy-1-cyclohexylmethyl)-9-(4-phenyloxyphenylmethyl)-1,4,9-triazaspiro[5.5]undecane.hydrochloride

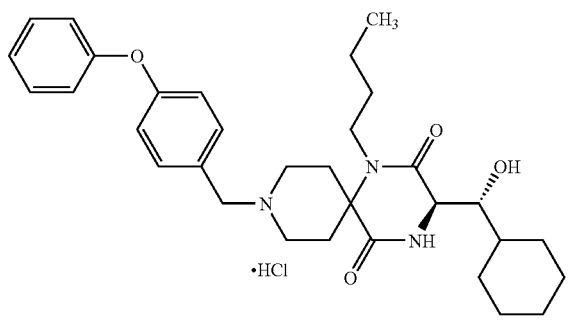

TLC: Rf 0.44 (chloroform:methanol=10:1); NMR (CD$_3$OD): δ 7.55-7.51 (m, 2H), 7.42-7.36 (m, 2H), 7.18 (tt, J=7.5, 1.0 Hz, 1H), 7.08-7.01 (m, 4H), 4.32 (s, 2H), 4.15 (d, J=2.0 Hz, 1H), 3.98 (dt, J=3.5, 12.5 Hz, 1H), 3.73 (dt, J=3.5, 12.5 Hz, 1H), 3.57-3.39 (m, 3H), 3.26 (d, J=2.0 Hz, 1H), 3.20 (m, 1H), 2.52-2.39 (m, 2H), 2.30 (m, 1H), 2.12 (d, J=15.5 Hz, 1H), 2.04-1.92 (m, 2H), 1.80-1.62 (m, 5H), 1.48-1.11 (m, 6H), 1.01-0.82 (m, 5H).

EXAMPLE 47(2)

(3R*)-1-butyl-2,5-dioxo-3-((1R*)-1-hydroxy-1-cyclohexylmethyl)-9-(3,5-dimethyl-1-phenylpyrazol-4-ylmethyl)-1,4,9-triazaspiro[5.5]undecane.2 hydrochloride

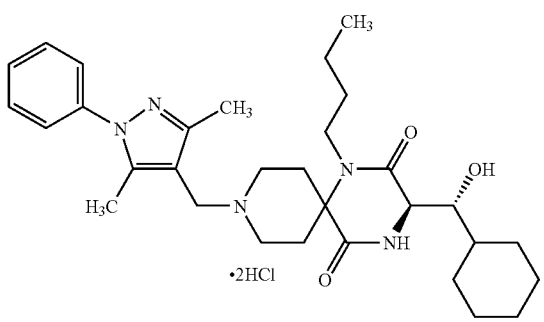

TLC: Rf 0.41 (chloroform:methanol=10:1); NMR (CD$_3$OD): δ 7.60-7.50 (m, 5H), 4.33 (s, 2H), 4.17 (d, J=2.5 Hz, 1H), 4.04 (m, 1H), 3.85-3.75 (m, 1H), 3.61-3.51 (m, 3H), 3.35-3.27 (m, 2H), 2.62 (m, 1H), 2.49-2.44 (m, 5H), 2.41 (s, 3H), 2.15 (m, 1H), 2.05-1.92 (m, 2H), 1.77-1.65 (m, 5H), 1.44-1.15 (m, 6H), 1.01-0.85 (m, 5H).

EXAMPLE 47(3)

(3R*)-1-butyl-2,5-dioxo-3-((1R*)-1-hydroxy-1-cyclohexylmethyl)-9-(4-isopropylphenylmethyl)-1,4,9-triazaspiro[5.5]undecane.hydrochloride

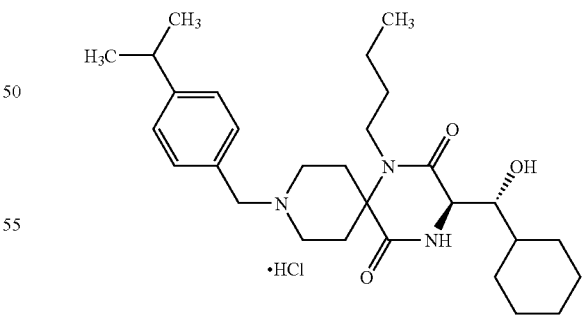

TLC: Rf 0.69 (chloroform:methanol=10:1); NMR (CD$_3$OD): δ 7.48 (d, J=8.4 Hz, 2H), 7.36 (d, J=8.4 Hz, 2H), 4.31 (s, 2H), 4.14 (d, J=2.1 Hz, 1H), 3.98 (m, 1H), 3.72 (m, 1H), 3.55-3.40 (m, 3H), 3.29-3.16 (m, 2H), 2.95 (m, 1H), 2.52-2.24 (m, 3H), 2.15-1.86 (m, 3H), 1.80-1.60 (m, 5H), 1.48-1.10 (m, 6H), 1.25 (d, J=6.9 Hz, 6H), 1.02-0.82 (m, 5H).

EXAMPLE 47(4)

(3R*)-1-butyl-2,5-dioxo-3-((1R*)-1-hydroxy-1-cyclohexylmethyl)-9-(4-(6-methylpyridin-3-yloxy)phenylmethyl)-1,4,9-triazaspiro[5.5]undecane.2 hydrochloride

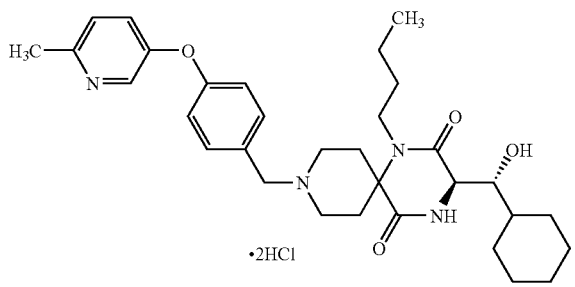

TLC: Rf 0.51 (ethyl acetate:methanol=10:1); NMR (CD$_3$OD): δ 8.59 (d, J=2.7 Hz, 1H), 8.19 (dd, J=9.0, 2.7 Hz, 1H), 7.91 (d, J=9.0 Hz, 1H), 7.75 (d, J=8.4 Hz, 2H), 7.30 (d, J=8.4 Hz, 2H), 4.39 (s, 2H), 4.15 (d, J=2.0 Hz, 1H), 3.99 (m, 1H), 3.73 (m, 1H), 3.61-3.46 (m, 3H), 3.37-3.26 (m, 2H), 2.77 (s, 3H), 2.62 (m, 1H), 2.45 (m, 1H), 2.13-1.92 (m, 3H), 1.73 (m, 4H), 1.40-1.14 (m, 8H), 1.01-0.86 (m, 2H), 0.95 (t, J=7.0 Hz, 3H).

EXAMPLE 47(5)

(3R*)-1-butyl-2,5-dioxo-3-((1R*)-1-hydroxy-1-cyclohexylmethyl)-9-(3,5-dimethyl-1-(4-fluorophenyl)pyrazol-4-ylmethyl)-1,4,9-triazaspiro[5.5]undecane.2 hydrochloride

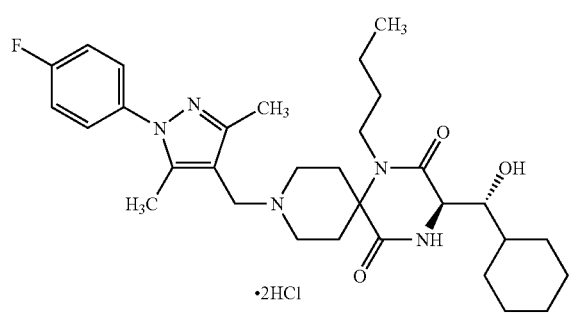

TLC: Rf 0.49 (ethyl acetate:methanol=10:1); NMR (CD$_3$OD): δ 7.57 (m, 2H), 7.37-7.31 (m, 2H), 4.32 (s, 2H), 4.16 (d, J=2.0 Hz, 1H), 4.08-4.00 (m, 1H), 3.79 (m, 1H), 3.63-3.52 (m, 3H), 3.37-3.27 (m, 2H), 2.65 (m, 1H), 2.48 (m, 1H), 2.45 (s, 3H), 2.39 (s, 3H), 2.16-1.92 (m, 3H), 1.73 (m, 4H), 1.42-1.15 (m, 8H), 1.01-0.88 (m, 2H), 0.95 (t, J=7.0 Hz, 3H).

EXAMPLE 47(6)

(3R*)-1-butyl-2,5-dioxo-3-((1R*)-1-hydroxy-1-cyclohexylmethyl)-9-(4-(4-methoxyphenyloxy)phenylmethyl)-1,4,9-triazaspiro[5.5]undecane.hydrochloride

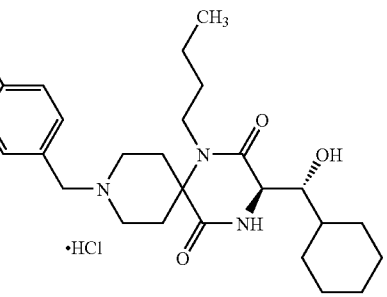

TLC: Rf 0.25 (chloroform:methanol=10:1); NMR (CD$_3$OD): δ 7.47 (d, J=9.0 Hz, 2H), 7.00 (d, J=9.0 Hz, 2H), 6.99-6.92 (m, 4H), 4.30 (s, 2H), 4.16 (d, J=2.1 Hz, 1H), 3.98 (m, 1H), 3.80 (s, 3H), 3.72 (m, 1H), 3.58-3.38 (m, 3H), 3.30-3.08 (m, 2H), 2.54-1.88 (m, 6H), 1.82-1.60 (m, 5H), 1.50-1.10 (m, 6H), 0.96 (t, J=7.5 Hz, 3H), 0.96 (m, 2H).

EXAMPLE 47(7)

(3R*)-1-butyl-2,5-dioxo-3-((1R*)-1-hydroxy-1-cyclohexylmethyl)-9-(4-(4-fluorophenyloxy)phenylmethyl)-1,4,9-triazaspiro[5.5]undecane.hydrochloride TLC: Rf 0.28 (chloroform:methanol=10:1); NMR (CD$_3$OD): δ 7.51 (d, J=8.7 Hz, 2H), 7.13 (d, J=8.7 Hz, 2H), 7.10-7.04 (m, 4H), 4.33 (s, 2H), 4.16 (d, J=2.1 Hz, 1H), 4.00 (m, 1H), 3.72 (m, 1H), 3.58-3.40 (m, 3H), 3.30-3.08 (m, 2H), 2.56-1.88 (m, 6H), 1.82-1.60 (m, 5H), 1.54-1.10 (m, 6H), 0.96 (t, J=7.2 Hz, 3H), 0.96 (m, 2H).

EXAMPLE 47(8)

(3R*)-1-butyl-2,5-dioxo-3-((1R*)-1-hydroxy-1-cyclohexylmethyl)-9-(4-(4-methylsulfonylaminophenyloxy)phenylmethyl)-1,4,9-triazaspiro[5.5]undecane.hydrochloride

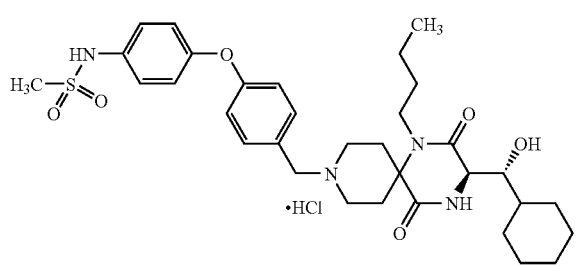

TLC: Rf 0.52 (ethyl acetate:methanol=10:1); NMR (CD₃OD): δ 7.53 (d, J=8.1 Hz, 2H), 7.30 (d, J=9.0 Hz, 2H), 7.08 (d, J=8.1 Hz, 2H), 7.04 (d, J=9.0 Hz, 2H), 4.34 (s, 2H), 4.16 (d, J=2.1 Hz, 1H), 4.00 (m, 1H), 3.76 (m, 1H), 3.58-3.42 (m, 3H), 3.30-3.08 (m, 2H), 2.96 (s, 3H), 2.54-1.88 (m, 6H), 1.82-1.62 (m, 5H), 1.50-1.14 (m, 6H), 0.96 (t, J=7.2 Hz, 3H), 0.96 (m, 2H).

EXAMPLE 48

(3R*)-1-(2-butynyl)-2,5-dioxo-3-((1R*)-1-hydroxy-1-cyclohexylmethyl)-9-allyloxycarbonyl-1,4,9-triazaspiro[5.5]undecane

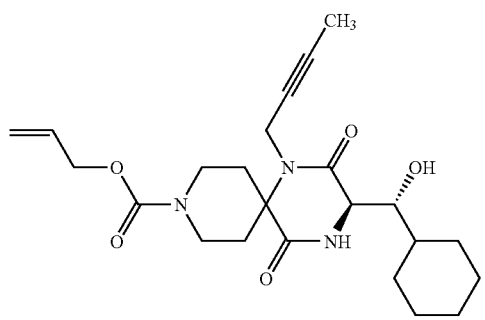

By the same procedure as described in Reference Example 3→Reference Example 6→Example 1 using Resin (3) prepared in Reference Example 2, N-allyloxycarbonyl-4-piperidone, 2-butynylamine, and (2R*,3R*)-N-(t-butyloxycarbonyl)-2-amino-3-hydroxy-3-cyclohexylpropanoic acid, the compound of the present invention having the following physical data was obtained.

TLC: Rf 0.32 (chloroform:methanol=15:1); NMR (CD₃OD): δ 6.04-5.91 (m, 1H), 5.35-5.27 (m, 1H), 5.23-5.19 (m, 1H), 4.60-4.58 (m, 2H), 4.27 (dq, J=17.5, 2.5 Hz, 1H), 4.19 (d, J=2.5 Hz, 1H), 4.07-4.01 (m, 2H), 3.89 (dq, J=17.5, 2.5 Hz, 1H), 3.75-3.50 (m, 2H), 3.38 (dd, J=9.0, 2.5 Hz, 1H), 2.32-2.17 (m, 2H), 2.07-1.70 (m, 11H), 1.33-1.14 (m, 3H), 1.00-0.85 (m, 2H).

EXAMPLE 49

(3R*)-1-(2-butynyl)-2,5-dioxo-3-((1R*)-1-hydroxy-1-cyclohexylmethyl)-1,4,9-triazaspiro[5.5]undecane

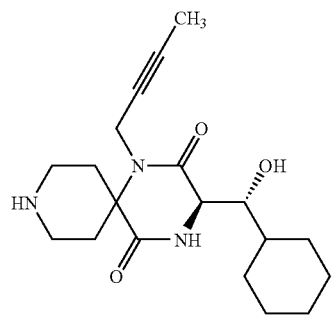

By the same procedure as described in Reference Example 4 using the compound prepared in Example 48, the compound of the present invention having the following physical data was obtained.

TLC: Rf 0.33 (chloroform:methanol:acetic acid=20:6:1); NMR (CD₃OD): δ 4.28 (dq, J=17.5, 2.5 Hz, 1H), 4.18 (d, J=2.5 Hz, 1H), 4.03 (dq, J=17.5, 2.5 Hz, 1H), 3.48-3.29 (m, 3H), 2.99-2.90 (m, 2H), 2.26-1.73 (m, 14H), 1.32-1.18 (m, 3H), 1.01-0.91 (m, 2H).

EXAMPLE 50(1) TO 50(6)

By the same procedure as described in Example 10 using the compound prepared in Example 49 and the corresponding aldehyde compounds, the following compounds of the present invention were obtained.

EXAMPLE 50(1)

(3R*)-1-(2-butynyl)-2,5-dioxo-3-((1R*)-1-hydroxy-1-cyclohexylmethyl)-9-(3,5-dimethyl-1-phenylpyrazol-4-ylmethyl)-1,4,9-triazaspiro[5.5]undecane.2 hydrochloride

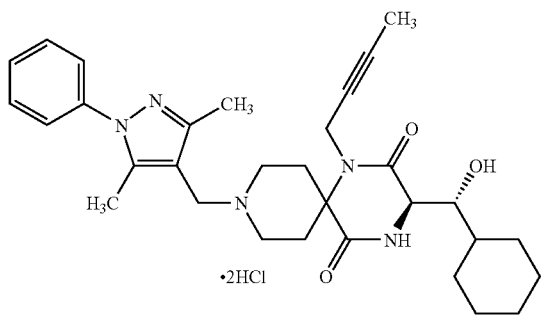

TLC: Rf 0.37 (chloroform:methanol=10:1); NMR (CD₃OD): δ 7.60-7.50 (m, 5H), 4.42-4.33 (m, 3H), 4.21 (d, J=2.5 Hz, 1H), 4.08-3.99 (m, 2H), 3.85-3.75 (m, 1H), 3.65-3.57 (m, 2H), 3.32 (m, 1H), 2.79 (m, 1H), 2.48-2.43 (m, 5H), 2.40 (s, 3H), 2.22 (m, 1H), 2.05-1.93 (m, 2H), 1.80-1.64 (m, 7H), 1.39-1.11 (m, 3H), 1.03-0.84 (m, 2H).

EXAMPLE 50(2)

(3R*)-1-(2-butynyl)-2,5-dioxo-3-((1R*)-1-hydroxy-1-cyclohexylmethyl)-9-(3,5-dimethyl-1-(4-methylphenyl)pyrazol-4-ylmethyl)-1,4,9-triazaspiro[5.5]undecane.2 hydrochloride

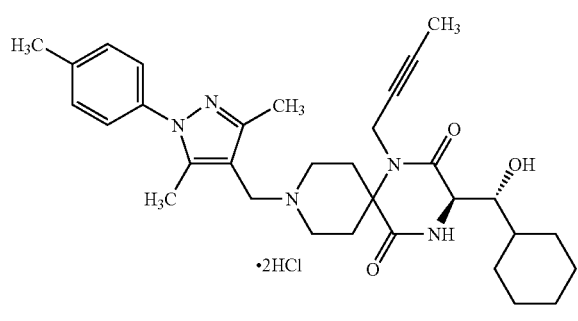

TLC: Rf 0.35 (chloroform:methanol=10:1); NMR (CD$_3$OD): δ 7.40 (s, 4H), 4.45-4.30 (m, 3H), 4.20 (m, 1H), 4.16-3.98 (m, 2H), 3.78 (m, 1H), 3.68-3.56 (m, 2H), 3.30 (m, 1H), 2.82 (m, 1H), 2.56-2.42 (m, 8H), 2.39 (s, 3H), 2.28-1.88 (m, 3H), 1.80-1.60 (m, 7H), 1.40-1.10 (m, 3H), 1.12-0.82 (m, 2H).

EXAMPLE 50(3)

(3R*)-1-(2-butynyl)-2,5-dioxo-3-((1R*)-1-hydroxy-1-cyclohexylmethyl)-9-(4-isopropylphenylmethyl)-1,4,9-triazaspiro[5.5]undecane.hydrochloride

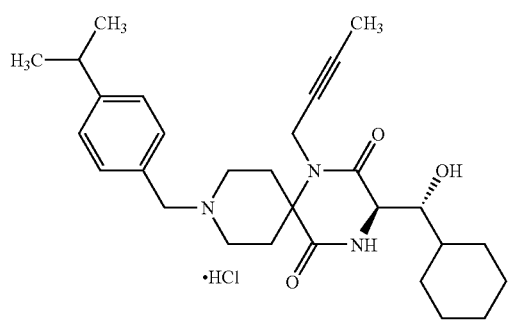

TLC: Rf 0.33 (chloroform:methanol=10:1); NMR (CD$_3$OD): δ 7.47 (d, J=8.1 Hz, 2H), 7.36 (d, J=8.1 Hz, 2H), 4.38-4.28 (m, 3H), 4.17 (m, 1H), 4.04-3.88 (m, 2H), 3.74 (m, 1H), 3.50-3.40 (m, 2H), 3.28 (m, 1H), 2.92 (m, 1H), 2.64 (m, 1H), 2.50-1.86 (m, 5H), 1.80-1.62 (m, 7H), 1.36-1.04 (m, 3H), 1.25 (d, J=7.2 Hz, 6H), 1.00-0.82 (m, 2H).

EXAMPLE 50(4)

(3R*)-1-(2-butynyl)-2,5-dioxo-3-((1R*)-1-hydroxy-1-cyclohexylmethyl)-9-(4-phenyloxyphenylmethyl)-1,4,9-triazaspiro[5.5]undecane.hydrochloride

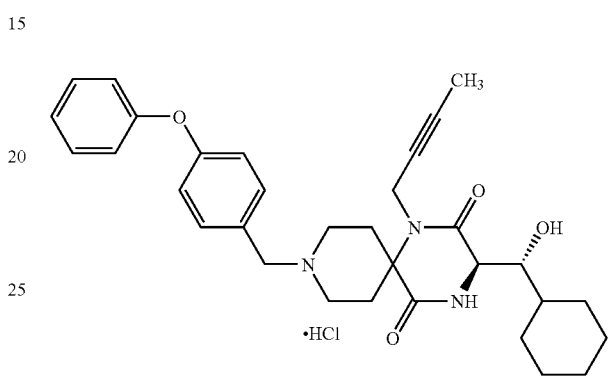

TLC: Rf 0.39 (chloroform:methanol=10:1); NMR (CD$_3$OD): δ 7.53 (d, J=9.0 Hz, 2H), 7.42-7.37 (m, 2H), 7.17 (t, J=7.5 Hz, 1H), 7.06-7.02 (m, 4H), 4.40-4.30 (m, 3H), 4.18 (m, 1H), 4.04-3.90 (m, 2H), 3.72 (m, 1H), 3.30-3.20 (m, 2H), 3.28 (m, 1H), 2.68 (m, 1H), 2.52-1.86 (m, 5H), 1.80-1.60 (m, 7H), 1.38-1.10 (m, 3H), 1.02-0.82 (m, 2H).

EXAMPLE 50(5)

(3R*)-1-(2-butynyl)-2,5-dioxo-3-((1R*)-1-hydroxy-1-cyclohexylmethyl)-9-(4-(4-methylphenyloxy)phenylmethyl)-1,4,9-triazaspiro[5.5]undecane.hydrochloride TLC: Rf 0.45 (chloroform:methanol=10:1); NMR (CD$_3$OD): δ 7.50 (d, J=8.4 Hz, 2H), 7.20 (d, J=8.7 Hz, 2H), 7.01 (d, J=8.7 Hz, 2H), 6.92 (d, J=8.4 Hz, 2H), 4.40-4.28 (m, 3H), 4.18 (m, 1H), 4.04-3.88 (m, 2H), 3.74 (m, 1H), 3.52-3.40 (m, 2H), 3.26 (m, 1H), 2.64 (m, 1H), 2.54-1.86 (m, 5H), 2.33 (s, 3H), 1.80-1.62 (m, 7H), 1.38-1.10 (m, 3H), 1.02-0.82 (m, 2H).

EXAMPLE 50(6)

(3R*)-1-(2-butynyl)-2,5-dioxo-3-((1R*)-1-hydroxy-1-cyclohexylmethyl)-9-(1,4-benzodioxan-6-ylmethyl)-1,4,9-triazaspiro[5.5]undecane.hydrochloride

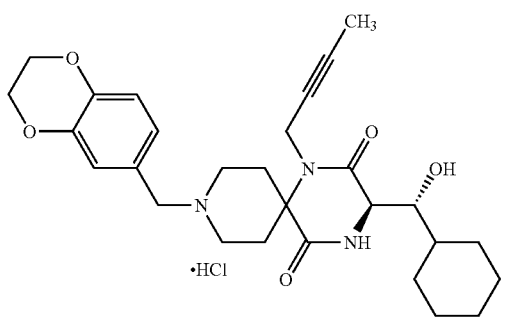

TLC: Rf 0.33 (chloroform:methanol=10:1); NMR (CD$_3$OD): δ 7.04 (s, 1H), 6.99-6.91 (m, 2H), 4.35 (m, 1H), 4.27 (s, 4H), 4.24 (s, 2H), 4.18 (m, 1H), 4.04-3.84 (m, 2H), 3.70 (m, 1H), 3.56-3.38 (m, 2H), 3.28 (m, 1H), 2.68-1.88 (m, 6H), 1.80-1.60 (m, 7H), 1.40-1.10 (m, 3H), 1.02-0.80 (m, 2H).

EXAMPLE 51

(3R*)-1-(2-butynyl)-2,5-dioxo-3-((1R*)-1-hydroxy-2-methylpropyl)-1,4,9-triazaspiro[5.5]undecane.acetate

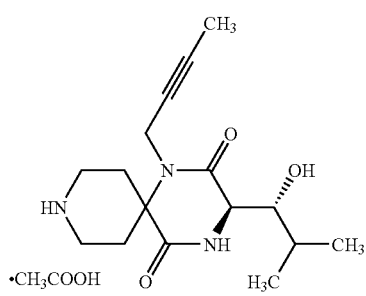

By the same procedure as described in Example 48→Example 49 using (2R*,3R*)-N-(t-butyloxycarbonyl)-2-amino-3-hydroxy-4-methylpentanoic acid instead of (2R*,3R*)-N-(t-butyloxycarbonyl)-2-amino-3-hydroxy-3-cyclohexylpropanoic acid, the compound of the present invention having the following physical data was obtained.

TLC: Rf 0.22 (chloroform:methanol:acetic acid=20:6:1); NMR (CD$_3$OD): δ 4.36 (dq, J=17.0, 2.5 Hz, 1H), 4.19 (d, J=2.0 Hz, 1H), 3.95-3.79 (m, 2H), 3.62 (dt, J=3.5, 13.0 Hz, 1H), 3.34-3.26 (m, 2H), 3.22 (dd, J=9.5, 2.0 Hz, 1H); 2.54-2.43 (m, 1H), 2.37 (m, 1H), 2.20-1.98 (m, 3H), 1.91 (s, 3H), 1.75 (t, J=2.5 Hz, 3H), 1.01-0.97 (m, 6H).

EXAMPLE 52(1) TO 52(5)

By the same procedure as described in Example 10 using the compound prepared in Example 51 and the corresponding aldehyde compounds, the following compounds of the present invention were obtained.

EXAMPLE 52(1)

(3R*)-1-(2-butynyl)-2,5-dioxo-3-((1R*)-1-hydroxy-2-methylpropyl)-9-(3,5-dimethyl-1-(4-methylphenyl)pyrazol-4-ylmethyl)-1,4,9-triazaspiro[5.5]undecane.hydrochloride

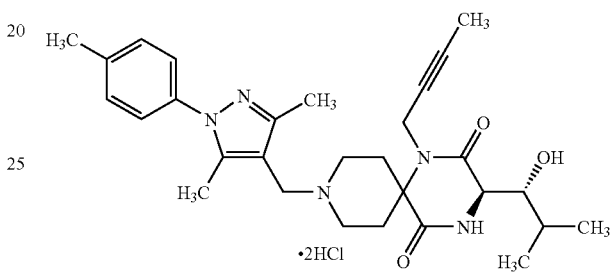

TLC: Rf 0.28 (chloroform:methanol=10:1); NMR (CD$_3$OD): δ 7.38 (d, J=3.9 Hz, 2H), 7.35 (d, J=3.9 Hz, 2H), 4.33 (s, 2H), 4.20 (d, J=2.1 Hz, 1H), 4.10-3.90 (m, 2H), 3.78 (m, 1H), 3.68-3.52 (m, 2H), 3.22 (dd, J=9.3, 2.1 Hz, 1H), 2.74 (m, 1H), 2.54-2.20 (m, 3H), 2.44 (s, 3H), 2.40 (s, 3H), 2.36 (s, 3H), 1.98 (m, 1H), 1.75 (t, J=2.1 Hz, 3H), 1.01 (d, J=6.6 Hz, 3H), 0.99 (d, J=6.6 Hz, 3H).

EXAMPLE 52(2)

(3R*)-1-(2-butynyl)-2,5-dioxo-3-((1R*)-1-hydroxy-2-methylpropyl)-9-(4-(4-methylphenyloxy)phenylmethyl)-1,4,9-triazaspiro[5.5]undecane.hydrochloride

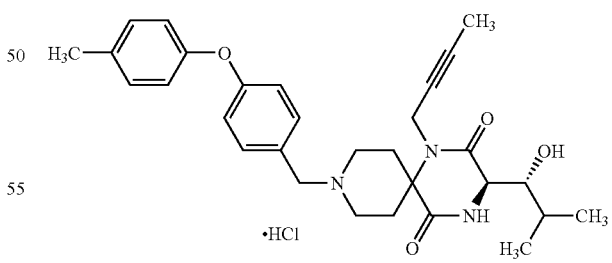

TLC: Rf 0.26 (chloroform:methanol=10:1); NMR (CD$_3$OD): δ 7.49 (d, J=9.0 Hz, 2H), 7.21 (d, J=8.4 Hz, 2H), 7.04 (d, J=9.0 Hz, 2H), 6.93 (d, J=8.4 Hz, 2H), 4.40 (m, 1H), 4.34 (s, 2H), 4.19 (d, J=2.1 Hz, 1H), 4.08-3.82 (m, 2H), 3.76 (m, 1H), 3.58-3.40 (m, 2H), 3.20 (dd, J=9.6, 2.1 Hz, 1H), 2.72-2.42 (m, 2H), 2.35 (s, 3H), 2.35-2.18 (m, 2H), 2.00 (m, 1H), 1.74 (t, J=2.1 Hz, 3H), 1.00 (d, J=6.6 Hz, 3H), 0.98 (d, J=6.6 Hz, 3H).

EXAMPLE 52(3)

(3R*)-1-(2-butynyl)-2,5-dioxo-3-((1R*)-1-hydroxy-2-methylpropyl)-9-(1,4-benzodioxan-6-ylmethyl)-1,4,9-triazaspiro[5.5]undecane.hydrochloride

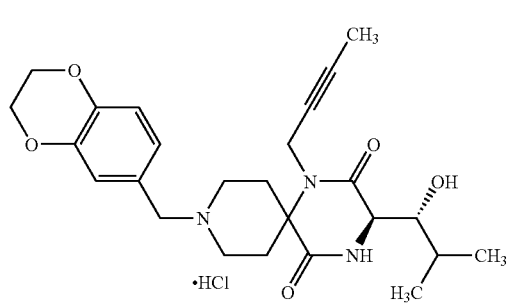

TLC: Rf 0.34 (chloroform:methanol=10:1); NMR (CD$_3$OD): δ 7.06-6.92 (m, 3H), 4.38 (m, 1H), 4.28 (s, 4H), 4.25 (s, 2H), 4.19 (d, J=2.1 Hz, 1H), 4.02-3.84 (m, 2H), 3.70 (m, 1H), 3.52-3.36 (m, 2H), 3.20 (dd, J=9.6, 2.1 Hz, 1H), 2.60 (m, 1H), 2.48 (m, 1H), 2.32-2.16 (m, 2H), 2.00 (m, 1H), 1.74 (t, J=2.1 Hz, 3H), 1.00 (d, J=6.6 Hz, 3H), 0.98 (d, J=6.6 Hz, 3H).

EXAMPLE 52(4)

(3R*)-1-(2-butynyl)-2,5-dioxo-3-((1R*)-1-hydroxy-2-methylpropyl)-9-(4-isopropylphenylmethyl)-1,4,9-triazaspiro[5.5]undecane.hydrochloride

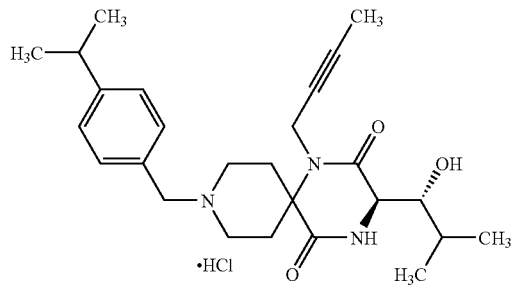

TLC: Rf 0.29 (chloroform:methanol=10:1); NMR (CD$_3$OD): δ 7.47 (d, J=8.1 Hz, 2H), 7.38 (d, J=8.1 Hz, 2H), 4.40 (m, 1H), 4.33 (s, 2H), 4.19 (d, J=2.1 Hz, 1H), 4.08-3.84 (m, 2H), 3.76 (m, 1H), 3.52-3.40 (m, 2H), 3.20 (dd, J=9.6, 2.1 Hz, 1H), 2.96 (m, 1H), 2.62 (m, 1H), 2.48 (m, 1H), 2.36-2.12 (m, 2H), 2.00 (m, 1H), 1.74 (t, J=2.1 Hz, 3H), 1.24 (d, J=7.2 Hz, 6H), 1.00 (d, J=6.6 Hz, 3H), 0.98 (d, J=6.6 Hz, 3H).

EXAMPLE 52(5)

(3R*)-1-(2-butynyl)-2,5-dioxo-3-((1R*)-1-hydroxy-2-methylpropyl)-9-(4-phenyloxyphenylmethyl)-1,4,9-triazaspiro[5.5]undecane.hydrochloride

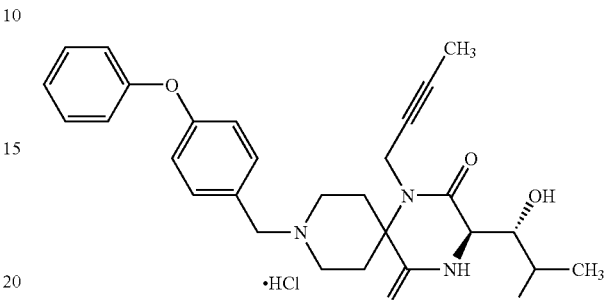

TLC: Rf 0.24 (chloroform:methanol=10:1); NMR (CD$_3$OD): δ 7.52 (d, J=9.0 Hz, 2H), 7.41 (t, J=7.2 Hz, 2H), 7.19 (t, J=7.2 Hz, 1H), 7.09-7.03 (m, 4H), 4.40 (m, 1H), 4.35 (s, 2H), 4.19 (d, J=2.1 Hz, 1H), 4.08-3.84 (m, 2H), 3.78 (m, 1H), 3.58-3.42 (m, 2H), 3.21 (dd, J=9.6, 2.1 Hz, 1H), 2.72-2.42 (m, 2H), 2.38-2.18 (m, 2H), 2.00 (m, 1H), 1.74 (t, J=2.1 Hz, 3H), 1.00 (d, J=6.6 Hz, 3H), 0.98 (d, J=6.6 Hz, 3H).

EXAMPLE 53

(3R*)-1-butyl-2,5-dioxo-3-((1S*)-1-hydroxy-1-cyclohexylmethyl)-9-benzyl-1,4,9-triazaspiro[5.5]undecane

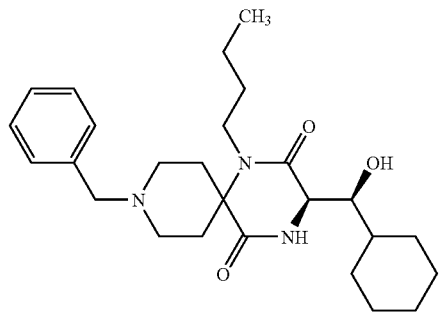

By the same procedure as described in Reference Example 3→Reference Example 6→Example 1 using Resin (3) prepared in Reference Example 2, N-benzyl-4-piperidone, n-butylamine, (2R*,3S*)-N-(t-butyloxycarbonyl)-2-amino-3-hydroxy-3-cyclohexylpropanoic acid, the compound of the present invention having the following physical data was obtained.

TLC: Rf 0.33 (chloroform:methanol=10:1); NMR (CD$_3$OD): δ 7.40-7.20 (m, 5H), 4.04 (d, J=1.5 Hz, 1H), 3.65-3.45 (m, 2H), 3.57 (s, 2H), 3.30 (m, 1H), 3.05 (m 1H), 2.86-2.77 (m, 3H), 2.30-2.00 (m, 4H), 1.90-1.60 (m, 6H), 1.60-1.10 (m, 9H), 1.10-0.90 (m, 2H), 0.95 (t, J=7.2 Hz, 3H).

EXAMPLE 54

(3R*)-1-butyl-2,5-dioxo-3-((1S*)-1-hydroxy-1-cyclohexylmethyl)-1,4,9-triazaspiro[5.5]undecane.hydrochlorde

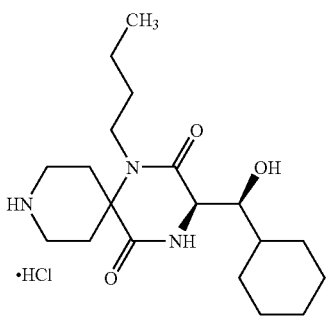

By the same procedure as described in Example 9 using the compound prepared in Example 53, the compound of the present invention having the following physical data was obtained.

TLC: Rf 0.59 (chloroform:methanol:acetic acid=10:2:1); NMR (CD$_3$OD): δ 4.08 (d, J=1.5 Hz, 1H), 4.03 (m, 1H), 3.70-3.12 (m, 7H), 2.50-2.02 (m, 5H), 1.85-1.66 (m, 5H), 1.55-1.10 (m, 7H), 1.10-0.85 (m, 2H), 0.97 (t, J=6.9 Hz, 3H).

EXAMPLE 55(1) TO 55(3)

By the same procedure as described in Example 10 using the compound prepared in Example 54 and the corresponding aldehyde compounds, the following compounds of the present invention were obtained.

EXAMPLE 55(1)

(3R*)-1-butyl-2,5-dioxo-3-((1S*)-1-hydroxy-1-cyclohexylmethyl)-9-(4-phenyloxyphenylmethyl)-1,4,9-triazaspiro[5.5]undecane.hydrochloride

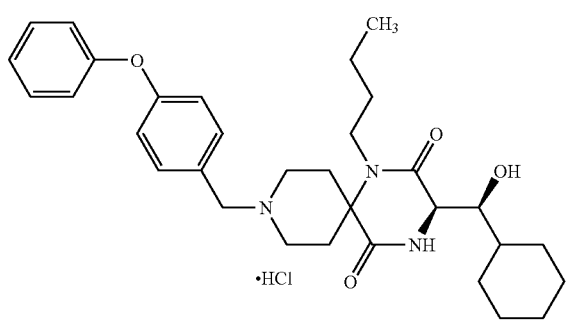

TLC: Rf 0.46 (chloroform:methanol=10:1); NMR (CD$_3$OD): δ 7.50 (d, J=8.7 Hz, 2H), 7.39 (dd, J=8.7, 7.5 Hz, 2H), 7.17 (t, J=7.5 Hz, 1H), 7.09-7.00 (m, 4H), 4.30 (brs, 2H), 4.08 (d, J=1.2 Hz, 1H), 4.04 (m, 1H), 3.74-3.36 (m, 5H), 3.16 (m, 1H), 2.55-2.33 (m, 2H), 2.32-2.09 (m, 2H), 2.04 (m, 1H), 1.84-1.61 (m, 5H), 1.53-1.12 (m, 7H), 1.04-0.86 (m, 5H).

EXAMPLE 55(2)

(3R*)-1-butyl-2,5-dioxo-3-((1S*)-1-hydroxy-1-cyclohexylmethyl)-9-(1,4-benzodioxan-6-ylmethyl)-1,4,9-triazaspiro[5.5]undecane.hydrochloride

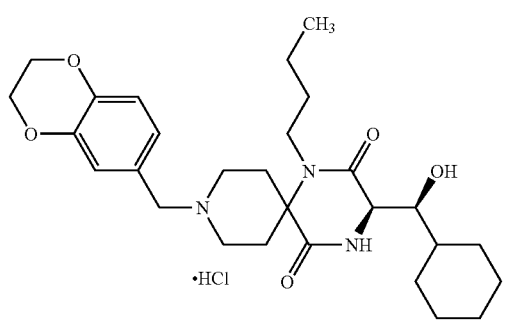

TLC: Rf 0.41 (chloroform:methanol=10:1); NMR (CD$_3$OD): δ 7.04 (d, J=2.1 Hz, 1H), 6.97 (dd, J=8.1, 2.1 Hz, 1H), 6.92 (d, J=8.1 Hz, 1H), 4.26 (s, 4H), 4.21 (s, 2H), 4.07 (d, J=1.2 Hz, 1H), 4.01 (m, 1H), 3.70-3.34 (m, 5H), 3.16 (m, 1H), 2.53-2.32 (m, 2H), 2.31-2.08 (m, 2H), 2.03 (m, 1H), 1.84-1.60 (m, 5H), 1.52-1.12 (m, 7H), 1.04-0.85 (m, 5H).

EXAMPLE 55(3)

(3R*)-1-butyl-2,5-dioxo-3-((1S*)-1-hydroxy-1-cyclohexylmethyl)-9-(3,5-dimethyl-1-phenylpyrazol-4-ylmethyl)-1,4,9-triazaspiro[5.5]undecane.2 hydrochloride

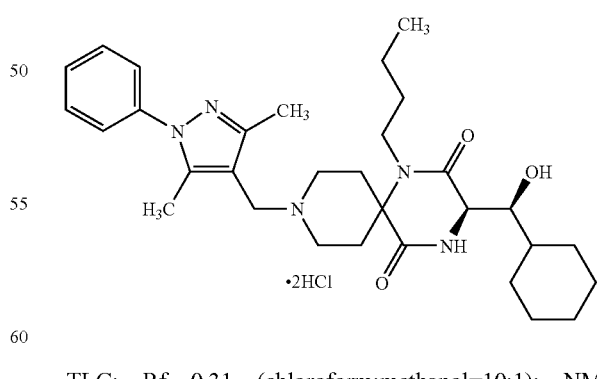

TLC: Rf 0.31 (chloroform:methanol=10:1); NMR (CD$_3$OD): δ 7.61-7.44 (m, 5H), 4.31 (s, 2H), 4.19-4.06 (m, 2H), 3.73 (m, 1H), 3.66-3.52 (m, 4H), 3.26 (m, 1H), 2.62-2.48 (m, 2H), 2.45-2.30 (m, 7H), 2.19 (m, 1H), 2.04 (m, 1H), 1.84-1.63 (m, 5H), 1.54-1.12 (m, 7H), 1.05-0.86 (m, 5H).

EXAMPLE 56

(3S)-1-butyl-2,5-dioxo-3-((1S)-1-hydroxy-2-methyl-propyl)-1,4,9-triazaspiro[5.5]undecane.hydrochloride

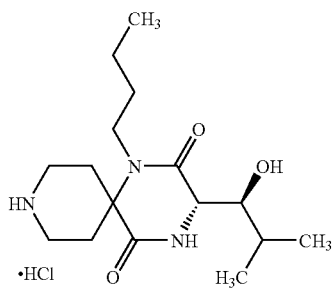

By the same procedure as described in Example 42→Example 43 using (2S,3S)-N-(t-butyloxycarbonyl)-2-amino-3-hydroxy-4-methylpentanoic acid instead of (2R*,3R*)-N-(t-butyloxycarbonyl)-2-amino-3-hydroxy-4-methylpentanoic acid, the compound of the present invention having the following physical data was obtained.

TLC: Rf 0.08 (chloroform:methanol=10:1); NMR (CD$_3$OD): δ 4.15 (d, J=2.0 Hz, 1H), 3.96 (dt, J=13.0, 4.0 Hz, 1H), 3.71 (dt, J=13.0, 4.0 Hz, 1H), 3.57-3.47 (m, 1H), 3.40-3.34 (m, 2H), 3.23-3.12 (m, 2H), 2.47-2.30 (m, 2H), 2.25-1.98 (m, 3H), 1.79-1.66 (m, 1H), 1.52-1.28 (m, 3H), 1.07-0.94 (m, 9H); Optical rotation: [α]$_D$ –13.8 (c 1.00, methanol).

EXAMPLE 57(1) TO 57(4)

By the same procedure as described in Example 10 using the compound prepared in Example 56 and the corresponding aldehyde compounds, the following compounds of the present invention were obtained.

EXAMPLE 57(1)

(3S)-1-butyl-2,5-dioxo-3-((1S)-1-hydroxy-2-methyl-propyl)-9-(3,5-dimethyl 1-phenylpyrazol-4-ylmethyl)-1,4,9-triazaspiro[5;5]undecane.2 hydrochloride

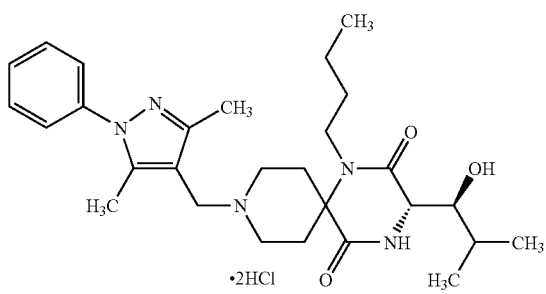

TLC: Rf 0.43 (chloroform:methanol=10:1); NMR (CD$_3$OD): δ 7.61-7.43 (m, 5H), 4.32 (s, 2H), 4.16 (d, J=2.1 Hz, 1H), 4.12-3.99 (m, 1H), 3.90-3.72 (m, 1H), 3.64-3.44 (m, 3H), 3.30-3.12 (m, 1H), 3.20 (dd, J=9.3, 2.1 Hz, 1H), 2.60-2.30 (m, 9H), 2.24-2.10 (m, 1H), 2.10-1.95 (m, 1H), 1.78-1.60 (m, 1H), 1.54-1.30 (m, 3H), 1.00 (d, J=6.6 Hz, 3H), 0.98 (d, J=6.6 Hz, 3H), 0.96 (t, J=6.9 Hz, 3H).

EXAMPLE 57(2)

(3S)-1-butyl-2,5-dioxo-3-((1S)-1-hydroxy-2-methyl-propyl)-9-(4-phenyloxyphenylmethyl)-1,4,9-triazaspiro[5.5]undecane.hydrochloride

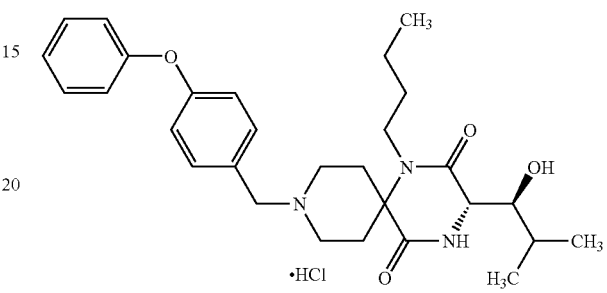

TLC: Rf 0.51 (chloroform:methanol=10:1); NMR (CD$_3$OD): δ 7.52 (d, J=8.7 Hz, 2H), 7.43-7.36 (m, 2H), 7.21-7.14 (m, 1H), 7.10-7.00 (m, 4H), 4.33 (s, 2H), 4.14 (d, J=2.1 Hz, 1H), 4.06-3.92 (m, 1H), 3.81-3.66 (m, 1H), 3.58-3.40 (m, 3H), 3.30-3.10 (m, 1H), 3.19 (dd, J=9.6, 2.1 Hz, 1H), 2.53-2.37 (m, 2H), 2.37-2.18 (m, 1H), 2.18-2.08 (m, 1H), 2.06-1.95 (m, 1H), 1.78-1.60 (m, 1H), 1.50-1.26 (m, 3H), 0.99 (d, J=6.6 Hz, 3H), 0.97 (d, J=6.6 Hz, 3H), 0.95 (t, J=7.2 Hz, 3H).

EXAMPLE 57(3)

(3S)-1-butyl-2,5-dioxo-3-((1S)-1-hydroxy-2-methyl-propyl)-9-(1,4-benzodioxan-6-ylmethyl)-1,4,9-triazaspiro[5.5]undecane.hydrochloride

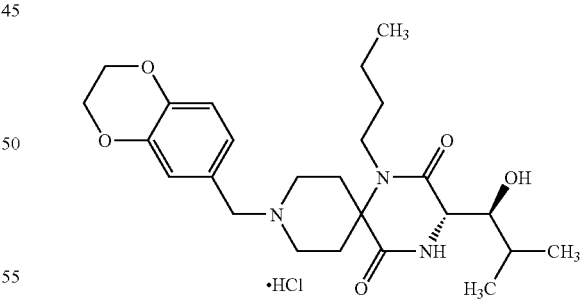

TLC: Rf 0.43 (chloroform:methanol=10:1); NMR (CD$_3$OD): δ 7.06 (d, J=2.1 Hz, 1H), 6.98 (dd, J=8.1, 2.1 Hz, 1H), 6.92 (d, J=8.1 Hz, 1H), 4.26 (s, 4H), 4.23 (s, 2H), 4.13 (d, J=2.4 Hz, 1H), 4.02-3.87 (m, 1H), 3.77-3.62 (m, 1H), 3.57-3.35 (m, 3H), 3.28-3.08 (m, 1H), 3.19 (dd, J=9.6, 2.4 Hz, 1H), 2.51-2.35 (m, 2H), 2.35-2.18 (m, 1H), 2.17-2.05 (m, 1H), 2.05-1.90 (m, 1H), 1.80-1.58 (m, 1H), 1.50-1.26 (m, 3H), 0.98 (d, J=6.6 Hz, 3H), 0.97 (d, J=6.6 Hz, 3H), 0.95 (t, J=7.2 Hz, 3H).

EXAMPLE 57(4)

(3S)-1-butyl-2,5-dioxo-3-((1S)-1-hydroxy-2-methyl-propyl)-9-(4-(4-methylsulfonylaminophenyloxy)phenylmethyl)-1,4,9-triazaspiro[5.5]undecane.hydrochloride

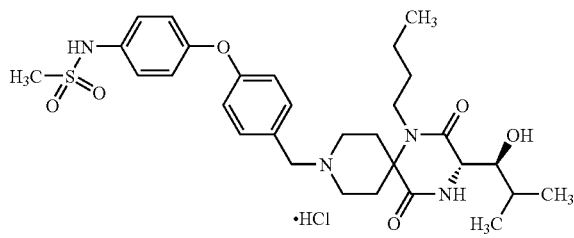

TLC: Rf 0.35 (chloroform:methanol=10:1); NMR (CD$_3$OD): δ 7.53 (d, J=8.7 Hz, 2H), 7.29 (d, J=9.0 Hz, 2H), 7.10-7.00 (m, 4H), 4.33 (s, 2H), 4.14 (d, J=2.1 Hz, 1H), 4.06-3.92 (m, 1H), 3.81-3.66 (m, 1H), 3.58-3.40 (m, 3H), 3.25-3.10 (m, 1H), 3.19 (dd, J=9.6, 2.1 Hz, 1H), 2.95 (s, 3H), 2.54-2.37 (m, 2H), 2.37-2.22 (m, 1H), 2.18-2.08 (m, 1H), 2.08-1.92 (m, 1H), 1.78-1.60 (m, 1H), 1.50-1.28 (m, 3H), 0.99 (d, J=6.6 Hz, 3H), 0.97 (d, J=6.6 Hz, 3H), 0.95 (t, J=7.5 Hz, 3H).

EXAMPLE 58

(3R)-1-butyl-2,5-dioxo-3-((1R)-1-hydroxy-2-methylpropyl)-1,4,9-triazaspiro[5.5]undecane.hydrochloride

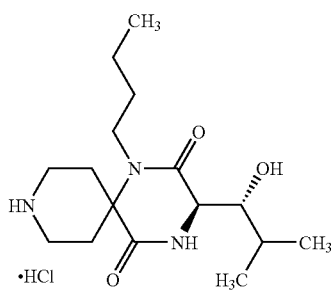

By the same procedure as described in Example 42→Example 43 using (2R,3R)-N-(t-butyloxycarbonyl)-2-amino-3-hydroxy-4-methylpentanoic acid instead of (2R*,3R*)-N-(t-butyloxycarbonyl)-2-amino-3-hydroxy-4-methylpentanoic acid, the compound of the present invention having the following physical data was obtained.

TLC: Rf 0.08 (chloroform:methanol=10:1); NMR (CD$_3$OD): δ 4.15 (d, J=2.0 Hz, 1H), 3.96 (dt, J=13.0, 4.0 Hz, 1H), 3.71 (dt, J=13.0, 4.0 Hz, 1H), 3.57-3.47 (m, 1H), 3.40-3.34 (m, 2H), 3.23-3.12 (m, 2H), 2.47-2.30 (m, 2H), 2.25-1.98 (m, 3H), 1.79-1.66 (m, 1H), 1.52-1.28 (m, 3H), 1.07-0.94 (m, 9H); Optical rotation: [α]$_D$+13.9 (c 1.00, methanol).

EXAMPLE 59(1) TO 59(4)

By the same procedure as described in Example 10 using the compound prepared in Example 58 and the corresponding aldehyde compounds, the following compounds of the present invention were obtained.

EXAMPLE 59(1)

(3R)-1-butyl-2,5-dioxo-3-((1R)-1-hydroxy-2-methylpropyl)-9-(3,5-dimethyl-1-phenylpyrazol-4-ylmethyl)-1,4,9-triazaspiro[5.5]undecane.2 hydrochloride

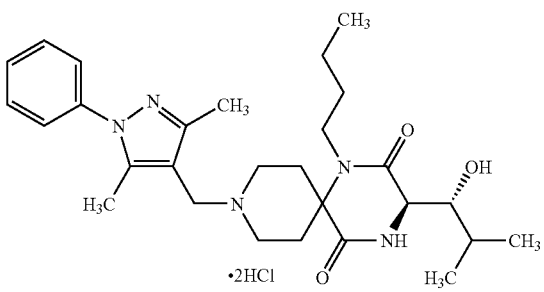

TLC: Rf 0.43 (chloroform:methanol=10:1); NMR (CD$_3$OD): δ 7.61-7.43 (m, 5H), 4.32 (s, 2H), 4.16 (d, J=2.1 Hz, 1H), 4.12-3.99 (m, 1H), 3.90-3.72 (m, 1H), 3.64-3.44 (m, 3H), 3.30-3.12 (m, 1H), 3.20 (dd, J=9.3, 2.1 Hz, 1H), 2.60-2.30 (m, 9H), 2.24-2.10 (m, 1H), 2.10-1.95 (m, 1H), 1.78-1.60 (m, 1H), 1.54-1.30 (m, 3H), 1.00 (d, J=6.6 Hz, 3H), 0.98 (d, J=6.6 Hz, 3H), 0.96 (t, J=6.9 Hz, 3H).

EXAMPLE 59(2)

(3R)-1-butyl-2,5-dioxo-3-((1R)-1-hydroxy-2-methylpropyl)-9-(4-phenyloxyphenylmethyl)-1,4,9-triazaspiro[5.5]undecane.hydrochloride

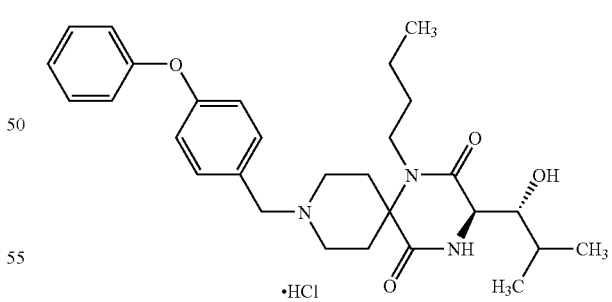

TLC: Rf 0.51 (chloroform:methanol=10:1); NMR (CD$_3$OD): δ 7.52 (d, J=8.7 Hz, 2H), 7.43-7.36 (m, 2H), 7.21-7.14 (m, 1H), 7.10-7.00 (m, 4H), 4.33 (s, 2H), 4.14 (d, J=2.1 Hz, 1H), 4.06-3.92 (m, 1H), 3.81-3.66 (m, 1H), 3.58-3.40 (m, 3H), 3.30-3.10 (m, 1H), 3.19 (dd, J=9.6, 2.1 Hz, 1H), 2.53-2.37 (m, 2H), 2.37-2.18 (m, 1H), 2.18-2.08 (m, 1H), 2.06-1.95 (m, 1H), 1.78-1.60 (m, 1H), 1.50-1.26 (m, 3H), 0.99 (d, J=6.6 Hz, 3H), 0.97 (d, J=6.6 Hz, 3H), 0.95 (t, J=7.2 Hz, 3H).

EXAMPLE 59(3)

(3R)-1-butyl-2,5-dioxo-3-((1R)-1-hydroxy-2-methylpropyl)-9-(1,4-benzodioxan-6-ylmethyl)-1,4,9-triazaspiro[5.5]undecane.hydrochloride

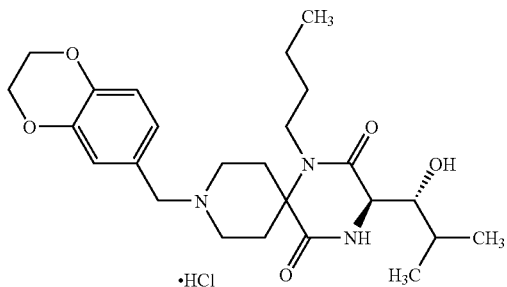

TLC: Rf 0.43 (chloroform:methanol=10:1); NMR (CD$_3$OD): δ 7.06 (d, J=2.1 Hz, 1H), 6.98 (dd, J=8.1, 2.1 Hz, 1H), 6.92 (d, J=8.1 Hz, 1H), 4.26 (s, 4H), 4.23 (s, 2H), 4.13 (d, J=2.4 Hz, 1H), 4.02-3.87 (m, 1H), 3.77-3.62 (m, 1H), 3.57-3.35 (m, 3H), 3.28-3.08 (m, 1H), 3.19 (dd, J=9.6, 2.4 Hz, 1H), 2.51-2.35 (m, 2H), 2.35-2.18 (m, 1H), 2.17-2.05 (m, 1H), 2.05-1.90 (m, 1H), 1.80-1.58 (m, 1H), 1.50-1.26 (m, 3H), 0.98 (d, J=6.6 Hz, 3H), 0.97 (d, J=6.6 Hz, 3H), 0.95 (t, J=7.2 Hz, 3H).

EXAMPLE 59(4)

(3R)-1-butyl-2,5-dioxo-3-((1R)-1-hydroxy-2-methylpropyl)-9-(4-(4-methylsulfonylaminophenyloxy)phenylmethyl)-1,4,9-triazaspiro[5.5]undecane.hydrochloride

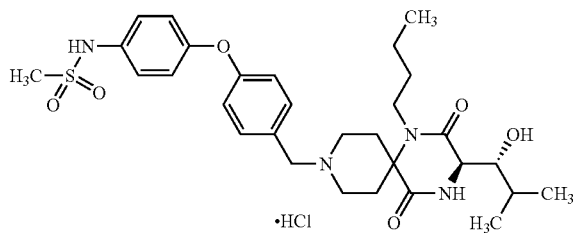

TLC: Rf 0.35 (chloroform:methanol=10:1); NMR (CD$_3$OD): δ 7.53 (d, J=8.7 Hz, 2H), 7.29 (d, J=9.0 Hz, 2H), 7.10-7.00 (m, 4H), 4.33 (s, 2H), 4.14 (d, J=2.1 Hz, 1H), 4.06-3.92 (m, 1H), 3.81-3.66 (m, 1H), 3.58-3.40 (m, 3H), 3.25-3.10 (m, 1H), 3.19 (dd, J=9.6, 2.1 Hz, 1H), 2.95 (s, 3H), 2.54-2.37 (m, 2H), 2.37-2.22 (m, 1H), 2.18-2.08 (m, 1H), 2.08-1.92 (m, 1H), 1.78-1.60 (m, 1H), 1.50-1.28 (m, 3H), 0.99 (d, J=6.6 Hz, 3H), 0.97 (d, J=6.6 Hz, 3H), 0.95 (t, J=7.5 Hz, 3H).

EXAMPLE 60

(3R)-1-butyl-2,5-dioxo-3-((1S)-1-hydroxy-2-methylpropyl)-1,4,9-triazaspiro[5.5]undecane.hydrochloride

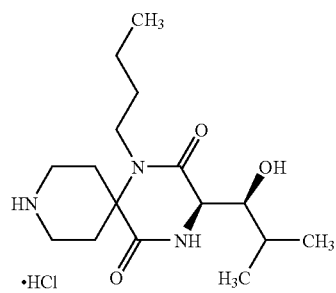

By the same procedure as described in Example 53→Example 54 using (2R,3S)-N-(t-butyloxycarbonyl)-2-amino-3-hydroxy-4-methylpentanoic acid instead of (2R*, 3S*)-N-(t-butyloxycarbonyl)-2-amino-3-hydroxy-3-cyclohexylpropanoic acid, the compound of the present invention having the following physical data was obtained.

TLC: Rf 0.51 (chloroform:methanol:acetic acid=10:2:1); NMR (CD$_3$OD): δ 4.08 (d, J=1.5 Hz, 1H), 4.02 (dt, J=12.6, 3.9 Hz, 1H), 3.70-3.00 (m, 6H), 2.50-2.10 (m, 4H), 1.80-1.60 (m, 2H), 1.55-1.35 (m, 3H), 1.02 (d, J=6.6 Hz, 3H), 0.99 (t, J=6.6 Hz, 3H), 0.93 (d, J=6.6 Hz, 3H); Optical rotation: [α]$_D$+21.2 (c 1.00, methanol).

EXAMPLE 61(1) TO 61(3)

By the same procedure as described in Example 10 using the compound prepared in Example 60 and the corresponding aldehyde compounds, the following compounds of the present invention were obtained.

EXAMPLE 61 (1)

(3R)-1-butyl-2,5-dioxo-3-((1S)-1-hydroxy-2-methylpropyl)-9-(3,5-dimethyl-1-phenylpyrazol-4-ylmethyl)-1,4,9-triazaspiro[5.5]undecane.2 hydrochloride

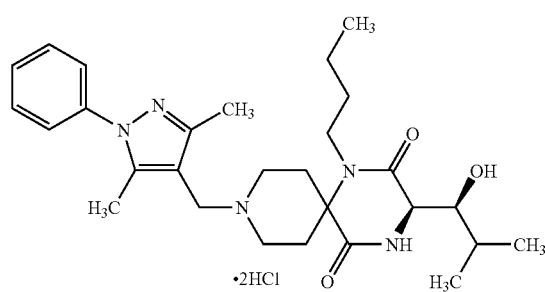

TLC: Rf 0.44 (chloroform:methanol=10:1); NMR (CD$_3$OD): δ 7.64-7.46 (m, 5H), 4.32 (s, 2H), 4.19-4.06 (m, 1H), 4.10 (d, J=1.5 Hz, 1H), 3.80-3.53 (m, 4H), 3.51 (dd, J=10.2, 1.5 Hz, 1H), 3.40-3.20 (m, 1H), 2.70-2.30 (m, 9H), 2.23-2.10 (m, 1H), 1.83-1.60 (m, 2H), 1.53-1.30 (m, 3H), 1.02 (d, J=6.6 Hz, 3H), 0.96 (t, J=7.2 Hz, 3H), 0.93 (d, J=6.6 Hz, 3H).

EXAMPLE 61(2)

(3R)-1-butyl-2,5-dioxo-3-((1S)-1-hydroxy-2-methyl-propyl)-9-(1,4-benzodioxan-6-ylmethyl)-1,4,9-triazaspiro[5.5]undecane.hydrochloride

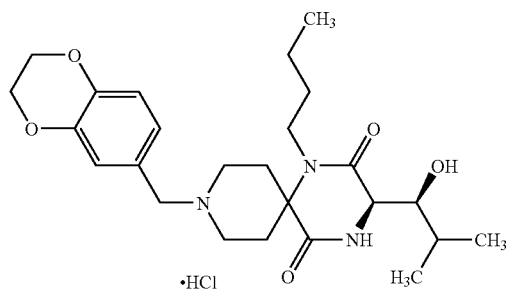

TLC: Rf 0.44 (chloroform:methanol=10:1); NMR (CD$_3$OD): δ 7.06 (d, J=2.1 Hz, 1H), 6.98 (dd, J=8.1, 2.1 Hz, 1H), 6.92 (d, J=8.1 Hz, 1H), 4.26 (s, 4H), 4.23 (s, 2H), 4.08 (d, J=1.5 Hz, 1H), 4.08-3.96 (m, 1H), 3.72-3.35 (m, 4H), 3.49 (dd, J=10.2, 1.5 Hz, 1H), 3.28-3.08 (m, 1H), 2.55-2.35 (m, 2H), 2.35-2.18 (m, 1H), 2.18-2.08 (m, 1H), 1.82-1.62 (m, 2H), 1.52-1.25 (m, 3H), 1.01 (d, J=6.6 Hz, 3H), 0.95 (t, J=7.2 Hz, 3H), 0.92 (d, J=6.6 Hz, 3H).

EXAMPLE 61(3)

(3R)-1-butyl-2,5-dioxo-3-((1S)-1-hydroxy-2-methyl-propyl)-9-(4-(4-methylsulfonylaminophenyloxy)phenylmethyl)-1,4,9-triazaspiro[5.5]undecane.hydrochloride

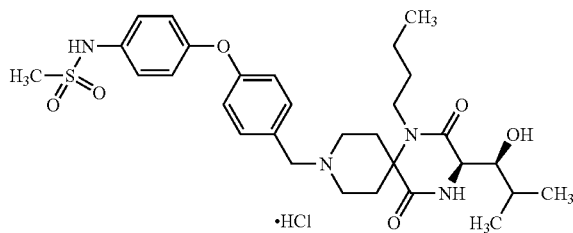

TLC: Rf 0.42 (chloroform:methanol=10:1); NMR (CD$_3$OD): δ 7.53 (d, J=8.7 Hz, 2H), 7.29 (d, J=9.0 Hz, 2H), 7.07 (d, J=8.7 Hz, 2H), 7.03 (d, J=9.0 Hz, 2H), 4.33 (s, 2H), 4.13-4.00 (m, 1H), 4.09 (d, J=1.5 Hz, 1H), 3.75-3.62 (m, 1H), 3.62-3.39 (m, 3H), 3.49 (dd, J=10.5, 1.5 Hz, 1H), 3.26-3.12 (m, 1H), 2.95 (s, 3H), 2.56-2.37 (m, 2H), 2.37-2.20 (m, 1H), 2.20-2.10 (m, 1H), 1.82-1.63 (m, 2H), 1.50-1.30 (m, 3H), 1.01 (d, J=6.6 Hz, 3H), 0.95 (t, J=7.2 Hz, 3H), 0.92 (d, J=6.6 Hz, 3H).

EXAMPLE 62

(3S)-1-butyl-2,5-dioxo-3-((1R)-1-hydroxy-2-methyl-propyl)-1,4,9-triazaspiro[5.5]undecane.hydrochloride

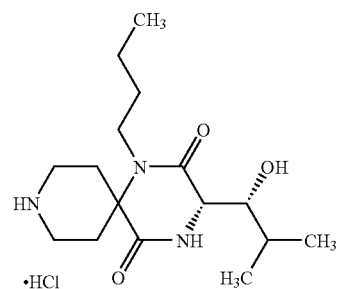

By the same procedure as described in Example 53→Example 54 using (2S,3R)-N-(t-butyloxycarbonyl)-2-amino-3-hydroxy-4-methylpentanoic acid instead of (2R*, 3S*)-N-(t-butyloxycarbonyl)-2-amino-3-hydroxy-3-cyclohexylpropanoic acid, the compound of the present invention having the following physical data was obtained.

TLC: Rf 0.51 (chloroform:methanol:acetic acid=10:2:1); NMR (CD$_3$OD): δ 4.08 (d, J=1.5 Hz, 1H), 4.02 (dt, J=12.6, 3.9 Hz, 1H), 3.70-3.00 (m, 6H), 2.50-2.10 (m, 4H), 1.80-1.60 (m, 2H), 1.55-1.35 (m, 3H), 1.02 (d, J=6.6 Hz, 3H), 0.99 (t, J=6.6 Hz, 3H), 0.93 (d, J=6.6 Hz, 3H); Optical rotation: [α]$_D$ −23.4 (c 1.00, methanol).

EXAMPLE 63(1) TO 63(3)

By the same procedure as described in Example 10 using the compound prepared in Example 62 and the corresponding aldehyde compounds, the following compounds of the present invention were obtained.

EXAMPLE 63(1)

(3S)-1-butyl-2,5-dioxo-3-((1R)-1-hydroxy-2-methyl-propyl)-9-(3,5-dimethyl-1-phenylpyrazol-4-ylmethyl)-1,4,9-triazaspiro[5.5]undecane.2 hydrochloride

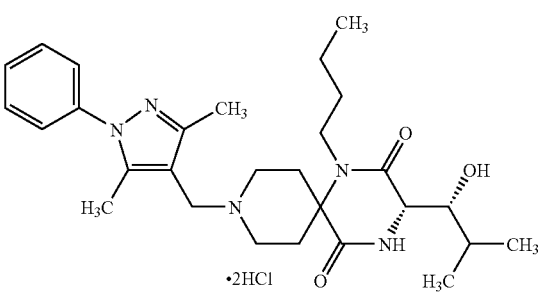

TLC: Rf 0.44 (chloroform:methanol=10:1); NMR (CD$_3$OD): δ 7.64-7.46 (m, 5H), 4.32 (s, 2H), 4.19-4.06 (m, 1H), 4.10 (d, J=1.5 Hz, 1H), 3.80-3.53 (m, 4H), 3.51 (dd, J=10.2, 1.5 Hz, 1H), 3.40-3.20 (m, 1H), 2.70-2.30 (m, 9H), 2.23-2.10 (m, 1H), 1.83-1.60 (m, 2H), 1.53-1.30 (m, 3H), 1.02 (d, J=6.6 Hz, 3H), 0.96 (t, J=7.2 Hz, 3H), 0.93 (d, J=6.6 Hz, 3H).

EXAMPLE 63(2)

(3S)-1-butyl-2,5-dioxo-3-((1R)-1-hydroxy-2-methylpropyl)-9-(1,4-benzodioxan-6-ylmethyl)-1,4,9-triazaspiro[5.5]undecane.hydrochloride

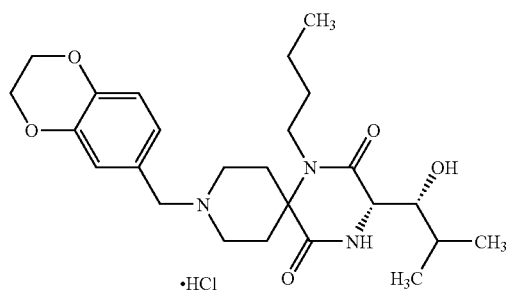

TLC: Rf 0.44 (chloroform:methanol=10:1); NMR (CD$_3$OD): δ 7.06 (d, J=2.1 Hz, 1H), 6.98 (dd, J=8.1, 2.1 Hz, 1H), 6.92 (d, J=8.1 Hz, 1H), 4.26 (s, 4H), 4.23 (s, 2H), 4.08 (d, J=1.5 Hz, 1H), 4.08-3.96 (m, 1H), 3.72-3.35 (m, 4H), 3.49 (dd, J=10.2, 1.5 Hz, 1H), 3.28-3.08 (m, 1H), 2.55-2.35 (m, 2H), 2.35-2.18 (m, 1H), 2.18-2.08 (m, 1H), 1.82-1.62 (m, 2H), 1.52-1.25 (m, 3H), 1.01 (d, J=6.6 Hz, 3H), 0.95 (t, J=7.2 Hz, 3H), 0.92 (d, J=6.6 Hz, 3H).

EXAMPLE 63(3)

(3S)-1-butyl-2,5-dioxo-3-((1R)-1-hydroxy-2-methylpropyl)-9-(4-(4-methylsulfonylaminophenyloxy)phenylmethyl)-1,4,9-triazaspiro[5.5]undecane.hydrochloride

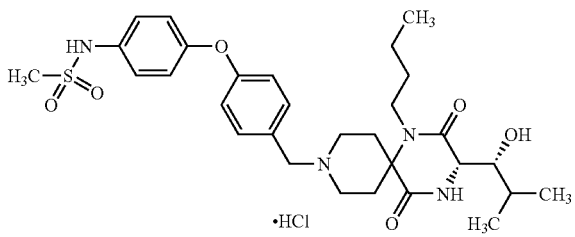

TLC: Rf 0.42 (chloroform:methanol=10:1); NMR (CD$_3$OD): δ 7.53 (d, J=8.7 Hz, 2H), 7.29 (d, J=9.0 Hz, 2H), 7.07 (d, J=8.7 Hz, 2H), 7.03 (d, J=9.0 Hz, 2H), 4.33 (s, 2H), 4.13-4.00 (m, 1H), 4.09 (d, J=1.5 Hz, 1H), 3.75-3.62 (m, 1H), 3.62-3.39 (m, 3H), 3.49 (dd, J=10.5, 1.5 Hz, 1H), 3.26-3.12 (m, 1H), 2.95 (s, 3H), 2.56-2.37 (m, 2H), 2.37-2.20 (m, 1H), 2.20-2.10 (m, 1H), 1.82-1.63 (m, 2H), 1.50-1.30 (m, 3H), 1.01 (d, J=6.6 Hz, 3H), 0.95 (t, J=7.2 Hz, 3H), 0.92 (d, J=6.6 Hz, 3H).

EXAMPLE 64

(3S)-2,5-dioxo-3-(3-benzyloxycarbonylaminopropyl)-9-(2-phenylethyl)-1,4,9-triazaspiro[5.5]undecane.hydrochloride

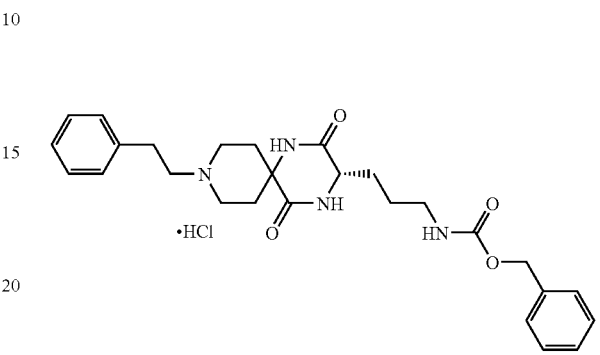

By the same procedure as described in Reference Example 9→Reference Example 10→Example 1 using Resin (3) prepared in Reference Example 2, N-(2-phenylethyl)-4-piperidone, 2,4,6-trimethoxybenzylamine and N$^α$-(t-butyloxycarbonyl)-Nδ-(benzyloxycarbonyl)-L-ornithine, the compound of the present invention having the following physical data was obtained.

TLC: Rf 0.33 (chloroform:methanol=10:1); NMR (DMSO-d$_6$): δ 10.80-10.00 (m, 1H), 8.65-8.45 (m, 1H), 8.33 (s, 1H), 7.50-7.20 (m, 10H), 5.01 (s, 2H), 4.01 (m, 1H), 3.70-3.45 (m, 3H), 3.45-3.20 (m, 3H), 3.15-2.90 (m, 4H), 2.50-2.30 (m, 2H), 2.10-1.90 (m, 1H), 1.87-1.60 (m, 3H), 1.60-1.35 (m, 2H).

EXAMPLE 65

(3S)-1-methyl-2,5-dioxo-3-(3-benzyloxycarbonylaminopropyl)-9-(2-phenylethyl)-1,4,9-triazaspiro[5.5]undecane.acetate

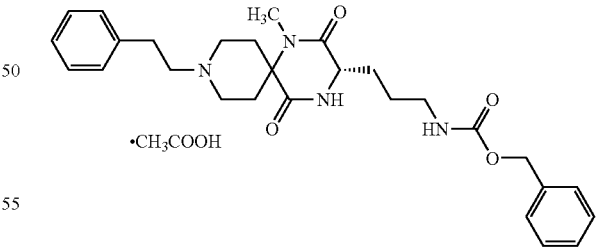

By the same procedure as described in Example 19 using Resin (3) prepared in Reference Example 2, N-(2-phenylethyl)-4-piperidone, methylamine and N$^α$-(t-butyloxycarbonyl)-N$^δ$-(benzyloxycarbonyl)-L-ornithine, the compound of the present invention having the following physical data was obtained.

TLC: Rf 0.36 (chloroform:methanol=10:1); MS (ESI, Pos., 40 V): 493(M+H)$^+$; HPLC condition: F; HPLC retention time: 3.36 min.

EXAMPLE 66

(3S)-1-butyl-2,5-dioxo-3-cyclohexylmethyl-9-(4-phenyloxyphenylmethyl)-9-oxido-1,4,9-triazaspiro[5.5]undecane

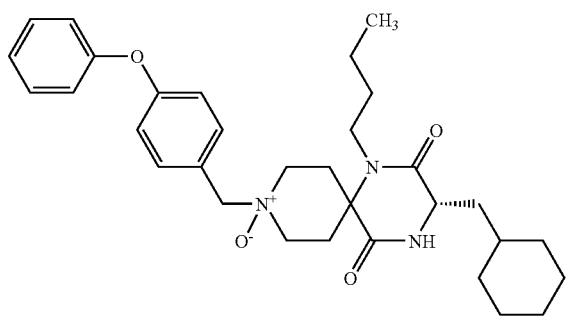

To a solution of the compound prepared in Example 40(90) (104 mg) in acetone (4 ml) were added water (1 ml), sodium hydrogen carbonate (210 mg) and OXONE (615 mg) (brand name). The reaction mixture was stirred for 1 hour at room temperature. The reaction mixture was diluted with ethyl acetate, washed with saturated aqueous solution of sodium hydrogen carbonate, and saturated aqueous solution of sodium chloride, dried over anhydrous magnesium sulfate, and concentrated. The residue was purified by preparative thin layer chromatography (chloroform:methanol=30:1, 20:1) to give the compound of the present invention (73 mg) having the following physical data.

TLC: Rf 0.50 (chloroform:methanol=9:1); NMR (CDCl$_3$): δ 7.49 (dt, J=8.7, 2.1 Hz, 2H), 7.36 (ddt, J=8.7, 7.2, 2.1 Hz, 2H), 7.14 (tt, J=7.2, 1.2 Hz, 1H), 7.04 (dq, J=8.7, 1.2 Hz, 2H), 7.01 (dt, J=8.7, 2.1 Hz, 2H), 5.82 (brs, 1H), 4.32 (s, 2H), 4.07-3.85 (m, 3H), 3.55-3.46 (m, 2H), 3.19-2.97 (m, 4H), 2.02-1.49 (m, 11H), 1.48-1.12 (m, 6H), 1.08-0.90 (m, 2H), 0.90 (t, J=7.2 Hz, 3H).

REFERENCE EXAMPLE 13

(2R,3R)-2-(t-butoxycarbonylamino)-3-hydroxy-4-methyl-N-butyl-N-[4-benzylaminocarbonyl-1-benzylpiperidin-4-yl]pentanamide

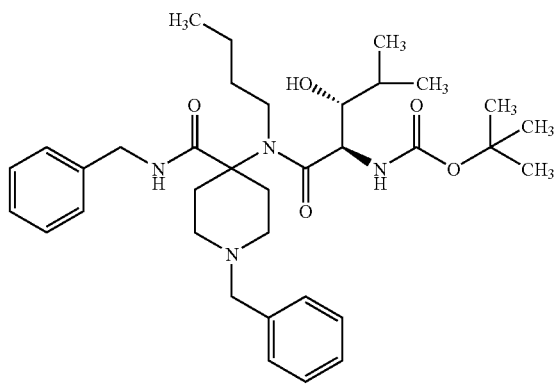

To a solution of (2R,3R)-2-(t-butoxycarbonylamino)-3-hydroxy-4-methylpentanoic acid (10.5 g) in methanol (340 ml) was added n-butylamine (4.2 ml), N-benzyl-4-piperidone (7.9 ml) and benzylisonitrile (5.2 ml). The reaction mixture was stirred overnight at 55° C. The reaction mixture was concentrated. The obtained residue was purified by column chromatography on silica gel (chloroform:methanol=100:1→75:1→50:1) to give the title compound (19.8 g) having the following physical data.

TLC: Rf 0.49 (chloroform:methanol=10:1); NMR (CD$_3$OD): δ 7.38-7.15 (m, 10H), 4.58 (d, J=9.6 Hz, 1H), 4.39 (d, J=15.0 Hz, 1H), 4.23 (d, J=15.0 Hz, 1H), 3.70-3.30 (m, 3H), 3.50 (s, 2H), 2.79-2.30 (m, 6H), 2.08-1.88 (m, 2H), 1.88-1.70 (m, 3H), 1.50-1.28 (m, 2H), 1.38 (s, 9H), 0.98 (t, J=7.2 Hz, 3H), 0.96 (d, J=6.6 Hz, 3H), 0.91 (d, J=6.6 Hz, 3H).

REFERENCE EXAMPLE 14

(2R,3R)-2-amino-3-hydroxy-4-methyl-N-butyl-N-[4-benzylaminocarbonyl-1-benzyl-piperidin-4-yl]pentanamide

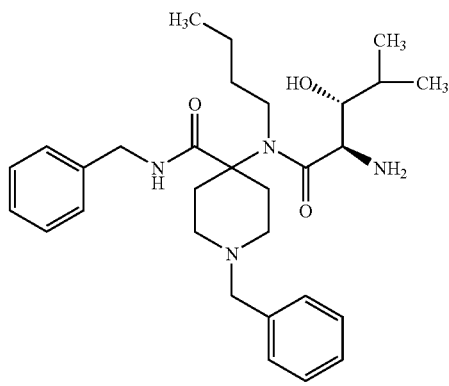

To a solution of the compound (19.8 g) prepared in Reference example 13 in dichloromethane (65 ml) was added trifluoroacetic acid (50 ml) under ice bath. The reaction mixture was stirred for 1 hr at room temperature. To the reaction mixture was added dichloromethane, neutrified with aqueous solution of sodium carbonate and extracted. The extract was washed with water and saturated aqueous solution of sodium chloride, dried over anhydrous sodium sulfate and concentrated to give the title compound having the following physical data. The obtained residue was used in the next reaction without further purification.

TLC:Rf 0.38 (chloroform:methanol=10:1).

EXAMPLE 67

(3R)-1-butyl-2,5-dioxo-3-((1R)-1-hydroxy-2-propyl)-9-benzyl-1,4,9-triazaspiro[5.5]undecane

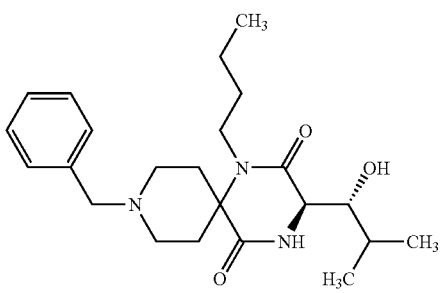

To a solution of the compound prepared in Reference example 14 in toluene (200 ml) was added acetic acid (15 ml). The reaction mixture was stirred for 45 minutes at 80° C. The reaction mixture was diluted with ethyl acetate, neutrified with aqueous solution of sodium carbonate and extracted. The extract was washed with saturated aqueous solution of sodium chloride, dried over anhydrous sodium sulfate and concentrated. The obtained residue purified by column chromatography on silica gel (ethyl acetate:methanol=25:1) to give the title compound (12.9 g) having the following physical data.

TLC: Rf 0.49 (chloroform:methanol=10:1); NMR (CD$_3$OD): δ 7.36-7.22 (m, 5H), 4.10 (d, J=2.7 Hz, 1H), 3.60 (s, 2H), 3.47 (m, 1H), 3.38-3.25 (m, 2H), 2.96 (m, 1H), 2.87-2.73 (m, 3H), 2.25-1.94 (m, 4H), 1.82 (m, 1H), 1.64 (m, 1H), 1.53-1.27 (m, 3H), 0.96 (d, J=6.6 Hz, 6H), 0.95 (t, J=7.5 Hz, 3H).

REFERENCE EXAMPLE 15

(3R)-1-butyl-2,5-dioxo-3-((1R)-1-hydroxy-2-methylpropyl)-1,4,9-triazaspiro[5.5]undecane.hydrochloride

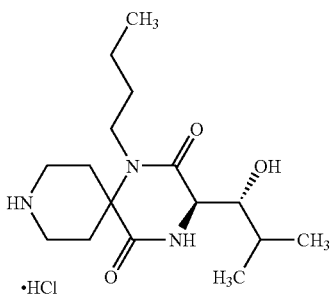

Under an atmosphere of argon, to a solution of the compound (12.67 g) prepared in Example 67 in methanol (160 ml) was added 20% palladium hydroxide on carbon (1.3 g). Under an atmosphere of hydrogen, the reaction mixture was stirred for 12 hours at room temperature. The reaction mixture was filtrated with Celite (brand name) and the filtrate was concentrated. The obtained residue was purified by column chromatography on silica gel (chloroform:hexane=3:1→chloroform:methanol=100:1→50:1→30:1→20:1→10:1). The obtained compound was added 4N hydrogen chloride/ethyl acetate solution and concentrated to give the title compound (8.6 g) having the following physical data.

TLC: Rf 0.16 (chloroform:methanol:acetic acid=20:4:1); NMR (CD$_3$OD): δ 4.15 (d, J=2.1 Hz, 1H), 3.95 (m, 1H), 3.71 (m, 1H), 3.52 (m, 1H), 3.42-3.31 (m, 2H), 3.21 (m, 1H), 3.21 (dd, J=9.6, 2.1 Hz, 1H), 2.48-2.32 (m, 2H), 2.23 (m, 1H), 2.14-1.96 (m, 2H), 1.72 (m, 1H), 1.55-1.33 (m, 3H), 1.02-0.92 (m, 9H); Optical rotation: [α]$_D$+13.9 (c 1.00, methanol, 28° C.).

REFERENCE EXAMPLE 15(1) TO 15(9)

By the same procedure described in Reference example 13→Reference example 14→Example 67→Reference example 15 using the corresponding amino acid derivatives respectively instead of (2R,3R)-2-(t-butoxycarbonylamino)-3-hydroxy-4-methylpentanoic acid, using the corresponding amine derivatives respectively instead of n-butylamine, the following compounds were obtained.

REFERENCE EXAMPLE 15(1)

(3S)-1-butyl-2,5-dioxo-3-(2-methylpropyl)-1,4,9-triazaspiro[5.5]undecane.hydrochloride

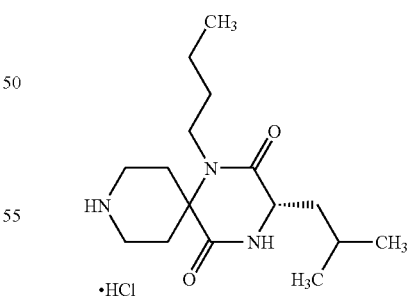

TLC: Rf 0.18 (chloroform:methanol=4:1); NMR (CD$_3$OD): δ 4.02 (dd, J=7.8, 4.6 Hz, 1H), 3.82-3.70 (m, 2H), 3.39 (m, 4H), 2.34-2.09 (m, 4H), 1.88-1.50 (m, 5H), 1.37 (m, 2H), 0.97 (t, J=7.5 Hz, 3H), 0.95 (d, J=6.5 Hz, 3H), 0.94 (d, J=6.5 Hz, 3H); Optical rotation:[α]$_D$–38.8 (c 1.04, methanol, 23° C.).

REFERENCE EXAMPLE 15(2)

(3S)-1-butyl-2,5-dioxo-3-cyclohexylmethyl-1,4,9-triazaspiro[5.5]undecane.hydrochloride

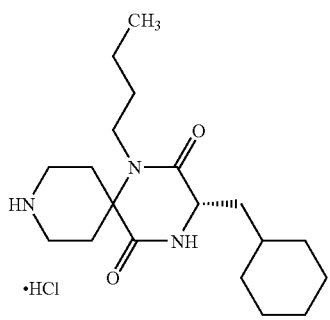

TLC: Rf 0.08 (chloroform:methanol:acetic acid=90:10:1); NMR (CD$_3$OD): δ 4.05 (dd, J=7.8, 4.8 Hz, 1H), 3.84-3.68 (m, 2H), 3.46-3.34 (m, 4H), 2.40-2.04 (m, 4H), 1.83-1.46 (m, 10H), 1.39 (sextet, J=7.5 Hz, 2H), 1.05-0.86 (m, 2H), 0.97 (t, J=7.2 Hz, 3H); Optical rotation: [α]$_D$–37.5 (c 1.04, methanol, 18° C.).

REFERENCE EXAMPLE 15(3)

(3R)-1-butyl-2,5-dioxo-3-((1R)-1-hydroxy-1-cyclohexyl)-1,4,9-triazaspiro[5.5]undecane.hydrochloride

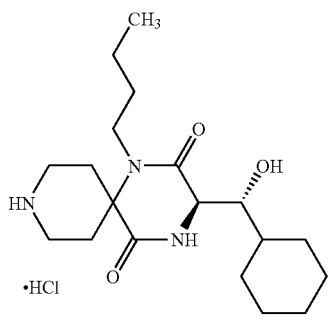

TLC: Rf 0.32 (butanol:acetic acid:water=4:2:1); NMR (CD$_3$OD): δ 4.16 (d, J=2.0 Hz, 1H), 3.95 (m, 1H), 3.70 (m, 1H), 3.52 (m, 1H), 3.37 (m, 1H), 3.28 (m, 1H), 3.22-3.13 (m, 2H), 2.46-1.93 (m, 6H), 1.80-1.64 (m, 5H), 1.48-1.15 (m, 6H), 1.02-0.87 (m, 5H); Optical rotation: [α]$_D$+1.22 (c 1.04, methanol, 26° C.).

REFERENCE EXAMPLE 15(4)

(3R)-1-butyl-2,5-dioxo-3-((1R)-1-hydroxy-1-(3,4,5,6-tetrahydropyran-4-yl)methyl)-1,4,9-triazaspiro[5.5]undecane.hydrochloride

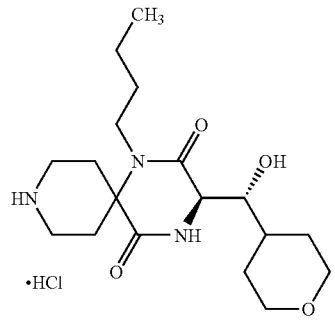

TLC: Rf 0.05 (chloroform:methanol=10:1); NMR (CD$_3$OD): δ 4.13 (d, J=2.0 Hz, 1H), 4.01-3.91 (m, 3H), 3.70 (m, 1H), 3.59-3.32 (m, 6H), 3.20 (m, 1H), 2.47-2.19 (m, 3H), 2.11-1.69 (m, 5H), 1.47-1.17 (m, 5H), 0.70 (t, J=7.0 Hz, 3H).

REFERENCE EXAMPLE 15(5)

(3R)-1-butyl-2,5-dioxo-3-((1R)-1-hydroxy-1-cyclopentyl)-1,4,9-triazaspiro[5.5]undecane.hydrochloride

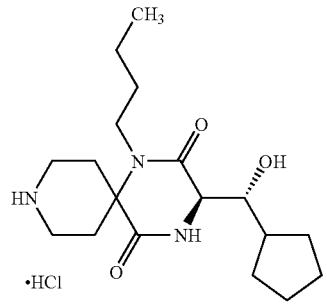

TLC: Rf 0.04 (chloroform:methanol=10:1); NMR (CD$_3$OD): δ 4.00 (d, J=2.0 Hz, 1H), 3.95 (m, 1H), 3.70 (m, 1H), 3.53 (m, 1H), 3.40-3.34 (m, 3H), 3.21 (m, 1H), 2.46-2.19 (m, 4H), 2.08 (m, 1H), 1.92-1.83 (m, 2H), 1.70-1.50 (m, 6H), 1.45-1.26 (m, 5H), 0.97 (t, J=7.0 Hz, 3H).

REFERENCE EXAMPLE 15(6)

(3R)-1-propyl-2,5-dioxo-3-((1R)-1-hydroxy-2-methylpropyl)-1,4,9-triazaspiro[5.5]undecane.hydrochloride

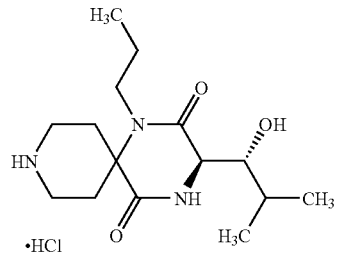

TLC: Rf 0.15 (chloroform:methanol:acetic acid=20:4:1); NMR (CD$_3$OD): δ 4.15 (d, J=2.1 Hz, 1H), 3.96 (m, 1H), 3.71 (m, 1H), 3.56-3.25 (m, 3H), 3.20 (dd, J=9.6, 2.1 Hz, 1H), 3.13 (m, 1H), 2.51-1.95 (m, 5H), 1.75 (m, 1H), 1.49 (m, 1H), 0.99 (d, J=6.6 Hz, 3H), 0.98 (d, J=6.6 Hz, 3H), 0.95 (t, J=7.5 Hz, 3H).

REFERENCE EXAMPLE 15(7)

(3R)-1-propyl-2,5-dioxo-3-((1R)-1-hydroxy-1-cyclohexyl)-1,4,9-triazaspiro[5.5]undecane.hydrochloride

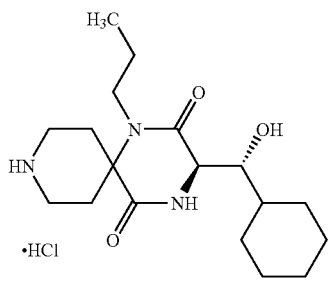

TLC: Rf 0.16 (chloroform:methanol:acetic acid=20:4:1); NMR (CD$_3$OD): δ 4.16 (d, J=2.1 Hz, 1H), 3.95 (m, 1H), 3.70 (m, 1H), 3.47 (m, 1H), 3.41-3.24 (m, 4H), 3.12 (m, 1H), 2.44 (m, 1H), 2.33 (m, 1H), 2.19 (m, 1H), 2.08 (m, 1H), 2.03-1.89 (m, 2H), 1.84-1.62 (m, 4H), 1.50 (m, 1H), 1.40-1.10 (m, 3H), 1.05-0.80 (m, 2H), 0.95 (t, J=7.5 Hz, 3H); Optical rotation: [α]$_D$–2.92 (c 1.06, methanol, 25° C.).

REFERENCE EXAMPLE 15(8)

(3S)-1-butyl-2,5-dioxo-3-((1S)-1-hydroxy-2-methylpropyl)-1,4,9-triazaspiro[5.5]undecane.hydrochloride

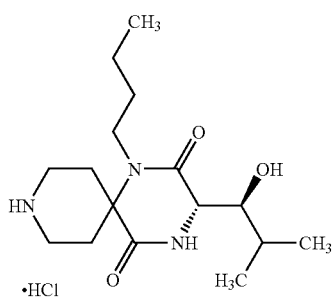

TLC: Rf 0.16 (chloroform:methanol:acetic acid=20:4:1); NMR (CD$_3$OD): δ 4.15 (d, J=2.1 Hz, 1H), 3.95 (m, 1H), 3.71 (m, 1H), 3.52 (m, 1H), 3.42-3.31 (m, 2H), 3.21 (m, 1H), 3.21 (dd, J=9.6, 2.1 Hz, 1H), 2.48-2.32 (m, 2H), 2.23 (m, 1H), 2.14-1.96 (m, 2H), 1.72 (m, 1H), 1.55-1.33 (m, 3H), 1.02-0.92 (m, 9H); Optical rotation: [α]$_D$–13.8 (c 1.00, methanol, 28° C.).

REFERENCE EXAMPLE 15(9)

(3S)-1-butyl-2,5-dioxo-3-((1S)-1-hydroxy-1-cyclohexyl)-1,4,9-triazaspiro[5.5]undecane.hydrochloride

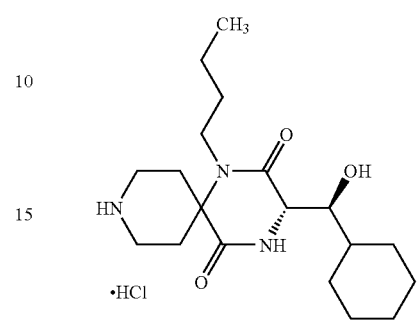

TLC: Rf 0.17 (chloroform:methanol:acetic acid=20:4:1); NMR (CD$_3$OD): δ 4.16 (d, J=2.1 Hz, 1H), 3.95 (m, 1H), 3.70 (m, 1H), 3.52 (m, 1H), 3.42-3.25 (m, 3H), 3.17 (m, 1H), 2.49-2.38 (m, 2H), 2.21 (m, 1H), 2.14-1.90 (m, 3H), 1.84-1.61 (m, 5H), 1.55-1.13 (m, 6H), 1.04-0.81 (m, 2H), 0.97 (t, J=7.2 Hz, 3H); Optical rotation:[α]$_D$–1.29 (c 1.09, methanol, 26° C.).

EXAMPLE 68

(3R)-1-butyl-2,5-dioxo-3-((1R)-1-hydroxy-2-methylpropyl)-9-(6-phenyloxypyridin-3-ylmethyl)-1,4,9-triazaspiro[5.5]undecane.2hydrochloride

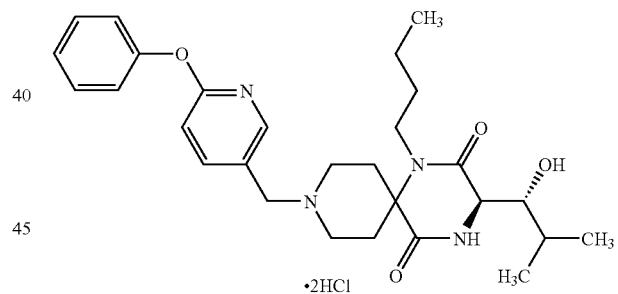

To a solution of the compound prepared in Reference example 15 (120 mg) in dimethylformamide (1 ml) was added acetic acid (59 μl). The reaction mixture was added sodium triacetoxyborohydride (146 mg) and 3-formyl-6-phenyloxypyridine (89 mg). The reaction mixture was stirred overnight at room temperature. The reaction mixture was added methanol and concentrated. The obtained residue was purified by column chromatography on silica gel (ethyl acetate→chloroform:methanol=25:1) and the obtained compound was conversed to hydrochloride salt by using a conventional method to give the title compound (118 mg) having the following physical data.

TLC: Rf 0.48 (chloroform:methanol=10:1); NMR (CD$_3$OD): δ 8.35 (d, J=2.1 Hz, 1H), 8.12 (dd, J=8.7, 2.1 Hz, 1H), 7.49-7.40 (m, 2H), 7.27 (t, J=7.8 Hz, 1H), 7.15 (d, J=7.8 Hz, 2H), 7.06 (d, J=8.7 Hz, 1H), 4.39 (s, 2H), 4.14 (d, J=2.1 Hz, 1H), 4.07-3.93 (m, 1H), 3.82-3.67 (m, 1H), 3.58-3.40 (m, 3H), 3.30-3.15 (m, 1H), 3.19 (dd, J=9.6, 2.1

Hz, 1H), 2.60-2.28 (m, 3H), 2.18-2.05 (m, 1H), 2.05-1.90 (m, 1H), 1.80-1.55 (m, 1H), 1.50-1.25 (m, 3H), 0.99 (d, J=6.6 Hz, 3H), 0.97 (d, J=6.6 Hz, 3H), 0.95 (t, J=7.2 Hz, 3H); Optical rotation: [α]$_D$+10.80 (c 1.05, methanol, 24° C.); HPLC conditions column: CHIRALCEL OJ-R, 0.46×15 cm, DAICEL, OJR0CD-JB026: flow rate: 0.7 ml/min; solvent A solution: 0.1M aqueous solution of potassium dihydrogen phosphate, B solution: acetonitrile (A:B=76:24); UV: 225 nm; retention time: 11.53 min.

EXAMPLE 68(1) TO 68(59)

By the same procedure as described in Example 68 using the corresponding aldehyde derivatives instead of 3-formyl-6-phenyloxypyridine, the following compounds were obtained.

EXAMPLE 68(1)

(3R)-1-butyl-2,5-dioxo-3-((1R)-1-hydroxy-2-methylpropyl)-9-(4-(4-methoxyphenyloxy)phenylmethyl)-1,4,9-triazaspiro[5.5]undecane.hydrochloride

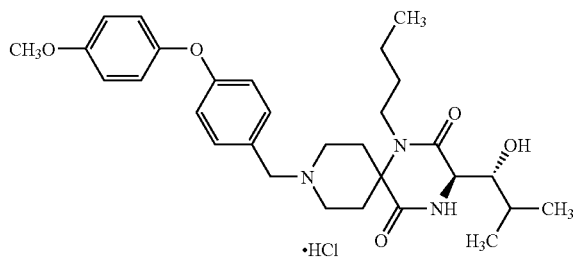

TLC: Rf 0.36 (ethyl acetate:methanol=10:1); NMR (CD$_3$OD): δ 7.45 (d, J=8.7 Hz, 2H), 7.00-6.96 (m, 6H), 4.27 (s, 2H), 4.14 (d, J=2.1 Hz, 1H), 3.94-3.69 (m, 2H), 3.79 (s, 3H), 3.60-3.05 (m, 5H), 2.50-1.95 (m, 5H), 1.70 (m, 1H), 1.50-1.30 (m, 3H), 1.00-0.93 (m, 9H).

EXAMPLE 68(2)

(3R)-1-butyl-2,5-dioxo-3-((1R)-1-hydroxy-2-methylpropyl)-9-(4-(3-methoxyphenyloxy)phenylmethyl)-1,4,9-triazaspiro[5.5]undecane.hydrochloride

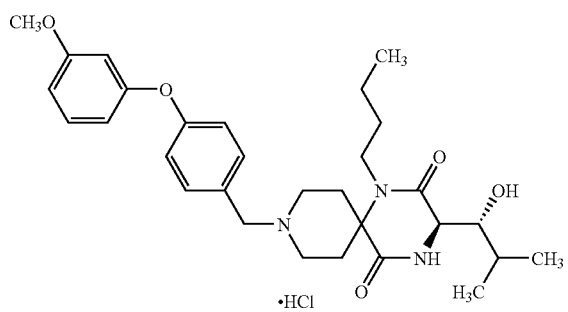

TLC: Rf 0.41 (ethyl acetate:methanol=10:1); NMR (CD$_3$OD): δ 7.51 (d, J=8.4 Hz, 2H), 7.28 (t, J=8.4 Hz, 1H), 7.08 (d, J=9.0 Hz, 2H), 6.75 (m, 1H), 6.61-6.57 (m, 2H), 4.32 (s, 2H), 4.14 (d J=2.1 Hz, 1H), 3.99-3.73 (m, 2H), 3.77 (s, 3H), 3.60-3.10 (m, 5H), 2.55-1.95 (m, 5H), 1.70 (m, 1H), 1.50-1.30 (m, 3H), 1.00-0.93 (m, 9H).

EXAMPLE 68(3)

(3R)-1-butyl-2,5-dioxo-3-((1R)-1-hydroxy-2-methylpropyl)-9-(4-(4-fluorophenyloxy)phenylmethyl)-1,4,9-triazaspiro[5.5]undecane.hydrochloride

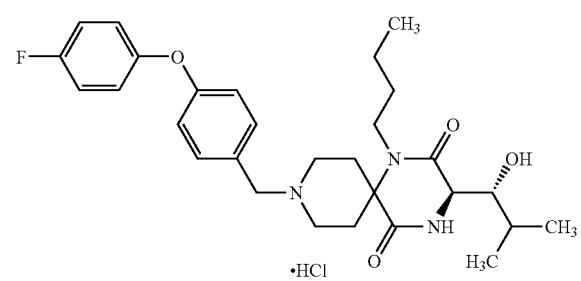

TLC: Rf 0.33 (ethyl acetate:methanol=10:1); NMR (CD$_3$OD): δ 7.50 (d, J=8.7 Hz, 2H), 7.17-7.03 (m, 6H), 4.30 (s, 2H), 4.14 (d, J=2.1 Hz, 1H), 3.97-3.71 (m, 2H), 3.60-3.10 (m, 5H), 2.55-1.95 (m, 5H), 1.70 (m, 1H), 1.50-1.30 (m, 3H), 1.00-0.93 (m, 9H).

EXAMPLE 68(4)

(3R)-1-butyl-2,5-dioxo-3-((1R)-1-hydroxy-2-methylpropyl)-9-(4-(4-chlorophenyloxy)phenylmethyl)-1,4,9-triazaspiro[5.5]undecane.hydrochloide

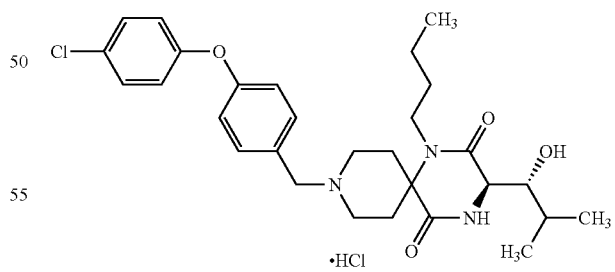

TLC: Rf 0.31 (ethyl acetate:methanol=10:1); NMR (CD$_3$OD): δ 7.53 (d, J=8.7 Hz, 2H), 7.38 (d, J=9.3 Hz, 2H), 7.09 (d, J=8.7 Hz, 2H), 7.02 (d, J=9.3 Hz, 2H), 4.32 (s, 2H), 4.14 (d, J=1.8 Hz, 1H), 3.98-3.72 (m, 2H), 3.60-3.10 (m, 5H), 2.55-2.00 (m, 5H), 1.70 (m, 1H), 1.50-1.30 (m, 3H), 1.00-0.93 (m, 9H).

EXAMPLE 68(5)

(3R)-1-butyl-2,5-dioxo-3-((1R)-1-hydroxy-2-methylpropyl)-9-(4-(phenylcarbonyl)phenylmethyl)-1,4,9-triazaspiro[5.5]undecane.hydrochloride

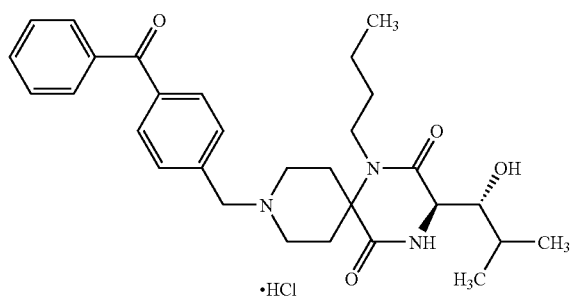

TLC: Rf 0.57 (chloroform:methanol=10:1); NMR (CD$_3$OD): δ 7.87 (d, J=8.4 Hz, 2H), 7.83-7.72 (m, 4H), 7.67 (m, 1H), 7.59-7.48 (m, 2H), 4.48 (s, 2H), 4.14 (d, J=2.1 Hz, 1H), 4.05 (m, 1H), 3.80 (m, 1H), 3.59-3.37 (m, 3H), 3.20 (m, 1H), 3.19 (dd, J=9.6, 2.1 Hz, 1H), 2.60-2.28 (m, 3H), 2.14 (m, 1H), 2.00 (m, 1H), 1.70 (m, 1H), 1.52-1.23 (m, 3H), 0.99 (d, J=6.6 Hz, 3H), 0.97 (d, J=6.6 Hz, 3H), 0.95 (t, J=7.2 Hz, 3H).

EXAMPLE 68(6)

(3R)-1-butyl-2,5-dioxo-3-((1R)-1-hydroxy-2-methylpropyl)-9-(4-(1-phenyl-1-hydroxymethyl)phenylmethyl)-1,4,9-triazaspiro[5.5]undecane.hydrochloride

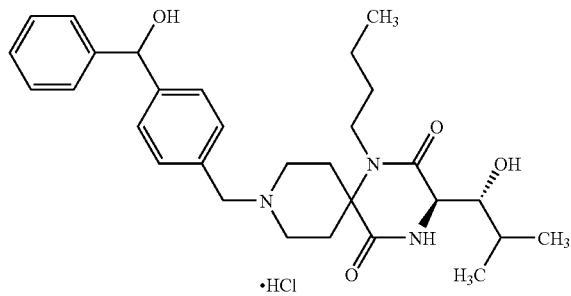

TLC: Rf 0.32 (chloroform:methanol=10:1); NMR (CD$_3$OD): δ 7.62-7.40 (m, 4H), 7.40-7.18 (m, 5H), 5.81 (s, 1H), 4.32 (s, 2H), 4.13 (d, J=2.1 Hz, 1H), 3.99 (m, 1H), 3.73 (m, 1H), 3.55-3.38 (m, 3H), 3.13 (m, 1H), 3.19 (dd, J=9.6, 2.1 Hz, 1H), 2.52-2.33 (m, 2H), 2.24 (m, 1H), 2.09 (m, 1H), 1.98 (m, 1H), 1.67 (m, 1H), 1.50-1.25 (m, 3H), 0.98 (d, J=6.6 Hz, 3H), 0.96 (d, J=6.6 Hz, 3H), 0.93 (t, J=7.2 Hz, 3H).

EXAMPLE 68(7)

(3R)-1-butyl-2,5-dioxo-3-((1R)-1-hydroxy-2-methylpropyl)-9-(4-(4-(morpholin-4-ylcarbonyl)phenyloxy)phenylmethyl)-1,4,9-triazaspiro[5.5]undecane.hydochloride

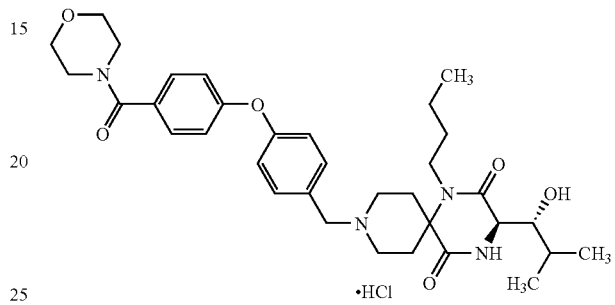

TLC: Rf 0.47 (chloroform:methanol=10:1); NMR (CD$_3$OD): δ 7.59 (d, J=8.7 Hz, 2H), 7.48 (d, J=8.7 Hz, 2H), 7.14 (d, J=8.7 Hz, 2H), 7.10 (d, J=8.7 Hz, 2H), 4.35 (s, 2H), 4.14 (d, J=1.8 Hz, 1H), 3.99 (m, 1H), 3.85-3.35 (m, 12H), 3.23 (m, 1H), 3.19 (dd, J=9.3, 1.8 Hz, 1H), 2.55-2.41 (m, 2H), 2.32 (m, 1H), 2.12 (m, 1H), 2.01 (m, 1H), 1.68 (m, 1H), 1.50-1.25 (m, 3H), 0.99 (d, J=6.6 Hz, 3H), 0.97 (d, J=6.6 Hz, 3H), 0.95 (t, J=7.2 Hz, 3H).

EXAMPLE 68(8)

(3R)-1-butyl-2,5-dioxo-3-((1R)-1-hydroxy-2-methylpropyl)-9-(4-(6-methylpyridin-3-yloxy)phenylmethyl)-1,4,9-triazaspiro[5.5]undecane.2hydrochloride

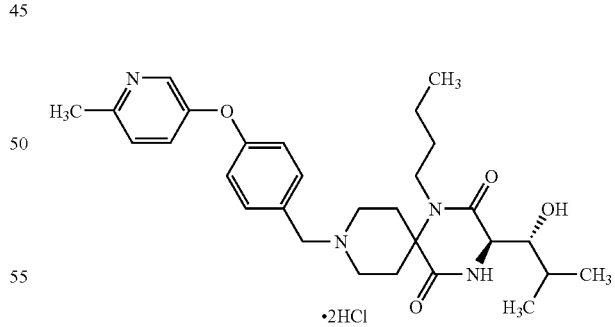

TLC: Rf 0.19 (ethyl acetate:methanol=10:1); NMR (CD$_3$OD): δ 8.58 (d, J=2.7, 0.6 Hz, 1H), 8.17 (dd, J=9.0, 2.7 Hz, 1H), 7.89 (d, J=9.0 Hz, 1H), 7.74 (d, J=9.0 Hz, 2H), 7.31 (d, J=9.0 Hz, 2H), 4.40 (s, 2H), 4.15 (d, J=2.1 Hz, 1H), 4.02 (m, 1H), 3.78 (m, 1H), 3.60-3.42 (m, 3H), 3.30-3.16 (m, 2H), 2.76 (s, 3H), 2.64-2.32 (m, 3H), 2.18-1.94 (m, 2H), 1.70 (m, 1H), 1.48-1.26 (m, 3H), 1.00 (d, J=6.3 Hz, 3H), 0.98 (d, J=6.3 Hz, 3H), 0.96 (t, J=7.2 Hz, 3H).

EXAMPLE 68(9)

(3R)-1-butyl-2,5-dioxo-3-((1R)-1-hydroxy-2-methylpropyl)-9-(4-(pyridin-1-oxido-3-yloxy)phenylmethyl)-1,4,9-triazaspiro[5.5]undecane.hydrochloride

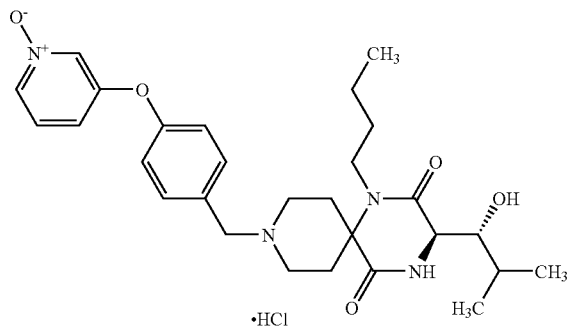

TLC: Rf 0.54 (chloroform:methanol=5:1); NMR (CD$_3$OD): δ 8.56 (m, 1H), 8.45 (m, 1H), 7.81-7.68 (m, 2H), 7.75 (d, J=8.4 Hz, 2H), 7.33 (d, J=8.4 Hz, 2H), 4.41 (s, 2H), 4.15 (d, J=1.8 Hz, 1H), 4.00 (m, 1H), 3.78 (m, 1H), 3.58-3.42 (m, 3H), 3.28-3.16 (m, 2H), 2.64-2.26 (m, 3H), 2.20-1.92 (m, 2H), 1.68 (m, 1H), 1.52-1.28 (m, 3H), 1.00 (d, J=6.6 Hz, 3H), 0.98 (d, J=6.6 Hz, 3H), 0.96 (t, J=7.2 Hz, 3H).

EXAMPLE 68(10)

(3R)-1-butyl-2,5-dioxo-3-((1R)-1-hydroxy-2-methylpropyl)-9-(4-(4-hydroxypiperidin-1-ylmethyl)phenylmethyl)-1,4,9-triazaspiro[5.5]undecane.2hydrochloride

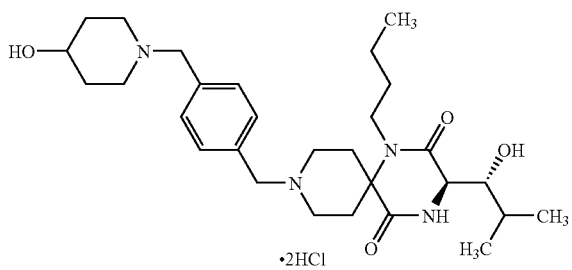

TLC: Rf 0.69 (chloroform:methanol:28% aqueous solution of ammonia=100:10:1); NMR (CD$_3$OD): δ 7.75 (d, J=8.4 Hz, 2H), 7.67 (d, J=8.4 Hz, 2H), 4.41 (s, 2H), 4.38 (s, 2H), 4.14 (d, J=2.1 Hz, 1H), 4.14-3.94 (m, 2H), 3.78 (m, 1H), 3.58-3.40 (m, 4H), 3.30-3.00 (m, 4H), 2.68-2.36 (m, 3H), 2.20-1.58 (m, 8H), 1.50-1.26 (m, 3H), 0.99 (d, J=6.6 Hz, 3H), 0.98 (d, J=6.6 Hz, 3H), 0.95 (t, J=6, 9 Hz, 3H).

EXAMPLE 68(11)

(3R)-1-butyl-2,5-dioxo-3-((1R)-1-hydroxy-2-methylpropyl)-9-(3,5-dimethyl-1-cyclohexylpyrazol-4-ylmethyl)-1,4,9-triazaspiro[5.5]undecane.2hydrochloride

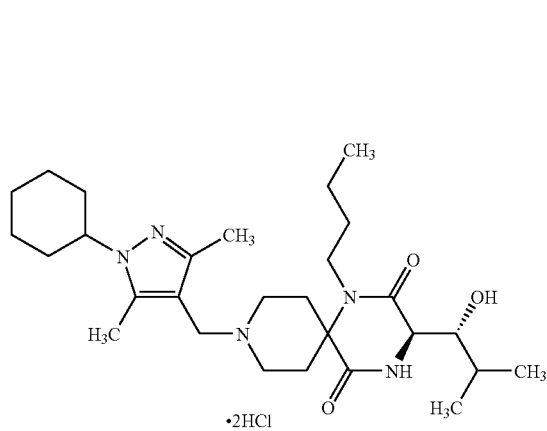

TLC: Rf 0.65 (chloroform:methanol=5:1); NMR (CD$_3$OD): δ 4.32 (m, 1H), 4.27 (s, 2H), 4.15 (d, J=2.1 Hz, 1H), 4.00 (m, 1H), 3.76 (m, 1H), 3.60-3.42 (m, 3H), 3.36-3.16 (m, 2H), 2.64-2.42 (m, 3H), 2.49 (s, 3H), 2.44 (s, 3H), 2.18-1.22 (m, 16H), 1.00 (d, J=6.6 Hz, 3H), 0.99 (d, J=6.6 Hz, 3H), 0.95 (t, J=7.5 Hz, 3H).

EXAMPLE 68(12)

(3R)-1-butyl-2,5-dioxo-3-((1R)-1-hydroxy-2-methylpropyl)-9-(1,3,5-trimethylpyrazol-4-ylmethyl)-1,4,9-triazaspiro[5.5]undecane.2hydrochloride

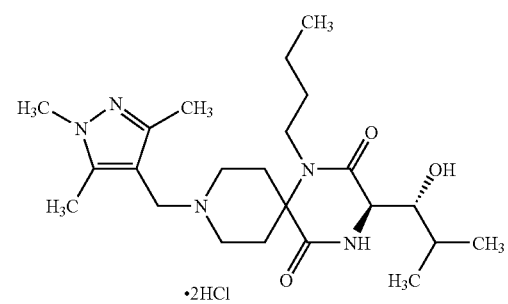

TLC: Rf 0.50 (chloroform:methanol=5:1); NMR (CD$_3$OD): δ 4.27 (s, 2H), 4.15 (d, J=2.1 Hz, 1H), 4.00 (m, 1H), 3.85 (s, 3H), 3.76 (m, 1H), 3.60-3.44 (m, 3H), 3.28-3.16 (m, 2H), 2.64-2.32 (m, 3H), 2.44 (s, 3H), 2.40 (s, 3H), 2.18-1.92 (m, 2H), 1.70 (m, 1H), 1.48-1.26 (m, 3H), 1.00 (d, J=6.6 Hz, 3H) 0.99 (d, J=6.6 Hz, 3H), 0.95 (t, J=7.5 Hz, 3H).

EXAMPLE 68(13)

(3R)-1-butyl-2,5-dioxo-3-((1R)-1-hydroxy-2-methylpropyl)-9-(4-(4-aminosulfonylphenyloxy)phenylmethyl)-1,4,9-triazaspiro[5.5]undecane.hydrochloride

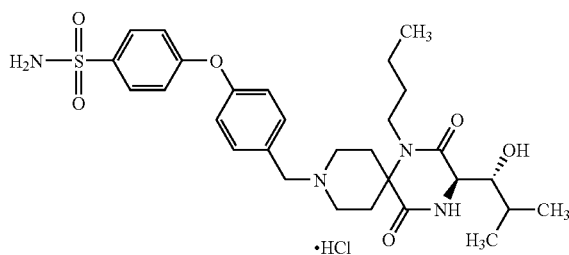

TLC: Rf 0.50 (chloroform:methanol=5:1); NMR (CD$_3$OD): δ 7.91 (d, J=8.7 Hz, 2H), 7.60 (d, J=8.7 Hz, 2H), 7.19 (d, J=8.7 Hz, 2H), 7.14 (d, J=8.7 Hz, 2H), 4.35 (s, 2H), 4.15 (d, J=2.4 Hz, 1H), 3.98 (m, 1H), 3.72 (m, 1H), 3.58-3.38 (m, 3H), 3.28-3.18 (m, 2H), 2.56-1.92 (m, 5H), 1.70 (m, 1H), 1.54-1.28 (m, 3H), 1.00 (d, J=6.9 Hz, 3H), 0.98 (d, J=6.9 Hz, 3H), 0.96 (t, J=7.5 Hz, 3H).

EXAMPLE 68(14)

(3R)-1-butyl-2,5-dioxo-3-((1R)-1-hydroxy-2-methylpropyl)-9-(4-(4-methylthiophenyloxy)phenylmethyl)-1,4,9-triazaspiro[5.5]undecane.hydrochloride

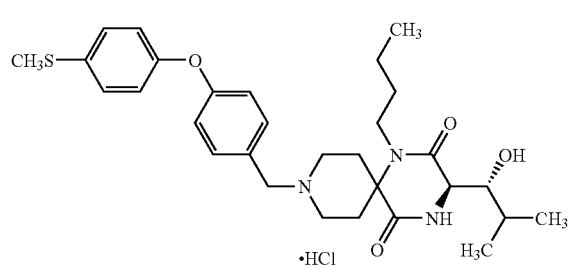

TLC: Rf 0.45 (chloroform:methanol=10:1); NMR (CD$_3$OD): δ 7.53 (d, J=9.0 Hz, 2H), 7.32 (d, J=9.0 Hz, 2H), 7.05 (d, J=9.0 Hz, 2H), 6.99 (d, J=9.0 Hz, 2H), 4.33 (s, 2H), 4.14 (d, J=2.1 Hz, 1H), 3.98 (m, 1H), 3.72 (m, 1H), 3.58-3.40 (m, 3H), 3.28-3.10 (m, 2H), 2.52-1.92 (m, 5H), 2.47 (s, 3H), 1.70 (m, 1H), 1.50-1.28 (m, 3H), 1.02-0.86 (m, 9H).

EXAMPLE 68(15)

(3R)-1-butyl-2,5-dioxo-3-((1R)-1-hydroxy-2-methylpropyl)-9-(4-(4-methylsulfonylphenyloxy)phenylmethyl)-1,4,9-triazaspiro[5.5]undecane.hydrochloride

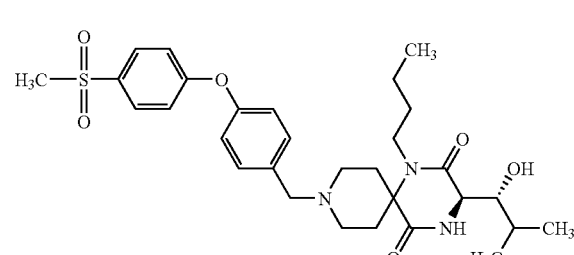

TLC: Rf 0.36 (chloroform:methanol=10:1); NMR (CD$_3$OD): δ 7.95 (d, J=9.0 Hz, 2H), 7.63 (d, J=8.1 Hz, 2H), 7.24-7.18 (m, 4H), 4.39 (s, 2H), 4.14 (d, J=2.4 Hz, 1H), 4.02 (m, 1H), 3.78 (m, 1H), 3.60-3.46 (m, 3H), 3.28-3.10 (m, 2H), 3.12 (s, 3H), 2.54-1.94 (m, 5H), 1.70 (m, 1H), 1.50-1.30 (m, 3H), 1.02-0.86 (m, 9H).

EXAMPLE 68(16)

(3R)-1-butyl-2,5-dioxo-3-((1R)-1-hydroxy-2-methylpropyl)-9-(4-(4-cyanophenyloxy)phenylmethyl)-1,4,9-triazaspiro[5.5]undecane.hydrochloride

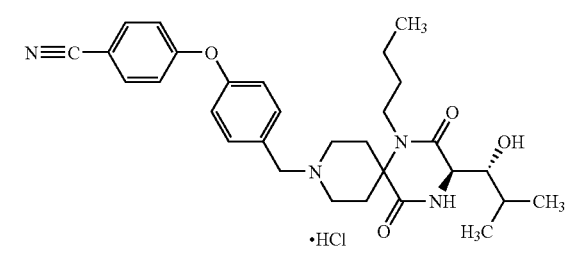

TLC: Rf 0.36 (chloroform:methanol=10:1); NMR (CD$_3$OD): δ 7.73 (d, J=8.7 Hz, 2H), 7.64 (d, J=9.0 Hz, 2H), 7.21 (d, J=9.0 Hz, 2H), 7.14 (d, J=8.7 Hz, 2H), 4.38 (s, 2H), 4.14 (d, J=2.1 Hz, 1H), 4.02 (m, 1H), 3.76 (m, 1H), 3.60-3.40 (m, 3H), 3.28-3.14 (m, 2H), 2.54-2.26 (m, 3H), 2.20-1.90 (m, 2H), 1.66 (m, 1H), 1.50-1.28 (m, 3H), 1.02-0.84 (m, 9H).

EXAMPLE 68(17)

(3R)-1-butyl-2,5-dioxo-3-((1R)-1-hydroxy-2-methylpropyl)-9-(4-(phenylthio)phenylmethyl)-1,4,9-triazaspiro[5.5]undecane.hydrochloride

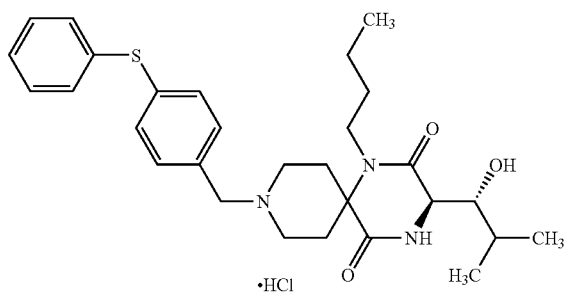

TLC: Rf 0.36 (chloroform:methanol=10:1); NMR (CD$_3$OD): δ 7.50-7.34 (m, 7H), 7.30 (d, J=8.4 Hz, 2H), 4.31 (s, 2H), 4.13 (d, J=2.1 Hz, 1H), 3.98 (m, 1H), 3.72 (m, 1H), 3.56-3.36 (m, 3H), 3.24-3.08 (m, 2H), 2.50-2.18 (m, 3H), 2.18-1.94 (m, 2H), 1.68 (m, 1H), 1.50-1.28 (m, 3H), 1.10-0.88 (m, 9H).

EXAMPLE 68(18)

(3R)-1-butyl-2,5-dioxo-3-((1R)-1-hydroxy-2-methylpropyl)-9-(3,5-dimethyl-1-(4-hydroxyphenyl)pyrazol-4-ylmethyl)-1,4,9-triazaspiro[5.5]undecane.2hydrochloride

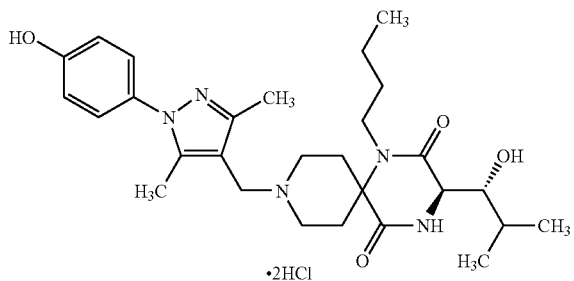

TLC: Rf 0.70 (chloroform:methanol=5:1); NMR (CD$_3$OD): δ 7.31 (d, J=8.7 Hz, 2H), 6.94 (d, J=8.7 Hz, 2H), 4.32 (s, 2H), 4.15 (d, J=2.1 Hz, 1H), 4.04 (m, 1H), 3.80 (m, 1H), 3.64-3.48 (m, 3H), 3.38-3.18 (m, 2H), 2.70-2.30 (m, 3H), 2.44 (s, 3H), 2.36 (s, 3H), 2.20-1.94 (m, 2H), 1.68 (m, 1H), 1.50-1.26 (m, 3H), 1.02-0.84 (m, 9H).

EXAMPLE 68(19)

(3R)-1-butyl-2,5-dioxo-3-((1R)-1-hydroxy-2-methylpropyl)-9-(3,5-dimethyl-1-(4-methylsulfonylaminophenyl)pyrazol-4-ylmethyl)-1,4,9-triazaspiro[5.5]undecane.2hydrochloride

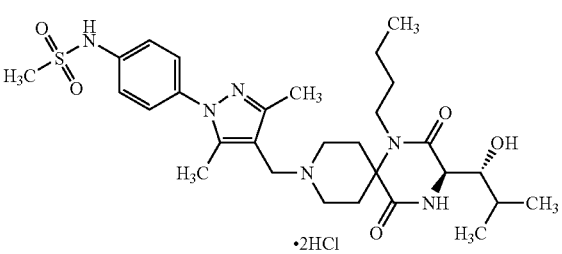

TLC: Rf 0.72 (chloroform:methanol=10:1); NMR (CD$_3$OD): δ 7.47 (d, J=9.0 Hz, 2H), 7.41 (d, J=9.0 Hz, 2H), 4.31 (s, 2H), 4.15 (d, J=1.8 Hz, 1H), 4.02 (m, 1H), 3.78 (m, 1H), 3.62-3.48 (m, 3H), 3.38-3.18 (m, 2H), 3.04 (s, 3H), 2.68-2.36 (m, 3H), 2.41 (s, 3H), 2.39 (s, 3H), 2.20-1.96 (m, 2H), 1.68 (m, 1H), 1.50-1.30 (m, 3H), 1.02-0.88 (m, 9H).

EXAMPLE 68(20)

(3R)-1-butyl-2,5-dioxo-3-((1R)-1-hydroxy-2-methylpropyl)-9-(3,5-dimethyl-1-(4-(2-(N,N-dimethylamino)ethylaminosulfonyl)phenyl)pyrazol-4-ylmethyl)-1,4,9-triazaspiro[5.5]undecane.3hydrochloride

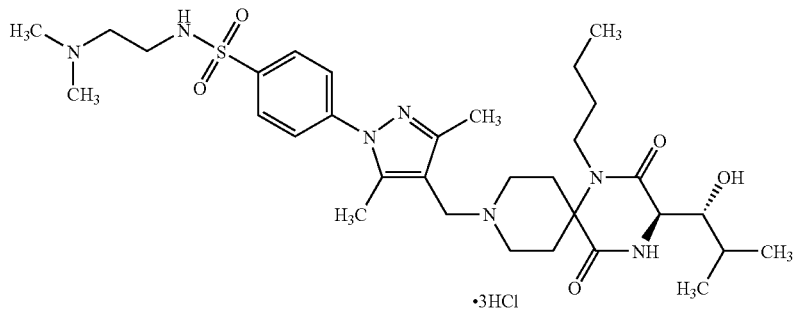

TLC: Rf 0.12 (chloroform:methanol=5:1); NMR (CD$_3$OD):δ 8.07 (d, J=9.0 Hz, 2H), 7.78 (d, J=9.0 Hz, 2H), 4.30 (s, 2H), 4.15 (d, J=2.1 Hz, 1H), 4.02 (m, 1H), 3.76 (m, 1H), 3.62-3.48 (m, 3H), 3.40-3.18 (m, 6H), 2.95 (s, 6H), 2.64 (m, 1H), 2.49 (s, 3H), 2.42-2.36 (m, 2H), 2.41 (s, 3H), 2.18-1.96 (m, 2H), 1.68 (m, 1H), 1.50-1.32 (m, 3H), 1.08-0.90 (m, 9H).

EXAMPLE 68(21)

(3R)-1-butyl-2,5-dioxo-3-((1R)-1-hydroxy-2-methylpropyl)-9-(3,5-dimethyl-1-(4-(pyrrolidin-1-ylsulfonyl)phenyl)pyrazol-4-ylmethyl)-1,4,9-triazaspiro[5.5]undecane.2hydrochloride

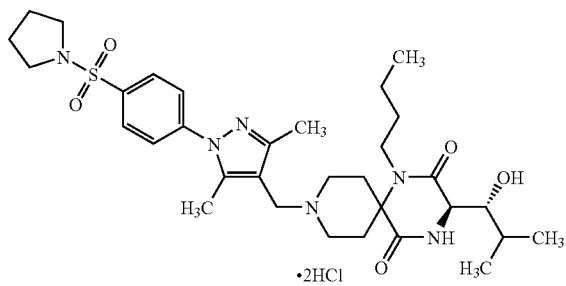

TLC: Rf 0.36 (chloroform:methanol=10:1); NMR (CD$_3$OD):δ 8.01 (d, J=8.7 Hz, 2H), 7.77 (d, J=8.7 Hz, 2H), 4.31 (s, 2H), 4.15 (d, J=1.8 Hz, 1H), 4.04 (m, 1H), 3.78 (m, 1H), 3.62-3.48 (m, 3H), 3.40-3.18 (m, 6H), 2.66 (m, 1H), 2.54-2.38 (m, 2H), 2.49 (s, 3H), 2.42 (s, 3H), 2.20-1.94 (m, 2H), 1.82-1.62 (m, 5H), 1.50-1.30 (m, 3H), 1.02-0.88 (m, 9H).

EXAMPLE 68(22)

(3R)-1-butyl-2,5-dioxo-3-((1R)-1-hydroxy-2-methylpropyl)-9-(4-(6-methylpyridin-1-oxido-3-yloxy)phenylmethyl)-1,4,9-triazaspiro[5.5]undecane.hydrochloride

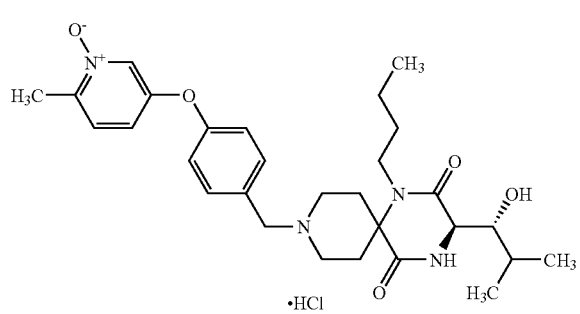

TLC: Rf 0.26 (chloroform:methanol=10:1); NMR (CD$_3$OD):δ 8.58 (m, 1H), 7.81-7.71 (m, 2H), 7.73 (d, J=8.4 Hz, 2H), 7.30 (d, J=8.4 Hz, 2H), 4.40 (s, 2H), 4.15 (d, J=2.1 Hz, 1H), 4.00 (m, 1H), 3.78 (m, 1H), 3.62-3.40 (m, 3H), 3.30-3.16 (m, 2H), 2.66-2.38 (m, 3H), 2.66 (s, 3H), 2.18-1.94 (m, 2H), 1.70 (m, 1H), 1.50-1.28 (m, 3H), 1.00 (d, J=6.6 Hz, 3H), 0.98 (d, J=6.6 Hz, 3H), 0.96 (t, J=6.9 Hz, 3H).

EXAMPLE 68(23)

(3R)-1-butyl-2,5-dioxo-3-((1R)-1-hydroxy-2-methylpropyl)-9-(4-(4-hydroxyphenyloxy)phenylmethyl)-1,4,9-triazaspiro[5.5]undecane.hydrochlode

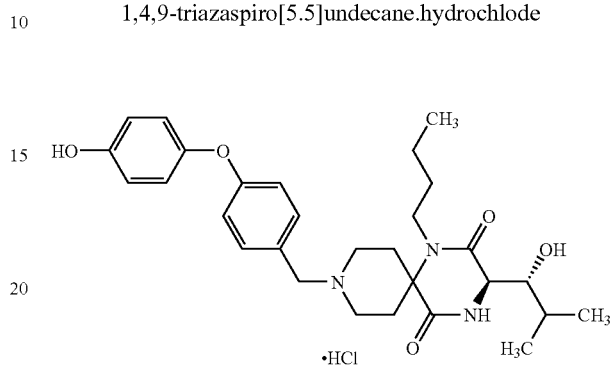

TLC: Rf 0.48 (ethyl acetate:methanol=10:1); NMR (CD$_3$OD):δ 7.46 (d, J=8.7 Hz, 2H), 6.97 (d, J=8.7 Hz, 2H), 6.88 (d, J=9.0 Hz, 2H), 6.80 (d, J=9.0 Hz, 2H), 4.30 (s, 2H), 4.13 (d, J=2.0 Hz, 1H), 3.98 (m, 1H), 3.72 (m, 1H), 3.53-3.42 (m, 3H), 3.23-3.11 (m, 2H), 2.50-1.97 (m, 6H), 1.70 (m, 1H), 1.39-1.30 (m, 3H), 0.98 (d, J=6.5 Hz, 3H), 0.96 (d, J=6.5 Hz, 3H), 0.95 (t, J=7.0 Hz, 3H).

EXAMPLE 68(24)

(3R)-1-butyl-2,5-dioxo-3-((1R)-1-hydroxy-2-methylpropyl)-9-(6-(4-methoxyphenyloxy)pyridin-3-ylmethyl)-1,4,9-triazaspiro[5.5]undecane.2hydrochloride

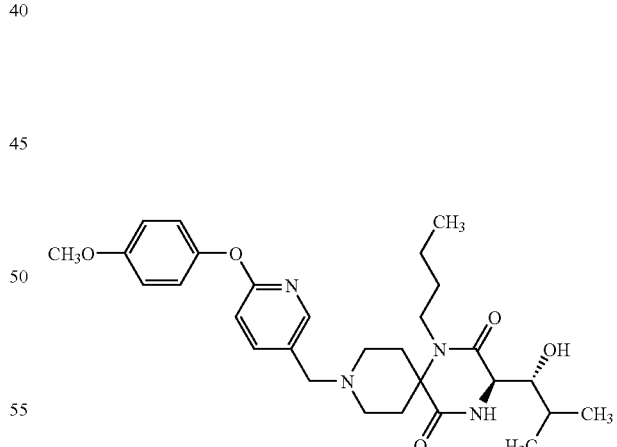

TLC: Rf 0.42 (chloroform:methanol=10:1); NMR (CD$_3$OD):δ 8.41 (m, 1H), 8.18 (m, 1H), 7.13-6.99 (m, 5H), 4.40 (s, 2H), 4.13 (d, J=2.0 Hz, 1H), 4.00 (m, 1H), 3.82 (s, 3H), 3.75 (m, 1H), 3.53-3.45 (m, 3H), 3.24 (m, 1H), 3.19 (dd, J=9.5, 2.0 Hz, 1H), 2.59-2.39 (m, 3H), 2.15-1.95 (m, 2H), 1.70 (m, 1H), 1.40-1.31 (m, 3H), 0.98 (d, J=6.5 Hz, 3H), 0.97 (d, J=6.5 Hz, 3H), 0.94 (t, J=7.5 Hz, 3H).

EXAMPLE 68(25)

(3R)-1-butyl-2,5-dioxo-3-((1R)-1-hydroxy-2-methylpropyl)-9-(3,5-dimethyl-1-(4-(methylaminosulfonyl)phenyl)pyrazol-4-ylmethyl)-1,4,9-triazaspiro[5.5]undecane.2hydrochloride

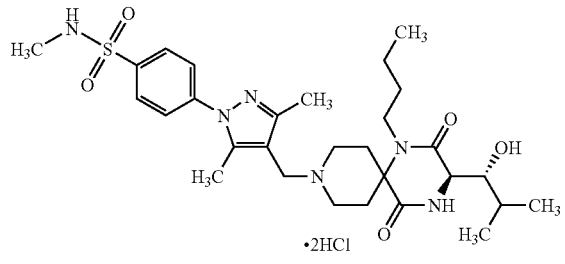

TLC: Rf 0.29 (ethyl acetate:methanol=4:1); NMR (CD$_3$OD):δ 8.00 (d, J=9.0 Hz, 2H), 7.73 (d, J=9.0 Hz, 2H), 4.32 (s, 2H), 4.16 (d, J=2.0 Hz, 1H), 4.05 (m, 1H), 3.79 (m, 1H), 3.64-3.50 (m, 3H), 3.29-3.19 (m, 2H), 2.59-2.35 (m, 3H), 2.58 (s, 3H), 2.47 (s, 3H), 2.40 (s, 3H), 2.15 (m, 1H), 2.02 (m, 1H), 1.72 (m, 1H), 1.41-1.35 (m, 3H), 0.99 (d, J=6.5 Hz, 3H), 0.98 (d, J=6.5 Hz, 3H), 0.96 (t, J=7.5 Hz, 3H).

EXAMPLE 68(26)

(3R)-1-butyl-2,5-dioxo-3-((1R)-1-hydroxy-2-methylpropyl)-9-(3,5-dimethyl-1-(4-(N-methyl-N-(2-hydroxyethyl)aminosulfonyl)phenyl)pyrazol-4-ylmethyl)-1,4,9-triazaspiro[5.5]undecane.2hydrochloride

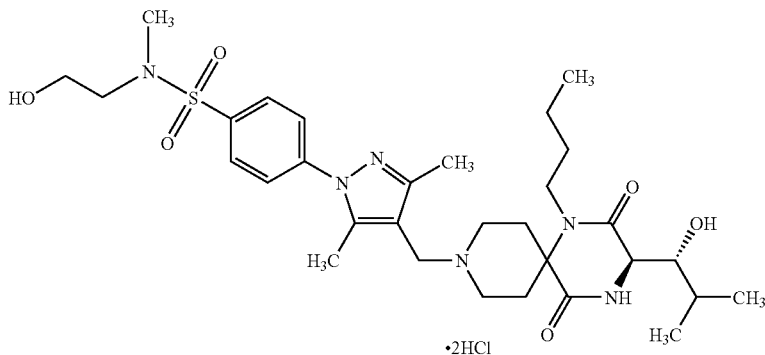

TLC: Rf 0.21 (ethyl acetate:methanol=4:1); NMR (CD$_3$OD):δ 7.98 (d, J=8.5 Hz, 2H), 7.75 (d, J=8.5 Hz, 2H), 4.31 (s, 2H), 4.15 (d, J=2.0 Hz, 1H), 4.04 (m, 1H), 3.79 (m, 1H), 3.69 (t, J=6.0 Hz, 2H), 3.61-3.51 (m, 3H), 3.23-3.17 (m, 4H), 2.87 (s, 3H), 2.58-2.44 (m, 3H), 2.48 (s, 3H), 2.40 (s, 3H), 2.15 (m, 1H), 2.02 (m, 1H), 1.71 (m, 1H), 1.41-1.35 (m, 3H), 0.99 (d, J=6.5 Hz, 3H), 0.98 (d, J=6.5 Hz, 3H), 0.95 (t, J=7.0 Hz, 3H).

EXAMPLE 68(27)

(3R)-1-butyl-2,5-dioxo-3-((1R)-1-hydroxy-2-methylpropyl)-9-(3,5-dimethyl-1-(4-(2-hydroxyethylaminosulfonyl)phenyl)pyrazol-4-ylmethyl)-1,4,9-triazaspiro[5.5]undecane.2hydrochloride

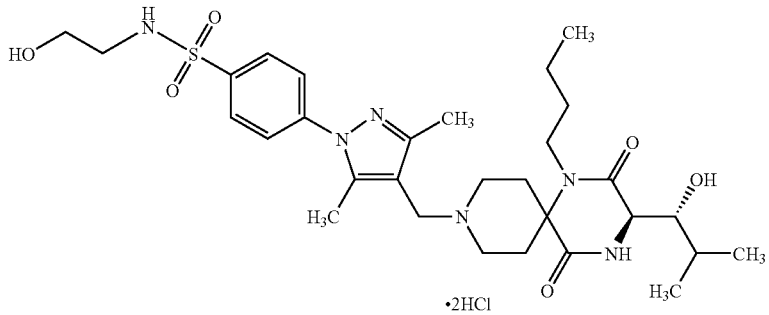

TLC: Rf 0.20 (ethyl acetate:methanol=4:1); NMR (CD$_3$OD):δ 8.03 (d, J=8.7 Hz, 2H), 7.72 (d, J=8.7 Hz, 2H), 4.31 (s, 2H), 4.15 (d, J=2.0 Hz, 1H), 4.04 (m, 1H), 3.79 (m, 1H), 3.63-3.51 (m, 3H), 3.56 (t, J=6.0 Hz, 2H), 3.34-3.29 (m, 1H), 3.20 (dd, J=9.5, 2.0 Hz, 1H), 3.01 (t, J=6.0 Hz, 2H), 2.59-2.43 (m, 3H), 2.47 (s, 3H), 2.40 (s, 3H), 2.15 (m, 1H), 2.02 (m, 1H), 1.71 (m, 1H), 1.41-1.35 (m, 3H), 0.99 (d, J=6.5 Hz, 3H), 0.98 (d, J=6.5 Hz, 3H), 0.95 (t, J=7.2 Hz, 3H).

EXAMPLE 68(28)

(3R)-1-butyl-2,5-dioxo-3-((1R)-1-hydroxy-2-methylpropyl)-9-(3,5-dimethyl-1-(4-(N,N-dimethylaminocarbonyl)phenyl)pyrazol-4-ylmethyl)-1,4,9-triazaspiro[5.5]undecane.2hydrochlode

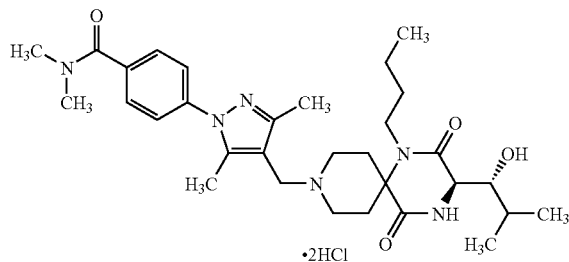

TLC: Rf 0.35 (ethyl acetate:methanol=2:1); NMR (CD$_3$OD):δ 7.62 (d, J=9.0 Hz, 2H), 7.58 (d, J=9.0 Hz, 2H), 4.32 (s, 2H), 4.16 (d, J=2.0 Hz, 1H), 4.05 (m, 1H), 3.79 (m, 1H), 3.61-3.49 (m, 3H), 3.34-3.29 (m, 1H), 3.20 (dd, J=9.5, 2.0 Hz, 1H), 3.13 (s, 3H), 3.04 (s, 3H), 2.55-2.34 (m, 3H), 2.42 (s, 3H), 2.39 (s, 3H), 2.18 (m, 1H), 2.02 (m, 1H), 1.73 (m, 1H), 1.41-1.34 (m, 3H), 0.99 (d, J=6.5 Hz, 3H), 0.98 (d, J=6.5 Hz, 3H), 0.96 (t, J=7.0 Hz, 3H).

EXAMPLE 68(29)

(3R)-1-butyl-2,5-dioxo-3-((1R)-1-hydroxy-2-methylpropyl)-9-(3,5-dimethyl-1-(4-(2-(morpholin-4-yl)ethylaminosulfonyl)phenyl)pyrazol-4-ylmethyl)-1,4,9-triazaspiro[5.5]undecane.3hydrochloride TLC: Rf 0.33 (ethyl acetate:methanol=2:1); NMR (CD$_3$OD):δ 8.06 (d, J=8.7 Hz, 2H), 7.77 (d, J=8.7 Hz, 2H), 4.31 (s, 2H), 4.15 (d, J=2.0 Hz, 1H), 4.10-4.01 (m, 3H), 3.88-3.76 (m, 3H), 3.61-3.53 (m, 5H), 3.37-3.19 (m, 8H), 2.59-2.37 (m, 3H), 2.48 (s, 3H), 2.40 (s, 3H), 2.15 (m, 1H), 2.02 (m, 1H), 1.71 (m, 1H), 1.40-1.35 (m, 3H), 0.99 (d, J=6.5 Hz, 3H), 0.98 (d, J=6.5 Hz, 3H), 0.95 (t, J=7.0 Hz, 3H).

EXAMPLE 68(30)

(3R)-1-butyl-2,5-dioxo-3-((1R)-1-hydroxy-2-methylpropyl)-9-(3,5-dimethyl-1-(4-(pyrrolidin-1-ylcarbonyl)phenyl)pyrazol-4-ylmethyl)-1,4,9-triazaspiro[5.5]undecane.2hdrochloride

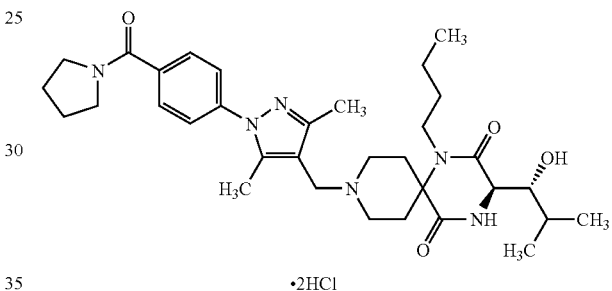

TLC: Rf 0.41 (chloroform:methanol=10:1); NMR (CD$_3$OD):δ 7.72 (d, J=8.7 Hz, 2H), 7.59 (d, J=8.7 Hz, 2H), 4.31 (s, 2H), 4.15 (d, J=2.1 Hz, 1H), 4.05 (m, 1H), 3.79 (m, 1H), 3.66-3.46 (m, 7H), 3.25 (m, 1H), 3.21 (dd, J=9.6, 2.1 Hz, 1H), 2.65-2.35 (m, 3H), 2.43 (s, 3H), 2.40 (s, 3H), 2.16 (m, 1H), 2.09-1.87 (m, 5H), 1.70 (m, 1H), 1.53-1.30 (m, 3H), 1.00 (d, J=6.6 Hz, 3H), 0.98 (d, J=6.6 Hz, 3H), 0.95 (t, J=7.2 Hz, 3H).

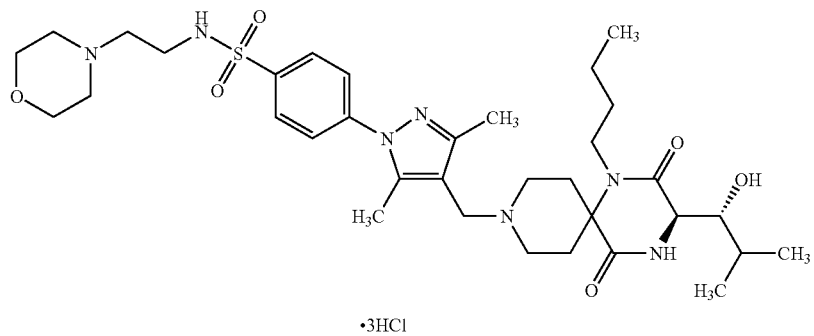

EXAMPLE 68(31)

(3R)-1-butyl-2,5-dioxo-3-((1R)-1-hydroxy-2-methylpropyl)-9-(4-(4-methylsulfinylphenyloxy)phenylmethyl)-1,4,9-triazaspiro[5.5]undecane.hydrochloride

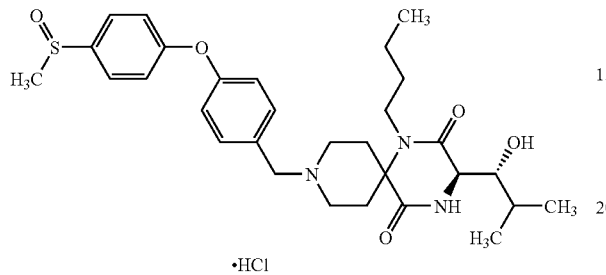

TLC: Rf 0.39 (chloroform:methanol=10:1); NMR (CD$_3$OD):δ 7.74 (d, J=8.7 Hz, 2H), 7.60 (d, J=8.7 Hz, 2H), 7.22 (d, J=8.7 Hz, 2H), 7.17 (d, J=8.7 Hz, 2H), 4.37 (s, 2H), 4.14 (d, J=2.4 Hz, 1H), 4.02 (m, 1H), 3.76 (m, 1H), 3.58-3.42 (m, 3H), 3.25-3.14 (m, 2H), 2.80 (s, 3H), 2.55-2.38 (m, 2H), 2.29 (m, 1H), 2.15 (m, 1H), 2.01 (m, 1H), 1.70 (m, 1H), 1.50-1.27 (m, 3H), 1.04-0.90 (m, 9H).

EXAMPLE 68(32)

(3R)-1-butyl-2,5-dioxo-3-((1R)-1-hydroxy-2-methylpropyl)-9-(3,5-dimethyl-1-(4-(N,N-dimethylaminosulfonyl)phenyl)pyrazol-4-ylmethyl)-1,4,9-triazaspiro[5.5]undecane.2hydrochloride

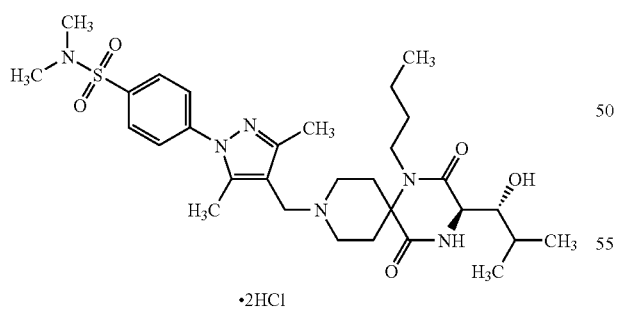

TLC: Rf 0.31 (chloroform:methanol=10:1); NMR (CD$_3$OD):δ 7.96 (d, J=8.7 Hz, 2H), 7.77 (d, J=8.7 Hz, 2H), 4.32 (s, 2H), 4.15 (d, J=2.4 Hz, 1H), 4.06 (m, 1H), 3.79 (m, 1H), 3.64-3.46 (m, 3H), 3.29-3.14 (m, 2H), 2.73 (s, 6H), 2.59-2.44 (m, 2H), 2.47 (s, 3H), 2.39 (s, 3H), 2.35 (m, 1H), 2.17 (m, 1H), 2.02 (m, 1H), 1.71 (m, 1H), 1.51-1.26 (m, 3H), 1.05-0.89 (m, 9H).

EXAMPLE 68(33)

(3R)-1-butyl-2,5-dioxo-3-((1R)-1-hydroxy-2-methylpropyl)-9-(3,5-dimethyl-1-(4-(morpholin-4-ylsulfonyl)phenyl)pyrazol-4-ylmethyl)-1,4,9-triazaspiro[5.5]undecane.2hydrochloride

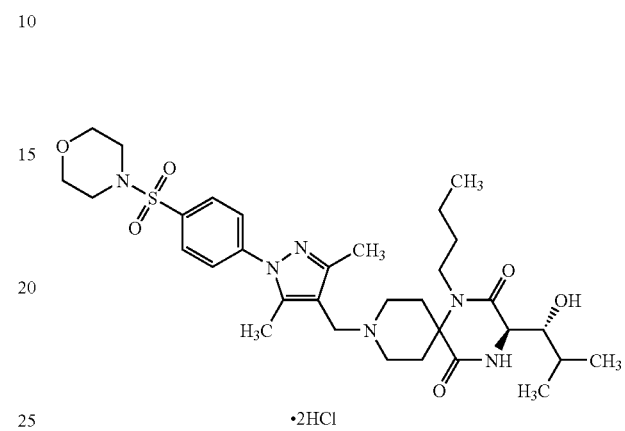

TLC: Rf 0.25 (chloroform:methanol=10:1); NMR (CD$_3$OD):δ 7.95 (d, J=8.7 Hz, 2H), 7.78 (d, J=8.7 Hz, 2H), 4.32 (s, 2H), 4.15 (d, J=2.1 Hz, 1H), 4.06 (m, 1H), 3.80 (m, 1H), 3.74-3.68 (m, 4H), 3.64-3.48 (m, 3H), 3.28-3.14 (m, 2H), 3.05-2.98 (m, 4H), 2.59-2.44 (m, 2H), 2.47 (s, 3H), 2.39 (s, 3H), 2.35 (m, 1H), 2.17 (m, 1H), 2.02 (m, 1H), 1.71 (m, 1H), 1.52-1.30 (m, 3H), 1.05-0.90 (m, 9H).

EXAMPLE 68(34)

(3R)-1-butyl-2,5-dioxo-3-((1R)-1-hydroxy-2-methylpropyl)-9-(4-(4-aminocarbonylphenyloxy)phenylmethyl)-1,4,9-triazaspiro[5.5]undecane.hydrochloride TLC: Rf 0.22 (chloroform:methanol=10:1); NMR (CD$_3$OD):δ 7.92 (d, J=8.7 Hz, 2H), 7.62 (d, J=8.7 Hz, 2H), 7.16 (d, J=8.7 Hz, 2H), 7.09 (d, J=8.7 Hz, 2H), 4.37 (s, 2H), 4.15 (d, J=2.1 Hz, 1H), 4.00 (m, 1H), 3.78 (m, 1H), 3.60-3.38 (m, 3H), 3.28-3.10 (m, 2H), 2.60-2.26 (m, 3H), 2.20-1.88 (m, 2H), 1.68 (m, 1H), 1.54-1.22 (m, 3H), 1.00 (d, J=6.6 Hz, 3H), 0.98 (d, J=6.6 Hz, 3H), 0.96 (t, J=7.5 Hz, 3H).

EXAMPLE 68(35)

(3R)-1-butyl-2,5-dioxo-3-((1R)-1-hydroxy-2-methylpropyl)-9-(4-(4-methylaminocarbonylphenyloxy)phenylmethyl)-1,4,9-triazaspiro[5.5]undecane.hydrochloride

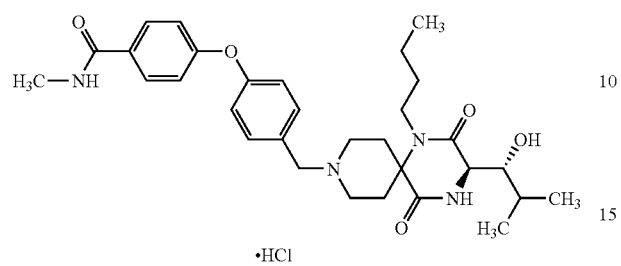

TLC: Rf 0.24 (chloroform:methanol=10:1); NMR (CD$_3$OD):δ 7.85 (d, J=8.7 Hz, 2H), 7.62 (d, J=8.7 Hz, 2H), 7.15 (d, J=8.7 Hz, 2H), 7.08 (d, J=8.7 Hz, 2H), 4.37 (s, 2H), 4.15 (d, J=2.1 Hz, 1H), 4.00 (m, 1H), 3.76 (m, 1H), 3.56-3.42 (m, 3H), 3.26-3.18 (m, 2H), 2.92 (s, 3H), 2.60-2.28 (m, 3H), 2.18-1.94 (m, 2H), 1.70 (m, 1H), 1.50-1.30 (m, 3H), 1.00 (d, J=6.6 Hz, 3H), 0.98 (d, J=6.6 Hz, 3H), 0.96 (t, J=7.5 Hz, 3H).

EXAMPLE 68(36)

(3R)-1-butyl-2,5-dioxo-3-((1R)-1-hydroxy-2-methylpropyl)-9-(3,5-dimethyl-1-(4-methylphenyl)pyrazol-4-ylmethyl)-1,4,9-triazaspiro[5.5]undecane.2hydrochloride

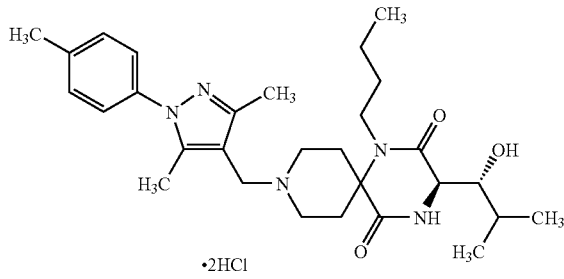

TLC: Rf 0.46 (chloroform:methanol=10:1); NMR (CD$_3$OD):δ 7.41 (s, 4H), 4.34 (s, 2H), 4.15 (d, J=2.1 Hz, 1H), 4.04 (m, 1H), 3.79 (m, 1H), 3.65-3.50 (m, 3H), 3.34 (m, 1H), 3.21 (dd, J=9.6, 2.1 Hz, 1H), 2.66 (m, 1H), 2.55-2.42 (m, 2H), 2.47 (s, 3H), 2.45 (s, 3H), 2.40 (s, 3H), 2.14 (m, 1H), 2.01 (m, 1H), 1.69 (m, 1H), 1.52-1.30 (m, 3H), 1.00 (d, J=6.6 Hz, 3H), 0.98 (d, J=6.6 Hz, 3H), 0.95 (t, J=7.2 Hz, 3H).

EXAMPLE 68(37)

(3R)-1-butyl-2,5-dioxo-3-((1R)-1-hydroxy-2-methylpropyl)-9-(3,5-dimethyl-1-(4-(N,N-diethylaminosulfonyl)phenyl)pyrazol-4-ylmethyl)-1,4,9-triazaspiro[5.5]undecane

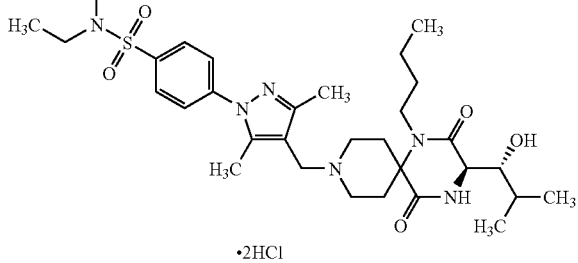

TLC: Rf 0.35 (chloroform:methanol=9:1); NMR (CD$_3$OD):δ 7.99 (d, J=8.7 Hz, 2H), 7.72 (d, J=8.7 Hz, 2H), 4.32 (s, 2H), 4.16 (d, J=2.1 Hz, 1H), 4.06 (m, 1H), 3.80 (m, 1H), 3.63-3.48 (m, 3H), 3.32-3.17 (m, 2H), 3.29 (q, J=7.2 Hz, 4H), 2.54-2.13 (m, 4H), 2.45 (s, 3H), 2.39 (s, 3H), 2.02 (m, 1H), 1.72 (m, 1H), 1.52-1.33 (m, 3H), 1.15 (t, J=7.2 Hz, 6H), 1.00 (d, J=6.6 Hz, 3H), 0.98 (d, J=6.6 Hz, 3H), 0.96 (t, J=6.9 Hz, 3H).

EXAMPLE 68(38)

(3R)-1-butyl-2,5-dioxo-3-((1R)-1-hydroxy-2-methylpropyl)-9-(3,5-dimethyl-1-(4-(4-methylpiperazin-1-ylsulfonyl)phenyl)pyrazol-4-ylmethyl)-1,4,9-triazaspiro[5.5]undecane.3hydrochloride

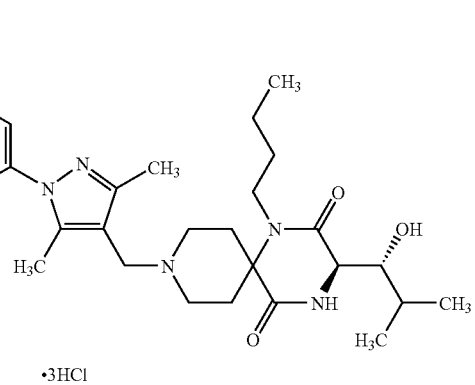

TLC: Rf 0.22 (chloroform:methanol=10:1); NMR (CD₃OD):δ 8.01 (d, J=8.7 Hz, 2H), 7.82 (d, J=8.7 Hz, 2H), 4.31 (s, 2H), 4.15 (d, J=1.8 Hz, 1H), 4.11-3.94 (m, 3H), 3.80 (m, 1H), 3.65-3.48 (m, 5H), 3.34-3.18 (m, 4H), 2.91 (s, 3H), 2.86-2.70 (m, 2H), 2.68-2.36 (m, 3H), 2.49 (s, 3H), 2.40 (s, 3H), 2.15 (m, 1H), 2.02 (m, 1H), 1.70 (m, 1H), 1.50-1.27 (m, 3H), 1.05-0.90 (m, 9H).

EXAMPLE 68(39)

(3R)-1-butyl-2,5-dioxo-3-((1R)-1-hydroxy-2-methylpropyl)-9-(5-chloro-3-methyl-1-phenylpyrazol-4-ylmethyl)-1,4,9-triazaspiro[5.5]undecane.2hydrochloride

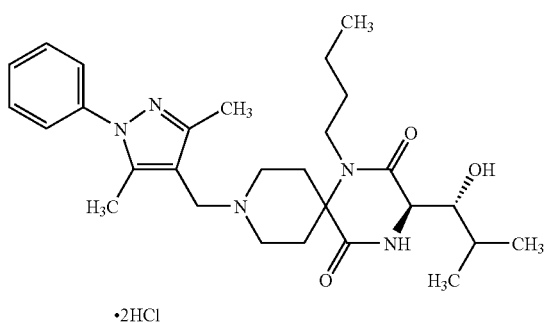

TLC: Rf 0.53 (chloroform:methanol=10:1); NMR (CD₃OD):δ 7.63-7.48 (m, 5H), 4.33 (s, 2H), 4.14 (d, J=1.8 Hz, 1H), 4.10 (m, 1H), 3.83 (m, 1H), 3.66-3.45 (m, 3H), 3.29-3.16 (m, 2H), 2.62-2.32 (m, 3H), 2.44 (s, 3H), 2.17 (m, 1H), 2.01 (m, 1H), 1.71 (m, 1H), 1.52-1.11 (m, 3H), 1.05-0.88 (m, 9H).

EXAMPLE 68(40)

(3R)-1-butyl-2,5-dioxo-3-((1R)-1-hydroxy-2-methylpropyl)-9-(3,5-dimethyl-1-(4-(morpholin-4-ylcarbonyl)phenyl)pyrazol-4-ylmethyl)-1,4,9-triazaspiro[5.5]undecane.2hydrochloride

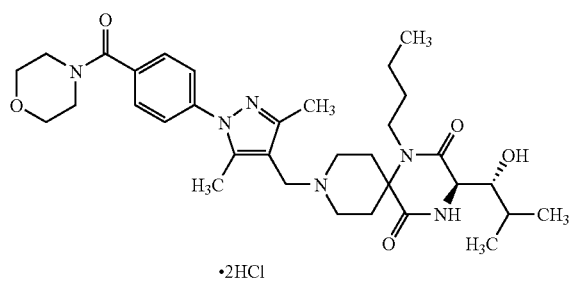

TLC: Rf 0.39 (chloroform:methanol=10:1); NMR (CD₃OD):δ 7.66-7.57 (m, 4H), 4.31 (s, 2H), 4.15 (d, J=2.1 Hz, 1H), 4.05 (m, 1H), 3.88-3.39 (m, 12H), 3.25 (m, 1H), 3.20 (dd, J=9.6, 2.1 Hz, 1H), 2.65-2.27 (m, 3H), 2.43 (s, 3H), 2.40 (s, 3H), 2.17 (m, 1H), 2.02 (m, 1H), 1.71 (m, 1H), 1.54-1.27 (m, 3H), 1.00 (d, J=6.6 Hz, 3H), 0.98 (d, J=6.6 Hz, 3H), 0.96 (t, J=7.2 Hz, 3H).

EXAMPLE 68(41)

(3R)-1-butyl-2,5-dioxo-3-((1R)-1-hydroxy-2-methylpropyl)-9-(3,5-dimethyl-1-(4-(2-hydroxyethylaminocarbonyl)phenyl)pyrazol-4-ylmethyl)-1,4,9-triazaspiro[5.5]undecane.2hydrochloride

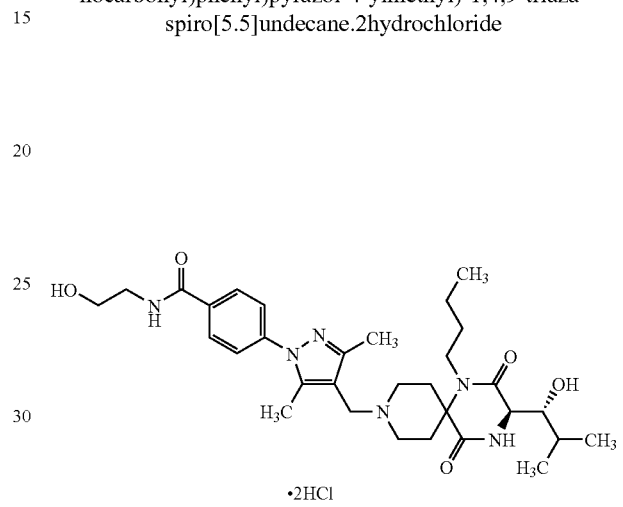

TLC: Rf 0.42 (chloroform:methanol=5:1); NMR (CD₃OD):δ 8.03 (d, J=8.7 Hz, 2H), 7.61 (d, J=8.7 Hz, 2H), 4.32 (s, 2H), 4.16 (d, J=1.8 Hz, 1H), 4.04 (m, 1H), 3.80 (m, 1H), 3.74 (t, J=5.7 Hz, 2H), 3.64-3.48 (m, 3H), 3.54 (t, J=5.7 Hz, 2H), 3.30-3.16 (m, 2H), 2.64-2.34 (m, 3H), 2.45 (s, 3H), 2.41 (s, 3H), 2.22-1.92 (m, 2H), 1.72 (m, 1H), 1.52-1.26 (m, 3H), 1.01 (d, J=6.6 Hz, 3H), 0.99 (d, J=6.6 Hz, 3H), 0.96 (t, J=7.2 Hz, 3H).

EXAMPLE 68(42)

(3R)-1-butyl-2,5-dioxo-3-((1R)-1-hydroxy-2-methylpropyl)-9-(4-(4-(2-(N,N-dimethylamino)ethylaminocarbonyl)phenyloxy)phenylmethyl)-1,4,9-triazaspiro[5.5]undecane.2hydrochloride

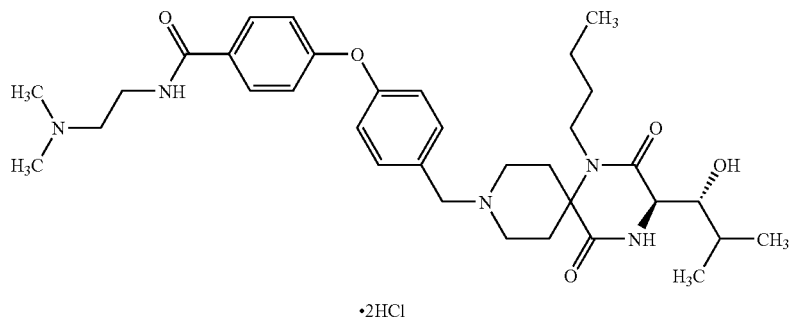

TLC: Rf 0.19 (chloroform:methanol=5:1); NMR (CD₃OD):δ 7.93 (d, J=9.0 Hz, 2H), 7.61 (d, J=8.4 Hz, 2H), 7.18-7.08 (m, 4H), 4.36 (s, 2H), 4.14 (d, J=1.8 Hz, 1H), 4.00 (m, 1H), 3.80-3.70 (m, 3H), 3.54-3.42 (m, 3H), 3.38 (t, J=6.3 Hz, 2H), 3.26-3.18 (m, 2H), 2.98 (s, 6H), 2.60-2.30 (m, 3H), 2.18-1.96 (m, 2H), 1.68 (m, 1H), 1.50-1.30 (m, 3H), 1.00-0.90 (m, 9H).

EXAMPLE 68(43)

(3R)-1-butyl-2,5-dioxo-3-((1R)-1-hydroxy-2-methylpropyl)-9-(4-(pyridin-3-yloxy)phenylmethyl)-1,4,9-triazaspiro[5.5]undecane.2hydrochloride

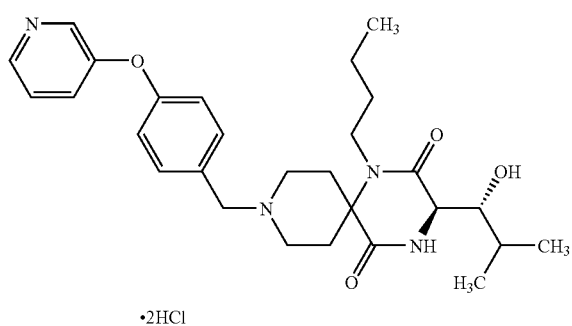

TLC: Rf 0.31 (chloroform:methanol=10:1); NMR (CD₃OD):δ 8.74 (m, 1H), 8.62 (d, J=5.4 Hz, 1H), 8.24 (m, 1H), 8.14 (m, 1H), 7.76 (d, J=8.4 Hz, 2H), 7.34 (d, J=8.4 Hz, 2H), 4.40 (s, 2H), 4.14 (d, J=2.1 Hz, 1H), 4.00 (m, 1H), 3.76 (m, 1H), 3.60-3.44 (m, 3H), 3.30-3.16 (m, 2H), 2.60 (m, 1H), 2.50-2.40 (m, 2H), 2.26-1.86 (m, 2H), 1.66 (m, 1H), 1.50-1.30 (m, 3H), 1.02-0.88 (m, 9H).

EXAMPLE 68(44)

(3R)-1-butyl-2,5-dioxo-3-((1R)-1-hydroxy-2-methylpropyl)-9-(4-(4-carboxyphenyloxy)phenylmethyl)-1,4,9-triazaspiro[5.5]undecane.hydrochloride

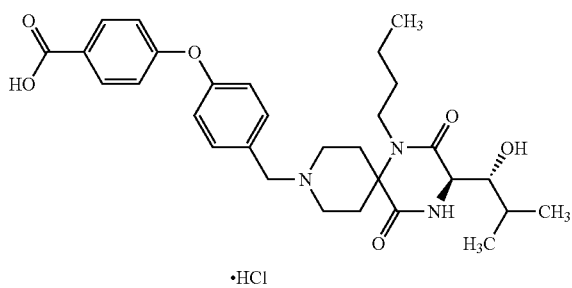

TLC: Rf 0.42 (chloroform:methanol=5:1); NMR (CD₃OD):δ 8.04 (d, J=8.7 Hz, 2H), 7.59 (d, J=8.4 Hz, 2H), 7.18 (d, J=8.4 Hz, 2H), 7.07 (d, J=8.7 Hz, 2H), 4.37 (s, 2H), 4.15 (d, J=2.4 Hz, 1H), 4.02 (m, 1H), 3.76 (m, 1H), 3.60-3.44 (m, 3H), 3.24-3.08 (m, 2H), 2.56-1.92 (m, 5H), 1.70 (m, 1H), 1.50-1.26 (m, 3H), 1.08-0.90 (m, 9H).

EXAMPLE 68(45)

(3R)-1-butyl-2,5-dioxo-3-((1R)-1-hydroxy-2-methylpropyl)-9-(4-(4-methylphenyloxy)phenylmethyl)-1,4,9-triazaspiro[5.5]undecane.hydrochloride

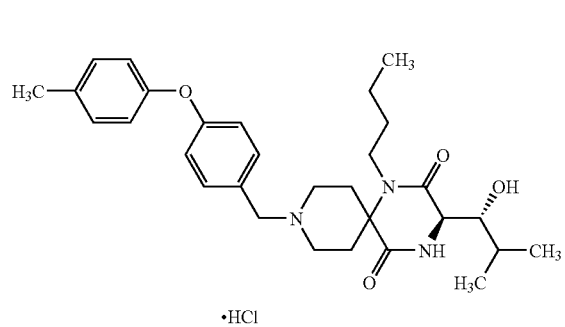

TLC: Rf 0.36 (chloroform:methanol=10:1); NMR (CD₃OD):δ 7.49 (d, J=9.0 Hz, 2H), 7.20 (d, J=9.0 Hz, 2H), 7.02 (d, J=9.0 Hz, 2H), 6.92 (d, J=9.0 Hz, 2H), 4.32 (s, 2H), 4.14 (d, J=2.1 Hz, 1H), 3.98 (m, 1H), 3.72 (m, 1H), 3.58-3.36 (m, 3H), 3.26-3.08 (m, 2H), 2.52-1.82 (m, 5H), 2.33 (s, 3H), 1.68 (m, 1H), 1.50-1.28 (m, 3H), 1.02-0.86 (m, 9H).

EXAMPLE 68(46)

(3R)-1-butyl-2,5-dioxo-3-((1R)-1-hydroxy-2-methylpropyl)-9-(3,5-dimethyl-1-(2,4-difluorophenyl)pyrazol-4-ylmethyl)-1,4,9-triazaspiro[5.5]undecane.2hydrochloride

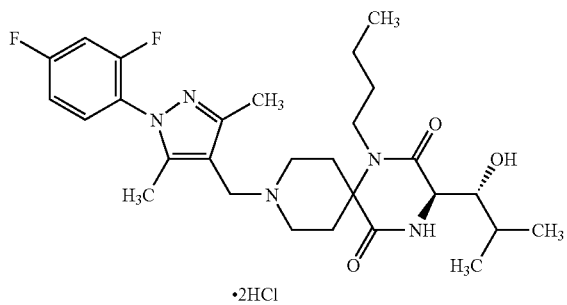

TLC: Rf 0.63 (chloroform:methanol=5:1); NMR (CD₃OD):δ 7.56 (m, 1H), 7.33-7.16 (m, 2H), 4.32 (s, 2H), 4.16 (d, J=2.1 Hz, 1H), 4.06 (m, 1H), 3.80 (m, 1H), 3.62-3.44 (m, 3H), 3.28-3.16 (m, 2H), 2.62-1.84 (m, 5H), 2.39 (s, 3H), 2.28 (s, 3H), 1.72 (m, 1H), 1.54-1.28 (m, 3H), 1.01 (d, J=6.6 Hz, 3H), 0.99 (d, J=6.6 Hz, 3H), 0.97 (t, J=7.2 Hz, 3H).

EXAMPLE 68(47)

(3R)-1-butyl-2,5-dioxo-3-((1R)-1-hydroxy-2-methylpropyl)-9-(3,5-dimethyl-1-(pyridin-2-yl)pyrazol-4-ylmethyl)-1,4,9-triazaspiro[5.5]undecane.2hydrochloride

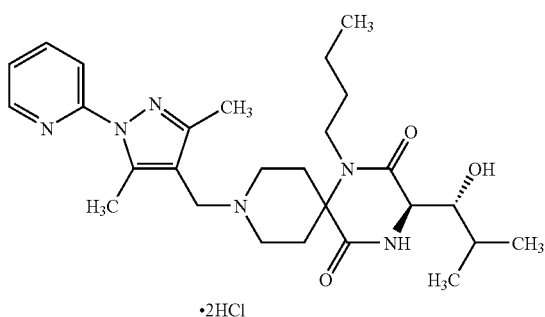

TLC: Rf 0.28 (chloroform:methanol=10:1); NMR (CD$_3$OD):δ 8.52 (m, 1H), 8.01 (m, 1H), 7.81 (m, 1H), 7.41 (m, 1H), 4.33 (s, 2H), 4.16 (d, J=1.8 Hz, 1H), 4.06 (m, 1H), 3.80 (m, 1H), 3.64-3.46 (m, 3H), 3.26-3.12 (m, 2H), 2.68 (s, 3H), 2.58-2.24 (m, 3H), 2.41 (s, 3H), 2.18 (m, 1H), 2.04 (m, 1H), 1.70 (m, 1H), 1.54-1.26 (m, 3H), 1.00 (d, J=6.6 Hz, 3H), 0.99 (d, J=6.6 Hz, 3H), 0.96 (t, J=7.5 Hz, 3H).

EXAMPLE 68(48)

(3R)-1-butyl-2,5-dioxo-3-((1R)-1-hydroxy-2-methylpropyl)-9-(3,5-dimethyl-1-(4-methylaminocarbonylphenyl)pyrazol-4-ylmethyl)-1,4,9-triazaspiro[5.5]undecane.2hydrochloride

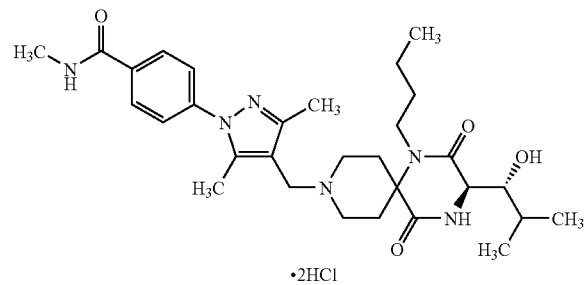

TLC: Rf 0.18 (chloroform:methanol=10:1); NMR (CD$_3$OD):δ 7.99 (d, J=8.7 Hz, 2H), 7.61 (d, J=8.7 Hz, 2H), 4.31 (s, 2H), 4.15 (d, J=2.1 Hz, 1H), 4.04 (m, 1H), 3.79 (m, 1H), 3.64-3.49 (m, 3H), 3.30-3.17 (m, 2H), 2.94 (s, 3H), 2.59 (m, 1H), 2.51-2.36 (m, 2H), 2.44 (s, 3H), 2.41. (s, 3H), 2.15 (m, 1H), 2.02 (m, 1H), 1.70 (m, 1H), 1.52-1.27 (m, 3H), 1.05-0.91 (m, 9H).

EXAMPLE 68(49)

(3R)-1-butyl-2,5-dioxo-3-((1R)-1-hydroxy-2-methylpropyl)-9-(4-cyclohexyloxyphenylmethyl)-1,4,9-triazaspiro[5.5]undecane.hydrochloride

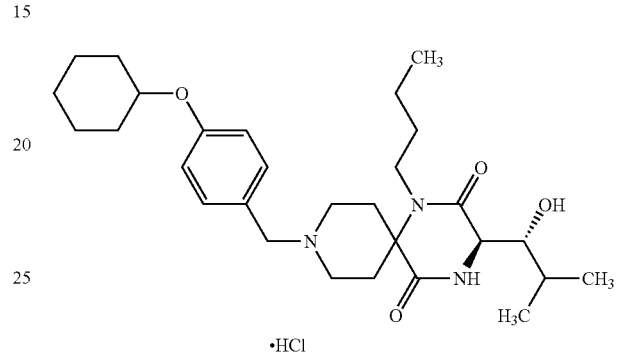

TLC: Rf 0.44 (chloroform:methanol=10:1); NMR (CD$_3$OD):δ 7.44 (d, J=8.7 Hz, 2H), 7.01 (d, J=8.7 Hz, 2H), 4.38 (m, 1H), 4.27 (s, 2H), 4.14 (d, J=2.1 Hz, 1H), 3.96 (m, 1H), 3.70 (m, 1H), 3.58-3.36 (m, 3H), 3.26-3.08 (m, 2H), 2.54-1.26 (m, 19H), 0.99 (d, J=6.6 Hz, 3H), 0.98 (d, J=6.6 Hz, 3H), 0.96 (t, J=7.5 Hz, 3H).

EXAMPLE 68(50)

(3R)-1-butyl-2,5-dioxo-3-((1R)-1-hydroxy-2-methylpropyl)-9-(4-(3,4,5,6-tetrahydropyran-4-yloxy)phenylmethyl)-1,4,9-triazaspiro[5.5]undecane.hydrochloride

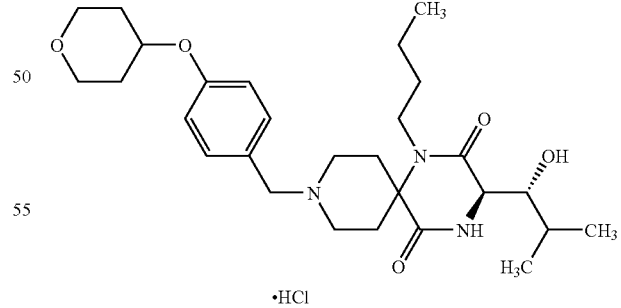

TLC: Rf 0.33 (chloroform:methanol=10:1); NMR (CD$_3$OD):δ 7.47 (d, J=8.7 Hz, 2H), 7.07 (d, J=8.7 Hz, 2H), 4.64 (m, 1H), 4.29 (s, 2H), 4.14 (d, J=2.4 Hz, 1H), 4.04-3.86 (m, 3H), 3.80-3.36 (m, 6H), 3.26-3.08 (m, 2H), 2.52-1.90 (m, 7H), 1.80-1.58 (m, 3H), 1.50-1.26 (m, 3H), 0.99 (d, J=6.6 Hz, 3H), 0.98 (d, J=6.6 Hz, 3H), 0.96 (t, J=7.5 Hz, 3H).

EXAMPLE 68(51)

(3R)-1-butyl-2,5-dioxo-3-((1R)-1-hydroxy-2-methylpropyl)-9-(4-(4-methoxyphenylmethylaminocarbonyl)phenylmethyl)-1,4,9-triazaspiro[5.5]undecane.hydrochloride

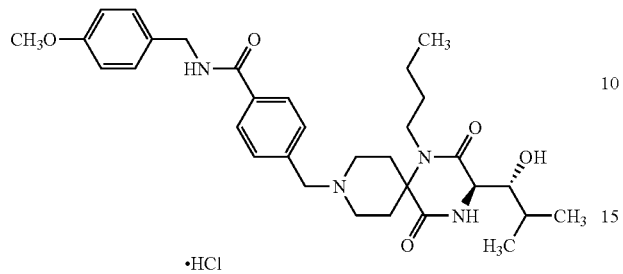

TLC: Rf 0.37 (chloroform:methanol=10:1); NMR (CD₃OD):δ 7.96 (d, J=8.4 Hz, 2H), 7.67 (d, J=8.4 Hz, 2H), 7.28 (d, J=8.4 Hz, 2H), 6.88 (d, J=8.4 Hz, 2H), 4.52 (s, 2H), 4.43 (s, 2H), 4.14 (d, J=2.1 Hz, 1H), 4.04 (m, 1H), 3.77 (s, 3H), 3.77 (m, 1H), 3.58-3.40 (m, 3H), 3.26-3.10 (m, 2H), 2.54-2.22 (m, 3H), 2.20-1.90 (m, 2H), 1.66 (m, 1H), 1.50-1.26 (m, 3H), 0.99 (d, J=6.6 Hz, 3H), 0.98 (d, J=6.6 Hz, 3H), 0.95 (t, J=7.5 Hz, 3H).

EXAMPLE 68(52)

(3R)-1-butyl-2,5-dioxo-3-((1R)-1-hydroxy-2-methylpropyl)-9-(4-(cyclohexylaminocarbonyl)phenylmethyl)-1,4,9-triazaspiro[5.5]undecane.hydrochloride

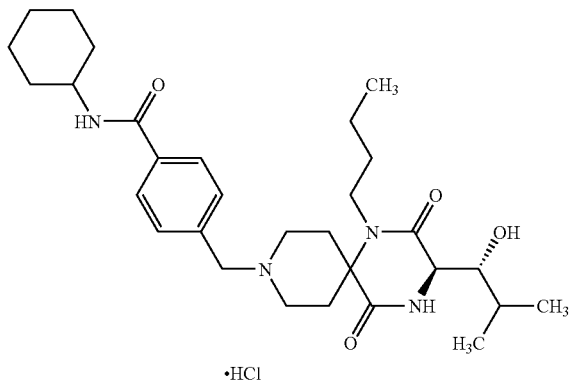

TLC: Rf 0.44 (ethyl acetate:methanol=4:1); NMR (CD₃OD):δ 7.91 (d, J=8.3 Hz, 2H), 7.66 (d, J=8.3 Hz, 2H), 4.42 (s, 2H), 4.13 (d, J=2.0 Hz, 1H), 4.03 (m 1H), 3.90-3.72 (m, 2H), 3.56-3.43 (m, 3H), 3.25 (m, 1H), 3.18 (dd, J=9.6, 2.0 Hz, 1H), 2.53-2.40 (m, 2H), 2.30 (m, 1H), 2.14 (m, 1H), 2.06-1.67 (m, 8H), 1.50-1.33 (m, 7H), 0.98 (d, J=6.6 Hz, 3H), 0.96 (d, J=6.6 Hz, 3H), 0.94 (t, J=7.5 Hz, 3H).

EXAMPLE 68(53)

(3R)-1-butyl-2,5-dioxo-3-((1R)-1-hydroxy-2-methylpropyl)-9-(4-(4-(pyrrolidin-1-ylcarbonyl)phenyloxy)phenylmethyl)-1,4,9-triazaspiro[5.5]undecane.hydrochloride

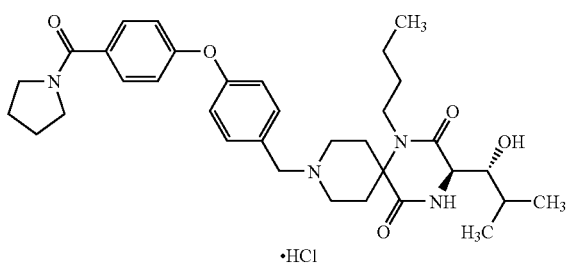

TLC: Rf 0.34 (ethyl acetate:methanol=4:1); NMR (CD₃OD):δ 7.61-7.57 (m, 4H), 7.14 (d, J=8.7 Hz, 2H), 7.09 (d, J=8.7 Hz, 2H), 4.36 (s, 2H), 4.14 (d, J=2.0 Hz, 1H), 4.00 (m, 1H), 3.74 (m, 1H), 3.62-3.45 (m, 7H), 3.24(m, 1H), 3.19 (dd, J=9.6, 2.0 Hz, 1H), 2.56-2.29 (m, 3H), 2.15-1.89 (m, 6H), 1.70 (m, 1H), 1.40-1.33 (m, 3H), 0.98 (d, J=6.6 Hz, 3H), 0.97 (d, J=6.6 Hz, 3H), 0.95 (t, J=7.2 Hz, 3H).

EXAMPLE 68(54)

(3R)-1-butyl-2,5-dioxo-3-((1R)-1-hydroxy-2-methylpropyl)-9-(3,5-dimethyl-1-(4-fluorophenyl)pyrazol-4-ylmethyl)-1,4,9-triazaspiro[5.5]undecane.2hydrochloride

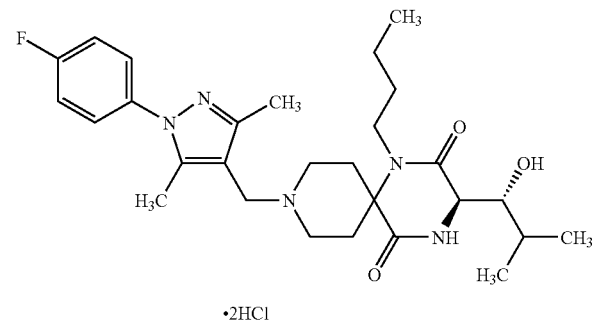

TLC: Rf 0.37 (ethyl acetate:methanol=4:1); NMR (CD₃OD):δ 7.56-7.51 (m, 2H), 7.35-7.28 (m, 2H), 4.31 (s, 2H), 4.15 (d, J=2.0 Hz, 1H), 4.03 (m, 1H), 3.78 (m, 1H), 3.61-3.49 (m, 3H), 3.34 (m, 1H), 3.20 (dd, J=9.6, 2.0 Hz, 1H), 2.68-2.42 (m, 6H), 2.38 (s, 3H), 2.17 (m, 1H), 2.02 (m, 1H), 1.70 (m, 1H), 1.50-1.35 (m, 3H), 0.99 (d, J=6.6 Hz, 3H), 0.98 (d, J=6.6 Hz, 3H), 0.95 (t, J=7.2 Hz, 3H).

EXAMPLE 68(55)

(3R)-1-butyl-2,5-dioxo-3-((1R)-1-hydroxy-2-methylpropyl)-9-(3,5-dimethyl-1-(4-(2-phenylethyl)phenyl)pyrazol-4-ylmethyl)-1,4,9-triazaspiro[5.5]undecane.2hydrochloride

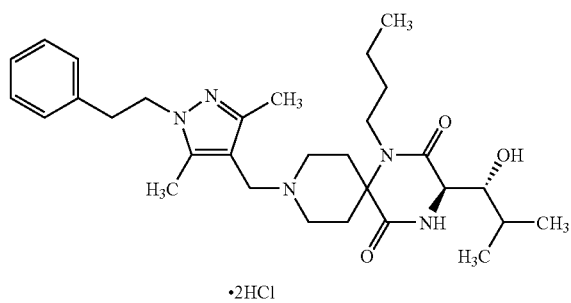

TLC: Rf 0.13 (chloroform:methanol=10:1); NMR (CD₃OD):δ 7.32-7.20 (m, 3H), 7.11-7.08 (m, 2H), 4.45 (t, J=6.6 Hz, 2H), 4.20 (s, 2H), 4.16 (d, J=1.8 Hz, 1H), 3.90 (m, 1H), 3.70-3.48 (m, 3H), 3.42-3.30 (m, 2H), 3.21 (m, 1H), 3.14 (t, J=6.6 Hz, 2H), 2.76-2.38 (m, 3H), 2.50 (s, 3H), 2.20-1.88 (m, 2H), 1.97 (s, 3H), 1.74 (m, 1H), 1.56-1.34 (m, 3H), 1.01 (d, J=6.6 Hz, 3H), 1.00 (d, J=6.6 Hz, 3H), 0.97 (t, J=6.9 Hz, 3H).

EXAMPLE 68(56)

(3R)-1-butyl-2,5-dioxo-3-((1R)-1-hydroxy-2-methylpropyl)-9-(3,5-dimethyl-1-(1-benzyloxycarbonylpiperidin-4-yl)pyrazol-4-ylmethyl)-1,4,9-triazaspiro[5.5]undecane.2hydrocloride

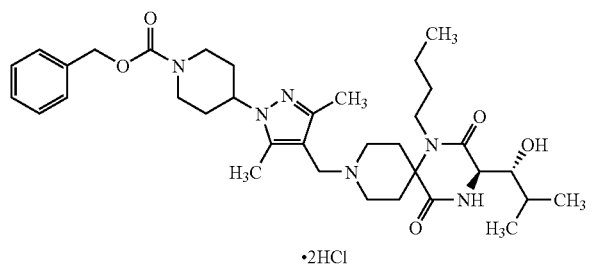

TLC: Rf 0.13 (chloroform:methanol=10:1); NMR (CD₃OD):δ 7.44-7.24 (m, 5H), 5.16 (s, 2H), 4.54 (m, 1H), 4.40-4.20 (m, 2H), 4.25 (s, 2H), 4.15 (d, J=2.1 Hz, 1H), 4.00 (m, 1H), 3.82-3.42 (m, 5H), 3.30-2.88 (m, 3H), 2.64-2.30 (m, 3H), 2.47 (s, 3H), 2.37 (s, 3H), 2.20-1.84 (m, 6H), 1.70 (m, 1H), 1.52-1.26 (m, 3H), 1.00 (d, J=6.6 Hz, 3H), 0.98 (d, J=6.6 Hz, 3H), 0.95 (t, J=7.5 Hz, 3H).

EXAMPLE 68(57)

(3R)-1-butyl-2,5-dioxo-3-((1R)-1-hydroxy-2-methylpropyl)-9-(4-(4-(2-hydroxyethylaminocarbonyl)phenyloxy)phenylmethyl)-1,4,9-triazaspiro[5.5]undecane.hydrochloride

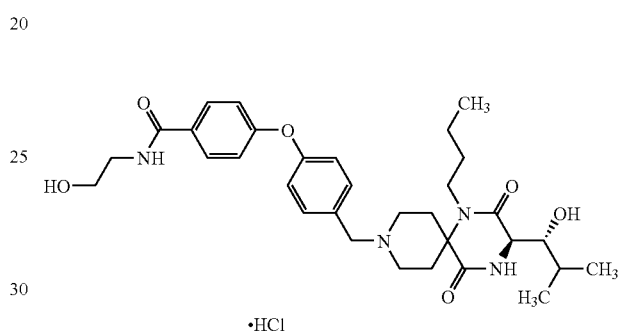

TLC: Rf 0.47 (chloroform:methanol=5:1); NMR (CD₃OD):δ 7.89 (d, J=9.0 Hz, 2H), 7.61 (d, J=9.0 Hz, 2H), 7.16 (d, J=9.0 Hz, 2H), 7.09 (d, J=9.0 Hz, 2H), 4.37 (s, 2H), 4.16 (d, J=2.1 Hz, 1H), 4.00 (m, 1H), 3.78 (m, 1H), 3.71 (t, J=5.7 Hz, 2H), 3.60-3.40 (m, 3H), 3.51 (t, J=5.7 Hz, 2H), 3.30-3.12 (m, 2H), 2.60-2.24 (m, 3H), 2.22-1.92 (m, 2H), 1.70 (m, 1H), 1.56-1.24 (m, 3H), 1.00 (d, J=6.6 Hz, 3H), 0.98 (d, J=6.6 Hz, 3H), 0.96 (t, J=7.5 Hz, 3H).

EXAMPLE 68(58)

(3R)-1-butyl-2,5-dioxo-3-((1R)-1-hydroxy-2-methylpropyl)-9-(3,5-dimethyl-1-(1-methylsulfonylpiperidin-4-yl)pyrazol-4-ylmethyl)-1,4,9-triazaspiro[5.5]undecane.2hydrochloride

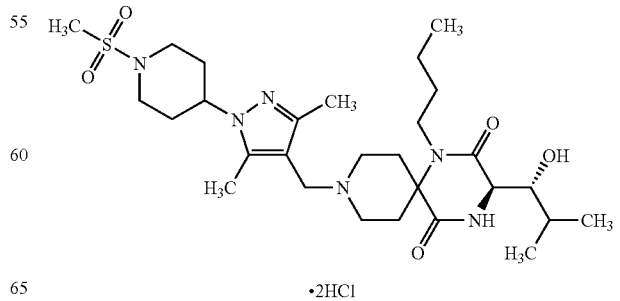

TLC: Rf 0.41 (chloroform:methanol=5:1); NMR (CD$_3$OD):δ 4.44 (m, 1H), 4.25 (s, 2H), 4.15 (d, J=2.1 Hz, 1H), 4.06-3.64 (m, 4H), 3.60-3.44 (m, 3H), 3.28-3.16 (m, 2H), 3.06-2.92 (m, 2H), 2.90 (s, 3H), 2.64-1.90 (m, 9H), 2.47 (s, 3H), 2.37 (s, 3H), 1.68 (m, 1H), 1.50-1.24 (m, 3H), 1.00 (d, J=6.6 Hz, 3H), 0.99 (d, J=6.6 Hz, 3H), 0.95 (t, J=7.5 Hz, 3H).

EXAMPLE 68(59)

(3R)-1-butyl-2,5-dioxo-3-((1R)-1-hydroxy-2-methylpropyl)-9-(4-(4-hydroxymethylphenyloxy)phenylmethyl)-1,4,9-triazaspiro[5.5]undecane

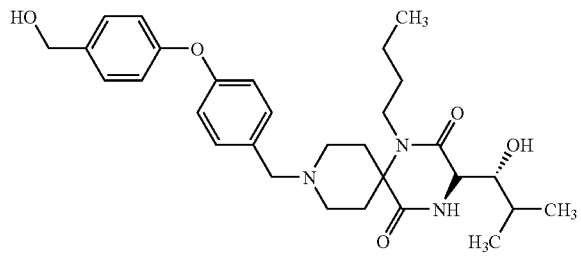

TLC: Rf 0.32 (chloroform:methanol=10:1); NMR (CD$_3$OD):δ 7.36 (d, J=8.4 Hz, 2H), 7.35 (d, J=8.4 Hz, 2H), 6.97 (d, J=8.4 Hz, 4H), 4.58 (s, 2H), 4.12 (d, J=2.4 Hz, 1H), 3.73 (s, 2H), 3.47 (m, 1H), 3.30-2.90 (m, 6H), 2.31-1.83 (m, 5H), 1.64 (m, 1H), 1.55-1.23 (m, 3H), 0.97 (d, J=6.6 Hz, 6H), 0.95 (t, J=7.5 Hz, 3H).

EXAMPLE 69

(3S)-1-butyl-2,5-dioxo-3-((1S)-1-hydroxy-2-methylpropyl)-9-(6-phenyloxypyridin-3-ylmethyl)-1,4,9-triazaspiro[5.5]undecane.2hydrochloride

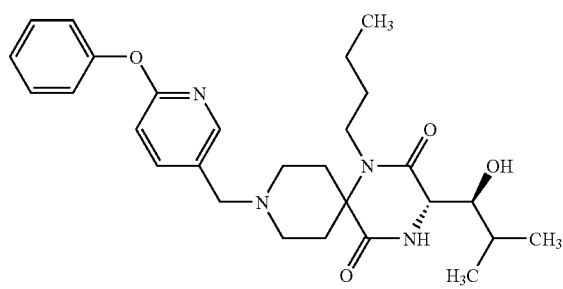

•2HCl

By the same procedure described in Example 68 using the compound prepared in Reference example 15(8) instead of the compound prepared in Reference example 3, the title compound (110 mg) having the following physical data was obtained.

TLC: Rf 0.48 (chloroform:methanol=10:1); NMR (CD$_3$OD):δ 8.35 (d, J=2.1 Hz, 1H), 8.12 (dd, J=8.7, 2.1 Hz, 1H), 7.49-7.40 (m, 2H), 7.27 (t, J=7.8 Hz, 1H), 7.15 (d, J=7.8 Hz, 2H), 7.06 (d, J=8.7 Hz, 1H), 4.39 (s, 2H), 4.14 (d, J=2.1 Hz, 1H), 4.07-3.93 (m, 1H), 3.82-3.67 (m, 1H), 3.58-3.40 (m, 3H), 3.30-3.15 (m, 1H), 3.19 (dd, J=9.6, 2.1 Hz, 1H), 2.60-2.28 (m, 3H), 2.18-2.05 (m, 1H), 2.05-1.90 (m, 1H), 1.80-1.55 (m, 1H), 1.50-1.25 (m, 3H), 0.99 (d, J=6.6 Hz, 3H), 0.97 (d, J=6.6 Hz, 3H), 0.95 (t, J=7.2 Hz, 3H); Optical rotation:[α]$_D$–10.1 (c 1.04, methanol, 25° C.); HPLC conditions column: CHIRALCEL OJ-R, 0.46×15 cm, DAICEL, OJR0CD-JB026; flow rate: 0.7 ml/min; solvent A solution: 0.1M aqueous solution of potassium dihydrogen phosphate, B solution: acetonitrile (A:B=76:24); UV: 225 nm; retention time: 8.65 min.

EXAMPLE 70

(3S)-1-butyl-2,5-dioxo-3-(2-methylpropyl)-9-(3,5-dimethyl-1-(4-(N,N-dimethylaminocarbonyl)phenyl) pyrazol-4-ylmethyl)-1,4,9-triazaspiro[5.5] undecane.2hydrochloride

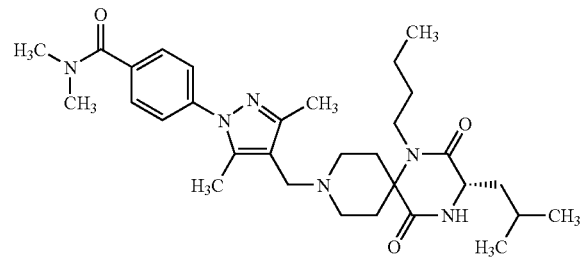

•2HCl

By the same procedure described in Example 68 using the compound prepared in Reference example 15(1) instead of the compound prepared in Reference example 15, and using [4-(4-formyl-3,5-dimethylpyrazolyl)phenyl]-N,N-dimethylcarboxamide instead of 3-formyl-6-phenyloxypyridine, the title compound having the following physical data was obtained.

TLC: Rf 0.62 (chloroform:methanol=5:1); NMR (CD$_3$OD):δ 7.65-7.52 (m, 4H), 4.33 (s, 2H), 4.03 (dd, J=7.8, 4.5 Hz, 1H), 3.96-3.72 (m, 2H), 3.64-3.54 (m, 2H), 3.50-3.36 (m, 2H), 3.14 (s, 3H), 3.05 (s, 3H), 2.60-2.42 (m, 2H), 2.44 (s, 3H), 2.41 (s, 3H), 2.36-2.10 (m, 2H), 1.90-1.24 (m, 7H), 0.97 (t, J=7.2 Hz, 3H), 0.96 (d, J=6.6 Hz, 3H), 0.95 (d, J=6.6 Hz, 3H).

EXAMPLE 70(1) TO 70(43)

By the same procedure as described in Example 70 using the corresponding aldehyde derivatives respectively instead of [4-(4-formyl-3,5-dimethylpyrazolyl)phenyl]-N,N-dimethylcarboxamide, the following compounds having the following physical data were obtained.

EXAMPLE 70(1)

(3S)-1-butyl-2,5-dioxo-3-(2-methylpropyl)-9-(3,5-dimethyl-1-(4-(pyrrolidin-1-ylcarbonyl)phenyl)pyrazol-4-ylmethyl)-1,4,9-triazaspiro[5.5]undecane.2hydrochloride

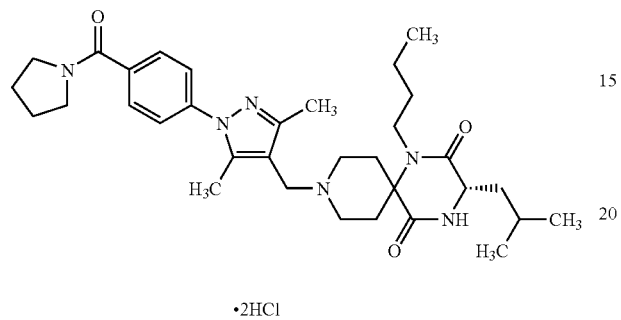

•2HCl

TLC: Rf 0.56 (chloroform:methanol=5:1); NMR (CD₃OD):δ 7.73 (d, J=8.7 Hz, 2H), 7.60 (d, J=8.7 Hz, 2H), 4.33 (s, 2H), 4.03 (dd, J=7.5, 4.5 Hz, 1H), 3.96-3.74 (m, 2H), 3.66-3.36 (m, 8H), 2.58-2.40 (m, 2H), 2.44 (s, 3H), 2.41 (s, 3H), 2.34-2.12 (m, 2H), 2.06-1.26 (m, 11H), 0.97 (t, J=7.2 Hz, 3H), 0.96 (d, J=6.3 Hz, 3H), 0.95 (d, J=6.3 Hz, 3H).

EXAMPLE 70(2)

(3S)-1-butyl-2,5-dioxo-3-(2-methylpropyl)-9-(3,5-dimethyl-1-(4-(morpholin-4-ylcarbonyl)phenyl)pyrazol-4-ylmethyl)-1,4,9-triazaspiro[5.5]undecane.2hydrochloride

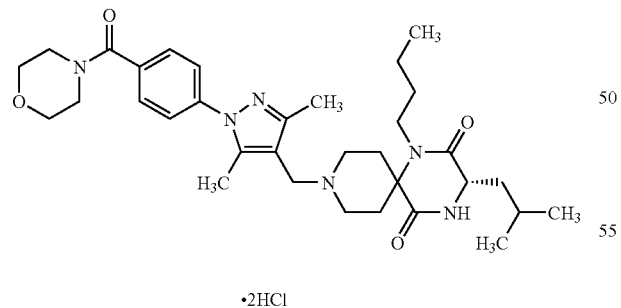

•2HCl

TLC: Rf 0.57 (chloroform:methanol=5:1); NMR (CD₃OD):δ 7.64 (d, J=9.0 Hz, 2H), 7.60 (d, J=9.0 Hz, 2H), 4.33 (s, 2H), 4.03 (dd, J=7.5, 4.5 Hz, 1H), 3.98-3.36 (m, 14H), 2.58-2.36 (m, 2H), 2.44 (s, 3H), 2.40 (s, 3H), 2.32-2.14 (m, 2H), 1.90-1.24 (m, 7H), 0.97 (t, J=7.2 Hz, 3H), 0.96 (d, J=6.3 Hz, 3H), 0.95 (d, J=6.3 Hz, 3H).

EXAMPLE 70(3)

(3S)-1-butyl-2,5-dioxo-3-(2-methylpropyl)-9-(4-methylsulfonylphenylmethyl)-1,4,9-triazaspiro[5.5]undecane.hydrochloride

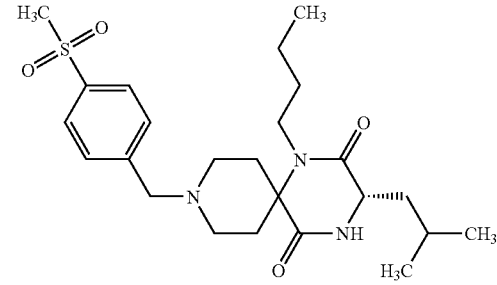

•HCl

TLC: Rf 0.49 (chloroform:methanol=10:1); NMR (CD₃OD):δ 8.09 (d, J=8.4 Hz, 2H), 7.85 (d, J=8.4 Hz, 2H), 4.48 (s, 2H), 4.02 (dd, J=7.8, 4.5 Hz, 1H), 3.92-3.70 (m, 2H), 3.56-3.36 (m, 4H), 3.16 (s, 3H), 2.48-2.30 (m, 2H), 2.28-2.06 (m, 2H), 1.90-1.24 (m, 7H), 0.96 (t, J=7.2 Hz, 3H), 0.95 (d, J=6.3 Hz, 3H), 0.94 (d, J=6.3 Hz, 3H).

EXAMPLE 70(4)

(3S)-1-butyl-2,5-dioxo-3-(2-methylpropyl)-9-(4-(4-methylsulfonylphenyloxy)phenylmethyl)-1,4,9-triazaspiro[5.5]undecane.hydrochloride

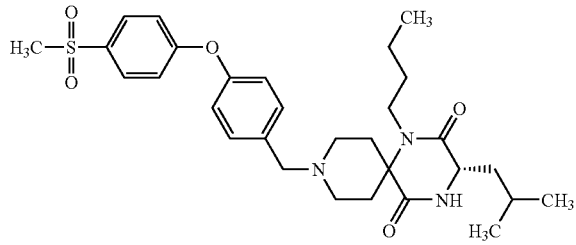

•HCl

TLC: Rf 0.45 (chloroform:methanol=10:1); NMR (CD₃OD):δ 7.96 (d, J=8.7 Hz, 2H), 7.66 (d, J=8.7 Hz, 2H), 7.23 (d, J=8.7 Hz, 2H), 7.21 (d, J=8.7 Hz, 2H), 4.40 (s, 2H), 4.02 (dd, J=7.5, 4.5 Hz, 1H), 3.94-3.72 (m, 2H), 3.58-3.36 (m, 4H), 3.12 (s, 3H), 2.54-2.36 (m, 2H), 2.18-2.08 (m, 2H), 1.88-1.26 (m, 7H), 0.96 (t, J=6.9 Hz, 3H), 0.95 (d, J=6.3 Hz, 3H), 0.94 (d, J=6.3 Hz, 3H).

EXAMPLE 70(5)

(3S)-1-butyl-2,5-dioxo-3-(2-methylpropyl)-9-(3,5-dimethyl-1-(4-(2-(morpholin-4-yl)ethylaminosulfonyl)phenyl)pyrazol-4-ylmethyl)-1,4,9-triazaspiro[5.5]undecane.3hydrochloride

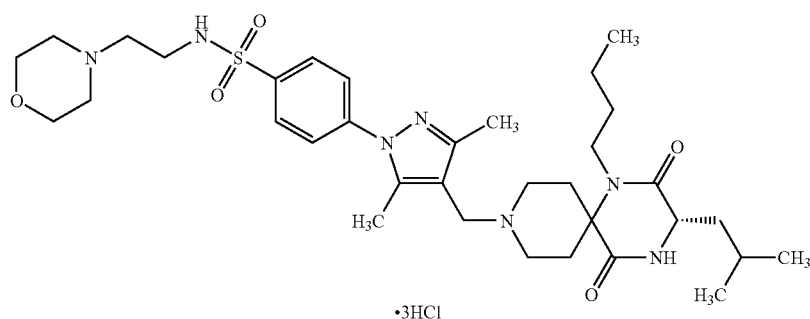

TLC: Rf 0.60 (chloroform:methanol=5:1); NMR (CD$_3$OD):δ 8.07 (d, J=8.4 Hz, 2H), 7.78 (d, J=8.4 Hz, 2H), 4.32 (s, 2H), 4.16-3.98 (m, 3H), 3.94-3.76 (m, 4H), 3.64-3.40 (m, 6H), 3.38-3.18 (m, 6H), 2.62-2.44 (m, 2H), 2.49 (s, 3H), 2.41 (s, 3H), 2.36-2.12 (m, 2H), 1.90-1.24 (m, 7H), 0.97 (t, J=6.6 Hz, 3H), 0.96 (d, J=6.3 Hz, 3H), 0.95 (d, J=6.3 Hz, 3H).

EXAMPLE 70(6)

(3S)-1-butyl-2,5-dioxo-3-(2-methylpropyl)-9-(3,5-dimethyl-1-(4-(4-methylpiperazin-1-ylsulfonyl)phenyl)pyrazol-4-ylmethyl)-1,4,9-triazaspiro[5.5]undecane.3hydrochlorie

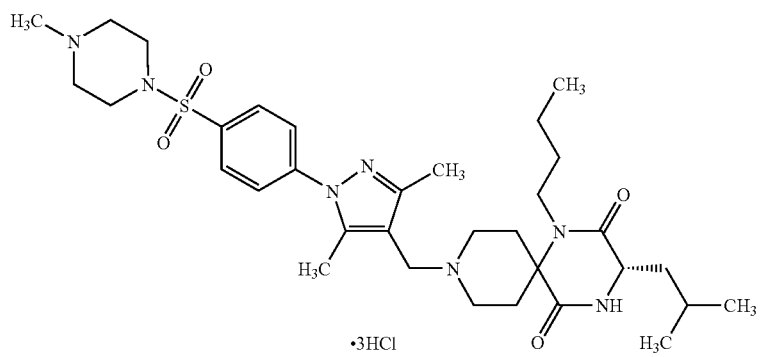

TLC: Rf 0.50 (chloroform:methanol=5:1); NMR (CD$_3$OD):δ 8.02 (d, J=9.0 Hz, 2H), 7.83 (d, J=9.0 Hz, 2H), 4.32 (s, 2H), 4.03 (dd, J=7.8, 4.5 Hz, 1H), 4.03-3.76 (m, 4H), 3.68-3.56 (m, 4H), 3.54-3.42 (m, 2H), 3.30-3.20 (m, 2H), 2.92 (s, 3H), 2.86-2.72 (m, 2H), 2.64-2.48 (m, 2H), 2.51 (s, 3H), 2.42 (s, 3H), 2.32-2.12 (m, 2H), 1.90-1.26 (m, 7H), 0.97 (t, J=6.6 Hz, 3H), 0.96 (d, J=6.3 Hz, 3H), 0.95 (d, J=6.3 Hz, 3H).

EXAMPLE 70(7)

(3S)-1-butyl-2,5-dioxo-3-(2-methylpropyl)-9-(4-(4-methylsulfinylphenyloxy)phenylmethyl)-1,4,9-triazaspiro[5.5]undecane.hydrochloride

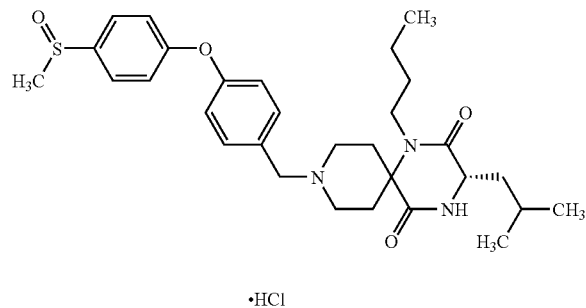

TLC: Rf 0.28 (chloroform:methanol=10:1); NMR (CD$_3$OD):δ 7.75 (d, J=9.0 Hz, 2H), 7.62 (d, J=9.0 Hz, 2H), 7.23 (d, J=9.0 Hz, 2H), 7.18 (d, J=9.0 Hz, 2H), 4.38 (s, 2H), 4.02 (dd, J=7.5, 4.5 Hz, 1H), 3.92-3.72 (m, 2H), 3.58-3.36 (m, 4H), 2.81 (s, 3H), 2.52-2.36 (m, 2H), 2.30-2.10 (m, 2H), 1.90-1.26 (m, 7H), 0.96 (t, J=7.2 Hz, 3H), 0.95 (d, J=6.3 Hz, 3H), 0.94 (d, J=6.3 Hz, 3H).

EXAMPLE 70(8)

(3S)-1-butyl-2,5-dioxo-3-(2-methylpropyl)-9-(4-(pyridin-1-oxido-3-yloxy)phenylmethyl)-1,4,9-triazaspiro[5.5]undecane.hydrochloride

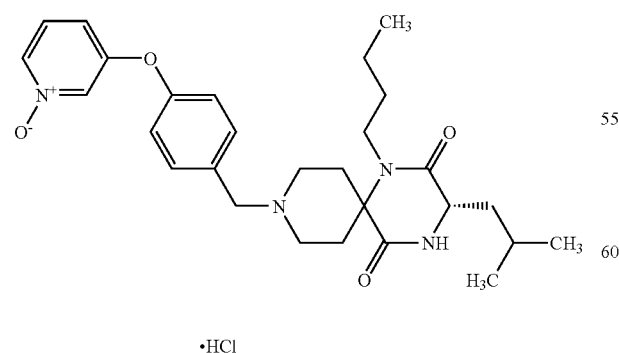

TLC: Rf 0.48 (chloroform:methanol=5:1); NMR (CD$_3$OD): 8.66 (s, 1H), 8.53-8.52 (m, 1H), 7.88-7.78 (m, 2H), 7.77 (d, J=8.7 Hz, 2H), 7.34 (d, J=8.7 Hz, 2H), 4.41 (s, 2H), 4.03 (dd, J=7.5, 4.5 Hz, 1H), 3.92-3.70 (m, 2H), 3.66-3.40 (m, 4H), 2.66-2.48 (m, 2H), 2.26-2.08 (m, 2H), 1.90-1.26 (m, H), 0.96 (t, J=7.5 Hz, 3H), 0.95 (d, J=6.6 Hz, 3H), 0.94 (d, J=6.6 Hz, 3H).

EXAMPLE 70(9)

(3S)-1-butyl-2,5-dioxo-3-(2-methylpropyl)-9-(3,5-dimethyl-1-(4-(2-hydroxyethylaminocarbonyl)phenyl)pyrazol-4-ylmethyl)-1,4,9-triazaspiro[5.5]undecane.2hydrochloride

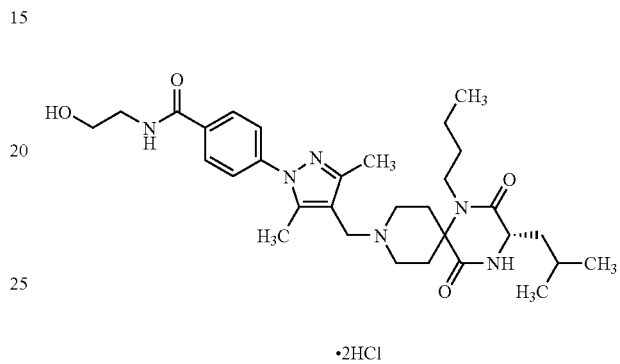

TLC: Rf 0.53 (chloroform:methanol=5:1); NMR (CD$_3$OD):δ 8.03 (d, J=8.4 Hz, 2H), 7.62 (d, J=8.4 Hz, 2H), 4.33 (s, 2H), 4.03 (dd, J=7.8, 4.5 Hz, 1H), 3.98-3.76 (m, 2H), 3.74 (t, J=5.7 Hz, 2H), 3.68-3.58 (m, 2H), 3.54 (t, J=5.7 Hz, 2H), 3.54-3.40 (m, 2H), 2.64-2.48 (m, 2H), 2.46 (s, 3H), 2.43 (s, 3H), 2.32-2.10 (m, 2H), 1.90-1.30 (m, 7H), 0.97 (t, J=6.6 Hz, 3H), 0.96 (d, J=6.3 Hz, 3H), 0.95 (d, J=6.3 Hz, 3H).

EXAMPLE 70(10)

(3S)-1-butyl-2,5-dioxo-3-(2-methylpropyl)-9-(4-(4-(morpholin-4-ylcarbonyl)phenyloxy)phenylmethyl)-1,4,9-triazaspiro[5.5]undecane.hydrochloride

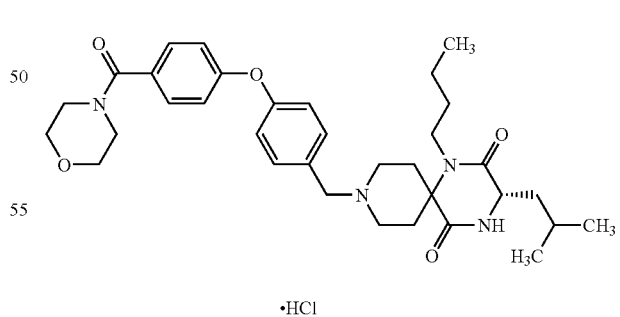

TLC: Rf 0.55 (chloroform:methanol=5:1); NMR (CD$_3$OD):δ 7.61 (d, J=8.7 Hz, 2H), 7.49 (d, J=8.7 Hz, 2H), 7.15 (d, J=8.7 Hz, 2H), 7.11 (d, J=8.7 Hz, 2H), 4.37 (s, 2H), 4.02 (dd, J=7.8, 4.8 Hz, 1H), 3.90-3.36 (m, 14H), 2.58-2.38 (m, 2H), 2.28-2.08 (m, 2H), 1.88-1.28 (m, 7H), 0.96 (t, J=7.2 Hz, 3H), 0.95 (d, J=6.3 Hz, 3H), 0.94 (d, J=6.3 Hz, 3H).

EXAMPLE 70(11)

(3S)-1-butyl-2,5-dioxo-3-(2-methylpropyl)-9-(3,5-dimethyl-1-(4-(N,N-diethylaminosulfonyl)phenyl)pyrazol-4-ylmethyl)-1,4,9-triazaspiro[5.5]undecane.2hydrochloride

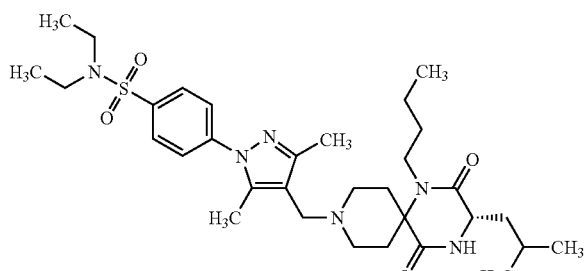

TLC: Rf 0.66 (chloroform:methanol=5:1); NMR (CD$_3$OD):δ 8.00 (d, J=8.4 Hz, 2H), 7.73 (d, J=8.4 Hz, 2H), 4.34 (s, 2H), 4.04 (dd, J=7.8, 4.5 Hz, 1H), 3.96-3.76 (m, 2H), 3.68-3.56 (m, 2H), 3.48-3.38 (m, 2H), 3.36-3.22 (m, 4H), 2.52-2.38 (m, 2H), 2.46 (s, 3H), 2.40 (s, 3H), 2.36-2.14 (m, 2H), 1.90-1.28 (m, 7H), 1.20-1.08 (m, 6H), 0.97 (t, J=7.5 Hz, 3H), 0.96 (d, J=6.3 Hz, 3H), 0.95 (d, J=6.3 Hz, 3H).

EXAMPLE 70(12)

(3S)-1-butyl-2,5-dioxo-3-(2-methylpropyl)-9-(4-(4-(2-hydroxyethylaminocarbonyl)phenyloxy)phenylmethyl)-1,4,9-triazaspiro[5.5]undecane.hydrochloride

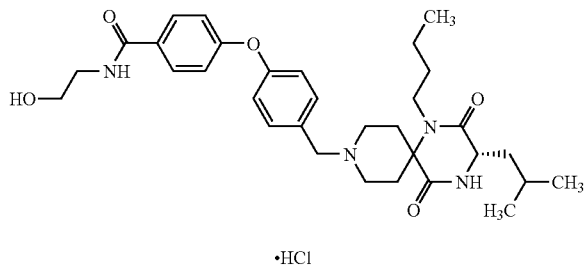

TLC: Rf 0.36 (chloroform:methanol=10:1); NMR (CD$_3$OD):δ 7.88 (d, J=8.7 Hz, 2H), 7.60 (d, J=8.4 Hz, 2H), 7.15 (d, J=8.4 Hz, 2H), 7.07 (d, J=8.7 Hz, 2H), 4.36 (s, 2H), 4.01 (dd, J=7.8, 4.5 Hz, 1H), 3.90-3.76 (m, 2H), 3.70 (t, J=6.0 Hz, 2H), 3.56-3.36 (m, 4H), 3.50 (t, J=6.0 Hz, 2H), 2.52-2.38 (m, 2H), 2.24-2.08 (m, 2H), 1.88-1.16 (m, 7H), 1.02-0.88 (m, 9H).

EXAMPLE 70(13)

(3S)-1-butyl-2,5-dioxo-3-(2-methylpropyl)-9-(4-(4-(pyrrolidin-1-ylcarbonyl)phenyloxy)phenylmethyl)-1,4,9-triazaspiro[5.5]undecane.hydrochloride

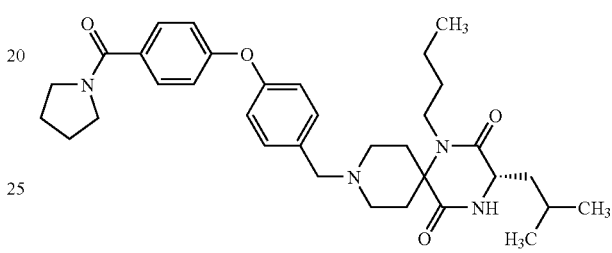

TLC: Rf 0.22 (ethyl acetate:methanol 10:1); NMR (CD$_3$OD):δ 7.59 (d, J=8.4 Hz, 2H), 7.58 (d, J=8.4 Hz, 2H), 7.16 (d, J=8.4 Hz, 2H), 7.09 (d, J=8.4 Hz, 2H), 4.38 (s, 2H), 4.02 (dd, J=7.5, 4.5 Hz, 1H), 3.92-3.72 (m, 2H), 3.64-3.36 (m, 8H), 2.48-2.10 (m, 4H), 2.04-1.26 (m, 11H), 0.96 (t, J=6.9 Hz, 3H), 0.95 (d, J=6.3 Hz, 3H), 0.94 (d, J=6.3 Hz, 3H).

EXAMPLE 70(14)

(3S)-1-butyl-2,5-dioxo-3-(2-methylpropyl)-9-(3,5-dimethyl-1-(4-(cyclohexylaminosulfonyl)phenyl)pyrazol-4-ylmethyl)-1,4,9-triazaspiro[5.5]undecane.2hydrochloride

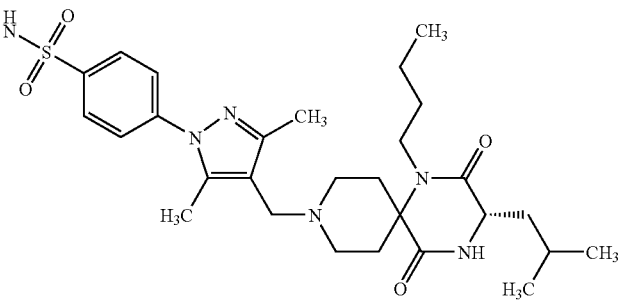

TLC: Rf 0.42 (chloroform:methanol=10:1); NMR (CD₃OD):δ 8.02 (d, J=8.4 Hz, 2H), 7.70 (d, J=8.4 Hz, 2H), 4.31 (s, 2H), 4.05 (dd, J=7.8, 4.8 Hz, 1H), 3.92-3.72 (m, 2H), 3.68-3.58 (m, 2H), 3.56-3.44 (m, 2H), 3.06 (m, 1H), 2.68-2.50 (m, 2H), 2.47 (s, 3H), 2.41 (s, 3H), 2.38-2.08 (m, 2H), 1.82-1.06 (m, 25H), 1.02-0.86 (m, 5H).

EXAMPLE 70(15)

(3S)-1-butyl-2,5-dioxo-3-(2-methylpropyl)-9-(3,5-dimethyl-1-(4-(3-methoxypropylaminosulfonyl)phenyl)pyrazol-4-ylmethyl)-1,4,9-triazaspiro[5.5]undecane.2hydrochloride

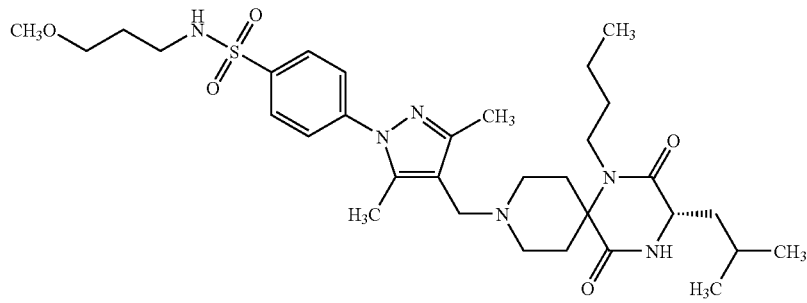

TLC: Rf 0.42 (chloroform:methanol=10:1); NMR (CD₃OD):δ 8.01 (d, J=8.7 Hz, 2H), 7.73 (d, J=8.7 Hz, 2H), 4.31 (s, 2H), 4.02 (dd, J=7.8, 4.8 Hz, 1H), 3.94-3.72 (m, 2H), 3.68-3.58 (m, 2H), 3.56-3.46 (m, 2H), 3.39 (t, J=6.0 Hz, 2H), 3.26 (s, 3H), 2.98 (t, J=6.9 Hz, 2H), 2.72-2.58 (m, 2H), 2.48 (s, 3H), 2.42 (s, 3H), 2.26-2.10 (m, 2H), 1.90-1.28 (m, 9H), 0.98-0.90 (m, 9H).

EXAMPLE 70(16)

(3S)-1-butyl-2,5-dioxo-3-(2-methylpropyl)-9-(4-methylsulfinylphenylmethyl)-1,4,9-triazaspiro[5.5]undecane.hydrochloride

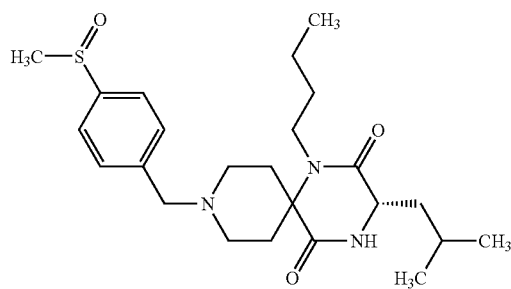

TLC: Rf 0.13 (ethyl acetate:methanol=10:1); NMR (CD₃OD):δ 7.88 (d, J=8.7 Hz, 2H), 7.81 (d, J=8.7 Hz, 2H), 4.47 (s, 2H), 4.02 (dd, J=7.8, 4.8 Hz, 1H), 3.96-3.74 (m, 2H), 3.56-3.36 (m, 4H), 2.83 (s, 3H), 2.52-2.34 (m, 2H), 2.28-2.08 (m, 2H), 1.90-1.26 (m, 7H), 0.95 (t, J=7.2 Hz, 3H), 0.95 (d, J=6.3 Hz, 3H), 0.94 (d, J=6.3 Hz, 3H).

EXAMPLE 70(17)

(3S)-1-butyl-2,5-dioxo-3-(2-methylpropyl)-9-(3,5-dimethyl-1-propylpyrazol-4-ylmethyl)-1,4,9-triazaspiro[5.5]undecane.2hydrochloride

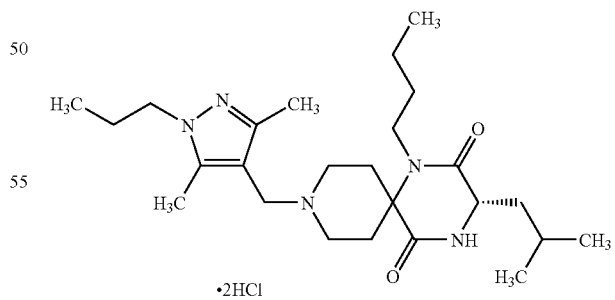

TLC: Rf 0.58 (chloroform:methanol=5:1); NMR (CD₃OD):δ 4.26 (s, 2H), 4.10 (t, J=7.2 Hz, 2H), 4.02 (dd, J=7.5, 4.5 Hz, 1H), 3.90-3.68 (m, 2H), 3.58-3.36 (m, 4H), 2.58-2.38 (m, 2H), 2.44 (s, 3H), 2.38 (s, 3H), 2.30-2.10 (m, 2H), 1.92-1.24 (m, 9H), 0.96 (t, J=7.2 Hz, 6H), 0.96 (d, J=6.6 Hz, 3H), 0.95 (d, J=6.6 Hz, 3H).

EXAMPLE 70(18)

(3S)-1-butyl-2,5-dioxo-3-(2-methylpropyl)-9-(3,5-dimethyl-1-ethylpyrazol-4-ylmethyl)-1,4,9-triazaspiro[5.5]undecane.2hydrochloride

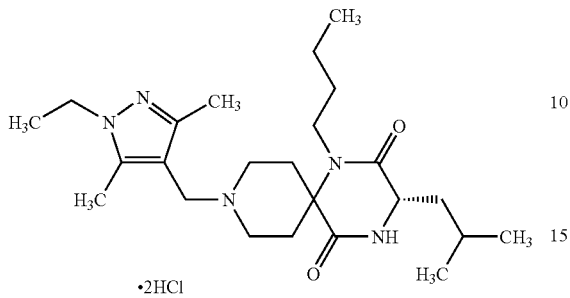

TLC: Rf 0.58 (chloroform:methanol=10:1); NMR (CD$_3$OD):δ 4.34-4.24 (m, 4H), 4.01 (dd, J=7.8, 4.5 Hz, 1H), 3.92-3.68 (m, 2H), 3.62-3.46 (m, 4H), 2.74-2.60 (m, 2H), 2.53 (s, 3H), 2.50 (s, 3H), 2.24-2.06 (m, 2H), 1.88-1.26 (m, 10H), 1.02-0.86 (m, 9H).

EXAMPLE 70(19)

(3S)-1-butyl-2,5-dioxo-3-(2-methylpropyl)-9-(3,5-dimethyl-1-cyclopentylpyrazol-4-ylmethyl)-1,4,9-triazaspiro[5.5]undecane.2hydrochloride

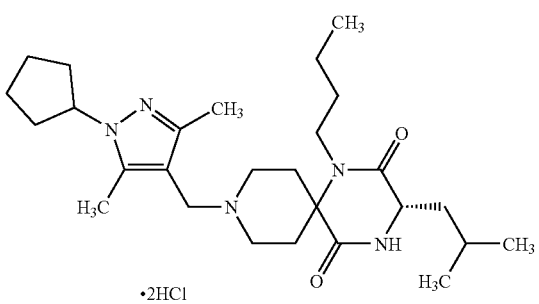

TLC: Rf 0.53 (chloroform:methanol=10:1); NMR (CD$_3$OD):δ 5.00-4.82 (m, 1H), 4.31 (s, 2H), 4.01 (dd, J=7.5, 4.5 Hz, 1H), 3.92-3.70 (m, 2H), 3.62-3.46 (m, 4H), 2.78-2.58 (m, 2H), 2.55 (s, 3H), 2.53 (s, 3H), 2.32-2.04 (m, 4H), 2.04-1.26 (m, 13H), 0.98-0.84 (m, 9H).

EXAMPLE 70(20)

(3S)-1-butyl-2,5-dioxo-3-(2-methylpropyl)-9-(3,5-dimethyl-1-(1,1-dimethylethyl)pyrazol-4-ylmethyl)-1,4,9-triazaspiro[5.5]undecane.2hydrochloride

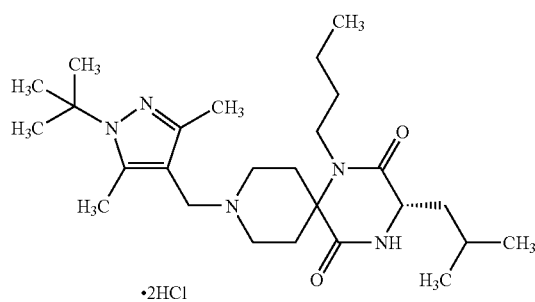

TLC: Rf 0.15 (ethyl acetate:methanol=10:1); NMR (CD$_3$OD):δ 4.23 (s, 2H), 4.02 (dd, J=7.5, 4.5 Hz, 1H), 3.90-3.68 (m, 2H), 3.58-3.36 (m, 4H), 2.56 (s, 3H), 2.56-2.38 (m, 2H), 2.32 (s, 3H), 2.32-2.10 (m, 2H), 1.88-1.26 (m, 7H), 1.67 (s, 9H), 0.96 (t, J=7.2 Hz, 3H), 0.96 (d, J=6.3 Hz, 3H), 0.95 (d, J=6.3 Hz, 3H).

EXAMPLE 70(21)

(3S)-1-butyl-2,5-dioxo-3-(2-methylpropyl)-9-(3,5-dimethyl-1-(1-benzyloxycarbonylpiperidin-4-yl)pyrazol-4-ylmethyl)-1,4,9-triazaspiro[5.5]undecane.2hydrochloride

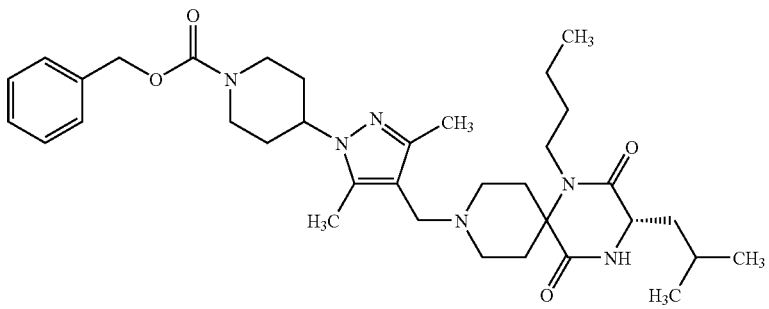

TLC: Rf 0.17 (ethyl acetate:methanol=10:1); NMR (CD$_3$OD):δ 7.42-7.26 (m, 5H), 5.15 (s, 2H), 4.48-4.22 (m, 3H), 4.23 (s, 2H), 4.02 (dd, J=7.8, 4.5 Hz, 1H), 3.88-3.68 (m, 2H), 3.58-3.36 (m, 4H), 3.12-2.90 (m, 2H), 2.50-1.28 (m, 15H), 2.42 (s, 3H), 2.30 (s, 3H), 0.96 (t, J=6.9 Hz, 3H), 0.95 (d, J=6.3 Hz, 3H), 0.94 (d, J=6.3 Hz, 3H).

EXAMPLE 70(22)

(3S)-1-butyl-2,5-dioxo-3-(2-methylpropyl)-9-(4-((4-methoxyphenyl)methylaminocarbonyl)phenylmethyl)-1,4,9-triazaspiro[5.5]undecane.hydrochloride

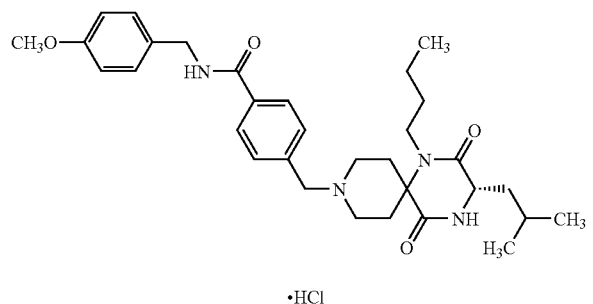

TLC: Rf 0.50 (chloroform:methanol=9:1); NMR (CD$_3$OD):δ 7.95 (d, J=8.7 Hz, 2H), 7.67 (d, J=8.7 Hz, 2H), 7.27 (d, J=8.7 Hz, 2H), 6.87 (d, J=8.7 Hz, 2H), 4.51 (s, 2H), 4.42 (s, 2H), 4.00 (dd, J=7.5, 4.8 Hz, 1H), 3.91-3.72 (m, 2H), 3.76 (s, 3H), 3.53-3.35 (m, 4H), 2.50-2.35 (m, 2H), 2.26-2.08 (m, 2H), 1.87-1.28 (m, 7H), 0.94 (t, J=7.5 Hz, 3H), 0.94 (d, J=6.6 Hz, 3H), 0.93 (d, J=6.6 Hz, 3H).

EXAMPLE 70(23)

(3S)-1-butyl-2,5-dioxo-3-(2-methylpropyl)-9-(4-(3-methoxypropylaminocarbonyl)phenylmethyl)-1,4,9-triazaspiro[5.5]undecane.hydrochloride

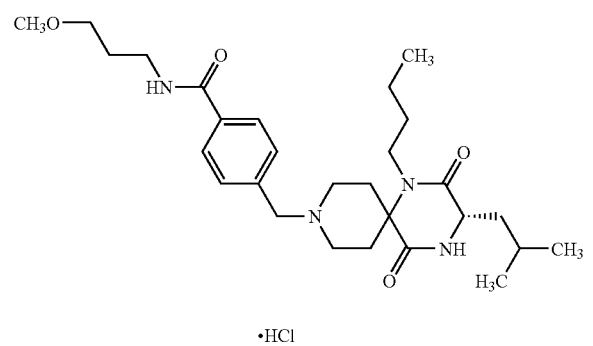

TLC: Rf 0.48 (chloroform:methanol=9:1); NMR (CD$_3$OD):δ 7.92 (d, J=8.4 Hz, 2H), 7.67 (d, J=8.4 Hz, 2H), 4.43 (s, 2H), 4.00 (dd, J=7.8, 4.5 Hz, 1H), 3.92-3.75 (m, 2H), 3.53-3.35 (m, 8H), 3.34 (s, 3H), 2.50-2.35 (m, 2H), 2.27-2.10 (m, 2H), 1.92-1.28 (m, 9H), 0.94 (t, J=7.2 Hz, 3H), 0.94 (d, J=6.6 Hz, 3H), 0.93 (d, J=6.6 Hz, 3H).

EXAMPLE 70(24)

(3S)-1-butyl-2,5-dioxo-3-(2-methylpropyl)-9-(3,5-dimethyl-1-(4-methoxycarbonylphenyl)pyrazol-4-ylmethyl)-1,4,9-triazaspiro[5.5]undecane.2hydrochloride

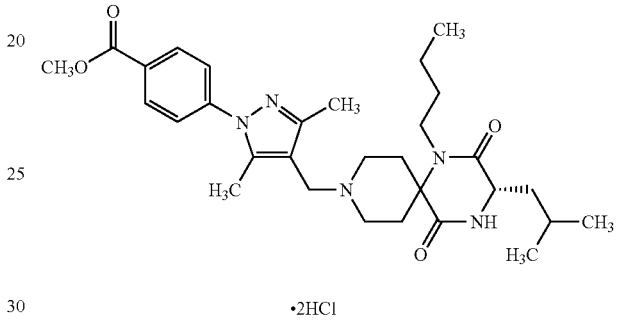

TLC: Rf 0.29 (ethyl acetate:methanol=10:1); NMR (CD$_3$OD):δ 8.19 (d, J=9.0 Hz, 2H), 7.63 (d, J=9.0 Hz, 2H), 4.28 (s, 2H), 4.03 (m, 1H), 3.94 (s, 3H), 3.95-3.30 (m, 6H), 2.50-2.15 (m, 4H), 2.44 (s, 3H), 2.39 (s, 3H), 1.90-1.30 (m, 7H), 0.96 (t, J=7.2 Hz, 3H), 0.95 (d, J=6.6 Hz, 3H) 0.94 (d, J=6.6 Hz, 3H).

EXAMPLE 70(25)

(3S)-1-butyl-2,5-dioxo-3-(2-methylpropyl)-9-(3,5-dimethyl-1-(4-methoxyphenyl)pyrazol-4-ylmethyl)-1,4,9-triazaspiro[5.5]undecane.2hydrochloride

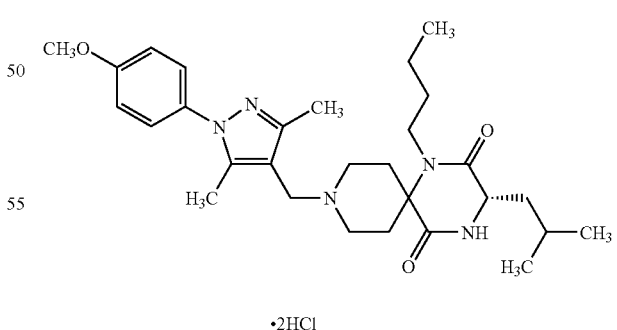

TLC: Rf 0.31 (ethyl acetate:methanol=10:1); NMR (CD$_3$OD):δ 7.37 (d, J=9.0 Hz, 2H), 7.09 (d, J=9.0 Hz, 2H), 4.31 (s, 2H), 4.02 (m, 1H), 4.00-3.30 (m, 6H), 3.86 (s, 3H), 2.65-2.15 (m, 4H), 2.39 (s, 3H), 2.34 (s, 3H), 1.90-1.30 (m, 7H), 0.96 (t, J=7.2 Hz, 3H), 0.95 (d, J=6.6 Hz, 3H) 0.94 (d, J=6.6 Hz, 3H).

EXAMPLE 70(26)

(3S)-1-butyl-2,5-dioxo-3-(2-methylpropyl)-9-(3,5-dimethyl-1-(4-(3-(morpholin-4-yl)propylaminosulfonyl)phenyl)pyrazol-4-ylmethyl)-1,4,9-triazaspiro[5.5]undecane.3hydrochloride

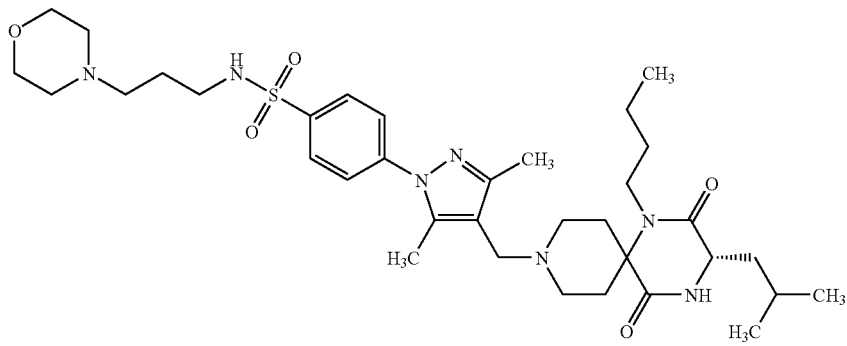

TLC: Rf 0.18 (ethyl acetate:methanol=3:1); NMR (CD$_3$OD):δ 8.02 (d, J=8.7 Hz, 2H), 7.74 (d, J=8.7 Hz, 2H), 4.31 (s, 2H), 4.10-4.00 (m, 3H), 4.00-3.00 (m, 16H), 2.70-2.10 (m, 4H), 2.48 (s, 3H), 2.40 (s, 3H), 2.10-1.90 (m, 2H), 1.90-1.30 (m, 7H), 0.96 (t, J=7.2 Hz, 3H), 0.95 (d, J=6.6 Hz, 3H), 0.94 (d, J=6.6 Hz, 3H).

EXAMPLE 70(27)

(3S)-1-butyl-2,5-dioxo-3-(2-methylpropyl)-9-(4-(pyrrolidin-1-ylcarbonyl)phenylmethyl)-1,4,9-triazaspiro[5.5]undecane.hydrochloride

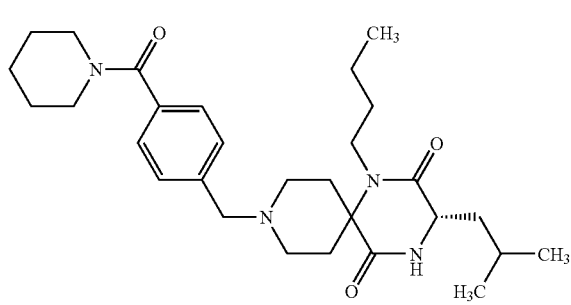

TLC: Rf 0.55 (chloroform:methanol=10:1); NMR (CD$_3$OD):δ 7.71-7.59 (m, 4H), 4.41 (s, 2H), 4.01 (dd, J=7.8, 4.5 Hz, 1H), 3.83-3.72 (m, 2H), 3.60 (t, J=6.9 Hz, 2H), 3.55-3.32 (m, 4H), 3.45 (t, J=6.9 Hz, 2H), 2.57-2.37 (m, 2H), 2.27-2.08 (m, 2H), 2.05-1.44 (m, 9H), 1.44-1.27 (m, 2H), 0.99-0.90 (m, 9H).

EXAMPLE 70(28)

(3S)-1-butyl-2,5-dioxo-3-(2-methylpropyl)-9-(4-(piperidin-1-ylcarbonyl)phenylmethyl)-1,4,9-triazaspiro[5.5]undecane.hydrochloride

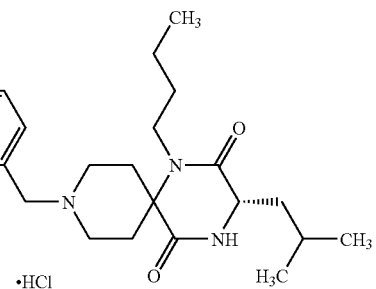

TLC: Rf 0.60 (chloroform:methanol=10:1); NMR (CD$_3$OD):δ 7.69 (d, J=8.4 Hz, 2H), 7.50 (d, J=8.4 Hz, 2H), 4.41 (s, 2H), 4.01 (dd, J=7.5, 4.5 Hz, 1H), 3.93-3.72 (m, 4H), 3.55-3.30 (m, 6H), 2.57-2.39 (m, 2H), 2.26-2.07 (m, 2H), 1.90-1.44 (m, 11H), 1.44-1.26 (m, 2H), 0.98-0.90 (m, 9H).

EXAMPLE 70(29)

(3S)-1-butyl-2,5-dioxo-3-(2-methylpropyl)-9-(4-(morpholin-4-ylcarbonyl)phenylmethyl)-1,4,9-triazaspiro[5.5]undecane.hydrocloride

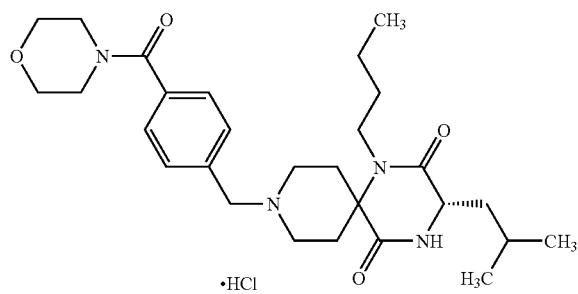

TLC: Rf 0.59 (chloroform:methanol=10:1); NMR (CD$_3$OD):δ 7.69 (d, J=8.1 Hz, 2H), 7.55 (d, J=8.1 Hz, 2H), 4.41 (s, 2H), 4.01 (dd, J=7.8, 4.5 Hz, 1H), 3.93-3.55 (m, 8H), 3.55-3.34 (m, 6H), 2.55-2.36 (m, 2H), 2.27-2.08 (m, 2H), 1.88-1.44 (m, 5H), 1.44-1.28 (m, 2H), 0.98-0.90 (m, 9H).

EXAMPLE 70(30)

(3S)-1-butyl-2,5-dioxo-3-(2-methylpropyl)-9-(4-(N-methylN-(2-(pyridin-2-yl)ethyl)aminocarbonyl)phenylmethyl)-1,4,9-triazaspiro[5.5]undecane.2hydrochloride

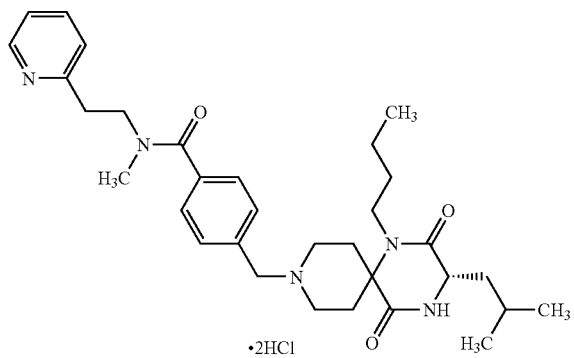

TLC: Rf 0.49 (chloroform:methanol=10:1); NMR (CD$_3$OD):δ 8.80 (d, J=6.0 Hz, 1H), 8.58 (m, 1H), 8.10 (d, J=8.4 Hz, 1H), 7.98 (m, 1H), 7.70 (d, J=7.8 Hz, 2H), 7.41 (d, J=7.8 Hz, 2H), 4.39 (s, 2H), 4.05-3.95 (m, 3H), 3.94-3.69 (m, 2H), 3.60-3.37 (m, 6H), 3.08 (s, 3H), 2.70-2.43 (m, 2H), 2.26-2.05 (m, 2H), 1.90-1.44 (m, 5H), 1.44-1.26 (m, 2H), 0.99-0.90 (m, 9H).

EXAMPLE 70(31)

(3S)-1-butyl-2,5-dioxo-3-(2-methylpropyl)-9-(4-(cyclohexylaminocarbonyl)phenylmethyl)-1,4,9-triazaspiro[5.5]undecane.hydrochloride

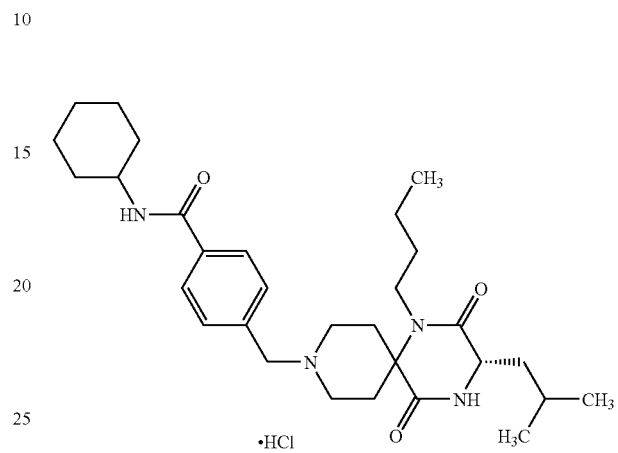

TLC: Rf 0.33 (ethyl acetate:methanol=10:1); NMR (CD$_3$OD):δ 7.92 (d, J=8.1 Hz, 2H), 7.69 (d, J=8.1 Hz, 2H), 4.43 (s, 2H), 4.01 (dd, J=7.5, 4.5 Hz, 1H), 3.96-3.70 (m, 2H), 3.58-3.36 (m, 4H), 2.58-2.38 (m, 2H), 2.28-2.06 (m, 2H), 2.04-1.12 (m, 18H), 0.95 (t, J=6.9 Hz, 3H), 0.94 (d, J=6.3 Hz, 3H), 0.93 (d, J=6.3 Hz, 3H).

EXAMPLE 70(32)

(3S)-1-butyl-2,5-dioxo-3-(2-methylpropyl)-9-(4-(N,N-dimethylaminosulfonyl)phenylmethyl)-1,4,9-triazaspiro[5.5]undecane.hydrochloride

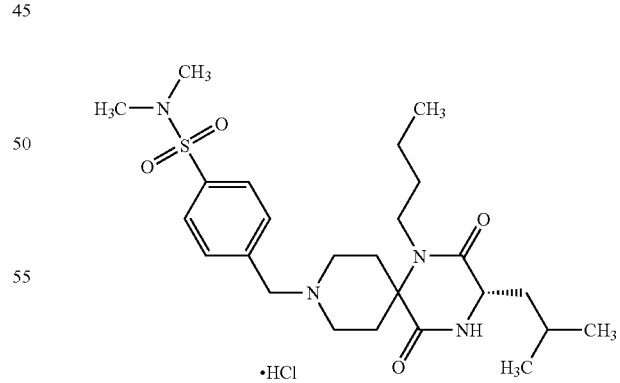

TLC: Rf 0.44 (ethyl acetate:methanol=10:1); NMR (CD$_3$OD):δ 7.91 (d, J=8.7 Hz, 2H), 7.86 (d, J=8.7 Hz, 2H), 4.49 (s, 2H), 4.02 (dd, J=7.5, 4.8 Hz, 1H), 3.96-3.76 (m, 2H), 3.56-3.38 (m, 4H), 2.72 (s, 6H), 2.60-2.40 (m, 2H), 2.28-2.06 (m, 2H), 1.90-1.28 (m, 7H), 0.95 (t, J=7.2 Hz, 3H), 0.95 (d, J=6.3 Hz, 3H), 0.94 (d, J=6.3 Hz, 3H).

EXAMPLE 70(33)

(3S)-1-butyl-2,5-dioxo-3-(2-methylpropyl)-9-(4-(4-methoxycarbonylphenyloxy)phenylmethyl)-1,4,9-triazaspiro[5.5]undecane.hydrochloride

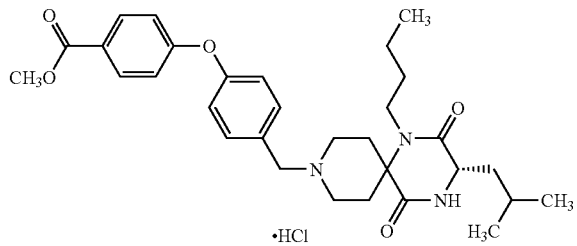

TLC: Rf 0.50 (ethyl acetate:methanol=10:1); NMR (CD$_3$OD):δ 8.04 (d, J=9.0 Hz, 2H), 7.63 (d, J=9.0 Hz, 2H), 7.19 (d, J=9.0 Hz, 2H), 7.08 (d, J=9.0 Hz, 2H), 4.38 (s, 2H), 4.02 (dd, J=7.5, 4.5 Hz, 1H), 3.90 (s, 3H), 3.88-3.72 (m, 2H), 3.58-3.36 (m, 4H), 2.58-2.38 (m, 2H), 2.30-2.08 (m, 2H), 1.90-1.28 (m, 7H), 0.96 (t, J=6.9 Hz, 3H), 0.95 (d, J=6.3 Hz, 3H), 0.94 (d, J=6.3 Hz, 3H).

EXAMPLE 70(34)

(3S)-1-butyl-2,5-dioxo-3-(2-methylpropyl)-9-(3,5-dimethyl-1-(1-methylpiperidin-4-yl)pyrazol-4-ylmethyl)-1,4,9-triazaspiro[5.5]undecane.3hydrochloride

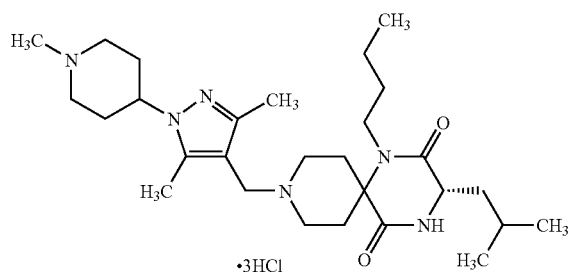

TLC: Rf 0.15 (chloroform:methanol=5:1); NMR (CD$_3$OD):δ 4.56 (m, 1H), 4.20 (s, 2H), 4.01 (dd, J=7.8, 4.8 Hz, 1H), 3.86-3.42 (m, 8H), 3.30-3.20 (m, 2H), 2.93 (s, 3H), 2.64-2.48 (m, 2H), 2.44-2.28 (m, 2H), 2.44 (s, 3H), 2.31 (s, 3H), 2.22-2.06 (m, 4H), 1.86-1.28 (m, 7H), 0.98-0.88 (m, 9H).

EXAMPLE 70(35)

(3S)-1-butyl-2,5-dioxo-3-(2-methylpropyl)-9-(3,5-dimethyl-1-(1-methylsulfonylpiperidin-4-yl)pyrazol-4-ylmethyl)-1,4,9-triazaspiro[5.5]undecane.2hydrochloride

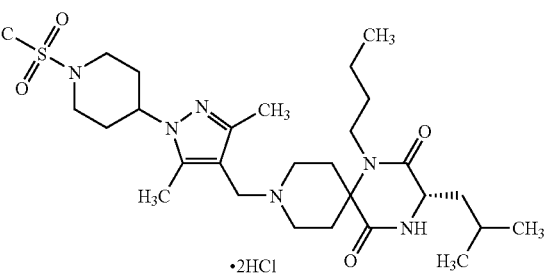

TLC: Rf 0.36 (chloroform:methanol=10:1); NMR (CD$_3$OD):δ 4.46 (m, 1H), 4.25 (s, 2H), 4.01 (dd, J=7.8, 4.8 Hz, 1H), 3.92-3.68 (m, 4H), 3.60-3.42 (m, 4H), 3.04-2.90 (m, 2H), 2.89 (s, 3H), 2.62-2.46 (m, 2H), 2.48 (s, 3H), 2.38 (s, 3H), 2.24-1.98 (m, 6H), 1.90-1.28 (m, 7H), 0.98-0.90 (m, 9H).

EXAMPLE 70(36)

(3S)-1-butyl-2,5-dioxo-3-(2-methylpropyl)-9-(3,5-dimethyl-1-(4-(3-(N,N-dimethylamino)propylaminosulfonyl)phenyl)pyrazol-4-ylmethyl)-1,4,9-triazaspiro[5.5]undecane.3hydrochloride

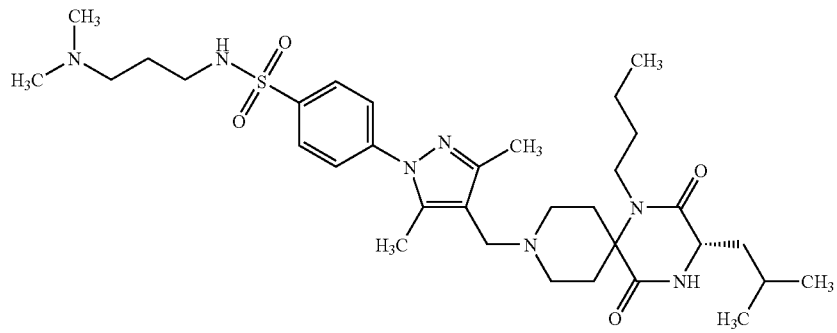

TLC: Rf 0.22 (chloroform:methanol:28% aqueous solution of ammonia=100:10:1); NMR (CD$_3$OD):δ 8.02 (d, J=8.7 Hz, 2H), 7.74 (d, J=8.7 Hz, 2H), 4.30 (s, 2H), 4.02 (dd, J=7.8, 4.5 Hz, 1H), 3.84-3.73 (m, 2H), 3.66-3.56 (m, 2H), 3.55-3.44 (m, 2H), 3.27-3.18 (m, 2H), 3.02 (t, J=6.3 Hz, 2H), 2.89 (s, 6H), 2.70-2.52 (m, 2H), 2.48 (s, 3H), 2.40 (s, 3H), 2.28-2.11 (m, 2H), 2.00-1.28 (m, 9H), 1.00-0.90 (m, 9H).

EXAMPLE 70(37)

(3S)-1-butyl-2,5-dioxo-3-(2-methylpropyl)-9-(4-(4-(N,N-dimethylamino)phenyloxy)phenylmethyl)-1,4,9-triazaspiro[5.5]undecane.2hydrochloride

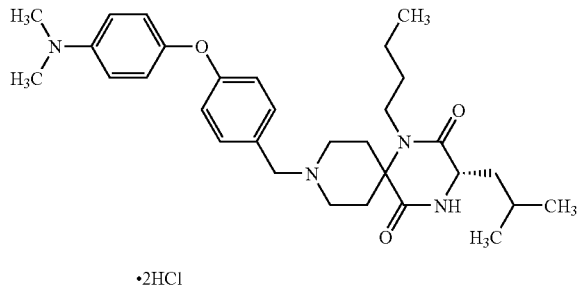

TLC: Rf 0.61 (chloroform:methanol=10:1); NMR (CD$_3$OD):δ 7.68-7.60 (m, 4H), 7.21 (d, J=8.7 Hz, 2H), 7.14 (d, J=8.7 Hz, 2H), 4.35 (s, 2H), 4.00 (dd, J=7.8, 4.8 Hz, 1H), 3.89-3.77 (m, 2H), 3.54-3.40 (m, 4H), 3.28 (s, 6H), 2.62-2.44 (m, 2H), 2.26-2.07 (m, 2H), 1.90-1.26 (m, 7H), 1.00-0.90 (m, 9H).

EXAMPLE 70(38)

(3S)-1-butyl-2,5-dioxo-3-(2-methylpropyl)-9-(3,5-dimethyl-1-(4-(N-methyl-N-(2-(N',N'-dimethylamino)ethyl)aminosulfonylphenyl)pyrazol-4-ylmethyl)-1,4,9-triazaspiro[5.5]undecane.3hydrochloride

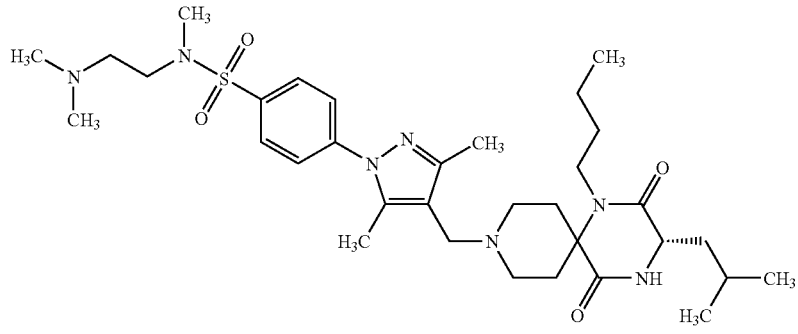

TLC: Rf 0.34 (chloroform:methanol:28% aqueous solution of ammonia=100:10:1); NMR (CD$_3$OD):δ 8.04 (d, J=8.7 Hz, 2H), 7.81 (d, J=8.7 Hz, 2H), 4.31 (s, 2H), 4.02 (dd, J=7.8, 4.5 Hz, 1H), 3.95-3.73 (m, 2H), 3.66-3.54 (m, 2H), 3.54-3.43 (m, 2H), 3.42 (s, 4H), 3.01 (s, 6H), 2.85 (s, 3H), 2.68-2.52 (m, 2H), 2.50 (s, 3H), 2.41 (s, 3H), 2.29-2.10 (m, 2H), 1.90-1.28 (m, 7H), 1.00-0.90 (m, 9H).

EXAMPLE 70(39)

(3S)-1-butyl-2,5-dioxo-3-(2-methylpropyl)-9-(4-(4-((N,N-dimethylamino)methyl)phenyloxy)phenylmethyl)-1,4,9-triazaspiro[5.5]undecane.2hydrochloride

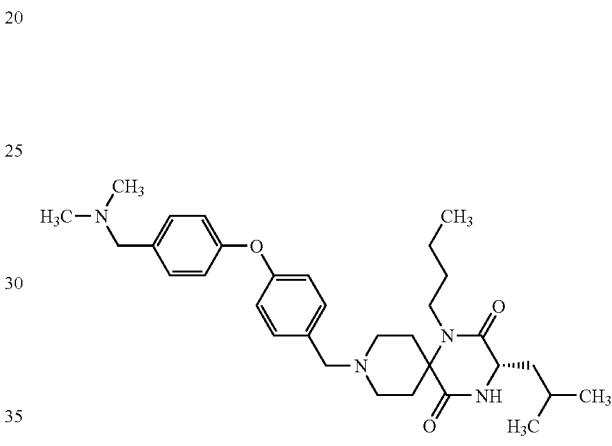

TLC: Rf 0.29 (chloroform:methanol:28%aqueous solution of ammonia=100:10:1); NMR (CD$_3$OD):δ 7.62 (d, J=8.7 Hz, 2H), 7.53 (d, J=8.7 Hz, 2H), 7.18-7.10 (m, 4H), 4.35 (s, 2H), 4.30 (s, 2H), 4.00 (dd, J.=7.8, 4.5 Hz, 1H), 3.88-3.68 (m, 2H), 3.54-3.38 (m, 4H), 2.86 (s, 6H), 2.59-2.42 (m, 2H), 2.26-2.07 (m, 2H), 1.88-1.25 (m, 7H), 1.02-0.89 (m, 9H).

EXAMPLE 70(40)

(3S)-1-butyl-2,5-dioxo-3-(2-methylpropyl)-9-(4-(4-carboxyphenyloxy)phenylmethyl)-1,4,9-triazaspiro[5.5]undecane.hydrochloride

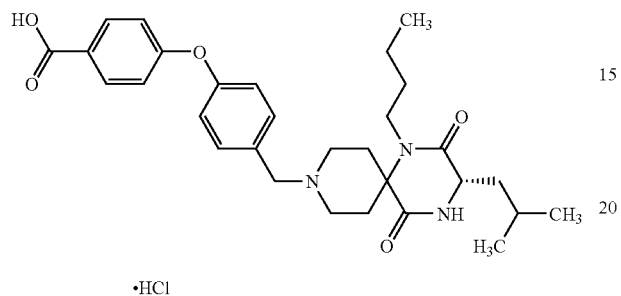

TLC: Rf 0.25 (chloroform:methanol=10:1); NMR (CD$_3$OD):δ 8.03 (d, J=8.7 Hz, 2H), 7.58 (d, J=8.7 Hz, 2H), 7.16 (d, J=8.7 Hz, 2H), 7.05 (d, J=8.7 Hz, 2H), 4.32 (s, 2H), 4.01 (dd, J=7.8, 4.5 Hz, 1H), 3.84-3.64 (m, 2H), 3.52-3.35 (m, 4H), 2.48-2.32 (m, 2H), 2.27-2.10 (m, 2H), 1.90-1.44 (m, 5H), 1.44-1.26 (m, 2H), 0.99-0.90 (m, 9H).

EXAMPLE 70(41)

(3S)-1-butyl-2,5-dioxo-3-(2-methylpropyl)-9-(3,5-dimethyl-1-(4-methylaminocarbonylphenyl)pyrazol-4-ylmethyl)-1,4,9-triazaspiro[5.5]undecane.2hydrochloride

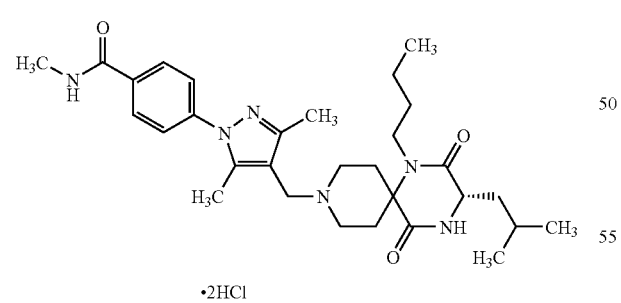

TLC: Rf 0.35 (chloroform:methanol=10:1); NMR (CD$_3$OD):δ 8.01 (d, J=8.7 Hz, 2H), 7.64 (d, J=8.7 Hz, 2H), 4.34 (s, 2H), 4.03 (dd, J=7.8, 4.8 Hz, 1H), 3.96-3.74 (m, 2H), 3.70-3.42 (m, 4H), 2.96 (s, 3H), 2.74-2.54 (m, 2H), 2.47 (s, 3H), 2.46 (s, 3H), 2.30-2.10 (m, 2H), 1.92-1.28 (m, 7H), 0.96 (t, J=6.9 Hz, 3H), 0.96 (d, J=6.6 Hz, 3H), 0.95 (d, J=6.6 Hz, 3H).

EXAMPLE 70(42)

(3S)-1-butyl-2,5-dioxo-3-(2-methylpropyl)-9-(4-((methoxycarbonyl)methylaminocarbonyl)phenylmethyl)-1,4,9-triazaspiro[5.5]undecane

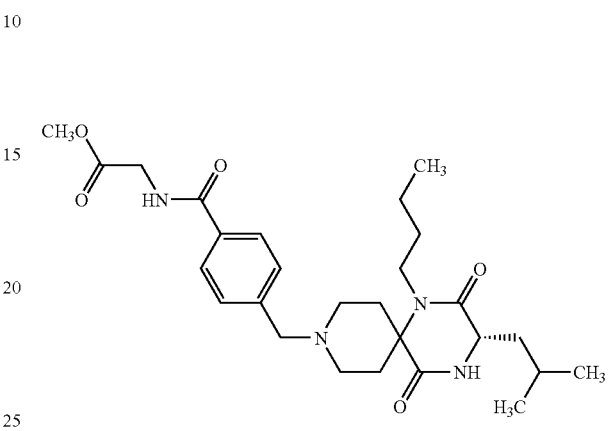

NMR (CDCl$_3$):δ 7.78 (d, J=8.1 Hz, 2H), 7.42 (d, J=8.1 Hz, 2H), 6.70 (t, J=4.8 Hz, 1H), 6.40 (brs, 1H), 4.26 (d, J=4.8 Hz, 2H), 3.96 (m, 1H), 3.81 (s, 3H), 3.62 (s, 2H), 3.50-3.28 (m, 2H), 3.00-2.48 (m, 8H), 2.26-1.20 (m, 7H), 0.99-0.94 (m, 9H).

EXAMPLE 70(43)

(3S)-1-butyl-2,5-dioxo-3-(2-methylpropyl)-9-(3-(3,5-dimethyl-1-phenylpyrazol-4-yl)-2E-propenyl)-1,4,9-triazspiro[5.5]undecane.2hydrochloride

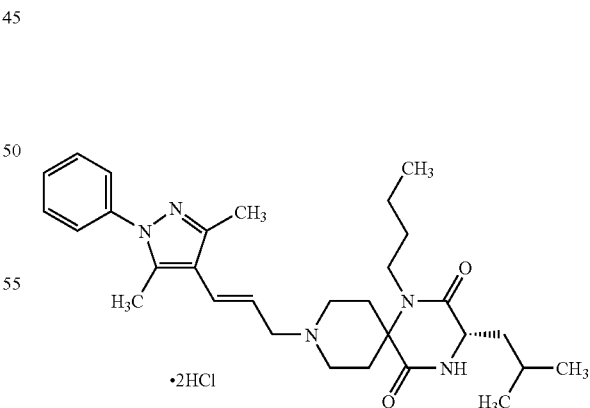

NMR (CDCl$_3$):δ 7.56-7.32 (m, 5H), 6.54 (m, 1H), 6.38 (brs, 1H), 5.96 (m, 1H), 4.00 (m, 1H), 3.76-2.90 (m, 8H), 2.38 (s, 3H), 2.34 (s, 3H), 2.14-1.22 (m, 11H), 1.00-0.86 (m, 9H).

EXAMPLE 71

(3S)-1-butyl-2,5-dioxo-3-(2-methylpropyl)-9-(4-(carboxymethylaminocarbonyl)phenylmethyl)-1,4,9-triazaspiro[5.5]undecane.hydrochloride

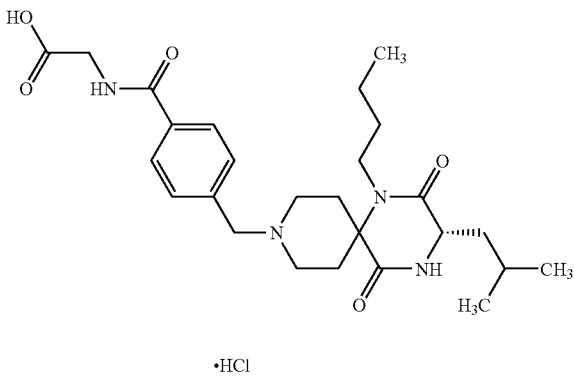

•HCl

To a solution of the compound prepared in Example 70(42) (106 mg) in methanol (3 ml) was added 5N aqueous solution of sodium hydroxide (0.1 ml). The reaction mixture was stirred for 3 hours at room temperature. The reaction mixture was concentrated and the residue was dissolved in dioxane. 4N hydrogen chloride/ethyl acetate solution was added to the solution. The reaction mixture was concentrated and the obtained residue was added dioxane and filtrated. The filtrate was concentrated and the obtained residue was washed with diethyl ether and dried to give the title compound (62 mg) having the following physical data.

TLC: Rf 0.28 (butanol:acetic acid:water=4:2:1); NMR (CD$_3$OD):δ 7.99 (d, J=8.7 Hz, 2H), 7.70 (d, J=8.7 Hz, 2H), 4.44 (s, 2H), 4.11 (s, 2H), 4.02 (dd, J=7.5, 4.8 Hz, 1H), 3.94-3.74 (m, 2H), 3.56-3.36 (m, 4H), 2.48-2.32 (m, 2H), 2.28-2.08 (m, 2H), 1.88-1.30 (m, 7H), 0.96 (t, J=7.2 Hz, 3H), 0.95 (d, J=6.3 Hz, 3H), 0.94 (d, J=6.3 Hz, 3H).

EXAMPLE 72

(3S)-1-butyl-2,5-dioxo-3-(2-methylpropyl)-9-(3-(3,5-dimethyl-1-phenylpyrazol-4-yl)propyl)-1,4,9-triazaspiro[5.5]undecane.2hydrochloride

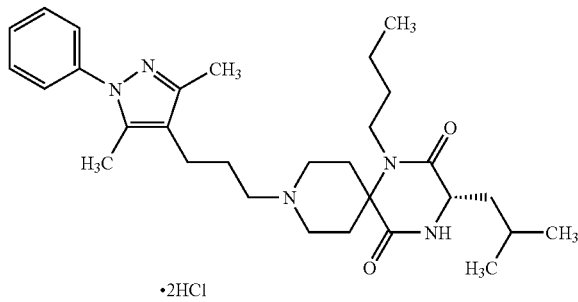

•2HCl

To a solution of the compound prepared in Example 70(43) (85 mg) in methanol (10 ml) solution was added 5% palladium on carbon (10 mg). Under an atmosphere of hydrogen, the reaction mixture was stirred for 22 hours at room temperature. The reaction mixture was filtrated through Celite(brand name) and the filtrate was concentrated. The obtained residue was purified by column chromatography on silica gel (ethyl acetate:methanol=15:1). To the solution of the obtained compound in methanol was added 4N hydrogen chloride/ethyl acetate solution. The reaction mixture was concentrated and the obtained residue was washed with diethyl ether and dried to give the title compound (23 mg) having the following physical data.

TLC: Rf 0.18 (chloroform:methanol=10:1); NMR (CD$_3$OD):δ 7.70-7.50 (m, 5H), 4.03 (dd J=7.2, 4.2 Hz, 1H), 3.86-3.68 (m, 2H), 3.66-3.40 (m, 4H), 3.30-3.16 (m, 2H), 2.74-2.48 (m, 4H), 2.46 (s, 3H), 2.35 (s, 3H), 2.28-1.98 (m, 4H), 1.90-1.24 (m, 7H), 0.97 (t, J=7.2 Hz, 3H), 0.96 (d, J=6.6 Hz, 3H), 0.95 (d, J=6.6 Hz, 3H).

EXAMPLE 73

(3S)-1-butyl-2,5-dioxo-3-cyclohexylmethyl-9-(3,5-dimethyl-1-(4-(N,N-dimethylaminocarbonyl)phenyl)pyrazol-4-ylmethyl)-1,4,9-triazaspiro[5.5]undecane.2hydrochloride

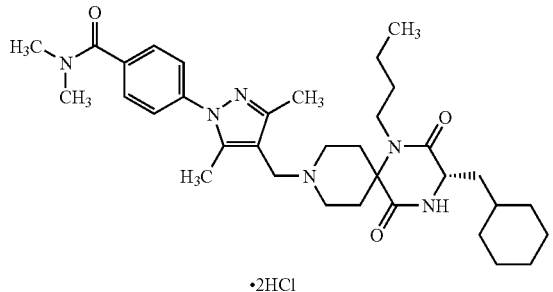

•2HCl

By the same procedure as described in Example 68 using the compound prepared in Reference example 15(2) instead of the compound prepared in Reference example 15, and using [4-(4-formyl-3,5-dimethylpyrazolyl)phenyl]-N,N-dimethylcarboxamide instead of 3-formyl-6-phenyloxypyridine, the title compound having the following physical data was obtained.

TLC: Rf 0.59 (chloroform:methanol=10:1); NMR (CD$_3$OD):δ 7.62 (d, J=9.0 Hz, 2H), 7.58 (d, J=9.0 Hz, 2H), 4.32 (s, 2H), 4.05 (dd, J=7.8, 4.5 Hz, 1H), 3.96-3.78 (m, 2H), 3.66-3.58 (m, 2H), 3.46-3.34 (m, 2H), 3.13 (s, 3H), 3.04 (s, 3H), 2.52-2.38 (m, 2H), 2.42 (s, 3H), 2.39 (s, 3H), 2.32-2.14 (m, 2H), 1.82-1.16 (m, 15H), 1.02-0.88 (m, 5H).

EXAMPLE 73(1) TO 73(41)

By the same procedure as described in Example 73 using the corresponding aldehyde derivatives respectively instead of [4-(4-formyl-3,5-dimethylpyrazolyl)phenyl]-N,N-dimethylcarboxamide, the following compounds were obtained.

EXAMPLE 73(1)

(3S)-1-butyl-2,5-dioxo-3-cyclohexylmethyl-9-(3,5-dimethyl-1-(4-(pyrrolidin-1-ylcarbonyl)phenyl)pyrazol-4-ylmethyl)-1,4,9-triazaspiro[5.5]undecane.2hydrochloride

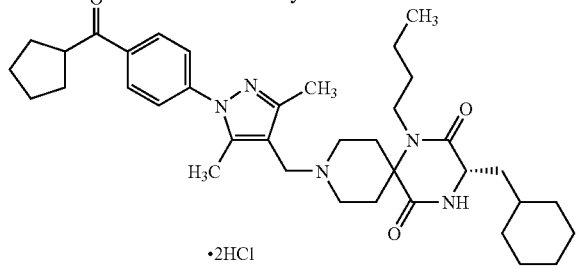

•2HCl

TLC: Rf 0.53 (chloroform:methanol=10:1); NMR (CD$_3$OD): δ 7.72 (d, J=8.7 Hz, 2H), 7.58 (d, J=8.7 Hz, 2H), 4.33 (s, 2H), 4.05 (dd, J=7.5, 4.5 Hz, 1H), 3.98-3.78 (m, 2H), 3.64-3.56 (m, 4H), 3.56-3.44 (m, 2H), 3.44-3.32 (m, 2H), 2.50-2.10 (m, 4H), 2.42 (s, 3H), 2.39 (s, 3H), 2.10-1.88 (m, 4H), 1.88-1.10 (m, 15H), 1.10-0.90 (m, 5H).

EXAMPLE 73(2)

(3S)-1-butyl-2,5-dioxo-3-cyclohexylmethyl-9-(3,5-dimethyl-1-(4-(morpholin-4-ylcarbonyl)phenyl)pyrazol-4-ylmethyl)-1,4,9-triazaspiro[5.5]undecane.2hydrochloride

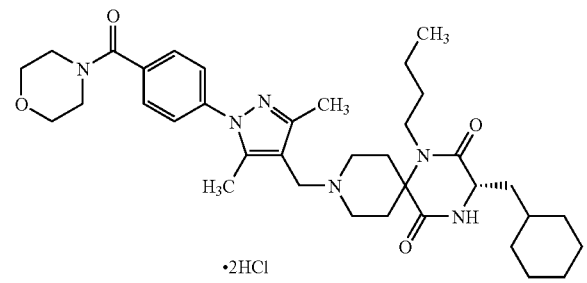

TLC: Rf 0.53 (chloroform:methanol=10:1); NMR (CD$_3$OD): δ 7.65-7.56 (m, 4H), 4.32 (s, 2H), 4.05 (dd, J=7.5, 4.5 Hz, 1H), 3.96-3.30 (m, 14H), 2.54-2.32 (m, 2H), 2.43 (s, 3H), 2.39 (s, 3H), 2.32-2.12 (m, 2H), 1.84-1.10 (m, 15H), 1.02-0.86 (m, 5H).

EXAMPLE 73(3)

(3S)-1-butyl-2,5-dioxo-3-cyclohexylmethyl-9-(3,5-dimethyl-1-(4-(2-(N,N-dimethylamino)ethylaminocarbonyl)phenyl)pyrazol-4-ylmethyl)-1,4,9-triazaspiro[5.5]undecane.3hydrochloride TLC: Rf 0.15 (chloroform:methanol=10:1); NMR (CD$_3$OD): δ 8.07 (d, J=8.1 Hz, 2H), 7.64 (d, J=8.1 Hz, 2H), 4.31 (s, 2H), 4.05 (dd, J=7.2, 5.1 Hz, 1H), 3.94-3.76 (m, 2H), 3.79 (t, J=6.0 Hz, 2H), 3.66-3.54 (m, 2H), 3.54-3.36 (m, 2H), 3.41 (t, J=6.0 Hz, 2H), 3.00 (s, 6H), 2.66-2.48 (m, 2H), 2.46 (s, 3H), 2.41 (s, 3H), 2.28-2.10 (m, 2H), 1.82-1.10 (m, 15H), 1.02-0.86 (m, 5H).

EXAMPLE 73(4)

(3S)-1-butyl-2,5-dioxo-3-cyclohexylmethyl-9-(4-(4-(morpholin-4-ylcarbonyl)phenyloxy)phenylmethyl)-1,4,9-triazaspiro[5.5]undecane.hydrochloride

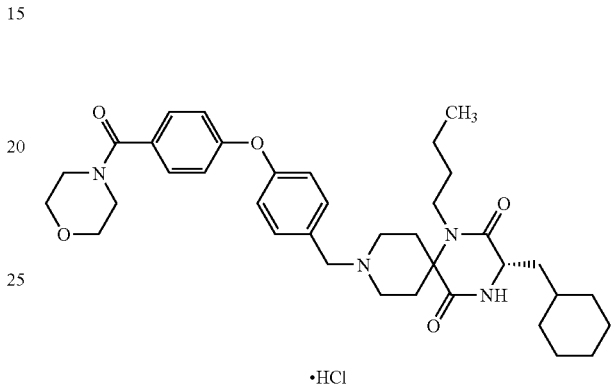

TLC: Rf 0.60 (chloroform:methanol=10:1); NMR (CD$_3$OD): δ 7.59 (d, J=8.4 Hz, 2H), 7.48 (d, J=8.7 Hz, 2H), 7.22-7.09 (m, 4H), 4.36 (s, 2H), 4.04 (dd, J=7.5, 4.8 Hz, 1H), 3.88-3.34 (m, 14H), 2.52-2.34 (m, 2H), 2.28-2.08 (m, 2H), 1.81-1.10 (m, 15H), 1.04-0.84 (m, 5H).

EXAMPLE 73(5)

(3S)-1-butyl-2,5-dioxo-3-cyclohexylmethyl-9-(4-methylsulfonylphenylmethyl)-1,4,9-triazaspiro[5.5]undecane.hydrochloride

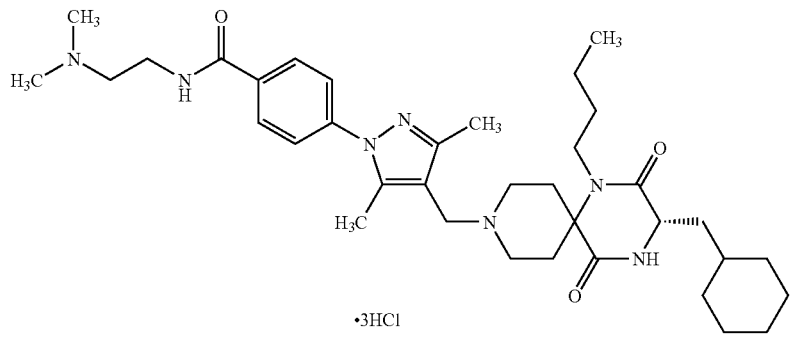

TLC: Rf 0.57 (chloroform:methanol=10:1); NMR (CD₃OD):δ 8.08 (d, J=8.4 Hz, 2H), 7.87 (d, J=8.4 Hz, 2H), 4.50 (s, 2H), 4.03 (dd, J=7.5, 4.5 Hz, 1H), 3.94-3.76 (m, 2H), 3.52-3.36 (m, 4H), 3.15 (s, 3H), 2.56-2.38 (m, 2H), 2.26-2.08 (m, 2H), 1.80-1.10 (m, 15H), 1.02-0.86 (m, 5H).

EXAMPLE 73(6)

(3S)-1-butyl-2,5-dioxo-3-cyclohexylmethyl-9-(4-(4-methylsulfonylphenyloxy)phenylmethyl)-1,4,9-triazaspiro[5.5]undecane.hydrochloride

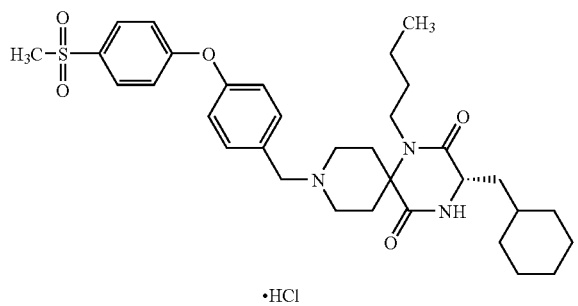

TLC: Rf 0.57 (chloroform:methanol=10:1); NMR (CD₃OD):δ 7.95 (d, J=9.0 Hz, 2H), 7.64 (d, J=8.7 Hz, 2H), 7.25-7.18 (m, 4H), 4.39 (s, 2H), 4.04 (dd, J=7.8, 4.8 Hz, 1H), 3.90-3.76 (m, 2H), 3.58-3.34 (m, 4H), 3.12 (s, 3H), 2.50-2.36 (m, 2H), 2.30-2.10 (m, 2H), 1.82-1.10 (m, 15H), 1.02-0.88 (m, 5H).

EXAMPLE 73(7)

(3S)-1-butyl-2,5-dioxo-3-cyclohexylmethyl-9-(3,5-dimethyl-1-(4-(2-(morpholin-4-yl)ethylaminosulfonyl)phenyl)pyrazol-4-ylmethyl)-1,4,9-triazaspiro[5.5]undecane.3hydrochloride TLC: Rf 0.43 (chloroform:methanol=10:1); NMR (CD₃OD):δ 8.06 (d, J=8.7 Hz, 2H), 7.57 (d, J=8.7 Hz, 2H), 4.31 (s, 2H), 4.12-4.01 (m, 3H), 3.92-3.76 (m, 4H), 3.65-3.40 (m, 6H), 3.40-3.16 (m, 6H), 2.64-2.44 (m, 2H), 2.48 (s, 3H), 2.41 (s, 3H), 2.28-2.12 (m, 2H), 1.84-1.10 (m, 15H), 1.02-0.86 (m, 5H).

EXAMPLE 73(8)

(3S)-1-butyl-2,5-dioxo-3-cyclohexylmethyl-9-(3,5-dimethyl-1-(4-(4-methylpiperazin-1-ylsulfonyl)phenyl)pyrazol-4-ylmethyl)-1,4,9-triazaspiro[5.5]undecane.3hydrochloride

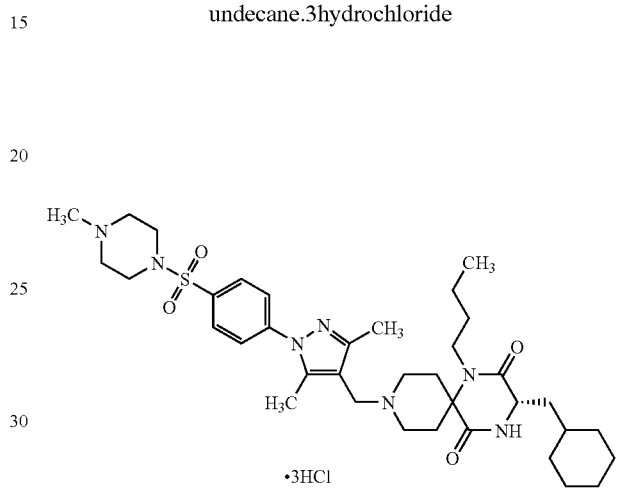

TLC: Rf 0.43 (chloroform:methanol=10:1); NMR (CD₃OD):δ 8.01 (d, J=8.7 Hz, 2H), 7.83 (d, J=8.7 Hz, 2H), 4.31 (s, 2H), 4.08-3.95 (m, 3H), 3.95-3.74 (m, 2H), 3.68-3.46 (m, 6H), 3.28-3.20 (m, 2H), 2.91 (s, 3H), 2.88-2.72 (m, 2H), 2.70-2.52 (m, 2H), 2.51 (s, 3H), 2.42 (s, 3H), 2.26-2.08 (m, 2H), 1.82-1.10 (m, 15H), 1.02-0.86 (m, 5H).

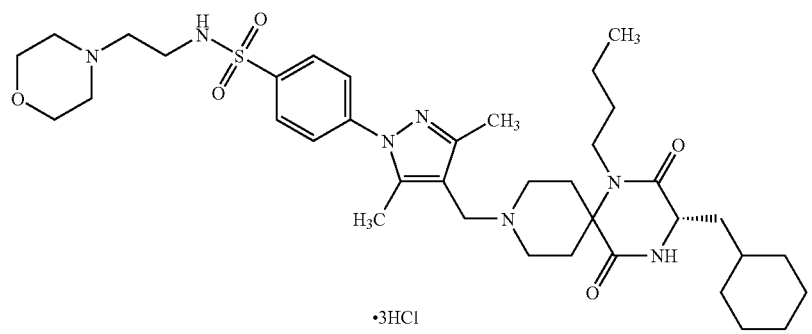

EXAMPLE 73(9)

(3S)-1-butyl-2,5-dioxo-3-cyclohexylmethyl-9-(4-(4-methylsulfinylphenyloxy)phenylmethyl)-1,4,9-triazaspiro[5.5]undecane.hydrochloride

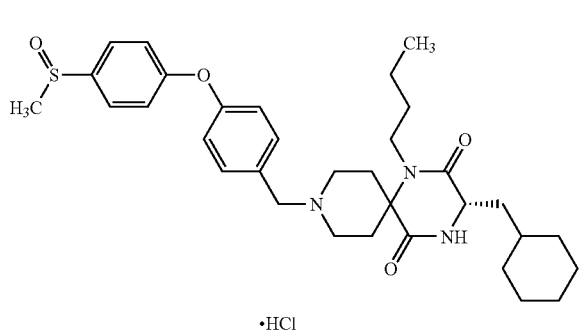

TLC: Rf 0.53 (chloroform:methanol=10:1); NMR (CD$_3$OD):δ7.74 (d, J=9.0 Hz, 2H), 7.62 (d, J=8.7 Hz, 2H), 7.25-7.14 (m, 4H), 4.37 (s, 2H), 4.04 (dd, J=7.5, 4.5 Hz, 1H), 3.88-3.72 (m, 2H), 3.54-3.36 (m, 4H), 2.80 (s, 3H), 2.52-2.36 (m, 2H), 2.26-2.10 (m, 2H), 1.80-1.10 (m, 15H), 1.02-0.86 (m, 5H).

EXAMPLE 73(10)

(3S)-1-butyl-2,5-dioxo-3-cyclohexylmethyl-9-(3,5-dimethyl-1-(4-(2-hydroxyethylaminocarbonyl)phenyl)pyrazol-4-ylmethyl)-1,4,9-triazaspiro[5.5]undecane.2hydrochloride

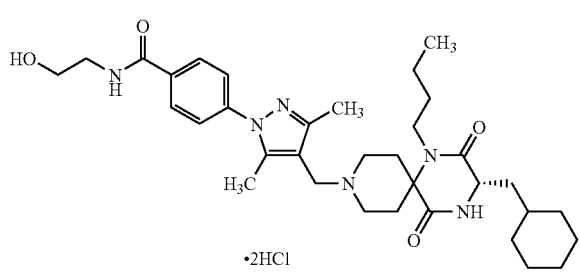

TLC: Rf 0.41 (chloroform:methanol=10:1); NMR (CD$_3$OD):δ 8.01 (d, J=8.7 Hz, 2H), 7.60 (d, J=8.7 Hz, 2H), 4.30 (s, 2H), 4.05 (dd, J=7.5, 4.2 Hz, 1H), 3.92-3.68 (m, 2H), 3.66-3.42 (m, 6H), 2.70-2.50 (m, 2H), 2.45 (s, 3H), 2.40 (s, 3H), 2.28-2.08 (m, 2H), 1.82-1.10 (m, 15H), 1.02-0.84 (m, 5H).

EXAMPLE 73(11)

(3S)-1-butyl-2,5-dioxo-3-cyclohexylmethyl-9-(4-(4-(2-hydroxyethylaminocarbonyl)phenyloxy)phenylmethyl)-1,4,9-triazaspiro[5.5]undecane.hydrochloride

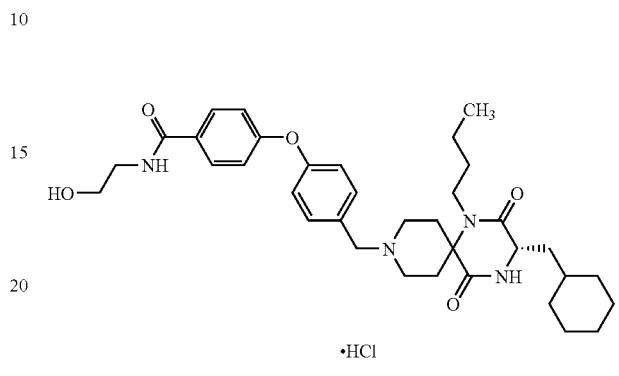

TLC: Rf 0.36 (chloroform:methanol=10:1); NMR (CD$_3$OD):δ 7.89 (d, J=9.0 Hz, 2H), 7.58 (d, J=8.7 Hz, 2H), 7.16 (d, J=8.7 Hz, 2H), 7.08 (d, J=9.0 Hz, 2H), 4.37 (s, 2H), 4.04 (dd, J=7.5, 4.5 Hz, 1H), 3.90-3.70 (m, 2H), 3.70 (t, J=6.0 Hz, 2H), 3.58-3.46 (m, 2H), 3.50 (t, J=6.0 Hz, 2H), 3.42-3.34 (m, 2H), 2.44-2.30 (m, 2H), 2.30-2.08 (m, 2H), 1.82-1.12 (m, 15H), 1.02-0.84 (m, 5H).

EXAMPLE 73(12)

(3S)-1-butyl-2,5-dioxo-3-cyclohexylmethyl-9-(4-(4-(pyrrolidin-1-ylcarbonyl)phenyloxy)phenylmethyl)-1,4,9-triazaspiro[5.5]undecane.hydrochloride

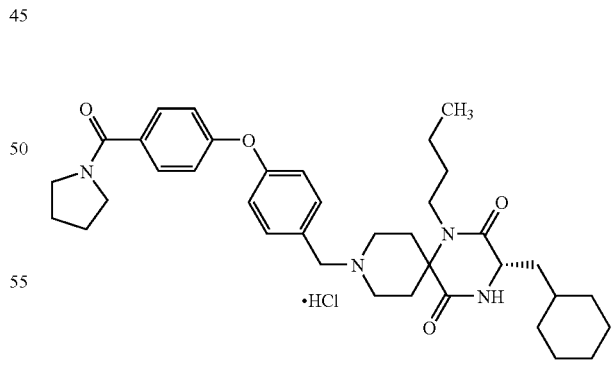

TLC: Rf 0.25(ethyl acetate:methanol=10:1); NMR (CD$_3$OD):δ 7.59 (d, J=8.7 Hz, 2H), 7.59 (d, J=8.7 Hz, 2H), 7.16 (d, J=8.7 Hz, 2H), 7.10 (d, J=8.7 Hz, 2H), 4.37 (s, 2H), 4.05 (dd, J=7.5, 4.8 Hz, 1H), 3.90-3.74 (m, 2H), 3.62-3.36 (m, 8H), 2.48-2.08 (m, 4H), 2.04-1.08 (m, 19H), 0.96 (t, J=7.2 Hz, 3H), 1.04-0.84 (m, 2H).

EXAMPLE 73(13)

(3S)-1-butyl-2,5-dioxo-3-cyclohexylmethyl-9-(3,5-dimethyl-1-(4-(cyclohexylaminosulfonyl)phenyl)pyrazol-4-ylmethyl)-1,4,9-triazaspiro[5.5]undecane.2hydrochloride

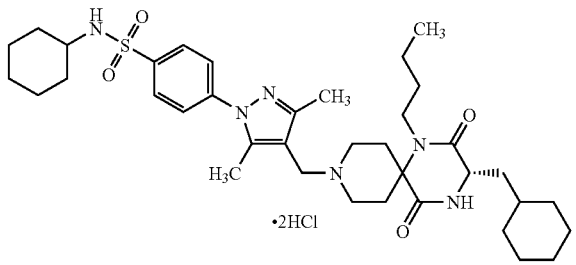

TLC: Rf 0.42 (chloroform:methanol=10:1); NMR (CD$_3$OD):δ 8.03 (d, J=8.7 Hz, 2H), 7.70 (d, J=8.7 Hz, 2H), 4.31 (s, 2H), 4.05 (dd, J=7.8, 4.8 Hz, 1H), 3.92-3.72 (m, 2H), 3.68-3.58 (m, 2H), 3.56-3.44 (m, 2H), 3.06 (m, 1H), 2.68-2.50 (m, 2H), 2.47 (s, 3H), 2.41 (s, 3H), 2.38-2.08 (m, 2H), 1.82-1.06 (m, 25H), 1.02-0.86 (m, 5H).

EXAMPLE 73(14)

(3S)-1-butyl-2,5-dioxo-3-cyclohexylmethyl-9-(3,5-dimethyl-1-(4-(3-methoxypropylaminosulfonyl)phenyl)pyrazol-4-ylmethyl)-1,4,9-triazaspiro[5.5]undecane.2hydrochloride

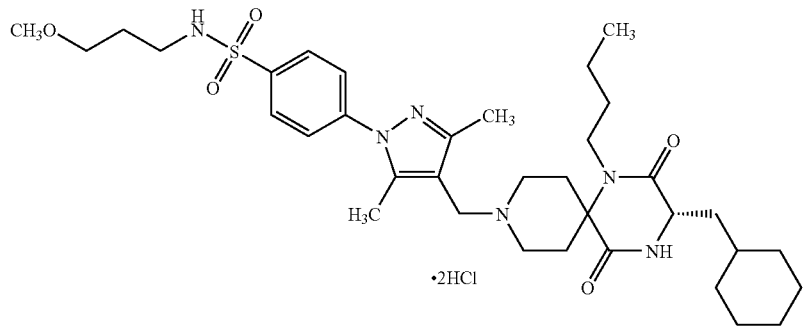

TLC: Rf 0.48 (chloroform:methanol=10:1); NMR (CD$_3$OD):δ 8.01 (d, J=8.4 Hz, 2H), 7.74 (d, J=8.4 Hz, 2H), 4.31 (s, 2H), 4.05 (dd, J=7.8, 4.8 Hz, 1H), 3.92-3.72 (m, 2H), 3.68-3.58 (m, 2H), 3.56-3.46 (m, 4H), 3.39 (t, J=6.0 Hz, 2H), 3.26 (s, 3H), 2.98 (t, J=6.9 Hz, 2H), 2.72-2.56 (m, 2H), 2.48 (s, 3H), 2.43 (s, 3H), 2.26-2.08 (m, 2H), 1.82-1.10 (m, 15H), 1.02-0.86 (m, 5H).

EXAMPLE 73(15)

(3S)-1-butyl-2,5-dioxo-3-cyclohexylmethyl-9-(4-methylsulfinylphenylmethyl)-1,4,9-triazaspiro[5.5]undecane.hydrochloride

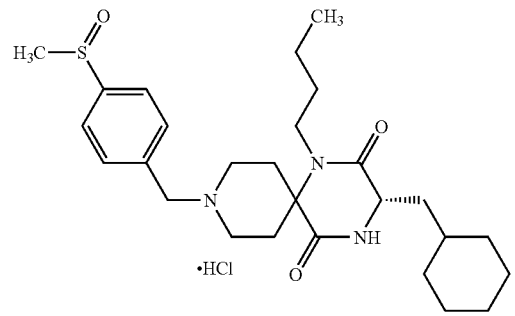

TLC: Rf 0.15 (ethyl acetate:methanol=10:1); NMR (CD$_3$OD):δ 7.85 (d, J=8.7 Hz, 2H), 7.81 (d, J=8.7 Hz, 2H), 4.47 (s, 2H), 4.05 (dd, J=7.2, 4.8 Hz, 1H), 3.94-3.76 (m, 2H), 3.58-3.36 (m, 4H), 2.83 (s, 3H), 2.54-2.34 (m, 2H), 2.18-2.06 (m, 2H), 1.82-1.10 (m, 15H), 0.96 (t, J=7.5 Hz, 3H), 1.06-0.86 (m, 2H).

EXAMPLE 73(16)

((3S)-1-butyl-2,5-dioxo-3-cyclohexylmethyl-9-(3,5-dimethyl-1-propylpyrazol-4-ylmethyl)-1,4,9-triazaspiro[5.5]undecane.2hydrochloride

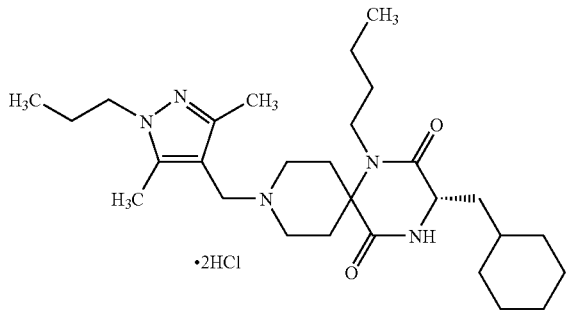

TLC: Rf 0.61 (chloroform:methanol=10:1); NMR (CD$_3$OD):δ 4.28 (s, 2H), 4.13 (t, J=7.2 Hz, 2H), 4.05 (dd, J=7.5, 4.5 Hz, 1H), 3.88-3.72 (m, 2H), 3.60-3.38 (m, 4H), 2.62-2.32 (m, 2H), 2.46 (s, 3H), 2.42 (s, 3H), 2.28-2.08 (m, 2H), 1.94-1.08 (m, 17H), 0.96 (t, J=7.2 Hz, 6H), 1.06-0.86 (m, 2H).

EXAMPLE 73(17)

(3S)-1-butyl-2,5-dioxo-3-cyclohexylmethyl-9-(3,5-dimethyl-1-ethylpyrazol-4-ylmethyl)-1,4,9-triazaspiro[5.5]undecane.2hydrochloride

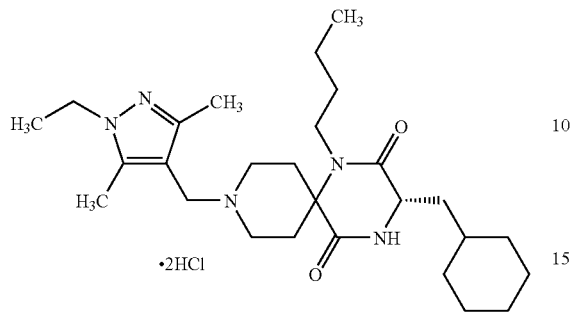

TLC: Rf 0.51 (chloroform:methanol=10:1); NMR (CD$_3$OD): δ 4.34-4.20 (m, 4H), 4.04 (dd, J=7.8, 4.8 Hz, 1H), 3.88-3.70 (m, 2H), 3.62-3.46 (m, 4H), 2.72-2.54 (m, 2H), 2.52 (s, 3H), 2.48 (s, 3H), 2.24-2.06 (m, 2H), 1.82-1.08 (m, 18H), 1.02-0.86 (m, 5H).

EXAMPLE 73(18)

(3S)-1-butyl-2,5-dioxo-3-cyclohexylmethyl-9-(3,5-dimethyl-1-cyclopentylpyrazol-4-ylmethyl)-1,4,9-triazaspiro[5.5]undecane.2hydrochloride

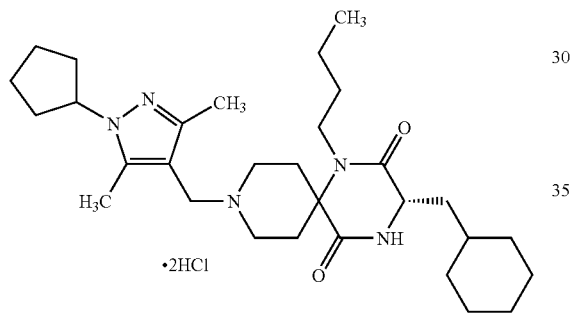

TLC: Rf 0.49 (chloroform:methanol=10:1); NMR (CD$_3$OD): δ 5.02-4.82 (m, 1H), 4.33 (s, 2H), 4.04 (dd, J=7.5, 4.8 Hz, 1H), 3.90-3.70 (m, 2H), 3.64-3.48 (m, 4H), 2.80-2.60 (m, 2H), 2.58 (s, 3H), 2.57 (s, 3H), 2.36-1.08 (m, 25H), 1.04-0.84 (m, 5H).

EXAMPLE 73(19)

(3S)-1-butyl-2,5-dioxo-3-cyclohexylmethyl-9-(3,5-dimethyl-1-(4-(3-(morpholin-4-yl)propylaminosulfonyl)phenyl)pyrazol-4-ylmethyl)-1,4,9-triazaspiro[5.5]undecane.3hydrochlorie

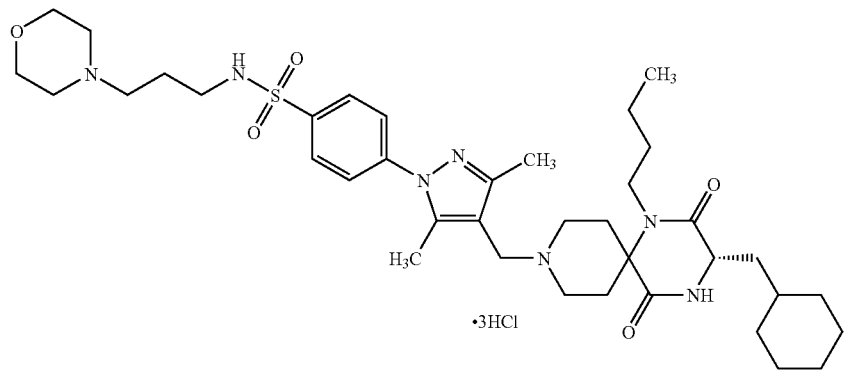

TLC: Rf 0.20 (ethyl acetate:methanol=3:1); NMR (CD$_3$OD): δ 8.02 (d, J=8.7 Hz, 2H), 7.74 (d, J=8.7 Hz, 2H), 4.31 (s, 2H), 4.10-4.00 (m, 3H), 4.00-3.00 (m, 16H), 2.65-2.10 (m, 4H), 2.47 (s, 3H), 2.40 (s, 3H), 2.05-1.95 (m, 2H), 1.85-1.15 (m, 15H), 1.10-0.90 (m, 2H), 0.95 (t, J=7.2 Hz, 3H).

EXAMPLE 73(20)

(3S)-1-butyl-2,5-dioxo-3-cyclohexylmethyl-9-(4-(N,N-dimethylaminosulfonyl)phenylmethyl)-1,4,9-triazaspiro[5.5]undecane.hydrochloride

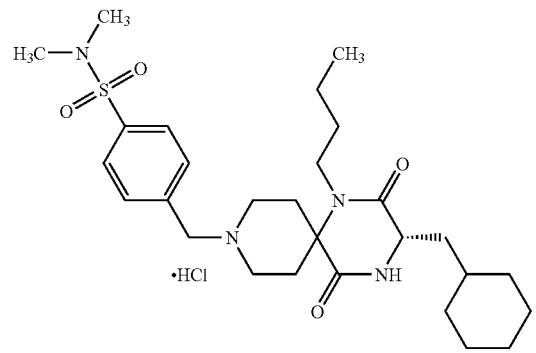

TLC: Rf 0.60 (chloroform:methanol=10:1); NMR (CD$_3$OD): δ 7.90 (d, J=8.4 Hz, 2H), 7.84 (d, J=8.4 Hz, 2H), 4.48 (s, 2H), 4.04 (dd, J=7.5, 4.5 Hz, 1H), 3.94-3.76 (m, 2H), 3.56-3.36 (m, 4H), 2.71 (s, 6H), 2.56-2.36 (m, 2H), 2.28-2.06 (m, 2H), 1.83-1.10 (m, 15H), 1.08-0.85 (m, 2H), 0.95 (t, J=7.2 Hz, 3H).

EXAMPLE 73(21)

(3S)-1-butyl-2,5-dioxo-3-cyclohexylmethyl-9-(4-(pyrrolidin-1-ylcarbonyl)phenylmethyl)-1,4,9-triazaspiro[5.5]undecane.hydrochloride

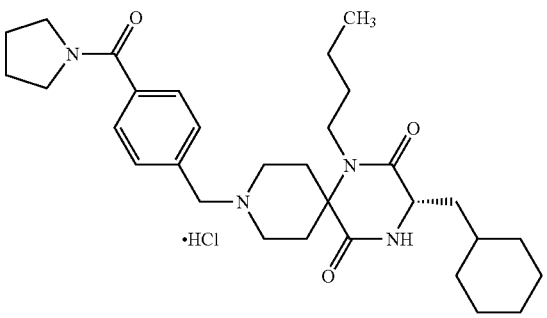

TLC: Rf 0.59 (chloroform:methanol=10:1); NMR (CD₃OD):δ 7.68 (d, J=8.7 Hz, 2H), 7.63 (d, J=8.7 Hz, 2H), 4.41 (s, 2H), 4.04 (dd, J=7.5, 4.5 Hz, 1H), 3.92-3.73 (m, 2H), 3.60 (t, J=6.9 Hz, 2H), 3.55-3.34 (m, 4H), 3.45 (t, J=6.9 Hz, 2H), 2.56-2.36 (m, 2H), 2.27-2.07 (m, 2H), 2.06-1.84 (m, 4H), 1.83-1.10 (m, 15H), 1.06-0.83 (m, 2H), 0.95 (t, J=7.2 Hz, 3H).

EXAMPLE 73(22)

(3S)-1-butyl-2,5-dioxo-3-cyclohexylmethyl-9-(4-(4-(N,N-dimethylamino)phenyloxy)phenylmethyl)-1,4,9-triazaspiro[5.5]undecane.2hydrochlride

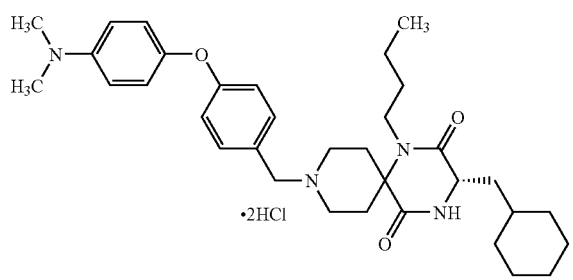

TLC: Rf 0.51 (chloroform:methanol=10:1); NMR (CD₃OD):δ 7.70-7.62 (m, 4H), 7.22 (d, J=9.0 Hz, 2H), 7.14 (d, J=8.4 Hz, 2H), 4.36 (s, 2H), 4.03 (dd, J=7.5, 4.5 Hz, 1H), 3.86-3.70 (m, 2H), 3.52-3.40 (m, 4H), 3.30 (s, 6H), 2.62-2.44 (m, 2H), 2.24-2.06 (m, 2H), 1.80-1.14 (m, 15H), 1.02-0.86 (m, 5H).

EXAMPLE 73(23)

(3S)-1-butyl-2,5-dioxo-3-cyclohexylmethyl-9-(4-(cyclohexylaminocarbonyl)phenylmethyl)-1,4,9-triazaspiro[5.5]undecane.hydrochloride

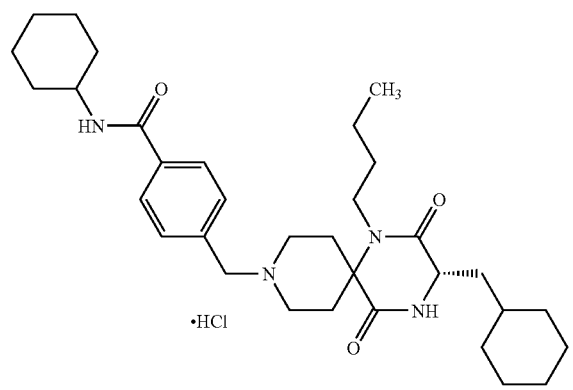

TLC: Rf 0.38 (chloroform:methanol=10:1); NMR (CD₃OD):δ 7.91 (d, J=8.1 Hz, 2H), 7.68 (d, J=8.1 Hz, 2H), 4.42 (s, 2H), 4.03 (dd, J=7.5, 4.5 Hz, 1H), 3.90-3.72 (m, 3H), 3.52-3.36 (m, 4H), 2.56-2.38 (m, 2H), 2.24-2.06 (m, 2H), 2.00-1.10 (m, 25H), 1.04-0.86 (m, 5H).

EXAMPLE 73(24)

(3S)-1-butyl-2,5-dioxo-3-cyclohexylmethyl-9-(3,5-dimethyl-1-(4-methoxycarbonylphenyl)pyrazol-4-ylmethyl)-1,4,9-triazaspiro[5.5]undecane.2hydrochloride

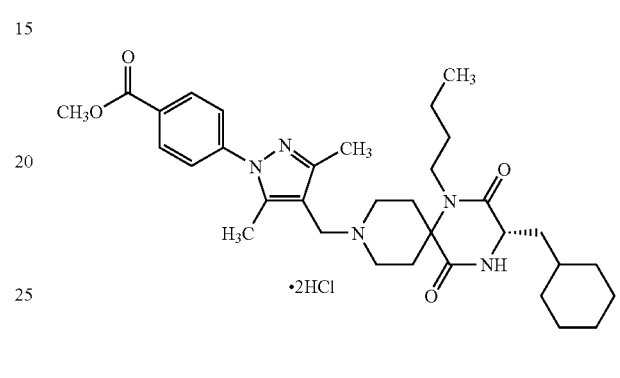

TLC: Rf 0.33 (ethyl acetate:methanol=10:1); NMR (CD₃OD):δ 8.18 (d, J=8.7 Hz, 2H), 7.64 (d, J=8.7 Hz, 2H), 4.31 (s, 2H), 4.05 (m, 1H), 3.94 (s, 3H), 3.94-3.45 (m, 6H), 2.70-2.50 (m, 2H), 2.46 (s, 3H), 2.41 (s, 3H), 2.30-2.10 (m, 2H), 1.85-1.10 (m, 15H), 1.10-0.90 (m, 2H), 0.95 (t, J=6.9 Hz, 3H).

EXAMPLE 73(25)

(3S)-1-butyl-2,5-dioxo-3-cyclohexylmethyl-9-(4-(3-methoxypropylaminocarbonyl)phenylmethyl)-1,4,9-triazaspiro[5.5]undecane.hydrochloride

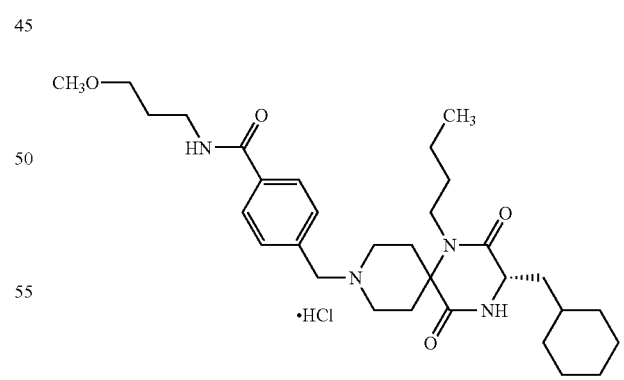

TLC: Rf 0.18 (ethyl acetate:methanol=10:1); NMR (CD₃OD):δ 7.93 (d, J=8.4 Hz, 2H), 7.69 (d, J=8.4 Hz, 2H), 4.44 (s, 2H), 4.04 (dd, J=7.5, 4.8 Hz, 1H), 3.92-3.74 (m, 2H), 3.58-3.36 (m, 10H), 3.35 (s, 3H), 2.54-2.36 (m, 2H), 2.28-2.06 (m, 2H), 1.94-1.08 (m, 15H), 1.04-0.84 (m, 2H), 0.95 (t, J=6.9 Hz, 3H).

EXAMPLE 73(26)

(3S)-1-butyl-2,5-dioxo-3-cyclohexylmethyl-9-(4-(N-methyl-N-(2-(pyridin-2-yl)ethyl)aminocarbonyl)phenylmethyl)-1,4,9-triazaspiro[5.5]undecane.2hydrochloride

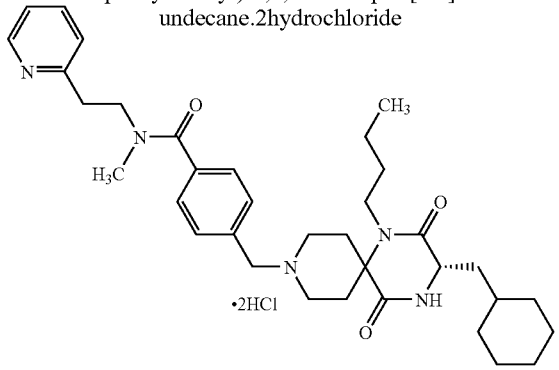

TLC: Rf 0.27 (ethyl acetate:methanol=10:1); NMR (CD$_3$OD):δ 8.81 (m, 1H), 8.59 (m, 1H), 8.16-7.94 (m, 2H), 7.71 (d, J=7.8 Hz, 2H), 7.42 (d, J=7.8 Hz, 2H), 4.40 (s, 2H), 4.06-3.70 (m, 5H), 3.60-3.36 (m, 6H), 3.09 (s, 3H), 2.72-2.42 (m, 2H), 2.26-2.02 (m, 2H), 1.84-1.14 (m, 15H), 1.06-0.84 (m, 2H), 0.95 (t, J=6.9 Hz, 3H).

EXAMPLE 73(27)

(3S)-1-butyl-2,5-dioxo-3-cyclohexylmethyl-9-(4-((4-methoxyphenyl)methylaminocarbonyl)phenylmethyl)-1,4,9-triazaspiro[5.5]undecane.hydrochloride

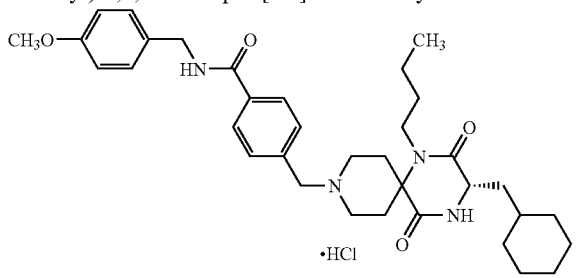

TLC: Rf 0.38 (chloroform:methanol=10:1); NMR (CD$_3$OD):δ 7.96 (d, J=9.0 Hz, 2H), 7.69 (d, J=9.0 Hz, 2H), 7.28 (d, J=9.0 Hz, 2H), 6.88 (d, J=9.0 Hz, 2H), 4.52 (s, 2H), 4.43 (s, 2H), 4.04 (dd, J=7.5, 4.5 Hz, 1H), 3.92-3.78 (m, 2H), 3.77 (s, 3H), 3.56-3.36 (m, 4H), 2.52-2.34 (m, 2H), 2.26-2.06 (m, 2H), 1.82-1.10 (m, 15H), 1.06-0.84 (m, 2H), 0.95 (t, J=7.2 Hz, 3H).

EXAMPLE 73(28)

(3S)-1-butyl-2,5-dioxo-3-cyclohexylmethyl-9-(4-(4-methoxycarbonylphenyloxy)phenylmethyl)-1,4,9-triazaspiro[5.5]undecane.hydrochloride

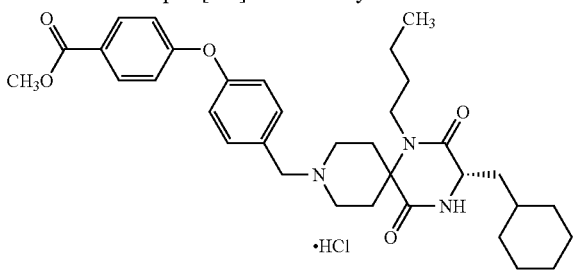

TLC: Rf 0.54 (chloroform:methanol=10:1); NMR (CD$_3$OD):δ 8.04 (d, J=9.0 Hz, 2H), 7.63 (d, J=9.0 Hz, 2H), 7.19 (d, J=9.0 Hz, 2H), 7.08 (d, J=9.0 Hz, 2H), 4.38 (s, 2H), 4.05 (dd, J=7.5, 4.5 Hz, 1H), 3.90 (s, 3H), 3.88-3.72 (m, 2H), 3.58-3.38 (m, 4H), 2.58-2.38 (m, 2H), 2.28-2.08 (m, 2H), 1.84-1.08 (m, 15H), 1.06-0.86 (m, 2H), 0.96 (t, J=7.2 Hz, 3H).

EXAMPLE 73(29)

(3S)-1-butyl-2,5-dioxo-3-cyclohexylmethyl-9-(3,5-dimethyl-1-(4-methoxyphenyl)pyrazol-4-ylmethyl)-1,4,9-triazaspiro[5.5]undecane.2hydrochloride

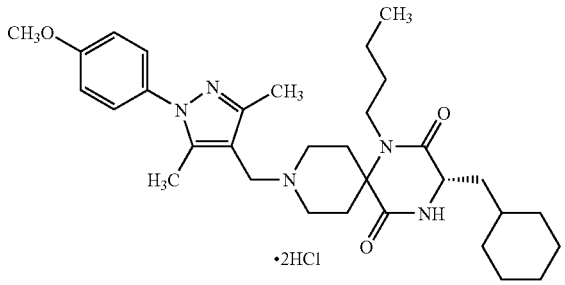

TLC: Rf 0.40 (chloroform:methanol=10:1); NMR (CD$_3$OD):δ 7.42 (d, J=9.0 Hz, 2H), 7.12 (d, J=9.0 Hz, 2H), 4.33 (s, 2H), 4.06 (dd, J=7.5, 4.5 Hz, 1H), 3.96-3.76 (m, 2H), 3.88 (s, 3H), 3.68-3.40 (m, 4H), 2.68-2.48 (m, 2H), 2.45 (s, 3H), 2.38 (s, 3H), 2.32-2.08 (m, 2H), 1.84-1.12 (m, 15H), 1.06-0.84 (m, 2H), 0.97 (t, J=7.2 Hz, 3H).

EXAMPLE 73(30)

(3S)-1-butyl-2,5-dioxo-3-cyclohexylmethyl-9-(3,5-dimethyl-1-(1-methylpiperidin-4-yl)pyrazol-4-ylmethyl)-1,4,9-triazaspiro[5.5]undecane.3hydrochloride

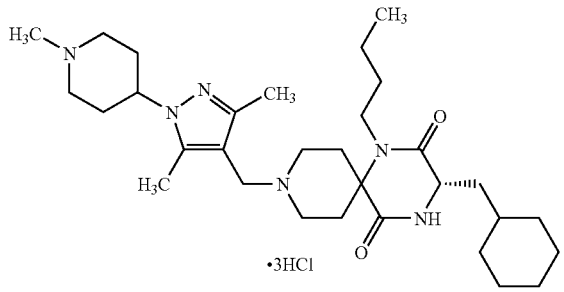

TLC: Rf 0.18 (chloroform:methanol=5:1); NMR (CD$_3$OD):δ 4.58 (m, 1H), 4.21 (s, 2H), 4.03 (dd, J=7.5, 4.5 Hz, 1H), 3.86-3.42 (m, 8H), 3.32-3.20 (m, 2H), 2.93 (s, 3H), 2.70-2.50 (m, 2H), 2.50-2.26 (m, 2H), 2.45 (s, 3H), 2.33 (s, 3H), 2.24-2.04 (m, 4H), 1.82-1.06 (m, 15H), 1.02-0.86 (m, 5H).

EXAMPLE 73(31)

(3S)-1-butyl-2,5-dioxo-3-cyclohexylmethyl-9-(3,5-dimethyl-1-(1-methylsulfonylpiperidin-4-yl)pyrazol-4-ylmethyl)-1,4,9-triazaspiro[5.5]undecane.2hydrochloride

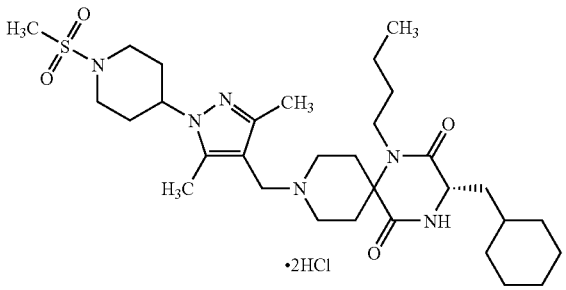

TLC: Rf 0.41 (chloroform:methanol=10:1); NMR (CD$_3$OD):δ 4.44 (m, 1H), 4.24 (s, 2H), 4.04 (dd, J=7.8, 4.8 Hz, 1H), 3.92-3.68 (m, 4H), 3.60-3.40 (m, 4H), 3.02-2.90 (m, 2H), 2.89 (s, 3H), 2.60-2.40 (m, 2H), 2.46 (s, 3H), 2.36 (s, 3H), 2.26-1.96 (m, 6H), 1.82-1.10 (m, 15H), 1.02-0.86 (m, 5H).

EXAMPLE 73(32)

(3S)-1-butyl-2,5-dioxo-3-cyclohexylmethyl-9-(3,5-dimethyl-1-(4-(3-(N,N-dimethylamino)propylaminosulfonyl)phenyl)pyrazol-4-ylmethyl)-1,4,9-triazaspiro[5.5]undecane.3hydrochloride

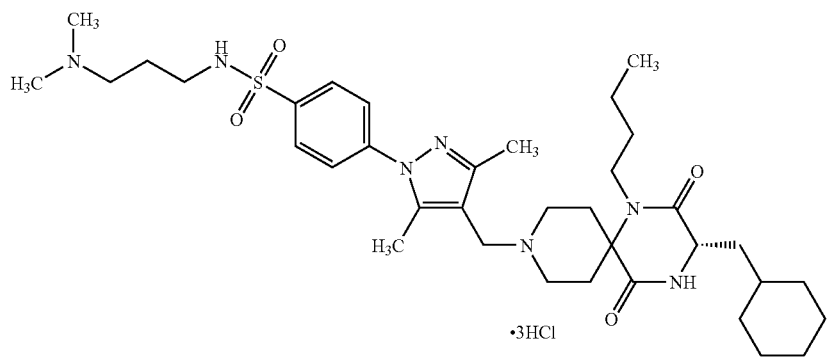

TLC: Rf 0.22 (chloroform:methanol:28% aqueous solution of ammonia=100:10:1); NMR (CD$_3$OD):δ 8.02 (d, J=8.7 Hz, 2H), 7.74 (d, J=8.7 Hz, 2H), 4.30 (s, 2H), 4.04 (dd, J=7.5, 4.5 Hz, 1H), 3.94-3.73 (m, 2H), 3.66-3.56 (m, 2H), 3.54-3.43 (m, 2H), 3.27-3.18 (m, 2H), 3.05-2.97 (m, 2H), 2.89 (s, 6H), 2.68-2.51 (m, 2H), 2.48 (s, 3H), 2.40 (s, 3H), 2.28-2.08 (m, 2H), 2.00-1.88 (m, 2H), 1.84-1.10 (m, 15H), 1.04-0.88 (m, 5H).

EXAMPLE 73(33)

(3S)-1-butyl-2,5-dioxo-3-cyclohexylmethyl-9-(3,5-dimethyl-1-(4-(N-methyl-N-(2-(N',N'-dimethylamino)ethyl)aminosulfonylphenyl)pyrazol-4-ylmethyl)-1,4,9-triazaspiro[5.5]undecane.3hydrochloride

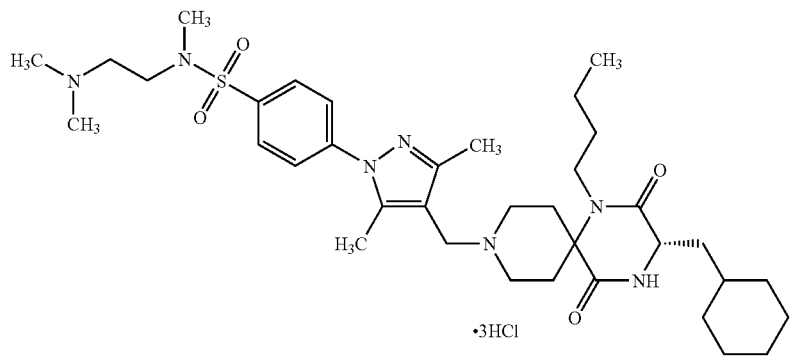

TLC: Rf 0.32 (chloroform:methanol:28% aqueous solution of ammonia=100:10:1); NMR (CD$_3$OD):δ 8.04 (d, J=8.7 Hz, 2H), 7.82 (d, J=8.7 Hz, 2H), 4.30 (s, 2H), 4.04 (dd, J=7.5, 4.5 Hz, 1H), 3.94-3.74 (m, 2H), 3.67-3.56 (m, 2H), 3.55-3.45 (m, 2H), 3.42 (s, 4H), 3.01 (s, 6H), 2.85 (s, 3H), 2.72-2.53 (m, 2H), 2.50 (s, 3H), 2.41 (s, 3H), 2.27-2.08 (m, 2H), 1.84-1.11 (m, 15H), 1.06-0.84 (m, 5H).

EXAMPLE 73(34)

(3S)-1-butyl-2,5-dioxo-3-cyclohexylmethyl-9-(4-(piperidin-1-ylcarbonyl)phenylmethyl)-1,4,9-triazaspiro[5.5]undecane.hydrochloride

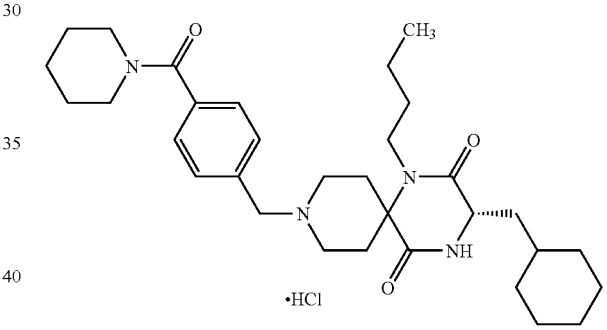

TLC: Rf 0.56 (chloroform:methanol=10:1); NMR (CD$_3$OD):δ 7.68 (d, J=8.1 Hz, 2H), 7.50 (d, J=8.1 Hz, 2H), 4.41 (s, 2H), 4.04 (dd, J=7.5, 4.8 Hz, 1H), 3.92-3.65 (m, 4H), 3.56-3.30 (m, 6H), 2.57-2.36 (m, 2H), 2.26-2.07 (m, 2H), 1.83-1.10 (m, 21H), 1.06-0.83 (m, 2H), 0.95 (t, J=7.2 Hz, 3H).

EXAMPLE 73(35)

(3S)-1-butyl-2,5-dioxo-3-cyclohexylmethyl-9-(4-(morpholin-4-ylcarbonyl)phenylmethyl)-1,4,9-triazaspiro[5.5]undecane.hydrochloride

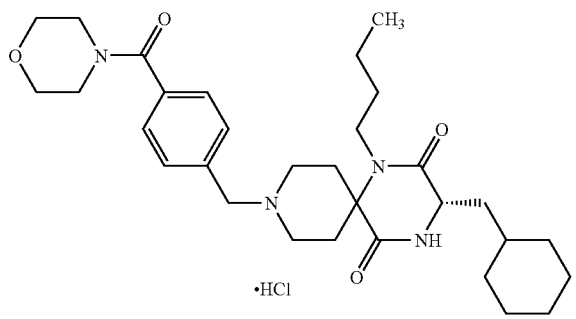

TLC: Rf 0.54 (chloroform:methanol=10:1); NMR (CD$_3$OD):δ 7.69 (d, J=8.1 Hz, 2H), 7.55 (d, J=8.1 Hz, 2H), 4.41 (s, 2H), 4.04 (dd, J=7.5, 4.5 Hz, 1H), 3.91-3.55 (m, 8H), 3.55-3.30 (m, 6H), 2.57-2.37 (m, 2H), 2.27-2.05 (m, 2H), 1.83-1.08 (m, 15H), 1.06-0.83 (m, 2H), 0.94 (t, J=7.2 Hz, 3H).

EXAMPLE 73(36)

(3S)-1-butyl-2,5-dioxo-3-cyclohexylmethyl-9-(4-(4-((N,N-dimethylamino)methyl)phenyloxy)phenylmethyl)-1,4,9-triazaspiro[5.5]undecane.2hydrochloride

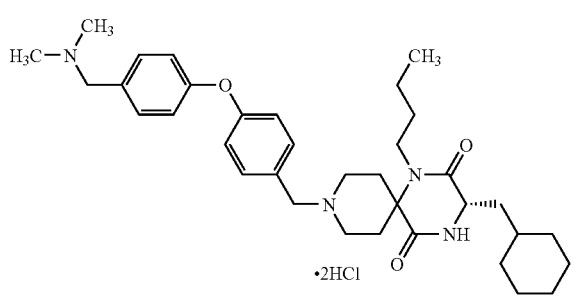

TLC: Rf 0.37 (chloroform:methanol=10:1); NMR (CD$_3$OD):δ 7.62 (d, J=8.7 Hz, 2H), 7.53 (d, J=8.7 Hz, 2H), 7.16-7.10 (m, 4H), 4.35 (s, 2H), 4.31 (s, 2H), 4.04 (dd, J=7.5, 4.5 Hz, 1H), 3.86-3.70 (m, 2H), 3.52-3.38 (m, 4H), 2.86 (s, 6H), 2.62-2.46 (m, 2H), 2.26-2.06 (m, 2H), 1.82-1.12 (m, 15H), 1.06-0.88 (m, 5H).

EXAMPLE 73(37)

(3S)-1-butyl-2,5-dioxo-3-cyclohexylmethyl-9-(3,5-dimethyl-1-(4-methylaminocarbonylphenyl)pyrazol-4-ylmethyl)-1,4,9-triazaspiro[5.5]undecane.2hydrochloride

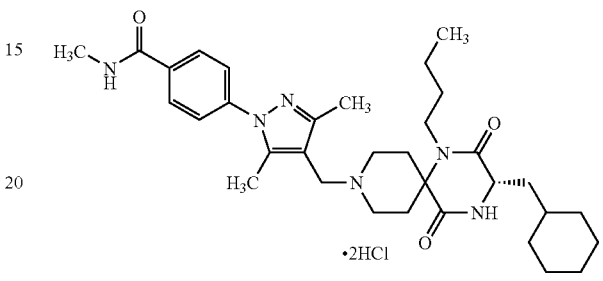

TLC: Rf 0.13 (ethyl acetate:methanol=10:1); NMR (CD$_3$OD):δ 8.00 (d, J=8.7 Hz, 2H), 7.61 (d, J=8.7 Hz, 2H), 4.33 (s, 2H), 4.06 (dd, J=7.8, 4.8 Hz, 1H), 3.94-3.76 (m, 2H), 3.66-3.56 (m, 2H), 3.52-3.40 (m, 2H), 2.95 (s, 3H), 2.62-2.38 (m, 2H), 2.50 (s, 3H), 2.42 (s, 3H), 2.32-2.10 (m, 2H), 1.84-1.18 (m, 15H), 1.06-0.84 (m, 2H), 0.97 (t, J=6.9 Hz, 3H).

EXAMPLE 73(38)

(3S)-1-butyl-2,5-dioxo-3-cyclohexylmethyl-9-(3,5-dimethyl-1-(1,1-dimethylethyl)pyrazol-4-ylmethyl)-1,4,9-triazaspiro[5.5]undecane.2hydrochloride TLC: Rf 0.38 (ethyl acetate:methanol=4:1); NMR (CD$_3$OD):δ 4.25 (s, 2H), 4.04 (dd, J=7.8, 4.8 Hz, 1H), 3.88-3.73 (m, 2H), 3.59-3.50 (m, 2H), 3.47-3.42 (m, 2H), 2.60 (s, 3H), 2.57-2.45 (m, 2H), 2.38 (s, 3H), 2.23-2.10 (m, 2H), 1.80-1.15 (m, 24H), 1.02-0.92 (m, 5H).

EXAMPLE 73(39)

(3S)-1-butyl-2,5-dioxo-3-cyclohexylmethyl-9-(3,5-dimethyl-1-(1-benzyl-oxycarbonylpiperidin-4-yl)pyrazol-4-ylmethyl)-1,4,9-triazaspiro[5.5]undecane.2hydrochloride

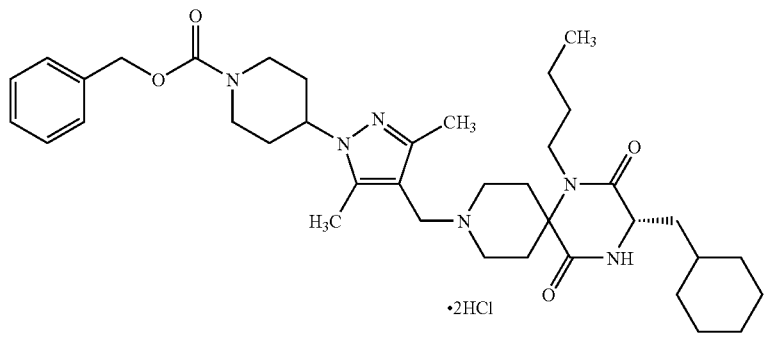

TLC: Rf 0.33 (ethyl acetate:methanol=4:1); NMR (CD$_3$OD):δ 7.39-7.29 (m, 5H), 5.14 (s, 2H), 4.52 (m, 1H), 4.33-4.29 (m, 2H), 4.25 (s, 2H), 4.04 (dd, J=7.8, 4.8 Hz, 1H), 3.87-3.72 (m, 2H), 3.55-3.42 (m, 4H), 3.10-2.98 (m, 2H), 2.60-2.43 (m, 5H), 2.36 (s, 3H), 2.23-1.95 (m, 6H), 1.80-1.15 (m, 15H), 1.02-0.92 (m, 5H).

EXAMPLE 73(40)

(3S)-1-butyl-2,5-dioxo-3-cyclohexylmethyl-9-(4-(4-hydroxymethylphenyloxy)phenylmethyl)-1,4,9-triazaspiro[5.5]undecane

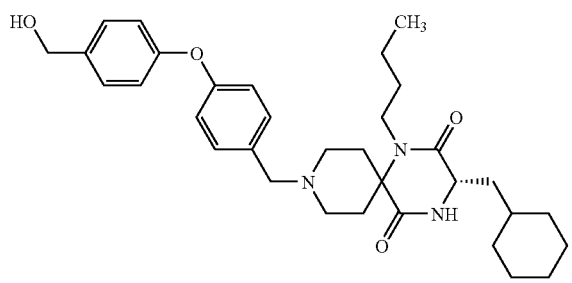

TLC: Rf 0.24 (chloroform:methanol=20:1); NMR (CD$_3$OD):δ 7.34 (d, J=8.7 Hz, 2H), 7.31 (d, J=8.7 Hz, 2H), 6.95 (d, J=8.7 Hz, 2H), 6.94 (d, J=8.7 Hz, 2H), 4.57 (s, 2H), 4.00 (dd, J=7.5, 4.5 Hz, 1H), 3.55 (s, 2H), 3.47-3.38 (m, 2H), 2.93-2.74 (m, 4H), 2.24-2.04 (m, 2H), 2.00-1.83 (m, 2H), 1.83-1.08 (m, 15H), 1.05-0.84 (m, 2H), 0.95 (t, J=7.5 Hz, 3H).

EXAMPLE 73(41)

(3S)-1-butyl-2,5-dioxo-3-cyclohexylmethyl-9-(4-((methoxycarbonyl)methylaminocarbonyl)phenylmethyl)-1,4,9-triazaspiro[5.5]undecane

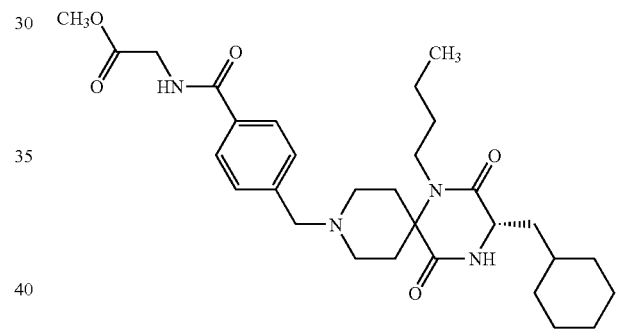

NMR (CDCl$_3$):δ 7.78 (d, J=8.1 Hz, 2H), 7.43 (d, J=8.1 Hz, 2H), 6.71 (t, J=4.8 Hz, 1H), 6.32 (brs, 1H), 4.26 (d, J=4.8 Hz, 2H), 4.00 (m, 1H), 3.81 (s, 3H), 3.64 (s, 2H), 3.54-3.28 (m, 2H), 3.06-2.72 (m, 8H), 2.26-1.10 (m, 15H), 1.06-0.82 (m, 2H), 0.94 (t, J=6.9 Hz, 3H).

EXAMPLE 74

(3S)-1-butyl-2,5-dioxo-3-cyclohexylmethyl-9-(4-(carboxymethylaminocarbonyl)phenylmethyl)-1,4,9-triazaspiro[5.5]undecane.hydrochloride

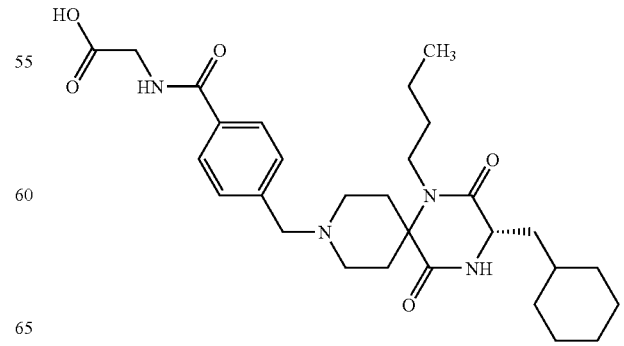

By the same procedure as described in Example 71 using the compound prepared in Example 73(41) instead of the compound prepared in Example 70(42), the title compound having the following physical data was obtained.

TLC: Rf 0.36 (butanol:acetic acid:water=4:2:1); NMR (CD$_3$OD): δ 7.99 (d, J=8.1 Hz, 2H), 7.70 (d, J=8.1 Hz, 2H), 4.45 (s, 2H), 4.11 (s, 2H), 4.04 (dd, J=7.2, 4.5 Hz, 1H), 3.94-3.74 (m, 2H), 3.58-3.36 (m, 4H), 2.56-2.34 (m, 2H), 2.30-2.06 (m, 2H), 1.84-1.16 (m, 15H), 1.06-0.86 (m, 2H), 0.96 (t, J=7.2 Hz, 3H).

EXAMPLE 75

(3R)-1-butyl-2,5-dioxo-3-((1R)-1-hydroxy-1-cyclohexylmethyl)-9-(4-phenyloxyphenylmethyl)-1,4,9-triazaspiro[5.5]undecane.hydrochloride

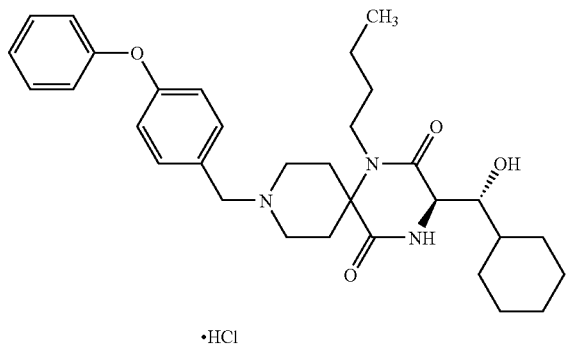

·HCl

By the same procedure as described in Example 68 using the compound prepared in Reference example 15(3) instead of the compound prepared in Reference example 15, using 4-phenyloxybenzaldehyde instead of 3-formyl-6-phenyloxypyridine, the title compound having the following physical data was obtained.

TLC: Rf 0.46 (ethyl acetate:methanol=10:1); NMR (CD$_3$OD): δ 7.50 (d, J=8.7 Hz, 2H), 7.42-7.37 (m, 2H), 7.18 (m, 1H), 7.07-7.01 (m, 4H), 4.31 (s, 2H), 4.15 (d, J=2.1 Hz, 1H), 3.97 (m, 1H), 3.71 (m, 1H), 3.60-3.05 (m, 5H), 2.55-1.90 (m, 6H), 1.90-1.60 (m, 5H), 1.60-1.10 (m, 6H), 1.10-0.90 (m, 2H), 0.95 (t, J=7.2 Hz, 3H).

EXAMPLE 75(1) TO 75(71)

By the same procedure as described in Example 75 using the corresponding aldehyde derivatives respectively instead of 4-phenyloxybenzaldehyde, the following compounds having the following physical data were obtained.

EXAMPLE 75(1)

(3R)-1-butyl-2,5-dioxo-3-((1R)-1-hydroxy-1-cyclohexylmethyl)-9-(6-phenyloxypyridin-3-ylmethyl)-1,4,9-triazaspiro[5.5]undecane.2hydrochloride

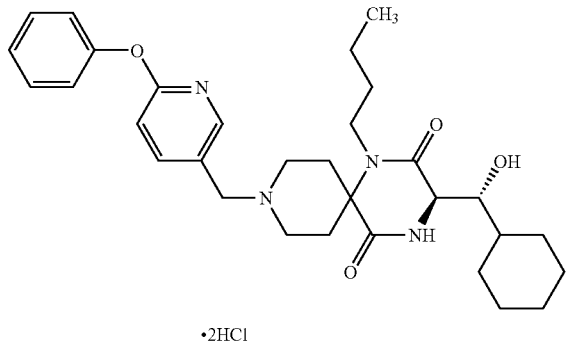

·2HCl

TLC: Rf 0.36 (ethyl acetate:methanol=10:1); NMR (CD$_3$OD): δ 8.28 (d, J=2.7 Hz, 1H), 8.01 (dd, J=8.4, 2.7 Hz, 1H), 7.43 (t, J=8.4 Hz, 2H), 7.25 (t, J=8.4 Hz, 1H), 7.13 (d, J=8.4 Hz, 2H), 7.06 (d, J=8.4 Hz, 1H), 4.38 (s, 2H), 4.15 (d, J=1.8 Hz, 1H), 4.02 (m, 1H), 3.77 (m, 1H), 3.60-3.05 (m, 5H), 2.55-1.90 (m, 6H), 1.90-1.60 (m, 5H), 1.60-1.10 (m, 6H), 1.10-0.90 (m, 2H), 0.95 (t, J=7.2 Hz, 3H).

EXAMPLE 75(2)

(3R)-1-butyl-2,5-dioxo-3-((1R)-1-hydroxy-1-cyclohexylmethyl)-9-(4-(4-fluorophenyloxy)phenylmethyl)-1,4,9-triazaspiro[5.5]undecane.hydrochloride

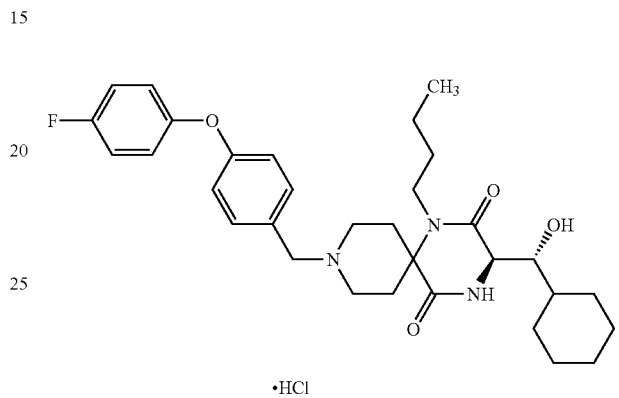

·HCl

TLC: Rf 0.48 (chloroform:methanol=9:1); NMR (CD$_3$OD): δ 7.54-7.48 (m, 2H), 7.14 (dd, J=9.6, 8.1 Hz, 2H), 7.09-7.02 (m, 4H), 4.33 (s, 2H), 4.15 (d, J=2.1 Hz, 1H), 4.00 (m, 1H), 3.73 (m, 1H), 3.57-3.40 (m, 3H), 3.33-3.08 (m, 2H), 2.54-1.88 (m, 6H), 1.82-1.63 (m, 5H), 1.48-1.12 (m, 6H), 1.03-0.85 (m, 2H), 0.95 (t, J=7.2 Hz, 3H).

EXAMPLE 75(3)

(3R)-1-butyl-2,5-dioxo-3-((1R)-1-hydroxy-1-cyclohexylmethyl)-9-(4-(4-chlorophenyloxy)phenylmethyl)-1,4,9-triazaspiro[5.5]undecane.hydrochloride

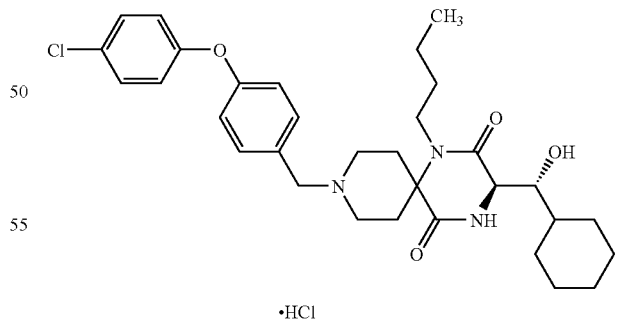

·HCl

TLC: Rf 0.50 (chloroform:methanol=9:1); NMR (CD$_3$OD): δ 7.58-7.51 (m, 2H), 7.38 (d, J=9.3 Hz, 2H), 7.09 (brd, J=8.4 Hz, 2H), 7.02 (d, J=9.3 Hz, 2H), 4.34 (s, 2H), 4.15 (d, J=2.1 Hz, 1H), 3.99 (m, 1H), 3.73 (m, 1H), 3.58-3.40 (m, 3H), 3.32-3.09 (m, 2H), 2.53-1.89 (m, 6H), 1.81-1.62 (m, 5H), 1.48-1.13 (m, 6H), 1.03-0.82 (m, 2H), 0.95 (t, J=7.2 Hz, 3H).

EXAMPLE 75(4)

(3R)-1-butyl-2,5-dioxo-3-((1R)-1-hydroxy-1-cyclo-hexylmethyl)-9-(4-(4-cyanophenyloxy)phenylmethyl)-1,4,9-triazaspiro[5.5]undecane.hydrochloride

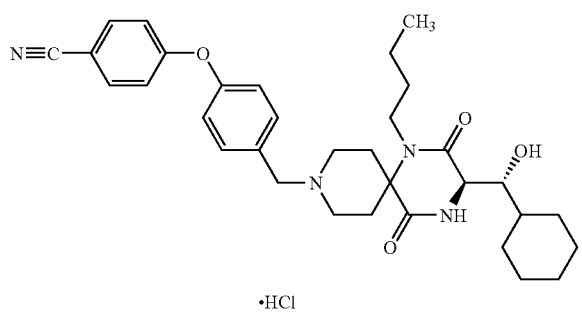

TLC: Rf 0.52 (chloroform:methanol=9:1); NMR (CD$_3$OD):δ 7.74 (d, J=9.0 Hz, 2H), 7.64-7.58 (m, 2H), 7.21 (d, J=8.4 Hz, 2H), 7.13 (d, J=9.0 Hz, 2H), 4.38 (s, 2H), 4.16 (d, J=2.1 Hz, 1H), 4.02 (m, 1H), 3.77 (m, 1H), 3.57-3.43 (m, 3H), 3.33-3.08 (m, 2H), 2.54-1.90 (m, 6H), 1.80-1.63 (m, 5H), 1.48-1.13 (m, 6H), 1.03-0.82 (m, 2H), 0.96 (t, J=7.2 Hz, 3H).

EXAMPLE 75(5)

(3R)-1-butyl-2,5-dioxo-3-((1R)-1-hydroxy-1-cyclo-hexylmethyl)-9-(4-(4-methylsulfonylaminophenyloxy)phenylmethyl)-1,4,9-triazaspiro[5.5]undecane.hydrochlorie

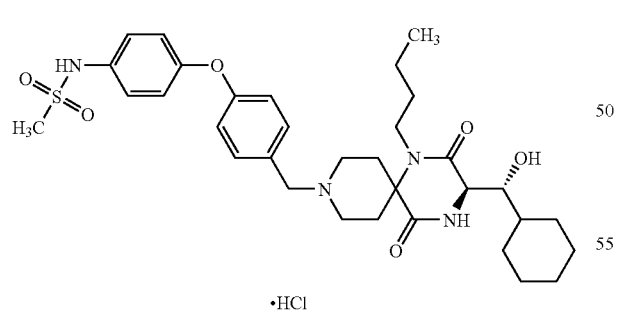

TLC: Rf 0.41 (chloroform:methanol=9:1); NMR (CD$_3$OD):δ 7.53 (d, J=8.7 Hz, 2H), 7.29 (d, J=8.7 Hz, 2H), 7.06 (d, J=8.7 Hz, 2H), 7.03 (d, J=8.7 Hz, 2H), 4.33 (s, 2H), 4.15 (d, J=1.8 Hz, 1H), 3.98 (m, 1H), 3.73 (m, 1H), 3.58-3.40 (m, 3H), 3.32-3.03 (m, 2H), 2.95 (s, 3H), 2.52-2.24 (m, 3H), 2.17-1.88 (m, 3H), 1.80-1.62 (m, 5H), 1.48-1.08 (m, 6H), 1.03-0.82 (m, 2H), 0.95 (t, J=7.2 Hz, 3H).

EXAMPLE 75(6)

(3R)-1-butyl-2,5-dioxo-3-((1R)-1-hydroxy-1-cyclo-hexylmethyl)-9-(4-(6-methylpyridin-3-yloxy)phenylmethyl)-1,4,9-triazaspiro[5.5]undecane.2hydrochloride

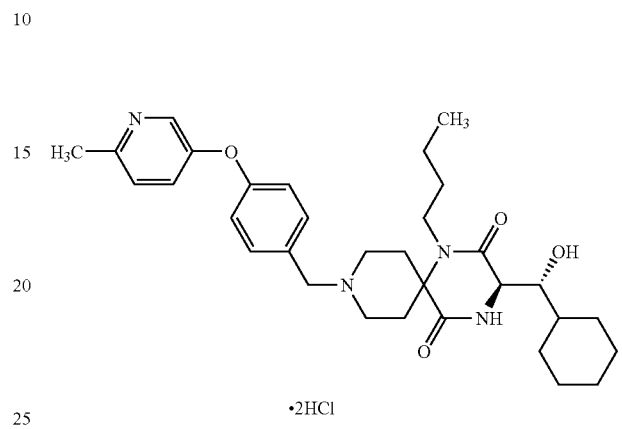

TLC: Rf 0.21 (ethyl acetate:methanol=10:1); NMR (CD$_3$OD):δ 8.54 (d, J=3.0 Hz, 1H), 8.08 (m, 1H), 7.82 (d, J=9.0 Hz, 1H), 7.70 (d, J=9.0 Hz, 2H), 7.28 (d, J=9.0 Hz, 2H), 4.39 (s, 2H), 4.10 (d, J=2.1 Hz, 1H), 4.01 (m, 1H), 3.75 (m, 1H), 3.60-3.20 (m, 5H), 2.73 (s, 3H), 2.70-2.35 (m, 3H), 2.20-1.90 (m, 3H), 1.90-1.60 (m, 5H), 1.50-1.15 (m, 6H), 1.10-0.90 (m, 2H), 0.95 (t, J=7.2 Hz, 3H).

EXAMPLE 75(7)

(3R)-1-butyl-2,5-dioxo-3-((1R)-1-hydroxy-1-cyclo-hexylmethyl)-9-(4-(1-methylethyl)phenylmethyl)-1,4,9-triazaspiro[5.5]undecane.hydrochloride

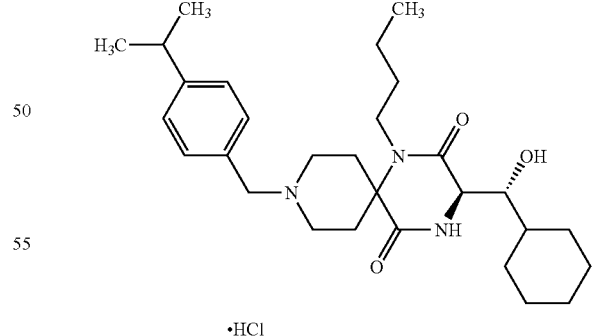

TLC: Rf 0.41 (ethyl acetate:methanol=10:1); NMR (CD$_3$OD):δ 7.45 (d, J=8.1 Hz, 2H), 7.37 (d, J=8.1 Hz, 2H), 4.30 (s, 2H), 4.15 (d, J=2.1 Hz, 1H), 3.98 (m, 1H), 3.72 (m, 1H), 3.60-3.05 (m, 5H), 2.95 (quint, J=6.9 Hz, 1H), 2.50-1.90 (m, 6H), 1.85-1.60 (m, 5H), 1.50-1.10 (m, 6H), 1.25 (d, J=6.9 Hz, 6H), 1.10-0.90 (m, 2H), 0.95 (t, J=6.9 Hz, 3H).

EXAMPLE 75(8)

(3R)-1-butyl-2,5-dioxo-3-((1R)-1-hydroxy-1-cyclohexylmethyl)-9-(4-(4-methylsulfylphenyloxy)phenylmethyl)-1,4,9-triazaspiro[5.5]undecane.hydrochloride

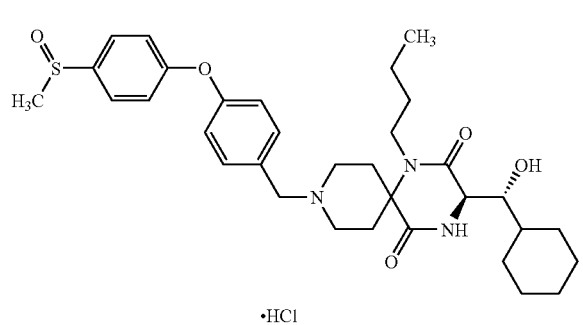

TLC: Rf 0.32 (chloroform:methanol=9:1); NMR (CD$_3$OD):δ 7.74 (d, J=9.0 Hz, 2H), 7.61 (d, J=9.0 Hz, 2H), 7.22 (d, J=9.0 Hz, 2H), 7.17 (d, J=9.0 Hz, 2H), 4.36 (s, 2H), 4.16 (d, J=2.1 Hz, 1H), 4.00 (dt, J=3.6, 12.6 Hz, 1H), 3.75 (dt, J=3.6, 12.6 Hz, 1H), 3.58-3.42 (m, 3H), 3.32-3.13 (m, 2H), 2.80 (s, 3H), 2.54-2.25 (m, 3H), 2.17-1.88 (m, 3H), 1.80-1.63 (m, 5H), 1.49-1.13 (m, 6H), 1.02-0.82 (m, 2H), 0.96 (t, J=7.2 Hz, 3H).

EXAMPLE 75(9)

(3R)-1-butyl-2,5-dioxo-3-((1R)-1-hydroxy-1-cyclohexylmethyl)-9-(4-(3,4,5,6-tetrahydropyran-4-yloxy)phenylmethyl)-1,4,9-triazaspiro[5.5]undecane.hydrochloride

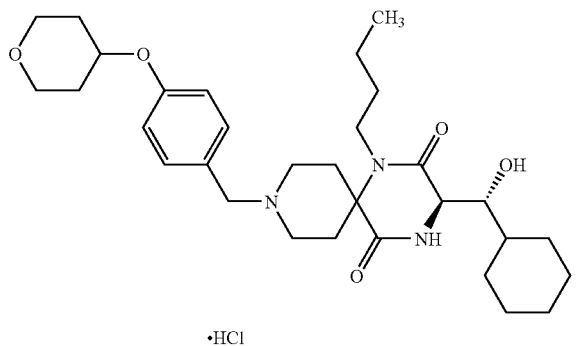

TLC: Rf 0.43 (ethyl acetate:methanol=4:1); NMR (CD$_3$OD):δ 7.45 (d, J=9.0 Hz, 2H), 7.06 (d, J=9.0 Hz, 2H), 4.63 (m, 1H), 4.28 (s, 2H), 4.15 (d, J=2.0 Hz, 1H), 4.01-3.90 (m, 3H), 3.72 (m, 1H), 3.63-3.53 (m, 2H), 3.50-3.41 (m, 3H), 3.27 (m, 1H), 3.15(m, 1H), 2.50-1.91 (m, 8H), 1.68-1.65 (m, 7H), 1.39-1.15 (m, 6H), 1.01-0.87 (m, 5H).

EXAMPLE 75(10)

(3R)-1-butyl-2,5-dioxo-3-((1R)-1-hydroxy-1-cyclohexylmethyl)-9-(4-phenylcarbonylphenylmethyl)-1,4,9-triazaspiro[5.5]undecane.hydrochloride

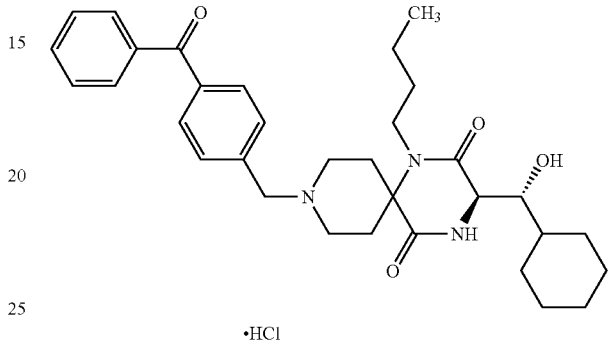

TLC: Rf 0.75 (ethyl acetate:methanol=4:1); NMR (CD$_3$OD):δ 7.87 (d, J=7.5 Hz, 2H), 7.81-7.72 (m, 4H), 7.67 (t, J=7.5 Hz, 1H), 7.54 (t, J=7.5 Hz, 2H), 4.48 (s, 2H), 4.16 (d, J=2.0 Hz, 1H), 4.07 (m, 1H), 3.81 (m, 1H), 3.53-3.47 (m, 3H), 3.33-3.17 (m, 2H), 2.51-2.31 (m, 3H), 2.17-1.92 (m, 3H), 1.76-1.70 (m, 5H), 1.40-1.15 (m, 6H), 1.01-0.87 (m, 5H).

EXAMPLE 75(11)

(3R)-1-butyl-2,5-dioxo-3-((1R)-1-hydroxy-1-cyclohexylmethyl)-9-(4-(1-phenyl-1-hydroxymethyl)phenylmethyl)-1,4,9-triazaspiro[5.5]undecane.hydrochloride

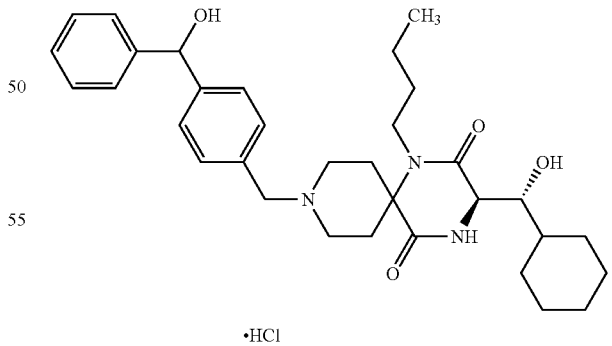

TLC: Rf 0.57 (ethyl acetate:methanol=4:1); NMR (CD$_3$OD):δ 7.53 (d, J=8.0 Hz, 2H), 7.48 (d, J=8.0 Hz, 2H), 7.39-7.20 (m, 5H), 5.81 (s, 1H), 4.33 (s, 2H), 4.14 (d, J=2.0 Hz, 1H), 4.00 (m, 1H), 3.74 (m, 1H), 3.45-3.41 (m, 3H), 3.26 (m, 1H), 3.10 (m, 1H), 2.48-1.91 (m, 6H), 1.80-1.60 (m, 5H), 1.44-1.14 (m, 6H), 1.00-0.86 (m, 5H).

EXAMPLE 75(12)

(3R)-1-butyl-2,5-dioxo-3-((1R)-1-hydroxy-1-cyclohexylmethyl)-9-(3,5-dimethyl-1-(4-(morpholin-4-ylsulfonyl)phenyl)pyrazol-4-ylmethyl)-1,4,9-triazaspiro[5.5]undecane.2hydrochloride

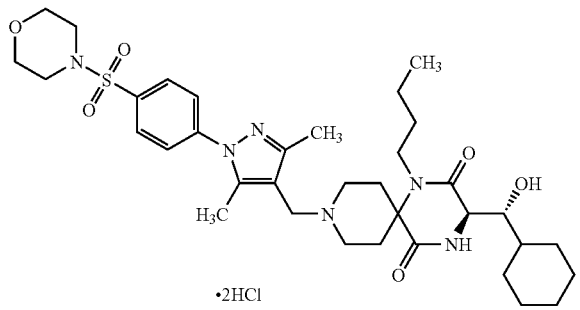

TLC: Rf 0.49 (chloroform:methanol=10:1); NMR (CD$_3$OD):δ 7.95 (d, J=8.7 Hz, 2H), 7.79 (d, J=8.7 Hz, 2H), 4.31 (s, 2H), 4.17 (d, J=2.1 Hz, 1H), 4.04 (m, 1H), 3.79 (m, 1H), 3.75-3.67 (m, 4H), 3.64-3.49 (m, 3H), 3.35-3.18 (m, 2H), 3.05-2.97 (m, 4H), 2.66-2.34 (m, 3H), 2.49 (s, 3H), 2.40 (s, 3H), 2.20-1.87 (m, 3H), 1.84-1.60 (m, 5H), 1.52-1.10 (m, 6H), 1.05-0.80 (m, 2H), 0.96 (t, J=7.2 Hz, 3H).

EXAMPLE 75(13)

(3R)-1-butyl-2,5-dioxo-3-((1R)-1-hydroxy-1-cyclohexylmethyl)-9-(3,5-dimethyl-1-(4-methylaminosulfonylphenyl)pyrazol-4-ylmethyl)-1,4,9-triazaspiro[5.5]undecane.2hydrochloride

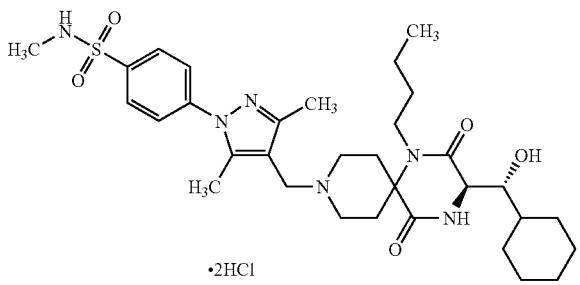

TLC: Rf 0.36 (ethyl acetate:methanol=4:1); NMR (CD$_3$OD):δ 8.01 (d, J=8.7 Hz, 2H), 7.73 (d, J=8.7 Hz, 2H), 4.31 (s, 2H), 4.16 (d, J=2.0 Hz, 1H), 4.05 (m, 1H), 3.80 (m, 1H), 3.63-3.53 (m, 3H), 3.34-3.23 (m, 2H), 2.59-2.34 (m, 3H), 2.57 (s, 3H), 2.46 (s, 3H), 2.39 (s, 3H), 2.16 (m, 1H), 2.05-1.93 (m, 2H), 1.77-1.66 (m, 5H), 1.45-1.17 (m, 6H), 1.01-0.88 (m, 5H).

EXAMPLE 75(14)

(3R)-1-butyl-2,5-dioxo-3-((1R)-1-hydroxy-1-cyclohexylmethyl)-9-(3,5-dimethyl-1-(4-(N-methyl-N-(2-hydroxyethyl)aminosulfonyl)phenyl)pyrazol-4-ylmethyl)-1,4,9-triazaspiro[5.5]undecane.2hydrochloride

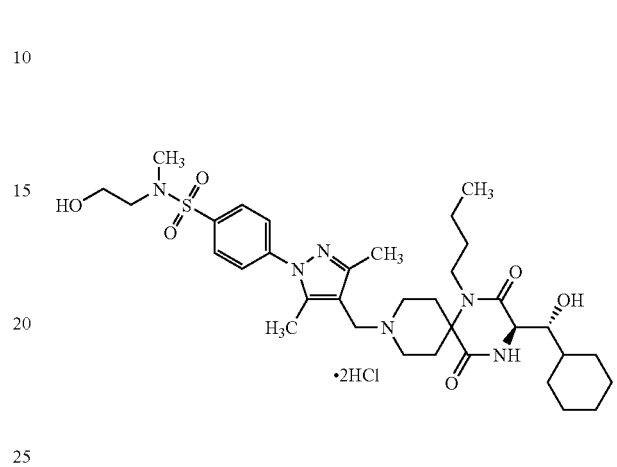

TLC: Rf 0.44 (chloroform:methanol=10:1); NMR (CD$_3$OD):δ 7.98 (d, J=8.7 Hz, 2H), 7.75 (d, J=8.7 Hz, 2H), 4.31 (s, 2H), 4.17 (d, J=2.0 Hz, 1H), 4.04 (m, 1H), 3.78 (m, 1H), 3.69 (t, J=5.7 Hz, 2H), 3.64-3.50 (m, 3H), 3.38-3.24 (m, 2H), 3.19 (t, J=5.7 Hz, 2H), 2.87 (s, 3H), 2.60-2.34 (m, 3H), 2.47 (s, 3H), 2.40 (s, 3H), 2.20-1.88 (m, 3H), 1.82-1.60 (m, 5H), 1.50-1.12 (m, 6H), 1.04-0.82 (m, 5H).

EXAMPLE 75(15)

(3R)-1-butyl-2,5-dioxo-3-((1R)-1-hydroxy-1-cyclohexylmethyl)-9-(3,5-dimethyl-1-(pyridin-2-yl)pyrazol-4-ylmethyl)-1,4,9-triazaspiro[5.5]undecane.2hydrochlorie

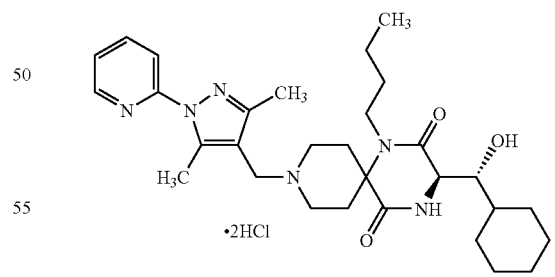

TLC: Rf 0.40 (ethyl acetate:methanol=4:1); NMR (CD$_3$OD):δ 8.51 (d, J=4.5 Hz, 1H), 8.01 (m, 1H), 7.80 (d, J=8.0Hz, 1H), 7.41 (m, 1H), 4.32 (s, 2H), 4.16 (d, J=2.0 Hz, 1H), 4.05 (m, 1H), 3.80 (m, 1H), 3.60-3.49 (m, 3H), 3.33-3.10 (m, 2H), 2.67 (s, 3H), 2.53-2.35 (m, 3H), 2.41 (s, 3H), 2.16 (m, 1H), 2.05-1.93 (m, 2H), 1.80-1.65 (m, 5H), 1.50-1.15 (m, 6H), 1.01-0.88 (m, 5H).

EXAMPLE 75(16)

(3R)-1-butyl-2,5-dioxo-3-((1R)-1-hydroxy-1-cyclohexylmethyl)-9-(3,5-dimethyl-1-cyclohexylpyrazol-4-ylmethyl)-1,4,9-triazaspiro[5.5]undecane.2hydrochloride

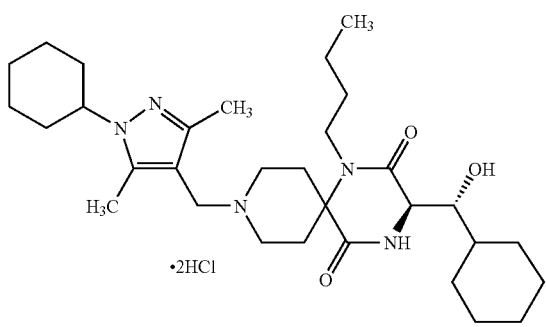

TLC: Rf 0.34 (ethyl acetate:methanol=4:1); NMR (CD$_3$OD):δ 4.32(m, 1H), 4.27 (s, 2H), 4.15 (d, J=2.0 Hz, 1H), 4.00 (m, 1H), 3.73 (m, 1H), 3.60-3.50 (m, 3H), 3.37-3.20 (m, 2H), 2.58-2.40 (m, 9H), 2.13-1.70 (m, 15H), 1.58-1.15 (m, 9H), 1.01-0.88 (m, 5H).

EXAMPLE 75(17)

(3R)-1-butyl-2,5-dioxo-3-((1R)-1-hydroxy-1-cyclohexylmethyl)-9-(1,3,5-trimethylpyrazol-4-ylmethyl)-1,4,9-triazaspiro[5.5]undecane.2hydrochloride

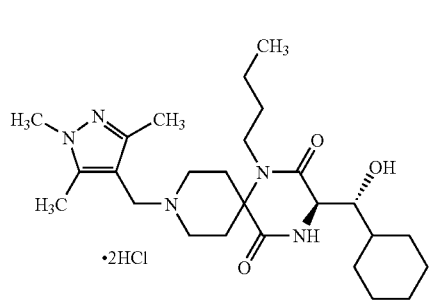

TLC: Rf 0.28 (chloroform:methanol=10:1); NMR (CD$_3$OD):δ 4.27 (s, 2H), 4.15 (d, J=2.1 Hz, 1H), 3.98 (m, 1H), 3.85 (s, 3H), 3.73 (m, 1H), 3.62-3.56 (m, 3H), 3.40-3.20 (m, 2H), 2.60 (m, 1H), 2.50-2.36 (m, 2H), 2.45 (s, 3H), 2.41 (s, 3H), 2.16-1.88 (m, 3H), 1.84-1.60 (m, 5H), 1.50-1.10 (m, 6H), 1.04-0.80 (m, 2H), 0.95 (t, J=7.2 Hz, 3H).

EXAMPLE 75(18)

(3R)-1-butyl-2,5-dioxo-3-((1R)-1-hydroxy-1-cyclohexylmethyl)-9-(3,5-dimethyl-1-(4-(N,N-dimethylaminocarbonyl)phenyl)pyrazol-4-ylmethyl)-1,4,9-triazaspiro[5.5]undecane.2hydrochloride

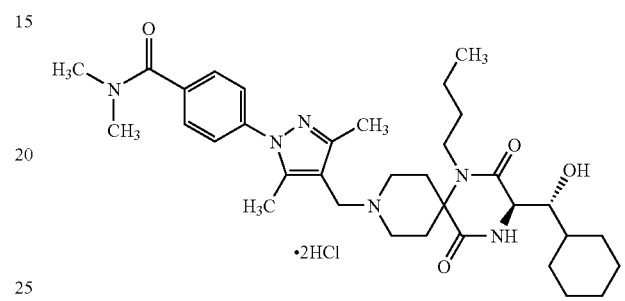

TLC: Rf 0.19 (ethyl acetate:methanol=4:1); NMR (CD$_3$OD):δ 7.62 (d, J=9.0 Hz, 2H), 7.58 (d, J=9.0 Hz, 2H), 4.32 (s, 2H), 4.17 (d, J=2.0 Hz, 1H), 4.05 (m, 1H), 3.80 (m, 1H), 3.60-3.53 (m, 3H), 3.33-3.27 (m, 2H), 3.13 (s, 3H), 3.04 (s, 3H), 2.53-2.35 (m, 3H), 2.42 (s, 3H), 2.39 (s, 3H), 2.17 (m, 1H), 2.05-1.92 (m, 2H), 1.77-1.65 (m, 5H), 1.39-1.15 (m, 6H), 1.01-0.88 (m, 5H).

EXAMPLE 75(19)

(3R)-1-butyl-2,5-dioxo-3-((1R)-1-hydroxy-1-cyclohexylmethyl)-9-(4-(N,N-bismethylsulfonyl)phenylmethyl)-1,4,9-triazaspiro[5.5]undecane.hydrochloride

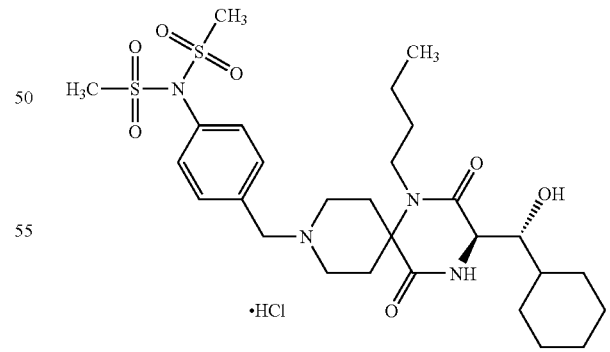

TLC: Rf 0.47 (ethyl acetate:methanol=10:1); NMR (CD$_3$OD):δ 7.69 (d, J=8.4 Hz, 2H), 7.60 (d, J=8.4 Hz, 2H), 4.42 (s, 2H), 4.16 (d, J=2.1 Hz, 1H), 4.06 (m, 1H), 3.80 (m, 1H), 3.60-3.10 (m, 5H), 3.46 (s, 6H), 2.55-1.90 (m, 6H), 1.90-1.60 (m, 5H), 1.50-1.10 (m, 6H), 1.10-0.90 (m, 2H), 0.95 (t, J=6.9 Hz, 3H).

EXAMPLE 75(20)

(3R)-1-butyl-2,5-dioxo-3-((1R)-1-hydroxy-1-cyclohexylmethyl)-9-(3,5-dimethyl-1-(4-methylsulfonylaminophenyl)pyrazol-4-ylmethyl)-1,4,9-triazaspiro[5.5]undecan.2hydrohloride

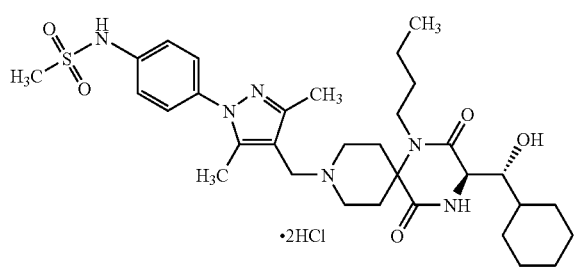

TLC: Rf 0.30 (chloroform:methanol=9:1); NMR (CD$_3$OD):δ 7.48-7.38 (m, 4H), 4.30 (s, 2H), 4.17 (d, J=2.1 Hz, 1H), 4.03 (m, 1H), 3.78 (m, 1H), 3.62-3.49 (m, 3H), 3.37-3.21 (m, 2H), 3.04 (s, 3H), 2.62-2.35 (m, 3H), 2.40 (s, 3H), 2.38 (s, 3H), 2.18-1.90 (m, 3H), 1.83-1.63 (m, 5H), 1.48-1.13 (m, 6H), 1.03-0.82 (m, 2H), 0.96 (t, J=7.2 Hz, 3H).

EXAMPLE 75(21)

(3R)-1-butyl-2,5-dioxo-3-((1R)-1-hydroxy-1-cyclohexylmethyl)-9-(3,5-dimethyl-1-(4-(N,N-dimethylsulfonyl)phenyl)pyrazol-4-ylmethyl)-1,4,9-triazaspiro[5.5]undecane.2hydrochloride

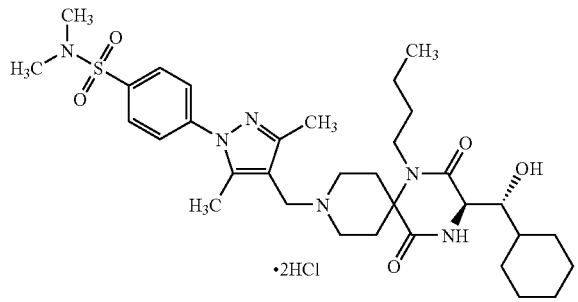

TLC: Rf 0.36 (chloroform:methanol=9:1); NMR (CD$_3$OD):δ 7.96 (d, J=8.7 Hz, 2H), 7.77 (d, J=8.7 Hz, 2H), 4.32 (s, 2H), 4.17 (d, J=2.1 Hz, 1H), 4.05 (m, 1H), 3.79 (m, 1H), 3.63-3.48 (m, 3H), 3.34-3.15 (m, 2H), 2.74 (s, 6H), 2.58-2.32 (m, 3H), 2.47 (s, 3H), 2.40 (s, 3H), 2.21-1.90 (m, 3H), 1.82-1.62 (m, 5H), 1.48-1.13 (m, 6H), 1.03-0.82 (m, 2H), 0.96 (t, J=7.2 Hz, 3H).

EXAMPLE 75(22)

(3R)-1-butyl-2,5-dioxo-3-((1R)-1-hydroxy-1-cyclohexylmethyl)-9-(3,5-dimethyl-1-(4-(pyrrolidin-1-ylcarbonyl)phenyl)pyrazol-4-ylmethyl)-1,4,9-triazaspiro[5.5]undecane.2hydrochloride

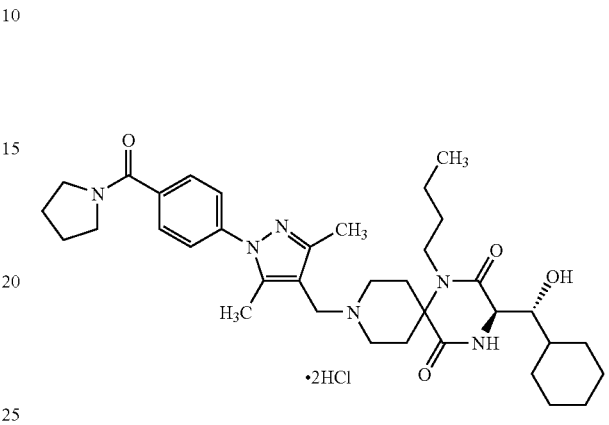

TLC: Rf 0.38 (chloroform:methanol=9:1); NMR (CD$_3$OD):δ 7.72 (d, J=8.7 Hz, 2H), 7.59 (d, J=8.7 Hz, 2H), 4.31 (s, 2H), 4.17 (d, J=2.4 Hz, 1H), 4.04 (m, 1H), 3.78 (m, 1H), 3.65-3.47 (m, 3H), 3.62 (t, J=6.6 Hz, 2H), 3.50 (t, J=6.6 Hz, 2H), 3.33-3.18 (m, 2H), 2.60-2.32 (m, 3H), 2.43 (s, 3H), 2.39 (s, 3H), 2.20-1.87 (m, 7H), 1.82-1.62 (m, 5H), 1.48-1.13 (m, 6H), 1.03-0.82 (m, 2H), 0.96 (t, J=7.2 Hz, 3H).

EXAMPLE 75(23)

(3R)-1-butyl-2,5-dioxo-3-((1R)-1-hydroxy-1-cyclohexylmethyl)-9-(3,5-dimethyl-1-(4-(morpholin-4-ylcarbonyl)phenyl)pyrazol-4-ylmethyl)-1,4,9-triazaspiro[5.5]undecane.2hydrochloride

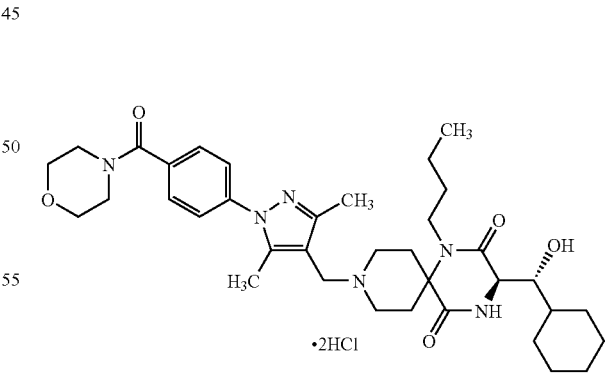

TLC: Rf 0.38 (chloroform:methanol=9:1); NMR (CD$_3$OD):δ 7.65-7.57 (m, 4H), 4.31 (s, 2H), 4.17 (d, J=2.4 Hz, 1H), 4.04 (m, 1H), 3.85-3.46 (m, 12H), 3.34-3.17 (m, 2H), 2.60-2.32 (m, 3H), 2.43 (s, 3H), 2.39 (s, 3H), 2.20-1.90 (m, 3H), 1.82-1.62 (m, 5H), 1.48-1.13 (m, 6H), 1.03-0.82 (m, 2H), 0.96 (t, J=7.2 Hz, 3H).

EXAMPLE 75(24)

(3R)-1-butyl-2,5-dioxo-3-((1R)-1-hydroxy-1-cyclohexylmethyl)-9-(4-aminocarbonylphenylmethyl)-1,4,9-triazaspiro[5.5]undecane.hydrochloride

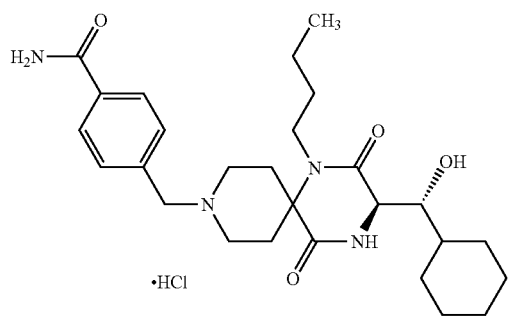

TLC: Rf 0.40 (ethyl acetate:methanol=3:1); NMR (CD$_3$OD):δ 7.99 (d, J=8.4 Hz, 2H), 7.70 (d, J=8.4 Hz, 2H), 4.44 (s, 2H), 4.16 (d, J=2.1 Hz, 1H), 4.04 (m, 1H), 3.78 (m, 1H), 3.60-3.38 (m, 3H), 3.30-3.08 (m, 2H), 2.60-2.24 (m, 3H), 2.20-1.86 (m, 3H), 1.82-1.58 (m, 5H), 1.50-1.06 (m, 6H), 1.04-0.80 (m, 2H), 0.96 (t, J=7.2 Hz, 3H).

EXAMPLE 75(25)

(3R)-1-butyl-2,5-dioxo-3-((1R)-1-hydroxy-1-cyclohexylmethyl)-9-(4-(4-aminocarbonylphenyloxy)phenylmethyl)-1,4,9-triazaspiro[5.5]undecane.hydrochloride

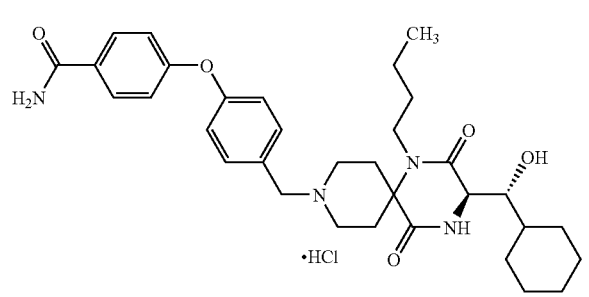

TLC: Rf 0.25 (chloroform:methanol=10:1); NMR (CD$_3$OD):δ 7.90 (d, J=8.7 Hz, 2H), 7.57 (d, J=8.7 Hz, 2H), 7.16 (d, J=8.7 Hz, 2H), 7.07 (d, J=8.7 Hz, 2H), 4.36 (s, 2H), 4.15 (d, J=2.1 Hz, 1H), 4.02 (m, 1H), 3.76 (m, 1H), 3.56-3.42 (m, 3H), 3.33-2.99 (m, 2H), 2.54-1.88 (m, 6H), 1.81-1.60 (m, 5H), 1.48-1.12 (m, 6H), 1.04-0.81 (m, 5H).

EXAMPLE 75(26)

(3R)-1-butyl-2,5-dioxo-3-((1R)-1-hydroxy-1-cyclohexylmethyl)-9-(4-(4-aminosulfonylphenyloxy)phenylmethyl)-1,4,9-triazaspiro[5.5]undecane.hydrochloride

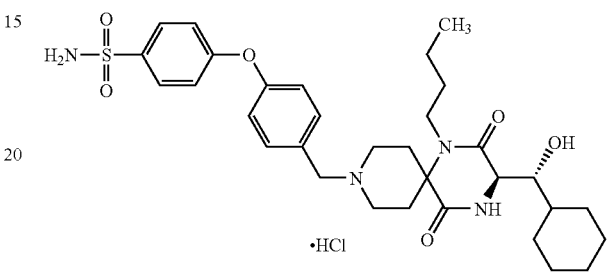

TLC: Rf 0.28 (chloroform:methanol=10:1); NMR (CD$_3$OD):δ 7.89 (d, J=8.7 Hz, 2H), 7.61 (d, J=8.7 Hz, 2H), 7.17 (d, J=8.7 Hz, 2H), 7.13 (d, J=8.7 Hz, 2H), 4.36 (s, 2H), 4.15 (d, J=2.1 Hz, 1H), 4.01 (m, 1H), 3.75 (m, 1H), 3.58-3.42 (m, 3H), 3.32-3.14 (m, 2H), 2.55-2.40 (m, 2H), 2.32 (m, 1H), 2.13 (m, 1H), 2.07-1.89 (m, 2H), 1.82-1.60 (m, 5H), 1.50-1.12 (m, 6H), 1.06-0.80 (m, 5H).

EXAMPLE 75(27)

(3R)-1-butyl-2,5-dioxo-3-((1R)-1-hydroxy-1-cyclohexylmethyl)-9-(4-(6-methylpyridin-1-oxido-3-yloxy)phenylmethyl)-1,4,9-triazaspiro[5.5]undecane.hydrochloride

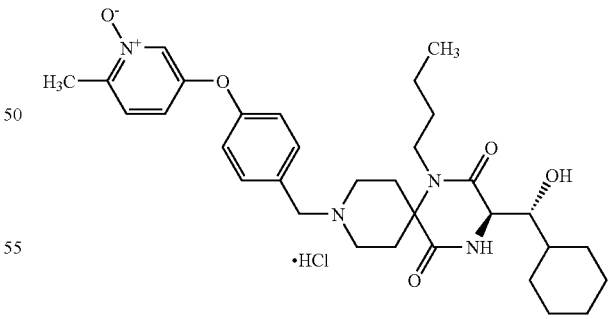

TLC: Rf 0.62 (chloroform:methanol=5:1); NMR (CD$_3$OD):δ 8.51 (s, 1H), 7.80-7.56 (m, 2H), 7.72 (d, J=8.7 Hz, 2H), 7.29 (d, J=8.7 Hz, 2H), 4.39 (s, 2H), 4.16 (d, J=2.1 Hz, 1H), 4.00 (m, 1H), 3.78 (m, 1H), 3.62-3.40 (m, 3H), 3.36-3.18 (m, 2H), 2.64-2.30 (m, 3H), 2.63 (s, 3H), 2.20-1.86 (m, 3H), 1.84-1.58 (m, 5H), 1.52-1.08 (m, 6H), 1.04-0.82 (m, 2H), 0.96 (t, J=7.2 Hz, 3H).

EXAMPLE 75(28)

(3R)-1-butyl-2,5-dioxo-3-((1R)-1-hydroxy-1-cyclohexylmethyl)-9-(4-(4-hydroxyphenyloxy)phenylmethyl)-1,4,9-triazaspiro[5.5]undecane.hydrochloride

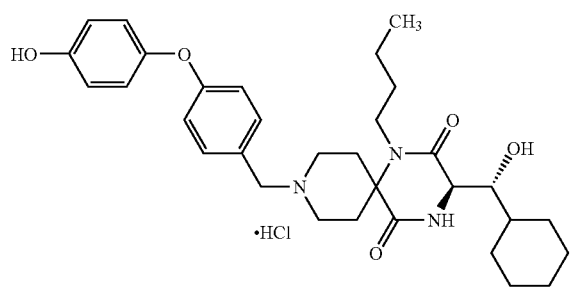

TLC: Rf 0.35 (chloroform:methanol=10:1); NMR (CD$_3$OD):δ 7.46 (d, J=9.0 Hz, 2H), 6.97 (d, J=9.0 Hz, 2H), 6.88 (d, J=9.0 Hz, 2H), 6.80 (d, J=9.0 Hz, 2H), 4.30 (s, 2H), 4.15 (d, J=2.1 Hz, 1H), 3.98 (m, 1H), 3.72 (m, 1H), 3.67-3.39 (m, 3H), 3.27 (m, 1H), 3.15 (m, 1H), 2.53-2.35 (m, 2H), 2.26 (m, 1H), 2.18-1.87 (m, 3H), 1.84-1.60 (m, 5H), 1.51-1.05 (m, 6H), 1.04-0.80 (m, 2H), 0.95 (t, J=7.2 Hz, 3H).

EXAMPLE 75(29)

(3R)-1-butyl-2,5-dioxo-3-((1R)-1-hydroxy-1-cyclohexylmethyl)-9-(3,5-dimethyl-1-(4-hydroxyphenyl)pyrazol-4-ylmethyl)-1,4,9-triazaspiro[5.5]undecane.2hydrochloride

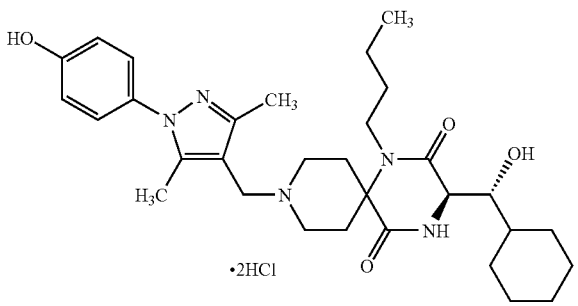

TLC: Rf 0.25 (chloroform:methanol=10:1); NMR (CD$_3$OD):δ 7.34 (d, J=8.7 Hz, 2H), 6.96 (d, J=8.7 Hz, 2H), 4.34 (s, 2H), 4.16 (d, J=2.1 Hz, 1H), 4.04 (m, 1H), 3.79 (m, 1H), 3.65-3.50 (m, 3H), 3.32 (m, 1H), 3.29 (m, 1H), 2.64 (m, 1H), 2.55-2.42 (m, 2H), 2.48 (s, 3H), 2.38 (s, 3H), 2.20-1.88 (m, 3H), 1.83-1.60 (m, 5H), 1.52-1.05 (m, 6H), 1.04-0.81 (m, 2H), 0.96 (t, J=6.9 Hz, 3H).

EXAMPLE 75(30)

(3R)-1-butyl-2,5-dioxo-3-((1R)-1-hydroxy-1-cyclohexylmethyl)-9-(3,5-dimethyl-1-(4-(2-hydroxyethylaminosulfonyl)phenyl)pyrazol-4-ylmethyl)-1,4,9-triazaspiro[5.5]undecane.2hydrochloride

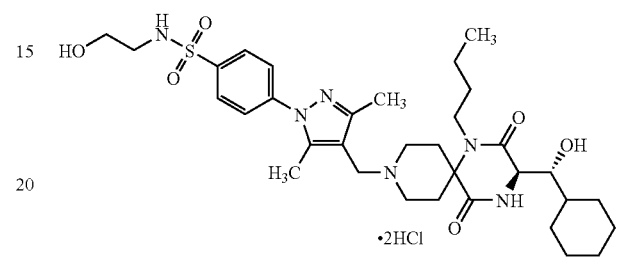

TLC: Rf 0.32 (chloroform:methanol=10:1); NMR (CD$_3$OD):δ 8.03 (d, J=8.7 Hz, 2H), 7.71 (d, J=8.7 Hz, 2H), 4.32 (s, 2H), 4.17 (d, J=2.1 Hz, 1H), 4.06 (m, 1H), 3.80 (m, 1H), 3.62-3.48 (m, 5H), 3.38-3.18 (m, 2H), 3.01 (t, J=5.7 Hz, 2H), 2.58-2.30 (m, 3H), 2.46 (s, 3H), 2.39 (s, 3H), 2.20-1.88 (m, 3H), 1.82-1.62 (m, 5H), 1.50-1.10 (m, 6H), 1.02-0.82 (m, 5H).

EXAMPLE 75(31)

(3R)-1-butyl-2,5-dioxo-3-((1R)-1-hydroxy-1-cyclohexylmethyl)-9-(3,5-dimethyl-1-(4-(pyrrolidin-1-ylsulfonyl)phenyl)pyrazol-4-ylmethyl)-1,4,9-triazaspiro[5.5]undecane.2hydrochloride

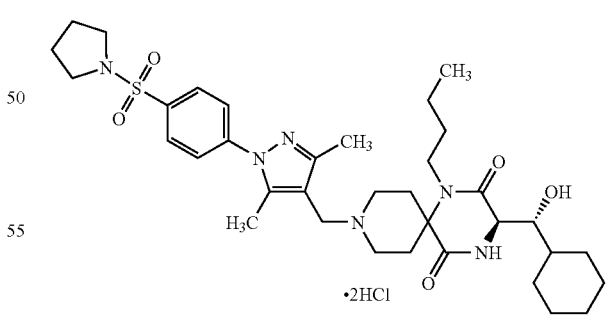

TLC: Rf 0.59 (chloroform:methanol=10:1); NMR (CD$_3$OD):δ 8.01 (d, J=8.7 Hz, 2H), 7.75 (d, J=8.7 Hz, 2H), 4.32 (s, 2H), 4.17 (d, J=2.4 Hz, 1H), 4.06 (m, 1H), 3.80 (m, 1H), 3.62-3.48 (m, 3H), 3.38-3.18 (m, 6H), 2.60-2.30 (m, 3H), 2.47 (s, 3H), 2.39 (s, 3H), 2.20-1.88 (m, 3H), 1.82-1.60 (m, 9H), 1.50-1.10 (m, 6H), 1.02-0.82 (m, 5H).

EXAMPLE 75(32)

(3R)-1-butyl-2,5-dioxo-3-((1R)-1-hydroxy-1-cyclohexylmethyl)-9-(5-chloro-3-methyl-1-phenylpyrazol-4-ylmethyl)-1,4,9-triazaspiro[5.5]undecane.2hydrochloride

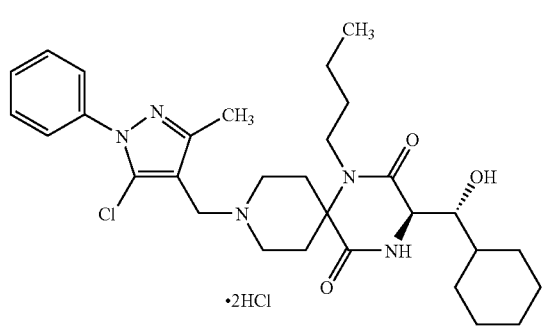

TLC: Rf 0.52 (chloroform:methanol=10:1); NMR (CD$_3$OD):δ 7.62-7.46 (m, 5H), 4.34 (s, 2H), 4.17 (d, J=1.8 Hz, 1H), 4.10 (m, 1H), 3.83 (m, 1H), 3.66-3.47 (m, 3H), 3.39-3.13 (m, 2H), 2.60-2.28 (m, 3H), 2.44 (s, 3H), 2.18 (m, 1H), 2.09-1.88 (m, 2H), 1.85-1.62 (m, 5H), 1.54-1.13 (m, 6H), 1.03-0.81 (m, 2H), 0.97 (t, J=7.2 Hz, 3H).

EXAMPLE 75(33)

(3R)-1-butyl-2,5-dioxo-3-((1R)-1-hydroxy-1-cyclohexylmethyl)-9-(4-(4-methoxyphenyloxy)phenylmethyl)-1,4,9-triazaspiro[5.5]undecane.hydrochloride

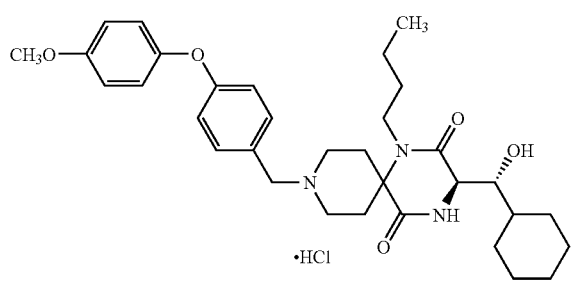

TLC: Rf 0.50 (chloroform:methanol=10:1); NMR (CD$_3$OD):δ 7.49 (d, J=8.7 Hz, 2H), 6.98 (d, J=8.7 Hz, 2H), 7.02-6.92 (m, 4H), 4.30 (s, 2H), 4.15 (d, J=2.1 Hz, 1H), 3.97 (m, 1H), 3.79 (s, 3H), 3.72 (m, 1H), 3.58-3.38 (m, 3H), 3.30-3.13 (m, 2H), 2.55-2.40 (m, 2H), 2.32 (m, 1H), 2.16-1.86 (m, 3H), 1.81-1.60 (m, 5H), 1.50-1.10 (m, 6H), 1.03-0.80 (m, 2H), 0.95 (t, J=7.2 Hz, 3H).

EXAMPLE 75(34)

(3R)-1-butyl-2,5-dioxo-3-((1R)-1-hydroxy-1-cyclohexylmethyl)-9-(4-(3-methoxyphenyloxy)phenylmethyl)-1,4,9-triazaspiro[5.5]undecane.hydrochloride

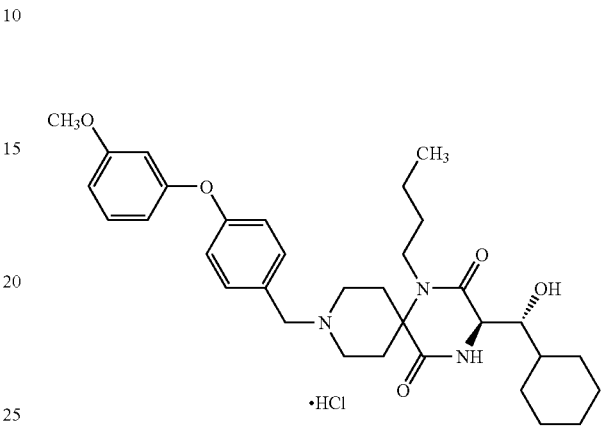

TLC: Rf 0.50 (chloroform:methanol=10:1); NMR (CD$_3$OD):δ 7.54 (d, J=8.7 Hz, 2H), 7.28 (m, 1H), 7.70 (d, J=8.7 Hz, 2H), 6.75 (ddd, J=8.7, 2.1, 1.2 Hz, 1H), 6.63-6.56 (m, 2H), 4.33 (s, 2H), 4.15 (d, J=2.1 Hz, 1H), 3.98 (m, 1H), 3.77 (s, 3H), 3.75 (m, 1H), 3.58-3.40 (m, 3H), 3.30-3.11 (m, 2H), 2.55-2.23 (m, 3H), 2.17-1.88 (m, 3H), 1.81-1.59 (m, 5H), 1.50-1.06 (m, 6H), 1.03-0.80 (m, 2H), 0.95 (t, J=7.2 Hz, 3H).

EXAMPLE 75(35)

(3R)-1-butyl-2,5-dioxo-3-((1R)-1-hydroxy-1-cyclohexylmethyl)-9-(4-(N,N-dimethylaminocarbonyl)phenylmethyl)-1,4,9-triazaspiro[5.5]undecane.hydrochloride

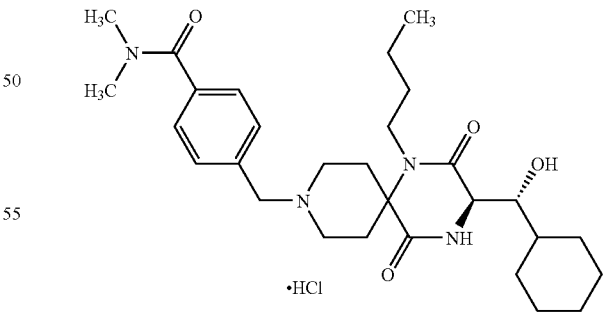

TLC: Rf 0.43 (chloroform:methanol=10:1); NMR (CD$_3$OD):δ 7.66 (d, J=8.4 Hz, 2H), 7.55 (d, J=8.4 Hz, 2H), 4.41 (s, 2H), 4.15 (d, J=1.8 Hz, 1H), 4.04 (m, 1H), 3.78 (m, 1H), 3.59-3.42 (m, 3H), 3.30-3.10 (m, 2H), 3.11 (s, 3H), 2.99 (s, 3H), 2.53-2.20 (m, 3H), 2.14 (m, 1H), 2.08-1.88 (m, 2H), 1.83-1.60 (m, 5H), 1.52-1.10 (m, 6H), 1.06-0.80 (m, 2H), 0.95 (t, J=7.2 Hz, 3H).

EXAMPLE 75(36)

(3R)-1-butyl-2,5-dioxo-3-((1R)-1-hydroxy-1-cyclohexylmethyl)-9-(3,5-dimethyl-1-phenylpyrazol-4-ylmethyl)-1,4,9-triazaspiro[5.5]undecane.2hydrochloride

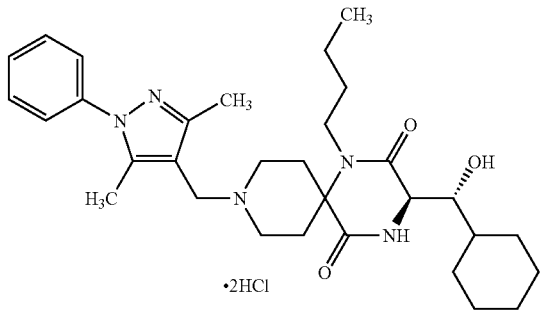

TLC: Rf 0.48 (chloroform:methanol=10:1); NMR (CD$_3$OD):δ 7.63-7.43 (m, 5H), 4.32 (s, 2H), 4.17 (d, J=2.1 Hz, 1H), 4.04 (m, 1H), 3.79 (m, 1H), 3.64-3.49 (m, 3H), 3.30-3.20 (m, 2H), 2.70-2.30 (m, 9H), 2.20-1.88 (m, 3H), 1.83-1.58 (m, 5H), 1.52-1.06 (m, 6H), 1.06-0.80 (m, 2H), 0.96 (t, J=7.2 Hz, 3H).

EXAMPLE 75(37)

(3R)-1-butyl-2,5-dioxo-3-((1R)-1-hydroxy-1-cyclohexylmethyl)-9-(3,5-dimethyl-1-(4-methylphenyl)pyrazol-4-ylmethyl)-1,4,9-triazaspiro[5.5]undecane.2hydrochloride

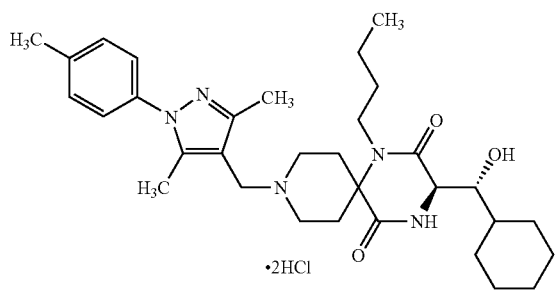

TLC: Rf 0.48 (chloroform:methanol=10:1); NMR (CD$_3$OD):δ 7.37 (d, J=8.7 Hz, 2H), 7.34 (d, J=8.7 Hz, 2H), 4.30 (s, 2H), 4.17 (d, J=2.1 Hz, 1H), 4.04 (m, 1H), 3.79 (m, 1H), 3.63-3.47 (m, 3H), 3.35-3.06 (m, 2H), 2.63-2.26 (m, 3H), 2.43 (s, 3H), 2.38 (s, 3H), 2.35 (s, 3H), 2.16 (m, 1H), 2.09-1.88 (m, 2H), 1.83-1.60 (m, 5H), 1.55-1.10 (m, 6H), 1.08-0.80 (m, 2H), 0.96 (t, J=7.2 Hz, 3H).

EXAMPLE 75(38)

(3R)-1-butyl-2,5-dioxo-3-((1R)-1-hydroxy-1-cyclohexylmethyl)-9-(3,5-dimethyl-1-(4-fluorophenyl)pyrazol-4-ylmethyl)-1,4,9-triazaspiro[5.5]undecane.2hydrochloride

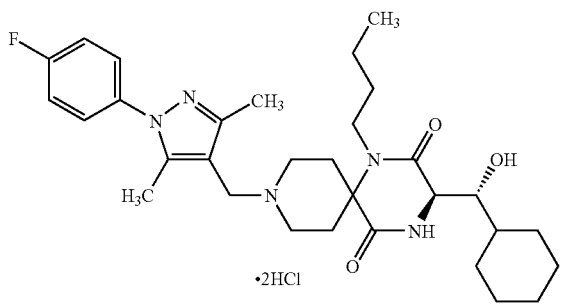

TLC: Rf 0.49 (chloroform:methanol=10:1); NMR (CD$_3$OD):δ 7.50 (dd, J=8.4, 4.8 Hz, 2H), 7.30 (dd, J=8.4, 8.4 Hz, 2H), 4.30 (s, 2H), 4.17 (d, J=2.1 Hz, 1H), 4.04 (m, 1H), 3.78 (m, 1H), 3.63-3.45 (m, 3H), 3.30-3.12 (m, 2H), 2.61-2.30 (m, 3H), 2.37 (s, 3H), 2.36 (s, 3H), 2.16 (m, 1H), 2.08-1.88 (m, 2H), 1.82-1.60 (m, 5H), 1.52-1.07 (m, 6H), 1.04-0.80 (m, 2H), 0.96 (t, J=7.2 Hz, 3H).

EXAMPLE 75(39)

(3R)-1-butyl-2,5-dioxo-3-((1R)-1-hydroxy-1-cyclohexylmethyl)-9-(6-(4-methoxyphenyloxy)pyridin-3-ylmethyl)-1,4,9-triazaspiro[5.5]undecane.hydrochloride

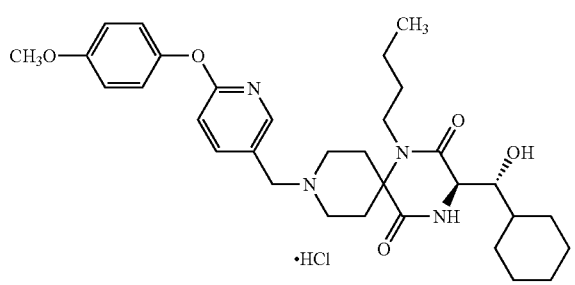

TLC: Rf 0.38 (chloroform:methanol=10:1); NMR (CD$_3$OD):δ 8.36 (m, 1H), 8.12 (m, 1H), 7.12-6.98 (m, 5H), 4.39 (s, 2H), 4.15 (d, J=2.1 Hz, 1H), 4.00 (m, 1H), 3.81 (s, 3H), 3.74 (m, 1H), 3.60-3.42 (m, 3H), 3.30-3.16 (m, 2H), 2.58-2.30 (m, 3H), 2.16-1.86 (m, 3H), 1.80-1.62 (m, 5H), 1.50-1.10 (m, 6H), 1.02-0.80 (m, 5H).

EXAMPLE 75(40)

(3R)-1-butyl-2,5-dioxo-3-((1R)-1-hydroxy-1-cyclohexylmethyl)-9-(4-(4-methylsulfonylphenyloxy)phenylmethyl)-1,4,9-triazaspiro[5.5]undecane.hydrochloride

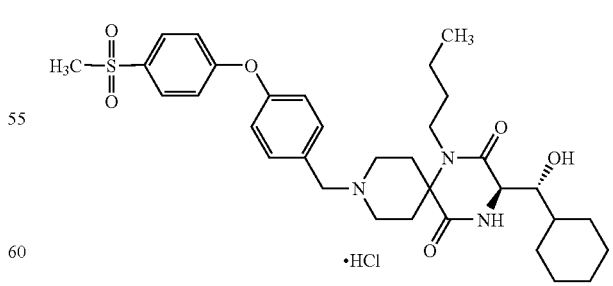

TLC: Rf 0.46 (chloroform:methanol=10:1); NMR (CD$_3$OD):δ 7.95 (d, J=9.0 Hz, 2H), 7.65 (d, J=8.4 Hz, 2H), 7.25-7.16 (m, 4H), 4.38 (s, 2H), 4.15 (d, J=2.4 Hz, 1H), 4.02 (m, 1H), 3.76 (m, 1H), 3.60-3.44 (m, 3H), 3.30-3.10 (m, 2H), 3.11 (s, 3H), 2.54-2.26 (m, 3H), 2.18-1.88 (m, 3H), 1.82-1.62 (m, 5H), 1.50-1.10 (m, 6H), 1.02-0.82 (m, 5H).

EXAMPLE 75(41)

(3R)-1-butyl-2,5-dioxo-3-((1R)-1-hydroxy-1-cyclo-hexylmethyl)-9-(4-(4-(2-(N,N-dimethylamino)ethylaminocarbonyl)phenyloxy)phenylmethyl)-1,4,9-triazaspiro[5.5]undecane.hydrochloride

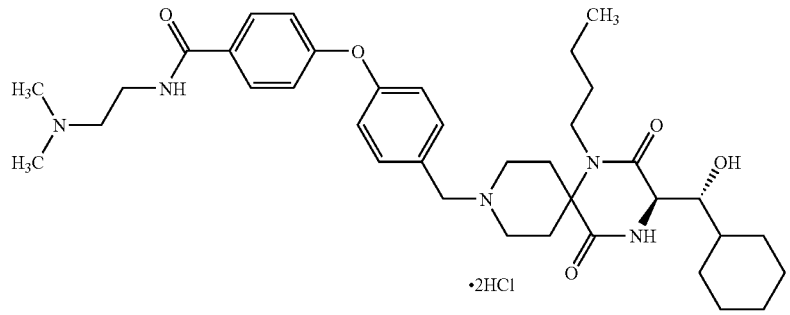

TLC: Rf 0.15 (chloroform:methanol=5:1); NMR (CD$_3$OD):δ 7.93 (d, J=9.0 Hz, 2H), 7.62 (d, J=8.4 Hz, 2H), 7.20-7.08 (m, 4H), 3.98 (s, 2H), 4.16 (d, J=2.1 Hz, 1H), 3.98 (m, 1H), 3.75 (m, 1H), 3.75 (t, J=5.4 Hz, 2H), 3.58-3.42 (m, 3H), 3.38 (t, J=5.4 Hz, 2H), 3.30-3.18 (m, 2H), 2.98 (s, 6H), 2.56-2.28 (m, 3H), 2.18-1.88 (m, 3H), 1.82-1.62 (m, 5H), 1.46-1.14 (m, 6H), 1.02-0.84 (m, 5H).

TLC: Rf 0.46 (chloroform:methanol=10:1); NMR (CD$_3$OD):δ 8.01 (d, J=8.7 Hz, 2H), 7.60 (d, J=8.7 Hz, 2H), 4.31 (s, 2H), 4.17 (d, J=2.4 Hz, 1H), 4.04 (m, 1H), 3.80 (m, 1H), 3.73 (t, J=6.0 Hz, 2H), 3.72-3.48 (m, 5H), 3.30-3.16 (m, 2H), 2.60-2.30 (m, 3H), 2.43 (s, 3H), 2.39 (s, 3H), 2.22-1.88 (m, 3H), 1.80-1.62 (m, 5H), 1.50-1.12 (m, 6H), 1.06-0.82 (m, 5H).

EXAMPLE 75(42)

(3R)-1-butyl-2,5-dioxo-3-((1R)-1-hydroxy-1-cyclo-hexylmethyl)-9-(3,5-dimethyl-1-(4-(2-hydroxyethy-laminocarbonyl)phenyl)pyrazol-4-ylmethyl)-1,4,9-triazaspiro[5.5]undecane.2hydrochloride

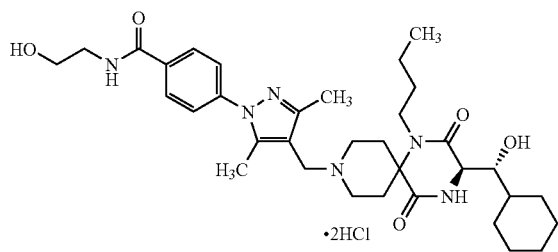

EXAMPLE 75(43)

(3R)-1-butyl-2,5-dioxo-3-((1R)-1-hydroxy-1-cyclo-hexylmethyl)-9-(3,5-dimethyl-1-(4-(2-(N,N-dim-ethylamino)ethylaminocarbonyl)phenyl)pyrazol-4-ylmethyl)-1,4,9-triazaspiro[5.5]undecane.3hydrochloride

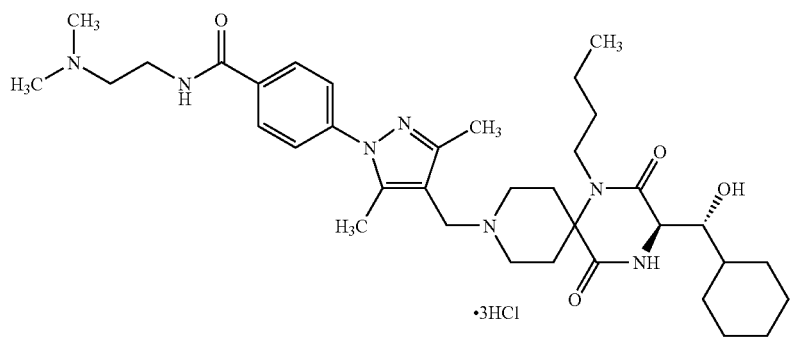

TLC: Rf 0.14 (chloroform:methanol:28% aqueous solution of ammonia=200:20:1); NMR (CD$_3$OD):δ 8.07 (d, J=8.7 Hz, 2H), 7.64 (d, J=8.7 Hz, 2H), 4.31 (s, 2H), 4.17 (d, J=2.1 Hz, 1H), 4.04 (m, 1H), 3.79 (t, J=5.7 Hz, 2H), 3.78 (m, 1H), 3.63-3.49 (m, 3H), 3.41 (t, J=5.7 Hz, 2H), 3.32-3.20 (m, 2H), 3.00 (s, 6H), 2.63-2.35 (m, 3H), 2.45 (s, 3H), 2.39 (s, 3H), 2.20-1.90 (m, 3H), 1.82-1.63 (m, 5H), 1.48-1.13 (m, 6H), 1.03-0.82 (m, 2H), 0.96 (t, J=7.2 Hz, 3H).

EXAMPLE 75(44)

(3R)-1-butyl-2,5-dioxo-3-((1R)-1-hydroxy-1-cyclohexylmethyl)-9-(3,5-dimethyl-1-(4-(2-(morpholin-4-yl)ethylaminosulfonyl)phenyl)pyrazol-4-ylmethyl)-1,4,9-triazaspiro[5.5]undecane.3hydrochloride TLC: Rf 0.31 (chloroform:methanol=10:1); NMR (CD$_3$OD):δ 7.58 (d, J=8.4 Hz, 2H), 7.48 (d, J=8.7 Hz, 2H), 7.18-7.06 (m, 4H), 4.36 (s, 2H), 4.16 (d, J=2.4 Hz, 1H), 4.00 (m, 1H), 3.82-3.40 (m, 12H), 3.38-3.12 (m, 2H), 2.52-2.24 (m, 3H), 2.18-1.86 (m, 3H), 1.82-1.62 (m, 5H), 1.50-1.10 (m, 6H), 1.02-0.82 (m, 5H).

EXAMPLE 75(46)

(3R)-1-butyl-2,5-dioxo-3-((1R)-1-hydroxy-1-cyclohexylmethyl)-9-(1,4-benzodioxan-6-ylmethyl)-1,4,9-triazaspiro[5.5]undecane.hydrochloride TLC: Rf 0.38 (chloroform:methanol=10:1); NMR (CD$_3$OD):δ 7.05 (d, J=2.1 Hz, 1H), 7.00-6.90 (m, 2H), 4.26 (s, 4H), 4.23 (s, 2H), 4.15 (d, J=1.8 Hz, 1H), 3.94 (m, 1H), 3.68 (m, 1H), 3.58-3.34 (m, 3H), 3.30-3.08 (m, 2H), 2.50-1.86 (m, 6H), 1.80-1.62 (m, 5H), 1.50-1.04 (m, 6H), 1.02-0.82 (m, 5H).

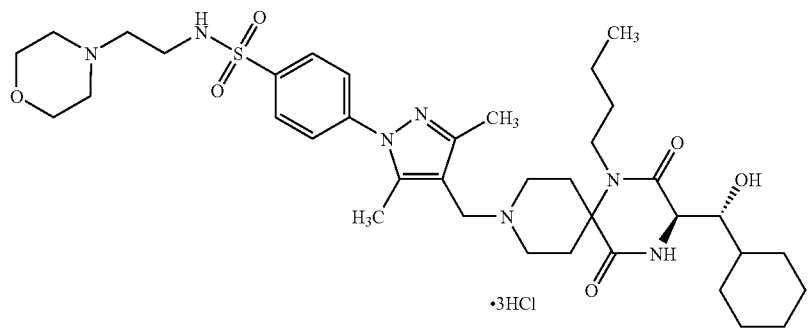

TLC: Rf 0.42 (chloroform:methanol=10:1); NMR (CD$_3$OD):δ 8.07 (d, J=9.0 Hz, 2H), 7.77 (d, J=9.0 Hz, 2H), 4.30 (s, 2H), 4.17 (d, J=2.4 Hz, 1H), 4.12-3.96 (m, 3H), 3.90-3.70 (m, 4H), 3.62-3.48 (m, 6H), 3.20-3.16 (m, 6H), 2.70-2.30 (m, 3H), 2.49 (s, 3H), 2.41 (s, 3H), 2.20-1.88 (m, 3H), 1.82-1.62 (m, 5H), 1.50-1.10 (m, 6H), 1.04-0.84 (m, 5H).

EXAMPLE 75(45)

(3R)-1-butyl-2,5-dioxo-3-((1R)-1-hydroxy-1-cyclohexylmethyl)-9-(4-(4-(morpholin-4-ylcarbonyl)phenyloxy)phenylmethyl)-1,4,9-triazaspiro[5.5]undecane.hydrochloride

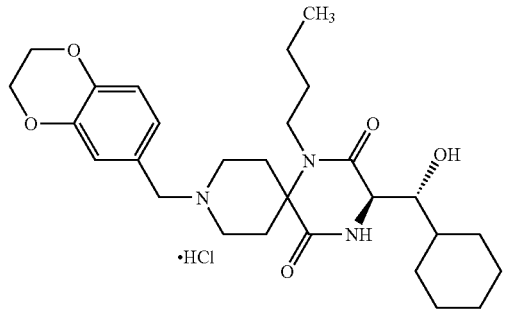

EXAMPLE 75(47)

(3R)-1-butyl-2,5-dioxo-3-((1R)-1-hydroxy-1-cyclohexylmethyl)-9-(3,5-dimethyl-1-(4-(N,N-diethylaminosulfonyl)phenyl)pyrazol-4-ylmethyl)-1,4,9-triazaspiro[5.5]undecane.2hydrochloride

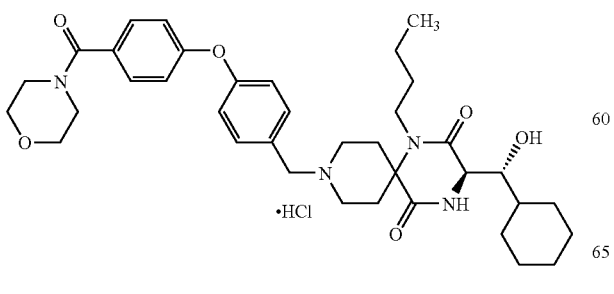

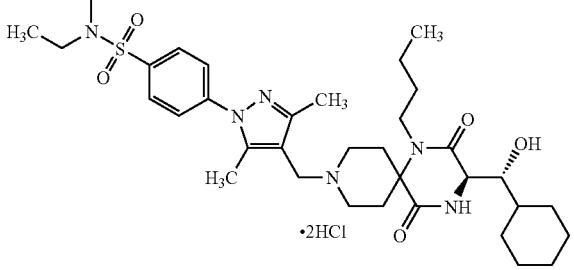

TLC: Rf 0.36 (chloroform:methanol=10:1); NMR (CD₃OD):δ 7.99 (d, J=9.0 Hz, 2H), 7.73 (d, J=9.0 Hz, 2H), 4.31 (s, 2H), 4.17 (d, J=2.1 Hz, 1H), 4.06 (m, 1H), 3.78 (m, 1H), 3.62-3.48 (m, 3H), 3.34-3.14 (m, 6H), 2.60-2.30 (m, 3H), 2.45 (s, 3H), 2.39 (s, 3H), 2.20-1.88 (m, 3H), 1.82-1.62 (m, 5H), 1.50-1.08 (m, 6H), 1.15 (t, J=7.5 Hz, 6H), 1.02-0.82 (m, 5H).

EXAMPLE 75(48)

(3R)-1-butyl-2,5-dioxo-3-((1R)-1-hydroxy-1-cyclohexylmethyl)-9-(4-(pyridin-1-oxido-3-yloxy)phenylmethyl)-1,4,9-triazaspiro[5.5]undecane.hydrochloride

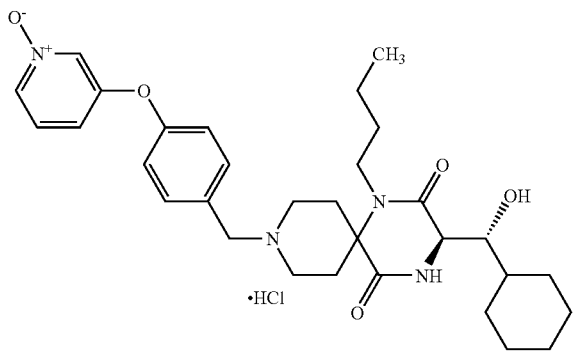

TLC: Rf 0.10 (ethyl acetate:methanol=3:1); NMR (CD₃OD):δ δ 8.48-8.37 (m, 2H), 7.73 (d, J=9.0 Hz, 2H), 7.73-7.60 (m, 2H), 7.31 (d, J=9.0 Hz, 2H), 4.39 (s, 2H), 4.15 (d, J=2.1 Hz, 1H), 4.01 (m, 1H), 3.76 (m, 1H), 3.60-3.20 (m, 5H), 2.70-2.40 (m, 3H), 2.20-1.90 (m, 3H), 1.90-1.60 (m, 5H), 1.60-1.10 (m, 6H), 1.10-0.80 (m, 2H), 0.95 (t, J=7.2 Hz, 3H).

EXAMPLE 75(49)

(3R)-1-butyl-2,5-dioxo-3-((1R)-1-hydroxy-1-cyclohexylmethyl)-9-(3,5-dimethyl-1-(4-(4-methylpiperazin-1-ylsulfonyl)phenyl)pyrazol-4-ylmethyl)-1,4,9-triazaspiro[5.5]undecane.3hydrochloride

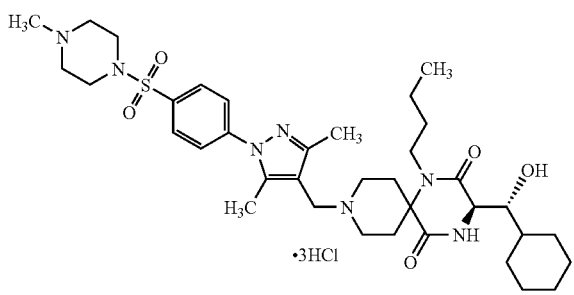

TLC: Rf 0.34 (chloroform:methanol=10:1); NMR (CD₃OD):δ 8.01 (d, J=8.7 Hz, 2H), 7.85 (d, J=8.7 Hz, 2H), 4.31 (s, 2H), 4.17 (d, J=2.4 Hz, 1H), 4.10-3.94 (m, 3H), 3.78 (m, 1H), 3.66-3.56 (m, 5H), 3.40-3.20 (m, 4H), 2.91 (s, 3H), 2.88-2.72 (m, 2H), 2.70-2.40 (m, 3H), 2.50 (s, 3H), 2.40 (s, 3H), 2.20-1.88 (m, 3H), 1.84-1.60 (m, 5H), 1.56-1.10 (m, 6H), 1.04-0.82 (m, 5H).

EXAMPLE 75(50)

(3R)-1-butyl-2,5-dioxo-3-((1R)-1-hydroxy-1-cyclohexylmethyl)-9-(4-(4-methylaminocarbonylphenyloxy)phenylmethyl)-1,4,9-triazaspiro[5.5]undecane.hydrochloride

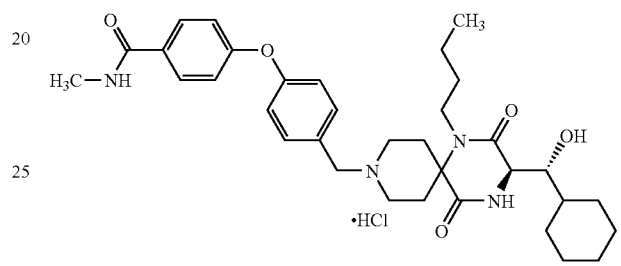

TLC: Rf 0.44 (chloroform:methanol=10:1); NMR (CD₃OD):δ 7.84 (d, J=9.0 Hz, 2H), 7.59 (d, J=8.7 Hz, 2H), 7.15 (d, J=8.7 Hz, 2H), 7.07 (d, J=9.0 Hz, 2H), 4.36 (s, 2H), 4.16 (d, J=2.1 Hz, 1H), 4.00 (m, 1H), 3.74 (m, 1H), 3.60-3.44 (m, 3H), 3.28-3.16 (m, 2H), 2.91 (s, 3H), 2.52-2.26 (m, 3H), 2.18-1.88 (m, 3H), 1.82-1.62 (m, 5H), 1.50-1.10 (m, 6H), 1.02-0.82 (m, 5H).

EXAMPLE 75(51)

(3R)-1-butyl-2,5-dioxo-3-((1R)-1-hydroxy-1-cyclohexylmethyl)-9-(3,5-dimethyl-1-(2,4-difluorophenyl)pyrazol-4-ylmethyl)-1,4,9-triazaspiro[5.5]undecane.3hydrochloride

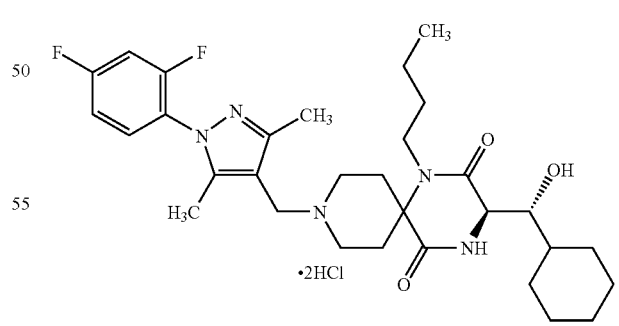

TLC: Rf 0.63 (chloroform:methanol=5:1); NMR (CD₃OD):δ 7.56 (m, 1H), 7.33-7.16 (m, 2H), 4.32 (s, 2H), 4.18 (d, J=2.4 Hz, 1H), 4.04 (m, 1H), 3.80 (m, 1H), 3.64-3.46 (m, 3H), 3.30-3.16 (m, 2H), 2.62-1.88 (m, 6H), 2.39 (s, 3H), 2.28 (s, 3H), 1.84-1.60 (m, 5H), 1.52-1.10 (m, 6H), 1.06-0.82 (m, 2H), 0.97 (t, J=6.9 Hz, 3H).

EXAMPLE 75(52)

(3R)-1-butyl-2,5-dioxo-3-((1R)-1-hydroxy-1-cyclo-hexylmethyl)-9-(3,5-dimethyl-1-(4-(2-(N,N-dim-ethylamino)ethylaminosulfonyl)phenyl)pyrazol-4-ylmethyl)-1,4,9-triazaspiro[5.5]undecane.3hydrochloride

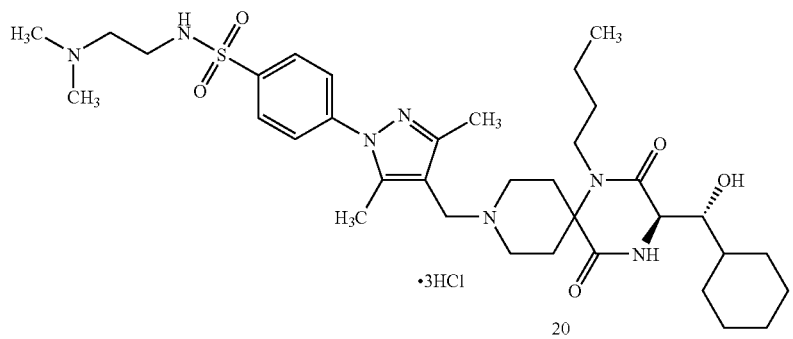

TLC: Rf 0.21 (chloroform:methanol:28% aqueous solution of ammonia=100:10:1); NMR (CD₃OD):δ 8.07 (d, J=8.7 Hz, 2H), 7.78 (d, J=8.7 Hz, 2H), 4.31 (s, 2H), 4.17 (d, J=2.1 Hz, 1H), 4.04 (m, 1H), 3.80 (m, 1H), 3.64-3.50 (m, 3H), 3.40-3.22 (m, 6H), 2.96 (s, 6H), 2.74-2.38 (m, 3H), 2.49 (s, 3H), 2.41 (s, 3H), 2.22-1.88 (m, 3H), 1.84-1.60 (m, 5H), 1.52-1.10 (m, 6H), 1.06-0.82 (m, 2H), 0.96 (t, J=7.2 Hz, 3H).

EXAMPLE 75(53)

(3R)-1-butyl-2,5-dioxo-3-((1R)-1-hydroxy-1-cyclo-hexylmethyl)-9-(3,5-dimethyl-1-(4-(methylaminocar-bonyl)phenyl)pyrazol-4-ylmethyl)-1,4,9-triazaspiro[5.5]undecane.2hydrochloride

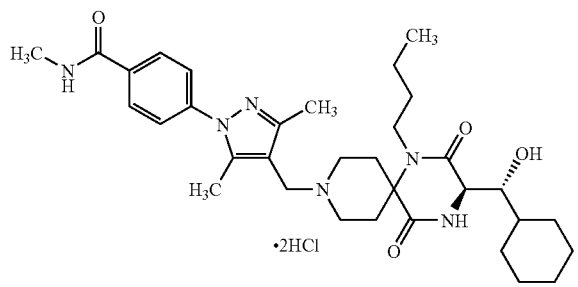

TLC: Rf 0.21 (chloroform:methanol=10:1); NMR (CD₃OD):δ 7.98 (d, J=8.7 Hz, 2H), 7.60 (d, J=8.7 Hz, 2H), 4.31 (s, 2H), 4.16 (d, J=2.1 Hz, 1H), 4.04 (m, 1H), 3.79 (m, 1H), 3.64-3.49 (m, 3H), 3.37-3.20 (m, 2H), 2.94 (s, 3H), 2.63-2.33 (m, 3H), 2.43 (s, 3H), 2.40 (s, 3H), 2.16 (m, 1H), 2.09-1.90 (m, 2H), 1.83-1.62 (m, 5H), 1.50-1.12 (m, 6H), 1.04-0.82 (m, 5H).

EXAMPLE 75(54)

(3R)-1-butyl-2,5-dioxo-3-((1R)-1-hydroxy-1-cyclo-hexylmethyl)-9-(4-(4-carboxyphenyloxy)phenylm-ethyl)-1,4,9-triazaspiro[5.5]undecane.hydrochloride

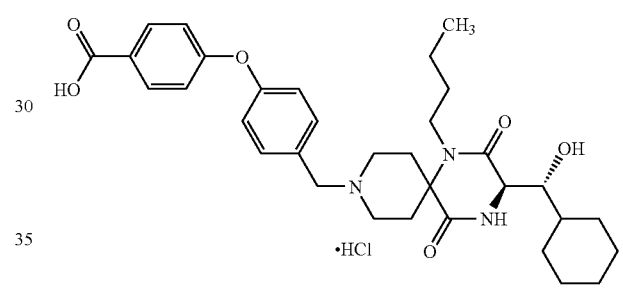

TLC: Rf 0.43 (chloroform:methanol=5:1); NMR (CD₃OD):δ 8.05 (d, J=9.0 Hz, 2H), 7.61 (d, J=9.0 Hz, 2H), 7.19 (d, J=9.0 Hz, 2H), 7.08 (d, J=9.0 Hz, 2H), 4.38 (s, 2H), 4.17 (d, J=2.1 Hz, 1H), 4.02 (m, 1H), 3.78 (m, 1H), 3.60-3.40 (m, 3H), 3.30-3.10 (m, 2H), 2.56-1.86 (m, 6H), 1.82-1.60 (m, 5H), 1.52-1.16 (m, 6H), 1.06-0.82 (m, 2H), 0.97 (t, J=7.2 Hz, 3H).

EXAMPLE 75(55)

(3R)-1-butyl-2,5-dioxo-3-((1R)-1-hydroxy-1-cyclo-hexylmethyl)-9-(4-((4-methoxyphenyl)methylami-nocarbonyl)phenylmethyl)-1,4,9-triazaspiro[5.5]undecane.hydrochloride

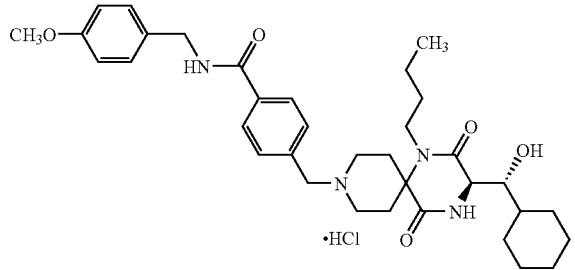

TLC: Rf 0.33 (chloroform:methanol=10:1); NMR (CD$_3$OD):δ 7.96 (d, J=8.4 Hz, 2H), 7.66 (d, J=8.4 Hz, 2H), 7.28 (d, J=8.4 Hz, 2H), 6.88 (d, J=8.4 Hz, 2H), 4.52 (s, 2H), 4.43 (s, 2H), 4.15 (d, J=2.1 Hz, 1H), 4.02 (m, 1H), 3.77 (s, 3H), 3.77 (m, 1H), 3.58-3.38 (m, 3H), 3.30-3.10 (m, 2H), 2.54-2.22 (m, 3H), 2.18-1.86 (m, 3H), 1.82-1.60 (m, 5H), 1.50-1.08 (m, 6H), 1.04-0.80 (m, 2H), 0.95 (t, J=6.9 Hz, 3H).

EXAMPLE 75(56)

(3R)-1-butyl-2,5-dioxo-3-((1R)-1-hydroxy-1-cyclo-hexylmethyl)-9-(4-(3-methoxypropylaminocarbonyl) phenylmethyl)-1,4,9-triazaspiro[5.5]undecane.hydro-chloride

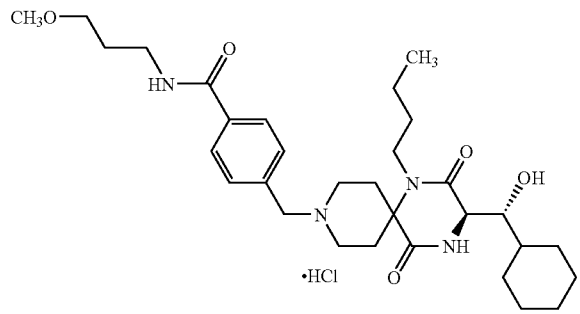

TLC: Rf 0.27 (chloroform:methanol=10:1); NMR (CD$_3$OD):δ 7.93 (d, J=8.1 Hz, 2H), 7.68 (d, J=8.1 Hz, 2H), 4.43 (s, 2H), 4.16 (d, J=1.8 Hz, 1H), 4.04 (m, 1H), 3.78 (m, 1H), 3.60-3.40 (m, 7H), 3.35 (s, 3H), 3.30-3.10 (m, 2H), 2.58-1.60 (m, 13H), 1.52-1.08 (m, 6H), 1.06-0.80 (m, 2H), 0.96 (t, J=7.2 Hz, 3H).

EXAMPLE 75(57)

(3R)-1-butyl-2,5-dioxo-3-((1R)-1-hydroxy-1-cyclo-hexylmethyl)-9-(4-(N-methyl-N-(2-(pyridin-2-yl) ethyl)aminocarbonyl)phenylmethyl)-1,4,9-triaza-spiro[5.5]undecane.2hydrochloride

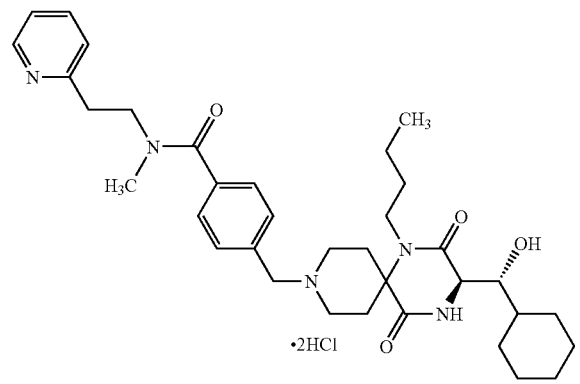

TLC: Rf 0.22 (chloroform:methanol=10:1); NMR (CD$_3$OD):δ 8.80 (m, 1H), 8.57 (m, 1H), 8.08 (m, 1H), 7.96 (m, 1H), 7.69 (d, J=8.4 Hz, 2H), 7.43 (d, J=8.4 Hz, 2H), 4.40 (s, 2H), 4.16 (d, J=2.1 Hz, 1H), 4.06-3.90 (m, 3H), 3.80 (m, 1H), 3.62-3.38 (m, 5H), 3.30-3.10 (m, 2H), 3.08 (s, 3H), 2.64-2.30 (m, 3H), 2.18-1.84 (m, 3H), 1.82-1.60 (m, 5H), 1.50-1.06 (m, 6H), 1.04-0.80 (m, 2H), 0.96 (t, J=7.2 Hz, 3H).

EXAMPLE 75(58)

(3R)-1-butyl-2,5-dioxo-3-((1R)-1-hydroxy-1-cyclo-hexylmethyl)-9-(4-(4-(pyrrolidin-1-ylcarbonyl)phe-nyloxy)phenylmethyl)-1,4,9-triazaspiro[5.5]unde-cane.hydrochloride

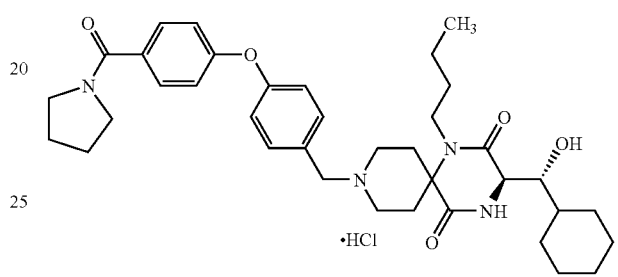

TLC: Rf 0.41 (ethyl acetate:methanol=4:1); NMR (CD$_3$OD):δ 7.59-7.56 (m, 4H), 7.15 (d, J=8.7 Hz, 2H), 7.09 (d, J=8.7 Hz, 2H), 4.36 (s, 2H), 4.15 (d, J=2.0 Hz, 1H), 4.01 (m, 1H), 3.75 (m, 1H), 3.60-3.46 (m, 7H), 3.30-3.13 (m, 2H), 2.51-2.11 (m, 4H), 2.04-1.89 (m, 6H), 1.80-1.65 (m, 5H), 1.50-1.15 (m, 6H), 1.00-0.87 (m, 5H).

EXAMPLE 75(59)

(3R)-1-butyl-2,5-dioxo-3-((1R)-1-hydroxy-1-cyclo-hexylmethyl)-9-(3,5-dimethyl-1-(4-chlorophenyl) pyrazol-4-ylmethyl)-1,4,9-triazaspiro[5.5] undecane.2hydrochloride

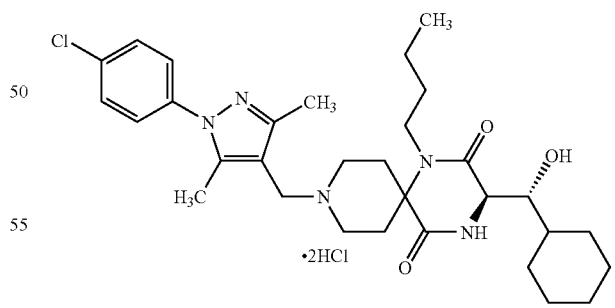

TLC: Rf 0.51 (chloroform:methanol=10:1); NMR (CD$_3$OD):δ 7.58 (d, J=9.0 Hz, 2H), 7.49 (d, J=9.0 Hz, 2H), 4.31 (s, 2H), 4.17 (d, J=2.1 Hz, 1H), 4.04 (m, 1H), 3.78 (m, 1H), 3.62-3.48 (m, 3H), 3.30-3.16 (m, 2H), 2.62-2.32 (m, 3H), 2.40 (s, 3H), 2.39 (s, 3H), 2.22-1.86 (m, 3H), 1.84-1.60 (m, 5H), 1.54-1.10 (m, 6H), 1.06-0.82 (m, 2H), 0.97 (t, J=7.2 Hz, 3H).

EXAMPLE 75(60)

(3R)-1-butyl-2,5-dioxo-3-((1R)-1-hydroxy-1-cyclohexylmethyl)-9-(3,5-dimethyl-1-(4-trifluoromethylphenyl)pyrazol-4-ylmethyl)-1,4,9-triazaspiro[5.5]undecane.2hydrochlride

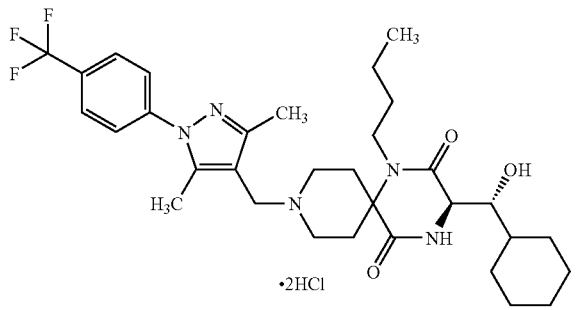

TLC: Rf 0.53 (chloroform:methanol=10:1); NMR (CD$_3$OD):δ 7.88 (d, J=8.7 Hz, 2H), 7.73 (d, J=8.7 Hz, 2H), 4.33 (s, 2H), 4.18 (d, J=2.1 Hz, 1H), 4.04 (m, 1H), 3.80 (m, 1H), 3.64-3.46 (m, 3H), 3.30-3.16 (m, 2H), 2.62-2.28 (m, 3H), 2.46 (s, 3H), 2.40 (s, 3H), 2.24-1.88 (m, 3H), 1.84-1.60 (m, 5H), 1.56-1.06 (m, 6H), 1.06-0.82 (m, 2H), 0.97 (t, J=7.2 Hz, 3H).

EXAMPLE 75(61)

(3R)-1-butyl-2,5-dioxo-3-((1R)-1-hydroxy-1-cyclohexylmethyl)-9-(3,5-dimethyl-1-(4-methoxyphenyl)pyrazol-4-ylmethyl)-1,4,9-triazaspiro[5.5]undecane.2hydrochloride

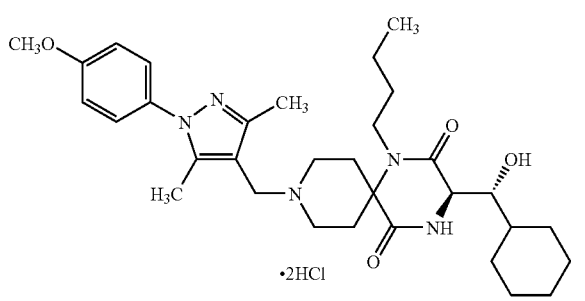

TLC: Rf 0.44 (chloroform:methanol=10:1); NMR (CD$_3$OD):δ 7.40 (d, J=8.7 Hz, 2H), 7.11 (d, J=8.7 Hz, 2H), 4.32 (s, 2H), 4.18 (d, J=2.4 Hz, 1H), 4.04 (m, 1H), 3.88 (s, 3H), 3.80 (m, 1H), 3.66-3.48 (m, 3H), 3.30-3.18 (m, 2H), 2.64-2.30 (m, 3H), 2.42 (s, 3H), 2.36 (s, 3H), 2.22-1.88 (m, 3H), 1.84-1.60 (m, 5H), 1.54-1.10 (m, 6H), 1.06-0.82 (m, 2H), 0.97 (t, J=7.2 Hz, 3H).

EXAMPLE 75(62)

(3R)-1-butyl-2,5-dioxo-3-((1R)-1-hydroxy-1-cyclohexylmethyl)-9-(3,5-dimethyl-1-ethylpyrazol-4-ylmethyl)-1,4,9-triazaspiro[5.5]undecane.2hydrochloride

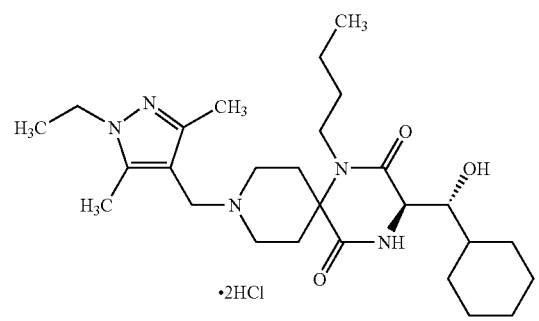

TLC: Rf 0.27 (chloroform:methanol=10:1); NMR (CD$_3$OD):δ 4.28 (s, 2H), 4.23 (q, J=7.2 Hz, 2H), 4.17 (d, J=2.4 Hz, 1H), 4.00 (m, 1H), 3.78 (m, 1H), 3.64-3.44 (m, 3H), 3.30-3.18 (m, 2H), 2.70-2.34 (m, 3H), 2.48 (s, 3H), 2.43 (s, 3H), 2.22-1.86 (m, 3H), 1.84-1.60 (m, 5H), 1.52-1.08 (m, 6H), 1.43 (t, J=7.2 Hz, 3H), 1.06-0.80 (m, 2H), 0.96 (t, J=7.2 Hz, 3H).

EXAMPLE 75(63)

(3R)-1-butyl-2,5-dioxo-3-((1R)-1-hydroxy-1-cyclohexylmethyl)-9-(3,5-dimethyl-1-propylpyrazol-4-ylmethyl)-1,4,9-triazaspiro[5.5]undecane.2hydrochloride

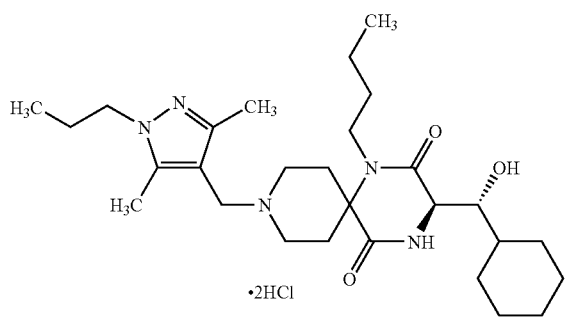

TLC: Rf 0.31 (chloroform:methanol=10:1); NMR (CD$_3$OD):δ 4.28 (s, 2H), 4.16 (d, J=2.4 Hz, 1H), 4.15 (t, J=7.2 Hz, 2H), 4.00 (m, 1H), 3.76 (m, 1H), 3.62-3.46 (m, 3H), 3.30-3.18 (m, 2H), 2.66-2.36 (m, 3H), 2.47 (s, 3H), 2.43 (s, 3H), 2.20-1.60 (m, 10H), 1.52-1.10 (m, 6H), 1.18 (t, J=7.2 Hz, 3H), 1.06-0.80 (m, 2H), 0.96 (t, J=7.2 Hz, 3H).

EXAMPLE 75(64)

(3R)-1-butyl-2,5-dioxo-3-((1R)-1-hydroxy-1-cyclohexylmethyl)-9-(3,5-dimethyl-1-(1,1-dimethylethyl)pyrazol-4-ylmethyl)-1,4,9-triazaspiro[5.5]undecane·2hydrochloride

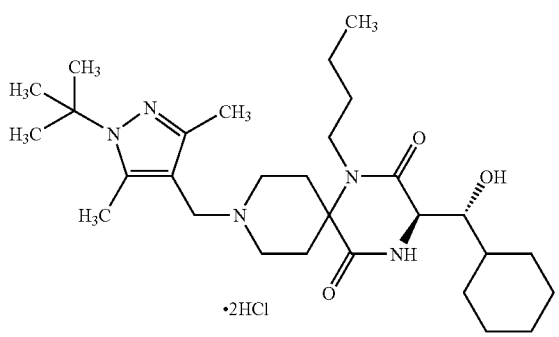

TLC: Rf 0.33 (chloroform:methanol=10:1); NMR (CD$_3$OD): δ 4.26 (s, 2H), 4.17 (d, J=2.4 Hz, 1H), 4.02 (m, 1H), 3.78 (m, 1H), 3.62-3.46 (m, 3H), 3.30-3.22 (m, 2H), 2.64-2.40 (m, 3H), 2.63 (s, 3H), 2.42 (s, 3H), 2.20-1.86 (m, 3H), 1.84-1.62 (m, 5H), 1.72 (s, 9H), 1.54-1.16 (m, 6H), 1.04-0.82 (m, 2H), 0.96 (t, J=6.9 Hz, 3H).

EXAMPLE 75(65)

(3R)-1-butyl-2,5-dioxo-3-((1R)-1-hydroxy-1-cyclohexylmethyl)-9-(3,5-dimethyl-1-cyclopentylpyrazol-4-ylmethyl)-1,4,9-triazaspiro[5.5]undecane·2 hydrochloride

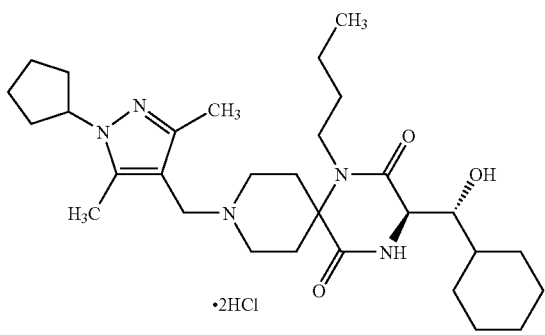

TLC: Rf 0.33 (chloroform:methanol=10:1); NMR (CD$_3$OD): δ 4.27 (s, 2H), 4.16 (d, J=2.1 Hz, 1H), 4.00 (m, 1H), 3.78 (m, 1H), 3.64-3.44 (m, 4H), 3.30-3.20 (m, 2H), 2.66-2.36 (m, 3H), 2.47 (s, 3H), 2.42 (s, 3H), 2.28-1.60 (m, 16H), 1.58-1.10 (m, 6H), 1.08-0.82 (m, 2H), 0.96 (t, J=6.9 Hz, 3H).

EXAMPLE 75(66)

(3R)-1-butyl-2,5-dioxo-3-((1R)-1-hydroxy-1-cyclohexylmethyl)-9-(3,5-dimethyl-1-(2-phenylethyl)pyrazol-4-ylmethyl)-1,4,9-triazaspiro[5.5]undecane·2hydrochloride

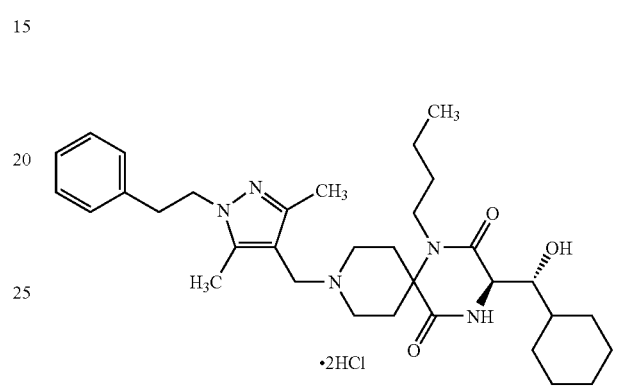

TLC: Rf 0.25 (chloroform:methanol=10:1); NMR (CD$_3$OD): δ 7.36-7.18 (m, 3H), 7.16-7.00 (m, 2H), 4.39 (t, J=6.3 Hz, 2H), 4.18 (s, 2H), 4.17 (d, J=2.4 Hz, 1H), 3.88 (m, 1H), 3.72-3.46 (m, 2H), 3.42-3.22 (m, 4H), 3.12 (t, J=6.3 Hz, 2H), 2.66-2.34 (m, 3H), 2.44 (s, 3H), 2.18-1.86 (m, 3H), 1.92 (s, 3H), 1.84-1.62 (m, 5H), 1.54-1.10 (m, 6H), 1.06-0.82 (m, 2H), 0.97 (t, J=6.9 Hz, 3H).

EXAMPLE 75(67)

(3R)-1-butyl-2,5-dioxo-3-((1R)-1-hydroxy-1-cyclohexylmethyl)-9-(3,5-dimethyl-1-(1-benzyl-oxycarbonylpiperidin-4-yl)pyrazol-4-ylmethyl)-1,4,9-triazaspiro[5.5]undecane·2hydrochloride

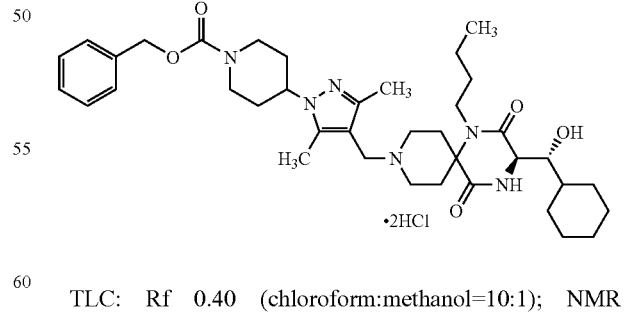

TLC: Rf 0.40 (chloroform:methanol=10:1); NMR (CD$_3$OD): δ 7.42-7.25 (m, 5H), 5.14 (s, 2H), 4.56 (m, 1H), 4.36-4.25 (m, 2H), 4.25 (s, 2H), 4.15 (d, J=2.1 Hz, 1H), 3.98 (m, 1H), 3.73 (m, 1H), 3.62-3.45 (m, 3H), 3.40-3.20 (m, 2H), 3.18-2.94 (m, 2H), 2.67-2.30 (m, 9H), 2.20-1.85 (m, 7H), 1.83-1.58 (m, 5H), 1.50-1.08 (m, 6H), 1.05-0.80 (m, 2H), 0.95 (t, J=7.2 Hz, 3H).

EXAMPLE 75(68)

(3R)-1-butyl-2,5-dioxo-3-((1R)-1-hydroxy-1-cyclohexylmethyl)-9-(4-(cyclohexylaminocarbonyl)phenylmethyl)-1,4,9-triazaspiro[5.5]undecane.hydrochloride

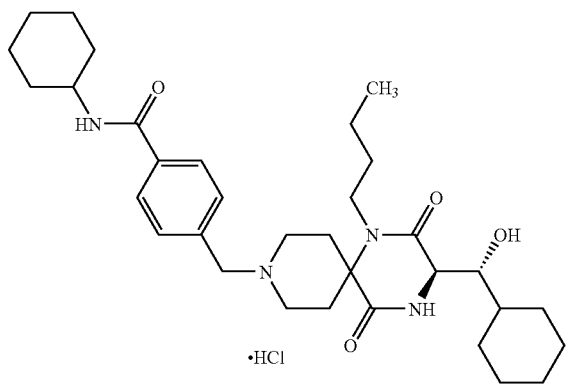

TLC: Rf 0.45 (chloroform:methanol=10:1); NMR (CD$_3$OD): 7.92 (d, J=8.7 Hz, 2H), 7.67 (d, J=8.7 Hz, 2H), 4.42 (s, 2H), 4.15 (d, J=2.1 Hz, 1H), 4.02 (m, 1H), 3.92-3.69 (m, 2H), 3.60-3.39 (m, 3H), 3.30-3.12 (m, 2H), 2.56-2.26 (m, 3H), 2.17-1.58 (m, 14H), 1.51-1.08 (m, 10H), 1.06-0.80 (m, 2H), 0.95 (t, J=6.9 Hz, 3H).

EXAMPLE 75(69)

(3R)-1-butyl-2,5-dioxo-3-((1R)-1-hydroxy-1-cyclohexylmethyl)-9-(3,5-dimethyl-1-(1-methylsulfonylpiperidin4-yl)pyrazol-4-ylmethyl)-1,4,9-triazaspiro[5.5]undecane.2hydrochloride

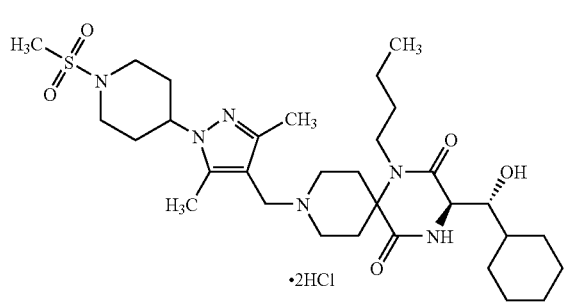

TLC: Rf 0.26 (chloroform:methanol=10:1); NMR (CD$_3$OD):δ 4.48 (m, 1H), 4.25 (s, 2H), 4.15 (d, J=2.1 Hz, 1H), 4.05-3.83 (m, 3H), 3.74 (m, 1H), 3.60-3.46 (m, 3H), 3.40-3.20 (m, 2H), 3.05-2.92 (m, 2H), 2.90 (s, 3H), 2.60 (m, 1H), 2.52-2.40 (m, 2H), 2.49 (s, 3H), 2.39 (s, 3H), 2.26-1.88 (m, 7H), 1.84-1.60 (m, 5H), 1.50-1.10 (m, 6H), 1.05-0.80 (m, 2H), 0.95 (t, J=6.9 Hz, 3H).

EXAMPLE 75(70)

(3R)-1-butyl-2,5-dioxo-3-((1R)-1-hydroxy-1-cyclohexylmethyl)-9-(4-(4-(2-hydroxyethylaminocarbonyl)phenyloxy)phenye.hydrochloride

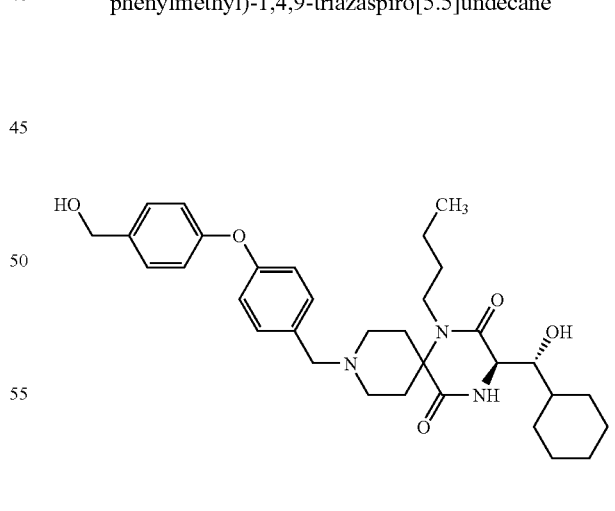

TLC: Rf 0.50 (chloroform:methanol=5:1); NMR (CD$_3$OD):δ 7.89 (d, J=9.0 Hz, 2H), 7.60 (d, J=9.0 Hz, 2H), 7.16 (d, J=9.0 Hz, 2H), 7.09 (d, J=9.0 Hz, 2H), 4.37 (s, 2H), 4.17 (d, J=2.1 Hz, 1H), 4.02 (m, 1H), 3.78 (m, 1H), 3.71 (t, J=5.7 Hz, 2H), 3.60-3.40 (m, 3H), 3.51 (t, J=5.7 Hz, 2H), 3.30-3.10 (m, 2H), 2.58-1.84 (m, 6H), 1.82-1.56 (m, 5H), 1.54-1.06 (m, 6H), 1.04-0.80 (m, 2H), 0.96 (t, J=6.9 Hz, 3H).

EXAMPLE 75(71)

(3R)-1-butyl-2,5-dioxo-3-((1R)-1-hydroxy-1-cyclohexylmethyl)-9-(4-(4-hydroxymethylphenyloxy)phenylmethyl)-1,4,9-triazaspiro[5.5]undecane TLC: Rf 0.37 (chloroform:methanol=10:1); NMR (CD$_3$OD):δ 7.34 (d, J=8.7 Hz, 4H), 6.97 (d, J=8.7 Hz, 2H), 6.96 (d, J=8.7 Hz, 2H), 4.57 (s, 2H), 4.13 (d, J=2.1 Hz, 1H), 3.71 (s, 2H), 3.47 (m, 1H), 3.35 (dd, J=9.0, 2.1 Hz, 1H), 3.30-2.88 (m, 5H), 2.31-1.81 (m, 6H), 1.81-1.58 (m, 5H), 1.55-1.05 (m, 6H), 1.05-0.83 (m, 2H), 0.95 (t, J=7.2 Hz, 3H).

EXAMPLE 76

(3S)-1-butyl-2,5-dioxo-3-((1S)-1-hydroxy-1-cyclohexylmethyl)-9-(4-(4-methylsulfonylaminophenyloxy)phenylmethyl)-1,4,9-triazaspiro[5.5]undecane.hydrochloride

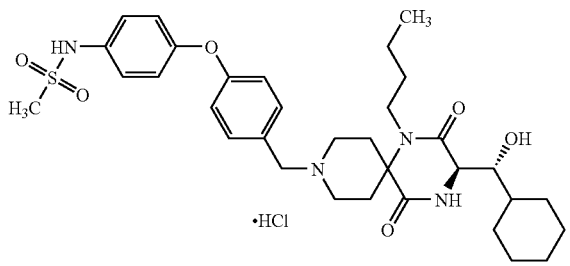

By the same procedure as described in Example 68 using the compound prepared in Reference example 15(9) instead of the compound prepared in Reference example 15, and using 4-(4-methylsulfonylaminophenyloxy)benzaldehyde instead of 3-formyl-6-phenyloxypyridine, the title compound having the following physical data was obtained.

TLC: Rf 0.54 (ethyl acetate:methanol=4:1); NMR (CD$_3$OD):δ 7.54 (d, J=8.4 Hz, 2H), 7.29 (d, J=8.7 Hz, 2H), 7.06 (d, j=8.4 Hz, 2H), 7.03 (d, J=8.7 Hz, 2H), 4.32 (s, 2H), 4.15 (d, J=2.0 Hz, 1H), 3.98 (m, 1H), 3.73 (m, 1H), 3.55-3.43 (m, 3H), 3.30-3.16 (m, 2H), 2.95 (s, 3H), 2.52-2.28 (m, 3H), 2.14-1.91 (m, 3H), 1.76-1.65 (m, 5H), 1.50-1.15 (m, 6H), 1.00-0.86 (m, 5H).

EXAMPLE 77

(3R)-1-butyl-2,5-dioxo-3-((1R)-1-hydroxy-1-(3,4,5,6-tetrahydropyran-4-yl)methyl)-9-(3,5-dimethyl-1-phenylpyrazol-4-ylmethyl)-1,4,9-triazaspiro[5.5]undecane.2hydrochloride

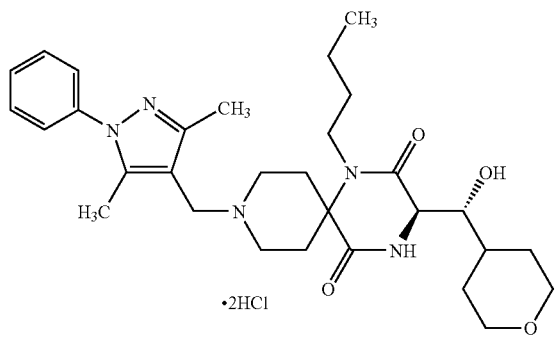

By the same procedure as described in Example 68 using the compound prepared in Reference example 15(4) instead of the compound prepared in Reference example 15, and using 4-formyl-3,5-dimethyl-1-phenylpyrazole instead of 3-formyl-6-phenyloxypyridine, the title compound having the following physical data was obtained.

TLC: Rf 0.31 (ethyl acetate:methanol=4:1); NMR (CD$_3$OD):δ 7.67-7.56 (m, 5H), 4.37 (s, 2H), 4.13 (d, J=2.0 Hz, 1H), 4.06 (m, 1H), 3.98-3.91 (m, 2H), 3.80 (m, 1H), 3.64-3.53 (m, 4H), 3.46-3.37 (m, 3H), 2.80-2.52 (m, 5H), 2.45 (s, 3H), 2.16-2.01 (m, 2H), 1.91-1.82 (m, 2H), 1.71 (m, 1H), 1.50-1.17 (m, 6H), 0.95 (t, J=7.5 Hz, 3H).

EXAMPLE 77(1) TO 77(5)

By the same procedure as described in Example 77 using the corresponding aldehyde derivatives respectively instead of 4-formyl-3,5-dimethyl-1-phenylpyrazole, the following compounds having the following physical data were obtained.

EXAMPLE 77(1)

(3R)-1-butyl-2,5-dioxo-3-((1R)-1-hydroxy-1-(3,4,5,6-tetrahydropyran-4-yl)methyl)-9-(4-(4-methylaminocarbonylphenyloxy)phenylmethyl)-1,4,9-triazaspiro[5.5]undecane.hydrochloride

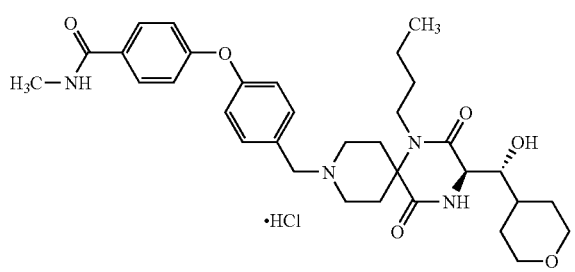

TLC: Rf 0.28 (ethyl acetate:methanol=4:1); NMR (CD$_3$OD):δ 7.84 (d, J=8.7 Hz, 2H), 7.59 (d, J=8.7 Hz, 2H), 7.15 (d, J=8.7 Hz, 2H), 7.07 (d, J=8.7 Hz, 2H), 4.36 (s, 2H), 4.12 (d, J=2.0 Hz, 1H), 4.06-3.90 (m, 3H), 3.75 (m, 1H), 3.56-3.34 (m, 5H), 3.30-3.20 (m, 2H), 2.91 (s, 3H), 2.51-2.28 (m, 3H), 2.16-1.69 (m, 5H), 1.50-1.15 (m, 5H), 0.95 (t, J=7.0 Hz, 3H).

EXAMPLE 77(2)

(3R)-1-butyl-2,5-dioxo-3-((1R)-1-hydroxy-1-(3,4,5,6-tetrahydropyran-4-yl)methyl)-9-(4-(4-(4-methoxyphenylmethylaminocarbonyl)phenylmethyl)-1,4,9-triazaspiro[5.5]undecane.hydrochloride

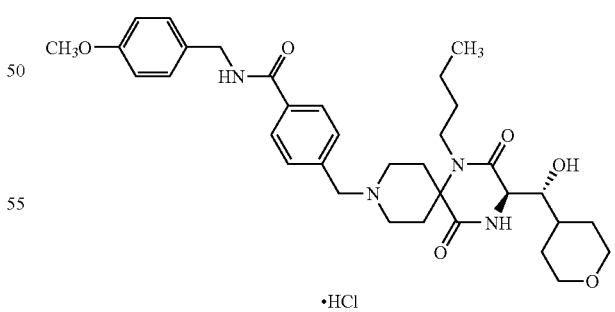

TLC: Rf 0.36 (ethyl acetate:methanol=4:1); NMR (CD$_3$OD):δ 7.95 (d, J=8.3 Hz, 2H), 7.66 (d, J=8.3 Hz, 2H), 7.27 (d, J=8.8 Hz, 2H), 6.87 (d, J=8.8 Hz, 2H), 4.51 (s, 2H), 4.42 (s, 2H), 4.11 (d, J=2.0 Hz, 1H), 4.04-3.91 (m, 3H), 3.76 (m, 1H), 3.76 (s, 3H), 3.56-3.37 (m, 5H), 3.30-3.13 (m, 2H), 2.50-1.70 (m, 8H), 1.39-1.15 (m, 5H), 0.95 (t, J=7.0 Hz, 3H).

EXAMPLE 77(3)

(3R)-1-butyl-2,5-dioxo-3-((1R)-1-hydroxy-1-(3,4,5,6-tetrahydropyran-4-yl)methyl)-9-(3,5-dimethyl-1-(4-(N,N-dimethylaminocarbonyl)phenylpyrazol-4-ylmethyl)-1,4,9-triazaspiro[5.5]undecane.2hydrochloride

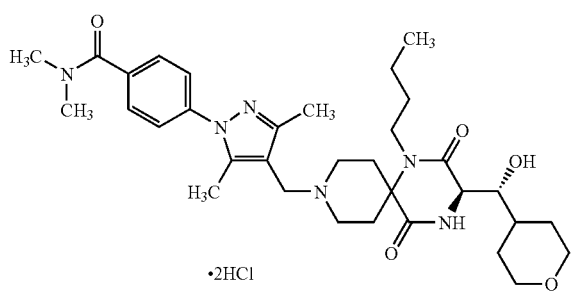

TLC: Rf 0.55 (chloroform:methanol=4:1); NMR (CD$_3$OD):δ 7.63 (d, J=9.0 Hz, 2H), 7.60 (d, J=9.0 Hz, 2H), 4.32 (s, 2H), 4.13 (d, J=2.0 Hz, 1H), 4.06 (m, 1H), 4.00-3.91 (m, 2H), 3.79 (m, 1H), 3.63-3.52 (m, 4H), 3.46-3.34 (m, 3H), 3.13 (s, 3H), 3.04 (s, 3H), 2.62-2.37 (m, 2H), 2.44 (s, 3H), 2.41 (s, 3H), 2.15 (m, 1H), 2.03 (m, 1H), 1.90-1.70 (m, 3H), 1.50-1.15 (m, 6H), 0.96 (t, J=7.0 Hz, 3H).

EXAMPLE 77(4)

(3R)-1-butyl-2,5-dioxo-3-((1R)-1-hydroxy-1-(3,4,5,6-tetrahydropyran-4-yl)methyl)-9-(4-(4-carboxyphenyloxy)phenylmethyl)-1,4,9-triazaspiro[5.5]undecane.hydrochloride

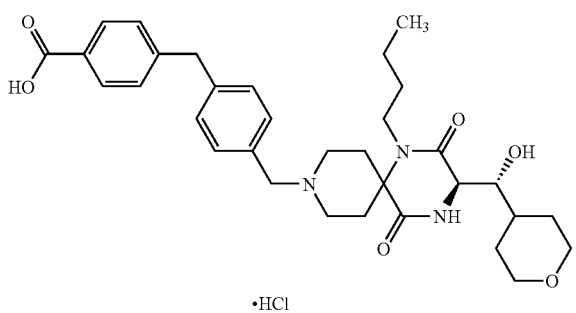

TLC: Rf 0.30 (chloroform:methanol=4:1); NMR (CD$_3$OD):δ 8.04 (d, J=9.0 Hz, 2H), 7.60 (d, J=8.5 Hz, 2H), 7.18 (d, J=8.5 Hz, 2H), 7.07 (d, J=9.0 Hz, 2H), 4.37 (s, 2H), 4.12 (d, J=2.0 Hz, 1H), 4.08-3.93 (m, 3H), 3.75 (m, 1H), 3.57-3.34 (m, 5H), 3.30-3.15 (m, 2H), 2.52-1.69 (m, 8H), 1.50-1.18 (m, 5H), 0.96 (t, J=7.2 Hz, 3H).

EXAMPLE 77(5)

(3R)-1-butyl-2,5-dioxo-3-((1R)-1-hydroxy-1-(3,4,5,6-tetrahydropyran-4-yl)methyl)-9-(4-(4-methylsulfonylaminophenyloxy)phenylmethyl)-1,4,9-triazaspiro[5.5]undecane.hydrochloride

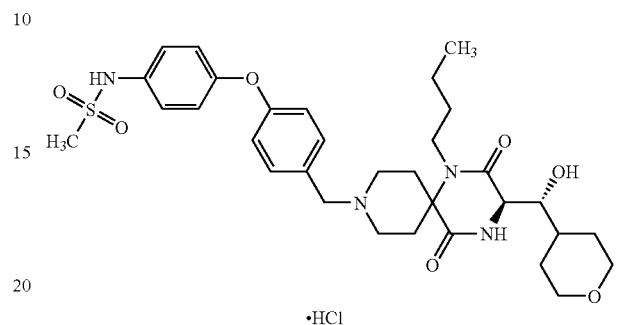

TLC: Rf 0.35 (ethyl acetate:methanol=4:1); NMR (CD$_3$OD):δ 7.53 (d, J=8.7 Hz, 2H), 7.29 (d, J=8.7 Hz, 2H), 7.06 (d, J=8.7 Hz, 2H), 7.03 (d, J=8.7 Hz, 2H), 4.33 (s, 2H), 4.12 (d, J=2.0 Hz, 1H), 4.04-3.92 (m, 3H), 3.72 (m, 1H), 3.54-3.38 (m, 5H), 3.30-3.13 (m, 2H), 2.95 (s, 3H), 2.51-2.26 (m, 3H), 2.16-2.00 (m, 2H), 1.89-1.70 (m, 3H), 1.50-1.15 (m, 5H), 0.95 (t, J=7.0 Hz, 3H).

EXAMPLE 78

(3R)-1-butyl-2,5-dioxo-3-((1R)-1-hydroxy-1-cyclopentylmethyl)-9-(3,5-dimethyl-1-phenylpyrazol-4-ylmethyl)-1,4,9-triazaspiro[5.5]undecane.2 hydrochloride

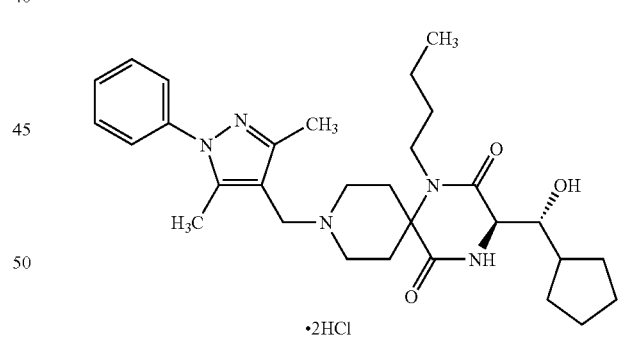

By the same procedure as described in Example 68 using the compound prepared in Reference example 15(5) instead of the compound prepared in Reference example 15, and using 4-formyl-3,5-dimethyl-1-phenylpyrazole instead of 3-formyl-6-phenyloxypyridine, title compound having the following physical data was obtained.

TLC: Rf 0.45 (ethyl acetate:methanol=4:1); NMR (CD$_3$OD):δ 7.64-7.51 (m, 5H), 4.34 (s, 2H), 4.05 (m, 1H), 4.01 (d, J=2.0 Hz, 1H), 3.79 (m, 1H), 3.63-3.52 (m, 3H), 3.39 (dd, J=9.9, 2.0 Hz, 1H), 3.30 (m, 1H), 2.64 (m, 1H), 2.48 (m, 1H), 2.47 (s, 3H), 2.42 (s, 3H), 2.37-2.12 (m, 2H), 1.90-1.82 (m, 2H), 1.74-1.15 (m, 11H), 0.96 (t, J=7.5 Hz, 3H).

EXAMPLE 78(1) TO 78(3)

By the same procedure as described in Example 78 using the corresponding aldehyde derivatives respectively instead of 4-formyl-3,5-dimethyl-1-phenylpyrazole, the following compounds were obtained.

EXAMPLE 78(1)

(3R)-1-butyl-2,5-dioxo-3-((1R)-1-hydroxy-1-cyclopentylmethyl)-9-(4-(4-(4-methoxyphenylmethylaminocarbonyl)phenylmethyl)-1,4,9-triazaspiro[5.5]undecane.hydrochloride

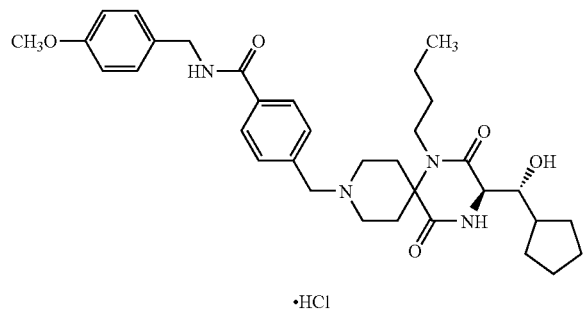

TLC: Rf 0.35 (chloroform:methanol=10:1); NMR (CD$_3$OD):δ 7.96 (d, J=8.7 Hz, 2H), 7.66 (d, J=8.7 Hz, 2H), 7.28 (d, J=8.7 Hz, 2H), 6.88 (d, J=8.7 Hz, 2H), 4.52 (s, 2H), 4.42 (s, 2H), 4.02 (m, 1H), 4.00 (d, J=1.8 Hz, 1H), 3.77 (s, 3H), 3.77 (m, 1H), 3.60-3.02 (m, 5H), 2.58-2.04 (m, 5H), 2.00-1.06 (m, 12H), 0.96 (t, J=7.5 Hz, 3H).

EXAMPLE 78(2)

(3R)-1-butyl-2,5-dioxo-3-((1R)-1-hydroxy-1-cyclopentylmethyl)-9-(4-(4-methylaminocarbonylphenyloxy)phenylmethyl)-1,4,9-triazaspiro[5.5]undecane.hydrochloride

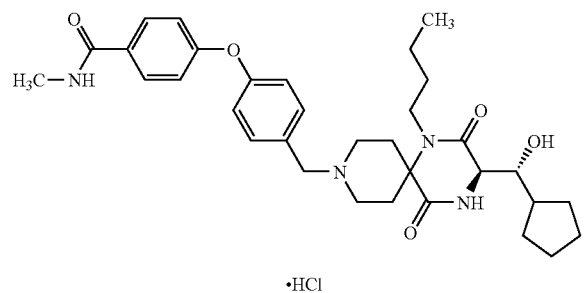

TLC: Rf 0.25 (chloroform:methanol=10:1); NMR (CD$_3$OD):δ 7.85 (d, J=8.7 Hz, 2H), 7.60 (d, J=8.7 Hz, 2H), 7.16 (d, J=8.7 Hz, 2H), 7.08 (d, J=8.7 Hz, 2H), 4.37 (s, 2H), 4.02 (m, 1H), 4.01 (d, J=2.1 Hz, 1H), 3.78 (m, 1H), 3.40-3.12 (m, 5H), 2.92 (s, 3H), 2.60-2.06 (m, 5H), 2.00-1.08 (m, 12H), 0.96 (t, J=7.2 Hz, 3H).

EXAMPLE 78(3)

(3R)-1-butyl-2,5-dioxo-3-((1R)-1-hydroxy-1-cyclopentylmethyl)-9-(4-(4-carboxyphenyloxy)phenylmethyl)-1,4,9-triazaspiro[5.5]undecane.hydrochloride

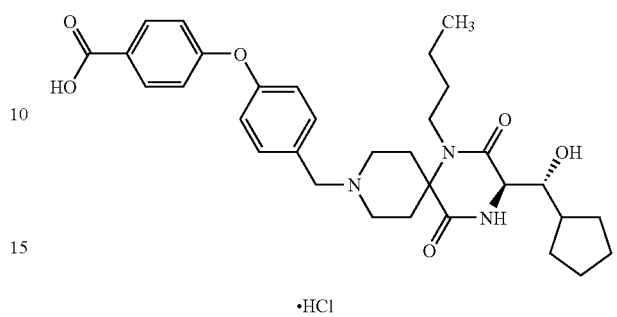

TLC: Rf 0.36 (chloroform:methanol=5:1); NMR (CD$_3$OD):δ 8.05 (d, J=8.7 Hz, 2H), 7.61 (d, J=8.7 Hz, 2H), 7.19 (d, J=8.7 Hz, 2H), 7.08 (d, J=8.7 Hz, 2H), 4.38 (s, 2H), 4.02 (m, 1H), 4.01 (d, J=1.8 Hz, 1H), 3.78 (m, 1H), 3.62-3.08 (m, 5H), 2.60-2.06 (m, 5H), 2.00-1.08 (m, 12H), 0.96 (t, J=6.9 Hz, 3H).

EXAMPLE 79

(3R)-1-propyl-2,5-dioxo-3-((1R)-1-hydroxy-2-methylpropyl)-9-(4-(4-methylaminocarbonylphenyloxy)phenylmethyl)-1,4,9-triazaspiro[5.5]undecane.hydrochloride

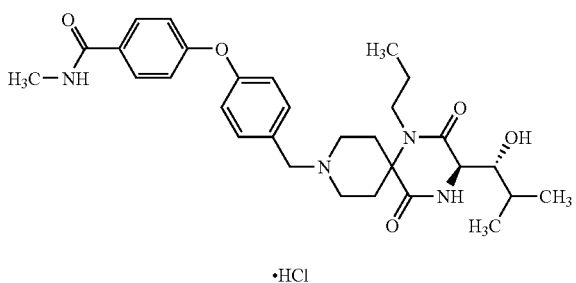

By the same procedure as described in Example 68 using the compound prepared in Reference example 15(6) instead of the compound prepared in Reference example 15, using 4-(4-methylaminocarobonylphenyloxy)benzaldehyde instead of 3-formyl-6-phenyloxypyridine, the title compound having the following physical data was obtained.

TLC: Rf 0.35 (chloroform:methanol=10:1); NMR (CD$_3$OD):δ 7.84 (d, J=9.0 Hz, 2H), 7.61 (d, J=8.7 Hz, 2H), 7.14 (d, J=8.7 Hz, 2H), 7.07 (d, J=9.0 Hz, 2H), 4.36 (s, 2H), 4.14 (d, J=1.8 Hz, 1H), 3.99 (m, 1H), 3.74 (m, 1H), 3.55-3.40 (m, 3H), 3.20 (m, 1H), 3.19 (dd, J=9.6, 1.8 Hz, 1H), 2.91 (s, 3H), 2.59-2.29 (m, 3H), 2.12 (m, 1H), 2.00 (m, 1H), 1.74 (m, 1H), 1.46 (m, 1H), 0.99 (d, J=6.6 Hz, 3H), 0.97 (d, J=6.6 Hz, 3H), 0.93 (t, J=7.5 Hz, 3H).

EXAMPLE 79(1) AND 79(2)

By the same procedure as described in Example 79 using the corresponding aldehyde derivatives respectively instead of 4-(4-methylaminocarobonylphenyloxy)benzaldehyde, the following compounds were obtained.

EXAMPLE 79(1)

(3R)-1-propyl-2,5-dioxo-3-((1R)-1-hydroxy-2-methylpropyl)-9-(3,5-dimethyl-1-cyclohexylpyrazol-4-ylmethyl)-1,4,9-triazaspiro[5.5]undecane.2hydrochlorie

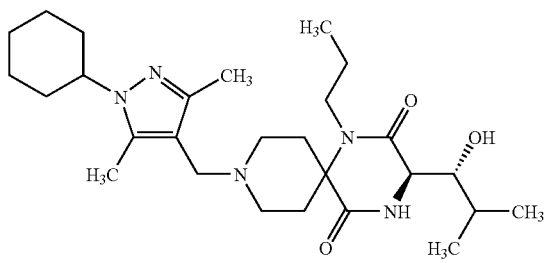

·2HCl

TLC: Rf 0.39 (chloroform:methanol=10:1); NMR (CD$_3$OD):δ 4.40 (m, 1H), 4.30 (s, 2H), 4.14 (d, J=2.1 Hz, 1H), 4.00 (m, 1H), 3.76 (m, 1H), 3.59-3.43 (m, 3H), 3.22 (m, 1H), 3.20 (dd, J=9.6, 2.1 Hz, 1H), 2.66 (m, 1H), 2.53 (s, 3H), 2.49 (s, 3H), 2.50-2.38 (m, 2H), 2.15-1.10 (m, 14H), 0.99 (d, J=6.6 Hz, 3H), 0.98 (d, J=6.6 Hz, 3H), 0.93 (t, J=7.5 Hz, 3H).

EXAMPLE 79(2)

(3R)-1-propyl-2,5-dioxo-3-((1R)-1-hydroxy-2-methylpropyl)-9-(4-(4-methoxyphenylmethylaminocarbonyl)phenylmethyl)-1,4,9-triazaspiro[5.5]undecane.hydrochloride

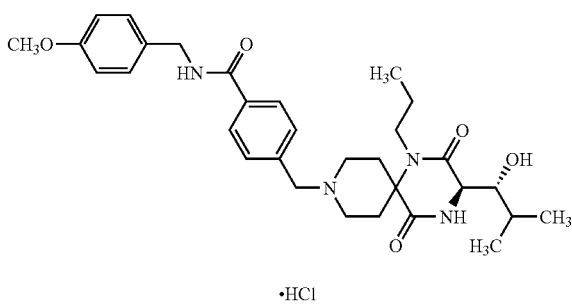

·HCl

TLC: Rf 0.41 (chloroform:methanol=10:1); NMR (CD$_3$OD):δ 7.95 (d, J=8.7 Hz, 2H), 7.69 (d, J=8.7 Hz, 2H), 7.27 (d, J=8.7 Hz, 2H), 6.87 (d, J=8.7 Hz, 2H), 4.51 (s, 2H), 4.42 (s, 2H), 4.13 (d, J=2.1 Hz, 1H), 4.01 (m, 1H), 3.76 (m, 1H), 3.76 (s, 3H), 3.54-3.39 (m, 3H), 3.19 (m, 1H), 3.18 (dd, J=9.6, 2.1 Hz, 1H), 2.58-2.26 (m, 3H), 2.10 (m, 1H), 1.99 (m, 1H), 1.72 (m, 1H), 1.46 (m, 1H), 0.98 (d, J=6.6 Hz, 3H), 0.96 (d, J=6.6 Hz, 3H), 0.92 (t, J=7.5 Hz, 3H).

EXAMPLE 80

(3R)-1-propyl-2,5-dioxo-3-((1R)-1-hydroxy-1-cyclohexylmethyl)-9-(4-(4-methylaminocarbonylphenyloxy)phenylmethyl)-1,4,9-triazaspiro[5.5]undecane-.hydrochloride

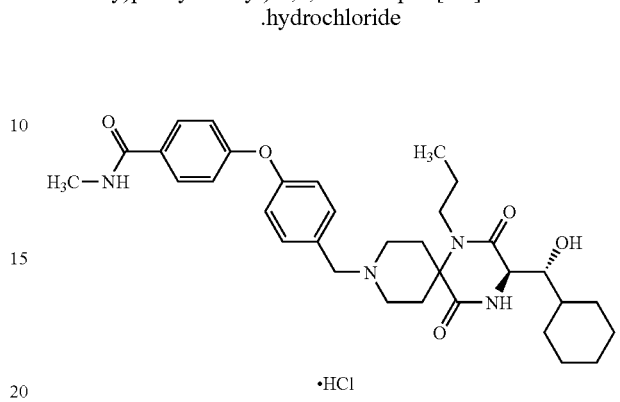

·HCl

By the same procedure as described in Example 68 using the compound prepared in Reference example 15(7) instead of the compound prepared in Reference example 15, and using 4-(4-methylaminocarobonylphenyloxy)benzaldehyde instead of 3-formyl-6-phenyloxypyridine, the title compound having the following physical data was obtained.

TLC: Rf 0.38 (chloroform:methanol=10:1); NMR (CD$_3$OD):δ 7.84 (d, J=9.0 Hz, 2H), 7.60 (d, J=9.0 Hz, 2H), 7.15 (d, J=9.0 Hz, 2H), 7.07 (d, J=9.0 Hz, 2H), 4.36 (s, 2H), 4.15 (d, J=2.1 Hz, 1H), 3.99 (m, 1H), 3.75 (m, 1H), 3.54-3.39 (m, 3H), 3.30-3.10 (m, 2H), 2.91 (s, 3H), 2.56-2.27 (m, 3H), 2.18-1.88 (m, 3H), 1.83-1.60 (m, 5H), 1.46 (m, 1H), 1.37-1.11 (m, 3H), 1.04-0.80 (m, 2H), 0.93 (t, J=7.5 Hz, 3H).

EXAMPLE 80(1) TO 80(5)

By the same procedure as described in Example 80 using the corresponding aldehyde derivatives respectively instead of 4-(4-methylaminocarobonylphenyloxy)benzaldehyde, the following compounds were obtained.

EXAMPLE 80(1)

(3R)-1-propyl-2,5-dioxo-3-((1R)-1-hydroxy-1-cyclohexylmethyl)-9-(3,5-dimethyl-1-cyclohexylpyrazol-4-ylmethyl)-1,4,9-triazaspiro[5.5]undecane.2hydrochloride

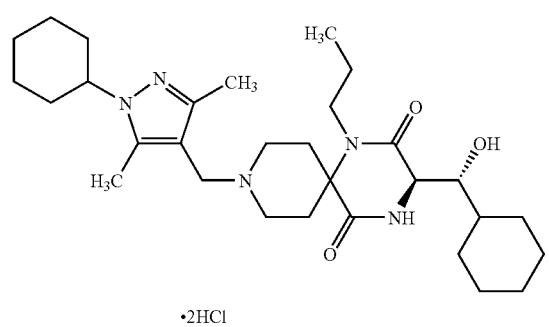

·2HCl

TLC: Rf 0.41 (chloroform:methanol=10:1); NMR (CD₃OD):δ 4.39 (m, 1H), 4.29 (s, 2H), 4.15 (d, J=2.1 Hz, 1H), 4.00 (m, 1H), 3.76 (m, 1H), 3.60-3.42 (m, 3H), 3.40-3.20 (m, 2H), 2.65 (m, 1H), 2.53 (s, 3H), 2.49 (s, 3H), 2.53-2.35 (m, 2H), 2.15-1.05 (m, 22H), 1.05-0.80 (m, 2H), 0.93 (t, J=7.2 Hz, 3H).

EXAMPLE 80(2)

(3R)-1-propyl-2,5-dioxo-3-((1R)-1-hydroxy-1-cyclohexylmethyl)-9-(4-(4-methoxyphenylmethylaminocarbonyl)phenylmethyl)-1,4,9-triazaspiro[5.5]undecane.hydrochloride

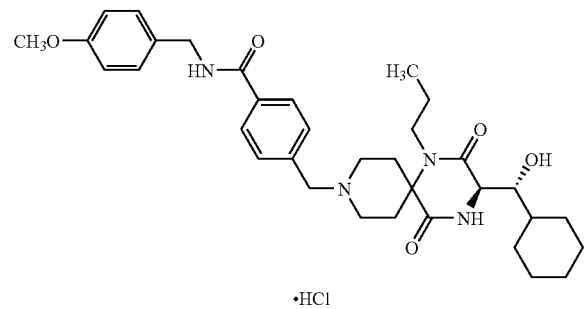

TLC: Rf 0.42 (chloroform:methanol=10:1); NMR (CD₃OD):δ 7.94 (d, J=8.7 Hz, 2H), 7.68 (d, J=8.7 Hz, 2H), 7.27 (d, J=8.7 Hz, 2H), 6.87 (d, J=8.7 Hz, 2H), 4.51 (s, 2H), 4.41 (s, 2H), 4.14 (d, J=1.8 Hz, 1H), 4.01 (m, 1H), 3.76 (m, 1H), 3.76 (s, 3H), 3.54-3.38 (m, 3H), 3.27 (dd, J=9.6, 1.8 Hz, 1H), 3.18 (m, 1H), 2.57-2.26 (m, 3H), 2.16-1.86 (m, 3H), 1.82-1.60 (m, 5H), 1.54-1.05 (m, 4H), 1.03-0.80 (m, 2H), 0.92 (t, J=7.5 Hz, 3H).

EXAMPLE 80(3)

(3R)-1-propyl-2,5-dioxo-3-((1R)-1-hydroxy-1-cyclohexylmethyl)-9-(3,5-dimethyl-1-(4-(N,N-dimethylaminocarbonyl)phenyl)pyrazol-4-ylmethyl)-1,4,9-triazaspiro[5.5]undecane.2hydrochloride

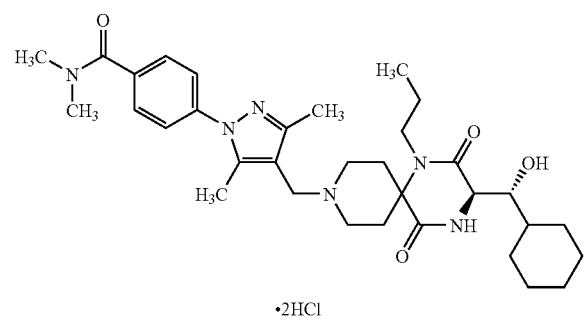

TLC: Rf 0.36 (chloroform:methanol=10:1); NMR (CD₃OD):δ 7.63 (s, 4H), 4.32 (s, 2H), 4.16 (d, J=2.1 Hz, 1H), 4.04 (m, 1H), 3.79 (m, 1H), 3.64-3.43 (m, 3H), 3.34-3.20 (m, 2H), 3.13 (s, 3H), 3.04 (s, 3H), 2.62 (m, 1H), 2.53-2.39 (m, 2H), 2.45 (s, 3H), 2.44 (s, 3H), 2.19-1.88 (m, 3H), 1.83-1.60 (m, 5H), 1.46 (m, 1H), 1.38-1.10 (m, 3H), 1.05-0.80 (m, 2H), 0.95 (t, J=7.5 Hz, 3H).

EXAMPLE 80(4)

(3R)-1-propyl-2,5-dioxo-3-((1R)-1-hydroxy-1-cyclohexylmethyl)-9-(4-(4-carboxyphenyloxy)phenylmethyl)-1,4,9-triazaspiro[5.5]undecane.hydrochloride

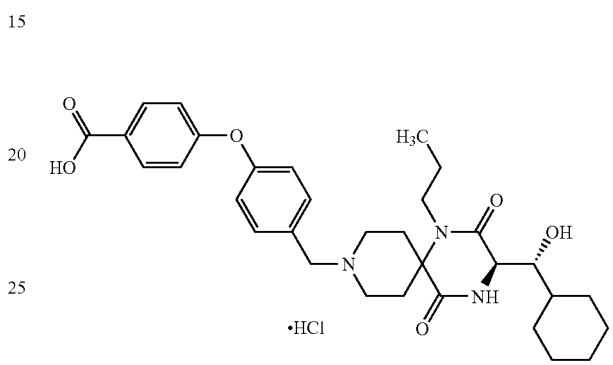

TLC: Rf 0.21 (chloroform:methanol:acetic acid=20:2:1); NMR (CD₃OD):δ 8.04 (d, J=9.0 Hz, 2H), 7.62 (d, J=8.4 Hz, 2H), 7.17 (d, J=8.4 Hz, 2H), 7.07 (d, J=9.0 Hz, 2H), 4.37 (s, 2H), 4.15 (d, J=2.1 Hz, 1H), 4.01 (m, 1H), 3.75 (m, 1H), 3.55-3.38 (m, 3H), 3.30-3.09 (m, 2H), 2.55-2.26 (m, 3H), 2.18-1.88 (m, 3H), 1.83-1.60 (m, 5H), 1.57-1.10 (m, 4H), 1.04-0.80 (m, 2H), 0.93 (t, J=7.5 Hz, 3H).

EXAMPLE 80(5)

(3R)-1-propyl-2,5-dioxo-3-((1R)-1-hydroxy-1-cyclohexylmethyl)-9-(4-(4-methoxycarbonylphenyloxy)phenylmethyl)-1,4,9-triazaspiro[5.5]undecane.hydrochloride

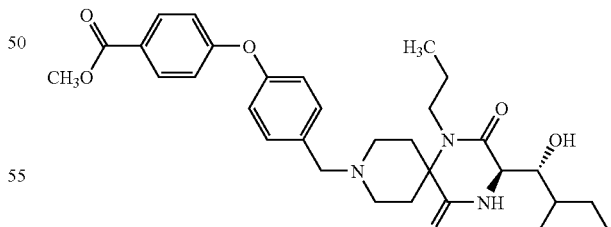

TLC: Rf 0.54 (chloroform:methanol=10:1); NMR (CD₃OD):δ 8.03 (d, J=8.7 Hz, 2H), 7.62 (d, J=8.7 Hz, 2H), 7.17 (d, J=8.7 Hz, 2H), 7.07 (d, J=8.7 Hz, 2H), 4.37 (s, 2H), 4.15 (d, J=2.1 Hz, 1H), 4.00 (m, 1H), 3.88 (s, 3H), 3.75 (m, 1H), 3.54-3.41 (m, 3H), 3.30-3.10 (m, 2H), 2.58-2.27 (m, 3H), 2.18-1.87 (m, 3H), 1.84-1.61 (m, 5H), 1.56-1.08 (m, 4H), 1.04-0.80 (m, 2H), 0.94 (t, J=7.2 Hz, 3H).

EXAMPLE 81

(3R)-1-propyl-2,5-dioxo-3-(1-cyclohexylmethylidene)-9-(4-(4-carboxyphenyloxy)phenylmethyl)-1,4,9-triazaspiro[5.5]undecane.hydrochloride

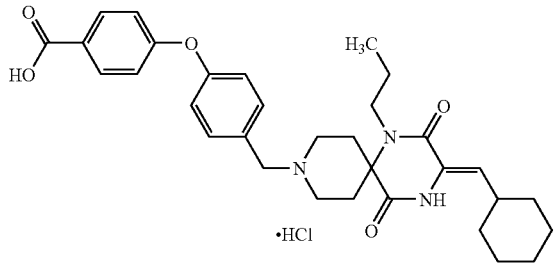

By the same procedure as described in Example 71 using the compound prepared in Example 80(5) instead of the compound prepared in Example 70(42), the title compound having the following physical data was obtained.

TLC: Rf 0.42 (chloroform:methanol=10:1); NMR (CD$_3$OD):δ 8.03 (d, J=8.7 Hz, 2H), 7.62 (d, J=8.7 Hz, 2H), 7.17 (d, J=8.7 Hz, 2H), 7.07 (d, J=8.7 Hz, 2H), 5.87 (d, J=10.5 Hz, 1H), 4.37 (s, 2H), 3.78-3.62 (m, 2H), 3.58-3.38 (m, 4H), 2.54-2.36 (m, 3H), 2.27-2.15 (m, 2H), 1.80-1.51 (m, 7H), 1.50-1.08 (m, 5H), 0.93 (t, J=7.2 Hz, 3H).

EXAMPLE 82

(3S)-1-propyl-2,5-dioxo-3-(2-methylpropyl)-9-(3,5-dimethyl-1-cyclohexylpyrazol-4-ylmethyl)-1,4,9-triazaspiro[5.5]undecane.2hydrochloride

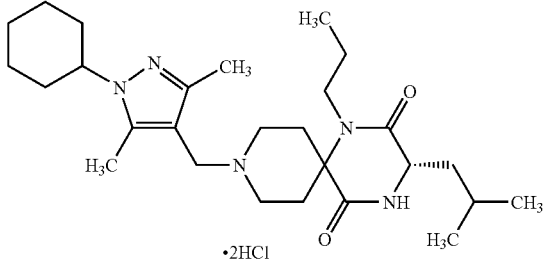

By the same procedure as described in Reference example 13→Reference example 14→Example 67→Reference example 15→Example 68 using the corresponding amino acid derivative instead of (2R,3R)-2-(t-butoxycarbonylamino)-3-hydroxy4-methylpentanoic acid, and using the corresponding amine derivative instead of n-butylamine, and using the corresponding aldehyde derivative instead of 3-formyl-6-phenyloxypyridine, the title compound having the following physical data was obtained.

TLC: Rf 0.51 (chloroform:methanol=10:1); NMR (CD$_3$OD):δ 4.39-4.27 (m, 1H), 4.28 (s, 2H), 4.01 (dd, J=7.8, 4.5 Hz, 1H), 3.92-3.68 (m, 2H), 3.61-3.50 (m, 2H), 3.47-3.38 (m, 2H), 2.68-2.50 (m, 2H), 2.49 (s, 3H), 2.45 (s, 3H), 2.25-2.05 (m, 2H), 2.03-1.20 (m, 15H), 0.98-0.89 (m, 9H).

EXAMPLE 82(1) TO 82(6)

By the same procedure as described in Example 82 using the corresponding aldehyde derivatives respectively instead of 1-cyclohexyl-4-formyl-3,5-dimethylpyrazole, the following compounds having the following physical data were obtained.

EXAMPLE 82(1)

(3S)-1-propyl-2,5-dioxo-3-(2-methylpropyl)-9-(4-(4-methylsulfonylaminophenyloxy)phenylmethyl)-1,4,9-triazaspiro[5.5]undecane.hydrochloride

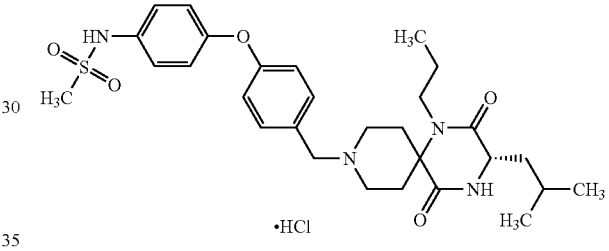

TLC: Rf 0.53 (chloroform:methanol=10:1); NMR (CD$_3$OD):δ 7.53 (d, J=8.7 Hz, 2H), 7.29 (d, J=9.0 Hz, 2H), 7.07 (d, J=8.7 Hz, 2H), 7.03 (d, J=9.0 Hz, 2H), 4.34 (s, 2H), 4.01 (dd, J=7.8, 4.8 Hz, 1H), 3.90-3.69 (m, 2H), 3.55-3.43 (m, 2H), 3.39-3.30 (m, 2H), 2.95 (s, 3H), 2.48-2.29 (m, 2H), 2.28-2.09 (m, 2H), 1.90-1.44 (m, 5H), 0.94 (d, J=6.6 Hz, 3H), 0.93 (d, J=6.6 Hz, 3H), 0.93 (t, J=7.5 Hz, 3H).

EXAMPLE 82(2)

(3S)-1-propyl-2,5-dioxo-3-(2-methylpropyl)-9-(3,5-dimethyl-1-(4-(2-(N,N-dimethylamino)ethylaminosulfonyl)phenyl)pyrazol-4-ylmethyl)-1,4,9-triazaspiro[5.5]undecane.3hydrochloride

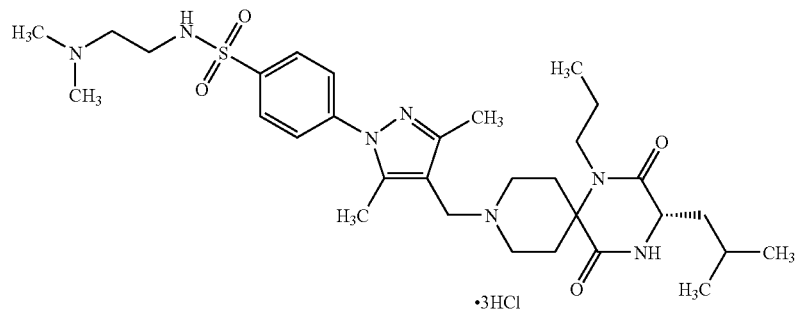

TLC: Rf 0.09 (chloroform:methanol:acetic acid=10:5:1); NMR (CD$_3$OD):δ 8.07 (d, J=9.0 Hz, 2H), 7.78 (d, J=9.0 Hz, 2H), 4.31 (s, 2H), 4.02 (dd, J=7.8, 4.5 Hz, 1H), 3.95-3.73 (m, 2H), 3.66-3.56 (m, 2H), 3.50-3.40 (m, 2H), 3.35-3.20 (m, 4H), 2.95 (s, 6H), 2.72-2.53 (m, 2H), 2.49 (s, 3H), 2.41 (s, 3H), 2.30-2.08 (m, 2H), 1.92-1.45 (m, 5H), 0.99-0.89 (m, 9H).

EXAMPLE 82(3)

(3S)-1-propyl-2,5-dioxo-3-cyclohexylmethyl-9-(3,5-dimethyl-1-cyclohexylpyrazol-4-ylmethyl)-1,4,9-triazaspiro[5.5]undecane.2hydrochlide

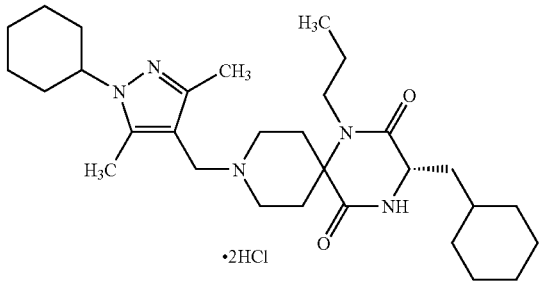

TLC: Rf 0.57 (chloroform:methanol=10:1); NMR (CD$_3$OD):δ 4.43-4.25 (m, 1H), 4.29 (s, 2H), 4.04 (dd, J=7.8, 4.5 Hz, 1H), 3.92-3.70 (m, 2H), 3.60-3.50 (m, 2H), 3.48-3.38 (m, 2H), 2.70-2.50 (m, 2H), 2.51 (s, 3H), 2.47 (s, 3H), 2.25-2.03 (m, 2H), 2.03-1.40 (m, 19H), 1.40-1.08 (m, 4H), 1.05-0.83 (m, 2H), 0.93 (t, J=7.5 Hz, 3H).

EXAMPLE 82(4)

(3S)-1-propyl-2,5-dioxo-3-cyclohexylmethyl-9-(4-(4-methylsulfonylaminophenyloxy)phenylmethyl)-1,4,9-triazaspiro[5.5]undecane.hydrochloride

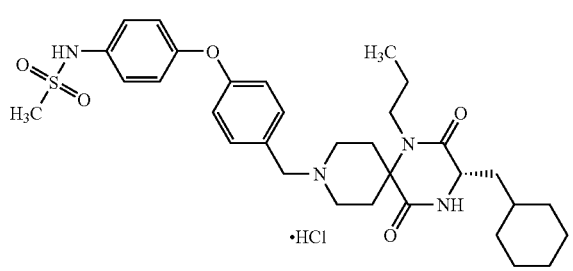

TLC: Rf 0.55 (chloroform:methanol=10:1); NMR (CD$_3$OD):δ 7.53 (d, J=9.0 Hz, 2H), 7.29 (d, J=9.0 Hz, 2H), 7.07 (d, J=9.0 Hz, 2H), 7.03 (d, J=9.0 Hz, 2H), 4.33 (s, 2H), 4.04 (dd, J=7.5, 4.5 Hz, 1H), 3.89-3.69 (m, 2H), 3.54-3.43 (m, 2H), 3.39-3.30 (m, 2H), 2.95 (s, 3H), 2.50-2.30 (m, 2H), 2.28-2.06 (m, 2H), 1.83-1.40 (m, 10H), 1.40-1.10 (m, 3H), 1.05-0.85 (m, 2H), 0.93 (t, J=7.5 Hz, 3H).

EXAMPLE 82(5)

1-butyl-2,5-dioxo-9-(4-(4-methylsulfonylaminophenyloxy)phenylmethyl)-1,4,9-triazaspiro[5.5]undecane.hydrochloride

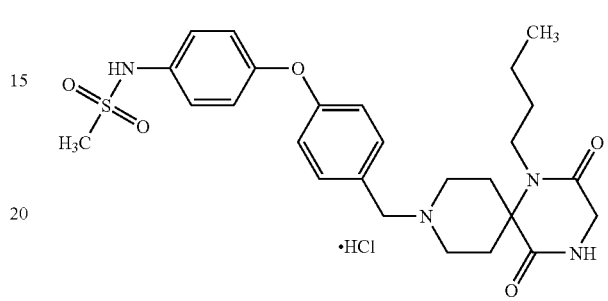

TLC: Rf 0.48 (chloroform:methanol=10:1); NMR (CD$_3$OD):δ 7.54 (d, J=8.7 Hz, 2H), 7.29 (d, J=8.7 Hz, 2H), 7.06 (d, J=8.7 Hz, 2H), 7.03 (d, J=8.7 Hz, 2H), 4.32 (s, 2H), 3.97 (s, 2H), 3.77-3.62 (m, 2H), 3.55-3.35 (m, 4H), 2.95 (s, 3H), 2.48-2.33 (m, 2H), 2.33-2.22 (m, 2H), 1.60-1.46 (m, 2H), 1.43-1.26 (m, 2H), 0.95 (t, J=7.2 Hz, 3H).

EXAMPLE 82(6)

1-butyl-2,5-dioxo-9-(3,5-dimethyl-1-cyclohexylpyrazol-4-ylmethyl)-1,4,9-triazaspiro[5.5]undecane.2hydrochloride

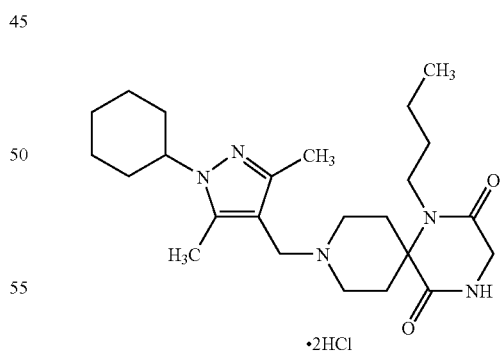

TLC: Rf 0.50 (chloroform:methanol=10:1); NMR (CD$_3$OD):δ 4.34 (m, 1H), 4.27 (s, 2H), 3.97 (s, 2H), 3.78-3.65 (m, 2H), 3.62-3.47 (m, 4H), 2.65-2.50 (m, 2H), 2.50 (s, 3H), 2.45 (s, 3H), 2.31-2.20 (m, 2H), 2.04-1.70 (m, 6H), 1.65-1.42 (m, 4H), 1.42-1.20 (m, 4H), 0.94 (t, J=7.2 Hz, 3H).

EXAMPLE 83

(3R)-1-(2-butynyl)-2,5-dioxo-3-((1R)-1-hydroxy-1-cyclohexylmethyl)-9-(3,5-dimethyl-1-phenylpyrazol-4-ylmethyl)-1,4,9-triazaspiro[5.5]undecane.2hydrochloride

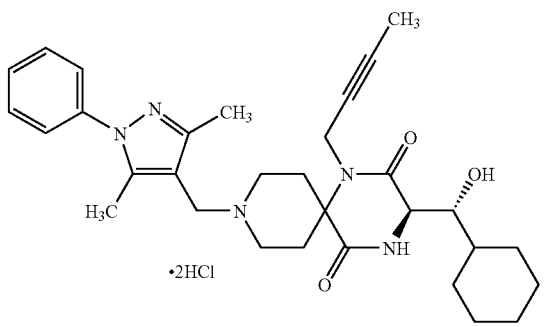

By the same procedure as described in Reference example 13→Reference example 14→Example 67 using (2R,3R)-2-(t-butoxycarbonylamino)-3-cyclohexyl-3-hydroxypropanoic acid instead of (2R,3R)-2-(t-butoxycarbonylamino)-3-hydroxy-4-methylpentanoic acid, 2-butynylamine instead of n-butylamine, N-(3,5-dimethyl-1-phenylpyrazol-4-yl)methyl-4-piperidone instead of N-benzyl-4-piperidone, and n-butylisonitrile instead of benzylisonitrile, the title compound having the following physical data was obtained.

TLC: Rf 0.45 (chloroform:methanol=10:1); NMR (CD$_3$OD):δ 7.60-7.45 (m, 5H), 4.44-4.28 (m, 3H), 4.21 (d, J=2.1 Hz, 1H), 4.10-3.94 (m, 2H), 3.79 (m, 1H), 3.66-3.54 (m, 2H), 3.32 (m, 1H), 2.74 (m, 1H), 2.56-2.34 (m, 8H), 2.24 (m, 1H), 2.08-1.90 (m, 2H), 1.84-1.62 (m, 7H), 1.44-1.12 (m, 3H), 1.05-0.82 (m, 2H).

EXAMPLE 83(1)

(3S)-1-(2-butynyl)-2,5-dioxo-3-((1S)-1-hydroxy-1-cyclohexylmethyl)-9-(3,5-dimethyl-1-phenylpyrazol-4-ylmethyl)-1,4,9-triazaspiro[5.5]undecane.2hydrochloride

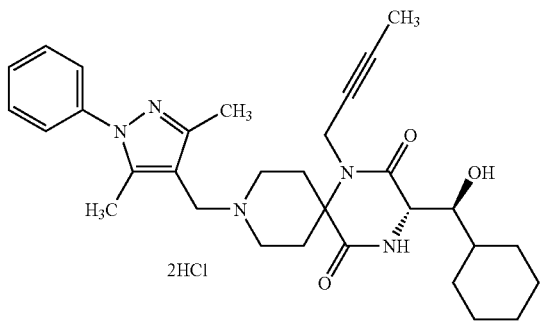

By the same procedure as described in Example 83, using (2S,3S)-2-(t-butoxycarbonylamino)-3-cyclohexyl-3-hydroxypropanoic acid instead of (2R,3R)-2-(t-butoxycarbonylamino)-3-cyclohexyl-3-hydroxypropanoic acid, the title compound having the following physical data was obtained.

TLC: Rf 0.45 (chloroform:methanol=10:1); NMR (CD$_3$OD):δ 7.60-7.45 (m, 5H), 4.44-4.28 (m, 3H), 4.21 (d, J=2.1 Hz, 1H), 4.10-3.94 (m, 2H), 3.79 (m, 1H), 3.66-3.54 (m, 2H), 3.32 (m, 1H), 2.74 (m, 1H), 2.56-2.34 (m, 8H), 2.24 (m, 1H), 2.08-1.90 (m, 2H), 1.84-1.62 (m, 7H), 1.44-1.12 (m, 3H), 1.05-0.82 (m, 2H).

EXAMPLE 84

(3S)-1-butyl-2,5-dioxo-3-cyclohexylmethyl-9-(2-(4-phenyloxyphenyl)ethyl)-1,4,9-triazaspiro[5.5]undecane.hydrochloride

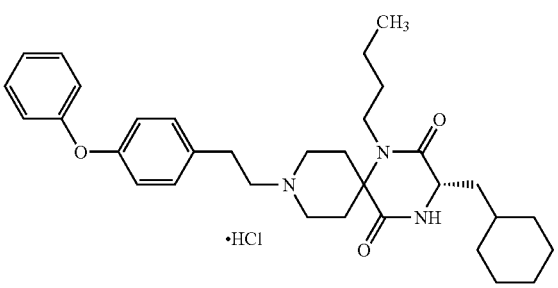

To the PS-TsCl-HL resin (brand name of Argonaut Technologies, catalog number 800366) (305 mg) was added a solution of 2-(4-phenyloxyphenyl)ethylalcohol (112 mg) in dichloromethane (2 ml) and pyridine (2 ml). The reaction mixture was stirred for 5 hours at room temperature. The resin was washed with dichloromethane for 3 times, dimethylformamide for 5 times, dimethylformamide:water=3:1 for 5 times, tetrahydrofuran for 3 times, dichloromethane for 3 times and acetonitrile for 3 times. The obtained resin was added a solution of the compound prepared in Reference example 15(2) (116 mg) in acetonitrile (5 ml) and diisopropylethylamine (0.366 ml). The reaction mixture was stirred for 18 hours at 70° C. After cooling it, the resin was washed with acetonitrile, the obtained washings were concentrated. The obtained residue was purified by column chromatography on silica gel (ethyl acetate:methanol=20:1), and the obtained compound was treated with hydrochloric acid to give the title compound (82 mg) having the following physical data was obtained.

TLC: Rf 0.54 (ethyl acetate:methanol=10:1); NMR (CD$_3$OD):δ 7.37-7.29 (m, 4H), 7.11 (t, J=7.2 Hz, 1H), 6.97-6.95 (m, 4H), 4.06 (d, J=7.5, 4.5 Hz, 1H), 3.88-3.77 (m, 2H), 3.65 (m, 2H), 3.46-3.36 (m, 4H), 3.13-3.07 (m, 2H), 2.48 (m, 2H), 2.28-2.14 (m, 2H), 1.80-1.21 (m, 15H), 0.98 (t, J=7.0 Hz, 3H), 0.99-0.91 (m, 2H).

EXAMPLE 84(1) and 84(2)

By the same procedure as described in Example 84 using the corresponding alcohol derivatives respectively instead of 2-(4-phenyloxyphenyl)ethylalcohol, and using the compound prepared in Reference example 15(1) instead of the compound prepared in Reference example 15(2), the following compounds having the following physical data were obtained.

EXAMPLE 84(1)

(3S)-1-butyl-2,5-dioxo-3-(2-methylpropyl)-9-(2-(4-phenyloxyphenyl)ethyl)-1,4,9-triazaspiro[5.5]undecane.hydrochloride

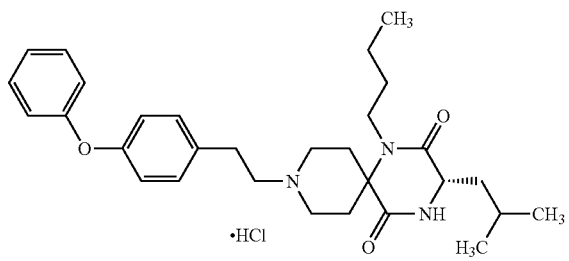

TLC: Rf 0.37 (ethyl acetate:methanol=10:1); NMR (CD$_3$OD):δ 7.37-7.29 (m, 4H), 7.11 (t, J=7.5 Hz, 1H), 6.98-6.95 (m, 4H), 4.03 (d, J=7.5, 4.5 Hz, 1H), 3.89-3.77 (m, 2H), 3.64 (m, 2H), 3.42-3.32 (m, 4H), 3.12-3.07 (m, 2H), 2.45 (m, 2H), 2.29-2.16 (m, 2H), 1.88-1.36 (m, 7H), 0.98 (t, J=7.0 Hz, 3H), 0.95 (d, J=6.3 Hz, 3H), 0.94 (d, J=6.3 Hz, 3H).

EXAMPLE 84(2)

(3S)-1-butyl-2,5-dioxo-3-(2-methylpropyl)-9-(2-(4-methoxyphenyl)ethyl)-1,4,9-triazaspiro[5.5]undecane.hydrochloride

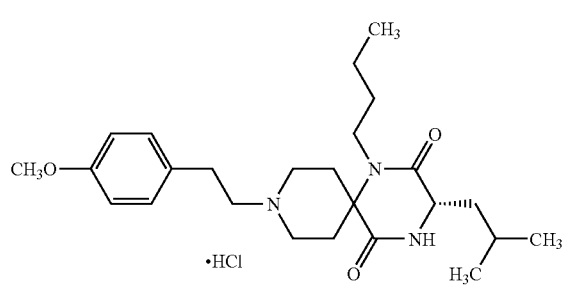

TLC: Rf 0.37 (ethyl acetate:methanol=10:1); NMR (CD$_3$OD):δ 7.22 (d, J=9.0 Hz, 2H), 6.90 (d, J=9.0 Hz, 2H), 4.01 (d, J=7.5, 4.5 Hz, 1H), 3.87-3.77 (m, 2H), 3.77 (s, 3H), 3.63 (m, 2H), 3.43-3.32 (m, 4H), 3.03 (m, 2H), 2.44 (m, 2H), 2.28-2.15 (m, 2H), 1.85-1.36(m, 7H), 0.97 (t, J=7.5 Hz, 3H), 0.95 (d, J=6.3 Hz, 3H), 0.94 (d, J=6.3 Hz, 3H).

EXAMPLE 85

(3S)-1-butyl-2,5-dioxo-3-cyclohexylmethyl-9-(4-ethoxycarbonylphenyl)-1,4,9-triazaspiro[5.5]undecane.hydrochloride

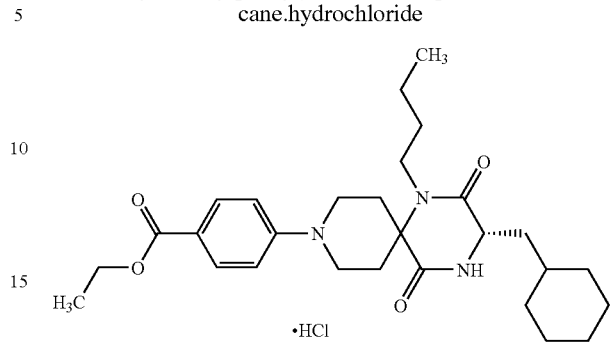

To a solution of the compound prepared in Reference example 15(2) (186 mg) in dimethylsulfoxide (3 ml) was added ethyl 4-fluorobenzoate (164 mg) and potassium carbonate (141 mg). The reaction mixture was stirred for 24 hours at 140° C. The reaction mixture was added water and t-butylmethyl ether and extracted. The extract was washed with saturated aqueous solution of sodium chloride, dried over anhydrous magnesium sulfate and concentrated. The obtained residue was purified by column chromatography on silica gel (hexane:ethyl acetate=4:1→3:1), and the obtained compound was treated with 4N hydrogen chloride/ethyl acetate to give the title compound (67 mg) having the following physical data.

TLC: Rf 0.27 (hexane:ethyl acetate=2:1); NMR (CD$_3$OD):δ 8.13 (d, J=8.7 Hz, 2H), 7.59 (d, J=8.7 Hz, 2H), 4.37 (q, J=7.2 Hz, 2H), 4.31-4.15 (m, 2H), 4.07 (dd, J=7.5, 4.5 Hz, 1H), 3.85-3.75 (m, 2H), 3.47-3.38 (m, 2H), 2.67-2.50 (m, 2H), 2.30-2.12 (m, 2H), 1.85-1.46 (m, 10H), 1.44-1.19 (m, 5H), 1.38 (t, J=7.2 Hz, 3H), 1.05-0.88 (m, 2H), 0.95 (t, J=7.2 Hz, 3H).

REFERENCE EXAMPLE 16

(3S)-1-butyl-2,5-dioxo-3-cyclohexylmethyl-9-benzyloxycarbonyl-1,4,9-triazaspiro[5.5]undecane

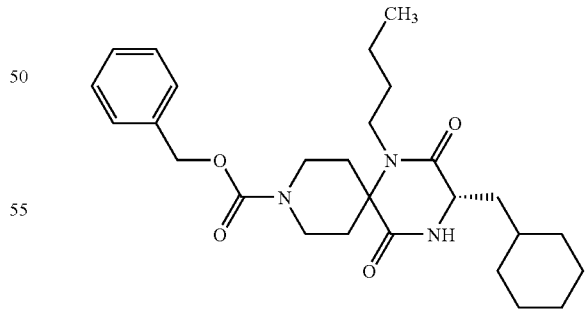

By the same procedure as described in Reference example 13→Reference example 14→Example 67 using (3S)-2-(t-butoxycarbonylamino)-3-cyclohexylpropanoic acid instead of (2R,3R)-2-(t-butoxycarbonylamino)-3-hydroxy-4-methylpentanoic acid, and N-benzyloxycarbonyl-4-piperidone instead of N-benzyl-4-piperidone, the title compound having the following physical data was obtained.

TLC: Rf 0.35 (hexane:ethyl acetate=1:1); NMR (CD$_3$OD):δ 7.39-7.31 (m, 5H), 6.48 (brs, 1H), 5.16 (s, 2H), 4.15 (brs, 2H), 4.00 (ddd, J=9.6, 4.8, 1.5 Hz, 1H), 3.76-3.16 (m, 4H), 2.02-1.12 (m, 19H), 1.08-0.88 (m, 2H), 0.92 (t, J=7.2 Hz, 3H).

REFERENCE EXAMPLE 17

(3S)-1-butyl-2,5-dioxo-3-cyclohexylmethyl-4-methyl-9-benzyloxycarbonyl-1,4,9-triazaspiro[5.5]undecane

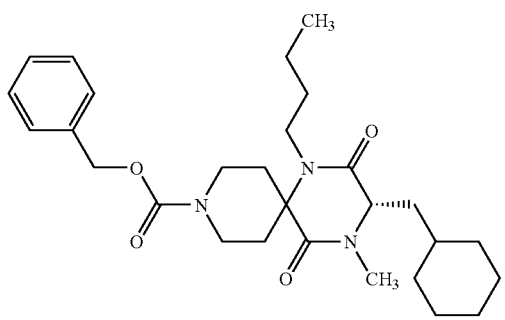

To a solution of the compound prepared in Reference example 16(1 g) in dimethylformamide (20 ml) was added 60% sodium hydride (164 mg) under ice bath. The reaction mixture was stirred for 1 hour at room temperature. The reaction mixture was added methyl iodide (0.3 ml) under ice bath. The reaction mixture was stirred overnight at room temperature. The reaction mixture was added ice water and extracted with ethyl acetate. The extract was washed with water and saturated aqueous solution of sodium chloride, dried over anhydrous magnesium sulfate and concentrated. The obtained residue was purified by column chromatography on silica gel (hexane:ethyl acetate=2:1) to give the title compound (1 g) having the following physical data.

TLC: Rf 0.34 (hexane:ethyl acetate=1:1); NMR (CD$_3$OD):δ 7.40-7.32 (m, 5H), 5.16 (s, 2H), 4.12 (brs, 2H), 3.91 (t, J=5.7 Hz, 1H), 3.88 (brs, 1H), 3.49 (m, 1H), 3.35 (m, 1H), 2.92 (s, 3H), 2.90 (m, 1H), 2.04-1.10 (m, 19H), 1.04-0.82 (m, 2H), 0.92 (t, J=7.2 Hz, 3H).

REFERENCE EXAMPLE 18

(3S)-1-butyl-2,5-dioxo-3-cyclohexylmethyl-4-methyl-1,4,9-triazaspiro[5.5]undecane.hydrochloride

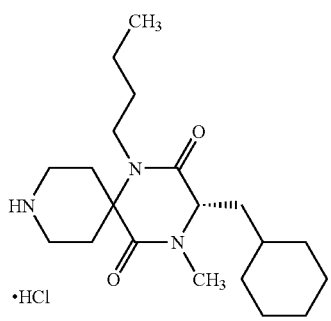

To a solution of the compound prepared in Reference example 17(1 g) in methanol (20 ml) was added 10% palladium on carbon (60 mg). Under an atmosphere of hydrogen, the reaction mixture was stirred for 8 hours at room temperature. The reaction mixture was filtrated through Celite (brand name) and the filtrate was added 4N hydrogen chloride ethyl acetate solution and concentrated to give the title compound (799 mg) having the following physical data.

TLC: Rf 0.28 (chloroform:methanol:acetic acid=90:10:1); NMR (CD$_3$OD):δ 4.05 (dd, J=7.5, 4.2 Hz, 1H), 4.01 (dt, J=4.2, 12.9 Hz, 1H), 3.59 (dt, J=3.3, 12.9 Hz, 1H), 3.51 (m, 1H), 3.40 (brd, J=5.4 Hz, 1H), 3.36 (brd, J=5.4 Hz, 1H), 3.25 (m, 1H), 2.93 (s, 3H), 2.37 (dt, J=5.4, 14.4 Hz, 1H), 2.32 (dt, J=5.4, 14.4 Hz, 1H), 2.11 (brd, J=14.4 Hz, 1H), 1.99 (brd, J=14.4 Hz, 1H), 1.86-1.14 (m, 15H), 1.07-0.87 (m, 2H), 0.97 (t, J=7.2 Hz, 3H).

EXAMPLE 86

(3S)-1-butyl-2,5-dioxo-3-cyclohexylmethyl-4-methyl-9-(4-phenyloxyphenymethyl)-1,4,9-triazaspiro[5.5]undecane.hydrochloride

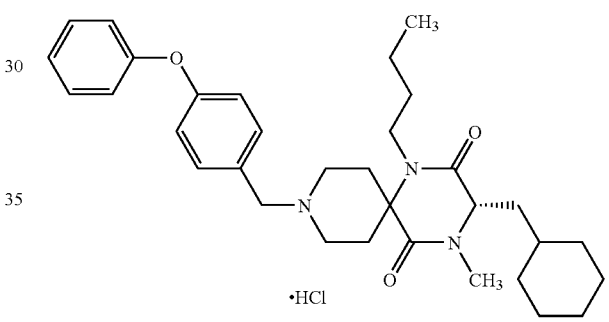

By the same procedure as described in Example 68 using the compound prepared in Reference example 18 instead of the compound prepared in Reference example 15, the title compound having the following physical data was obtained.

TLC: Rf 0.32 (ethyl acetate); NMR (CD$_3$OD):δ7.53 (d, J=8.7 Hz, 2H), 7.39 (dd, J=8.7, 7.5 Hz, 2H), 7.18 (t, J=7.5 Hz, 1H), 7.09-7.01 (m, 4H), 4.34 (s, 2H), 4.05 (m, 1H), 4.04 (dd, J=7.2, 3.9 Hz, 1H), 3.68-3.43 (m, 4H), 3.27 (m, 1H), 2.93 (s, 3H), 2.48 (dd, J=14.4, 5.4 Hz, 1H), 2.39 (dd, J=14.4, 5.4 Hz, 1H), 2.16 (brd, J=14.4 Hz, 1H), 2.03 (brd, J=14.4 Hz, 1H), 1.86-1.58 (m, 8H), 1.53-1.14 (m, 7H), 1.07-0.86 (m, 2H), 0.95 (t, J=7.5 Hz, 3H).

By the same procedure as described in Example 68 using the compound prepared in Reference example 15(3) instead of the compound prepared in Reference example 15, and using 4-(2-methylpropanoylamino)benzaldehyde instead of 3-formyl-6-phenyloxypyridine the title compound having the following physical data was obtained.

TLC: Rf 0.28 (chloroform:methanol=10:1); NMR (d$_6$-DMSO):δ 10.6 (s, 1H), 10.0 (s, 1H), 8.02 (m, 1H), 7.68 (d, J=8.7 Hz, 2H), 7.52 (d, J=8.7 Hz, 2H), 5.24 (s, 1H), 4.22 (s, 2H), 3.96 (m, 1H), 3.70 (m, 1H), 3.66-3.12 (m, 6H), 2.68-2.20 (m, 4H), 2.02-1.42 (m, 8H), 1.40-1.00 (m, 6H), 1.10 (d, J=6.9 Hz, 6H), 0.98-0.64 (m, 2H), 0.88 (t, J=6.9 Hz, 3H).

EXAMPLE 87(1) TO 87(6)

By the same procedure as described in Example 87 using the corresponding aldehyde derivatives respectively instead of 4-(2-methylpropanoylamino)benzaldehyde, the following compounds having the following physical data were obtained.

EXAMPLE 87(1)

(3R)-1-butyl-2,5-dioxo-3-((1R)-1-hydroxy-1-cyclohexylmethyl)-9-(4-(2-methoxyacetylamino)phenylmethyl)-1,4,9-triazaspiro[5.5]undecane.hydrochloride

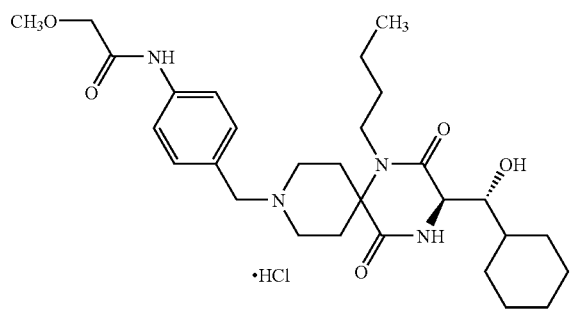

TLC: Rf 0.36 (chloroform:methanol=10:1); NMR (d$_6$-DMSO):δ 10.5 (s, 1H), 9.95 (s, 1H), 8.02 (m, 1H), 7.75 (d, J=8.4 Hz, 2H), 7.55 (d, J=8.4 Hz, 2H), 4.26 (s, 2H), 4.02 (s, 2H), 3.96 (m, 1H), 3.80-3.10 (m, 7H), 3.38 (s, 3H), 2.60-2.18 (m, 4H), 2.02-1.44 (m, 8H), 1.40-1.00 (m, 6H), 0.98-0.64 (m, 2H), 0.88 (t, J=7.2 Hz, 3H).

EXAMPLE 87(2)

(3R)-1-butyl-2,5-dioxo-3-((1R)-1-hydroxy-1-cyclohexylmethyl)-9-(4-(2-phenylacetylamino)phenylmethyl)-1,4,9-triazaspiro[5.5]undecane.hydrochloride

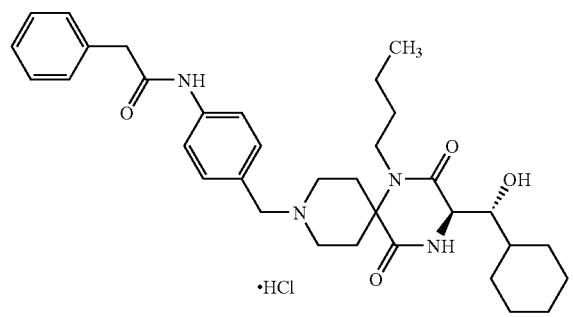

TLC: Rf 0.27 (chloroform:methanol=10:1); NMR (d$_6$-DMSO):δ 10.6 (s, 1H), 10.4 (s, 1H), 8.01 (m, 1H), 7.67 (d, J=9.0 Hz, 2H), 7.54 (d, J=9.0 Hz, 2H), 7.40-7.18 (m, 5H), 4.24 (s, 2H), 3.96 (s, 1H), 3.84-3.10 (m, 8H), 2.62-2.18 (m, 4H), 2.04-1.42 (m, 8H), 1.40-1.00 (m, 6H), 0.98-0.64 (m, 2H), 0.88 (t, J=7.2 Hz, 3H).

EXAMPLE 87(3)

(3R)-1-butyl-2,5-dioxo-3-((1R)-1-hydroxy-1-cyclohexylmethyl)-9-(4-(2-(4-fluorophenyl)acetylamino)phenylmethyl)-1,4,9-triazaspiro[5.5]undecane.hydrochlode

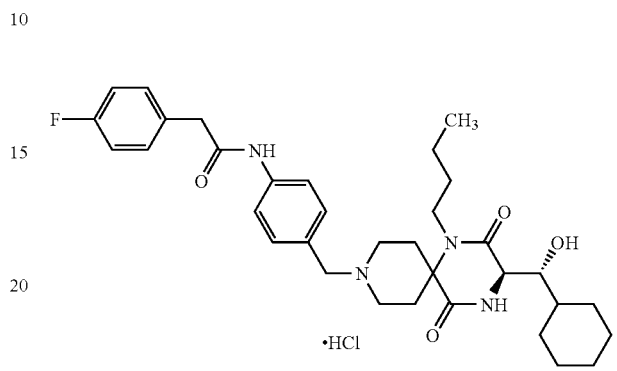

TLC: Rf 0.26 (chloroform:methanol=10:1); NMR (d$_6$-DMSO):δ 10.8 (s, 1H), 10.4 (s, 1H), 8.01 (m, 1H), 7.66 (d, J=8.4 Hz, 2H), 7.54 (d, J=8.4 Hz, 2H), 7.37 (dd, J=8.4, 5.4 Hz, 2H), 7.14 (t, J=8.4 Hz, 2H), 4.34-3.10 (m, 8H), 4.24 (s, 2H), 3.96 (s, 1H), 2.66-2.18 (m, 4H), 2.02-1.42 (m, 8H), 1.40-1.00 (m, 6H), 0.98-0.64 (m, 2H), 0.88 (t, J=6.9 Hz, 3H).

EXAMPLE 87(4)

(3R)-1-butyl-2,5-dioxo-3-((1R)-1-hydroxy-1-cyclohexylmethyl)-9-(4-(4-methoxycarbonylphenylaminocarbonyl)phenylmethyl)-1,4,9-triazaspiro[5.5]undecane.hydrochloride

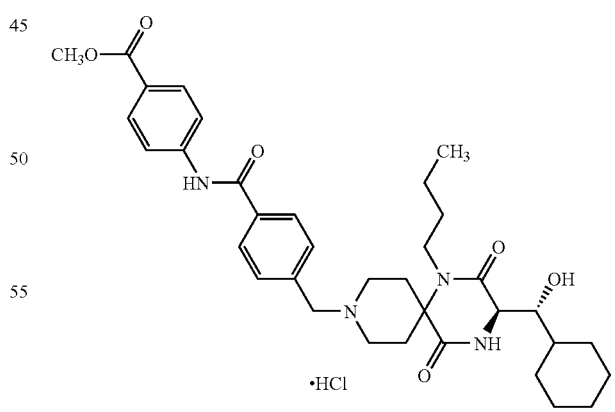

TLC: Rf 0.35 (chloroform:methanol=10:1); NMR (d$_6$-DMSO):δ 10.90 (br.s, 1H), 10.70 (s, 1H), 8.05 (m, 1H), 8.04 (d, J=8.4 Hz, 2H), 7.97 (s, 4H), 7.83 (d, J=8.4 Hz, 2H), 5.24 (m, 1H), 4.43 (s, 2H), 3.97 (m, 1H), 3.90-3.06 (m, 7H), 3.84 (s, 3H), 2.62-2.20 (m, 3H), 2.06-1.42 (m, 8H), 1.40-1.02 (m, 6H), 0.98-0.66 (m, 2H), 0.89 (t, J=6.9 Hz, 3H).

EXAMPLE 87(5)

(3R)-1-butyl-2,5-dioxo-3-((1R)-1-hydroxy-1-cyclo-hexylmethyl)-9-(4-(4-methoxyphenylmethyloxycarbonyl)phenylmethyl)-1,4,9-triazaspiro[5.5]undecane.hydrochloride

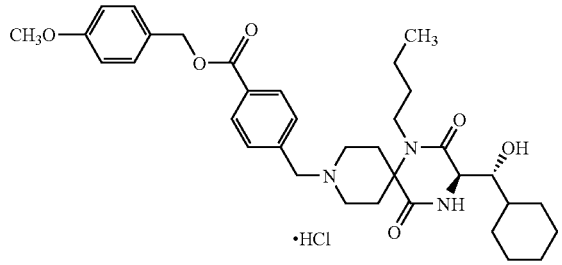

TLC: Rf 0.41 (chloroform:methanol=10:1); NMR (d6-DMSO):δ 10.6 (s, 1H), 8.03 (d, J=8.7 Hz, 2H), 8.02 (m, 1H), 7.78 (d, J=8.7 Hz, 2H), 7.42 (d, J=8.7 Hz, 2H), 6.96 (d, J=8.7 Hz, 2H), 5.30 (s, 2H), 5.24 (m, 1H), 4.42 (s, 2H), 3.96 (m, 1H), 3.86-3.10 (m, 7H), 3.76 (s, 3H), 2.64-2.20 (m, 3H), 2.02-1.42 (m, 8H), 1.40-1.00 (m, 6H), 0.96-0.68 (m, 2H), 0.88 (t, J=6.3 Hz, 3H).

EXAMPLE 87(6)

(3R)-1-butyl-2,5-dioxo-3-((1R)-1-hydroxy-1-cyclo-hexylmethyl)-9-(2-(4-methylaminocarbonylphenyloxy)pyridin-5-ylmethyl)-1,4,9-triazaspiro[5.5]undecane.hydrochloride

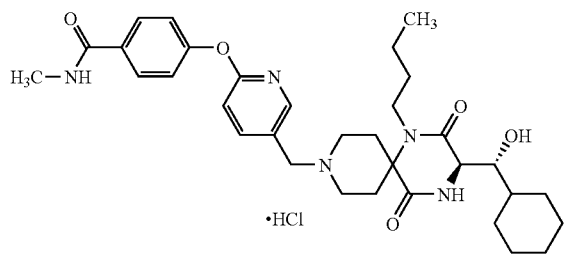

TLC: Rf 0.37 (chloroform:methanol=9:1); NMR (CD3OD):δ 8.35 (d, J=2.5 Hz, 1H), 8.15 (dd, J=8.5, 2.5 Hz, 1H), 7.89 (d, J=8.5 Hz, 2H), 7.23 (d, J=8.5 Hz, 2H), 7.14 (d, J=8.5 Hz, 1H), 4.39 (s, 2H), 4.15 (d, J=2.0 Hz, 1H), 4.00 (m, 1H), 3.75 (m, 1H), 3.57-3.45 (m, 3H), 3.30-3.22 (m, 2H), 2.92 (s, 3H), 2.56 (m, 1H), 2.50-2.39 (m, 2H), 2.14-1.91 (m, 3H), 1.80-1.60 (m, 5H), 1.50-1.10 (m, 6H), 1.00-0.87 (m, 2H), 0.95 (t, J=7.0 Hz, 3H).

EXAMPLE 88

(3S)-1-butyl-2,5-dioxo-3-((1S)-1-hydroxy-1-cyclo-hexylmethyl)-9-(4-(4-carboxyphenyloxy)phenylmethyl)-1,4,9-triazaspiro[5.5]undecane.hydrochloride

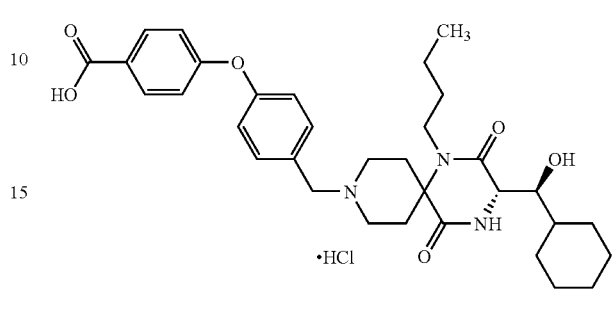

By the same procedure as described in Example 68 using the compound prepared in Reference example 15(9) instead of the compound prepared in Reference example 15, using 4-(4-carboxyphenyloxy)benzaldehyde instead of 3-formyl-6-phenyloxypyridine, the title compound having the following physical data was obtained.

TLC: Rf 0.45 (chloroform:methanol=5:1); NMR (d6-DMSO):δ 10.4 (s, 1H), 8.05 (m, 1H), 7.97 (d, J=8.7 Hz, 2H), 7.69 (d, J=8.7 Hz, 2H), 7.19 (d, J=8.7 Hz, 2H), 7.09 (d, J=8.7 Hz, 2H), 5.28 (d, J=6.9 Hz, 1H) 4.35 (s, 2H), 3.97 (m, 1H), 3.88-3.12 (m, 7H), 2.64-2.20 (m, 3H), 2.06-1.42 (m, 8H), 1.40-1.00 (m, 6H), 0.89 (t, J=6.9 Hz, 3H), 0.80 (m, 2H).

EXAMPLE 89

(3S)-1-butyl-2,5-dioxo-3-(pyridin-3-ylmethyl)-9-(4-(4-methylaminocarbonylphenyloxy)phenylmethyl)-1,4,9-triazaspiro[5.5]undecane.2hydrochloride

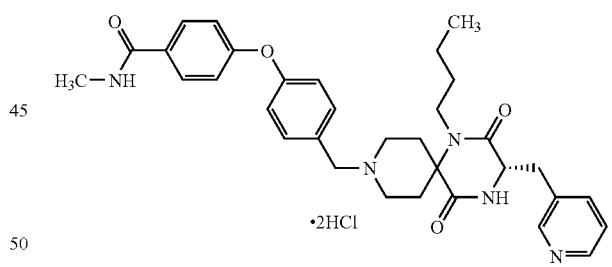

By the same procedure as described in Reference example 13→Reference example 14→Example 67 using N-t-butoxycarbonyl-3-pyridyl-L-alanine instead of (2R,3R)-2-(t-butoxycarbonylamino)-3-hydroxy-4-methylpentanoic acid, and using N-benzyl-4-piperidone-2-morpholinoethylisonitrile instead of N-(4-(4-methylaminocarobonylphenyloxy)phenylmethyl)-4-piperidone the title compound having the following physical data was obtained.

TLC: Rf 0.25 (chloroform:methanol=10:1); NMR (CD3OD):δ 8.82-8.76 (m, 2H), 8.55 (d, J=8.4 Hz, 1H), 8.06 (dd, J=7.8, 5.7 Hz, 1H), 7.84 (d, J=9.0 Hz, 2H), 7.63 (d, J=8.7 Hz, 2H), 7.15-7.02 (m, 4H), 4.55 (t, J=5.4 Hz, 1H), 4.33 (s, 2H), 3.80 (m, 1H), 3.68-3.28 (m, 7H), 2.91 (s, 3H), 2.56-2.40 (m, 2H), 2.20 (m, 1H), 1.70 (m, 1H), 1.50-1.20 (m, 4H), 0.92 (t, J=6.9 Hz, 3H).

EXAMPLE 89(1) TO 89(5)

By the same procedure as described in Example 89 using the corresponding amino acid derivatives respectively instead of N-t-butoxycarbonyl-3-pyridyl-L-alanine, the following compounds having the following physical data were obtained.

EXAMPLE 89(1)

(3S)-1-butyl-2,5-dioxo-3-phenylmethyl-9-(4-(4-methylaminocarbonylphenyloxy)phenylmethyl)-1,4,9-triazaspiro[5.5]undecane.hydrochloride

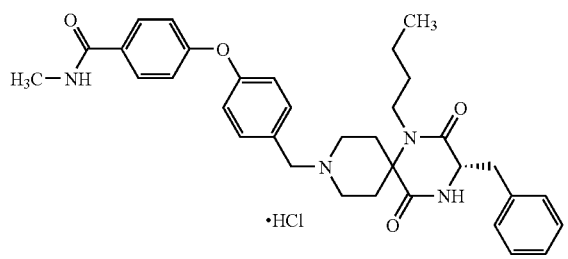

TLC: Rf 0.51 (chloroform:methanol:acetic acid=20:2:1); NMR (CD$_3$OD):δ 7.84 (d, J=9.0 Hz, 2H), 7.56 (d, J=9.0 Hz, 2H), 7.30-7.04 (m, 9H), 4.36 (dd, J=4.5, 3.6 Hz, 1H), 4.25 (s, 2H), 3.78 (m, 1H), 3.50-3.02 (m, 6H), 3.00-2.84 (m, 4H), 2.38 (m, 1H), 2.02 (m, 1H), 1.86 (m, 1H), 1.60-1.24 (m, 4H), 0.93 (t, J=6.9 Hz, 3H), 0.04 (m, 1H).

EXAMPLE 89(2)

(3S)-1-butyl-2,5-dioxo-3-(pyridin-2-ylmethyl)-9-(4-(4-methylaminocarbonylphenyloxy)phenylmethyl)-1,4,9-triazaspiro[5.5]undecane.2hydrochlori

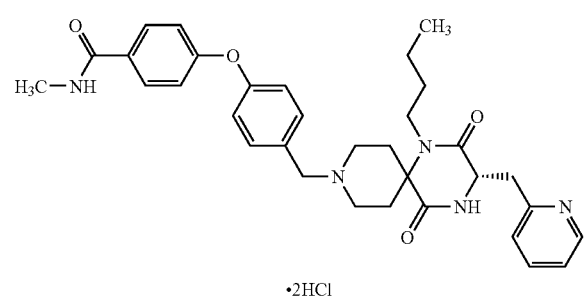

TLC: Rf 0.46 (chloroform:methanol:acetic acid=20:2:1); NMR (CD$_3$OD):δ 8.78 (dd, J=7.5, 1.5 Hz, 1H), 8.57 (td, J=7.8, 1.5 Hz, 1H), 8.06 (d, J=8.4 Hz, 1H), 8.00 (m, 1H), 7.84 (d, J=8.2 Hz, 2H), 7.64 (d, J=6.6 Hz, 2H), 7.16-7.04 (m, 4H), 4.68 (dd, J=6.9, 5.7 Hz, 1H), 4.38 (s, 2H), 3.84 (m, 1H), 3.70-3.32 (m, 7H), 2.91 (s, 3H), 2.64-2.44 (m, 2H), 2.16 (m, 1H), 2.06 (m, 1H), 1.50-1.22 (m, 4H), 0.91 (t, J=6.9 Hz, 3H).

EXAMPLE 89(3)

(3S)-1-butyl-2,5-dioxo-3-hydroxymethyl-9-(4-(4-methylaminocarbonylphenyloxy)phenylmethyl)-1,4,9-triazaspiro[5.5]undecane.hydrochloride

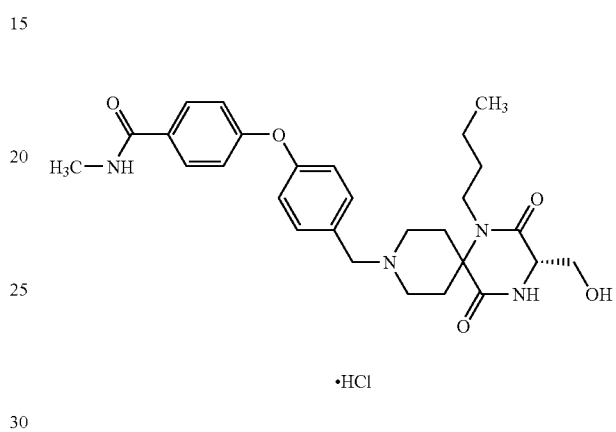

TLC: Rf 0.28 (chloroform:methanol:acetic acid=20:2:1); NMR (CD$_3$OD):δ 7.84 (d, J=9.0 Hz, 2H), 7.61 (d, J=8.7 Hz, 2H), 7.14 (d, J=8.7 Hz, 2H), 7.07 (d, J=9.0 Hz, 2H), 4.36 (s, 2H), 4.02-3.88 (m, 3H), 3.80-3.44 (m, 5H), 3.30 (m, 1H), 2.91 (s, 3H), 2.60-2.36 (m, 3H), 2.18 (m, 1H), 1.64 (m, 1H), 1.50-1.26 (m, 3H), 1.02-0.90 (m, 3H).

EXAMPLE 89(4)

(3S)-1-butyl-2,5-dioxo-3-(pyridin-1-oxido-2-ylmethyl)-9-(4-(4-methylaminocarbonylphenyloxy)phenylmethyl)-1,4,9-triazaspiro[5.5]undecane.hydrochloride

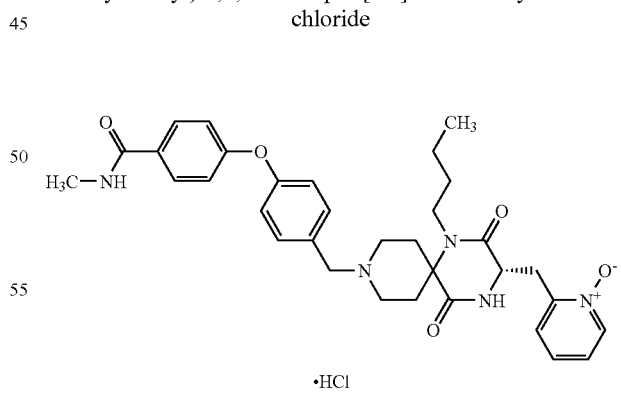

TLC: Rf 0.86 (chloroform:methanol:acetic acid=10:2:1); NMR (CD$_3$OD):δ 8.70 (dd, J=5.4, 1.0 Hz, 1H), 8.05 (td, J=6.6, 1.2 Hz, 1H), 7.92-7.72 (m, 4H), 7.64 (d, J=9.0 Hz, 2H), 7.20-7.06 (m, 4H), 4.67 (d, J=6.3 Hz, 1H), 4.36 (s, 2H), 3.86-3.18 (m, 8H), 2.91 (s, 3H), 2.70-2.26 (m, 2H), 2.34-2.06 (m, 2H), 1.60-1.44 (m, 2H), 1.44-1.24 (m, 2H), 0.92 (t, J=7.5 Hz, 3H).

EXAMPLE 89(5)

(3S)-1-butyl-2,5-dioxo-3-(pyridin-1-oxido-3-ylmethyl)-9-(4-(4-methylaminocarbonylphenyloxy)phenylmethyl)-1,4,9-triazaspiro[5.5]undecane.hydrochloride

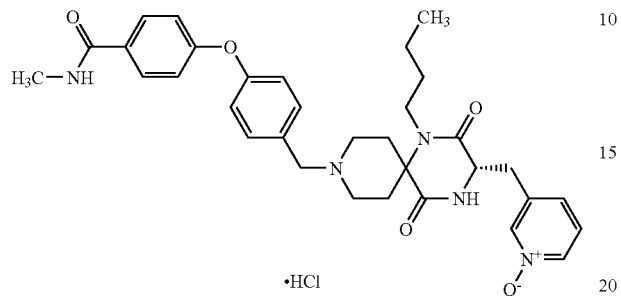

TLC: Rf 0.65 (chloroform:methanol:acetic acid 10:2:1); NMR (CD$_3$OD):δ 8.74-8.60 (m, 2H), 8.06 (d, J=7.8 Hz, 1H), 7.88 (m, 1H), 7.84 (d, J=8.7 Hz, 2H), 7.62 (d, J=8.7 Hz, 2H), 7.12 (d, J=8.7 Hz, 2H), 7.06 (d, J=8.7 Hz, 2H), 4.52 (t, J=5.1 Hz, 1H), 4.33 (s, 2H), 4.00 (m, 1H), 3.78 (m, 1H), 3.60 (m, 1H), 3.56-3.18 (m, 5H), 2.91 (s, 3H), 2.56-2.18 (m, 2H), 2.20 (m, 1H), 1.66 (m, 1H), 1.52-1.22 (m, 4H), 0.93 (t, J=6.9 Hz, 3H).

EXAMPLE 90

(3R)-1-(4-methoxyphenylmethyl)-2,5-dioxo-3-((1R)-1-hydroxy-1-cyclohexylmethyl)-9-(4-(4-methylaminocarbonylphenyloxy)phenylmethyl)-1,4,9-triazaspiro[5.5]undecane.hydrochloride

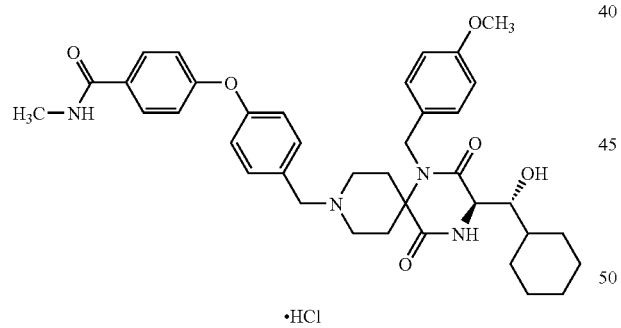

By the same procedure as described in Reference example 13→Reference example 14→Example 67 using (2R,3R)-2-(t-butoxycarbonylamino)-3-cyclohexyl-3-hydroxypropanoic acid instead of (2R,3R)-2-(t-butoxycarbonylamino)-3-hydroxy-4-methylpentanoic acid, and using 4-methoxybenzylamine instead of n-butylamine, using N-(4-(4-methylaminocarobonylphenyloxy)phenylmethyl)-4-piperidone instead of N-benzyl-4-piperidone, using 2-morpholinoethylisonitrile instead of benzylisonitrile, the title compound having the following physical data was obtained.

TLC: Rf 0.24 (chloroform:methanol=10:1); NMR (CD$_3$OD):δ 7.84 (d, J=8.7 Hz, 2H), 7.56 (d, J=8.7 Hz, 2H), 7.18 (d, J=8.7 Hz, 2H), 7.13 (d, J=8.7 Hz, 2H), 7.07 (d, J=8.7 Hz, 2H), 6.85 (d, J=8.7 Hz, 2H), 4.48 (m, 1H), 4.33 (s, 4H), 3.96 (m, 1H), 3.75 (m, 1H), 3.75 (s, 3H), 3.58-3.18 (m, 3H), 2.92 (s, 3H), 2.66-2.28 (m, 3H), 2.16-1.58 (m, 7H), 1.40-0.82 (m, 5H).

EXAMPLE 90(1) TO 90(4)

By the same procedure as described in Example 90 using the corresponding amines instead of 4-methoxybenzylamine, the title compounds were obtained.

EXAMPLE 90(1)

(3R)-1-phenylmethyl-2,5-dioxo-3-((1R)-1-hydroxy-1-cyclohexylmethyl)-9-(4-(4-methylaminocarbonylphenyloxy)phenylmethyl)-1,4,9-triazaspiro[5.5]undecane.hydrochloride

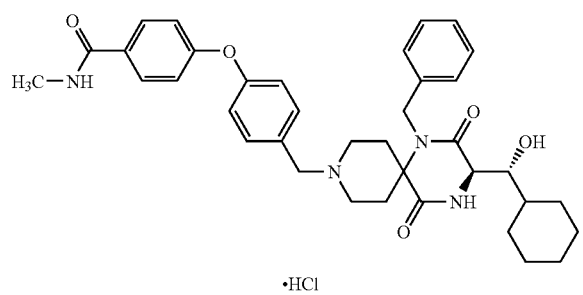

TLC: Rf 0.28 (chloroform:methanol=10:1); NMR (CD$_3$OD):δ 7.85 (d, J=8.7 Hz, 2H), 7.56 (d, J=8.7 Hz, 2H), 7.40-7.02 (m, 5H), 7.13 (d, J=8.7 Hz, 2H), 7.06 (d, J=8.7 Hz, 2H), 4.58 (m, 1H), 4.33 (s, 4H), 3.96 (m, 1H), 3.76 (m, 1H), 3.54-3.18 (m, 3H), 2.92 (s, 3H), 2.64-2.28 (m, 3H), 2.14-1.58 (m, 7H), 1.40-0.80 (m, 5H).

EXAMPLE 90(2)

(3R)-1-(2-methoxyethyl)-2,5-dioxo-3-((1R)-1-hydroxy-1-cyclohexylmethyl)-9-(4-(4-methylaminocarbonylphenyloxy)phenylmethyl)-1,4,9-triazaspiro[5.5]undecane.hydrochloride

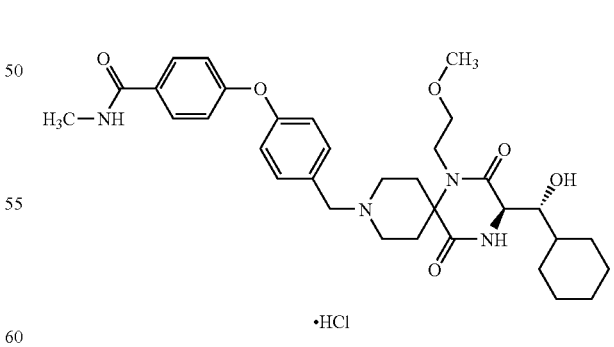

TLC: Rf 0.35 (chloroform:methanol=10:1); NMR (CD$_3$OD):δ 7.84 (d, J=8.7 Hz, 2H), 7.57 (d, J=8.7 Hz, 2H), 7.15 (d, J=8.7 Hz, 2H), 7.07 (d, J=8.7 Hz, 2H), 4.36 (s, 2H), 4.18 (d, J=2.1 Hz, 1H), 3.98 (m, 1H), 3.86-3.18 (m, 8H), 3.31 (s, 3H), 2.91 (s, 3H), 2.60-1.58 (m, 10H), 1.42-0.80 (m, 5H).

EXAMPLE 90(3)

(3R)-1-(pyridin-2-ylmethyl)-2,5-dioxo-3-((1R)-1-hydroxy-1-cyclohexylmethyl)-9-(4-(4-methylaminocarbonylphenyloxy)phenylmethyl)-1,4,9-triazaspiro[5.5]undecane.2hydrochloride

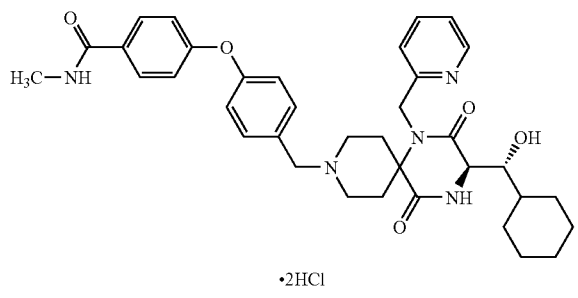

·2HCl

TLC: Rf 0.83 (chloroform:methanol:acetic acid=10:2:1); NMR (CD$_3$OD):δ 8.76 (dd, J=6.6, 1.8 Hz, 1H), 8.54 (td, J=8.4, 1.8 Hz, 1H), 8.12 (d, J=8.4 Hz, 1H), 7.93 (dd, J=8.4, 6.6 Hz, 1H), 7.83 (d, J=9.0 Hz, 2H), 7.65 (d, J=8.7 Hz, 2H), 7.14-7.02 (m, 4H), 5.34-5.20 (m, 2H), 4.38 (s, 2H), 4.30 (d, J=1.8 Hz, 1H), 3.96 (m, 1H), 3.78 (m, 1H), 3.52-3.38 (m, 2H), 3.32 (m, 1H), 2.90 (s, 3H), 2.72-2.54 (m, 3H), 2.30 (m, 1H), 2.06 (m, 1H), 1.88 (m, 1H), 1.82-1.50 (m, 4H), 1.28-1.06 (m, 3H), 1.06-0.80 (m, 2H).

EXAMPLE 90(4)

(3R)-1-(pyridin-3-ylmethyl)-2,5-dioxo-3-((1R)-1-hydroxy-1-cyclohexylmethyl)-9-(4-(4-methylaminocarbonylphenyloxy)phenylmethyl)-1,4,9-triazaspiro[5.5]undecane.2hydrochloride

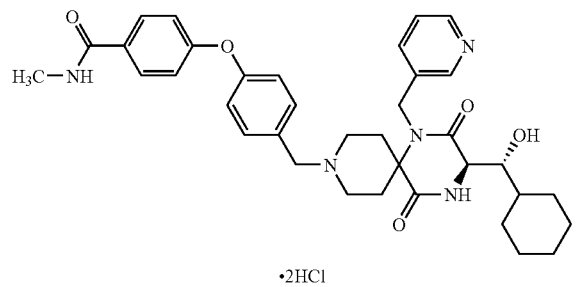

·2HCl

TLC: Rf 0.58 (chloroform:methanol:acetic acid=10:2:1); NMR (CD$_3$OD):δ 8.89 (s, 1H), 8.73 (d, J=5.7 Hz, 1H), 8.64 (d, J=8.1 Hz, 1H), 8.03 (dd, J=8.1, 5.7 Hz, 1H), 7.83 (d, J=8.7 Hz, 2H), 7.65 (d, J=8.4 Hz, 2H), 7.18-7.02 (m, 4H), 5.19 (d, J=18.0 Hz, 1H), 5.11 (d, J=18.0 Hz, 1H), 4.40-4.26 (m, 3H), 3.90 (m, 1H), 3.78 (m, 1H), 3.50-3.38 (m, 2H), 3.30 (m, 1H), 2.90 (s, 3H), 2.74-2.42 (m, 3H), 2.20-1.88 (m, 3H), 1.82-1.56 (m, 4H), 1.32-1.06 (m, 3H), 1.02-0.80 (m, 2H).

REFERENCE EXAMPLE 19

(3R)-1-butyl-2,5-dioxo-3-cyclohexylmethyl-1,4,9-triazaspiro[5.5]undecane.hydrochloride

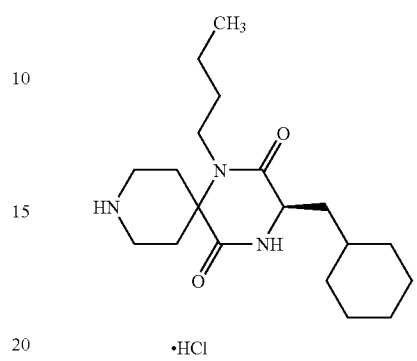

·HCl

By the same procedure as described in Reference example 13→Reference example 14→Example 67→Reference example 15 using N-t-butoxycarbonyl-D-cyclohexylalanine instead of (2R,3R)-2-(t-butoxycarbonylamino)-3-hydroxy-4-methylpentanoic acid, the title compound having the following physical data was obtained.

TLC: Rf 0.59 (n-butanol:acetic acid:H$_2$O=4:2:1); NMR (CD$_3$OD):δ 4.05 (dd, J=7.5, 4.8 Hz, 1H), 3.83-3.69 (m, 2H), 3.42-3.37 (m, 4H), 2.39-2.07 (m, 4H), 1.80-1.49 (m, 10H), 1.45-1.19 (m, 5H), 1.03-0.91 (m, 5H); Optical rotation: [α]$_D$+35.5 (c 1.05, methanol, 21° C.).

EXAMPLE 91

(3R)-1-butyl-2,5-dioxo-3-cyclohexylmethyl-9-(4-(4-carboxyphenyloxy)phenylmethyl)-1,4,9-triazaspiro[5.5]undecane.hydrochloride

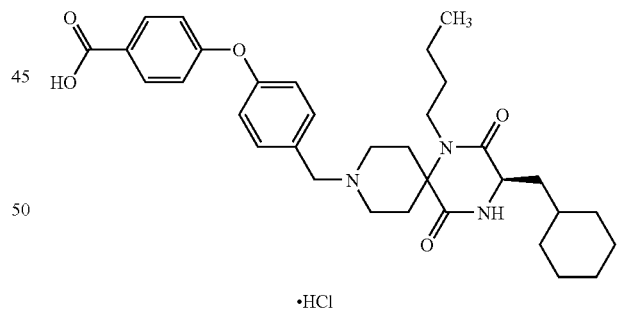

·HCl

By the same procedure as described in Example 68 using the compound prepared in Reference example 19 instead of the compound prepared in Reference example 15, and using 4-(4-carboxyphenyloxy)benzaldehyde instead of 3-formyl-6-phenyloxypyridine, the title compound having the following physical data was obtained.

TLC: Rf 0.36 (chloroform:methanol=10:1); NMR (d$_6$-DMSO):δ 10.92 (br-s, 1H), 8.41 (br-s, 1H), 7.95 (d, J=8.7 Hz, 2H), 7.69 (d, J=8.7 Hz, 2H), 7.17 (d, J=8.7 Hz, 2H), 7.07 (d, J=8.7 Hz, 2H), 4.32 (s, 2H), 3.91 (m, 1H), 3.59-3.35 (m, 6H), 2.56-2.35 (m, 2H), 2.10 (m, 1H), 1.98 (m, 1H), 1.72-1.35 (m, 10H), 1.32-1.14 (m, 5H), 0.90-0.78 (m, 5H).

EXAMPLE 92

(3S)-1-butyl-2,5-dioxo-3-(pyridin-1-oxido-2-ylmethyl)-9-(4-(4-methylaminocarbonylphenyloxy)phenylmethyl)-1,4,9-triazaspiro[5.5]undecane.9-oxide

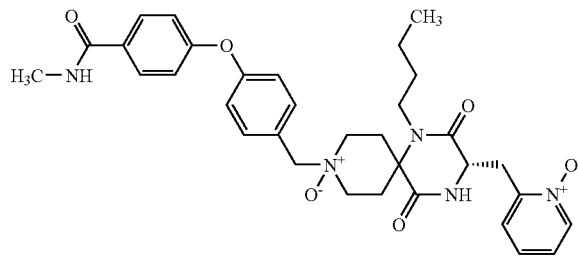

To a solution of the free form of the compound prepared in Example 89(2) (117 mg) in chloroform (10 ml) was added dropwise the solution (4 ml) of 3-chloroperbenzoic acid (114 mg). After the reaction mixture was stirred overnight at room temperature, the solvent was evaporated. The obtained residue was purified by column chromatography on silica gel (Fuji Silysia Chemical Ltd., N H-DM1020, chloroform) to give the title compound (100 mg) having the following physical data.

TLC: Rf 0.23 (chloroform:methanol:acetic acid=20:2:1); NMR (CDCl$_3$):δ 8.81 (s, 1H), 8.28 (dd, J=6.0, 1.2 Hz, 1H), 7.77 (d, J=8.7 Hz, 2H), 7.52-7.46 (m, 3H), 7.32-7.22 (m, 2H), 7.16-6.98 (m, 4H), 6.32 (m, 1H), 4.40-4.24 (m, 4H), 3.87 (dd, J=11.0, 5.1 Hz, 1H), 3.66-3.34 (m, 4H), 3.16-2.86 (m, 4H), 3.01 (d, J=4.5 Hz, 3H), 1.84-1.20 (m, 6H), 0.90 (t, J=7.2 Hz, 3H).

REFERENCE EXAMPLE 20

1-butyl-2,5-dioxo-3-(morpholin-4-ylmethyl)-1,4,9-triazaspiro[5.5]undecane.2hydrochloride

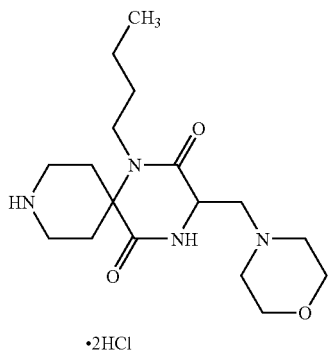

By the same procedure as described in Reference example 13→Reference example 14→Example 67→Reference example 15 using 2-(t-butoxycarbonylamino)-3-(morpholin-4-yl)propanoic acid instead of (2R,3R)-2-(t-butoxycarbonylamino)-3-hydroxy-4-methylpentanoic acid, the title compound having the following physical data was obtained.

TLC: Rf 0.07 (chloroform:methanol=10:1); NMR (CD$_3$OD):δ 4.76 (dd, J=8.4, 4.8 Hz, 1H), 4.05-3.82 (m, 6H), 3.71-3.40 (m, 10H), 2.41 (m, 1H), 2.31-2.21 (m, 3H), 1.98-1.54 (m, 2H), 1.46-1.36 (m, 2H), 0.97 (t, J=7.5 Hz, 3H).

EXAMPLE 93

1-butyl-2,5-dioxo-3-(morpholin-4-ylmethyl)9-(4-(4-methylaminocarbonylphenyloxy)phenylmethyl)-1,4,9-triazaspiro[5.5]undecane.2hydrochloride

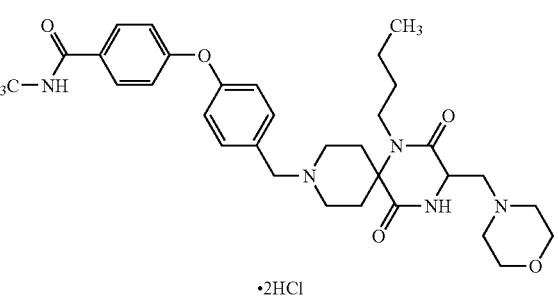

By the same procedure as described in Example 68 using the compound prepared in Reference example 20 instead of the compound prepared in Reference example 15, and using 4-(4-methylaminocarobonyl)phenyloxybenzaldehyde instead of 3-formyl-6-phenyloxypyridine, the title compound having the following physical data was obtained.

TLC: Rf 0.41 (chloroform:methanol=10:1); NMR (CD$_3$OD):δ 7.84 (d, J=9.0 Hz, 2H), 7.63 (d, J=8.5 Hz, 2H), 7.14 (d, J=8.5 Hz, 2H), 7.07 (d, J=9.0 Hz, 2H), 4.73 (dd, J=8.1, 5.1 Hz, 1H), 4.37 (s, 2H), 4.10-3.85 (m, 5H), 3.76-3.43 (m, 9H), 3.40-3.20 (m, 2H), 2.91 (s, 3H), 2.63-2.43 (m, 2H), 2.33-2.24 (m, 2H), 1.65-1.50 (m, 2H), 1.44-1.34 (m, 2H), 0.96 (t, J=7.0 Hz, 3H).

EXAMPLE 94

(3R)-1-butyl-2,5-dioxo-3-((1R)-1-hydroxy-1-cyclohexylmethyl)-9-(4-(4-(N-hydroxycarbamoyl)phenyloxy)phenylmethyl)-1,4,9-triazaspiro[5.5]undecane-.hydrochloride

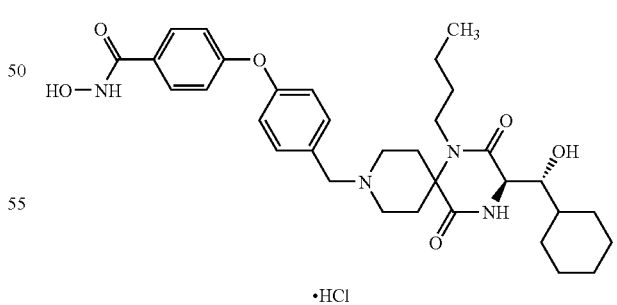

To a suspension of the compound prepared in Example 75(54) (120 mg) and (1-methoxyisopropyl)oxyamine (31 mg) in dimethylformamide (1.6 ml) was added diisopropylethylamine (68 μl), 1-ethyl-3-[3-(dimethylamino)propyl] carbodiimide.hydrochloride (56 mg) and 1-hydroxybenztriazole (40 mg). The reaction mixture was stirred for 1 hour at room temperature. The reaction mixture was added 1N

443 hydrochloric acid (2 ml) and stirred for 15 minutes at room temperature. The reaction mixture was diluted with water and extracted with ethyl acetate. The extract was washed with water, saturated aqueous solution of sodium bicarbonate and saturated aqueous solution of sodium chloride and the obtained residue was dried over anhydrous sodium sulfate and concentrated. To a solution of the obtained residue in methanol was added 4N hydrogen chloride/ethyl acetate solution and concentrated. The obtained residue was washed with ethyl acetate to give the title compound (116 mg) having the following physical data.

TLC: Rf 0.43 (chloroform:methanol:acetic acid=20:4:1); NMR (CD$_3$OD):δ 7.79 (d, J=8.7 Hz, 2H), 7.60 (d, J=8.7 Hz, 2H), 7.14 (d, J=8.7 Hz, 2H), 7.06 (d, J=8.7 Hz, 2H), 4.36 (s, 2H), 4.15 (d, J=2.1 Hz, 1H), 4.00 (m, 1H), 3.75 (m, 1H), 3.60-3.40 (m, 3H), 3.30-3.11 (m, 2H), 2.58-2.27 (m, 3H), 2.19-1.96 (m, 3H), 1.93-1.60 (m, 5H), 1.50-1.09 (m, 6H), 1.05-0.80 (m, 2H), 0.94 (t, J=7.2 Hz, 3H).

EXAMPLE 95

(3R)-1-butyl-2,5-dioxo-3-((1R)-1-hydroxy-1-cyclohexylmethyl)-9-(4-(4-methylaminocarbonylphenyloxy)phenylcarbonyl)-1,4,9-triazaspiro[5.5]undecan

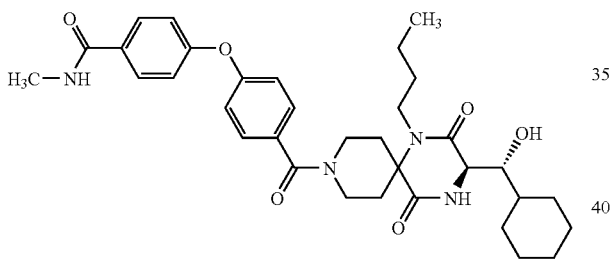

To a solution of 4-(4-methylaminocarobonylphenyloxy) benzoic acid (53.8 mg) in dimethylformamide (4 ml) was added 1-hydroxybenztriazole (34.9 mg) and 1-ethyl-3-[3-(dimethylamino)propyl]carbodiimide-hydrochloride (49.5 mg). The reaction mixture was stirred for 40 minutes at room temperature. The reaction mixture was added the compound prepared in Example 69(3) (100 mg) and stirred for 19 hours at room temperature. The reaction mixture was diluted with methylene dichloride, added water, and extracted with methylene dichloride. The extract was washed with 10% aqueous solution of citric acid and saturated aqueous solution of sodium chloride, dried over anhydrous sodium sulfate and concentrated. The obtained residue was purified by column chromatography on silica gel (ethyl acetate:methanol=10:1) and washed with diethyl ether to give the title compound (56.1 mg) having the following physical data.

TLC: Rf 0.41 (ethyl acetate:methanol=10:1); NMR (CD$_3$OD):δ 7.84 (d, J=8.7 Hz, 2H), 7.49 (t, J=8.7 Hz, 2H), 7.13-7.06 (m, 4H), 3.70 (m, 1H), 4.16 (m, 1H), 4.12-2.98 (m, 6H), 2.91 (s, 3H), 2.42-0.80 (m, 19H), 0.96 (t, J=6.9 Hz, 3H).

444

EXAMPLE 96

(3R)-1-butyl-2,5-dioxo-3-((1R)-1-hydroxy-1-cyclohexylmethyl)-9-(4-(4-methylaminocarbonylphenyloxy)phenyl)-1,4,9-triazaspiro[5.5]undecane.hydrochloride

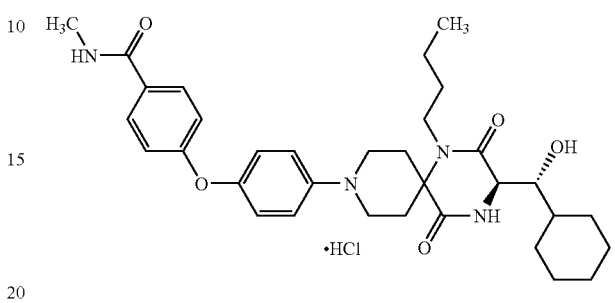

By the same procedure as described in Reference example 13→Reference example 14→Example 67 using (2R,3R)-2-(t-butoxycarbonylamino)-3-cyclohexyl-3-hydroxypropanoic acid instead of (2R,3R)-2-(t-butoxycarbonylamino)-3-hydroxy-4-methylpentanoic acid, and using N-(4-(4-methylaminocarobonylphenyloxy)phenyl)-4-piperidone instead of N-benzyl-4-piperidone, and using 2-morpholinoethylisonitrile instead of benzylisonitrile, the title compound having the following physical data was obtained.

TLC: Rf 0.40 (ethyl acetate); NMR (CD$_3$OD):δ 7.87 (d, J=9.0 Hz, 2H), 7.78 (d, J=9.0 Hz, 2H), 7.25 (d, J=9.0 Hz, 2H), 7.10 (d, J=9.0 Hz, 2H), 4.65 (m, 1H), 4.39 (m, 1H), 4.20 (d, J=1.8 Hz, 1H), 3.73-3.65 (m, 3H), 3.43-3.27 (m, 2H), 2.91 (s, 3H), 2.90-2.52 (m, 3H), 2.25 (m, 1H), 2.10-1.90 (m, 2H), 1.85-1.60 (m, 5H), 1.60-1.10 (m, 6H), 0.99 (t, J=7.2 Hz, 3H), 1.00-0.82 (m, 2H).

EXAMPLE 97

Inhibiting Activity to HIV-1 Infection to Human PBMC

Human PBMC (peripheral blood mononuclear cell) was isolated from HIV-negative healthy persons by a Ficol-Hipaque density-gradient centrifugation and incubated for 3 days in the presence of 10 µg/ml PHA (phytohemagglutinin). PHA-stimulated PBMC was suspended in RPMI 1640 containing 10% serum to give a density of $1 \times 10^5$ cells/ml and poured into a 96-well microplate. Furthermore, in the presence of a sole test compound in various concentrations or in the co-presence with other anti-HIV inhibitor (such as AZT (zidovudin) or AMD 3100), various HIV-1 cell lines of 50 TCID$_{50}$ (such as HIV-1$_{LAI}$, HIV-1$_{NL4-3}$, HIV-1$_{BaL}$, HIV-1$_{JRFL}$, HIV-1$_{89.6}$, HIV-1 HIV-1$_{ERS104pre}$, HIV-1$_{JSL}$, HIV-1$_{MM}$, HIV-1$_{TM}$ and HIV-1$_{MOKW}$) were exposed. After being incubated for 7 days, the amount of HIV-1p24 antigen on the supernatant liquid of the incubation was measured by an EIA method using Lumipulse F (Fuji Rebio).

Inhibiting effect to HIV-1 infection to human PBMC was investigated by the joint use of the compound of Example 2(1) with AMD 3100. The compound of Example 2(1) in various concentrations and AMD 3100 were added either solely or combinably and an assay was carried out. Results of the compound of Example 2(1) to HIV-1$_{89.6}$ and to a mixed virus of HIV-1$_{BaL}$ and HIV-1$_{NL4-3}$ are shown in Tables 1 and 2. Inhibiting effects of both compounds when the p24 amount where the compounds are not added is defined as 100% are shown in terms of % control.

TABLE 1

Inhibiting Effect of Combination of Compound of Example 2(1) with AMD 3100 to HIV-1$_{89.6}$

|  |  | Compound of Example 2(1) | | |
| --- | --- | --- | --- | --- |
|  | (μM) | 0 | 0.1 | 1 |
| AMD 3100 | 0 | 100 | 72.0 | 64.5 |
|  | 0.01 | 58.3 | 38.0 | 15.1 |
|  | 0.1 | 6.9 | 6.0 | 0.7 |
|  |  |  |  | % control |

TABLE 2

Inhibiting Effect of Combination of Compound of Example 2(1) with AMD 3100 to Mixed Virus of HIV-1$_{BaL}$ and HIV-1$_{NL4-3}$ (1:1)

|  |  | Compound of Example 2(1) | | |
| --- | --- | --- | --- | --- |
|  | (μM) | 0 | 0.1 | 1 |
| AMD 3100 | 0 | 100 | 63.8 | 52.4 |
|  | 0.01 | 59.1 | 32.1 | 10.5 |
|  | 0.1 | 44.2 | 17.8 | 1.5 |
|  |  |  |  | % control |

Inhibiting effect of the compound of Example 2(1) to human PBMC infected by wild-type HIV-1 (HIV-1$_{MOKW}$) and by multidrug resistant HIV-1 (HIV-1$_{JSL}$ and HIV-1$_{MM}$) to reverse transcriptase inhibitor and protease inhibitor was investigated. Inhibiting effect (IC$_{50}$ values) of the compound of Example 2(1) to various kinds of viruses is shown in Table 3.

TABLE 3

Inhibiting Effect to Infection of Multidrug Resistant HIV-1 Strains (HIV-1$_{JSL}$ and HIV-1$_{MM}$) to Reverse Transcriptase Inhibitor and Protease Inhibitor to Human PBMC

|  | IC$_{50}$ (μM) | | |
| --- | --- | --- | --- |
|  | Wild-Type HIV | Multidrug Resistant HIV-1 | |
|  | HIV-1$_{MOKW}$ | HIV-1$_{JSL}$ | HIV-1$_{MM}$ |
| Compound of Ex. 2(1) | 0.040 ± 0.029 | 0.064 ± 0.011 | 0.048 ± 0.062 |

Inhibiting effect to human PBMC infected by HIV-1 HIV-1$_{BaL}$ by the joint use of the compound of Example 2(1) and saquinavir (SQV) which is an anti-HIV inhibitor was investigated. The effects of the compound of Example 2(1) and saquinavir (SQV) used either solely or combinably are shown in Table 4. Inhibiting effects of both compounds when the p24 amount where the compounds are not added is defined as 100% are shown in terms of % control.

TABLE 4

Inhibiting Effect by Combination of Compound of Example 2(1) with Saquinavir to HIV-1$_{BaL}$ Infected to Human PBMC

|  |  | Compound of Example 2(1) | |
| --- | --- | --- | --- |
|  | (μM) | 0 | 0.1 |
| Saquinavir | 0 | 100 | 75.4 |
|  | 0.01 | 53.8 | 44.3 |
|  |  |  | % control |

Inhibiting effect to human PBMC infected by HIV-1 HIV-1BaL by the joint use of the compound of Example 75(54) and saquinavir (SQV) which is an anti-HIV inhibitor 10 was investigated. The effects of the compound of Example 75(54) and saquinavir (SQV) used either solely or combinably are shown in Table 5. Inhibiting effects of both compounds when the p24 amount where the compounds are not added is defined as 100% are shown in terms of % control.

TABLE 5

Inhibiting Effect by Combination of Compound of Example 75(54) with Saquinavir to HIV-1$_{BaL}$ Infected to Human PBMC

|  |  | Compound of Example 75(54) | | | |
| --- | --- | --- | --- | --- | --- |
|  | (nM) | 0 | 0.2 | 1 | 5 |
| Saquinavir | 0 | 100 | 64.2 | 34.2 | 10.6 |
|  | 1 | 78.1 | 66.0 | 32.8 | 10.8 |
|  | 5 | 67.7 | 52.0 | 29.3 | 6.1 |
|  | 25 | 5.9 | 5.7 | 3.8 | 1.6 |
|  |  |  |  |  | % control |

FORMULATION EXAMPLE 1

The following components were admixed in a conventional manner, punched out to give 100 tablets each containing 50 mg of active ingredient.

| 9-(1,4-benzodioxan-6-ylmethyl)-1-butyl-3-cyclohexylmethyl-2,5-dioxo-1,4,9-triazaspiro[5.5]undecane.hydrochloride | 5.0 g |
| --- | --- |
| calcium carboxymethyl cellulose (disintegrant) | 0.2 g |
| magnesium stearate (lubricant) | 0.1 g |
| microcrystalline cellulose | 4.7 g |

FORMULATION EXAMPLE 2

The following components were admixed in a conventional technique. The solution was sterilized in a conventional technique, filled in ampoules 5 ml each and freeze-dried over in a conventional technique to give 100 ampoules each containing 20 mg of active ingredient.

| 9-(1,4-benzodioxan-6-ylmethyl)-1-butyl-3-cyclohexylmethyl-2,5-dioxo-1,4,9-triazaspiro[5.5]undecane.hydrochloride | 2.0 g |
| --- | --- |
| mannitol | 20 g |
| distilled water | 500 mL |

The invention claimed is:

1. A method for treatment of a disease selected from the group consisting of HIV infection, AIDS, and HIV infection acquiring multidrug resistance, which comprises administering to a subject in need thereof an effective amount of a triazaspiro[5.5]undecane compound represented by formula (I):

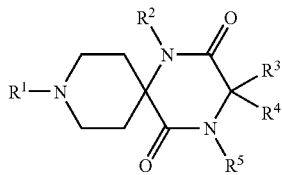

wherein $R^1$ is
(1) hydrogen,
(2) C1-18 alkyl,
(3) C2-18 alkenyl,
(4) C2-18 alkynyl,
(5) —$COR^6$,
(6) —$CONR^7R^8$,
(7) —$COOR^9$,
(8) —$SO_2R^{10}$,
(9) —$COCOOR^{11}$,
(10) —$CONR^{12}COR^{13}$,
(11) Cyc1 or
(12) C1-18 alkyl, C2-18 alkenyl or C2-18 alkynyl substituted by 1-5 substituents selected from the group consisting of (a) halogen, (b) —$CONR^7R^8$, (c) —$COOR^9$, (d) —$OR^{14}$, (e) —$SR^{15}$, (f) —$NR^{16}R^{17}$, (g) —$NR^{18}COR^{19}$, (h) —$SO_2NR^{20}R^{21}$, (i) —$OCOR^{22}$, (j) —$NR^{23}SO_2R^{24}$, (k) —$NR^{25}COOR^{26}$, (l) —$NR^{27}CONR^{28}R^{29}$, (m) Cyc1, (n) keto and (o) —$N(SO_2R^{24})_2$, $R^6$-$R^9$, $R^{11}$-$R^{21}$, $R^{23}$, $R^{25}$ and $R^{27}$-$R^{29}$ are each independently
(1) hydrogen,
(2) C1-8 alkyl,
(3) C2-8 alkenyl,
(4) C2-8 alkynyl,
(5) Cyc1 or
(6) C1-8 alkyl, C2-8 alkenyl or C2-8 alkynyl substituted by 1-5 substituents selected from the group consisting of (a) Cyc1, (b) halogen, (c) —$OR^{30}$, (d) —$SR^{31}$, (e) —$NR^{32}R^{33}$, (f) —$COOR^{34}$, (g) —$CONR^{35}R^{36}$, (h) —$NR^{37}COR^{38}$, (i) —$NR^{39}SO_2R^{40}$ and (j) —$N(SO_2R^{40})_2$, $R^7$ and $R^8$, $R^{20}$ and $R^{21}$, or $R^{28}$ and $R^{29}$, taken together, are
1) C2-6 alkylene,
2) —(C2-6 alkylene)-O—(C2-6 alkylene)-,
3) —(C2-6 alkylene)-S—(C2-6 alkylene)- or
4) —(C2-6 alkylene)-$NR^{195}$—(C2-6 alkylene)-, wherein $R^{195}$ is hydrogen, C1-8 alkyl, phenyl, or C1-8 alkyl substituted by phenyl, $R^{10}$, $R^{22}$, $R^{24}$ and $R^{26}$ are each independently
(1) C1-8 alkyl,
(2) C2-8 alkenyl,
(3) C2-8 alkynyl,
(4) Cyc1 or
(5) C1-8 alkyl, C2-8 alkenyl or C2-8 alkynyl substituted by 1-5 substituents selected from the group consisting of (a) Cyc1, (b) halogen, (c) —$OR^{30}$, (d) —$SR^{31}$, (e) —$NR^{32}R^{33}$, (f) —$COOR^{34}$, (g) —$CONR^{35}R^{36}$, (h) —$NR^{37}COR^{38}$, (i) —$NR^{39}SO_2R^{40}$ and (j) —$N(SO_2R^{40})_2$, $R^{30}$-$R^{37}$ and $R^{39}$ are each independently hydrogen, C1-8 alkyl, Cyc1 or C1-8 alkyl substituted by Cyc1, $R^{35}$ and $R^{36}$, taken together, are
1) C2-6 alkylene,
2) —(C2-6 alkylene)-O—(C2-6 alkylene)-,
3) —(C2-6 alkylene)-S—(C2-6 alkylene)- or
4) —(C2-6 alkylene)-$NR^{196}$—(C2-6 alkylene)- wherein $R^{196}$ is hydrogen, C1-8 alkyl, phenyl or C1-8 alkyl substituted by phenyl, $R^{38}$ and $R^{40}$ are each independently C1-8 alkyl, Cyc1 or C1-8 alkyl substituted by Cyc1, Cyc1 is C3-15 mono-, bi- or tri-(fused or spiro)carbocyclic ring or 3-15 membered mono-, bi- or tri-(fused or spiro)cyclic hetero ring containing 1-4 nitrogen atoms, 1-3 oxygen atoms and/or 1-3 sulfur atoms, wherein Cyc1 may be substituted by 1-5 of $R^{51}$, $R^{51}$ is
(1) C1-8 alkyl,
(2) C2-8 alkenyl,
(3) C2-8 alkynyl,
(4) halogen,
(5) nitro,
(6) trifluoromethyl,
(7) trifluoromethoxy,
(8) nitrile,
(9) keto,
(10) Cyc2,
(11) —$OR^{52}$,
(12) —$SR^{53}$,
(13) —$NR^{54}R^{55}$,
(14) —$COOR^{56}$,
(15) —$CONR^{57}R^{58}$,
(16) —$NR^{59}COR^{60}$,
(17) —$SO_2NR^{61}R^{62}$,
(18) —$OCOR^{63}$,
(19) —$NR^{64}SO_2R^{65}$,
(20) —$NR^{66}COOR^{67}$,
(21) —$NR^{68}CONR^{69}R^{70}$,
(22) —$B(OR^{71})_2$,
(23) —$SO_2R^{72}$,
(24) —$N(SO_2R^{72})_2$,
(25) —$S(O)R^{72}$ or
(26) C1-8 alkyl, C2-8 alkenyl or C2-8 alkynyl substituted by 1-5 substituents selected from the group consisting of (a) halogen, (b) Cyc2, (c) —$OR^{52}$, (d) —$SR^{53}$, (e) —$NR^{54}R^{55}$, (f) —$COOR^{56}$, (g) —$CONR^{57}R^{58}$, (h) —$NR^{59}COR^{60}$, (i) —$SO_2NR^{61}R^{62}$, (j) —$OCOR^{63}$, (k) —$NR^{64}SO_2R^{65}$, (l) —$NR^{66}COOR^{67}$, (m) —$R^{68}CONR^{69}R^{70}$, (n) —$B(OR^{71})_2$, (o) —$SO_2R^{72}$, (p) —$N(SO_2R^{72})_2$, (q) —$S(O)R^{72}$ and (r) keto, $R^{52}$-$R^{62}$, $R^{64}$, $R^{66}$ and $R^{68}$-$R^{71}$ are each independently
1) hydrogen,
2) C1-8 alkyl,
3) C2-8 alkenyl,
4) C2-8 alkynyl,
5) Cyc2 or
6) C1-8 alkyl, C2-8 alkenyl or C2-8 alkynyl substituted by Cyc2, —$OR^{73}$, —$COOR^{74}$ or —$NR^{75}R^{76}$, $R^{57}$ and $R^{58}$, $R^{61}$ and $R^{62}$ or $R^{69}$ and $R^{70}$ taken together, are
1) C2-6 alkylene,
2) —(C2-6 alkylene)-O—(C2-6 alkylene)-, 3) —(C2-6 alkylene)-S—(C2-6 alkylene)- or
4) —(C2-6 alkylene)-NR$^{197}$—(C2-6 alkylene)-, wherein R$^{197}$ is hydrogen, C1-8 alkyl, phenyl or C1-8 alkyl substituted by phenyl,
R$^{63}$, R$^{65}$, R$^{67}$ and R$^{72}$ are each independently
1) C1-8 alkyl,
2) C2-8 alkenyl,
3) C2-8 alkynyl,
4) Cyc2 or
5) C1-8 alkyl, C2-8 alkenyl or C2-8 alkynyl substituted by Cyc2, —OR$^{73}$, —COOR$^{74}$ or —NR$^{75}$R$^{76}$,
R$^{73}$-R$^{76}$ are each independently hydrogen, C1-8 alkyl, Cyc2 or C1-8 alkyl substituted by Cyc2,
Cyc2 has the same meaning as Cyc1, wherein Cyc2 may be substituted by 1-5 of R$^{77}$,
R$^{77}$ is
1) C1-8 alkyl,
2) halogen,
3) nitro,
4) trifluoromethyl,
5) trifluoromethoxy,
6) nitrile,
7) —OR$^{78}$,
8) —NR$^{79}$R$^{80}$,
9) —COOR$^{81}$,
10) —SR$^{82}$,
11) —CONR$^{83}$R$^{84}$,
12) C2-8 alkenyl,
13) C2-8 alkynyl,
14) keto,
15) Cyc6,
16) —NR$^{161}$COR$^{162}$,
17) —SO$_2$NR$^{63}$R$^{164}$,
18) —OCOR$^{165}$,
19) —NR$^{166}$SO$_2$R$^{167}$,
20) —NR$^{168}$COOR$^{169}$,
21) —NR$^{170}$CONR$^{171}$R$^{172}$,
22) —SO$_2$R$^{173}$,
23) —N(SO$_2$R$^{167}$)$_2$,
24) —S(O)R$^{173}$ or
25) C1-8 alkyl, C2-8 alkenyl or C2-8 alkynyl substituted by 1-5 substituents selected from the group consisting of (a) halogen, (b) —OR$^{78}$, (c) —NR$^{79}$R$^{80}$, (d) —COOR$^{81}$, (e) —SR$^{82}$, (f) —CONR$^{83}$R$^{84}$, (g) keto, (h) Cyc6, (i) —N$^{161}$COR$^{162}$, (j) —SO$_2$NR$^{163}$R$^{164}$, (k) —OCOR$^{165}$, (l) —NR$^{166}$SO$_2$R$^{167}$, (m) —NR$^{168}$COOR$^{169}$, (n) —NR$^{170}$CONR$^{171}$R$^{172}$, (o) —SO$_2$R$^{173}$, (p) —N(SO$_2$R$^{167}$)$_2$ and (q) —S(O)R$^{173}$,
R$^{78}$-R$^{84}$, R$^{161}$-R$^{164}$, R$^{166}$, R$^{168}$ and R$^{170}$-R$^{172}$ are each independently, (a) hydrogen, (b) C1-8 alkyl, (c) C2-8 alkenyl, (d) C2-8 alkynyl, (e) Cyc6, (f) C1-8 alkyl, C2-8 alkenyl or C2-8 alkynyl substituted by Cyc6, —OR$^{174}$, —COOR$^{175}$, —NR$^{176}$R$^{177}$ or —CONR$^{178}$R$^{179}$,
R$^{83}$ and R$^{84}$, R$^{163}$ and R$^{164}$, or R$^{171}$ and R$^{172}$, taken together, are
1) C2-6 alkylene,
2) —(C2-6 alkylene)-O—(C2-6 alkylene)-,
3) —(C2-6 alkylene)-S—(C2-6 alkylene)- or
4) —(C2-6 alkylene)-NR$^{198}$—(C2-6 alkylene)-, wherein R$^{198}$ is hydrogen, C1-8 alkyl, phenyl or C1-8 alkyl substituted by phenyl,
R$^{165}$, R$^{167}$, R$^{169}$ and R$^{173}$ are each independently (a) C1-8 alkyl, (b) C2-8 alkenyl, (c) C2-8 alkynyl, (d) Cyc6 or (e) C1-8 alkyl, C2-8 alkenyl or C2-8 alkynyl substituted by Cyc6, —OR$^{174}$, —COOR$^{175}$, —NR$^{176}$R$^{177}$ or —CONR$^{178}$R$^{179}$, R$^{174}$-R$^{177}$ are each independently
1) hydrogen,
2) C1-8 alkyl,
3) Cyc6 or
4) C1-8 alkyl substituted by Cyc6,
R$^{178}$ and R$^{179}$, taken together, are
1) C2-6 alkylene,
2) —(C2-6 alkylene)-O—(C2-6 alkylene)-,
3) —(C2-6 alkylene)-S—(C2-6 alkylene)- or
4) —(C2-6 alkylene)-NR$^{199}$—(C2-6 alkylene)-, wherein R$^{199}$ is hydrogen, C1-8 alkyl, phenyl or C1-8 alkyl substituted by phenyl,
Cyc6 is C3-8 mono-carbocyclic ring or 3-8 membered mono-cyclic hetero ring containing 1-4 nitrogen atoms, 1-2 oxygen atoms and/or 1-2 sulfur atoms, wherein Cyc6 may be substituted by 1-5 of R$^{180}$,
R$^{180}$ is
(1) C1-8 alkyl,
(2) halogen,
(3) nitro,
(4) trifluoromethyl,
(5) trifluoromethoxy,
(6) nitrile,
(7) —OR$^{181}$,
(8) —NR$^{182}$R$^{183}$,
(9) —COOR$^{184}$,
(10) —SR$^{185}$ or
(11) —CONR$^{186}$R$^{187}$,
R$^{181}$-R$^{187}$ are each independently
1) hydrogen,
2) C1-8 alkyl,
3) phenyl or
4) C1-8 alkyl substituted by phenyl,
R$^{182}$ and R$^{183}$ or R$^{186}$ and R$^{187}$, taken together, are
1) C2-6 alkylene,
2) —(C2-6 alkylene)-O—(C2-6 alkylene)-,
3) —(C2-6 alkylene)-S—(C2-6 alkylene)- or
4) —(C2-6 alkylene)-NR$^{200}$—(C2-6 alkylene)-, wherein R$^{200}$ is hydrogen, C1-8 alkyl, phenyl, C1-8 alkyl substituted by phenyl,
R$^2$ is
(1) hydrogen,
(2) C1-8 alkyl,
(3) C2-8 alkenyl,
(4) C2-8 alkynyl,
(5) —OR$^{90}$,
(6) Cyc3 or
(7) C1-8 alkyl, C2-8 alkenyl or C2-8 alkynyl substituted by 1-5 substituents selected from the group consisting of (a) halogen, (b) —OR$^{90}$, (c) —SR$^{91}$, (d) —NR$^{92}$R$^{93}$, (e) —COOR$^{94}$, (f) —CONR$^{95}$R$^{96}$, (g) —NR$^{97}$R$^{98}$, (h) —SO$_2$NR$^{99}$R$^{100}$, (i) —OCOR$^{101}$, (j) —NR$^{102}$SO$_2$R$^{103}$, (k) —NR$^{104}$COOR$^{105}$, (l) —NR$^{106}$CONR$^{107}$R$^{108}$, (m) Cyc3, (n) keto and (o) —N(SO$_2$R$^{103}$)$_2$,
R$^{90}$-R$^{100}$, R$^{102}$, R$^{104}$ and R$^{106}$-R$^{108}$ are each independently
1) hydrogen,
2) C1-8 alkyl,
3) C2-8 alkenyl,
4) C2-8 alkynyl,
5) Cyc3 or
6) C1-8 alkyl, C2-8 alkenyl or C2-8 alkynyl substituted by Cyc3, R$^{95}$ and R$^{96}$, R$^{99}$ and R$^{100}$, or R$^{107}$ and R$^{108}$, taken together, are
1) C2-6 alkylene,
2) —(C2-6 alkylene)-O—(C2-6 alkylene)-, 3) —(C2-6 alkylene)-S—(C2-6 alkylene)- or
4) —(C2-6 alkylene)-NR$^{201}$—(C2-6 alkylene)-, R$^{201}$ is hydrogen, C1-8 alkyl, phenyl or C1-8 alkyl substituted by phenyl, R$^{101}$, R$^{103}$ and R$^{105}$ are each independently
1) C1-8 alkyl,
2) C2-8 alkenyl,
3) C2-8 alkynyl or
4) Cyc3, or C1-8 alkyl, C2-8 alkenyl or C2-8 alkynyl substituted by Cyc3, Cyc3 has the same meaning as Cyc1,
wherein Cyc3 may be substituted by 1-5 of R$^{109}$, and R$^{109}$ has the same meaning as R$^{51}$,
R$^3$ and R$^4$ are each independently
(1) hydrogen,
(2) C1-8 alkyl,
(3) C2-8 alkenyl,
(4) C2-8 alkynyl,
(5) —COOR$^{120}$,
(6) —CONR$^{121}$R$^{122}$,
(7) Cyc4 or
(8) C1-8 alkyl, C2-8 alkenyl or C2-8 alkynyl substituted by 1-5 substituents selected from the group consisting of (a) halogen, (b) nitrile, (c) Cyc4, (d) —COOR$^{120}$, (e) —CONR$^{121}$R$^{122}$, (f) —OR$^{123}$, (g) —SR$^{124}$, (h) —NR$^{125}$R$^{126}$, (i) —NR$^{127}$COR$^{128}$, (j) —SO$_2$NR$^{129}$R$^{130}$, (k) —OCOR$^{131}$, (l) —NR$^{132}$SO$_2$R$^{133}$, (m) —NR$^{134}$COOR$^{135}$, (n) —NR$^{136}$CONR$^{137}$R$^{138}$, (o) —S—SR$^{139}$, (p) —NHC(=NH)NHR$^{140}$, (q) keto, (r) —NR$^{145}$CONR$^{146}$COR$^{147}$ and (s) —N(SO$_2$R$^{133}$)$_2$,
R$^{120}$-R$^{130}$, R$^{132}$, R$^{134}$, R$^{136}$-R$^{138}$, R$^{145}$ and R$^{146}$ are each independently
1) hydrogen,
2) C1-8 alkyl,
3) C2-8 alkenyl,
4) C2-8 alkynyl,
5) Cyc4 or
6) C1-8 alkyl, C2-8 alkenyl or C2-8 alkynyl substituted by Cyc4, halogen, —OR$^{148}$, —SR$^{149}$, —COOR$^{150}$ or —NHCOR$^{141}$,
R$^{121}$ and R$^{122}$, R$^{129}$ and R$^{130}$, or R$^{137}$ and R$^{138}$, taken together, are
1) C2-6 alkylene,
2) —(C2-6 alkylene)-O—(C2-6 alkylene)-,
3) —(C2-6 alkylene)-S—(C2-6 alkylene)- or
4) —(C2-6 alkylene)-NR$^{202}$—(C2-6 alkylene)-, wherein R$^{202}$ is hydrogen, C1-8 alkyl, phenyl, C1-8 alkyl substituted by phenyl,
R$^{131}$, R$^{133}$, R$^{135}$, R$^{139}$ and R$^{147}$ are each independently
1) C1-8 alkyl,
2) C2-8 alkenyl,
3) C2-8 alkynyl,
4) Cyc4 or
5) C1-8 alkyl, C2-8 alkenyl or C2-8 alkynyl substituted by Cyc4, halogen, —OR$^{148}$, —SR$^{149}$, —COOR$^{150}$ or —NHCOR$^{141}$,
R$^{140}$ is hydrogen, —COOR$^{142}$ or —SO$_2$R$^{143}$,
R$^{141}$-R$^{143}$ are each independently
1) C1-8 alkyl,
2) C2-8 alkenyl,
3) C2-8 alkynyl,
4) Cyc4 or
5) C1-8 alkyl, C2-8 alkenyl or C2-8 alkynyl substituted by Cyc4,
R$^{148}$-R$^{150}$ are each independently
1) hydrogen,
2) C1-8 alkyl,
3) C2-8 alkenyl,
4) C2-8 alkynyl,
5) Cyc4 or
6) C1-8 alkyl, C2-8 alkenyl or C2-8 alkynyl substituted by Cyc4, Cyc4 has the same meaning as Cyc1, wherein Cyc4 may be substituted by 1-5 of R$^{144}$, and R$^{144}$ has the same meaning as R$^{51}$,
R$^3$ and R$^4$, taken together, are

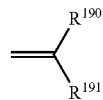

wherein R$^{190}$ and R$^{191}$ each independently has the same meaning as R$^3$ or R$^4$,
R$^5$ is
(1) hydrogen,
(2) C1-8 alkyl,
(3) Cyc5 or
(4) C1-8 alkyl substituted by Cyc5,
wherein Cyc5 has the same meaning as Cyc1, and Cyc5 may be substituted by 1-5 of R$^{160}$,
R$^{160}$ has the same meaning as R$^{51}$,
a quaternary ammonium salt thereof, an N-oxide thereof, or a non-toxic salt thereof.

2. The method according to claim 1, wherein the disease is AIDS.

3. The method according to claim 1, wherein said disease is HIV infection acquiring multidrug resistance.

4. The method according to claim 1, wherein the triazaspiro[5.5]undecane compound represented by formula (I), a quaternary ammonium salt thereof, an N-oxide thereof, or a non-toxic salt thereof is administered with at least one additional HIV infection treating agent.

5. The method according to claim 2, wherein the triazaspiro[5.5]undecane compound represented by formula (I), a quaternary ammonium salt thereof, an N-oxide thereof, or a non-toxic salt thereof is administered with at least one additional HIV infection treating agent.

6. The method according to claim 3, wherein the triazaspiro[5.5]undecane compound represented by formula (I), a quaternary ammonium salt thereof, an N-oxide thereof, or a non-toxic salt thereof is administered with at least one additional HIV infection treating agent.

7. The method according to any one of claims 4, 5 and 6, wherein said at least one additional HIV infection treating agent is a protease inhibitor, a reverse transcriptase inhibitor, a fusion inhibitor or a chemokine regulator.

* * * * *